(12) United States Patent
Kumaran et al.

(10) Patent No.: US 11,952,608 B2
(45) Date of Patent: *Apr. 9, 2024

(54) METHODS FOR PRODUCTION OF OXYGENATED TERPENES

(71) Applicant: Manus Bio Inc., Cambridge, MA (US)

(72) Inventors: Ajikumar Parayil Kumaran, Watertown, MA (US); Chin Giaw Lim, Cambridge, MA (US); Liwei Li, Cambridge, MA (US); Souvik Ghosh, Cambridge, MA (US); Christopher Pirie, Cambridge, MA (US); Anthony Qualley, Cambridge, MA (US)

(73) Assignee: Manus Bio Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/141,758

(22) Filed: Jan. 5, 2021

(65) Prior Publication Data

US 2021/0292798 A1 Sep. 23, 2021

Related U.S. Application Data

(63) Continuation of application No. 15/505,503, filed as application No. PCT/US2015/046369 on Aug. 21, 2015, now Pat. No. 10,934,564.

(60) Provisional application No. 62/040,284, filed on Aug. 21, 2014.

(51) Int. Cl.
| | |
|---|---|
| C12N 9/02 | (2006.01) |
| A01N 27/00 | (2006.01) |
| A23L 27/12 | (2016.01) |
| C12P 5/00 | (2006.01) |
| C12P 7/26 | (2006.01) |

(52) U.S. Cl.
CPC ............. C12P 7/26 (2013.01); A01N 27/00 (2013.01); A23L 27/13 (2016.08); C12N 9/0073 (2013.01); C12P 5/002 (2013.01); C12Y 114/13078 (2013.01); A23V 2002/00 (2013.01); C07K 2319/03 (2013.01)

(58) Field of Classification Search
None
See application file for complete search history.

(56) References Cited

U.S. PATENT DOCUMENTS

| | | | |
|---|---|---|---|
| 6,890,960 B1 | 5/2005 | Henderson et al. | |
| 8,415,136 B1 | 4/2013 | Gardner et al. | |
| 8,512,988 B2 | 8/2013 | Ajikumar et al. | |
| 8,927,241 B2 | 1/2015 | Ajikumar et al. | |
| 9,284,570 B2 | 3/2016 | Stephanopoulos et al. | |
| 9,359,624 B2 | 6/2016 | Ajikumar et al. | |
| 9,404,130 B2 | 8/2016 | Ajikumar et al. | |
| 9,957,527 B2 | 5/2018 | Ajikumar et al. | |
| 10,501,760 B2 | 12/2019 | Kumaran et al. | |
| 10,934,564 B2* | 3/2021 | Kumaran | C12P 5/002 |
| 11,180,782 B2 | 11/2021 | Kumaran et al. | |
| 11,618,908 B2* | 4/2023 | Philippe | C12N 9/0006 435/148 |
| 2007/0172934 A1 | 7/2007 | Muller et al. | |
| 2012/0107893 A1 | 5/2012 | Ajikumar et al. | |
| 2012/0246767 A1 | 9/2012 | Amick et al. | |
| 2017/0002366 A1 | 1/2017 | Ajikumar et al. | |
| 2017/0002382 A1 | 1/2017 | Ajikumar et al. | |

FOREIGN PATENT DOCUMENTS

| | | |
|---|---|---|
| EP | 1033076 | 9/2000 |
| JP | 2004067723 | 3/2004 |
| WO | 2006079020 | 7/2006 |

OTHER PUBLICATIONS

Wriessnegger et al., "Production of the sesquiterpenoid (+)-nootkatone by metabolic engineering of Pichia pastoris", Metabolic Engineering, vol. 24, Apr. 16, 2014, pp. 18-29.
Seifert et al., "Rational Design of a Minimal and Highly Enriched CYP102A1 Mutant Library with Improved Regio-, Stereo- and Chemoselectivity", Chembiochem, 2009, vol. 10, pp. 853-861.
Humphrey et al., "Spatial organisation of four enzymes from Stevia rebaudiana that are involved in steviol glycoside synthesis", Plant Molecular Biology, vol. 61, No. 1-2, 2006, pp. 47-62.
Hotze et al., "Cinnamate 4-hydroxylase from Catharanthus Roseusand a Strategy for the Functional Expression of Plant Cytochrome P450 Proteins as Translational Fusions with P450 Reductase in *Escherichia coli*", FEBS Letters, 1995, vol. 374, pp. 345-350.
Schuckel et al., "A Gene-Fusion Approach to Enabling Plant Cytochromes P450 for Biocatalysis", Chembiochem, vol. 13, No. 18, Nov. 5, 2012, pp. 2758-2763, XP002752378.
Drew et al., "Transcriptome Analysisof Thapsia laciniata Rouy Provides Insights into Terpenoid Biosynthesis and Diversity in Apiaceae", 2013, International Journal of Molecular Sciences, 2013, vol. 14, pp. 9080-9098.
King et al., "Production of Bioactive Diterpenoids in the Euphorbiaceae Depends on Evolutionarily Conserved Gene Clusters", The Plant Cell, 2014, vol. 26, pp. 3286-3298.
International Search Report and Written Opinion for PCT/US2015/046421, dated Mar. 22, 2016, 26 pages.
International Search Report and Written Opinion for PCT/US2015/46369, dated Dec. 14, 2015, 9 pages.
Frohwitter et al., "Production of the sesquiterpene (+)-valencene by metabolicallyengineered Corynebacterium glutamicum", J. Biotechnol. 191 :205-213, 2014.
Okamoto et al., "A short-chain dehydrogenase involved in terpene metabolism from Zingiber zerumbet", FEBS J. 278:2892-2900, 2011.
Lange et al., "Isoprenoid biosynthesis: The evolution of two ancient and distinct pathways across genomes", PNAS 97:13172-13177, 2000.
Singh, G., "Chemistry of Terpenoids and Carotenoids", Discovery Publishing House, New Delhi, 2007, pp. 3 and 4.

* cited by examiner

*Primary Examiner* — David Steadman
(74) *Attorney, Agent, or Firm* — Morgan, Lewis & Bockius LLP

(57) ABSTRACT

The present invention relates to methods for producing oxygenated terpenoids. Polynucleotides, derivative enzymes, and host cells for use in such methods are also provided.

5 Claims, 74 Drawing Sheets

Specification includes a Sequence Listing.

Figure 3A

>VvVS [Vitis vinifera]

MSTQVSASSLAQIPQPKNRPVANFHPNIWGDQFITYTPEDKVTRACKEEQIEDLKKEVKRKLTA
AAVANPSQLLNFIDAVQRLGVAYHFEQEIEEALQHICNSFHDCNDMDGDLYNIALGFRLLRQQG
YTISCDIFNKFTDERGRFKEALISDVRGMLGLYEAAHLRVHGEDILAKALAFTTTHLKAMVESL
GYHLAEQVAHALNRPIRKGLERLEARWYISVYQDEAFHDKTLLELAKLDFNLVQSLHKEELSNL
ARWWKELDFATKLPFARDRLVEGYFWMHGVYFEPQYLRGRRILTKVIAMTSILDDIHDAYGTPE
ELKLFIEAIERWDINSINQLPEYMKLCYVALLDVYKEIEEEMEKEGNQYRVHYAKEVMKNQVRA
YFAEAKWLHEEHVPAFEEYMRVALASSGYCLLATTSFVGMGEIATKEAFDWVTSDPKIMSSSNF
ITRLMDDIKSHKFEQKRGHVTSAVECYMKQYGVSEEQVYSEFQKQIENAWLDINQECLKPTAVS
MPLLARLLNFTRTMDVIYKEQDSYTHVGKVMRDNIASVFINAVI (SEQ ID NO: 1)

ATGGCTACGCAGGTCTCAGCCTCGTCACTGGCACAAATCCCGCAGCCGAAAAATCGTCCGGTGG
CGAACTTCCATCCGAATATCTGGGGTGACCAGTTTATCACGTATACCCCGGAAGATAAAGTGAC
CCGTGCGTGCAAGGAAGAACAAATTGAAGACCTGAAAAAGGAAGTCAAACGCAAGCTGACCGCA
GCAGCAGTGGCAAACCCGTCTCAGCTGCTGAATTTTATCGATGCGGTTCAACGTCTGGGCGTCG
CCTATCATTTCGAACAGGAAATTGAAGAAGCACTGCAACATATCTGCAACAGCTTTCACGATTG
TAATGATATGGACGGCGATCTGTATAACATTGCTCTGGGTTTCCGTCTGCTGCGCCAGCAAGGC
TACACGATTTCCTGTGACATCTTTAATAAATTCACCGATGAACGTGGTCGCTTTAAGGAAGCGC
TGATCTCAGACGTTCGTGGCATGCTGGGTCTGTATGAAGCTGCGCATCTGCGCGTCCACGGCGA
AGATATTCTGGCCAAAGCACTGGCTTTCACCACGACCCACCTGAAGGCGATGGTCGAATCTCTG
GGTTACCATCTGGCAGAACAGGTGGCACACGCCCTGAACCGTCCGATCCGCAAAGGCCTGGAAC
GTCTGGAAGCGCGCTGGTATATTAGTGTGTACCAGGACGAAGCATTTCATGATAAAACCCTGCT
GGAACTGGCTAAGCTGGATTTCAACCTGGTTCAATCTCTGCACAAAGAAGAACTGAGTAATCTG
GCCCGTTGGTGGAAAGAACTGGACTTTGCGACCAAGCTGCCGTTCGCCCGTGATCGCCTGGTTG
AAGGCTATTTTTGGATGCATGGTGTCTATTTCGAACCGCAGTACCTGCGCGGTCGTCGCATTCT
GACGAAAGTGATCGCAATGACCTCGATTCTGGATGACATCCACGACGCTTACGGCACCCCGGAA
GAACTGAAACTGTTTATTGAAGCGATCGAACGTTGGGATATTAACAGCATCAATCAGCTGCCGG
AATATATGAAACTGTGCTACGTGGCCCTGCTGGATGTTTACAAGGAAATCGAAGAAGAAATGGA
AAAGGAAGGTAACCAGTATCGTGTTCATTACGCGAAAGAAGTCATGAAGAATCAAGTGCGCGCC
TACTTTGCAGAAGCTAAATGGCTGCATGAAGAACACGTGCCGGCGTTCGAAGAATATATGCGCG
TTGCGCTGGCCAGCTCTGGCTACTGTCTGCTGGCCACGACCTCTTTTGTGGGCATGGGTGAAAT
TGCAACGAAAGAAGCGTTTGACTGGGTTACCAGTGATCCGAAGATTATGAGTTCCTCAAACTTT
ATCACCCGTCTGATGGATGACATTAAATCCCATAAGTTCGAACAGAAACGCGGTCACGTCACCT
CAGCCGTGGAATGCTATATGAAACAGTACGGCGTTTCGGAAGAACAAGTCTATAGCGAATTTCA
GAAACAAATCGAAACGCATGGCTGGATATTAATCAGGAATGTCTGAAACCGACGGCAGTCTCC
ATGCCGCTGCTGGCTCGTCTGCTGAATTTTACGCGCACGATGGATGTGATCTATAAAGAACAGG
ATTCGTACACCCATGTGGGCAAGGTTATGCGCGATAACATTGCAAGCGTGTTCATTAATGCTGT
TATCTAA (SEQ ID NO: 2)

Figure 3A (Continued)

>Vv1M1 | engineered valencene synthase

MATQVSASSLAQIPQPKNRPVANFHPNIWGDQFITYTPEDKVTRACKEEQIEDLKKEVKRKLTA
AAVANPSQLLNFIDAVQRLGVAYHFEQEIEEALQHICNSFHDCNDMDGDLYNIALGFRLLRQQG
YTISCDIFNKFTDERGRFKEALISDVRGMLGLYEAAHLRVHGEDILAKALAFTTTHLKAMVESL
GYHLAEQVAHALNRPIRKGLERLEARWYISVYQDEAFHDKTLLELAKLDFNLVQSLHKEELSNL
ARWWKELDFATKLPFARDRLVEGYFWMHGVYFEPQYLRGRRILTKVIAMTSILDDIHDAYGSPE
ELKLFIEAIEKWDESSINQLPEYMKLCFVALIDVYNEIEEEMEKEGNQYRIHYLKEVMKNQVRA
YFAEAKWLHDEHVPAFEEYMRVALASSGYCLLAVTSFVGMGEIVTKEAFDWVTSDPKLMSSSNF
ITRLMDDIKSHKFEQKRGHVTSAVECYMKQYGVTEEQVYSEFKKQIENAWLDINQECLKPTAVP
MPLLARLLNFTRTMDVIYKEQDSYTHVGKVMRDNIASVFINPVI  (SEQ ID NO: 3)

ATGGCAACCCAGGTGAGTGCAAGCAGCCTGGCCCAAATCCCTCAGCCGAAAAACCGCCCGGTT
GCAAACTTCCACCCTAATATCTGGGGCGATCAGTTCATCACCTATACCCCGGAAGATAAAGTG
ACAAGGGCCTGCAAAGAGGAGCAGATCGAGGACCTGAAAAAAGAGGTGAAGCGCAAGCTGACC
GCAGCCGCAGTGGCAAACCCGAGCCAACTGTTAAACTTCATCGATGCCGTGCAGCGCCTGGGC
GTTGCCTATCACTTCGAGCAGGAAATCGAAGAAGCCCTACAGCACATCTGTAACAGCTTCCAC
GATTGTAACGACATGGATGGCGACTTATACAACATAGCATTAGGTTTCCGCTTACTGCGTCAG
CAGGGCTACACCATAAGCTGCGACATCTTTAACAAGTTTACCGACGAGCGCGGTCGTTTTAAA
GAGGCGCTGATTAGCGACGTTCGCGGCATGTTAGGTCTGTACGAAGCCGCACATCTGCGCGTG
CACGGCGAAGACATTCTGGCGAAGGCGCTGGCATTCACAACCACACACCTGAAGGCAATGGTG
GAAAGTCTGGGCTACCACTTAGCCGAGCAGGTTGCCCATGCACTGAATCGCCCGATTCGTAAG
GGCCTGGAACGCCTGGAAGCCCGCTGGTACATCAGTGTTTATCAGGATGAAGCCTTTCATGAT
AAGACCCTGCTGGAGCTGGCAAAGCTGGATTTCAACCTGGTTCAGAGCCTGCATAAGGAAGAG
CTGAGCAACCTGGCCCGTTGGTGGAAGGAGCTGGATTTCGCAACCAAGCTGCCGTTCGCCAGG
GACAGGTTAGTTGAAGGCTACTTCTGGATGCACGGCGTTTACTTCGAGCCGCAATACCTGCGT
GGCCGCCGCATCCTGACGAAGGTGATCGCCATGACCAGCATTCTGGACGACATCCACGATGCG
TACGGGAGCCCTGAGGAGTTAAAGCTGTTCATCGAGGCAATCGAGAAGTGGGATGAGAGTAGC
ATCAACCAACTGCCGGAGTATATGAAACTGTGCTTCGTGGCCCTGATTGATGTTTACAATGAG
ATTGAAGAGGAGATGGAGAAAGAGGGGAACCAGTACCGCATCCACTACCTGAAAGAGGTGATG
AAGAATCAGGTGCGCGCATACTTCGCAGAGGCCAAATGGCTGCATGATGAGCATGTTCCTGCC
TTCGAGGAGTACATGCGCGTGGCATTAGCCAGCAGTGGTTACTGTCTGTTAGCCGTTACGAGC
TTCGTGGGTATGGGCGAGATCGTGACCAAAGAGGCATTCGACTGGGTGACGAGCGACCCGAAG
CTGATGAGCAGCAGCAACTTCATCACCCGTCTGATGGACGACATCAAGAGCCACAAGTTCGAG
CAGAAACGCGGTCACGTTACCAGCGCCGTGGAGTGCTACATGAAGCAGTACGGCGTGACAGAG
GAGCAAGTGTACAGCGAGTTCAAGAAACAAATCGAGAACGCCTGGCTGGACATCAACCAAGAG
TGCCTGAAACCGACCGCAGTGCCGATGCCTCTGTTAGCCCGTCTGCTGAATTTCACACGCACG
ATGGACGTTATCTACAAGGAGCAGGATAGCTACACCCACGTTGGTAAGGTGATGCGCGACAAC
ATCGCCAGTGTGTTCATCAACCCGGTGATCTAA  (SEQ ID NO: 4)

Figure 3A (Continued)

>Vv2M1 | engineered valencene synthase

MATQVSASSLAQIPQPKNRPVANFHPNIWGDQFITYTPEDKVTRACKEEQIEDLKKEVKRKLTA
AAVANPSQLLNFIDAVQRLGVAYHFEQEIEEALQHICNSFHDCNDMDGDLYNIALGFRLLRQQG
YTISCDIFNKFTDERGRFKEALISDVRGMLGLYEAAHLRVHGEDILAKALAFTTTHLKAMVESL
GYHLAEQVAHALNRPIRKGLERLEARWYISVYQDEAFHDKTLLELAKLDFNLVQSLHKEELSNL
ARWWKELDFATKLPFARDRLVEGYFWMHGVYFEPQYLRGRRILTKVIALTSILDDIHDAYGTPE
ELKLFIEAIEKWDESSINQLPEYMKLCYVALLDVYNEIEEEMEKEGNQYRIHYLKEVMKNQVRA
YFAEAKWLHDEHVPAFEEYMRVALASSGYCLLAVTSFVGMGEIVTKEAFDWVTSDPRIMSSSNF
ITRLMDDIKSHKFEQKRGHVTSAVECYMKQYAVTEEQVYSEFKKQIENAWLDINQECLKPTAVP
MPLLARLLNFTRTMDVIYKEQDSYTHVGKTMRDNIASVFINPVI (SEQ ID NO: 5)

ATGGCAACCCAGGTGAGTGCAAGCAGCCTGGCCCAAATCCCTCAGCCGAAAAACCGCCCGGTTG
CAAACTTCCACCCTAATATCTGGGGCGATCAGTTCATCACCTATACCCCGGAAGATAAAGTGAC
AAGGGCCTGCAAAGAGGAGCAGATCGAGGACCTGAAAAAAGAGGTGAAGCGCAAGCTGACCGCA
GCCGCAGTGGCAAACCCGAGCCAACTGTTAAACTTCATCGATGCCGTGCAGCGCCTGGGCGTTG
CCTATCACTTCGAGCAGGAAATCGAAGAAGCCCTACAGCACATCTGTAACAGCTTCCACGATTG
TAACGACATGGATGGCGACTTATACAACATAGCATTAGGTTTCCGCTTACTGCGTCAGCAGGGC
TACACCATAAGCTGCGACATCTTTAACAAGTTTACCGACGAGCGCGGTCGTTTTAAAGAGGCGC
TGATTAGCGACGTTCGCGGCATGTTAGGTCTGTACGAAGCCGCACATCTGCGCGTGCACGGCGA
AGACATTCTGGCGAAGGCGCTGGCATTCACAACCACACACCTGAAGGCAATGGTGGAAAGTCTG
GGCTACCACTTAGCCGAGCAGGTTGCCCATGCACTGAATCGCCCGATTCGTAAGGGCCTGGAAC
GCCTGGAAGCCCGCTGGTACATCAGTGTTTATCAGGATGAAGCCTTTCATGATAAGACCCTGCT
GGAGCTGGCAAAGCTGGATTTCAACCTGGTTCAGAGCCTGCATAAGGAAGAGCTGAGCAACCTG
GCCCGTTGGTGGAAGGAGCTGGATTTCGCAACCAAGCTGCCGTTCGCCAGGGACAGGTTAGTTG
AAGGCTACTTCTGGATGCACGGCGTTTACTTCGAGCCGCAATACCTGCGTGGCCGCCGCATCCT
GACGAAGGTGATCGCCCTGACCAGCATTCTGGACGACATCCACGATGCGTACGGGACCCCTGAG
GAGTTAAAGCTGTTCATCGAGGCAATCGAGAAGTGGGATGAGAGTAGCATCAACCAACTGCCGG
AGTATATGAAACTGTGCTATGTGGCCCTGCTGGATGTTTACAATGAGATTGAAGAGGAGATGGA
GAAAGAGGGGAACCAGTACCGCATCCACTACCTGAAAGAGGTGATGAAGAATCAGGTGCGCGCA
TACTTCGCAGAGGCCAAATGGCTGCATGATGAGCATGTTCCTGCCTTCGAGGAGTACATGCGCG
TGGCATTAGCCAGCAGTGGTTACTGTCTGTTAGCCGTTACGAGCTTCGTGGGTATGGGCGAGAT
CGTGACCAAAGAGGCATTCGACTGGGTGACGAGCGACCCGCGTATTATGAGCAGCAGCAACTTC
ATCACCCGTCTGATGGACGACATCAAGAGCCACAAGTTCGAGCAGAAACGCGGTCACGTTACCA
GCGCCGTGGAGTGCTACATGAAGCAGTACGCAGTGACAGAGGAGCAAGTGTACAGCGAGTTCAA
GAAACAAATCGAGAACGCCTGGCTGGACATCAACCAAGAGTGCCTGAAACCGACCGCAGTGCCG
ATGCCTCTGTTAGCCCGTCTGCTGAATTTCACACGCACGATGGACGTTATCTACAAGGAGCAGG
ATAGCTACACCCACGTTGGTAAGACCATGCGCGACAACATCGCCAGTGTGTTCATCAACCCGGT
GATCTAA (SEQ ID NO: 6)

Figure 3A (Continued)

\>Vv1M5 | engineered valencene synthase

MATQVSASSLAQIPQPKNRPVANFHPNIWGDQFITYTPEDKVTRAKKEEQIEDLKKEVKRKLTA
AAVANPSQLLNFIDAVQRLGVAYHFEQEIEEALQHICNSFHDCNDMDGDLYNIALGFRLLRQQG
YTISCDIFNKFTDERGRFKEALISDVRGMLGLYEAAHLRVHGEDILAKALAFTTTHLKAMVESL
GYHLAEQVAHALNRPIRKGLERLEARWYISVYQDEAFHDKTLLELAKLDFNLVQSLHKEELSNL
ARWWKELDFATKLPFARDRLVEGYFWMMGVYFEPQYLRGRRILTKVIAMTSILDDIHDAYGSPE
ELKLFIEAIEKWDESSINQLPEYMKLCFVALIDVYNEIEEEMEKEGNQYRIHYLKEVMKNQVRA
YFAEAKWLHDEHVPAFEEYMRVALASSGYCLLAVTSFVGMGEIVTKEAFDWVTSDPKLMSSSNT
ITRLMDDIKSHKFEQKRGHVTSAVECYMKQYGVTEEQVYSEFKKQIENAWLDINQECLKPTAVP
MPLLARLLNFTRTMDVIYKEEDSYTHVGKVMRDNIASVFINPVI  (SEQ ID NO: 7)

ATGGCAACCCAGGTGAGTGCAAGCAGCCTGGCCCAAATCCCTCAGCCGAAAAACCGCCCGGTTG
CAAACTTCCACCCTAATATCTGGGGCGATCAGTTCATCACCTATACCCCGGAAGATAAAGTGAC
AAGGGCCAAAAAAGAGGAGCAGATCGAGGACCTGAAAAAAGAGGTGAAGCGCAAGCTGACCGCA
GCCGCAGTGGCAAACCCGAGCCAACTGTTAAACTTCATCGATGCCGTGCAGCGCCTGGGCGTTG
CCTATCACTTCGAGCAGGAAATCGAAGAAGCCCTACAGCACATCTGTAACAGCTTCCACGATTG
TAACGACATGGATGGCGACTTATACAACATAGCATTAGGTTTCCGCTTACTGCGTCAGCAGGGC
TACACCATAAGCTGCGACATCTTTAACAAGTTTACCGACGAGCGCGGTCGTTTTAAAGAGGCGC
TGATTAGCGACGTTCGCGGCATGTTAGGTCTGTACGAAGCCGCACATCTGCGCGTGCACGGCGA
AGACATTCTGGCGAAGGCGCTGGCATTCACAACCACACACCTGAAGGCAATGGTGGAAAGTCTG
GGCTACCACTTAGCCGAGCAGGTTGCCCATGCACTGAATCGCCCGATTCGTAAGGGCCTGGAAC
GCCTGGAAGCCCGCTGGTACATCAGTGTTTATCAGGATGAAGCCTTTCATGATAAGACCCTGCT
GGAGCTGGCAAAGCTGGATTTCAACCTGGTTCAGAGCCTGCATAAGGAAGAGCTGAGCAACCTG
GCCCGTTGGTGGAAGGAGCTGGATTTCGCAACCAAGCTGCCGTTCGCCAGGGACAGGTTAGTTG
AAGGCTACTTCTGGATGATGGGCGTTTACTTCGAGCCGCAATACCTGCGTGGCCGCCGCATCCT
GACGAAGGTGATCGCCATGACCAGCATTCTGGACGACATCCACGATGCGTACGGGAGCCCTGAG
GAGTTAAAGCTGTTCATCGAGGCAATCGAGAAGTGGGATGAGAGTAGCATCAACCAACTGCCGG
AGTATATGAAACTGTGCTTCGTGGCCCTGATTGATGTTTACAATGAGATTGAAGAGGAGATGGA
GAAAGAGGGGAACCAGTACCGCATCCACTACCTGAAAGAGGTGATGAAGAATCAGGTGCGCGCA
TACTTCGCAGAGGCCAAATGGCTGCATGATGAGCATGTTCCTGCCTTCGAGGAGTACATGCGCG
TGGCATTAGCCAGCAGTGGTTACTGTCTGTTAGCCGTTACGAGCTTCGTGGGTATGGGCGAGAT
CGTGACCAAAGAGGCATTCGACTGGGTGACGAGCGACCCGAAGCTGATGAGCAGCAGCAACACC
ATCACCCGTCTGATGGACGACATCAAGAGCCACAAGTTCGAGCAGAAACGCGGTCACGTTACCA
GCGCCGTGGAGTGCTACATGAAGCAGTACGGCGTGACAGAGGAGCAAGTGTACAGCGAGTTCAA
GAAACAAATCGAGAACGCCTGGCTGGACATCAACCAAGAGTGCCTGAAACCGACCGCAGTGCCG
ATGCCTCTGTTAGCCCGTCTGCTGAATTTCACACGCACGATGGACGTTATCTACAAGGAGGAAG
ATAGCTACACCCACGTTGGTAAGGTGATGCGCGACAACATCGCCAGTGTGTTCATCAACCCGGT
GATCTAA  (SEQ ID NO: 8)

Figure 3A (Continued)

>Vv2M5 | engineered valencene synthase

MATQVSASSLAQIPQPKNRPVANFHPNIWGDQFITYTPEDKVTRAKKEEQIEDLKKEVKRKLTA
AAVANPSQLLNFIDAVQRLGVAYHFEQEIEEALQHICNSFHDCNDMDGDLYNIALGFRLLRQQG
YTISCDIFNKFTDERGRFKEALISDVRGMLGLYEAAHLRVHGEDILAKALAFTTTHLKAMVESL
GYHLAEQVAHALNRPIRKGLERLEARWYISVYQDEAFHDKTLLELAKLDFNLVQSLHKEELSNL
ARWWKELDFATKLPFARDRLVEGYFWMMGVYFEPQYLRGRRILTKVIALTSILDDIHDAYGTPE
ELKLFIEAIEKWDESSINQLPEYMKLCYVALLDVYNEIEEEMEKEGNQYRIHYLKEVMKNQVRA
YFAEAKWLHDEHVPAFEEYMRVALASSGYCLLAVTSFVGMGEIVTKEAFDWVTSDPRIMSSSNT
ITRLMDDIKSHKFEQKRGHVTSAVECYMKQYAVTEEQVYSEFKKQIENAWLDINQECLKPTAVP
MPLLARLLNFTRTMDVIYKEEDSYTHVGKTMRDNIASVFINPVI  (SEQ ID NO: 9)

ATGGCAACCCAGGTGAGTGCAAGCAGCCTGGCCCAAATCCCTCAGCCGAAAAACCGCCCGGTTG
CAAACTTCCACCCTAATATCTGGGGCGATCAGTTCATCACCTATACCCCGGAAGATAAAGTGAC
AAGGGCCAAAAAAGAGGAGCAGATCGAGGACCTGAAAAAAGAGGTGAAGCGCAAGCTGACCGCA
GCCGCAGTGGCAAACCCGAGCCAACTGTTAAACTTCATCGATGCCGTGCAGCGCCTGGGCGTTG
CCTATCACTTCGAGCAGGAAATCGAAGAAGCCCTACAGCACATCTGTAACAGCTTCCACGATTG
TAACGACATGGATGGCGACTTATACAACATAGCATTAGGTTTCCGCTTACTGCGTCAGCAGGGC
TACACCATAAGCTGCGACATCTTTAACAAGTTTACCGACGAGCGCGGTCGTTTTAAAGAGGCGC
TGATTAGCGACGTTCGCGGCATGTTAGGTCTGTACGAAGCCGCACATCTGCGCGTGCACGGCGA
AGACATTCTGGCGAAGGCGCTGGCATTCACAACCACACACCTGAAGGCAATGGTGGAAAGTCTG
GGCTACCACTTAGCCGAGCAGGTTGCCCATGCACTGAATCGCCCGATTCGTAAGGGCCTGGAAC
GCCTGGAAGCCCGCTGGTACATCAGTGTTTATCAGGATGAAGCCTTTCATGATAAGACCCTGCT
GGAGCTGGCAAAGCTGGATTTCAACCTGGTTCAGAGCCTGCATAAGGAAGAGCTGAGCAACCTG
GCCCGTTGGTGGAAGGAGCTGGATTTCGCAACCAAGCTGCCGTTCGCCAGGGACAGGTTAGTTG
AAGGCTACTTCTGGATGATGGGCGTTTACTTCGAGCCGCAATACCTGCGTGGCCGCCGCATCCT
GACGAAGGTGATCGCCCTGACCAGCATTCTGGACGACATCCACGATGCGTACGGGACCCCTGAG
GAGTTAAAGCTGTTCATCGAGGCAATCGAGAAGTGGGATGAGAGTAGCATCAACCAACTGCCGG
AGTATATGAAACTGTGCTATGTGGCCCTGCTGGATGTTTACAATGAGATTGAAGAGGAGATGGA
GAAAGAGGGGAACCAGTACCGCATCCACTACCTGAAAGAGGTGATGAAGAATCAGGTGCGCGCA
TACTTCGCAGAGGCCAAATGGCTGCATGATGAGCATGTTCCTGCCTTCGAGGAGTACATGCGCG
TGGCATTAGCCAGCAGTGGTTACTGTCTGTTAGCCGTTACGAGCTTCGTGGGTATGGGCGAGAT
CGTGACCAAAGAGGCATTCGACTGGGTGACGAGCGACCCGCGTATTATGAGCAGCAGCAACACC
ATCACCCGTCTGATGGACGACATCAAGAGCCACAAGTTCGAGCAGAAACGCGGTCACGTTACCA
GCGCCGTGGAGTGCTACATGAAGCAGTACGCAGTGACAGAGGAGCAAGTGTACAGCGAGTTCAA
GAAACAAATCGAGAACGCCTGGCTGGACATCAACCAAGAGTGCCTGAAACCGACCGCAGTGCCG
ATGCCTCTGTTAGCCCGTCTGCTGAATTTCACACGCACGATGGACGTTATCTACAAGGAGGAAG
ATAGCTACACCCACGTTGGTAAGACCATGCGCGACAACATCGCCAGTGTGTTCATCAACCCGGT
GATCTAA  (SEQ ID NO: 10)

>VS2 | engineered valencene synthase

MATQVSASSLAQIPQPKNRPVANFHPNIWGDQFITYTPEDKVTRAKKEEQIEDLKKEVKRKLTA
AAVANPSQLLNFIDAVQRLGVAYHFEQEIEEALQHICNSFHDCNDMDGDLYNIALGFRLLRQQG
YTISCDIFNKFTDERGRFKEALISDVRGMLGLYEAAHLRVHGEDILAKALAFTTTHLKAMVESL
GYHLAEQVAHALNRPIRKGLERLEARWYISVYQDEAFHDKTLLELAKLDFNLVQSLHKEELSNL
ARWWKELDFATKLPFARDRLVEGYFWMMGVYFEPQYLRGRRILTKVIALTSILDDIHDAYGTPE
ELKLFIEAIEKWDESSINQLPEYMKLCYVALLDVYNEIEEEMEKEGNQYRIHYLKEVMKNQVRA
YFAEAKWLHDEHVPAFEEYMRVALASSGYCLLAVTSFVGMGEIVTKEAFDWVTSDPRIMSSSNT
ITRLMDDIKSHKFEQKRGHVTSAVECYMKQYAVTEEQVYSEFKKQIENAWLDINQECLKPTAVP
MPLLARLLNFTRTMDVIYKEEDSYTHVGKTMRDNIASVFINPVI  (SEQ ID NO: 11)

Figure 3A (Continued)

>CsVS | Citrus sinensus valencene synthase

MASGETFRPTADFHPSLWRNHFLKGASDFKTVDHTATQERHEALKEEVRRMITDAEDKPVQKLR
LIDEVQRLGVAYHFEKEIGDAIQKLCPIYIDSNRADLHTVSLHFRLLRQQGIKISCDVFEKFKD
DEGRFKSSLINDVQGMLSLYEAAYMAVRGEHILDEAIAFTTTHLKSLVAQDHVTPKLAEQINHA
LYRPLRKTLPRLEARYFMSMINSTSDHLCNKTLLNFAKLDFNILLELHKEELNELTKWWKDLDF
TTKLPYARDRLVELYFWDLGTYFEPQYAFGRKIMTQLNYILSIIDDTYDAYGTLEELSLFTEAV
QRWNIEAVDMLPEYMKLIYRTLLDAFNEIEEDMAKQGRSHCVRYAKEENQKVIGAYSVQAKWFS
EGYVPTIEEYMPIALTSCAYTFVITNSFLGMGDFATKEVFEWISNNPKVVKAASVICRLMDDMQ
GHEFEQKRGHVASAIECYTKQHGVSKEEAIKMFEEEVANAWKDINEELMMKPTVVARPLLGTIL
NLARAIDFIYKEDDGYTHSYLIKDQIASVLGDHVPF  (SEQ ID NO: 12)

Figure 3B

```
Vv2M5    MATQVSASSLAQIPQPKNRPVANFHPNIWGDQFITYTPEDK-VTRAKKEEQIEDLKKEVK 59
VS2      MATQVSASSLAQIPQPKNRPVANFHPNIWGDQFITYTPEDK-VTRAKKEEQIEDLKKEVK 59
VvVS     MSTQVSASSLAQIPQPKNRPVANFHPNIWGDQFITYTPEDK-VTRACKEEQIEDLKKEVK 59
CsVS     MASGETF-----------RPTADFHPSLWRNHFLKGASDFKTVDHTATQERHEALKEEVR 49
         *::    :        **.*:***.:*  ::*:.  :.: *  *  ::  .:*: *  **:**:

Vv2M5    RKLTAAAVANPSQLLNFIDAVQRLGVAYHFEQEIEEALQHICNSFHDCNDMDGDLYNIAL 119
VS2      RKLTAAAVANPSQLLNFIDAVQRLGVAYHFEQEIEEALQHICNSFHDCNDMDGDLYNIAL 119
VvVS     RKLTAAAVANPSQLLNFIDAVQRLGVAYHFEQEIEEALQHICNSFHDCNDMDGDLYNIAL 119
CsVS     RMITDAEDK-PVQKLRLIDEVQRLGVAYHFEKEIGDAIQKLCPIYIDSNRAD---LHTVSL 106
         * :*  *    *  * *:** **********:** :*:*::*   *.*   *  *:.::*

Vv2M5    GFRLLRQQGYTISCDIFNKFTDERGRFKEALISDVRGMLGLYEAAHLRVHGEDILAKALA 179
VS2      GFRLLRQQGYTISCDIFNKFTDERGRFKEALISDVRGMLGLYEAAHLRVHGEDILAKALA 179
VvVS     GFRLLRQQGYTISCDIFNKFTDERGRFKEALISDVRGMLGLYEAAHLRVHGEDILAKALA 179
CsVS     HFRLLRQQGIKISCDVFEKFKDDEGRFKSSLINDVQGMLSLYEAAYMAVRGEHILDEAIA 166
          ******** .****:*:** *: .****:* .*:*****:: *:**.**  *:*:*

Vv2M5    FTTTHLKAMVES--LGYHLAEQVAHALNRPIRKGLERLEARWYISVY--QDEAFHDKTLL 235
VS2      FTTTHLKAMVES--LGYHLAEQVAHALNRPIRKGLERLEARWYISVY---QDEAFHDKTLL 235
VvVS     FTTTHLKAMVES--LGYHLAEQVAHALNRPIRKGLERLEARWYISVY--QDEAFHDKTLL 235
CsVS     FTTTHLKSLVAQDHVTPKLAEQINHALYRPLRKTLPRLEARYFMSMINSYSDHLCNKTLL 226
         *******::*.  .  : :****: ***  **:** * *****:::*:  .: : :****

Vv2M5    ELAKLDFNLVQSLHKEELSNLARWWKELDFATKLPFARDRLVEGYFWMMGVYFEPQYLRG 295
VS2      ELAKLDFNLVQSLHKEELSNLARWWKELDFATKLPFARDRLVEGYFWMMGVYFEPQYLRG 295
VvVS     ELAKLDFNLVQSLHKEELSNLARWWKELDFATKLPFARDRLVEGYFWMHGVYFEPQYLRG 295
CsVS     NFAKLDFNILLELHKEELNELTKWWKDLDFTTKLPYARDRLVELYFWDLGTYFEPQYAFG 286
         ::******::  .******.:*::***:***:***** ******* ***  *.****** *

Vv2M5    RRILTKVIALTSILDDIHDAYGTPEELKLFIEAIEKWDESSINQLPEYMKLCYVALLDVY 355
VS2      RRILTKVIALTSILDDIHDAYGTPEELKLFIEAIERWDESSINQLPEYMKLCYVALLDVY 355
VvVS     RRILTKVIAMTSILDDIHDAYGTPEELKLFIEAIERWDINSINQLPEYMKLCYVALLDVY 355
CsVS     RKIMTQLNYILSIIDDTYDAYGTLEELSLFTEAVQRWNIEAVDMLPEYMKLIYRTLLDAF 346
         *:*:*::   : **:** ***** ***.** **::*:  .:::  ******* *  :***.:

Vv2M5    NEIEEEMEKEGNQYRIHYLKEVMKNQVRAYFAEAKWLHDEHVPAFEEYMRVALASSGYCL 415
VS2      NEIEEEMEKEGNQYRIHYLKEVMKNQVRAYFAEAKWLHDEHVPAFEEYMRVALASSGYCL 415
VvVS     KEIEEEMEKEGNQYRVHYAKEVMKNQVRAYFAEAKWLHEEHVPAFEEYMRVALASSGYCL 415
CsVS     NEIEEDMAKQGRSHCVRYAKEENQKVIGAYSVQAKWFSEGYVPTIEEYMPIALTSCAYTF 406
         :****:* *:*.::  ::* **  :: :  **  .:***:  :  :**::****  :**:*..*  :

Vv2M5    LAVTSFVGMGEIVTKEAFDWVTSDPRIMSSSNTITRLMDDIKSHKFEQKRGHVTSAVECY 475
VS2      LAVTSFVGMGEIVTKEAFDWVTSDPRIMSSSNTITRLMDDIKSHKFEQKRGHVTSAVECY 475
VvVS     LATTSFVGMGEIATKEAFDWVTSDPKIMSSSNFITRLMDDIKSHKFEQKRGHVTSAVECY 475
CsVS     VITNSFLGMGDFATKEVFEWISNNPKVVKAASVICRLMDDMQGHEFEQKRGHVASAIECY 466
         : .. **:***.:*** **.*:*::.:*:::.::  * ******:*;********:**:***

Vv2M5    MKQYAVTEEQVYSEFKKQIENAWLDINQEC-LKPTAVPMPLLARLLNFTRTMDVIYKEED 534
VS2      MKQYAVTEEQVYSEFKKQIENAWLDINQEC-LKPTAVPMPLLARLLNFTRTMDVIYKEED 534
VvVS     MKQYGVSEEQVYSEFQKQIENAWLDINQEC-LKPTAVSMPLLARLLNFTRTMDVIYKEQD 534
CsVS     TKQHGVSKEEAIKMFEEEVANAWKDINEELMMKFTVVARPLLGTILNLARAIDFIYKEDD 526
         **:.*::**:. . *:::: *** ****:. :***.*. ***. :*:::*:**.****:*

Vv2M5    SYTHVGKTMRDNIASVFINPVI- 556
VS2      SYTHVGKTMRDNIASVFINPVI- 556
VvVS     SYTHVGKVMRDNIASVFINAVI- 556
CsVS     GYTHS-YLIKDQIASVLGDHVPF 548
         .***   ::*:*****: : *
```

Figure 4A

>ZzHO [Zingiber zerumbet]

MEAISLFSPFFFITLFLGFFITLLIKRSSRSSVHKQQVLLASLPPSPPRLPLIGNIHQLVGGNPHR
ILLQLARTHGPLICLRLGQVDQVVASSVEAVEEIIKRHDLKFADRPRDLTFSRIFFYDGNAVVMTP
YGGEWKQMRKIYAMELLNSRRVKSFAAIREDVARKLTGEIAHKAFAQTPVINLSEMVMSMINAIVI
RVAFGDKCKQQAYFLHLVKEAMSYVSSFSVADMYPSLKFLDTLTGLKSKLEGVHGKLDKVFDEIIA
QRQAALAAEQAEEDLIIDVLLKLKDEGNQEFPITYTSVKAIVMEIFLAGTETSSSVIDWVMSELIK
NPKAMEKVQKEMREAMQGKTKLEESDIPKFSYLNLVIKETLRLHPPGPLLFPRECRETCEVMGYRV
PAGARLLINAFALSRDEKYWGSDAESFKPERFEGISVDFKGSNFEFMPFGAGRRICPGMTFGISSV
EVALAHLLFHFDWQLPQGMKIEDLDMMEVSGMSATRRSPLLVLAKLIIPLP (SEQ ID No: 13 | Wild Type)

MALLLAVFFFFITLFLGFFITLLIKRS*SRS*SVHKQQVLLASLPPSPPRLPLIGNIHQLVGGNPHRI
LLQLARTHGPLICLRLGQVDQVVASSVEAVEEIIKRHDLKFADRPRDLTF*SRI*FFYDGNAVVMTPY
GGEWKQMRKIYAMELLN*SRR*VKSFAAIREDVARKLTGEIAHKAFAQTPVINLSEMVMSMINAIVIR
VAFGDKCKQQAYFLHLVKEAMSYVSSFSVADMYPSLKFLDTLTGLKSKLEGVHGKLDKVFDEIIAQ
RQAALAAEQAEEDLIIDVLLKLKDEGNQEFPITYTSVKAIVMEIFLAGTETSSSVIDWVMSELIKN
PKAMEKVQKEMREAMQGKTKLEESDIPKFSYLNLVIKETLRLHPPGPLLFPRECRETCEVMGYRVP
AGARLLINAFAL*SR*DEKYWGSDAESFKPERFEGISVDFKGSNFEFMPFGAGRRICPGMTFGISSVE
VALAHLLFHFDWQLPQGMKIEDLDMMEVSGMSATRRSPLLVLAKLIIPLP (SEQ ID NO: 14)

ATGGCTCTGTTATTAGCAGTGTTCTTCTTTTTCATTACGCTGTTTCTGGGTTTCTTTATTACGCTG
CTGATTAAACGCTCGTCCCGTAGCTCTGTCCATAAACAGCAAGTGCTGCTGGCCTCTCTGCCGCCG
AGTCCGCCGCGCCTGCCGCTGATTGGCAACATCCATCAACTGGTGGGCGGCAACCCGCATCGTATT
CTGCTGCAACTGGCGCGTACCCACGGCCCGCTGATCTGCCTGCGTCTGGGTCAGGTTGATCAAGTG
GTTGCAAGTTCCGTGGAAGCTGTTGAAGAAATTATCAAACGTCACGACCTGAAATTTGCAGATCGT
CCGCGCGACCTGACCTTTAGCCGTATTTTCTTTTATGATGGTAACGCTGTCGTGATGACGCCGTAC
GGCGGTGAATGGAAACAGATGCGTAAAATCTATGCAATGGAACTGCTGAACAGCCGTCGTGTGAAA
TCTTTTGCGGCCATTCGTGAAGACGTTGCACGCAAACTGACCGGCGAAATCGCTCACAAAGCATTC
GCTCAGACGCCGGTCATTAACCTGTCTGAAATGGTGATGAGTATGATCAATGCGATTGTCATCCGC
GTGGCCTTTGGTGATAAATGTAAACAGCAAGCATACTTCCTGCATCTGGTGAAAGAAGCTATGTCC
TATGTTTCATCGTTTTCAGTCGCGGATATGTACCCGTCCCTGAAATTCCTGGACACCCTGACGGGC
CTGAAAAGCAAACTGGAAGGCGTTCACGGTAAACTGGATAAAGTCTTCGACGAAATCATCGCACAG
CGTCAAGCAGCGCTGGCGGCGGAACAGGCTGAAGAAGATCTGATTATCGACGTGCTGCTGAAACTG
AAAGATGAAGGCAACCAGGAATTTCCGATTACCTATACGTCAGTTAAAGCGATTGTCATGGAAATC
TTCCTGGCCGGCACCGAAACCAGCAGCAGCGTGATTGACTGGGTTATGAGTGAACTGATCAAAAAC
CCGAAAGCGATGGAAAAAGTGCAGAAAGAAATGCGTGAAGCCATGCAAGGCAAAACCAAACTGGAA
GAATCGGATATTCCGAAATTTAGCTACCTGAATCTGGTTATCAAAGAAACCCTGCGTCTGCATCCG
CCGGGTCCGCTGCTGTTCCCGCGTGAATGCCGCGAAACCTGCGAAGTGATGGGCTATCGTGTTCCG
GCGGGTGCCCGCCTGCTGATTAACGCATTTGCTCTGTCTCGTGATGAAAAATACTGGGGTTCCGAC
GCCGAATCATTTAAACCGGAACGCTTTGAAGGCATCTCTGTGGATTTCAAAGGTAGTAATTTTGAA
TTTATGCCGTTCGGCGCGGGCCGTCGTATTTGTCCGGGCATGACCTTTGGTATCTCCTCAGTTGAA
GTCGCGCTGGCCCATCTGCTGTTTCACTTCGATTGGCAACTGCCGCAAGGCATGAAAATTGAAGAT
CTGGACATGATGGAAGTCTCGGGTATGAGCGCAACCCGTCGTAGCCCGCTGCTGGTTCTGGCCAAA
CTGATTATCCCGCTGCCG (SEQ ID NO: 15)

Figure 4A (Continued)

>BsGAO [Barnadesia spinosa]

MELTLTTSLGLAVFVFILFKLLTGSKSTKNSLPEAWRLPIIGHMHHLVGTLPHRGVTDMARKYGSL
MHLQLGEVSTIVVSSPRWAKEVLTTYDITFANRPETLTGEIVAYHNTDIVLSPYGEYWRQLRKLCT
LELLSAKKVKSFQSLREEECWNLVKEVRSSGSGSPVDLSESIFKLIATILSRAAFGKGIKDQREFT
EIVKEILRLTGGFDVADIFPSKKILHHLSGKRAKLTNIHNKLDSLINNIVSEHPGSRTSSSQESLL
DVLLRLKDSAELPLTSDNVKAVILDMFGAGTDTSSATIEWAISELIRCPRAMEKVQTELRQALNGK
ERIQEEDIQELSYLKLVIKETLRLHPPLPLVMPRECREPCVLAGYEIPTKTKLIVNVFAINRDPEY
WKDAETFMPERFENSPINIMGSEYEYLPFGAGRRMCPGAALGLANVELPLAHILYYFNWKLPNGAR
LDELDMSECFGATVQRKSELLLVPTAYKTANNSA  (SEQ ID No: 16 | Wild Type)

MALLLAVFLGLAVFVFILFKLLTGSKSTKNSLPEAWRLPIIGHMHHLVGTLPHRGVTDMARKYGSL
MHLQLGEVSTIVVSSPRWAKEVLTTYDITFANRPETLTGEIVAYHNTDIVLSPYGEYWRQLRKLCT
LELLSAKKVKSFQSLREEECWNLVKEVRSSGSGSPVDLSESIFKLIATIL*SR*AAFGKGIKDQREFT
EIVKEILRLTGGFDVADIFPSKKILHHLSGKRAKLTNIHNKLDSLINNIVSEHPG*SR*TSSSQESLL
DVLLRLKDSAELPLTSDNVKAVILDMFGAGTDTSSATIEWAISELIRCPRAMEKVQTELRQALNGK
ERIQEEDIQELSYLKLVIKETLRLHPPLPLVMPRECREPCVLAGYEIPTKTKLIVNVFAINRDPEY
WKDAETFMPERFENSPINIMGSEYEYLPFGAGRRMCPGAALGLANVELPLAHILYYFNWKLPNGAR
LDELDMSECFGATVQRKSELLLVPTAYKTANNSA  (SEQ ID NO: 17)

ATGGCTCTGTTATTAGCAGTTTTCCTGGGCCTGGCTGTCTTCGTCTTTATCCTGTTCAAACTGCTG
ACCGGCTCAAAATCAACCAAAAATTCACTGCCGGAAGCATGGCGTCTGCCGATCATTGGCCACATG
CATCACCTGGTTGGCACGCTGCCGCATCGCGGTGTGACCGACATGGCGCGTAAATACGGCAGCCTG
ATGCATCTGCAACTGGGCGAAGTGAGCACCATTGTCGTCTCATCGCCGCGTTGGGCAAAAGAAGTG
CTGACGACGTATGATATTACCTTTGCGAATCGCCCGGAAACCCTGACCGGCGAAATTGTTGCGTAC
CACAACACGGATATTGTGCTGTCACCGTATGGCGAATACTGGCGCCAACTGCGTAAACTGTGCACG
CTGGAACTGCTGAGCGCCAAAAAAGTGAAAAGTTTTCAGTCGCTGCGTGAAGAAGAATGCTGGAAT
CTGGTGAAAGAAGTGCGTTCGAGCGGCTCAGGTTCCCGGTCGATCTGTCGGAATCCATCTTTAAA
CTGATTGCAACCATTCTGAGCCGCGCAGCGTTTGGCAAAGGTATCAAAGATCAGCGTGAATTTACC
GAAATTGTGAAAGAAATCCTGCGCCTGACGGGCGGTTTTGATGTGGCGGATATTTTCCCGTCCAAA
AAGATCCTGCACCACCTGAGCGGCAAACGTGCGAAACTGACCAACATCCACAACAAACTGGATTCC
CTGATTAATAACATTGTTTCTGAACATCCGGGTTCGCGTACCTCGTCGAGCCAGGAAAGCCTGCTG
GATGTGCTGCTGCGCCTGAAAGATTCCGCGGAACTGCCGCTGACCTCGGACAATGTTAAAGCCGTG
ATCCTGGATATGTTCGGTGCGGGCACGGATACGTCGAGCGCCACGATTGAATGGCGATCAGCGAA
CTGATCCGCTGCCCGCGTGCAATGGAAAAAGTGCAAACGGAACTGCGTCAAGCGCTGAATGGTAAA
GAACGCATTCAGGAAGAAGATATTCAGGAACTGTCCTATCTGAAACTGGTCATTAAAGAAACCCTG
CGCCTGCATCCGCCGCTGCCGCTGGTGATGCCGCGTGAATGTCGTGAACCGTGTGTCCTGGCGGGT
TACGAAATCCCGACCAAAACGAAACTGATTGTGAATGTCTTTGCCATCAATCGTGACCCGGAATAC
TGGAAAGATGCAGAAACCTTCATGCCGGAACGCTTTGAAAACAGCCCGATTAACATCATGGGTAGT
GAATATGAATACCTGCCGTTTGGCGCAGGCCGCCGTATGTGTCCGGGTGCAGCTCTGGGTCTGGCG
AATGTGGAACTGCCGCTGGCGCACATCCTGTATTATTTAACTGGAAACTGCCGAATGGCGCTCGC
CTGGATGAACTGGATATGTCGGAATGCTTTGGCGCGACGGTCCAACGCAAAAGCGAACTGCTGCTG
GTCCCGACGGCATACAAAACGGCAAACAACTCCGCA  (SEQ ID NO: 18)

Figure 4A (Continued)

>HmPO [Hyoscyamus muticus]

MQFFSLVSIFLFLSFLFLLRKWKNSNSQSKKLPPGPWKLPLLGSMLHMVGGLPHHVLRDLAKKYGP
LMHLQLGEVSAVVVTSPDMAKEVLKTHDIAFASRPKLLAPEIVCYNRSDIAFCPYGDYWRQMRKIC
VLEVLSAKNVRSFSSIRRDEVLRLVNFVRSSTSEPVNFTERLFLFTSSMTCRSAFGKVFKEQETFI
QLIKEVIGLAGGFDVADIFPSLKFLHVLTGMEGKIMKAHHKVDAIVEDVINEHKKNLAMGKTNGAL
GGEDLIDVLLRLMNDGGLQFPITNDNIKAIIFDMFAAGTETSSSTLVWAMVQMMRNPTILAKAQAE
VREAFKGKETFDENDVEELKYLKLVIKETLRLHPPVPLLVPRECREETEINGYTIPVKTKVMVNVW
ALGRDPKYWDDADNFKPERFEQCSVDFIGNNFEYLPFGGGRRICPGISFGLANVYLPLAQLLYHFD
WKLPTGMEPKDLDLTELVGVTAARKSDLMLVATPYQPSRE  (SEQ ID NO: 19 | Wild Type)

MALLLAVFFFSLVSIFLFLSFLFLLRKWKNSNSQSKKLPPGPWKLPLLGSMLHMVGGLPHHVLRDLAKKYGP
LMHLQLGEVSAVVVTSPDMAKEVLKTHDIAFASRPKLLAPEIVCYNRSDIAFCPYGDYWRQMRKICVLEVLS
AKNVRSFSSIRRDEVLRLVNFVRSSTSEPVNFTERLFLFTSSMTCRSAFGKVFKEQETFIQLIKEVIGLAGG
FDVADIFPSLKFLHVLTGMEGKIMKAHHKVDAIVEDVINEHKKNLAMGKTNGALGGEDLIDVLLRLMNDGGL
QFPITNDNIKAIIFDMFAAGTETSSSTLVWAMVQMMRNPTILAKAQAEVREAFKGKETFDENDVEELKYLKL
VIKETLRLHPPVPLLVPRECREETEINGYTIPVKTKVMVNVWALGRDPKYWDDADNFKPERFEQCSVDFIGN
NFEYLPFGGGRRICPGISFGLANVYLPLAQLLYHFDWKLPTGMEPKDLDLTELVGVTAARKSDLMLVATPYQ
PSRE  (SEQ ID NO: 20)

ATGGCTCTGTTATTAGCAGTTTTCTTCTTCTCCCTGGTCTCAATCTTTCTGTTCCTGTCCTTTCTG
TTCCTGCTGCGTAAATGGAAAAACTCAAACTCCCAATCGAAAAACTGCCGCCGGGTCCGTGGAAA
CTGCCGCTGCTGGGCTCTATGCTGCACATGGTTGGCGGCCTGCCGCATCACGTTCTGCGTGATCTG
GCGAAAAAATATGGTCCGCTGATGCATCTGCAACTGGGCGAAGTCTCCGCCGTGGTTGTCACCTCA
CCGGATATGGCAAAAGAAGTGCTGAAAACGCATGACATTGCGTTCGCCTCCCGTCCGAAACTGCTG
GCCCCGGAAATTGTGTGCTACAACCGCTCAGATATTGCATTTTGTCCGTATGGTGACTACTGGCGT
CAAATGCGCAAATTTGCGTCCTGGAAGTGCTGTCGGCCAAAAATGTGCGCAGCTTTAGCTCTATT
CGTCGTGATGAAGTTCTGCGTCTGGTTAACTTCGTCCGCAGTTCCACCTCGGAGCCGGTGAATTTT
ACGGAACGTCTGTTTCTGTTCACCTCATCGATGACCTGCCGTAGCGCATTTGGTAAAGTTTTCAAA
GAACAGGAAACCTTCATTCAACTGATCAAAGAAGTCATTGGCCTGGCCGGCGGTTTTGATGTGGCA
GACATCTTTCCGAGTCTGAAATTCCTGCATGTTCTGACCGGCATGGAAGGCAAAATTATGAAAGCT
CATCACAAAGTCGATGCGATTGTGGAAGACGTTATCAACGAACACAAGAAAAACCTGGCGATGGGC
AAAACGAACGGCGCACTGGGCGGTGAAGATCTGATCGACGTTCTGCTGCGTCTGATGAATGATGGC
GGCCTGCAATTTCCGATCACCAACGATAATATCAAAGCTATTATCTTTGATATGTTTGCGGCGGGC
ACCGAAACCAGCAGCAGCACCCTGGTGTGGGCGATGGTGCAGATGATGCGTAACCCGACGATTCTG
GCAAAAGCTCAAGCGGAAGTGCGCGAAGCCTTCAAAGGCAAAGAAACCTTTGATGAAAATGACGTT
GAAGAACTGAAATATCTGAAACTGGTCATCAAAGAAACGCTGCGTCTGCATCCGCCGGTTCCGCTG
CTGGTCCCGCGTGAATGCCGCGAAGAAACCGAAATTAACGGTTATACCATCCCGGTTAAAACGAAA
GTGATGGTTAATGTCTGGGCTCTGGGCCGTGATCCGAAATACTGGGATGACGCGGACAACTTTAAA
CCGGAACGCTTTGAACAGTGCTCTGTGGATTTCATCGGCAACAACTTTGAATATCTGCCGTTTGGC
GGTGGCCGTCGCATTTGTCCGGGTATCAGCTTCGGCCTGGCTAATGTTTATCTGCCGCTGGCGCAA
CTGCTGTACCACTTTGATTGGAAACTGCCGACCGGCATGGAACCGAAAGATCTGGACCTGACCGAA
CTGGTGGGCGTTACGGCAGCTCGTAAATCTGATCTGATGCTGGTTGCGACCCCGTACCAGCCGAGC
CGTGAA  (SEQ ID NO: 21)

Figure 4A (Continued)

>LsGAO [Lactuca sativa]

MELSITTSIALATIVFFLYKLATRPKSTKKQLPEASRLPIIGHMHHLIGTMPHRGVMDLARKHGSL
MHLQLGEVSTIVVSSPKWAKEILTTYDITFANRPETLTGEIIAYHNTDIVLAPYGEYWRQLRKLCT
LELLSVKKVKSFQSIREEECWNLVKEVKESGSGKPINLSESIFTMIATILSRAAFGKGIKDQREFT
EIVKEILRQTGGFDVADIFPSKKFLHHLSGKRARLTSIHKKLDNLINNIVAEHHVSTSSKANETLL
DVLLRLKDSAEFPLTADNVKAIILDMFGAGTDTSSATVEWAISELIRCPRAMEKVQAELRQALNGK
EKIQEEDIQDLAYLNLVIRETLRLHPPLPLVMPRECREPVNLAGYEIANKTKLIVNVFAINRDPEY
WKDAEAFIPERFENNPNNIMGADYEYLPFGAGRRMCPGAALGLANVQLPLANILYHFNWKLPNGAS
HDQLDMTESFGATVQRKTELLLVPSF  (SEQ ID NO: 22 | Wild Type)

MALLLAVFIALATIVFFLYKLATRPKSTKKQLPEA*SRL*PIIGHMHHLIGTMPHRGVMDLARKHGSL
MHLQLGEVSTIVVSSPKWAKEILTTYDITFANRPETLTGEIIAYHNTDIVLAPYGEYWRQLRKLCT
LELLSVKKVKSFQSIREEECWNLVKEVKESGSGKPINLSESIFTMIATIL*SR*AAFGKGIKDQREFT
EIVKEILRQTGGFDVADIFPSKKFLHHLSGKRARLTSIHKKLDNLINNIVAEHHVSTSSKANETLL
DVLLRLKDSAEFPLTADNVKAIILDMFGAGTDTSSATVEWAISELIRCPRAMEKVQAELRQALNGK
EKIQEEDIQDLAYLNLVIRETLRLHPPLPLVMPRECREPVNLAGYEIANKTKLIVNVFAINRDPEY
WKDAEAFIPERFENNPNNIMGADYEYLPFGAGRRMCPGAALGLANVQLPLANILYHFNWKLPNGAS
HDQLDMTESFGATVQRKTELLLVPSF  (SEQ ID NO: 23)

ATGGCTCTGTTATTAGCAGTTTTCATCGCACTGGCTACCATCGTCTTCTTCCTGTATAAACTGGCA
ACGCGCCCGAAATCTACCAAAAAACAACTGCCGGAAGCGAGCCGTCTGCCGATTATCGGCCACATG
CATCACCTGATTGGCACCATGCCGCACCGTGGTGTCATGGATCTGGCCCGCAAACATGGCTCGCTG
ATGCATCTGCAACTGGGCGAAGTGAGCACCATTGTGGTTAGCTCTCCGAAATGGGCAAAAGAAATT
CTGACCACCTATGATATTACCTTTGCTAACCGCCCGGAAACCCTGACGGGCGAAATTATCGCGTAC
CATAATACGGACATTGTGCTGGCCCCGTATGGTGAATACTGGCGTCAACTGCGTAAACTGTGCACC
CTGGAACTGCTGTCCGTTAAAAAAGTCAAATCATTTCAATCGATTCGTGAAGAAGAATGTTGGAAC
CTGGTGAAAGAAGTTAAAGAAAGCGGCTCTGGTAAACCGATTAATCTGAGTGAATCCATCTTCACC
ATGATTGCGACGATCCTGAGTCGTGCGGCCTTTGGCAAAGGTATTAAAGATCAGCGCGAATTTACC
GAAATTGTCAAAGAAATCCTGCGTCAAACGGGCGGTTTCGATGTGGCAGACATTTTTCCGAGCAAA
AAATTCCTGCATCACCTGTCTGGCAAACGTGCTCGCCTGACCAGTATCCATAAAAAACTGGATAAC
CTGATCAACAATATCGTCGCGGAACATCATGTGAGCACCAGCAGCAAAGCGAATGAAACGCTGCTG
GATGTTCTGCTGCGCCTGAAAGACAGTGCCGAATTCCGCTGACCGCAGACAACGTCAAAGCTATT
ATCCTGGATATGTTCGGTGCAGGCACCGATACCAGCAGCGCAACGGTGGAATGGGCCATTAGCGAA
CTGATCCGTTGCCCGCGCGCAATGGAAAAAGTTCAGGCAGAACTGCGTCAAGCTCTGAACGGTAAA
GAAAAAATCCAGGAAGAAGATATTCAAGACCTGGCCTATCTGAATCTGGTGATTCGTGAAACCCTG
CGTCTGCACCCGCCGCTGCCGCTGGTTATGCCGCGTGAATGCCGTGAGCCGGTGAACCTGGCGGGC
TATGAAATCGCCAATAAAACCAAACTGATCGTCAATGTGTTTGCGATTAACCGTGACCCGGAATAC
TGGAAAGACGCGGAAGCCTTTATCCCGGAACGTTTTGAAAACAATCCGAACAATATCATGGGTGCA
GATTATGAATACCTGCCGTTTGGCGCTGGTCGTCGCATGTGTCCGGGCGCAGCTCTGGGTCTGGCA
AACGTTCAACTGCCGCTGGCGAACATTCTGTACCATTTCAACTGGAAACTGCCGAATGGCGCGTCC
CACGATCAACTGGACATGACCGAATCATTTGGTGCCACCGTGCAACGTAAAACGGAACTGCTGCTG
GTTCCGAGCTTC  (SEQ ID NO: 24)

Figure 4A (Continued)

>NtEAO [Nicotiani tabacum]

MQFFSLVSIFLFLSFLFLLRKWKNSNSQSKKLPPGPWKIPILGSMLHMIGGEPHHVLRDLAKKYGP
LMHLQLGEISAVVVTSRDMAKEVLKTHDVVFASRPKIVAMDIICYNQSDIAFSPYGDHWRQMRKIC
VMELLNAKNVRSFSSIRRDEVVRLIDSIRSDSSSGELVNFTQRIIWFASSMTCRSAFGQVLKGQDI
FAKKIREVIGLAEGFDVVDIFPTYKFLHVLSGMKRKLLNAHLKVDAIVEDVINEHKKNLAAGKSNG
ALGGEDLIDVLLRLMNDTSLQFPITNDNIKAVIVDMFAAGTETSSTTTVWAMAEMMKNPSVFTKAQ
AEVREAFRDKVSFDENDVEELKYLKLVIKETLRLHPPSPLLVPRECREDTDINGYTIPAKTKVMVN
VWALGRDPKYWDDAESFKPERFEQCSVDFFGNNFEFLPFGGGRRICPGMSFGLANLYLPLAQLLYH
FDWKLPTGIMPRDLDLTELSGITIARKGGLYLNATPYQPSRE  (SEQ ID NO: 25 | Wild Type)

MALLLAVFFFSLVSIFLFLSFLFLLRKWKNSNSQSKKLPPGPWKIPILGSMLHMIGGEPHHVLRDL
AKKYGPLMHLQLGEISAVVVTSRDMAKEVLKTHDVVFASRPKIVAMDIICYNQSDIAFSPYGDHWR
QMRKICVMELLNAKNVRSFSSIRRDEVVRLIDSIRSDSSSGELVNFTQRIIWFASSMTCRSAFGQV
LKGQDIFAKKIREVIGLAEGFDVVDIFPTYKFLHVLSGMKRKLLNAHLKVDAIVEDVINEHKKNLA
AGKSNGALGGEDLIDVLLRLMNDTSLQFPITNDNIKAVIVDMFAAGTETSSTTTVWAMAEMMKNPS
VFTKAQAEVREAFRDKVSFDENDVEELKYLKLVIKETLRLHPPSPLLVPRECREDTDINGYTIPAK
TKVMVNVWALGRDPKYWDDAESFKPERFEQCSVDFFGNNFEFLPFGGGRRICPGMSFGLANLYLPL
AQLLYHFDWKLPTGIMPRDLDLTELSGITIARKGGLYLNATPYQPSRE  (SEQ ID NO: 26)

ATGGCTCTGTTATTAGCAGTTTTCTTCTTCTCCCTGGTCTCAATCTTCCTGTTCCTGTCCTTTCTG
TTCCTGCTGCGTAAATGGAAAAACTCTAATAGCCAATCCAAAAAACTGCCGCCGGGTCCGTGGAAA
ATTCCGATCCTGGGCTCTATGCTGCACATGATTGGCGGTGAACCGCATCATGTGCTGCGTGATCTG
GCGAAAAAATATGGTCCGCTGATGCATCTGCAACTGGGCGAAATCTCTGCGGTGGTTGTCACGAGT
CGTGACATGGCCAAAGAAGTGCTGAAAACCCATGATGTGGTTTTTGCATCTCGCCCGAAAATCGTT
GCTATGGATATTATCTGCTATAACCAGTCGGACATCGCGTTCAGCCCGTACGGTGATCACTGGCGT
CAAATGCGCAAAATTTGTGTCATGGAACTGCTGAACGCCAAAAATGTGCGCAGTTTTAGCTCTATT
CGTCGTGATGAAGTCGTGCGTCTGATTGATTCCATCCGCTCAGACAGTTCCTCAGGCGAACTGGTG
AATTTTACGCAGCGTATTATCTGGTTCGCATCGAGCATGACCTGCCGCTCGGCTTTTGGTCAGGTT
CTGAAAGGCCAAGATATTTTTGCGAAGAAAATTCGTGAAGTGATCGGTCTGGCCGAAGGCTTCGAT
GTTGTGGATATTTTTCCGACCTATAAATTCCTGCATGTCCTGAGCGGTATGAAACGCAAACTGCTG
AACGCGCACCTGAAAGTTGATGCCATTGTCGAAGACGTGATCAACGAACATAAGAAAAACCTGGCG
GCGGGTAAATCCAACGGCGCACTGGGCGGTGAAGATCTGATTGACGTGCTGCTGCGTCTGATGAAT
GATACCAGCCTGCAATTTCCGATCACCAACGACAACATTAAAGCGGTGATCGTTGATATGTTCGCG
GCGGGCACCGAAACCTCTAGTACCACGACCGTTTGGGCGATGGCCGAAATGATGAAAAACCCGTCG
GTGTTTACCAAAGCACAAGCGGAAGTGCGTGAAGCGTTTCGTGATAAAGTTAGCTTCGATGAAAAT
GATGTGGAAGAACTGAAATACCTGAAACTGGTGATTAAAGAAACGCTGCGTCTGCATCCGCCGAGC
CCGCTGCTGGTTCCGCGTGAATGCCGTGAAGATACCGACATTAACGGTTATACGATCCCGGCAAAA
ACCAAAGTCATGGTGAATGTTTGGGCTCTGGGCCGTGACCCGAAATACTGGGATGACGCAGAATCC
TTTAAACCGGAACGCTTTGAACAGTGCTCAGTGGATTTCTTTGGTAACAACTTTGAATTTCTGCCG
TTTGGCGGTGGCCGTCGCATTTGTCCGGGTATGTCCTTCGGCCTGGCGAACCTGTATCTGCCGCTG
GCCCAACTGCTGTACCACTTTGATTGGAAACTGCCGACGGGTATTATGCCGCGTGATCTGGACCTG
ACGGAACTGTCTGGCATTACCATCGCACGCAAAGGTGGCCTGTATCTGAATGCTACCCCGTACCAG
CCGAGTCGTGAA (SEQ ID NO: 27)

Figure 4A (Continued)

>CpVO [Citrus x paradisi]

MELPLKSIALTIVIVTVLTWAWRVLNWVWLRPKKLEKFLRQQGLKGNSYRLLFGDLKENSIELKEA
KARPLSLDDDIAIRVNPFLHKLVNDYGKNSFMWFGPTPRVNIMNPDQIKAIFTKINDFQKVNSIPL
ARLLIVGLATLEGEKWAKHRKLINPAFHQEKLKLMLPAFYLSCIEIITKWEKQMSVEGSSELDVWP
YLANLTSDVISRTAFGSSYEEGRRIFQLQAELAELTMQVFRSVHIPGWRFLPTKRNRRMKEIDKEI
RASLMGIIKNREKAMRAGEAANNDLLGILMETSFREIEEHGNNKNVGFSMNDVIEECKLFYFAGQE
TTSVLLNWTMVLLSKHQDWQERARQEVLQVFGNNKPDYDGLNHLKIVQMILYEVLRLYPPVTVLSR
AVFKETKLGNLTLPAGVQIGLPMILVHQDPELWGDDAVEFKPERFAEGISKAAKNQVSYFPFALGP
RICVGQNFALVEAKMATAMILQNYSFELSPSYVHAPTAVPTLHPELGTQLILRKLWCKNN (SEQ
ID NO: 28 | Wild Type)

MALLLAVFIALTIVIVTVLTWAWRVLNWVWLRPKKLEKFLRQQGLKGNSYRLLFGDLKENSIELKE
AKARPLSLDDDIAIRVNPFLHKLVNDYGKNSFMWFGPTPRVNIMNPDQIKAIFTKINDFQKVNSIP
LARLLIVGLATLEGEKWAKHRKLINPAFHQEKLKLMLPAFYLSCIEIITKWEKQMSVEGSSELDVW
PYLANLTSDVI*SRT*AFGSSYEEGRRIFQLQAELAELTMQVFRSVHIPGWRFLPTKRNRRMKEIDKE
IRASLMGIIKNREKAMRAGEAANNDLLGILMETSFREIEEHGNNKNVGFSMNDVIEECKLFYFAGQ
ETTSVLLNWTMVLLSKHQDWQERARQEVLQVFGNNKPDYDGLNHLKIVQMILYEVLRLYPPVTVLS
RAVFKETKLGNLTLPAGVQIGLPMILVHQDPELWGDDAVEFKPERFAEGISKAAKNQVSYFPFALG
PRICVGQNFALVEAKMATAMILQNYSFELSPSYVHAPTAVPTLHPELGTQLILRKLWCKNN (SEQ
ID NO: 29)

ATGGCTCTGTTATTAGCAGTTTTCATTGCTCTGACGATTGTTATTGTTACGGTGCTGACCTGGGCG
TGGCGTGTGCTGAACTGGGTTTGGCTGCGTCCGAAAAAACTGGAAAAATTTCTGCGCCAGCAAGGC
CTGAAGGGTAACAGCTATCGTCTGCTGTTCGGCGATCTGAAAGAAAATTCTATTGAACTGAAAGAA
GCGAAAGCCCGTCCGCTGAGTCTGGATGACGATATTGCAATCCGCGTTAACCCGTTTCTGCATAAA
CTGGTCAACGATTACGGCAAAAATTCTTTTATGTGGTTCGGTCCGACCCCGCGCGTGAACATTATG
AACCCGGATCAGATTAAAGCGATCTTTACGAAAATCAACGATTTCCAAAAAGTTAATAGCATTCCG
CTGGCGCGTCTGCTGATCGTCGGCCTGGCCACCCTGGAAGGTGAAAAATGGGCAAAACATCGCAAA
CTGATTAACCCGGCTTTTCACCAAGAAAAACTGAAACTGATGCTGCCGGCGTTCTATCTGTCCTGC
ATCGAAATTATCACGAAATGGGAAAAACAGATGTCAGTGGAAGGTAGCTCTGAACTGGACGTTTGG
CCGTATCTGGCCAATCTGACCAGCGATGTTATTTCTCGTACGGCATTTGGCAGTTCCTACGAAGAA
GGTCGTCGCATCTTCCAGTTACAGGCGGAACTGGCCGAACTGACCATGCAGGTTTTTCGTTCTGTC
CATATTCCGGGCTGGCGTTTCCTGCCGACGAAACGCAACCGTCGCATGAAAGAAATTGACAAAGAA
ATCCGCGCCAGTCTGATGGGTATTATCAAAAATCGTGAAAAAGCAATGCGCGCTGGCGAAGCGGCC
AACAATGATCTGCTGGGTATTCTGATGGAAACCAGCTTTCGTGAAATCGAAGAACACGGCAACAAT
AAAAACGTCGGTTTCAGCATGAATGACGTGATCGAAGAATGTAAACTGTTTTATTTCGCTGGCCAG
GAAACCACGTCAGTTCTGCTGAACTGGACGATGGTGCTGCTGTCGAAACATCAGGATTGGCAAGAA
CGTGCCCGCCAGGAAGTCCTGCAAGTGTTTGGCAACAATAAACCGGACTACGATGGTCTGAACCAC
CTGAAAATTGTGCAGATGATCCTGTATGAAGTTCTGCGTCTGTATCCGCCGGTGACGGTGCTGAGC
CGTGCGGTGTTTAAAGAAACCAAACTGGGTAATCTGACGCTGCCGGCAGGCGTCCAGATTGGTCTG
CCGATGATCCTGGTGCACCAGGACCCGGAACTGTGGGCGACGATGCTGTGGAATTTAAACCGGAA
CGTTTCGCGGAAGGTATTAGTAAAGCAGCTAAAAATCAGGTTTCCTATTTTCCGTTCGCGCTGGGT
CCGCGTATTTGCGTCGGTCAAAACTTTGCACTGGTGGAAGCTAAAATGGCAACCGCTATGATCCTG
CAAAATTATAGCTTTGAACTGTCACCGAGCTATGTTCATGCGCCGACCGCCGTTCCGACGCTGCAC
CCGGAACTGGGCACGCAACTGATTCTGCGTAAACTGTGGTGTAAAAACAAT (SEQ ID NO: 30)

Figure 4A (Continued)

>AaAO [Artemesia annua]

MKSILKAMALSLTTSIALATILLFVYKFATRSKSTKKSLPEPWRLPIIGHMHHLIGTTPHRGVRDL
ARKYGSLMHLQLGEVPTIVVSSPKWAKEILTTYDITFANRPETLTGEIVLYHNTDVVLAPYGEYWR
QLRKICTLELLSVKKVKSFQSLREEECWNLVQEIKASGSGRPVNLSENVFKLIATILSRAAFGKGI
KDQKELTEIVKEILRQTGGFDVADIFPSKKFLHHLSGKRARLTSLRKKIDNLIDNLVAEHTVNTSS
KTNETLLDVLLRLKDSAEFPLTSDNIKAIILDMFGAGTDTSSSTIEWAISELIKCPKAMEKVQAEL
RKALNGKEKIHEEDIQELSYLNMVIKETLRLHPPLPLVLPRECRQPVNLAGYNIPNKTKLIVNVFA
INRDPEYWKDAEAFIPERFENSSATVMGAEYEYLPFGAGRRMCPGAALGLANVQLPLANILYHFNW
KLPNGVSYDQIDMTESSGATMQRKTELLLVPSF  (SEQ ID NO: 31 | Wild Type)

MALLLAVFIALATILLFVYKFATRSKSTKKSLPEPWRLPIIGHMHHLIGTTPHRGVRDLARKYGSL
MHLQLGEVPTIVVSSPKWAKEILTTYDITFANRPETLTGEIVLYHNTDVVLAPYGEYWRQLRKICT
LELLSVKKVKSFQSLREEECWNLVQEIKASGSGRPVNLSENVFKLIATIL*SR*AAFGKGIKDQKELT
EIVKEILRQTGGFDVADIFPSKKFLHHLSGKRARLTSLRKKIDNLIDNLVAEHTVNTSSKTNETLL
DVLLRLKDSAEFPLTSDNIKAIILDMFGAGTDTSSSTIEWAISELIKCPKAMEKVQAELRKALNGK
EKIHEEDIQELSYLNMVIKETLRLHPPLPLVLPRECRQPVNLAGYNIPNKTKLIVNVFAINRDPEY
WKDAEAFIPERFENSSATVMGAEYEYLPFGAGRRMCPGAALGLANVQLPLANILYHFNWKLPNGVS
YDQIDMTESSGATMQRKTELLLVPSF  (SEQ ID NO: 32)

ATGGCTCTGTTATTAGCAGTTTTCATCGCACTGGCAACCATTCTGCTGTTTGTGTATAAATTCGCT
ACCCGTTCCAAATCAACGAAAAAATCACTGCCGGAACCGTGGCGCCTGCCGATTATCGGTCACATG
CATCACCTGATCGGCACCACCCCGCATCGTGGCGTGCGTGATCTGGCACGCAAATATGGCTCGCTG
ATGCATCTGCAACTGGGTGAAGTCCCGACCATTGTGGTTAGCTCTCCGAAATGGGCGAAAGAAATC
CTGACCACCTATGATATTACCTTTGCCAACCGCCCGGAAACCCTGACGGGCGAAATCGTGCTGTAC
CACAATACGGATGTGGTGCTGGCGCCGTATGGTGAATACTGGCGTCAACTGCGTAAAATTTGCACC
CTGGAACTGCTGAGTGTGAAAAAAGTTAAATCTTTCCAGAGCCTGCGTGAAGAAGAATGTTGGAAC
CTGGTTCAAGAAATTAAAGCATCGGGCAGCGGTCGCCCGGTTAACCTGAGTGAAAATGTCTTTAAA
CTGATTGCTACCATCCTGTCCCGTGCGGCCTTCGGCAAAGGTATCAAAGATCAGAAAGAACTGACC
GAAATTGTCAAAGAAATCCTGCGCCAAACGGGCGGTTTTGATGTGGCGGACATTTTTCCGTCGAAA
AAATTCCTGCATCACCTGAGCGGTAAACGTGCCCGCCTGACCAGCCTGCGTAAGAAAATTGATAAC
CTGATCGACAATCTGGTCGCGGAACATACCGTGAACACGAGTTCCAAAACCAATGAAACGCTGCTG
GATGTGCTGCTGCGCCTGAAAGACTCCGCCGAATTTCCGCTGACCTCAGATAATATCAAAGCGATT
ATCCTGGATATGTTCGGTGCAGGCACCGATACCAGCAGCAGCACCATTGAATGGGCAATCTCAGAA
CTGATTAAATGCCCGAAAGCTATGGAAAAAGTCCAGGCAGAACTGCGCAAAGCTCTGAACGGCAAA
GAAAAAATCCATGAAGAAGATATTCAAGAACTGTCTTACCTGAACATGGTTATCAAAGAAACCCTG
CGTCTGCACCCGCCGCTGCCGCTGGTGCTGCCGCGTGAATGTCGCCAGCCGGTTAACCTGGCAGGC
TATAACATCCCGAATAAAACGAAACTGATCGTTAACGTCTTTGCTATTAACCGTGACCCGGAATAC
TGGAAAGACGCGGAAGCCTTTATCCCGGAACGCTTTGAAAACAGCAGCGCGACCGTGATGGGTGCC
GAATATGAATACCTGCCGTTTGGCGCGGGTCGTCGCATGTGTCCGGGCGCAGCTCTGGGTCTGGCA
AACGTGCAACTGCCGCTGGCTAATATCCTGTATCACTTCAACTGGAAACTGCCGAATGGCGTTAGC
TACGATCAAATTGACATGACCGAAAGCTCAGGTGCCACGATGCAACGCAAAACCGAACTGCTGCTG
GTGCCGTCCTTC  (SEQ ID NO: 33)

Figure 4A (Continued)

>AtKO [Arabidopsis thaliana]

MAFFSMISILLGFVISSFIFIFFFKKLLSFSRKNMSEVSTLPSVPVVPGFPVIGNLLQLKEKKPHK
TFTRWSEIYGPIYSIKMGSSSLIVLNSTETAKEAMVTRFSSISTRKLSNALTVLTCDKSMVATSDY
DDFHKLVKRCLLNGLLGANAQKRKRHYRDALIENVSSKLHAHARDHPQEPVNFRAIFEHELFGVAL
KQAFGKDVESIYVKELGVTLSKDEIFKVLVHDMMEGAIDVDWRDFFPYLKWIPNKSFEARIQQKHK
RRLAVMNALIQDRLKQNGSESDDDCYLNFLMSEAKTLTKEQIAILVWETIIETADTTLVTTEWAIY
ELAKHPSVQDRLCKEIQNVCGGEKFKEEQLSQVPYLNGVFHETLRKYSPAPLVPIRYAHEDTQIGG
YHVPAGSEIAINIYGCNMDKKRWERPEDWWPERFLDDGKYETSDLHKTMAFGAGKRVCAGALQASL
MAGIAIGRLVQEFEWKLRDGEEENVDTYGLTSQKLYPLMAIINPRRS (SEQ ID NO: 34 | Wild Type)

MALLLAVFSMISILLGFVISSFIFIFFFKKLLSF*SR*KNMSEVSTLPSVPVVPGFPVIGNLLQLKE
KKPHKTFTRWSEIYGPIYSIKMGSSSLIVLNSTETAKEAMVTRFSSISTRKLSNALTVLTCDKSM
VATSDYDDFHKLVKRCLLNGLLGANAQKRKRHYRDALIENVSSKLHAHARDHPQEPVNFRAIFEH
ELFGVALKQAFGKDVESIYVKELGVTLSKDEIFKVLVHDMMEGAIDVDWRDFFPYLKWIPNKSFE
ARIQQKHKRRLAVMNALIQDRLKQNGSESDDDCYLNFLMSEAKTLTKEQIAILVWETIIETADTT
LVTTEWAIYELAKHPSVQDRLCKEIQNVCGGEKFKEEQLSQVPYLNGVFHETLRKYSPAPLVPIR
YAHEDTQIGGYHVPAGSEIAINIYGCNMDKKRWERPEDWWPERFLDDGKYETSDLHKTMAFGAGK
RVCAGALQASLMAGIAIGRLVQEFEWKLRDGEEENVDTYGLTSQKLYPLMAIINPRRS (SEQ ID NO: 35)

ATGGCTCTGTTATTAGCAGTTTTTTCGATGATTTCTATCCTGCTGGGCTTTGTTATCTCGTCCTTT
ATCTTTATCTTCTTCTTCAAAAAACTGCTGTCGTTTTCTCGTAAAAACATGTCCGAAGTTTCAACC
CTGCCGAGTGTCCCGGTGGTTCCGGGTTTTCCGGTTATCGGTAATCTGCTGCAGCTGAAAGAAAAG
AAACCGCATAAGACCTTCACGCGCTGGTCCGAAATCTATGGCCCGATCTACTCAATTAAAATGGGT
AGCTCTAGTCTGATTGTGCTGAACTCTACCGAAACGGCAAAAGAAGCTATGGTTACCCGTTTTTCC
TCAATTTCGACGCGCAAGCTGAGCAATGCGCTGACCGTCCTGACGTGCGACAAATCTATGGTGGCC
ACCAGTGATTACGATGACTTCCATAAACTGGTTAAGCGTTGTCTGCTGAACGGCCTGCTGGGTGCG
AATGCCCAGAAGCGTAAGCGCCACTATCGCGACGCCCTGATTGAAAACGTGTCGAGCAAACTGCAT
GCACACGCTCGTGATCATCCGCAGGAACCGGTCAATTTTCGCGCAATCTTCGAACACGAACTGTTT
GGCGTGGCGCTGAAACAAGCCTTCGGCAAGGATGTTGAATCGATTTACGTCAAAGAACTGGGCGTG
ACCCTGAGCAAAGACGAAATCTTTAAGGTCCTGGTGCATGATATGATGGAAGGTGCAATTGACGTT
GATTGGCGTGATTTCTTTCCGTATCTGAAATGGATTCCGAACAAGTCATTCGAAGCTCGCATTCAG
CAAAAACACAAGCGTCGCCTGGCAGTGATGAACGCTCTGATTCAGGATCGTCTGAAACAAAATGGC
TCTGAAAGTGATGACGATTGCTATCTGAATTTTCTGATGTCCGAAGCAAAAACCCTGACGAAGGAA
CAGATTGCTATCCTGGTTTGGGAAACCATTATCGAAACGGCGGACACCACGCTGGTCACCACGGAA
TGGGCGATCTACGAACTGGCCAAGCATCCGAGCGTTCAGGATCGCCTGTGCAAAGAAATTCAAAAC
GTCTGTGGCGGTGAAAAATTTAAGGAAGAACAGCTGTCGCAAGTGCCGTATCTGAATGGTGTTTTC
CACGAAACCCTGCGTAAATATAGCCCGGCACCGCTGGTCCCGATCCGTTACGCCCATGAAGATACC
CAGATTGGCGGTTATCACGTGCCGGCAGGCAGTGAAATTGCTATCAACATTTACGGTTGCAATATG
GACAAAAAGCGTTGGGAACGCCCGGAAGATTGGTGGCCGGAACGTTTTCTGGACGATGGCAAATAT
GAAACCTCTGATCTGCATAAGACGATGGCGTTCGGTGCAGGTAAACGTGTGTGTGCAGGTGCACTG
CAAGCAAGTCTGATGGCAGGCATCGCTATTGGTCGTCTGGTGCAAGAATTTGAATGGAAACTGCGC
GACGGCGAAGAAGAAAACGTTGATACCTATGGTCTGACGTCCCAGAAACTGTACCCGCTGATGGCC
ATTATCAATCCGCGTCGCTCA (SEQ ID NO: 36)

Figure 4A (Continued)

>*Sr*KO [Stevia rebaudiana]

MDAVTGLLTVPATAITIGGTAVALAVALIFWYLKSYTSARRSQSNHLPRVPEVPGVPLLGNLLQLK
EKKPYMTFTRWAATYGPIYSIKTGATSMVVVSSNEIAKEALVTRFQSISTRNLSKALKVLTADKTM
VAMSDYDDYHKTVKRHILTAVLGPNAQKKHRIHRDIMMDNISTQLHEFVKNNPEQEEVDLRKIFQS
ELFGLAMRQALGKDVESLYVEDLKITMNRDEIFQVLVVDPMMGAIDVDWRDFFPYLKWVPNKKFEN
TIQQMYIRREAVMKSLIKEHKKRIASGEKLNSYIDYLLSEAQTLTDQQLLMSLWEPIIESSDTTMV
TTEWAMYELAKNPKLQDRLYRDIKSVCGSEKITEEHLSQLPYITAIFHETLRRHSPVPIIPLRHVH
EDTVLGGYHVPAGTELAVNIYGCNMDKNVWENPEEWNPERFMKENETIDFQKTMAFGGGKRVCAGS
LQALLTASIGIGRMVQEFEWKLKDMTQEEVNTIGLTTQMLRPLRAIIKPRI (SEQ ID NO: 37 |
Wild Type)

MALLLAVFAVALAVALIFWYLKSYTSARRSQSNHLPRVPEVPGVPLLGNLLQLKEKKPYMTFTRW
AATYGPIYSIKTGATSMVVVSSNEIAKEALVTRFQSISTRNLSKALKVLTADKTMVAMSDYDDYH
KTVKRHILTAVLGPNAQKKHRIHRDIMMDNISTQLHEFVKNNPEQEEVDLRKIFQSELFGLAMRQ
ALGKDVESLYVEDLKITMNRDEIFQVLVVDPMMGAIDVDWRDFFPYLKWVPNKKFENTIQQMYIR
REAVMKSLIKEHKKRIASGEKLNSYIDYLLSEAQTLTDQQLLMSLWEPIIESSDTTMVTTEWAMY
ELAKNPKLQDRLYRDIKSVCGSEKITEEHLSQLPYITAIFHETLRRHSPVPIIPLRHVHEDTVLG
GYHVPAGTELAVNIYGCNMDKNVWENPEEWNPERFMKENETIDFQKTMAFGGGKRVCAGSLQALL
TASIGIGRMVQEFEWKLKDMTQEEVNTIGLTTQMLRPLRAIIKPRI (SEQ ID NO: 38)

ATGGCTCTGTTATTAGCAGTTTTTGCCGTCGCTCTGGCGGTAGCACTGATCTTCTGGTATCTGAAA
TCTTACACTAGCGCGCGCCGCTCTCAGTCCAACCACCTGCCGCGTGTGCCGGAAGTTCCGGGTGTG
CCACTGCTGGGCAACCTGCTGCAACTGAAAGAAAAGAAACCGTACATGACCTTTACCCGCTGGGCA
GCGACTTATGGTCCTATCTACAGCATTAAAACCGGCGCTACGTCTATGGTTGTGGTTTCTTCCAAC
GAAATCGCGAAAGAAGCCCTGGTGACTCGTTTCCAGTCCATTAGCACCCGCAACCTGTCCAAAGCG
CTGAAGGTTCTGACGGCTGACAAGACTATGGTGGCTATGAGCGACTATGATGACTACCACAAAACC
GTTAAACGTCACATCCTGACCGCAGTACTGGGTCCGAACGCACAGAAAAAACATCGCATCCACCGC
GACATTATGATGGATAACATCTCCACGCAGCTGCATGAGTTCGTTAAGAACAATCCAGAACAGGAA
GAGGTAGATCTGCGTAAAATTTTTCAGTCCGAACTGTTCGGTCTGGCTATGCGTCAGGCGCTGGGC
AAAGACGTTGAAAGCCTGTATGTCGAAGACCTGAAAATTACCATGAACCGTGATGAGATCTTCCAG
GTTCTGGTTGTAGATCCGATGATGGGCGCCATCGACGTGGATTGGCGTGACTTCTTTCCGTACCTG
AAATGGGTCCCGAACAAGAAGTTCGAAAACACCATCCAGCAAATGTACATCCGTCGTGAAGCGGTG
ATGAAAAGCCTGATCAAGAACACAAAAGCGTATTGCTTCTGGTGAGAAACTGAACTCCTACATC
GATTATCTGCTGTCCGAAGCGCAGACCCTGACCGACCAACAGCTGCTGATGTCTCTGTGGGAACCG
ATTATCGAAAGCAGCGACACCACTATGGTCACTACCGAATGGGCAATGTATGAGCTGGCCAAAAAC
CCGAAACTGCAGGATCGTCTGTACCGTGACATCAAAAGCGTTTGCGGCTCCGAGAAAATCACTGAA
GAACACCTGTCTCAGCTGCCGTACATCACTGCTATTTTCCACGAAACCCTGCGTCGCCATTCTCCG
GTTCCGATCATTCCGCTGCGTCACGTTCACGAAGATACTGTGCTGGGTGGTTACCATGTACCGGCA
GGCACTGAACTGGCTGTCAACATCTACGGCTGTAACATGGATAAAAACGTTTGGGAGAATCCTGAA
GAATGGAACCCGGAACGCTTCATGAAAGAGAACGAAACCATCGACTTCCAGAAAACGATGGCTTTC
GGCGGTGGTAAACGTGTGTGCGCAGGTTCTCTGCAGGCGCTGCTGACGGCGTCCATTGGTATCGGT
CGCATGGTACAGGAATTTGAATGGAAGCTGAAAGACATGACCCAAGAAGAGGTGAATACCATTGGT
CTGACTACCCAGATGCTGCGTCCACTGCGTGCAATCATCAAACCTCGTATT (SEQ ID NO: 39)

Figure 4A (Continued)

>PpKO [Physcomitrella patens]

MAKHLATQLLQQWNEALKTMPPGFRTAGKILVWEELASNKVLITIALAWVLLFVARTCLRNKKRL
PPAIPGGLPVLGNLLQLTEKKPHRTFTAWSKEHGPIFTIKVGSVPQAVVNNSEIAKEVLVTKFAS
ISKRQMPMALRVLTRDKTMVAMSDYGEEHRMLKKLVMTNLLGPTTQNKNRSLRDDALIGMIEGVL
AELKASPTSPKVVNVRDYVQRSLFPFALQQVFGYIPDQVEVLELGTCVSTWDMFDALVVAPLSAV
INVDWRDFFPALRWIPNRSVEDLVRTVDFKRNSIMKALIRAQRMRLANLKEPPRCYADIALTEAT
HLTEKQLEMSLWEPIIESADTTLVTSEWAMYEIAKNPDCQDRLYREIVSVAGTERMVTEDDLPNM
PYLGAIIKETLRKYTPVPLIP*SRF*VEEDITLGGYDIPKGYQILVNLFAIANDPAVWSNPEKWDPE
RMLANKKVDMGFRDFSLMPFGAGKRMCAGITQAMFIIPMNVAALVQHCEWRLSPQEISNINNKIE
DVVYLTTHKLSPLSCEATPRISHRLP (SEQ ID NO: 40 | Wild Type)

MALLLAVFTQLLQQWNEALKTMPPGFRTAGKILVWEELASNKVLITIALAWVLLFVARTCLRNKK
RLPPAIPGGLPVLGNLLQLTEKKPHRTFTAWSKEHGPIFTIKVGSVPQAVVNNSEIAKEVLVTKF
ASISKRQMPMALRVLTRDKTMVAMSDYGEEHRMLKKLVMTNLLGPTTQNKNRSLRDDALIGMIEG
VLAELKASPTSPKVVNVRDYVQRSLFPFALQQVFGYIPDQVEVLELGTCVSTWDMFDALVVAPLS
AVINVDWRDFFPALRWIPNRSVEDLVRTVDFKRNSIMKALIRAQRMRLANLKEPPRCYADIALTE
ATHLTEKQLEMSLWEPIIESADTTLVTSEWAMYEIAKNPDCQDRLYREIVSVAGTERMVTEDDLP
NMPYLGAIIKETLRKYTPVPLIP*SRF*VEEDITLGGYDIPKGYQILVNLFAIANDPAVWSNPEKWD
PERMLANKKVDMGFRDFSLMPFGAGKRMCAGITQAMFIIPMNVAALVQHCEWRLSPQEISNINNK
IEDVVYLTTHKLSPLSCEATPRISHRLP (SEQ ID NO: 41)

ATGGCTCTGTTATTAGCAGTTTTTACGCAACTGCTGCAACAATGGAATGAAGCTCTGAAGACGAT
GCCGCCGGGTTTTCGCACCGCTGGCAAAATTCTGGTGTGGGAAGAACTGGCAAGCAATAAAGTTC
TGATTACGATCGCACTGGCTTGGGTCCTGCTGTTTGTGGCTCGTACCTGCCTGCGCAATAAAAAG
CGTCTGCCGCCGGCAATCCCGGGCGGTCTGCCGGTGCTGGGCAACCTGCTGCAGCTGACGGAAAA
GAAACCGCATCGTACCTTTACGGCGTGGAGCAAGGAACACGGCCCGATTTTCACCATCAAAGTCG
GTTCGGTGCCGCAGGCTGTGGTTAACAATAGCGAAATTGCGAAAGAAGTCCTGGTGACCAAGTTC
GCCAGCATCTCTAAACGTCAAATGCCGATGGCACTGCGCGTCCTGACGCGTGATAAAACGATGGT
GGCTATGTCTGACTATGGCGAAGAACATCGCATGCTGAAAAAGCTGGTGATGACGAATCTGCTGG
GTCCGACCACGCAGAACAAAAATCGTAGTCTGCGCGATGACGCACTGATTGGCATGATCGAAGGT
GTTCTGGCGGAACTGAAGGCCAGTCCGACCTCCCCGAAAGTCGTGAACGTTCGCGATTATGTCCA
GCGTTCTCTGTTTCCGTTCGCGCTGCAGCAAGTGTTTGGCTACATTCCGGATCAAGTTGAAGTCC
TGGAACTGGGCACGTGTGTTTCTACCTGGGATATGTTCGACGCACTGGTTGTCGCTCCGCTGAGT
GCGGTTATTAACGTCGATTGGCGTGACTTTTTCCCGGCCCTGCGCTGGATTCCGAATCGTTCCGT
GGAAGATCTGGTGCGCACCGTTGACTTTAAGCGTAACTCAATTATGAAAGCCCTGATCCGTGCAC
AGCGTATGCGCCTGGCTAACCTGAAGGAACCGCCGCGCTGCTACGCAGATATTGCTCTGACCGAA
GCGACGCACCTGACCGAAAACAACTGGAAATGAGTCTGTGGGAACCGATTATCGAATCCGCCGA
TACCACGCTGGTGACCTCAGAATGGGCTATGTATGAATTGCGAAAAATCCGGATTGTCAGGACC
GTCTGTACCGCGAAATCGTGTCCGTTGCCGGCACGGAACGCATGGTTACCGAAGATGACCTGCCG
AACATGCCGTATCTGGGTGCAATTATCAAAGAAACGCTGCGCAAGTACACCCCGGTTCCGCTGAT
TCCGAGTCGTTTTGTCGAAGAAGATATCACCCTGGGCGGTTATGACATTCCGAAAGGTTACCAGA
TCCTGGTCAACCTGTTCGCGATTGCCAATGATCCGGCCGTTTGGTCGAACCCGGAAAAATGGGAC
CCGGAACGCATGCTGGCAAATAAAAAGGTGGATATGGGCTTTCGTGACTTCAGCCTGATGCCGTT
TGGCGCCGGTAAACGCATGTGCGCCGGTATCACCCAAGCAATGTTCATTATCCCGATGAATGTGG
CGGCCCTGGTTCAGCATTGTGAATGGCGCCTGAGCCCGCAAGAAATCTCTAACATCAACAACAAG
ATCGAAGATGTGGTTTACCTGACCACGCATAAACTGTCACCGCTGTCGTGCGAAGCAACCCCGCG
TATCAGCCACCGTCTGCCG (SEQ ID NO: 42)

Figure 4A (Continued)

>BmVO [Bacillus megaterium]

MTIKEMPQPKTFGELKNLPLLNTDKPVQALMKIADELGEIFKFEAPGRVTRYLSSQRLIKEACDE*S
RF*DKNLSQALKFVRDFAGDGLATSWTHEKNWKKAHNILLPSFSQQAMKGYHAMMVDIAVQLVQKWE
RLNADEHIEVPEDMTRLTLDTIGLCGFNYRFNSFYRDQPHPFITSMVRALDEAMNKLQRANPDDPA
YDENKRQFQEDIKVMNDLVDKIIADRKASGEQSDDLLTHMLNGKDPETGEPLDDENIRYQIITFLI
AGHETTSGLLSFALYFLVKNPHVLQKAAEEAARVLVDPVPSYKQVKQLKYVGMVLNEALRLWPTIP
AFSLYAKEDTVLGGEYPLEKGDELMVLIPQLHRDKTIWGDDVEEFRPERFENPSAIPQHAFKPFGN
GQRACIGQQFALHEATLVLGMMLKHFDFEDHTNYELDIKETLTLKPEGFVVKAKSKKIPLGGIPSP
STEQSAKKVRKKAENAHNTPLLVLYGSNMGTAEGTARDLADIAMSKGFAPQVATLDSHAGNLPREG
AVLIVTASYNGHPPDNAKQFVDWLDQASADEVKGVRYSVFGCGDKNWATTYQKVPAFIDETLAAKG
AENIADRGEADASDDFEGTYEEWREHMWSDVAAYFNLDIENSEDNKSTLSLQFVDSAADMPLAKMH
GAFSTNVVASKELQQPGSARSTRHLEIELPKEASYQEGDHLGVIPRNYEGIVNRVTARFGLDASQQ
IRLEAEEEKLAHLPLAKTVSVEELLQYVELQDPVTRTQLRAMAAKTVCPPHKVELEALLEKQAYKE
QVLAKRLTMLELLEKYPACEMKFSEFIALLPSIRPRYYSISSSPRVDEKQASITVSVVSGEAWSGY
GEYKGIASNYLAELQEGDTITCFISTPQSEFTLPKDPETPLIMVGPGTGVAPFRGFVQARKQLKEQ
GQSLGEAHLYFGCRSPHEDYLYQEELENAQSEGIITLHTAF*SR*MPNQPKTYVQHVMEQDGKKLIEL
LDQGAHFYICGDGSQMAPAVEATLMKSYADVHQVSEADARLWLQQLEEKGRYAKDVWAG (SEQ ID NO: 43)

ATGACGATTAAAGAAATGCCGCAACCGAAGACGTTTGGCGAACTGAAGAACCTGCCGCTGCTGAA
CACGGATAAGCCGGTGCAAGCCCTGATGAAGATTGCTGATGAACTGGGCGAAATCTTTAAATTCG
AAGCGCCGGGTCGTGTGACCCGTTATCTGAGCAGCCAGCGTCTGATTAAAGAAGCCTGCGATGAA
TCGCGCTTTGACAAGAACCTGAGCCAGGCACTGAAATTTGTTCGTGATTTCGCAGGTGACGGTCT
GGCCACCAGCTGGACGCATGAAAAGAACTGGAAAAAGGCCCACAATATTCTGCTGCCGTCGTTCA
GCCAGCAAGCAATGAAAGGCTACCATGCTATGATGGTCGATATCGCGGTTCAGCTGGTCCAAAAA
TGGGAACGTCTGAATGCGGACGAACACATTGAAGTGCCGGAAGATATGACCCGCCTGACGCTGGA
CACCATCGGTCTGTGTGGCTTTAACTATCGTTTTAATTCGTTCTACCGCGATCAGCCGCATCCGT
TCATTACCAGCATGGTGCGTGCGCTGGACGAAGCCATGAACAAACTGCAGCGTGCAAACCCGGAT
GACCCGGCGTATGATGAAAACAAGCGTCAGTTTCAAGAAGACATCAAAGTGATGAATGATCTGGT
TGACAAGATTATCGCAGATCGCAAAGCGAGCGGCGAACAGTCAGATGACCTGCTGACGCACATGC
TGAACGGCAAAGACCCGGAAACCGGTGAACCGCTGGATGACGAAAACATCCGTTATCAGATCATC
ACCTTTCTGATCGCAGGCCATGAAACCACGTCGGGTCTGCTGAGCTTTGCGCTGTACTTCCTGGT
CAAGAACCCGCACGTGCTGCAGAAAGCGGCCGAAGAAGCAGCTCGTGTGCTGGTTGATCCGGTTC
CGTCGTATAAACAGGTCAAGCAACTGAAATACGTGGGTATGGTTCTGAATGAAGCGCTGCGCCTG
TGGCCGACGATTCCGGCATTTAGCCTGTATGCTAAGGAAGATACCGTTCTGGGCGGTGAATACCC
GCTGGAAAAAGGCGATGAACTGATGGTCCTGATTCCGCAGCTGCATCGCGACAAACCATCTGGG
GTGATGACGTGGAAGAATTTCGCCCGGAACGCTTCGAAAACCCGAGCGCGATTCCGCAGCATGCC
TTTAAACCGTTCGGCAATGGTCAACGTGCGTGCATCGGCCAGCAATTTGCGCTGCACGAAGCCAC
GCTGGTTCTGGGTATGATGCTGAAACATTTTGATTTCGAAGACCACACCAACTATGAACTGGATA
TTAAGGAAACCCTGACGCTGAAACCGGAAGGCTTCGTGGTTAAAGCGAAGTCTAAAAAGATTCCG
CTGGGCGGTATCCCGTCTCCGAGTACGGAACAGAGTGCCAAAAAGGTCCGTAAAAAGGCGGAAAA
CGCCCATAATACCCCGCTGCTGGTGCTGTATGGTTCTAACATGGGCACGGCAGAAGGCACCGCTC
GCGATCTGGCAGACATTGCTATGTCTAAAGGTTTTGCGCCGCAGGTGGCCACGCTGGATAGTCAT
GCAGGCAATCTGCCGCGTGAAGGTGCTGTCCTGATCGTGACCGCAAGCTACAACGGTCACCCGCC
GGATAATGCGAAGCAGTTCGTTGATTGGCTGGACCAAGCGTCGGCCGATGAAGTTAAAGGTGTCC
GCTATAGCGTGTTTGGCTGTGGTGACAAGAACTGGGCTACCACGTACCAGAAAGTTCCGGCGTTC
ATTGATGAAACGCTGGCGGCCAAAGGCGCAGAAAATATCGCTGATCGTGGTGAAGCAGACGCTTC
CGATGACTTTGAAGGCACCTATGAAGAATGGCGCGAACACATGTGGTCGGATGTGGCAGCTTACT
TCAACCTGGATATTGAAAACAGCGAAGACAATAAATCCACCCTGTCACTGCAGTTTGTTGATAGT
GCGGCCGACATGCCGCTGGCAAAGATGCACGGCGCTTTCTCCACGAATGTCGTGGCTTCAAAAGA
ACTGCAGCAACCGGGTTCGGCACGTAGCACCCGCCATCTGGAAATTGAACTGCCGAAAGAAGCCA
GCTATCAGGAAGGCGATCACCTGGGTGTGATTCCGCGTAACTACGAAGGCATCGTGAATCGTGTT

Figure 4A (Continued)

ACGGCCCGCTTTGGTCTGGATGCATCCCAGCAAATCCGCCTGGAAGCGGAAGAAGAAAAGCTGGC
GCATCTGCCGCTGGCCAAAACCGTCTCAGTGGAAGAACTGCTGCAGTATGTGGAACTGCAAGATC
CGGTTACCCGTACGCAGCTGCGTGCGATGGCGGCTAAGACCGTCTGCCCGCCGCACAAAGTGGAA
CTGGAAGCTCTGCTGGAAAAGCAGGCGTATAAAGAACAAGTGCTGGCGAAACGCCTGACCATGCT
GGAACTGCTGGAAAAGTACCCGGCCTGTGAAATGAAGTTCTCTGAATTTATCGCACTGCTGCCGT
CTATCCGTCCGCGTTATTACAGTATTAGTTCCTCACCGCGTGTGGATGAAAACAGGCCAGTATC
ACCGTTTCTGTTGTCAGTGGCGAAGCATGGTCTGGCTATGGTGAATACAAGGGTATCGCAAGTAA
CTACCTGGCTGAACTGCAGGAAGGCGATACCATTACGTGCTTTATCTCTACGCCGCAAAGTGAAT
TTACCCTGCCGAAAGACCCGGAAACGCCGCTGATCATGGTTGGCCCGGGCACCGGTGTCGCACCG
TTTCGTGGTTTCGTGCAGGCACGCAAGCAACTGAAAGAACAGGGCCAATCCCTGGGTGAAGCGCA
TCTGTATTTTGGCTGTCGCTCACCGCACGAAGATTATCTGTACCAGGAAGAACTGGAAAACGCGC
AATCCGAAGGTATTATCACGCTGCATACCGCCTTCTCACGTATGCCGAATCAGCCGAAAACCTAC
GTCCAGCACGTGATGGAACAAGATGGCAAAAAGCTGATTGAACTGCTGGACCAGGGTGCGCATTT
TTATATCTGCGGTGATGGCAGCCAAATGGCACCGGCAGTGGAAGCAACCCTGATGAAATCCTACG
CAGATGTTCACCAGGTCTCAGAAGCAGACGCTCGTCTGTGGCTGCAGCAACTGGAAGAAAAGGGC
CGCTATGCGAAAGATGTTTGGGCCGGTTAA (SEQ ID NO: 44)

>PsVO [Pleurotus sapidus]

MRYGCAAVALFYLTAMGKLHPLAIIPDYKGSMAASVTIFNKRTNPLDISVNQANDWPWRYAKTCVL
SSDWALHEMIIHLNNTHLVEEAVIVAAQRKLSPSHIVFRLLEPHWVVTLSLNALARSVLIPEVIVP
IAGFSAPHIFQFIRESFTNFDWKSLYVPADLE*SR*GFPVDQLNSPKFHNYAYARDINDMWTTLKKFV
SSVLQDAQYYPDDASVAGDTQIQAWCDEMRSGMGAGMTNFPESITTVDDLVNMVTMCIHIAAPQHT
AVNYLQQYYQTFVSNKPSALFSPLPTSIAQLQKYTESDLMAALPLNAKRQWLLMAQIPYLLSMQVQ
EDENIVTYAANASTDKDPIIASAGRQLAADLKKLAAVFLVNSAQLDDQNTPYDVLAPEQLANAIVI
(SEQ ID NO: 45)

ATGCGTTATGGCTGTGCTGCTGTGGCTCTGTTCTATCTGACCGCTATGGGCAAACTGCACCCGCTG
GCTATTATCCCGGACTACAAGGGTAGCATGGCGGCCTCTGTCACCATTTTTAACAAACGTACGAAT
CCGCTGGATATCAGCGTTAACCAGGCAAATGACTGGCCGTGGCGCTATGCTAAGACGTGCGTGCTG
AGCAGCGATTGGGCGCTGCATGAAATGATTATCCACCTGAACAATACCCATCTGGTGGAAGAAGCC
GTCATTGTGGCAGCTCAGCGTAAACTGTCACCGTCGCACATCGTTTTTCGCCTGCTGGAACCGCAT
TGGGTGGTTACCCTGTCGCTGAACGCACTGGCTCGTAGCGTGCTGATCCCGGAAGTTATTGTCCCG
ATCGCGGGTTTCTCTGCCCCGCACATTTTTCAGTTCATCCGCGAATCTTTTACCAATTTCGATTGG
AAAAGTCTGTACGTCCCGGCGGACCTGGAATCGCGTGGCTTTCCGGTGGATCAGCTGAACAGCCCG
AAGTTCCATAATTATGCGTACGCCCGCGATATCAACGACATGTGGACCACGCTGAAAAAGTTTGTG
AGTTCCGTTCTGCAGGATGCCCAATATTACCCGGATGACGCAAGTGTGGCTGGTGATACGCAGATT
CAAGCATGGTGCGACGAAATGCGTTCCGGCATGGGTGCGGGCATGACCAACTTCCCGGAATCAATC
ACCACGGTTGATGACCTGGTCAATATGGTGACCATGTGTATTCACATCGCGGCCCCGCAGCATACG
GCGGTTAACTATCTGCAGCAATACTACCAAACCTTCGTCAGTAACAAGCCGTCCGCACTGTTCTCA
CCGCTGCCGACCTCTATTGCTCAGCTGCAAAAATACACGGAAAGTGATCTGATGGCAGCTCTGCCG
CTGAACGCGAAGCGTCAGTGGCTGCTGATGGCCCAAATTCCGTATCTGCTGTCGATGCAGGTGCAA
GAAGATGAAAACATCGTTACCTACGCGGCCAATGCGTCCACGGATAAAGACCCGATTATCGCATCA
GCTGGCCGCCAGCTGGCAGCTGACCTGAAAAAGCTGGCGGCCGTTTTTCTGGTCAACTCAGCCCAG
CTGGATGACCAAAATACCCCGTATGATGTGCTGGCACCGGAACAGCTGGCGAATGCCATTGTTATC
TAA (SEQ ID NO: 46)

Figure 4A (Continued)

>PoLO [Pleurotus ostreatus]

MAPTMSL*SR*SALKNVHLPYMVQHPEPTDCSTAMKHAAEGYDRARQMIAFLFDILDYESSVPQKFTP
EEKKEKYTWSHSDKFPPHLAIIPEDIDVPAYIIFSIVRLVQTLSIMSGIQCNERLAPGPEQNTMEK
LTKWNAERHKNQGWVKDMFNEPNIGLRNDWYTDAVFAQQFFTGPNPTTITLASDTWMKAFTEEAAS
QGKRDLISLFRSAPPNSFYVQDFSDFRARMGAKPDEELCATSDGGVTRYGCAAVALFYLPPTGELH
PLAIVPDYKGSMAASITLFNKRVDPSDASVDQANDWPWRYAKTCVLSADWVLHEMIIHLNNTHLVQ
EAVIVAVQRTLPDSHIVFRLLKPHWVVTLSLNAQARSVLIPEVIVPIAGFSELRIFQFVGHAFTNF
DWKALYVPTDLEFRGFPLDRLDDDKFHNYAYAKDIKDMWMALRKFVSSVLKDGKYYPDDSAVAADA
QIQDWCDEMRSEKGAGMKKFPESISTLDDLIDMVTMCIHIAAPQHTAVNYLQQYYQTFVPNKPSAL
FSPLPTLLSQLESYTESDLMAALPLGAKQEWLLMAQVPYLLSKEVEQDGNIVTYAGTASNNEDPII
AAAGKELSADLVILAGVFLKNSEKLDDQNTAYNVLAPDQLANAIVI (SEQ ID NO: 47)

ATGGCCCCGACGATGTCACTGTCTCGCTCCGCACTGAAGAATGTCCACCTGCCGTATATGGTCCA
ACACCCGGAACCGACCGATTGCAGCACCGCGATGAAACACGCGGCCGAAGGTTATGATCGTGCTC
GCCAGATGATTGCGTTTCTGTTCGACATCCTGGATTACGAAAGCTCTGTTCCGCAAAAATTTACC
CCGGAAGAAAAGAAAGAAAAATATACGTGGTCACACTCGGATAAGTTCCCGCCGCATCTGGCCAT
TATCCCGGAAGACATTGATGTGCCGGCATACATTATCTTTAGCATCGTTCGTCTGGTCCAGACCC
TGAGTATTATGTCCGGCATCCAATGCAACGAACGTCTGGCACCGGGGCCGGAACAGAATACGATG
GAAAAACTGACGAAGTGGAACGCGGAACGTCATAAAAATCAAGGCTGGGTCAAGGATATGTTTAA
CGAACCGAATATTGGTCTGCGCAACGACTGGTATACCGATGCTGTGTTCGCGCAGCAATTTTTCA
CGGGTCCGAATCCGACCACGATTACCCTGGCCTCTGATACGTGGATGAAAGCATTTACCGAAGAA
GCAGCTAGTCAGGGCAAGCGTGACCTGATCAGCCTGTTTCGCTCTGCCCCGCCGAACTCCTTCTA
CGTTCAGGACTTTTCAGATTTCCGTGCTCGCATGGGCGCGAAACCGGACGAAGAACTGTGCGCGA
CCTCTGATGGCGGTGTTACCCGTTATGGCTGTGCAGCAGTCGCACTGTTTTACCTGCCGCCGACC
GGTGAACTGCATCCGCTGGCCATTGTGCCGGATTATAAAGGCAGTATGGCAGCTTCCATCACGCT
GTTCAACAAGCGTGTGGACCCGTCAGATGCCTCGGTTGACCAGGCAAATGATTGGCCGTGGCGCT
ACGCTAAAACCTGTGTTCTGTCCGCGGATTGGGTCCTGCATGAAATGATTATCCACCTGAACAAT
ACCCATCTGGTGCAGGAAGCCGTCATTGTGGCAGTTCAACGTACGCTGCCGGATTCACACATCGT
TTTTCGCCTGCTGAAACCGCATTGGGTGGTTACCCTGTCGCTGAATGCCCAGGCACGTAGCGTTC
TGATCCCGGAAGTCATTGTGCCGATCGCGGGCTTCAGTGAACTGCGCATCTTTCAGTTCGTTGGT
CACGCCTTTACCAACTTCGACTGGAAAGCACTGTATGTCCCGACGGATCTGGAATTTCGTGGTTT
CCCGCTGGACCGCCTGGATGACGATAAGTTCCATAACTATGCTTACGCGAAGGACATTAAGGATA
TGTGGATGGCCCTGCGTAAGTTCGTGAGTTCCGTTCTGAAAGATGGCAAGTATTACCCGGACGAT
TCGGCTGTTGCAGCAGACGCGCAGATTCAAGACTGGTGCGATGAAATGCGCAGCGAAAAAGGCGC
GGGTATGAAAAAGTTCCCGGAAAGCATTTCTACCCTGGACGATCTGATCGATATGGTGACGATGT
GTATTCACATCGCAGCTCCGCAGCATACCGCCGTGAACTATCTGCAGCAATATTACCAAACGTTT
GTTCCGAATAAACCGTCAGCACTGTTCTCGCCGCTGCCGACCCTGCTGAGCCAGCTGGAATCTTA
CACGGAAAGTGATCTGATGGCGGCCCTGCCGCTGGGTGCTAAACAGGAATGGCTGCTGATGGCGC
AAGTGCCGTATCTGCTGTCTAAGGAAGTCGAACAGGATGGCAACATTGTGACCTACGCCGGTACG
GCAAGTAACAATGAAGATCCGATTATCGCAGCTGCGGGCAAAGAACTGTCCGCTGACCTGGTCAT
CCTGGCGGGTGTGTTTCTGAAAAACTCAGAAAAGCTGGACGATCAGAACACCGCCTATAATGTCC
TGGCACCGGATCAACTGGCCAATGCAATTGTGATCTAA (SEQ ID NO: 48)

>CiVO [Cichorium intybus]

MEISIPTTLGLAVIIFIIFKLLTRTTSKKNLLPEPWRLPIIGHMHHLIGTMPHRGVMELARKHGSL
MHLQLGEVSTIVVSSPRWAKEVLTTYDITFANRPETLTGEIVAYHNTDIVLAPYGEYWRQLRKLCT
LELLSNKKVKSFQSLREEECWNLVKDIRSTGQGSPINLSENIFKMIATILSRAAFGKGIKDQMKFT
ELVKEILRLTGGFDVADIFPSKKLLHHLSGKRAKLTNIHNKLDNLINNIIAEHPGNRTSSSQETLL
DVLLRLKESAEFPLTADNVKAVILDMFGAGTDTSSATIEWAISELIRCPRAMEKVQTELRQALNGK
ERIQEEDLQELNYLKLVIKETLRLHPPLPLVMPRECREPCVLGGYDIPSKTKLIVNVFAINRDPEY

Figure 4A (Continued)

WKDAETFMPERFENSPITVMGSEYEYLPFGAGRRMCPGAALGLANVELPLAHILYFNWKLPNGKTF
EDLDMTESFGATVQRKTELLLVPTDFQTLTAST  (SEQ ID NO: 49 | Wild Type)

MALLLAVFLAVIIFIIFKLLTRTTSKKNLLPEPWRLPIIGHMHHLIGTMPHRGVMELARKHGSLMH
LQLGEVSTIVVSSPRWAKEVLTTYDITFANRPETLTGEIVAYHNTDIVLAPYGEYWRQLRKLCTLE
LLSNKKVKSFQSLREEECWNLVKDIRSTGQGSPINLSENIFKMIATIL*SR*AAFGKGIKDQMKFTEL
VKEILRLTGGFDVADIFPSKKLLHHLSGKRAKLTNIHNKLDNLINNIIAEHPGNRTSSSQETLLDV
LLRLKESAEFPLTADNVKAVILDMFGAGTDTSSATIEWAISELIRCPRAMEKVQTELRQALNGKER
IQEEDLQELNYLKLVIKETLRLHPPLPLVMPRECREPCVLGGYDIPSKTKLIVNVFAINRDPEYWK
DAETFMPERFENSPITVMGSEYEYLPFGAGRRMCPGAALGLANVELPLAHILYFNWKLPNGKTFED
LDMTESFGATVQRKTELLLVPTDFQTLTAST  (SEQ ID NO: 50)

ATGGCTCTGTTATTAGCAGTTTTTCTGGCTGTCATTATCTTTATCATCTTCAAACTGCTGACCCGC
ACCACCTCGAAGAAAAACCTGCTGCCGGAACCGTGGCGTCTGCCGATTATCGGCCACATGCATCAC
CTGATTGGCACCATGCCGCACCGTGGTGTGATGGAACTGGCGCGCAAACATGGCTCACTGATGCAC
CTGCAGCTGGGTGAAGTGAGCACCATCGTGGTTAGCTCTCCGCGTTGGGCGAAAGAAGTTCTGACC
ACGTATGATATTACCTTTGCCAACCGCCCGGAAACCCTGACGGGCGAAATCGTGGCATACCATAAT
ACGGACATTGTTCTGGCTCCGTATGGTGAATACTGGCGTCAGCTGCGCAAACTGTGCACCCTGGAA
CTGCTGAGTAACAAAAAAGTCAAATCTTTTCAAAGTCTGCGTGAAGAAGAATGTTGGAATCTGGTG
AAAGATATCCGCTCCACCGGCCAGGGTTCACCGATCAACCTGTCGGAAAACATCTTCAAAATGATC
GCGACGATCCTGTCTCGTGCGGCCTTTGGCAAAGGTATTAAAGACCAAATGAAATTCACCGAACTG
GTTAAAGAAATCCTGCGCCTGACGGGCGGTTTTGATGTCGCAGACATTTTCCCGAGTAAAAAACTG
CTGCATCACCTGTCCGGCAAACGTGCTAAACTGACCAACATCCATAACAAACTGGATAACCTGATC
AACAACATTATCGCCGAACACCCGGGTAATCGTACCAGTTCCTCACAGGAAACGCTGCTGGATGTT
CTGCTGCGCCTGAAAGAAAGCGCAGAATTTCCGCTGACCGCGGACAATGTTAAAGCCGTCATTCTG
GATATGTTCGGTGCAGGCACCGACACGTCGAGCGCAACCATTGAATGGGCTATCTCTGAACTGATT
CGTTGCCCGCGCGCGATGGAAAAAGTGCAGACGGAACTGCGTCAAGCCCTGAACGGCAAAGAACGC
ATCCAGGAAGAAGATCTGCAAGAACTGAACTACCTGAAACTGGTTATCAAAGAAACCCTGCGCCTG
CATCCGCCGCTGCCGCTGGTCATGCCGCGTGAATGCCGCGAACCGTGTGTGCTGGGCGGTTATGAT
ATCCCGAGCAAAACCAAACTGATCGTCAACGTGTTTGCAATTAATCGTGACCCGGAATACTGGAAA
GACGCTGAAACCTTTATGCCGGAACGCTTCGAAAACAGCCCGATTACGGTTATGGGTTCTGAATAT
GAATACCTGCCGTTTGGTGCAGGTCGTCGCATGTGTCCGGGTGCAGCTCTGGGTCTGGCGAATGTC
GAACTGCCGCTGGCCCACATCCTGTATTACTTCAACTGGAAACTGCCGAATGGCAAAACCTTTGAA
GATCTGGACATGACCGAATCCTTCGGTGCAACGGTGCAACGCAAAACCGAACTGCTGCTGGTGCCG
ACGGATTTCCAAACGCTGACCGCATCAACG  (SEQ ID NO: 51)

>HaGAO [Helianthus annuus]
MEVSLTTSIALATIVFFLYKLLTRPTSSKNRLPEPWRLPIIGHMHHLIGTMPHRGVMDLARKYGSL
MHLQLGEVSAIVVSSPKWAKEILTTYDIPFANRPETLTGEIIAYHNTDIVLAPYGEYWRQLRKLCT
LELLSVKKVKSFQSLREEECWNLVQEIKASGSGTPFNLSEGIFKVIATVL*SR*AAFGKGIKDQKQFT
EIVKEILRETGGFDVADIFPSKKFLHHLSGKRGRLTSIHNKLDSLINNLVAEHTVSKSSKVNETLL
DVLLRLKNSEEFPLTADNVKAIILDMFGAGTDTSSATVEWAISELIRCPRAMEKVQAELRQALNGK
ERIKEEEIQDLPYLNLVIRETLRLHPPLPLVMPRECRQAMNLAGYDVANKTKLIVNVFAINRDPEY
WKDAESFNPERFENSNTTIMGADYEYLPFGAGRRMCPGSALGLANVQLPLANILYYFKWKLPNGAS
HDQLDMTESFGATVQRKTELMLVPSF  (SEQ ID NO: 52 | Wild Type)

MALLLAVFIALATIVFFLYKLLTRPTSSKNRLPEPWRLPIIGHMHHLIGTMPHRGVMDLARKYGSL
MHLQLGEVSAIVVSSPKWAKEILTTYDIPFANRPETLTGEIIAYHNTDIVLAPYGEYWRQLRKLCT
LELLSVKKVKSFQSLREEECWNLVQEIKASGSGTPFNLSEGIFKVIATVL*SR*AAFGKGIKDQKQFT
EIVKEILRETGGFDVADIFPSKKFLHHLSGKRGRLTSIHNKLDSLINNLVAEHTVSKSSKVNETLL
DVLLRLKNSEEFPLTADNVKAIILDMFGAGTDTSSATVEWAISELIRCPRAMEKVQAELRQALNGK
ERIKEEEIQDLPYLNLVIRETLRLHPPLPLVMPRECRQAMNLAGYDVANKTKLIVNVFAINRDPEY

Figure 4A (Continued)

WKDAESFNPERFENSNTTIMGADYEYLPFGAGRRMCPGSALGLANVQLPLANILYYFKWKLPNGAS
HDQLDMTESFGATVQRKTELMLVPSF  (SEQ ID NO: 53)

ATGGCTCTGTTATTAGCAGTTTTCATCGCCCTGGCAACCATTGTCTTTTTCCTGTATAAACTGCTG
ACCCGTCCGACCTCATCTAAAAACCGTCTGCCGGAACCGTGGCGCCTGCCGATTATCGGCCACATG
CATCACCTGATTGGCACCATGCCGCACCGTGGTGTCATGGATCTGGCACGCAAATATGGCAGCCTG
ATGCATCTGCAACTGGGTGAAGTTTCTGCGATTGTGGTTAGCTCTCCGAAATGGGCCAAAGAAATT
CTGACCACCTATGATATTCCGTTTGCGAACCGCCCGGAAACCCTGACGGGCGAAATTATCGCATAC
CACAATACCGACATTGTGCTGGCTCCGTATGGTGAATACTGGCGTCAACTGCGTAAACTGTGCACG
CTGGAACTGCTGAGTGTTAAAAAAGTCAAAAGTTTCCAGAGCCTGCGTGAAGAAGAATGTTGGAAC
CTGGTTCAAGAAATTAAAGCGAGCGGCAGCGGCACCCCGTTTAATCTGAGTGAAGGTATTTTCAAA
GTGATTGCGACCGTGCTGAGCCGTGCGGCATTTGGTAAAGGTATCAAAGATCAGAAACAATTCACC
GAAATTGTCAAAGAAATCCTGCGCGAAACGGGCGGTTTTGATGTGGCGGACATCTTTCCGAGCAAA
AAATTCCTGCATCACCTGTCTGGCAAACGTGGTCGCCTGACCTCAATTCATAACAAACTGGATTCG
CTGATCAACAATCTGGTCGCCGAACATACCGTGAGCAAAAGCAGCAAAGTGAATGAAACGCTGCTG
GATGTCCTGCTGCGTCTGAAAAACTCGGAAGAATTTCCGCTGACCGCAGACAATGTGAAAGCTATT
ATCCTGGATATGTTCGGTGCAGGCACCGATACCAGCAGCGCAACGGTGGAATGGCCATTAGCGAA
CTGATCCGTTGCCCGCGCGCAATGGAAAAAGTTCAGGCAGAACTGCGTCAAGCTCTGAACGGCAAA
GAACGCATTAAAGAAGAAGAAATCCAGGATCTGCCGTATCTGAATCTGGTTATTCGTGAAACCCTG
CGTCTGCATCCGCCGCTGCCGCTGGTCATGCCGCGTGAATGTCGCCAAGCAATGAACCTGGCTGGC
TATGACGTGGCAAATAAAACCAAACTGATCGTCAATGTGTTTGCGATTAACCGTGACCCGGAATAC
TGGAAAGACGCGGAAAGTTTTAACCCGGAACGCTTTGAAAACAGCAACACCACGATTATGGGTGCG
GATTATGAATACCTGCCGTTTGGCGCCGGTCGTCGCATGTGTCCGGGCAGCGCGCTGGGTCTGGCC
AACGTTCAACTGCCGCTGGCCAATATCCTGTATTACTTCAAATGGAAACTGCCGAATGGCGCCTCA
CACGATCAACTGGACATGACCGAATCGTTTGGTGCAACCGTGCAACGCAAAACGGAACTGATGCTG
GTTCCGTCTTTC  (SEQ ID NO: 54)

Figure 4B

>n20yhcB-t29SrKO
MAWEYALIGLVVGIIIGAVAAWYLKSYTSARRSQSNHLPRVPEVPGVPLLGNLLQLKEKKPYMTFT
RWAATYGPIYSIKTGATSMVVVSSNEIAKEALVTRFQSISTRNLSKALKVLTADKTMVAMSDYDDY
HKTVKRHILTAVLGPNAQKKHRIHRDIMMDNISTQLHEFVKNNPEQEEVDLRKIFQSELFGLAMRQ
ALGKDVESLYVEDLKITMNRDEIFQVLVVDPMMGAIDVDWRDFFPYLKWVPNKKFENTIQQMYIRR
EAVMKSLIKEHKKRIASGEKLNSYIDYLLSEAQTLTDQQLLMSLWEPIIESSDTTMVTTEWAMYEL
AKNPKLQDRLYRDIKSVCGSEKITEEHLSQLPYITAIFHETLRRHSPVPIIPLRHVHEDTVLGGYH
VPAGTELAVNIYGCNMDKNVWENPEEWNPERFMKENETIDFQKTMAFGGGKRVCAGSLQALLTASI
GIGRMVQEFEWKLKDMTQEEVNTIGLTTQMLRPLRAIIKPRI (SEQ ID NO: 55)

>n22yhcB-t30VO1c9
MAWEYALIGLVVGIIIGAVAMRWYLKSYTSARRSQSNHLPRVPEVPGVPLLGNLLQLKEKKPYMTF
TRWAATYGPIYSIKTGATSVVVVSSNEIAKEAMVTRFQSISTRNLSKALKVLTADKTMVAMSDYDD
YHKTVKRHILTAVLGPNAQKKHRIHRDIMMDNISTQLHEFVKNNPEQEEVDLRKIFQSELFGLAMR
QALGKDVESLYVEDLKITMNRDEILQVLVVDPMMGAIDVDWRDFFPYLKWVPNKKFENTIQQMYIR
REAVMKSLIKEHKKRIASGEKLNSYIDYLLSEAQTLTDQQLLMSLWEPIIESSDTTMVTTEWAMYE
LAKNPKLQDRLYRDIKSVCGSEKITEEHLSQLPYITAIFHETLRKHSPVPILPLRHVHEDTVLGGY
HVPAGTELAVNIYGCNMDKNVWENPEEWNPERFMKENETIDFQKTMAFGGGKRVCAGSLQALLIAS
IGIGRMVQEFEWKLKDMTQEEVNTIGLTNQMLRPLRAIIKPRI (SEQ ID NO: 56)

>n22yhcB-t30VO1c12
MAWEYALIGLVVGIIIGAVAMRWYLKSYTSARRSQSNHLPRVPEVPGVPLLGNLLQLKEKKPYMTF
TKWAATYGPIYSIKTGATSMVVVSSNEIAKEAMVTRFQSISTRNLSKALKVLTADKQMVAMSDYDD
YHKTVKRHILTAVLGPNAQKKHRIHRDIMMDNISTQLHEFVKNNPEQEEVDLRKIFQSELFGLAMR
QALGKDVESLYVEDLKITMNRDEILQVLVVDPMMGAIDVDWRDFFPYLKWVPNKKFENTIQQMYIR
REAVMKSLIKEHKKRIASGEKLNSYIDYLLSEAQTLTDQQLLMSLWEPIIESSDTTMVTTEWAMYE
LAKNPKLQDRLYRDIKSVCGSEKITEEHLSQLPYITAIFHETLRKHSPVPILPLRHVHEDTVLGGY
HVPAGTELAVNIYGCNMDKNVWENPEEWNPERFMKENETIDFQKTMAFGGGKRVCAGSLQALLIAS
IGIGRMVQEFEWKLKDMTQEEVNTIGLTNQMLRPLRAIIKPRI (SEQ ID NO: 57)

>n22yhcB-t30VO1b4
MAWEYALIGLVVGIIIGAVAMRWYLKSYTSARRSQSNHLPRVPEVPGVPLLGNLLQLKEKKPYMTF
TRWAATYGPIYSIKTGATSVVVVSSNEIAKEAMVTRFQSISTRNLSKALKVLTADKQMVAMSDYDD
YHKTVKRHILTAVLGPNAQKKHRIHRDIMMDNISTQLHEFVKNNPEQEEVDLRKIFQSELFGLAMR
QALGKDVESLYVEDLKITMNRDEILQVLVVDPMMGAIDVDWRDFFPYLKWVPNKKFENTIQQMYIR
REAVMKSLIKEHKKRIASGEKLNSYIDYLLSEAQTLTDQQLLMSLWEPIIESSDTTMVTTEWAMYE
LAKNPKLQDRLYRDIKSVCGSEKITEEHLSQLPYITAIFHETLRKHSPVPILPLRHVHEDTVLGGY
HVPAGTELAVNIYGCNMDKNVWENPEEWNPERFMKENETIDFQKTMAFGGGKRVCAGSLQALLIAS
IGIGRMVQEFEWKLKDMTQEEVNTIGLTNQMLRPLRAIIKPRI (SEQ ID NO: 58)

>n20yhcB-t29VO1c11
MAWEYALIGLVVGIIIGAVAAWYLKSYTSARRSQSNHLPRVPEVPGVPLLGNLLQLKEKKPYMTFT
KWAATYGPIYSIKTGATSMVVVSSNEIAKEAMVTRFQSISTRNLSKALKVLTADKQMVAMSDYDDY
HKTVKRHILTAVLGPNAQKKHRIHRDIMMDNISTQLHEFVKNNPEQEEVDLRKIFQSELFGLAMRQ
ALGKDVESLYVEDLKITMNRDEILQVLVVDPMMGAIDVDWRDFFPYLKWVPNKKFENTIQQMYIRR
EAVMKSLIKEHKKRIASGEKLNSYIDYLLSEAQTLTDQQLLMSLWEPIIESSDTTMVTTEWAMYEL
AKNPKLQDRLYRDIKSVCGSEKITEEHLSQLPYITAIFHETLRKHSPVPILPLRHVHEDTVLGGYH
VPAGTELAVNIYGCNMDKNVWENPEEWNPERFMKENETIDFQKTMAFGGGKRVCAGSLQALLIASI
GIGRMVQEFEWKLKDMTQEEVNTIGLTNQMLRPLRAIIKPRI (SEQ ID NO: 59)

Figure 4B (Continued)

>n22yhcB-t30VO1b6

MAWEYALIGLVVGIIIGAVAMRWYLKSYTSARRSQSNHLPRVPEVPGVPLLGNLLQLKEKKPYMTF
TKWAATYGPIYSIKTGATSVVVVSSNEIAKEAMVTRFQSISTRNLSKALKVLTADKTMVAMSDYDD
YHKTVKRHILTAVLGPNAQKKHRIHRDIMMDNISTQLHEFVKNNPEQEEVDLRKIFQSELFGLAMR
QALGKDVESLYVEDLKITMNRDEILQVLVVDPMMGAIDVDWRDFFPYLKWVPNKKFENTIQQMYIR
REAVMKSLIKEHKKRIASGEKLNSYIDYLLSEAQTLTDQQLLMSLWEPIIESSDTTMVTTEWAMYE
LAKNPKLQDRLYRDIKSVCGSEKITEEHLSQLPYITAIFHETLRKHSPVPIIPLRHVHEDTVLGGY
HVPAGTELAVNIYGCNMDKNVWENPEEWNPERFMKENETIDFQKTMAFGGGKRVCAGSLQALLIAS
IGIGRMVQEFEWKLKDMTQEEVNTIGLTNQMLRPLRAIIKPRI  (SEQ ID NO: 60)

>n22yhcB-t30VO1c6 (VO2)

MAWEYALIGLVVGIIIGAVAMRWYLKSYTSARRSQSNHLPRVPEVPGVPLLGNLLQLKEKKPYMTF
TKWAATYGPIYSIKTGATSVVVVSSNEIAKEALVTRFQSISTRNLSKALKVLTADKQMVAMSDYDD
YHKTVKRHILTAVLGPNAQKKHRIHRDIMMDNISTQLHEFVKNNPEQEEVDLRKIFQSELFGLAMR
QALGKDVESLYVEDLKITMNRDEILQVLVVDPMMGAIDVDWRDFFPYLKWVPNKKFENTIQQMYIR
REAVMKSLIKEQKKRIASGEKLNSYIDYLLSEAQTLTDQQLLMSLWEPIIESSDTTMVTTEWAMYE
LAKNPKLQDRLYRDIKSVCGSEKITEEHLSQLPYITAIFHETLRKHSPVPILPLRHVHEDTVLGGY
HVPAGTELAVNIYGCNMDKNVWENPEEWNPERFMKENETIDFQKTMAFGGGKRVCAGSLQALLIAS
IGIGRMVQEFEWKLKDMTQEEVNTIGLTNQMLRPLRAIIKPRI  (SEQ ID NO: 61)

Figure 6A

>*Sr*CPR [Stevia rebaudiana]

MQSDSVKVSPFDLVSAAMNGKAMEKLNASESEDPTTLPALKMLVENRELLTLFTTSFAVLIGCLVF
LMWRRSSSKKLVQDPVPQVIVVKKKEKESEVDDGKKKVSIFYGTQTGTAEGFAKALVEEAKVRYEK
TSFKVIDLDDYAADDDEYEEKLKKESLAFFFLATYGDGEPTDNAANFYKWFTEGDDKGEWLKKLQY
GVFGLGNRQYEHFNKIAIVVDDKLTEMGAKRLVPVGLGDDDQCIEDDFTAWKELVWPELDQLLRDE
DDTSVTTPYTAAVLEYRVVYHDKPADSYAEDQTHTNGHVVHDAQHP*SR*SNVAFKKELHTSQSDRSC
THLEFDISHTGLSYETGDHVGVYSENLSEVVDEALKLLGLSPDTYFSVHADKEDGTPIGGASLPPP
FPPCTLRDALTRYADVLSSPKKVALLALAAHASDPSEADRLKFLASPAGKDEYAQWIVANQRSLLE
VMQSFPSAKPPLGVFFAAVAPRLQPRYYSISSSPKMSPNRIHVTCALVYETTPAGRIHRGLCSTWM
KNAVPLTESPDCSQASIFVRTSNFRLPVDPKVPVIMIGPGTGLAPFRGFLQERLALKESGTELGSS
IFFFGCRNRKVDFIYEDELNNFVETGALSELIVAF*SR*EGTAKEYVQHKMSQKASDIWKLLSEGAYL
YVCGDAKGMAKDVHRTLHTIVQEQGSLDSSKAELYVKNLQMSGRYLRDVW (SEQ ID NO: 62)

ATGCAGAGCGATTCTGTTAAAGTATCCCCGTTCGACCTGGTCTCTGCGGCTATGAACGGCAAAGCA
ATGGAGAAACTGAACGCGAGCGAATCTGAAGATCCAACCACCCTGCCGGCACTGAAAATGCTGGTA
GAAAACCGTGAACTGCTGACTCTGTTCACCACCTCCTTCGCCGTTCTGATTGGTTGCCTGGTCTTC
CTGATGTGGCGCCGTTCCTCTTCCAAGAAGCTGGTACAGGACCCGGTTCCTCAGGTGATCGTCGTT
AAAAAGAAAGAGAAGGAAAGCGAAGTCGATGACGGCAAAAAGAAGGTTTCCATTTTCTACGGTACT
CAGACCGGCACCGCTGAGGGTTTTGCCAAAGCACTGGTTGAAGAGGCAAAAGTGCGTTACGAAAAA
ACTTCCTTCAAAGTGATTGACCTGGACGACTATGCTGCGGATGATGATGAATACGAGGAAAAACTG
AAAAAAGAAAGCCTGGCCTTCTTCTTCCTGGCAACCTATGGCGATGGTGAACCGACCGACAACGCG
GCGAACTTCTACAAATGGTTTACCGAAGGCGACGACAAAGGTGAATGGCTGAAGAAACTGCAGTAT
GGTGTTTTCGGTCTGGGCAATCGCCAGTACGAACATTTTAACAAAATCGCAATCGTTGTTGATGAC
AAACTGACTGAAATGGGTGCGAAACGTCTGGTGCCGGTTGGCCTGGGTGACGATGATCAATGCATC
GAAGATGACTTCACCGCATGGAAAGAACTGGTTTGGCCGGAACTGGATCAGCTGCTGCGCGACGAA
GACGACACTTCCGTGACCACCCCGTATACCGCTGCAGTGCTGGAGTACCGTGTTGTTTACCACGAT
AAACCGGCGGACTCTTACGCCGAAGATCAGACTCACACTAACGGTCACGTCGTACATGACGCACAG
CACCCGTCTCGTAGCAATGTTGCGTTTAAGAAAGAGCTGCACACGAGCCAGTCCGACCGCTCTTGT
ACGCACCTGGAGTTCGATATCTCCCACACCGGTCTGTCCTATGAAACCGGTGACCATGTTGGCGTT
TACAGCGAAAACCTGAGCGAGGTAGTTGATGAAGCGCTGAAACTGCTGGGCCTGTCTCCAGACACC
TACTTTAGCGTGCATGCTGACAAGGAAGATGGTACTCCGATTGGCGGCGCTTCCCTGCCGCCACCG
TTTCCACCTTGCACTCTGCGTGATGCTCTGACTCGTTACGCTGATGTTCTGTCTAGCCCGAAAAAG
GTTGCGCTGCTGGCGCTGGCCGCACATGCTTCTGACCCGTCTGAAGCTGACCGTCTGAAATTCCTG
GCGTCTCCGGCCGGCAAAGACGAATACGCGCAGTGGATTGTCGCTAACCAGCGCTCTCTGCTGGAA
GTGATGCAGTCCTTCCCGTCTGCCAAACCGCCACTGGGCGTGTTTTCGCAGCTGTGGCTCCGCGC
CTGCAGCCGCGCTACTATTCTATCTCTAGCTCCCCGAAAATGAGCCCGAACCGCATCCACGTTACT
TGTGCTCTGGTTTACGAAACCACCCCTGCGGGCCGTATCCACCGTGGTCTGTGCTCTACGTGGATG
AAAAATGCCGTGCCGCTGACCGAATCCCCGGACTGCTCTCAGGCGTCCATCTTCGTGCGTACCTCT
AACTTCCGTCTGCCGGTGGACCCGAAAGTTCCTGTTATCATGATCGGTCCTGGCACGGGTCTGGCC
CCGTTTCGTGGTTTTCTGCAGGAGCGTCTGGCTCTGAAAGAATCCGGTACTGAGCTGGGCTCTTCC
ATCTTTTTCTTCGGTTGTCGTAACCGCAAAGTCGATTTCATCTATGAAGACGAACTGAACAACTTC
GTAGAGACTGGTGCACTGTCCGAACTGATTGTGGCATTCTCTCGTGAAGGCACGGCGAAAGAATAC
GTTCAACACAAAATGTCTCAGAAAGCGAGCGATATCTGGAAACTGCTGTCCGAGGGTGCGTATCTG
TATGTTTGTGGCGACGCGAAAGGCATGGCTAAAGATGTACACCGCACCCTGCACACCATTGTACAA
GAACAAGGCTCTCTGGATAGCTCCAAGGCAGAACTGTACGTGAAAAACCTGCAGATGTCTGGCCGT
TACCTGCGTGATGTATGGTAA (SEQ ID NO: 63)

Figure 6A (Continued)

>AtCPR [Arabidopsis thaliana]

MTSALYASDLFKQLKSIMGTDSLSDDVVLVIATTSLALVAGFVVLLWKKTTADRSGELKPLMIPKS
LMAKDEDDDLDLGSGKTRVSIFFGTQTGTAEGFAKALSEEIKARYEKAAVKVIDLDDYAADDDQYE
EKLKKETLAFFCVATYGDGEPTDNAARFSKWFTEENERDIKLQQLAYGVFALGNRQYEHFNKIGIV
LDEELCKKGAKRLIEVGLGDDDQSIEDDFNAWKESLWSELDKLLKDEDDKSVATPYTAVIPEYRVV
THDPRFTTQKSMESNVANGNTTIDIHHPCRVDVAVQKELHTHESDRSCIHLEFDI*SR*TGITYETGD
HVGVYAENHVEIVEEAGKLLGHSLDLVFSIHADKEDGSPLESAVPPPFPGPCTLGTGLARYADLLN
PPRKSALVALAAYATEPSEAEKLKHLTSPDGKDEYSQWIVASQRSLLEVMAAFPSAKPPLGVFFAA
IAPRLQPRYYSISSCQDWAP*SR*VHVTSALVYGPTPTGRIHKGVCSTWMKNAVPAEKSHECSGAPIF
IRASNFKLPSNPSTPIVMVGPGTGLAPFRGFLQERMALKEDGEELGSSLLFFGCRNRQMDFIYEDE
LNNFVDQGVISELIMAF*SR*EGAQKEYVQHKMMEKAAQVWDLIKEEGYLYVCGDAKGMARDVHRTLH
TIVQEQEGVSSSEAEAIVKKLQTEGRYLRDVW (SEQ ID NO: 64)

ATGACCAGCGCACTGTACGCAAGCGACCTGTTTAAGCAACTGAAGAGCATTATGGGCACCGATAGC
CTGAGCGATGATGTTGTCCTGGTCATTGCGACCACGAGCCTGGCACTGGTGGCTGGTTTTGTGGTT
CTGCTGTGGAAAAAGACCACGGCCGATCGTTCTGGCGAACTGAAACCGCTGATGATTCCGAAAAGT
CTGATGGCAAAGGACGAAGATGACGATCTGGATCTGGGCTCCGGTAAAACCCGTGTGTCAATCTTT
TTCGGTACCCAGACGGGCACCGCAGAAGGTTTCGCAAAAGCTCTGTCTGAAGAAATTAAGGCGCGC
TATGAAAAAGCGGCCGTTAAGGTCATCGATCTGGACGATTATGCAGCTGACGATGACCAGTACGAA
GAAAAACTGAAAAAGGAAACCCTGGCGTTTTTCTGCGTTGCCACCTACGGCGACGGTGAACCGACG
GATAACGCGGCCCGTTTTAGTAAATGGTTCACCGAAGAAAATGAACGCGACATTAAGCTGCAGCAA
CTGGCGTATGGCGTGTTTGCTCTGGGTAACCGTCAGTACGAACATTTCAACAAGATCGGTATCGTC
CTGGATGAAGAACTGTGTAAAAAGGGCGCGAAGCGCCTGATTGAAGTGGGCCTGGGTGATGACGAT
CAATCCATCGAAGACGATTTTAACGCCTGGAAAGAATCTCTGTGGAGTGAACTGGACAAACTGCTG
AAGGATGAAGACGATAAGAGCGTGGCGACGCCGTATACCGCCGTTATTCCGGAATACCGTGTCGTG
ACCCATGATCCGCGCTTCACCACGCAGAAAAGCATGGAATCAAATGTTGCGAACGGTAATACCACG
ATTGACATCCATCACCCGTGCCGTGTGGATGTTGCCGTCCAAAAAGAACTGCATACCCACGAATCG
GACCGTAGCTGTATCCACCTGGAATTTGATATTAGCCGCACGGGCATCACCTATGAAACGGGCGAC
CATGTGGGTGTTTACGCAGAAAACCACGTGGAAATTGTTGAAGAAGCTGGCAAACTGCTGGGTCAT
TCGCTGGATCTGGTTTTTAGCATCCACGCGGACAAGGAAGATGGTTCGCCGCTGGAAAGCGCAGTG
CCGCCGCCGTTCCCGGGTCCGTGCACCCTGGGTACGGGTCTGGCACGTTATGCAGATCTGCTGAAT
CCGCCGCGCAAATCCGCACTGGTGGCTCTGGCAGCTTACGCAACCGAACCGTCAGAAGCTGAAAAA
CTGAAGCATCTGACGTCGCCGGACGGTAAAGATGAATATAGCCAGTGGATTGTTGCGTCTCAACGC
AGTCTGCTGGAAGTCATGGCAGCATTTCCGTCGGCAAAACCGCCGCTGGGCGTGTTTTCGCAGCT
ATTGCACCGCGTCTGCAGCCGCGCTATTACAGCATCAGCTCTTGTCAAGATTGGGCGCCGTCTCGT
GTCCATGTGACCAGTGCACTGGTGTATGGTCCGACGCCGACCGGTCGCATTCACAAAGGCGTGTGC
TCTACCTGGATGAAAAACGCGGTTCCGGCCGAAAAGTCTCACGAATGTAGTGGTGCGCCGATTTTT
ATCCGTGCCAGTAACTTCAAACTGCCGTCCAATCCGTCAACCCCGATCGTTATGGTCGGTCCGGGT
ACGGGTCTGGCACCGTTTCGTGGTTTCCTGCAGGAACGCATGGCTCTGAAAGAAGATGGCGAAGAA
CTGGGTAGTTCCCTGCTGTTTTTCGGCTGCCGTAATCGCCAGATGGACTTCATCTACGAAGATGAA
CTGAACAACTTCGTCGATCAAGGTGTGATTTCCGAACTGATCATGGCATTTTCACGCGAAGGCGCT
CAGAAAGAATACGTCCAACATAAAATGATGGAAAAGGCGGCCCAAGTGTGGGATCTGATCAAAGAA
GAAGGCTATCTGTACGTTTGTGGCGACGCAAAGGGTATGGCTCGTGATGTCCATCGCACCCTGCAC
ACGATTGTTCAGGAACAAGAAGGTGTCTCATCGAGCGAAGCGGAAGCCATCGTGAAAAAGCTGCAG
ACCGAAGGCCGTTATCTGCGCGATGTTTGGTAA (SEQ ID NO: 65)

>TcCPR [Taxus cuspidata]

MQANSNTVEGASQGKSLLDI*SR*LDHIFALLLNGKGGDLGAMTGSALILTENSQNLMILTTALAVLV
ACVFFFVWRRGGSDTQKPAVRPTPLVKEEDEEEDDSAKKKVTIFFGTQTGTAEGFAKALAEEEAKA
RYEKAVFKVVDLDNYAADDEQYEEKLKKEKLAFFMLATYGDGEPTDNAARFYKWFLEGKEREPWLS
DLTYGVFGLGNRQYEHFNKVAKAVDEVLIEQGAKRLVPVGLGDDDQCIEDDFTAWREQVWPELDQL

Figure 6A (Continued)

LRDEDDEPTSATPYTAAIPEYRVEIYDSVVSVYEETHALKQNGQAVYDIHHPCRSNVAVRRELHTP
LSDRSCIHLEFDISDTGLIYETGDHVGVHTENSIETVEEAAKLLGYQLDTIFSVHGDKEDGTPLGG
SSLPPPFPGPCTLRTALARYADLLNPPRKAAFLALAAHASDPAEAERLKFLSSPAGKDEYSQWVTA
SQRSLLEIMAEFPSAKPPLGVFFAAIAPRLQPRYYSISSSPRFAP*SR*IHVTCALVYGPSPTGRIHK
GVCSNWMKNSLPSEETHDCSWAPVFVRQSNFKLPADSTTPIVMVGPGTGFAPFRGFLQERAKLQEA
GEKLGPAVLFFGCRNRQMDYIYEDELKGYVEKGILTNLIVAF*SR*EGATKEYVQHKMLEKASDTWSL
IAQGGYLYVCGDAKGMARDVHRTLHTIVQEQESVDSSKAEFLVKKLQMDGRYLRDIW (SEQ ID NO: 66)

ATGCAGGCTAATTCCAACACGGTGGAAGGTGCCTCCCAGGGGAAGAGCCTGCTGGACATATCTCGG
CTGGACCATATTTTTGCGCTGCTGTTGAACGGCAAGGGAGGAGATCTGGGAGCCATGACCGGCTCG
GCTTTGATTTTGACAGAGAATTCGCAGAATTTGATGATTTTGACCACGGCTTTGGCTGTTTTGGTC
GCGTGTGTTTTCTTCTTCGTTTGGAGGAGGGGAGGATCGGATACGCAGAAGCCGGCGGTGAGACCG
ACGCCTCTGGTGAAGGAGGAAGATGAGGAGGAAGAAGACGATTCTGCAAAGAAGAAAGTCACGATT
TTCTTTGGGACACAGACTGGGACGGCCGAGGGATTTGCCAAGGCTCTAGCAGAAGAGGCAAAGGCA
AGATATGAGAAAGCTGTGTTTAAAGTCGTAGATTTGGACAACTATGCAGCAGATGATGAGCAGTAT
GAAGAAAAATTGAAAAAGGAAAAATTAGCATTTTTTATGCTAGCAACGTATGGAGATGGGGAGCCC
ACTGACAATGCAGCAAGATTTTATAAGTGGTTTCTTGAGGGCAAGGAGAGGGAGCCATGGCTTTCT
GATCTCACTTATGGGGTGTTTGGATTAGGCAACAGACAATATGAACATTTTAATAAGGTGGCTAAA
GCAGTAGATGAAGTCTTAATTGAACAAGGTGCAAAGCGACTTGTTCCAGTGGGCCTTGGTGATGAT
GACCAATGCATTGAAGATGACTTTACTGCTTGGCGAGAGCAGGTTTGGCCTGAACTGGATCAGTTA
CTCCGGGATGAAGATGATGAGCCCACAAGTGCTACACCTTATACAGCTGCCATACCTGAGTATAGG
GTTGAAATTTATGATTCCGTGGTTTCAGTGTACGAGGAAACTCATGCTCTCAAGCAAAATGGCCAA
GCTGTTTATGATATCCATCACCCCTGCAGATCTAATGTGGCAGTGAGAAGAGAGCTTCATACACCT
TTGTCTGACCGCTCTTGCATCCATTTGGAATTTGATATATCAGACACTGGCCTTATATATGAGACA
GGAGATCATGTTGGTGTCCATACAGAAAACAGCATTGAAACTGTGGAGGAAGCAGCAAAGCTACTA
GGCTACCAATTGGACACTATATTCTCAGTCCACGGTGACAAAGAAGATGGCACGCCACTTGGAGGG
TCTTCTTTGCCACCACCTTTCCCTGGTCCATGCACCCTACGAACTGCTCTTGCTCGTTATGCTGAT
TTGCTGAATCCTCCTCGGAAGGCCGCCTTTCTTGCATTGGCAGCTCATGCATCTGATCCAGCAGAG
GCAGAGCGGTTGAAGTTCCTCTCATCACCAGCTGGAAAGGATGAATATTCTCAATGGGTCACTGCA
AGTCAGAGAAGTCTTTTAGAAATAATGGCAGAATTTCCATCAGCAAAACCACCCCTTGGTGTTTTC
TTTGCAGCAATAGCCCCTCGTCTGCAACCCCGATATTATTCTATTTCTTCCTCTCCCAGGTTTGCA
CCCTCAAGAATACATGTGACATGTGCTCTTGTTTACGGGCCCAGTCCAACCGGTAGAATTCACAAA
GGTGTTTGTTCTAACTGGATGAAGAATTCGCTACCCTCAGAAGAAACCCATGACTGTAGCTGGGCT
CCAGTCTTTGTCAGGCAATCAAATTTTAAATTGCCAGCAGATTCTACTACTCCTATTGTCATGGTG
GGTCCTGGAACTGGTTTTGCACCTTTTAGAGGTTTTTTGCAGGAAAGAGCAAAACTTCAAGAAGCT
GGTGAGAAGCTCGGTCCGGCTGTTTTATTTTTTGGGTGCAGGAATCGCCAAATGGACTACATTTAT
GAAGATGAGCTGAAGGGCTATGTGGAGAAAGGAATACTGACCAATCTCATTGTTGCTTTCTCTCGT
GAAGGAGCAACCAAAGAGTATGTCCAGCACAAGATGCTGGAAAAGGCATCCGATACCTGGAGTCTC
ATTGCTCAGGGTGGGTATCTTTATGTATGTGGTGATGCCAAGGGTATGGCTAGGGATGTACACAGG
ACACTGCACACTATTGTCCAAGAGCAGGAATCTGTGGATAGCAGCAAAGCAGAGTTTCTAGTGAAG
AAATTACAGATGGATGGAAGATACTTACGAGATATATGGTGA (SEQ ID NO: 67)

>AaCPR [Artemisia annua]

MAQSTTSVKLSPFDLMTALLNGKVSFDTSNTSDTNIPLAVFMENRELLMILTTSVAVLIGCVVVLV
WRRSSSAAKKAAESPVIVVPKKVTEDEVDDGRKKVTVFFGTQTGTAEGFAKALVEEAKARYEKAVF
KVIDLDDYAAEDDEYEEKLKKESLAFFFLATYGDGEPTDNAARFYKWFTEGEEKGEWLDKLQYAVF
GLGNRQYEHFNKIAKVVDEKLVEQGAKRLVPVGMGDDQCIEDDFTAWKELVWPELDQLLRDEDDT
SVATPYTAAVAEYRVVFHDKPETYDQDQLTNGHAVHDAQHPCRSNVAVKKELHSPLSDRSCTHLEF
DISNTGLSYETGDHVGVYVENLSEVVDEAEKLIGLPPHTYFSVHADNEDGTPLGGASLPPPFPPCT
LRKALASYADVLSSPKKSALLALAAHATDSTEADRLKFLASPAGKDEYAQWIVASHRSLLEVMEAF
PSAKPPLGVFFASVAPRLQPRYYSISSSPRFAPNRIHVTCALVYEQTPSGRVHKGVCSTWMKNAVP

Figure 6A (Continued)

MTESQDCSWAPIYVRTSNFRLPSDPKVPVIMIGPGTGLAPFRGFLQERLAQKEAGTELGTAILFFG
CRNRKVDFIYEDELNNFVETGALSELVTAFSREGATKEYVQHKMTQKASDIWNLLSEGAYLYVCGD
AKGMAKDVHRTLHTIVQEQGSLDSSKAELYVKNLQMAGRYLRDVW (SEQ ID NO: 68)

ATGGCGCAGTCTACCACCAGCGTGAAATTGTCCCCTTTTGATCTCATGACCGCTCTGCTGAATGGG
AAAGTCTCATTCGATACAAGCAACACAAGTGATACCAACATCCCTTTGGCGGTTTTTATGGAGAAT
AGAGAGTTACTCATGATTTTAACGACTTCCGTGGCCGTGCTCATTGGGTGCGTCGTCGTACTTGTC
TGGCGCCGGTCAAGTAGCGCAGCAAAGAAGGCGGCGGAGTCCCCGGTTATCGTCGTCCCAAAGAAG
GTTACAGAGGACGAGGTGGACGACGGACGCAAAAAAGTGACGGTATTCTTTGGTACACAGACCGGA
ACCGCGGAAGGATTTGCTAAAGCGCTGGTGGAAGAAGCTAAAGCCCGTTACGAAAAGCGGTATTC
AAAGTGATAGACCTGGATGACTATGCGGCAGAGGACGACGAGTACGAGGAAAAATTGAAAAAGAA
TCTCTTGCGTTCTTTTTTCTCGCCACTTACGGCGATGGAGAACCTACTGATAATGCGGCTCGGTTT
TATAAGTGGTTCACTGAGGGTGAAGAAAAGGTGAATGGCTGGACAAATTGCAGTACGCAGTATTT
GGACTCGGGAATCGTCAATATGAACATTTTAACAAAATTGCTAAGGTCGTCGATGAAAAACTGGTT
GAGCAGGGTGCGAAACGTCTGGTCCCGGTTGGAATGGGCGATGACGACCAGTGCATTGAAGACGAC
TTTACAGCATGGAAGGAACTGGTGTGGCCGGAACTGGACCAACTTTTGCGTGACGAGGATGACACA
TCTGTAGCTACGCCGTACACTGCTGCGGTAGCCGAGTATAGGGTCGTTTTTCACGATAAACCGGAA
ACCTACGACCAAGACCAGCTCACAAATGGTCATGCAGTACATGATGCGCAACATCCTTGCAGGTCA
AATGTGGCGGTGAAGAAAGAGCTGCACAGTCCTCTGTCAGATCGTTCTTGCACCCACCTGGAATTT
GACATATCCAATACGGGCCTTTCGTATGAAACCGGAGATCACGTTGGTGTCTATGTTGAAAATCTG
TCGGAAGTGGTTGATGAGGCGGAAAAACTTATCGGTCTGCCGCCTCATACGTACTTTTCAGTCCAC
GCTGATAATGAAGACGGAACCCCGCTGGGTGGCGCATCGTTACCCCCACCCTTTCCACCATGCACT
CTGCGTAAGGCGCTTGCCAGTTATGCTGATGTTTTGTCTAGTCCCAAAAAGAGTGCACTTCTCGCA
CTGGCGGCCCATGCCACTGATAGTACAGAGGCCGACAGGCTGAAATTTCTGGCGTCACCAGCGGGA
AAAGACGAATACGCCCAATGGATCGTTGCCAGTCATCGGTCTTTACTGGAAGTGATGGAAGCGTTC
CCTTCCGCTAAGCCACCTCTGGGGGTCTTTTTCGCTAGTGTGGCACCCCGTCTACAGCCCCGGTAT
TACTCAATATCTAGCTCACCCAGATTTGCTCCAATAGAATACACGTAACATGCGCGCTGGTCTAT
GAGCAGACCCCAAGTGGACGGGTGCATAAAGGGGTTTGTTCTACCTGGATGAAGAACGCCGTCCCA
ATGACCGAGTCTCAGGATTGTTCCTGGGCACCTATATATGTTAGAACATCAAACTTTCGACTGCCA
AGTGACCCGAAAGTTCCGGTAATTATGATAGGTCCAGGAACAGGGCTGGCTCCCTTTCGCGGGTTC
CTCCAGGAACGTCTGGCGCAGAAGGAGGCGGGAACTGAACTGGGGACGGCGATTTTATTTTTCGGG
TGTAGAAATCGTAAAGTCGATTTTATATATGAAGATGAGTTGAACAATTTCGTGGAAACCGGGGCA
TTATCGGAATTAGTTACGGCTTTTAGCAGGGAGGGGCGACTAAAGAGTATGTCCAGCACAAGATG
ACTCAGAAAGCCTCAGATATATGGAACCTGCTGTCGGAGGGAGCCTATCTTTATGTTTGCGGTGAT
GCAAAAGGAATGGCCAAAGATGTCCACCGGACCCTCCACACTATTGTGCAGGAACAGGGTTCATTA
GACTCAAGTAAAGCCGAACTTTACGTAAAAAATCTACAGATGGCGGGCCGTTACCTCCGTGACGTT
TGGTAA (SEQ ID NO: 69)

>AtCPR1 [Arabidopsis thaliana]

MATSALYASDLFKQLKSIMGTDSLSDDVVLVIATTSLALVAGFVVLLWKKTTADRSGELKPLMIPK
SLMAKDEDDDLDLGSGKTRVSIFFGTQTGTAEGFAKALSEEIKARYEKAAVKVIDLDDYAADDDQY
EEKLKKETLAFFCVATYGDGEPTDNAARFYKWFTEENERDIKLQQLAYGVFALGNRQYEHFNKIGI
VLDEELCKKGAKRLIEVGLGDDDQSIEDDFNAWKESLWSELDKLLKDEDDKSVATPYTAVIPEYRV
VTHDPRFTTQKSMESNVANGNTTIDIHHPCRVDVAVQKELHTHESDRSCIHLEFDISRTGITYETG
DHVGVYAENHVEIVEEAGKLLGHSLDLVFSIHADKEDGSPLESAVPPPFPGPCTLGTGLARYADLL
NPPRKSALVALAAYATEPSEAEKLKHLTSPDGKDEYSQWIVASQRSLLEVMAAFPSAKPPLGVFFA
AIAPRLQPRYYSISSSPRLAPSRVHVTSALVYGPTPTGRIHKGVCSTWMKNAVPAEKSHECSGAPI
FIRASNFKLPSNPSTPIVMVGPGTGLAPFRGFLQERMALKEDGEELGSSLLFFGCRNRQMDFIYED
ELNNFVDQGVISELIMAFSREGAQKEYVQHKMMEKAAQVWDLIKEEGYLYVCGDAKGMARDVHRTL
HTIVQEQEGVSSSEAEAIVKKLQTEGRYLRDVW (SEQ ID NO: 70)

Figure 6A (Continued)

```
ATGGCGACCAGCGCTCTGTATGCTAGTGACCTTTTTAAACAGCTCAAAAGCATCATGGGCACTGAT
AGCCTGTCCGACGATGTTGTCCTGGTAATCGCAACCACTTCCCTTGCGCTTGTTGCGGGCTTTGTG
GTGTTACTGTGGAAGAAGACTACCGCAGATAGGAGTGGTGAATTGAAACCGCTGATGATCCCAAAA
AGTCTGATGGCCAAAGATGAGGATGATGATCTGGATCTTGGATCAGGGAAGACGCGAGTCAGTATT
TTTTTCGGGACCCAGACGGGCACCGCGGAGGGCTTCGCCAAAGCTCTGTCCGAGGAAATAAAGGCC
AGATACGAGAAAGCCGCCGTAAAGGTTATAGACCTAGATGATTACGCCGCTGATGACGATCAGTAT
GAGGAGAAACTTAAAAAGGAGACTCTGGCGTTTTTTTGCGTGGCAACTTACGGAGACGGCGAGCCC
ACCGATAATGCAGCTAGGTTTTACAAGTGGTTTACCGAGGAGAACGAACGAGATATAAAGTTACAG
CAGTTGGCCTATGGCGTGTTTGCCCTGGGTAATCGGCAATATGAGCATTTCAACAAAATTGGCATC
GTTCTGGATGAGGAATTGTGCAAAAAGGGTGCAAAACGGCTGATAGAGGTGGGTCTAGGTGACGAT
GATCAATCTATAGAAGACGATTTTAATGCGTGGAAAGAGAGCTTATGGAGTGAACTGGATAAGCTC
TTGAAAGATGAAGACGACAAGTCAGTGGCGACCCCTTATACCGCGGTAATCCCGGAATACCGCGTC
GTGACACACGATCCGAGGTTTACAACCCAAAAATCTATGGAGTCTAATGTCGCCAATGGCAACACA
ACGATTGATATTCACCACCCCTGTCGTGTTGACGTGGCTGTTCAAAAAGAACTTCATACACACGAA
AGTGACCGAAGTTGCATACACTTGGAATTTGACATTAGTCGCACCGGAATTACGTATGAAACTGGT
GATCACGTGGGTGTATACGCAGAAAATCATGTCGAAATAGTAGAAGAAGCTGGCAAACTGCTGGGA
CATTCACTCGATCTAGTGTTTAGTATACATGCCGATAAAGAGGATGGCAGCCCATTGGAAAGTGCC
GTCCCTCCGCCGTTTCCTGGACCGTGTACTCTGGGGACGGGACTCGCCCGCTATGCTGACCTGTTA
AACCCCCCTCGTAAAAGCGCCCTTGTGGCCCTGGCGGCATACGCAACTGAACCGAGCGAAGCGGAG
AAGCTGAAACATCTGACATCACCGGATGGCAAAGACGAGTATAGTCAGTGGATAGTAGCCTCTCAG
CGCTCTCTGCTGGAAGTGATGGCCGCATTTCCGTCCGCCAAACCACCTTTGGGAGTATTTTTCGCT
GCTATCGCACCTCGGCTCCAGCCGCGCTATTACAGCATATCTTCAAGTCCCGCTTAGCACCGTCT
CGTGTCCATGTCACTTCTGCGTTGGTTTATGGTCCGACTCCAACAGGTCGCATCCACAAAGGTGTC
TGTTCAACCTGGATGAAAAACGCGGTGCCCGCGGAGAAATCTCATGAGTGCAGTGGTGCACCTATT
TTTATCCGCGCAAGTAACTTCAAACTCCCTTCTAATCCGAGCACGCCCATTGTGATGGTTGGCCCA
GGCACTGGCCTTGCTCCGTTTCGCGGTTTTCTACAGGAGCGGATGGCCCTTAAAGAAGATGGGGAA
GAATTGGGATCATCGTTGCTCTTTTTGGCTGCCGAAATCGCCAGATGGATTTTATCTACGAAGAC
GAGTTGAATAACTTTGTCGATCAAGGAGTAATTTCGGAGTTGATTATGGCATTTTCACGCGAAGGG
GCTCAGAAAGAGTATGTCCAACACAAGATGATGGAAAAAGCGGCACAAGTGTGGGATCTTATTAAA
GAAGAAGGCTATCTTTATGTATGTGGGGATGCGAAAGGTATGGCCCGTGATGTCCATCGCACCCTG
CACACGATTGTACAGGAACAGGAAGGTGTGTCCTCGTCCGAAGCAGAAGCAATCGTTAAAAAACTG
CAAACAGAGGGTCGTTACCTTCGCGACGTGTGGTAA (SEQ ID NO: 71)
```

>AtCPR2 [Arabidopsis thaliana]

```
MASSSSSSSTSMIDLMAAIIKGEPVIVSDPANASAYESVAAELSSMLIENRQFAMIVTTSIAVLIG
CIVMLVWRRSGSGNSKRVEPLKPLVIKPREEEIDDGRKKVTIFFGTQTGTAEGFAKALGEEAKARY
EKTRFKIVDLDDYAADDDEYEEKLKKEDVAFFFLATYGDGEPTDNAARFYKWFTEGNDRGEWLKNL
KYGVFGLGNRQYEHFNKVAKVVDDILVEQGAQRLVQVGLGDDDQCIEDDFTAWREALWPELDTILR
EEGDTAVATPYTAAVLEYRVSIHDSEDAKFNDINMANGNGYTVFDAQHPYKANVAVKRELHTPESD
RSCIHLEFDIAGSGLTYETGDHVGVLCDNLSETVDEALRLLDMSPDTYFSLHAEKEDGTPISSSLP
PPFPPCNLRTALTRYACLLSSPKKSALVALAAHASDPTEAERLKHLASPAGKDEYSKWVVESQRSL
LEVMAEFPSAKPPLGVFFAGVAPRLQPRFYSISSSPKIAETRIHVTCALVYEKMPTGRIHKGVCST
WMKNAVPYEKSENCSSAPIFVRQSNFKLPSDSKVPIIMIGPGTGLAPFRGFLQERLALVESGVELG
PSVLFFGCRNRRMDFIYEEELQRFVESGALAELSVAFSREGPTKEYVQHKMMDKASDIWNMISQGA
YLYVCGDAKGMARDVHRSLHTIAQEQGSMDSTKAEGFVKNLQTSGRYLRDVW (SEQ ID NO: 72)
```

```
ATGGCGTCCAGCAGTTCATCGAGTTCTACAAGCATGATCGATCTGATGGCCGCTATTATCAAAGGG
GAACCCGTAATTGTCTCTGATCCAGCAAATGCCTCGGCATACGAGTCGGTGGCTGCCGAATTATCA
TCTATGTTAATTGAAAATAGACAATTTGCCATGATTGTGACAACTTCTATTGCTGTGCTGATAGGT
TGCATCGTCATGCTCGTGTGGCGCCGTAGCGGATCAGGCAACTCAAAGCGCGTCGAGCCTTTGAAA
CCCCTGGTTATCAAACCGCGAGAGGAGGAAATCGATGATGGCAGAAAAAAGGTTACTATCTTTTTT
```

Figure 6A (Continued)

```
GGCACACAGACGGGGACAGCGGAAGGTTTCGCGAAAGCACTCGGAGAGGAAGCGAAAGCCCGATAC
GAGAAAACACGGTTCAAAATTGTGGATCTGGATGACTATGCGGCTGATGATGATGAGTATGAAGAA
AAACTGAAAAAAGAAGATGTGGCGTTTTTTTTCTTGCCACTTATGGCGACGGAGAGCCCACCGAT
AATGCAGCGCGGTTTTACAAGTGGTTCACCGAAGGAAATGATCGGGGAGAATGGTTAAAAAATCTG
AAATACGGTGTGTTCGGTCTTGGCAATCGCCAATATGAGCATTTTAATAAAGTCGCGAAAGTGGTC
GATGATATATTGGTAGAACAGGGCGCTCAGCGCCTCGTCCAGGTGGGGCTTGGCGACGATGATCAG
TGCATAGAAGATGATTTTACTGCATGGCGTGAAGCGCTGTGGCCGGAGCTGGACACCATTTTACGT
GAAGAGGGCGATACAGCAGTGGCAACCCCGTACACGGCTGCCGTCTTAGAGTATCGTGTGTCCATT
CATGATAGCGAGGATGCCAAATTCAATGACATCAATATGGCGAATGGAAATGGGTACACCGTGTTT
GACGCGCAGCACCCGTATAAGGCAAACGTTGCAGTCAAGAGGGAACTGCATACTCCTGAAAGTGAT
CGCAGTTGCATCCACCTGGAGTTCGATATTGCGGGATCAGGTTTAACGTACGAAACGGGCGACCAC
GTAGGTGTGCTGTGCGACAATCTTTCAGAGACAGTGGACGAAGCTCTGCGCCTGCTGGATATGAGC
CCGGATACCTATTTTAGCTTGCACGCTGAGAAGAAGATGGGACTCCAATTAGCAGTAGCTTACCT
CCACCCTTTCCGCCGTGTAATTTGCGTACCGCCCTTACGCGCTATGCGTGTCTGCTGAGTTCGCCA
AAGAAGTCGGCCCTTGTGGCACTGGCGGCACATGCAAGTGACCCGACCGAGGCGGAGAGGCTGAAA
CATCTGGCTTCTCCAGCGGGCAAAGATGAATACAGCAAATGGGTGGTAGAATCACAGCGTTCCCTA
CTAGAAGTAATGGCCGAATTTCCCTCAGCTAAACCACCGCTGGGAGTGTTCTTTGCGGGCGTTGCT
CCCCGCTTGCAACCACGCTTTTATTCAATTAGCTCAAGTCCTAAGATAGCGGAAACACGGATACAT
GTAACTTGCGCATTGGTTTATGAAAAAATGCCAACCGGGAGGATACATAAAGGCGTATGTTCAACC
TGGATGAAAAATGCTGTGCCATACGAAAGTCGGAGAATTGCTCCTCTGCCCCAATTTTCGTGCGT
CAAAGCAACTTTAAACTGCCGAGTGATTCAAAGGTGCCTATTATTATGATAGGCCCTGGTACAGGA
CTCGCCCCGTTTCGTGGTTTTCTTCAAGAAAGACTGGCTCTGGTCGAATCAGGCGTGGAATTAGGA
CCCTCCGTGTTATTTTTTGGCTGCCGCAACCGTCGAATGGACTTCATCTATGAAGAAGAATTGCAA
CGTTTTGTGGAGTCAGGCGCTCTGGCGGAACTATCCGTCGCCTTTAGTAGAGAAGGCCCAACCAAA
GAATACGTACAGCATAAGATGATGGATAAAGCGAGCGACATTTGGAATATGATCTCACAAGGGGCG
TACCTGTACGTATGTGGAGATGCCAAAGGAATGGCACGAGACGTACATAGATCGTTGCATACTATT
GCTCAAGAACAGGGAAGCATGGATTCGACTAAAGCAGAAGGCTTTGTTAAAAATCTACAGACATCT
GGTCGCTATCTGCGTGACGTGTGGTAA  (SEQ ID NO: 73)
```

\>ATR2 [Arabidopsis thaliana]

```
MASSSSSSSTSMIDLMAAIIKGEPVIVSDPANASAYESVAAELSSMLIENRQFAMIVTTSIAVLIG
CIVMLVWRRSGSGNSKRVEPLKPLVIKPREEEIDDGRKKVTIFFGTQTGTAEGFAKALGEEAKARY
EKTRFKIVDLDDYAADDDEYEEKLKKEDVAFFFLATYGDGEPTDNAARFYKWFTEGNDRGEWLKNL
KYGVFGLGNRQYEHFNKVAKVVDDILVEQGAQRLVQVGLGDDDQCIEDDFTAWREALWPELDTILR
EEGDTAVATPYTAAVLEYRVSIHDSEDAKFNDITLANGNGYTVFDAQHPYKANVAVKRELHTPESD
RSCIHLEFDIAGSGLTMKLGDHVGVLCDNLSETVDEALRLLDMSPDTYFSLHAEKEDGTPISSSLP
PPFPPCNLRTALTRYACLLSSPKKSALVALAAHASDPTEAERLKHLASPAGKDEYSKWVVESQRSL
LEVMAEFPSAKPPLGVFFAGVAPRLQPRFYSISSSPKIAETRIHVTCALVYEKMPTGRIHKGVCST
WMKNAVPYEKSEKLFLGRPIFVRQSNFKLPSDSKVPIIMIGPGTGLAPFRGFLQERLALVESGVEL
GPSVLFFGCRNRRMDFIYEEELQRFVESGALAELSVAFSREGPTKEYVQHKMMDKASDIWNMISQG
AYLYVCGDAKGMARDVHRSLHTIAQEQGSMDSTKAEGFVKNLQTSGRYLRDVW  (SEQ ID NO: 74)
```

```
ATGGCGAGCAGTTCGTCCTCCTCTTCTACCAGTATGATCGATCTGATGGCCGCTATTATAAAAGGA
GAACCAGTCATTGTGTCTGATCCTGCAAACGCATCAGCCTACGAATCTGTGGCTGCTGAACTGTCC
TCGATGCTGATCGAAAATCGCCAATTTGCAATGATTGTTACAACCAGCATCGCTGTTCTTATCGGG
TGTATTGTCATGCTGGTTTGGCGGCGGAGTGGCAGCGGCAATTCTAAAGAGTGGAGCCACTGAAG
CCTCTGGTAATCAAACCCCGCGAAGAAGAAATCGATGATGGACGTAAGAAAGTTACAATTTTTTTT
GGTACACAGACAGGTACAGCAGAGGGCTTTGCCAAAGCTCTTGGAGAAGAAGCAAAGCTCGATAT
GAGAAAACACGCTTCAAGATCGTCGATCTGGATGACTACGCGGCAGACGACGATGAGTACGAAGAA
AAACTCAAAAAGAGGATGTGGCTTTTTTTTCCTGGCAACTTATGGGACGGCGAGCCTACCGAC
AATGCAGCGCGGTTTTACAAATGGTTTACCGAAGGCAATGATAGAGGGGAGTGGCTCAAAAATCTC
```

Figure 6A (Continued)

```
AAATACGGAGTTTTCGGATTGGGGAATAGACAATACGAACACTTTAATAAGGTTGCGAAAGTGGTA
GATGATATTCTGGTCGAGCAGGGCGCGCAACGTTTAGTACAGGTCGGCCTGGGTGATGACGACCAG
TGCATCGAAGATGACTTTACGGCCTGGCGAGAAGCGCTCTGGCCGGAATTAGATACAATCCTTCGG
GAAGAGGGGGACACTGCTGTCGCTACCCCGTACACTGCCGCAGTGCTGGAATATCGTGTTTCAATA
CATGATTCGGAAGATGCCAAGTTTAATGACATCACCCTGGCAAACGGCAACGGATATACCGTATTT
GACGCTCAACATCCGTATAAGGCCAATGTAGCAGTAAAGCGGGAACTCCATACTCCCGAAAGTGAC
AGAAGTTGCATCCATCTGGAGTTCGATATAGCGGGAAGCGGACTGACTATGAAACTGGGAGATCAT
GTAGGGGTCCTGTGCGATAATTTGAGCGAAACCGTTGACGAAGCGCTCCGGCTTTTAGATATGTCC
CCTGATACTTATTTCTCTTTGCACGCCGAGAAGGAAGATGGTACACCTATATCCTCCTCGCTGCCG
CCGCCTTTTCCACCATGTAATCTGCGTACGGCCTTGACTAGGTATGCATGTCTTCTTAGCTCCCCG
AAAAAGTCCGCACTGGTAGCGTTGGCAGCTCATGCCAGCGATCCCACGGAGGCAGAGCGTTTAAAA
CACCTGGCGAGTCCTGCTGGCAAAGATGAATACAGCAAATGGGTGGTTGAGTCGCAGAGGTCCCTG
CTGGAAGTCATGGCTGAATTTCCGTCTGCGAAACCGCCTCTGGGAGTTTTCTTCGCAGGAGTAGCC
CCACGTTTACAACCGCGTTTCTATTCTATTTCTTCCTCCCCAAGATCGCGGAAACTCGAATACAC
GTAACGTGCGCATTGGTGTATGAAAGATGCCAACTGGTCGTATCCACAAGGGAGTGTGCTCAACC
TGGATGAAAACGCCGTTCCGTATGAAAAATCGGAAAAATTGTTTTTGGGTAGACCCATATTCGTT
CGGCAGTCAAACTTTAAACTACCTTCTGATAGCAAGGTTCCGATTATTATGATTGGACCGGGTACT
GGCCTGGCGCCGTTCCGTGGTTTCCTGCAAGAACGGTTGGCGCTGGTGGAATCCGGCGTGGAACTT
GGGCCATCGGTTTTGTTTTCGGGTGCCGCAATCGTCGCATGGACTTCATCTACGAGGAAGAACTC
CAGCGTTTTGTCGAAAGCGGTGCCCTTGCTGAATTGTCCGTTGCATTCAGCCGCGAAGGTCCAACT
AAGGAGTATGTGCAGCACAAAATGATGGACAAAGCGAGCGATATTTGGAATATGATTAGCCAGGGC
GCATACCTTTATGTGTGCGGTGATGCTAAGGGAATGGCGCGCGATGTCCATAGATCTTTACATACC
ATTGCACAGGAGCAGGGCTCTATGGATTCAACAAAAGCTGAAGGTTTTGTGAAAAACCTTCAGACC
AGCGGGCGGTATCTTCGCGATGTTTGGTAA (SEQ ID NO: 75)
```

>SrCPR1 [Stevia rebaudiana]

```
MAQSDSVKVSPFDLVSAAMNGKAMEKLNASESEDPTTLPALKMLVENRELLTLFTTSFAVLIGCLV
FLMWRRSSSKKLVQDPVPQVIVVKKKEKESEVDDGKKKVSIFYGTQTGTAEGFAKALVEEAKVRYE
KTSFKVIDLDDYAADDDEYEEKLKKESLAFFFLATYGDGEPTDNAANFYKWFTEGDDKGELLKKLQ
YGVFGLGNRQYEHFNKIAIVVDDKLTEMGAKRLVPVGLGDDDQCIEDDFTAWKELVWPELDQLLRD
EDDTSVTTPYTAAVLEYRVVYHDKPADSYAEDQTHTNGHVVHDAQHPSRSNVAFKKELHTSQSDRS
CTHLEFDISHTGLSYETGDHVGVYSENLSEVVDEALKLLGLSPDTYFSVHADKEDGTPIGGASLPP
PFPPCTLRDALTRYADVLSSPKKVALLALAAHASDPSEADRLKFLASPAGKDEYAQWIVANQRSLL
EVMQSFPSAKPPLGVFFAAVAPRLQPRYYSISSSPKMSPNRIHVTCALVYETTPAGRIHRGLCSTW
MKNAVPLTESPDCSQASIFVRTSNFRLPVDPKVPVIMIGPGTGLAPFRGFLQERLALKESGTELGS
SIFFFGCRNRKVDFIYEDELNNFVETGALSELIVAFSREGTAKEYVQHKMSQKASDIWKLLSEGAY
LYVCGDAKGMAKDVHRTLHTIVQEQGSLDSSKAELYVKNLQMSGRYLRDVW (SEQ ID NO: 76)
```

```
ATGGCTCAGAGCGATTCTGTTAAAGTATCCCCGTTCGACCTGGTCTCTGCGGCTATGAACGGCAAA
GCAATGGAGAAACTGAACGCGAGCGAATCTGAAGATCCAACCACCCTGCCGGCACTGAAAATGCTG
GTAGAAAACCGTGAACTGCTGACTCTGTTCACCACCTCCTTCGCCGTTCTGATTGGTTGCCTGGTC
TTCCTGATGTGGCGCCGTTCCTCTTCCAAGAAGCTGGTACAGGACCCGGTTCCTCAGGTGATCGTC
GTTAAAAAGAAAGAGAAGGAAAGCGAAGTCGATGACGGCAAAAAGAAGGTTTCCATTTTCTACGGT
ACTCAGACCGGCACCGCTGAGGGTTTTGCCAAAGCACTGGTTGAAGAGGCAAAAGTGCGTTACGAA
AAAACTTCCTTCAAAGTGATTGACCTGGACGACTATGCTGCGGATGATGATGAATACGAGGAAAAA
CTGAAAAAGAAAGCCTGGCCTTCTTCTTCCTGGCAACCTATGGCGATGGTGAACCGACCGACAAC
GCGGCGAACTTCTACAAATGGTTTACCGAAGGCGACGACAAAGGTGAATTGCTGAAGAAACTGCAG
TATGGTGTTTTCGGTCTGGGCAATCGCCAGTACGAACATTTTAACAAAATCGCAATCGTTGTTGAT
GACAAACTGACTGAAATGGGTGCGAAACGTCTGGTGCCGGTTGGCCTGGGTGACGATGATCAATGC
ATCGAAGATGACTTCACCGCATGGAAAGAACTGGTTTGGCCGGAACTGGATCAGCTGCTGCGCGAC
GAAGACGACACTTCCGTGACCACCCCGTATACCGCTGCAGTGCTGGAGTACCGTGTTGTTTACCAC
GATAAACCGGCGGACTCTTACGCCGAAGATCAGACTCACACTAACGGTCACGTCGTACATGACGCA
```

Figure 6A (Continued)

```
CAGCACCCGTCTCGTAGCAATGTTGCGTTTAAGAAAGAGCTGCACACGAGCCAGTCCGACCGCTCT
TGTACGCACCTGGAGTTCGATATCTCCCACACCGGTCTGTCCTATGAAACCGGTGACCATGTTGGC
GTTTACAGCGAAAACCTGAGCGAGGTAGTTGATGAAGCGCTGAAACTGCTGGGCCTGTCTCCAGAC
ACCTACTTTAGCGTGCATGCTGACAAGGAAGATGGTACTCCGATTGGCGGCGCTTCCCTGCCGCCA
CCGTTTCCACCTTGCACTCTGCGTGATGCTCTGACTCGTTACGCTGATGTTCTGTCTAGCCCGAAA
AAGGTTGCGCTGCTGGCGCTGGCCGCACATGCTTCTGACCCGTCTGAAGCTGACCGTCTGAAATTC
CTGGCGTCTCCGGCCGGCAAAGACGAATACGCGCAGTGGATTGTCGCTAACCAGCGCTCTCTGCTG
GAAGTGATGCAGTCCTTCCCGTCTGCCAAACCGCCACTGGGCGTGTTTTCGCAGCTGTGGCTCCG
CGCCTGCAGCCGCGCTACTATTCTATCTCTAGCTCCCCGAAAATGAGCCCGAACCGCATCCACGTT
ACTTGTGCTCTGGTTTACGAAACCACCCCTGCGGGCCGTATCCACCGTGGTCTGTGCTCTACGTGG
ATGAAAAATGCCGTGCCGCTGACCGAATCCCCGGACTGCTCTCAGGCGTCCATCTTCGTGCGTACC
TCTAACTTCCGTCTGCCGGTGGACCCGAAAGTTCCTGTTATCATGATCGGTCCTGGCACGGGTCTG
GCCCCGTTTCGTGGTTTTCTGCAGGAGCGTCTGGCTCTGAAAGAATCCGGTACTGAGCTGGGCTCT
TCCATCTTTTTCTTCGGTTGTCGTAACCGCAAAGTCGATTTCATCTATGAAGACGAACTGAACAAC
TTCGTAGAGACTGGTGCACTGTCCGAACTGATTGTGGCATTCTCTCGTGAAGGCACGGCGAAAGAA
TACGTTCAACACAAAATGTCTCAGAAAGCGAGCGATATCTGGAAACTGCTGTCCGAGGGTGCGTAT
CTGTATGTTTGTGGCGACGCGAAAGGCATGGCTAAAGATGTACACCGCACCCTGCACACCATTGTA
CAAGAACAAGGCTCTCTGGATAGCTCCAAGGCAGAACTGTACGTGAAAAACCTGCAGATGTCTGGC
CGTTACCTGCGTGATGTATGGTAA (SEQ ID NO: 77)
```

>SrCPR2 [Stevia rebaudiana]

```
MAQSESVEASTIDLMTAVLKDTVIDTANASDNGDSKMPPALAMMFEIRDLLLILTTSVAVLVGCFV
VLVWKRSSGKKSGKELEPPKIVVPKRRLEQEVDDGKKKVTIFFGTQTGTAEGFAKALFEEAKARYE
KAAFKVIDLDDYAADLDEYAEKLKKETYAFFFLATYGDGEPTDNAAKFYKWFTEGDEKGVWLQKLQ
YGVFGLGNRQYEHFNKIGIVVDDGLTEQGAKRIVPVGLGDDDQSIEDDFSAWKELVWPELDLLLRD
EDDKAAATPYTAAIPEYRVVFHDKPDAFSDDHTQTNGHAVHDAQHPCRSNVAVKKELHTPESDRSC
THLEFDISHTGLSYETGDHVGVYCENLIEVVEEAGKLLGLSTDTYFSLHIDNEDGSPLGGPSLQPP
FPPCTLRKALTNYADLLSSPKKSTLLALAAHASDPTEADRLRFLASREGKDEYAEWVVANQRSLLE
VMEAFPSARPPLGVFFAAVAPRLQPRYYSISSSPKMEPNRIHVTCALVYEKTPAGRIHKGICSTWM
KNAVPLTESQDCSWAPIFVRTSNFRLPIDPKVPVIMIGPGTGLAPFRGFLQERLALKESGTELGSS
ILFFGCRNRKVDYIYENELNNFVENGALSELDVAFSRDGPTKEYVQHKMTQKASEIWNMLSEGAYL
YVCGDAKGMAKDVHRTLHTIVQEQGSLDSSKAELYVKNLQMSGRYLRDVW (SEQ ID NO: 78)
```

```
ATGGCGCAATCTGAAAGTGTTGAGGCCAGTACCATCGACCTTATGACGGCAGTGTTGAAGGATACA
GTTATTGACACTGCAAATGCTTCAGATAACGGCGATTCTAAAATGCCTCCTGCGCTTGCGATGATG
TTCGAGATCCGCGATCTTCTGCTGATCCTTACCACATCAGTAGCGGTGCTGGTGGGATGCTTTGTG
GTACTCGTGTGGAAACGTTCGTCGGGCAAAAAATCAGGTAAGGAGCTGGAACCGCCTAAGATTGTC
GTACCGAAACGCCGACTGGAACAAGAAGTTGATGATGGCAAAAAAAAGTGACTATATTTTTGGG
ACACAGACAGGCACAGCGGAGGGATTTGCGAAAGCCTTATTCGAGGAGGCGAAGGCACGTTACGAG
AAAGCAGCTTTTAAAGTCATTGATCTGGATGACTATGCAGCAGACCTAGATGAATACGCAGAGAAA
CTGAAAAAAGAAACTTATGCGTTTTTCTTCCTGGCCACATACGGAGACGGTGAACCGACGGACAAT
GCCGCCAAGTTTTATAAGTGGTTCACTGAAGGGGATGAGAAAGGTGTATGGCTTCAGAAATTGCAA
TACGGAGTGTTCGGACTAGGAAATCGGCAATATGAGCACTTTAATAAAATAGGCATAGTAGTAGAC
GATGGGCTAACCGAGCAGGGGGCCAAACGGATTGTACCCGTGGGCCTGGGGGACGATGATCAGTCT
ATTGAGGATGATTTTAGTGCTTGGAAAGAGCTTGTTTGGCCTGAACTGGACTTACTCCTGCGTGAT
GAAGACGATAAAGCGGCAGCGACTCCATACACGGCAGCAATCCCCGAGTATAGAGTCGTATTCCAT
GATAAACCGGATGCTTTCTCTGATGACCATACCCAAACTAATGGTCATGCGGTCCATGATGCACAA
CATCCCTGCCGCAGCAATGTAGCGGTGAAAAAGGAGCTGCATACGCCTGAAAGTGATCGCTCATGT
ACGCATCTGGAGTTTGATATTTCACACACAGGTCTTAGCTACGAGACTGGAGATCACGTCGGAGTC
TATTGCGAAAATCTGATCGAAGTGGTTGAAGAGGCCGGGAAACTGTTGGGACTAAGTACAGATACT
TATTTTTCTTTACATATAGATAACGAGGATGGTTCCCCACTTGGCGGTCCATCTCTTCAGCCTCCA
```

Figure 6A (Continued)

```
TTCCCACCATGTACCTTACGCAAAGCGCTGACTAACTACGCAGATCTGCTGTCTAGCCCAAAGAAA
TCAACGCTTCTGGCGTTGGCTGCTCATGCCTCAGATCCGACCGAAGCTGATCGCCTTCGTTTTCTG
GCATCCCGAGAAGGTAAAGATGAATATGCAGAATGGGTGGTAGCGAATCAGCGTTCTTTGCTGGAA
GTCATGGAGGCATTCCCCAGCGCGCGCCCTCCGCTGGGTGTTTTCTTCGCAGCGGTGGCCCCGCGG
CTCCAGCCGCGTTATTATTCAATTAGCAGTTCTCCTAAGATGGAACCTAATCGAATCCATGTAACA
TGTGCATTGGTCTATGAGAAAACGCCGGCTGGCCGCATCCATAAAGGTATATGTAGCACATGGATG
AAAAATGCAGTACCCCTCACGGAGTCCCAGGATTGTAGTTGGGCGCCGATATTTGTTCGGACGAGC
AATTTTAGACTTCCTATAGACCCAAAGGTTCCAGTTATTATGATTGGTCCTGGCACCGGACTTGCG
CCATTCCGGGGGTTTCTGCAAGAAAGACTGGCTCTGAAAGAAAGCGGTACAGAACTCGGCTCCAGT
ATATTGTTTTTCGGCTGTCGCAACCGGAAAGTAGATTATATATATGAAAACGAGCTGAATAACTTC
GTTGAAAATGGTGCCCTGTCTGAACTCGATGTCGCTTTTTCGCGAGATGGCCCGACAAAAGAATAC
GTGCAGCATAAAATGACCCAGAAAGCAAGTGAAATCTGGAATATGCTGTCAGAAGGGGCATATCTG
TATGTGTGCGGAGATGCAAAGGGCATGGCCAAAGACGTTCACAGAACCTTGCATACCATAGTACAA
GAGCAGGGCTCTCTGGATAGCTCAAAAGCCGAGCTGTACGTGAAAAATCTCCAGATGAGTGGACGC
TACCTGAGGGATGTTTGGTAA (SEQ ID NO: 79)
```

Figure 6A (Continued)

>SrCPR3 [Stevia rebaudiana]

MAQSNSVKISPLDLVTALFSGKVLDTSNASESGESAMLPTIAMIMENRELLMILTTSVAVLIGCVV
VLVWRRSSTKKSALEPPVIVVPKRVQEEEVDDGKKKVTVFFGTQTGTAEGFAKALVEEAKARYEKA
VFKVIDLDDYAADDDEYEEKLKKESLAFFFLATYGDGEPTDNAARFYKWFTEGDAKGEWLNKLQYG
VFGLGNRQYEHFNKIAKVVDDGLVEQGAKRLVPVGLGDDDQCIEDDFTAWKELVWPELDQLLRDED
DTTVATPYTAAVAEYRVVFHEKPDALSEDYSYTNGHAVHDAQHPCRSNVAVKKELHSPESDRSCTH
LEFDISNTGLSYETGDHVGVYCENLSEVVNDAERLVGLPPDTYFSIHTDSEDGSPLGGASLPPPFP
PCTLRKALTCYADVLSSPKKSALLALAAHATDPSEADRLKFLASPAGKDEYSQWIVASQRSLLEVM
EAFPSAKPSLGVFFASVAPRLQPRYYSISSSPKMAPDRIHVTCALVYEKTPAGRIHKGVCSTWMKN
AVPMTESQDCSWAPIYVRTSNFRLPSDPKVPVIMIGPGTGLAPFRGFLQERLALKEAGTDLGLSIL
FFGCRNRKVDFIYENELNNFVETGALSELIVAFSREGPTKEYVQHKMSEKASDIWNLLSEGAYLYV
CGDAKGMAKDVHRTLHTIVQEQGSLDSSKAELYVKNLQMSGRYLRDVW (SEQ ID NO: 80)

ATGGCGCAATCTAATTCTGTGAAAATCTCTCCATTGGATCTGGTTACAGCACTCTTTAGCGGGAAG
GTACTGGATACAAGTAACGCCAGTGAAAGCGGGGAATCCGCGATGCTGCCAACAATCGCGATGATC
ATGGAAAATCGGGAACTGCTAATGATTCTGACAACGTCTGTAGCAGTTTTAATCGGTTGCGTTGTG
GTTCTGGTGTGGCGTCGATCATCCACGAAAAGAGCGCATTAGAACCGCCTGTTATCGTAGTACCA
AAAAGAGTTCAGGAGGAAGAGGTGGATGATGGGAAAAAAAAAGTCACCGTTTTCTTCGGGACCCAA
ACTGGTACGGCAGAAGGTTTTGCGAAAGCACTGGTCGAAGAGGCGAAAGCCCGCTATGAGAAGGCG
GTTTTTAAGGTTATTGACCTTGATGACTATGCGGCGGACGATGATGAATACGAAGAAAAATTAAAG
AAAGAATCACTTGCCTTTTTTTTTGGCAACATACGGTGATGGCGAGCCGACTGATAACGCGGCA
CGGTTTTACAAATGGTTTACCGAAGGCGACGCGAAGGGGAGTGGTTGAACAAGTTACAGTACGGT
GTGTTCGGCTTGGGGAACCGCCAGTACGAGCACTTTAACAAGATAGCTAAAGTTGTCGATGATGGT
CTGGTAGAACAGGGAGCGAAGCGTCTCGTGCCAGTAGGGCTGGGCGATGATGATCAGTGTATAGAA
GATGATTTTACGGCTTGGAAGGAGTTAGTTTGGCCGGAACTGGACCAACTGCTGCGCGATGAGGAT
GATACAACTGTCGCTACCCCGTATACAGCAGCGGTAGCTGAATACAGGGTGGTTTTTCACGAGAAA
CCTGATGCGCTGAGTGAGGACTATTCGTATACTAACGGCCATGCCGTTCACGATGCACAGCACCCG
TGCCGTTCTAATGTCGCCGTAAAAAAGGAACTGCATAGCCCGGAGTCGGACCGCAGTTGTACCCAT
CTGGAGTTTGATATTTCAAATACCGGGCTGAGTTACGAAACGGGCGATCACGTTGGCGTGTACTGT
GAGAATCTAAGCGAGGTTGTTAACGATGCAGAACGACTGGTCGGTTTGCCTCCAGATACTTATTTC
TCGATCCACACTGATAGCGAAGATGGCTCTCCACTCGGGGGGCGAGTCTGCCGCCCCGTTTCCC
CCGTGTACGCTGAGAAAGGCCCTTACATGTTATGCAGATGTACTCTCTTCCCCAAAAAAAGTGCC
TTGCTCGCATTAGCAGCCCACGCTACCGATCCCTCGGAAGCAGATCGTCTGAAATTCTTGGCATCG
CCGGCGGGCAAAGATGAATACAGCCAATGGATAGTTGCAAGTCAGCGCAGTCTCTTAGAAGTGATG
GAAGCGTTTCCGTCCGCAAAGCCGTCCTTAGGTGTGTTTTTCGCGTCCGTGGCACCGCGTCTTCAG
CCTAGATATTACAGCATTAGTTCCTCTCCAAAAATGGCCCCGGACCGTATTCACGTGACTTGTGCT
CTTGTATATGAGAAAACCCCGGCAGGTCGTATTCACAAAGGCGTGTGCAGCACCTGGATGAAGAAT
GCAGTGCCGATGACCGAAAGCCAGGATTGTTCATGGGCGCCAATCTATGTCAGGACAAGTAATTTC
AGACTTCCGTCTGATCCTAAAGTTCCAGTCATAATGATTGGCCCCGGCACGGGACTGGCTCCTTTT
CGTGGTTTCCTGCAAGAGCGCTTGGCACTGAAAGAAGCAGGCACTGACCTGGGACTGTCCATCCTG
TTCTTTGGGTGCCGTAATCGTAAGGTCGATTTTATATATGAAAATGAATTGAACAACTTTGTAGAA
ACAGGCGCATTATCCGAACTGATCGTAGCTTTTAGTAGAGAGGGGCCGACGAAAGAATATGTACAA
CACAAGATGTCTGAGAAGGCTTCGGATATATGGAACCTGCTCTCTGAGGGTGCCTATCTGTACGTT
TGCGGTGATGCCAAAGGAATGGCCAAAGATGTGCACCGCACTTTACATACAATCGTCCAAGAGCAG
GGTAGCTTGGACTCATCTAAAGCTGAACTGTATGTGAAGAACTTACAGATGAGCGGGCGCTATTTG
CGAGATGTTTGGTAA (SEQ ID NO: 81)

Figure 6A (Continued)

>PgCPR [Pelargonium graveolens]

```
MAQSSSGSMSPFDFMTAIIKGKMEPSNASLGAAGEVTAMILDNRELVMILTTSIAVLIGCVVVFIW
RRSSSQTPTAVQPLKPLLAKETESEVDDGKQKVTIFFGTQTGTAEGFAKALADEAKARYDKVTFKV
VDLDDYAADDEEYEEKLKKETLAFFFLATYGDGEPTDNAARFYKWFLEGKERGEWLQNLKFGVFGL
GNRQYEHFNKIAIVVDEILAEQGGKRLISVGLGDDDQCIEDDFTAWRESLWPELDQLLRDEDDTTV
STPYTAAVLEYRVVFHDPADAPTLEKSYSNANGHSVVDAQHPLRANVAVRRELHTPASDRSCTHLE
FDISGTGIAYETGDHVGVYCENLAETVEEALELLGLSPDTYFSVHADKEDGTPLSGSSLPPPFPPC
TLRTALTLHADLLSSPKKSALLALAAHASDPTEADRLRHLASPAGKDEYAQWIVASQRSLLEVMAE
FPSAKPPLGVFFASVAPRLQPRYYSISSSPRIAPSRIHVTCALVYEKTPTGRVHKGVCSTWMKNSV
PSEKSDECSWAPIFVRQSNFKLPADAKVPIIMIGPGTGLAPFRGFLQERLALKEAGTELGPSILFF
GCRNSKMDYIYEDELDNFVQNGALSELVLAFSREGPTKEYVQHKMMEKASDIWNLISQGAYLYVCG
DAKGMARDVHRTLHTIAQEQGSLDSSKAESMVKNLQMSGRYLRDVW
``` (SEQ ID NO: 82)

```
ATGGCGCAGTCAAGCAGTGGATCAATGAGCCCTTTCGATTTTATGACCGCTATAATAAAAGGTAAA
ATGGAGCCAAGTAATGCGTCTTTAGGAGCGGCAGGTGAAGTCACAGCAATGATACTTGATAATAGG
GAGCTGGTTATGATTCTGACGACCAGCATTGCAGTGCTGATCGGTTGCGTTGTAGTGTTCATTTGG
CGTCGTTCATCATCCCAGACCCCTACCGCGGTGCAGCCATTAAAACCACTTTTAGCGAAGGAAACA
GAGAGCGAAGTAGACGATGGCAAACAGAAAGTAACTATCTTTTTTGGTACTCAAACTGGAACCGCT
GAAGGTTTCGCGAAAGCGCTCGCAGACGAGGCCAAAGCACGGTATGATAAAGTCACTTTTAAAGTG
GTTGATCTGGACGATTATGCCGCAGATGACGAAGAATATGAAGAAAGCTGAAGAAGGAAACGTTA
GCATTCTTTTTCTTGCGACGTATGGAGATGGTGAACCTACTGACAATGCTGCAAGGTTTTATAAG
TGGTTTCTGGAAGGTAAAGAACGCGGAGAATGGCTTCAGAATCTAAAATTTGGTGTGTTTGGTTTA
GGCAACCGTCAGTATGAGCATTTCAATAAAATTGCCATTGTGGTTGATGAAATCCTTGCAGAACAA
GGTGGTAAGCGTCTCATTTCAGTTGGCCTGGGCGATGATGATCAGTGTATTGAGGATGACTTTACT
GCCTGGAGGGAATCGCTGTGGCCGGAGCTAGATCAGTTATTACGCGATGAGGATGATACTACGGTT
TCTACGCCGTATACCGCCGCGGTGCTGGAATACAGAGTCGTTTTTCATGATCCGGCAGATGCCCCA
ACTCTCGAAAAAGCTACAGCAACGCTAACGGGCATAGCGTGGTTGATGCGCAACATCCGTTACGG
GCAAATGTTGCCGTCAGACGGGAGTTGCATACTCCTGCGTCTGACCGCTCATGTACCCATCTGGAA
TTTGATATATCTGGTACTGGCATCGCATACGAGACGGGTGATCATGTTGGCGTGTATTGCGAGAAT
CTTGCAGAGACGGTAGAAGAAGCGTTGGAACTTTTAGGTCTTTCCCCGGATACATACTTCTCCGTA
CACGCAGATAAAGAGGACGGTACGCCTCTCTCAGGCTCATCTCTCCCGCCGCCATTTCCACCGTGC
ACTTTACGTACAGCCCTGACGTTACATGCTGACTTACTGTCTTCCCCAAAGAAATCTGCATTGCTC
GCGCTTGCAGCTCATGCATCAGACCCCACTGAAGCTGATCGATTGCGGCACCTAGCAAGCCCTGCG
GGCAAGGACGAATACGCTCAGTGGATAGTTGCTAGTCAGCGTTCCTTGCTGGAAGTGATGGCGGAG
TTCCCCAGTGCCAAGCCCCCGCTGGGAGTATTCTTCGCATCGGTTGCTCCAAGATTGCAGCCCCGG
TACTACTCTATTTCTTCTTCCCCAAGAATAGCGCCGTCTCGCATACACGTGACCTGCGCGTTAGTT
TACGAGAAAACACCTACGGGCAGAGTACACAAAGGAGTTTGCTCCACTTGGATGAAAAACTCAGTG
CCCTCTGAAAAGAGTGATGAATGTTCATGGGCACCAATTTTCGTACGACAGAGCAACTTTAAACTG
CCCGCCGATGCGAAAGTACCCATAATTATGATTGGTCCAGGAACGGGTCTGGCACCATTTCGCGGC
TTCCTCCAGGAGCGGCTTGCATTGAAAGAAGCAGGGACAGAACTGGGACCTTCCATATTATTTTTT
GGGTGCCGCAACAGCAAAATGGACTATATATACGAGGATGAACTGGATAATTTTGTACAGAATGGG
GCACTCTCTGAACTCGTGTTGGCGTTCTCACGTGAAGGTCCTACCAAAGAGTATGTGCAACATAAG
ATGATGGAGAAAGCCTCAGATATATGGAACCTTATTTCACAGGGAGCTTATTTGTATGTGTGCGGG
GACGCAAAAGGCATGGCGCGTGATGTGCACCGCACGTTACATACCATCGCTCAGGAGCAGGGGTCA
TTAGATAGCTCAAAAGCAGAGAGTATGGTGAAGAATCTTCAGATGTCAGGCAGATACCTGCGCGAT
GTCTGGGTAA
``` (SEQ ID NO: 83)

Figure 6B

```
AtCPR2    MASSSSSSSTSMIDLMAAIIKGE-PVIVSDPANASAYESVAAELSSMLIENRQFAMIVTT    59
ATR2      MASSSSSSSTSMIDLMAAIIKGE-PVIVSDPANASAYESVAAELSSMLIENRQFAMIVTT    59
AaCPR     MAQSTTSVKLSPFDLMTALLNG---KVSFDTSNTSDTN----IPLAVFMENRELLMILTT    53
AtCPR     --MTSALYASDLFKQLKSIMGTDS------------------------LSDDVLVIATT    34
AtCPR1    -MATSALYASDLFKQLKSIMGTDS------------------------LSDDVLVIATT    35
                   :::  :  ::::                                 :*  **

AtCPR2    SIAVLIGCIVMLVWRRSGSGNSKRVE-PLKPLVIKPREEE----IDDGRKKVTIFFGTQT   114
ATR2      SIAVLIGCIVMLVWRRSGSGNSKRVE-PLKPLVIKPREEE----IDDGRKKVTIFFGTQT   114
AaCPR     SVAVLIGCVVVLVWRRSSAAKKAAESPVIVVPKKVTEDE----VDDGRKKVTVFFGTQT   109
AtCPR     SLALVAG-FVVLLWKKTTADRSGELKPLMIPKSLMAKDEDDDLGSGKTRVSIFFGTQT    93
AtCPR1    SLALVAG-FVVLLWKKTTADRSGELKPLMIPKSLMAKDEDDDLGSGKTRVSIFFGTQT    94
           *:*:::  *  .*.*:*:::.       :.     :           :.. :*:*******

AtCPR2    GTAEGFAKALGEEAKARYEKTRFKIVDLDDYAADDDEYEEKLKKEDVAFFFLATYGDGEP   174
ATR2      GTAEGFAKALGEEAKARYEKTRFKIVDLDDYAADDDEYEEKLKKEDVAFFFLATYGDGEP   174
AaCPR     GTAEGFAKALVEEAKARYEKAVFKVIDLDDYAAEDDEYEEKLKKESLAFFFLATYGDGEP   169
AtCPR     GTAEGFAKALSEEIKARYEKAAVKVIDLDDYAADDDQYEEKLKKETLAFFCVATYGDGEP   153
AtCPR1    GTAEGFAKALSEEIKARYEKAAVKVIDLDDYAADDDQYEEKLKKETLAFFCVATYGDGEP   154
          ********** .** ****: .:*.*********:**:********..***. *******

AtCPR2    TDNAARFYKWFTEGNDRGEWLKNLKYGVFGLGNRQYEHFNKVAKVVDDILVEQGAQRLVQ   234
ATR2      TDNAARFYKWFTEGNDRGEWLKNLKYGVFGLGNRQYEHFNKVAKVVDDILVEQGAQRLVQ   234
AaCPR     TDNAARFYKWFTEGEEKGEWLDKLQYAVFGLGNRQYEHFNKIAKVVDEKLVEQGAKRLVP   229
AtCPR     TDNAARFSKWFTEENERDIKLQQLAYGVFALGNRQYEHFNKIGIVLDEELCKKGAKRLIE   213
AtCPR1    TDNAARFSKWFTEENERDIKLQQLAYGVFALGNRQYEHFNKIGIVLDEELCKKGAKRLIE   214
          *******.*****   :.  :*:* * *.*********:.:: *:  : :*.***:

AtCPR2    VGLGDDDQCIEDDFTAWREALWPELDTIIREEGDTAVATPYTAAVLEYRVSIHDSEDAKF   294
ATR2      VGLGDDDQCIEDDFTAWREALWPELDTIIREEGDTAVATPYTAAVLEYRVSIHDSEDAKF   294
AaCPR     VGMGDDDQCIEDDFTAWKELVWPELDQLLRDEDDTSVATPYTAVAEYRVVFHD-KPETY   288
AtCPR     VGLGDDDQSIEDDFNAWKESLWSELDKLLKDEDDKSVATPYTAVIPEYRVVTHDPRFTTQ   273
AtCPR1    VGLGDDDQSIEDDFNAWKESLWSELDKLLKDEDDKSVATPYTAVIPEYRVVTHDPRFTTQ   274
          **:*****.*****.**:*.:*.***::::**.*:*******.. ****   **  .
```

Figure 6B (Continued)

```
AtCPR2    NDINMANGNGYTVFDAQHPYKANVAVKRELHTPESDRSCIHLEFDIAGSGLTYETGDHVG 354
ATR2      NDITLANGNGYTVFDAQHPYKANVAVKRELHTPESDRSCIHLEFDIAGSGLTMKLGDHVG 354
AaCPR     DQDQLTNG--HAVHDAQHPCRSNVAVKKELHSPLSDRSCTHLEFDISNTGLSYETGDHVG 346
AtCPR     KSMESNVANGNTTIDIHHPCRVDVAVQKELHTHESDRSCIHLEFDISRTGITYETGDHVG 333
AtCPR1    KSMESNVANGNTTIDIHHPCRVDVAVQKELHTHESDRSCIHLEFDISRTGITYETGDHVG 334
             .  . *  :***  . .:****::****.  ****** ******.: .:*:: ******

AtCPR2    VLCDNLSETVDEALRLLDMSPDTYFSLHAEKEDGTPIS-SSLPPPFP-PCNLRTALTRYA 412
ATR2      VLCDNLSETVDEALRLLDMSPDTYFSLHAEKEDGTPIS-SSLPPPFP-PCNLRTALTRYA 412
AaCPR     VYVENLSEVVDEAEKLIGLPPHTYFSVHADNEDGTPLGGASLPPPFP-PCTLRKALASYA 405
AtCPR     VYAENHVEIVEEAGKLLGHSLDLVFSIHADKEDGSPLE-SAVPPPFPGPCTLGTGLARYA 392
AtCPR1    VYAENHVEIVEEAGKLLGHSLDLVFSIHADKEDGSPLE-SAVPPPFPGPCTLGTGLARYA 393
          *  :*  *:*.** :* :.     . **:**:: ****: . :::****** ** .. :**

AtCPR2    CLLSSPKKSALVALAAHASDPTEAERLKHLASPAGKDEYSKWVVESQRSLLEVMAEFPSA 472
ATR2      CLLSSPKKSALVALAAHASDPTEAERLKHLASPAGKDEYSKWVVESQRSLLEVMAEFPSA 472
AaCPR     DVLSPKKKSALLALAAHATDSTEADRLKFLASPAGKDEYAQWIVASHRSLLEVMEAFPSA 465
AtCPR     DLLNPPRKSALVALAAYATEPSEAEKLKHLTSPDGKDEYSQWIVASQRSLLEVMAAFPSA 452
AtCPR1    DLLNPPRKSALVALAAYATEPSEAEKLKHLTSPDGKDEYSQWIVASQRSLLEVMAAFPSA 453
           :*..*:::.***:*****:**:. :*:*.*:*:**.****: **:**:.*****.****

AtCPR2    KPPLGVFFAGVAPRLQPRFYSISSSPKIAETRIHVTCALVYEKMPTGRIHKGVCSTWMKN 532
ATR2      KPPLGVFFAGVAPRLQPRFYSISSSPKIAETRIHVTCALVYEKMPTGRIHKGVCSTWMKN 532
AaCPR     KPPLGVFFASVAPRLQPRYYSISSSPRFAPNRIHVTCALVYEQTPSGRVHKGVCSTWMKN 525
AtCPR     KPPLGVFFAAIAPRLQPRYYSISSCQDWAPSRVHVTSALVYGPTPTGRIHKGVCSTWMKN 512
AtCPR1    KPPLGVFFAAIAPRLQPRYYSISSSPRLAPSRVHVTSALVYGPTPTGRIHKGVCSTWMKN 513
          ********. ********:*****.  .  .*:*** *****  :*:**:**********

AtCPR2    AVPYEKSENCSS-APIFVRQSNFKLPSDSKVPIIMIGPGTGLAPFRGFLQERLALVESGV 591
ATR2      AVPYEKSEKLFLGRPIFVRQSNFKLPSDSKVPIIMIGPGTGLAPFRGFLQERLALVESGV 592
AaCPR     AVPMTESQDCSW-APIYVRTSNFRLPSDPKVPVIMIGPGTGLAPFRGFLQERLAQKEAGT 584
AtCPR     AVPAEKSHECSG-APIFIRASNFKLPSNPSTPIVMVGPGTGLAPFRGFLQERMALKEDGE 571
AtCPR1    AVPAEKSHECSG-APIFIRASNFKLPSNPSTPIVMVGPGTGLAPFRGFLQERMALKEDGE 572
          ***  :: .     **::  ***:***:   *::*:***************:*  * *
```

Figure 6B (Continued)

```
AtCPR2   ELGPSVLFFGCRNRRMDFIYEEELQRFVESGALAELSVAFSREGPTKEYVQHKMMDKASD 651
ATR2     ELGPSVLFFGCRNRRMDFIYEEELQRFVESGALAELSVAFSREGPTKEYVQHKMMDKASD 652
AaCPR    ELGTAILFFGCRNRKVDFIYEDELNNFVETGALSELVTAFSREGATKEYVQHKMTQKASD 644
AtCPR    ELGSSLLFFGCRNRQMDFIYEDELNNFVDQGVISELIMAFSREGAQKEYVQHKMMEKAAQ 631
AtCPR1   ELGSSLLFFGCRNRQMDFIYEDELNNFVDQGVISELIMAFSREGAQKEYVQHKMMEKAAQ 632
         ***.:::***********:::***:.**  *.::**  ********.  **.::

AtCPR2   IWNMISQGAYLYVCGDAKGMARDVHRSLHTIAQEQGSMDSTKAEGFVKNLQTSGRYLRDVW 712
ATR2     IWNMISQGAYLYVCGDAKGMARDVHRSLHTIAQEQGSMDSTKAEGFVKNLQTSGRYLRDVW 713
AaCPR    IWNLLSEGAYLYVCGDAKGMAKDVHRTLHTIVQEQGSLDSSKAELYVKNLQMAGRYLRDVW 705
AtCPR    VWDLIKEEGYLYVCGDAKGMARDVHRTLHTIVQEQEGVSSSEAEAIVKKLQTEGRYLRDVW 692
AtCPR1   VWDLIKEEGYLYVCGDAKGMARDVHRTLHTIVQEQEGVSSSEAEAIVKKLQTEGRYLRDVW 693
         :*:::::  .*****************:****.***.****..::*::** .********
```

Figure 6C

```
SrCPR2    MAQSESVEASTIDLMTAVLKDTVIDTANASDNGDSKMPPALAMFEIRDLLILTTSVAV    60
SrCPR3    MAQSNSVKISPLDLVTALFSGKVLDTSNASESGESAMLPTIAMIMENRELLMILTTSVAV   60
SrCPR     -MQSDSVKVSPFDLVSAAMNGKAMEKLNASESEDPTTLPALKMLVENRELLTLFTTSFAV   59
SrCPR1    MAQSDSVKVSPFDLVSAAMNGKAMEKLNASESEDPTTLPALKMLVENRELLTLFTTSFAV   60
           **: *.:***.::*  :......::  ***::.   *::.* *.**: ::***.**

SrCPR2    LVGCFVVLVWKRSSGKKKSGKELEPPKIVVPKRRLEQEVDDGKKKVTIFFGTQTGTAEGFA  120
SrCPR3    LIGCVVVLVWRRSSTKKS--ALEPPVIVPKRVQEEEVDDGKKKVTVFFGTQTGTAEGFA   118
SrCPR     LIGCLVFLMWRRSSSSKKLVQDPVPQVIVKKKEKESEVDDGKKKVSIFYGTQTGTAEGFA   119
SrCPR1    LIGCLVFLMWRRSSSSKKLVQDPVPQVIVKKKEKESEVDDGKKKVSIFYGTQTGTAEGFA   120
          *:***.*.:*:*:***. **         * *** *: .*********::*:********

SrCPR2    KALFEEAKARYEKAAFKVIDLDDYAADLDEYAEKLKKETYAFFLATYGDGEPTDNAAKF    180
SrCPR3    KALVEEAKARYEKAVFKVIDLDDYAADDDEYEEKLKKESLAFFFLATYGDGEPTDNAARF   178
SrCPR     KALVEEAKVRYEKTSFKVIDLDDYAADDDEYEEKLKKESLAFFFLATYGDGEPTDNAANF   179
SrCPR1    KALVEEAKVRYEKTSFKVIDLDDYAADDDEYEEKLKKESLAFFFLATYGDGEPTDNAANF   180
          ***.****.****::*********** :***:******* ***:**************.:

SrCPR2    YKWFTEGDEKGVWLQKLQYGVFGLGNRQYEHFNKIGIVDDGLTEQGAKRIVPVGLGDDD   240
SrCPR3    YKWFTEGDAKGEWLNKLQYGVFGLGNRQYEHFNKIAKVDDGLVEQGAKRLVPVGLGDDD   238
SrCPR     YKWFTEGDDKGEWLKKLQYGVFGLGNRQYEHFNKIAIVDDKLTEMGAKRLVPVGLGDDD   239
SrCPR1    YKWFTEGDDKGELLKKLQYGVFGLGNRQYEHFNKIAIVDDKLTEMGAKRLVPVGLGDDD   240
          ********  ** *.********************. *.  *  *:****:********

SrCPR2    QSIEDDFSAWKELVWPELDLLLRDEDDKAAATPYTAAIPEYRVVFHDKP-DAFSDDHTQT  299
SrCPR3    QCIEDDFTAWKELVWPELDQLLRDEDDTTVATPYTAAVAEYRVVFHEKP-DALSEDYSYT  297
SrCPR     QCIEDDFTAWKELVWPELDQLLRDEDDTSVTTPYTAAVLEYRVVYHDKPADSYAEDQTHT  299
SrCPR1    QCIEDDFTAWKELVWPELDQLLRDEDDTSVTTPYTAAVLEYRVVYHDKPADSYAEDQTHT  300
          * .:*****.********::**:***** .. :*****: *****:.*:  :  :  *

SrCPR2    NGHAVHDAQHPCRSNVAVKKELHTPESDRSCTHLEFDISHTGLSYETGDHVGVYCENLIE  359
SrCPR3    NGHAVHDAQHPCRSNVAVKKELHSPESDRSCTHLEFDISNTGLSYETGDHVGVYCENLSE  357
SrCPR     NGHVVHDAQHPSRSNVAFKKELHTSQSDRSCTHLEFDISHTGLSYETGDHVGVYSENLSE  359
SrCPR1    NGHVVHDAQHPSRSNVAFKKELHTSQSDRSCTHLEFDISHTGLSYETGDHVGVYSENLSE  360
          ***.*******.*****.:****:..**********:**:**********.****.
```

Figure 6C (Continued)

```
SrCPR2   VVEEAGKLLGLSTDTYFSLHIDNEDGSPLGGPSLQPPFPPCTLRKALTNYADLLSSPKKS  419
SrCPR3   VVNDAERLVGLPPDTYFSIHTDSEDGSPLGGASLPPPFPPCTLRKALTCYADVLSSPKKS  417
SrCPR    VVDEALKLLGLSPDTYFSVHADKEDGTPIGGASLPPPFPPCTLRDALTRYADVLSSPKKV  419
SrCPR1   VVDEALKLLGLSPDTYFSVHADKEDGTPIGGASLPPPFPPCTLRDALTRYADVLSSPKKV  420
         **::*: :*:::**..:*****:*:: *. *: ************** ***:******

SrCPR2   TLLALAAHASDPTEADRLRFLASREGKDEYAEWVVANQRSLLEVMEAFPSARPPLGVFFA  479
SrCPR3   ALLALAAHATDPSEADRLKFLASPAGKDEYSQWIVASQRSLLEVMEAFPSAKPSLGVFFA  477
SrCPR    ALLALAAHASDPSEADRLKFLASPAGKDEYAQWIVANQRSLLEVMQSFPSAKPPLGVFFA  479
SrCPR1   ALLALAAHASDPSEADRLKFLASPAGKDEYAQWIVANQRSLLEVMQSFPSAKPPLGVFFA  480
         :************.*******:**** .*****::*:*:********:.:**:*.*****

SrCPR2   AVAPRLQPRYYSISSSPKMEPNRIHVTCALVYEKTPAGRIHKGICSTWMKNAVPLTESQD  539
SrCPR3   SVAPRLQPRYYSISSSPKMAPDRIHVTCALVYEKTPAGRIHKGVCSTWMKNAVPMTESQD  537
SrCPR    AVAPRLQPRYYSISSSPKMSPNRIHVTCALVYETTPAGRIHRGLCSTWMKNAVPLTESPD  539
SrCPR1   AVAPRLQPRYYSISSSPKMSPNRIHVTCALVYETTPAGRIHRGLCSTWMKNAVPLTESPD  540
         :****************.*:************: ******:*:*********:*** *

SrCPR2   CSWAPIFVRTSNFRLPIDPKVPVIMIGPTGLAPFRGFLQERLALKESGTELGSSILFFG  599
SrCPR3   CSWAPIYVRTSNFRLPSDPKVPVIMIGPTGLAPFRGFLQERLALKEAGTELGSSILFFG  597
SrCPR    CSQASIFVRTSNFRLPVDPKVPVIMIGPTGLAPFRGFLQERLALKESGTELGSSIFFFG  599
SrCPR1   CSQASIFVRTSNFRLPVDPKVPVIMIGPTGLAPFRGFLQERLALKESGTELGSSIFFFG  600
         ** *.* .:********* *********************:*::*******:***

SrCPR2   CRNRKVDYIYENELNNFVENGALSELDVAFSRDGPTKEYVQHKMTQKASEIWNMLSEGAY  659
SrCPR3   CRNRKVDFIYENELNNFVETGALSELIVAFSREGPTKEYVQHKMSEKASDIWNLLSEGAY  657
SrCPR    CRNRKVDFIYEDELNNFVETGALSELIVAFSREGTAKEYVQHKMSQKASDIWKLLSEGAY  659
SrCPR1   CRNRKVDFIYEDELNNFVETGALSELIVAFSREGTAKEYVQHKMSQKASDIWKLLSEGAY  660
         *******:***:*******.******:*****:*. *******::.***:**::*****

SrCPR2   LYVCGDAKGMAKDVHRTLHTIVQEEQGSLDSSKAELYVKNLQMSGRYLRDVW  710
SrCPR3   LYVCGDAKGMAKDVHRTLHTIVQEEQGSLDSSKAELYVKNLQMSGRYLRDVW  708
SrCPR    LYVCGDAKGMAKDVHRTLHTIVQEEQGSLDSSKAELYVKNLQMSGRYLRDVW  710
SrCPR1   LYVCGDAKGMAKDVHRTLHTIVQEEQGSLDSSKAELYVKNLQMSGRYLRDVW  711
         ***************************************************
```

Figure 6D

```
ATR2     MASSSSSSTSMIDLMAAIIKGEPVIVSDPANASAYESVAAELSSMLIENRQFAMIVTTS  60
AtCPR2   MASSSSSSTSMIDLMAAIIKGEPVIVSDPANASAYESVAAELSSMLIENRQFAMIVTTS  60
PgCPR    MAQSSSGS-MSPFDFWTAIIKG-----KMEPSNAS--LGAAGEVTAMILDNRELVMILTTS  53
AaCPR    MAQSTTSVKLSPFDLMFALLNGKVS-FDTSNTSDTN----IP-LAVFMENRELLMILTTS  54
SrCPR3   MAQSN-SVKISPLDLVTIALFSGKV--LDTSNASESGESAMLPTIAMIMENRELLMILTTS  57
SrCPR    MAQSD-SVKVSPFDLVSAAMNGKA--MEKLNASESEDFTILPALKMLVENRELLTLFTTS  57
SrCPR2   MAQSE-SVEASTIDLMTAVLKDFV--IDTANASDNGDSKMPFALAMMFEIRDLLLLETTS  57
AtCPR1   MATSALYASDLFKQLKSIMGTDS--------------------LSDDVVLVIAFTS  36
         *  *                              .                 :  ***

ATR2     IAVLIGCIVMLVWRRSGSGNSKRVEPLKP--LVIKPR---EEEIDDGRKKVTIFFGTQTG  115
AtCPR2   IAVLIGCIVMLVWRRSGSGNSKRVEPLKP--LVIKPR---EEEIDDGRKKVTIFFGTQTG  115
PgCPR    IAVLIGCVVVFIWRRSSSQTFTAVQPLKP--LLAKET---ESEVDDGKQKVTIFFGTQTG  108
AaCPR    VAVLIGCVVVLVWRRSSSAAKKAAESP----VIVVPKKVTEDEVDDGRKKVTVFFGTQTG  110
SrCPR3   VAVLIGCVVVLVWRRSS-TKKSALEPP----VIVVPKRVQEEEVDDGKKKVTVFFGTQTG  112
SrCPR    FAVLIGCLVFLMWRRSS-SKKLVQDPVPQ--VIVVKKEKESEVDDGKKKVSIFYGTQTG  114
SrCPR2   VAVLVGCFVVLVWKRSS-GKKSGKELEPP--KIVVPKRRLEQEVDDGKKKVTIFFGTQTG  114
AtCPR1   LALVAG-FVVLLWKKTTADRSGELKPLMIPKSLMARDEDDLGSKTRVSIFFGTQTG  95
          .   .   . * ::.:                :    ::..*  .::*:*:******

ATR2     TAEGFAKALGEEAKARYEKTRFKIVDLDDYAADDDEYEEKLKKEDVAFFFLATYGDGEPT  175
AtCPR2   TAEGFAKALGEEAKARYEKTRFKIVDLDDYAADDDEYEEKLKKEDVAFFFLATYGDGEPT  175
PgCPR    TAEGFAKALADEAKARYEKARYDKVTFKVVDLDDYAADDEYEEKLKKETLAFFFLATYGDGEPT  168
AaCPR    TAEGFAKALVEEAKARYEKAVFKVIDLDLDDYAAEDEYEEKLKKESLAFFFLATYGDGEPT  170
SrCPR3   TAEGFAKALVEEAKARYEKARYDKVTFKVVDLDDYAADDDEYEEKLKKESLAFFFLATYGDGEPT  172
SrCPR    TAEGFAKALVEEAKVRYEKTSFKVIDLDDYAADLDEYAEKLKKETYAFFLATYGDGEPT  174
SrCPR2   TAEGFAKALFEEAKARYEKAAFKVIDLDDYAADLDEYAEKLKKETYAFFLATYGDGEPT  174
AtCPR1   TAEGFAKALSEEIKARYEKAAVKVIDLDDYAADDQYEEKLKKETLAFFCVATYGDGEPT  155
         *********: :** ****.: : *: :******: :*  ** :::*  .:*******

ATR2     DNAARFYKWFTEGNDRGEWLKNLKYGVFGLGNRQYEHFNKVAKVVDDILVEQGAQRLVQV  235
AtCPR2   DNAARFYKWFTEGNDRGEWLKNLKYGVFGLGNRQYEHFNKVAKVVDDILVEQGAQRLVQV  235
PgCPR    DNAARFYKWFPLEGKERGEWLQNLKFGVFGLGNRQYEHFNKIAIVVDRILAEQGGKRLISV  228
AaCPR    DNAARFYKWFTEGEERGEWLDKLQYAVFGLGNRQYEHFNKLAKVVDEKLVEQGAKRLVPV  230
SrCPR3   DNAARFYKWFTEGDARGEWLNKLQYGVFGLGNRQYEHFNKLAKVVDDGLVEQGAKRLVPV  232
SrCPR    DNAANFYKWFTEGDDRKGELLKKLQYGVFGLGNRQYEHFNKIALVVDDKLTEMGAKRLVPV  234
SrCPR2   DNAANFYKWFTEGDEKGVWLQKLQYGVFGLGNRQYEHFNKIGIVVDDGLTEQGARRLVPV  234
         ****.***** : *: : * *:*::::***********:* ***.  . ***::*:.*
```

Figure 6D (Continued)

```
AtCPR1   DNAARFYKWFTEENERDIKLQQLAYGVFALGNRQYEHFNKIGIVLDEELCKKGAKRLIEV  215
         ****.******  *   .    :.:** :.************:.  * :  * :.*:::  *

ATR2     GLGDDDQCIEDDFTAWREALWPELDTILREEGDTAVATPYTAAVLEYRVSIHDSE--DAK  293
AtCPR2   GLGDDDQCIEDDFTAWREALWPELDTILREEGDTAVATPYTAAVLEYRVSIHDSE--DAK  293
PgCPR    GLGDDDQCIEDDFTAWRESLWPELDQLLRDEDDITVSTPYTAAVLEYRVVFHDPA--DAP  286
AaCPR    GMGDDDQCIEDDFTAWKELVWPELDQLLRDEDDTTVATPYTAAVAEYRVVFHDKP--ETY  288
SrCPR3   GLGDDDQCIEDDFTAWKELVWPELDQLLRDEDDTTVATPYTAAVAEYRVVFHEKP--DAL  290
SrCPR    GLGDDDQSIEDDFTAWKELVWPELDQLLRDEDDISVTTPYTAAVLEYRVVYHDKPA-DSY  293
SrCPR2   GLGDDDQSIEDDFSAWKELVWPELDLLLRDEDDKAAATPYTAAIPEYRVVFHDKP--DAF  292
SrCPR1   GLGDDDQSIEDDFNAWKESLWSELDKLLKDEDDKSVATPYTAVIPEYRVVTHDPRFTTQK  275
         *:*****.***** *:***  *:** ::*:****:.  :.*****.:  * *  :

ATR2     FNDITLANGNGYTVFDAQHPYKANVAVKRELHTPESDRSCIHLEFDIAGSGLTMKLGDHV  353
AtCPR2   FNDINMANGNGYTVFDAQHPYKANVAVKRELHTPESDRSCIHLEFDIAGSGLTYETGDHV  353
PgCPR    TLEKSYSNANGHSVVDAQHPLRANVAVRRELRTPASDRSCTHLEFDISGTGLAYETGDHV  346
AaCPR    DQDQ-LTN--GHAVHDAQHPCRSNVAVKKELHSPLSDRSCTHLEFDISNTGLSYETGDHV  345
SrCPR3   SEDYSYTN--GHAVHDAQHPSRSNVAVKKELHTSQSDRSCTHLEFDISHTGLSYETGDHV  348
SrCPR    AEDQTHTN--GHVVHDAQHPCRSNVAVKKELHTPESDRSCTHLEFDISHTGLSYETGDHV  351
SrCPR2   SDDRTQTN--GHAVHDAQHPCRVDVAVQKELHTHESDRSCTHLEFDISRTGITYETGDHV  350
SrCPR1   SMESNVAN--GMTTIDIHHPCRVDVAVQKELTHESDRSLDLVESIHADREDGSPLE-SAVPFFFGPCTLGTGLARY  333
           :      *         :*:**   :* .:.:    *****  *: :.********

ATR2     GVLCDNLSETVDEALRLLDMSPDTYFSLHAEKEDGTPIS--SSLPPPFP--PCNLRTALTRY  411
AtCPR2   GVLCDNLSETVDEALRLLDMSPDTYFSLHAEKEDGTPIS--SSLPPPFP--PCNLRTALTRY  411
PgCPR    GVYCENLAETVEEALELLGLSPDTYFSVHADKEDGTPLSGSSLPPFP--PCTLRTALTLH  405
AaCPR    GVYVENLSEVVDEAERLIGLPHTYFSVHADNEDGTPLGGASLPPPFP--PCTLRKALASY  404
SrCPR3   GVYCENLSEVVNDAERLVGLPPDTYFSIHTDSEDGSPLGGASLPPFP--PCTLRKALTCY  407
SrCPR    GVYSENLSEVVDEALRLLGLSPDTYFSVHADKEDGTPIGGASLPPFP--PCTLRDALTRY  410
SrCPR2   GVYCENLLEVVEEAGKLLGLSTDTYFSLHIDNEDGSPLGGPSLQPFP--PCTLRKALTNY  409
SrCPR1   GVYAENHVEIVEEAGKLLGHSLDIVESIHADREDGSPLE--SAVPFFFGPCTLGTGLARY  392
         **  :*    :    *::  .  ::  :    :*  :     :****     **    *

ATR2     ACLLSSPKKSAIVALAAHASDPTEAERLIKHLASPAGKDEYSKWVVESQRSLLEVMAEFPS  471
AtCPR2   ACLLSSPKKSAIVALAAHASDPTEAERLIKHLASPAGKDEYSKWVVESQRSLLEVMAEFPS  471
PgCPR    ADLLSSPKKSALLALAAHASDPTEADRLRHLASPAGKDEYAQMIVASQRSLLEVMAEFPS  465
AaCPR    ADVLSSPKKSALLALAAHATDSTEADRLKFLASPAGKDEYAQMIVASHRSLLEVMEAFPS  464
SrCPR3   ADVLSSPKKSALLALAAHATDPSEADRLKFLASPAGKDEYSQMIVASQRSLLEVMEAFPS  467
SrCPR    ADVLSSPKKVALLALAAHASDPSEADRLKFLASPAGKDEYAQMIVANQRSLLEVMQSFPS  470
         *.:****** *::******:*.:**.**  *********::  :*.::*****  **
```

Figure 6D (Continued)

```
SrCPR2    ADLLSPKSTLLALAAHASDPTEADRLRFLASREGKDEYAEWVVANQRSLLEVMEAFPS    469
AtCPR1    ADLLNPFRKSALVALAAYATEPSEAEKLKHLTSPDGKDEYSQWIVASQRSLLEVMAAFPS   452
          * :*.*:* :*:;****  *.:*:*:.*:  * ****:::*:*  .:***********

ATR2      AKPPLGVFFAGVAPRLQPRFYSISSSPKIAETRIHVTICALVYEKMPTGRIHKGVCSTWMK   531
AtCPR2    AKPPLGVFFAGVAPRLQPRFYSISSSPKIAETRIHVTICALVYEKMPTGRIHKGVCSTWMK   531
PgCPR     AKPPLGVFFASVAPRLQPRFYSISSSPRLAPSRIHVTICALVYEKTPTGRVHKGVCSTWMK   525
AaCPR     AKPPLGVFFASVAPRLQPRYYSISSSPRFAPNRIHVTICALVYEQTPSGRVHKGVCSTWMK   524
SrCPR3    AKPSLGVFFASVAPRLQPRYYSISSSPKMAPDRIHVTICALVYEKTPAGRIHKGVCSTWMK   527
SrCPR     AKPPLGVFFAAVAPRLQPRYYSISSSPKMSPNRIHVTICALVYETTPAGRIHRGLCSTWMK   530
SrCPR2    ARPPLGVFFAAVAPRLQPRYYSISSSPKMEPNRIHVTICALVYEKTPAGRIHKGICSTWMK   529
AtCPR1    AKPPLGVFFAALAPRLQPRYYSISSSPRLAPSRVHVTISALVYGPTPTGRIHKGVCSTWMK   512
          *:*.********: ********.*******::    *:***:* .*  .**:*:*:******

ATR2      NAVPYEKSEKLFLGRPIFVRQSNFKLPSDSKVPIIMIGPGTGLAPFRGFLQERLALVESG   591
AtCPR2    NAVPYEKSENCSS-APIFVRQSNFKLPSDSKVPIIMIGPGTGLAPFRGFLQERLALVESG   590
PgCPR     NSVPSEKSDECSW-APIFVRQSNFKLPADAKVPIIMIGPGTGLAPFRGFLQERLALKEAG   584
AaCPR     NAVPMTESQDCSW-APIYVRTSNFRLPSDPKVPVIMIGPGTGLAPFRGFLQERLAQKEAG   583
SrCPR3    NAVPMTESQDCSW-APIYVRTSNFRLPSDPKVPVIMIGPGTGLAPFRGFLQERLALKEAG   586
SrCPR     NAVPLTESPDCSQ-ASIFVRTSNFRLPVDPKVPVIMIGPGTGLAPFRGFLQERLALKESG   589
SrCPR2    NAVPLTESQDCSW-APIFVRTSNFRLPIDPKVPVIMIGPGTGLAPFRGFLQERLALKESG   588
AtCPR1    NAVPAEKSHECSG-APIFIRASNFKLPSNPSTPIVMVGPGTGLAPFRGFLQERMALKEDG   571
          *:**   *.   *  ** :*:***:**   .* *::*****************:**:.*

ATR2      VELGPSVLFFGCRNRPRMDEIYEEELQRFVESGALAELSVAFSREGPTKEYVQHKMMDKAS   651
AtCPR2    VELGPSVLFFGCRNRPRMDEIYEEELQRFVESGALAELSVAFSREGPTKEYVQHKMMDRAS   650
PgCPR     TELGPSILFFGCRNSKMDYIYEDELDNFVQNGALSELVTFGALSELVIAFSREGATKEYVQHKMMERAS   644
AaCPR     TELGTAILFFGCRNRKVDFIYEDELNNFVETGALSELVIAFSREGATKEYVQHKMTQRAS   643
SrCPR3    TDLGLSILFFGCRNRKVDFIYENELNNFVETGALSELIVAFSREGPTKEYVQHKMSERAS   646
SrCPR     TELGSSILFFGCRNRKVDYIYENELNNFVENGALSELDVAFSRDGFTKEYVQHKMSQRAS   649
SrCPR2    TELGSSILFFGCRNRKVDFIYEDELNNFVENGALSELVAFSRDGFTKEYVQHKMTQRAS   648
AtCPR1    EELGSSLLFFGCRNRQMDFIYEDELMNFVDQGVISELIMAFSREGAQKEYVQHKMMEKAA   631
          :**   :::********    :*:::**  ..**   :   *****:**:****  :*:

ATR2      DIWNMISQGAYLYVCGDAKGMARDVHRSLHTIAQEQGSMDSTKAEGFVKNLQTSGRYLRDVW   713
AtCPR2    DIWNMISQGAYLYVCGDAKGMARDVHRSLHTIAQEQGSMDSTKAEGFVKNLQTSGRYLRDVW   712
PgCPR     DIWNLLSQGAYLYVCGDAKGMARDVHRTLHTIAQEQGSLDSSKAESMVKNLQMSGRYLRDVW   706
AaCPR     DIWNLLSEGAYLYVCGDAKGMAKDVHRTLHTIVQEQGSLDSSKAELYVKNLQMAGRYLRDVW   705
SrCPR3    DIWNLLSEGAYLYVCGDAKGMAKDVHRTLHTIVQEQGSLDSSKAELYVKNLQMSGRYLRDVW   708
          *****:*:**********:***:****:***.****:**:***  ****: ********
```

Figure 6D (Continued)

```
SrCPR   DIWKLLSEGAYLYVCGDAKGMAKDVHRTLHTIVQEQGSLDSSKAELYVKNLQMSGRYLRDVW 711
SrCPR2  EIWRMLSEGAYLYVCGDAKGMAKDVHRTLHTIVQEQGSLDSSKAELYVKNLQMSGRYLRDVW 710
AtCPR1  QVWDLIKEEGYLYVCGDAKGMARDVHRTLHTIVQEQEGVSSSEAEAIVKKLQTEGRYLRDVW 693
         :*. :: ..  ************:*****.***  .:.*;:**  **;:**  ********
```

Figure 11
| # | (+)-nootkatone Downstream Pathway Enzymes |
|---|---|
| 1 | Valencene synthase (VS) |
| 2 | Valencene oxygenase (VO) |
| 3 | P450 reductase (CPR) |
| 4 | Alcohol dehydrogenase (ADH) |
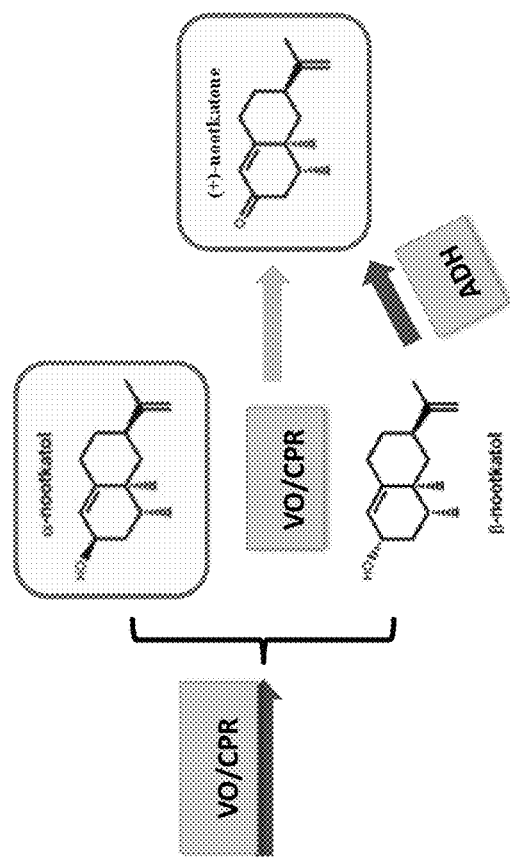
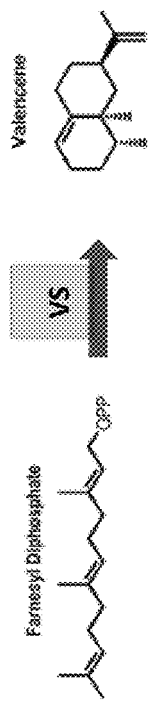

Figure 22A

>ReCDH [Rhodococcus erythropolis]

MARVEGQVALITGAARGQGRSHAIKLAEEGADVILVDVPNDVVDIGYPLGTADELDQTAKDVEN
LGRKAIVIHADVRDLESLTAEVDRAVSTLGRLDIVSANAGIASVPFLSHDIPDNTWRQMIDINL
TGVWHTAKVAVPHILAGERGGSIVLTSSAAGLKGYAQISHYSAAKHGVVGLMRSLALELAPHRV
RVNSLHPTQVNTPMIQNEGTYRIFSPDLENPTREDFEIASTTTNALPIPWVESVDVSNALLFLV
SEDARYITGAAIPVDAGTTLK (SEQ ID NO: 84)

ATGGCCCGTGTGGAAGGTCAAGTGGCTCTGATTACCGGCGCTGCTCGTGGTCAAGGTCGTAGTC
ATGCGATTAAACTGGCGGAAGAAGGCGCGGATGTGATTCTGGTTGACGTCCCGAATGATGTGGT
TGACATCGGCTATCCGCTGGGTACGGCAGATGAACTGGACCAGACCGCTAAAGATGTTGAAAAC
CTGGGTCGTAAGGCGATTGTCATCCATGCCGATGTGCGCGACCTGGAATCACTGACGGCAGAAG
TGGATCGTGCTGTTAGTACCCTGGGCCGCCTGGACATTGTTTCCGCAAATGCTGGTATCGCCAG
CGTCCCGTTTCTGTCTCACGATATTCCGGACAACACCTGGCGTCAGATGATTGATATCAATCTG
ACGGGCGTCTGGCATACCGCGAAAGTGGCCGTTCCGCACATTCTGGCCGGTGAACGCGGCGGTT
CCATCGTTCTGACCAGCTCTGCGGCCGGCCTGAAAGGTTATGCACAAATTAGTCATTACTCCGC
AGCTAAGCACGGCGTCGTGGGTCTGATGCGTTCACTGGCACTGGAACTGGCTCCGCATCGTGTC
CGCGTGAACTCGCTGCACCCGACGCAGGTGAACACCCCGATGATTCAAAATGAAGGCACGTATC
GTATCTTTAGCCCGGATCTGGAAAACCCGACCCGCGAAGACTTCGAAATTGCGTCTACCACGAC
CAATGCCCTGCCGATCCCGTGGGTGGAATCAGTTGATGTCTCGAACGCACTGCTGTTCCTGGTT
AGCGAAGACGCACGTTACATTACCGGTGCAGCAATCCCGGTGGATGCCGGTACGACCCTGAAGT
AA (SEQ ID NO: 85)

>CsDH [Citrus sinensus]

MATPPISSLISQRLLGKVALVTGGASGIGEGIVRLFHRHGAKVCFVDVQDELGYRLQESLVGDK
DSNIFYSHCDVTVEDDVRRAVDLTVTKFGTLDIMVNNAGISGTPSSDIRNVDVSEFEKVFDINV
KGVFMGMKYAASVMIPRKQGSIISLGSVGSVIGGIGPHHYISSKHAVVGLTRSIAAELGQHGIR
VNCVSPYAVPTNLAVAHLPEDERTEDMFTGFREFAKKNANLQGVELTVEDVANAVLFLASEDAR
YISGDNLIVDGGFTRVNHSFRVFR (SEQ ID NO: 86)

ATGGCAACGCCGCCGATTTCATCCCTGATTTCACAACGCCTGCTGGGTAAAGTCGCCCTGGTCA
CGGGTGGTGCTTCTGGTATTGGTGAAGGCATCGTGCGTCTGTTTCACCGTCATGGCGCGAAAGT
GTGCTTTGTTGATGTGCAGGATGAACTGGGCTACCGTCTGCAAGAATCTCTGGTGGGCGACAAA
GATTCAAACATCTTTTATAGCCACTGTGATGTCACCGTGGAAGACGATGTGCGCCGCGCTGTGG
ATCTGACCGTGACGAAATTCGGTACGCTGGATATTATGGTCAATAACGCGGGTATTAGTGGCAC
CCCGTCCAGCGATATTCGTAATGTTGATGTGAGCGAATTTGAAAAGTGTTTGATATTAACGTC
AAAGGCGTGTTTATGGGCATGAAATATGCCGCGAGCGTGATGATCCCGCGCAAACAGGGTAGCA
TCATCTCCCTGGGTTCTGTTGGCAGCGTGATCGGTGGCATTGGCCCGCACCATTATATCAGCTC
GAAACATGCGGTTGTGGGCCTGACCCGCAGCATTGCAGCGGAACTGGGTCAGCATGGCATTCGT
GTGAACTGTGTGTCTCCGTATGCGGTTCCGACCAATCTGGCGGTTGCACACCTGCCGGAAGATG
AACGTACCGAAGATATGTTTACGGGCTTCCGTGAATTTGCGAAAAGAATGCCAACCTGCAAGG
TGTTGAACTGACCGTCGAAGATGTGGCCAATGCGGTGCTGTTTCTGGCCAGCGAAGATGCACGC
TACATTAGCGGTGATAATCTGATCGTTGATGGCGGCTTTACCCGTGTGAACCACTCATTTCGTG
TTTTCCGTTAA (SEQ ID NO: 87)

>CsDH1 [Citrus sinensus]

MSKPRLQGKVAIIMGAASGIGEATAKLFAEHGAFVIIADIQDELGNQVVSSIGPEKASYRHCDV
RDEKQVEETVAYAIEKYGSLDIMYSNAGVAGPVGTILDLDMAQFDRTIATNLAGSVMAVKYAAR

Figure 22A (Continued)

VMVANKIRGSIICTTSTASTVGGSGPHAYTISKHGLLGLVRSAASELGKHGIRVNCVSPFGVAT
PFSAGTINDVEGFVCKVANLKGIVLKAKHVAEAALFLASDESAYVSGHDLVVDGGFTAVTNVMS
MLEGHG (SEQ ID NO: 88)

ATGTCAAAACCGCGTCTGCAAGGCAAAGTGGCTATTATTATGGGTGCTGCGTCTGGCATCGGTG
AAGCTACGGCTAAACTGTTCGCTGAACATGGCGCATTTGTGATTATCGCTGATATTCAGGACGA
ACTGGGCAACCAGGTGGTTAGCTCTATCGGCCCGGAAAAAGCGTCTTATCGTCACTGCGATGTG
CGTGATGAAAACAGGTTGAAGAAACCGTCGCGTATGCGATTGAAAATACGGCAGCCTGGATA
TTATGTACTCCAATGCGGGCGTGGCCGGTCCGGTTGGCACGATTCTGGATCTGGACATGGCCCA
ATTCGACCGTACCATCGCAACGAACCTGGCTGGTAGTGTTATGGCAGTCAAATATGCGGCCCGT
GTCATGGTGGCGAATAAAATTCGCGGTAGCATTATCTGTACCACGAGTACCGCCTCCACGGTGG
GCGGCAGCGGCCCGCACGCCTATACCATTAGCAAACACGGTCTGCTGGGCCTGGTTCGTTCAGC
AGCTTCGGAACTGGGTAAACATGGCATCCGCGTGAACTGCGTTAGCCCGTTTGGTGTTGCGACC
CCGTTCTCTGCCGGTACGATTAACGATGTCGAAGGCTTTGTCTGTAAAGTGGCGAATCTGAAAG
GCATCGTCCTGAAAGCGAAGCATGTGGCCGAAGCGGCCCTGTTCCTGGCAAGCGATGAATCTGC
TTATGTGAGCGGTCACGACCTGGTGGTGGATGGTGGCTTTACGGCAGTTACGAATGTCATGTCA
ATGCTGGAAGGTCACGGCTAA (SEQ ID NO: 89)

>CsDH2 [Citrus sinensus]

MSNPRMEGKVALITGAASGIGEAAVRLFAEHGAFVVAADVQDELGHQVAASVGTDQVCYHHCDV
RDEKQVEETVRYTLEKYGKLDVLFSNAGIMGPLTGILELDLTGFGNTMATNVCGVAATIKHAAR
AMVDKNIRGSIICTTSVASSLGGTAPHAYTTSKHALVGLVRTACSELGAYGIRVNCISPFGVAT
PLSCTAYNLRPDEVEANSCALANLKGIVLKAKHIAEAALFLASDESAYISGHNLAVDGGFTVVN
HSSSSAT (SEQ ID NO: 90)

ATGTCAAACCCGCGTATGGAAGGCAAAGTCGCACTGATTACGGGCGCAGCATCTGGTATCGGTG
AAGCAGCAGTCCGTCTGTTCGCTGAACATGGTGCGTTTGTCGTGGCGGCAGATGTGCAAGACGA
ACTGGGTCATCAGGTGGCGGCATCTGTGGGTACGGACCAGGTGTGCTACCATCACTGCGATGTG
CGCGATGAAAACAAGTGGAAGAAACCGTGCGTTATACCCTGGAAAAATACGGCAAACTGGATG
TCCTGTTTTCAAACGCGGGCATCATGGGTCCGCTGACCGGCATTCTGGAACTGGATCTGACCGG
CTTCGGTAACACGATGGCAACCAATGTGTGCGGTGTTGCCGCGACCATTAAACACGCGGCACGC
GCAATGGTGGACAAAAACATTCGCGGTAGCATTATCTGCACCACCAGCGTGGCTTCATCGCTGG
GTGGCACCGCGCCGCACGCATACACCACGAGCAAACACGCACTGGTGGGCCTGGTTCGTACGGC
ATGTTCGGAACTGGGTGCGTATGGCATTCGTGTGAACTGTATCAGCCCGTTTGGTGTTGCAACG
CCGCTGTCTTGCACGGCCTATAACCTGCGCCCGGATGAAGTGGAAGCAAACTCATGCGCACTGG
CGAACCTGAAAGGTATTGTGCTGAAAGCGAAACACATTGCGGAAGCAGCGCTGTTCCTGGCGAG
CGATGAAAGCGCGTATATTAGCGGTCATAATCTGGCGGTGGATGGTGGTTTCACGGTGGTTAAT
CATTCAAGTTCGTCGGCGACGTAA (SEQ ID NO: 91)

>CsDH3 [Citrus sinensus]

MTTAGSRDSPLVAQRLLGKVALVTGGATGIGESIVRLFHKHGAKVCVVDINDDLGQHLCQTLGP
TTRFIHGDVAIEDDVSRAVDFTVANFGTLDIMVNNAGMGGPPCPDIREFPISTFEKVFDINTKG
TFIGMKHAARVMIPSKKGSIVSISSVTSAIGGAGPHAYTASKHAVLGLTKSVAAELGQHGIRVN
CVSPYAILTNLALAHLHEDERTDDARAGFRAFIGKNANLQGVDLVEDDVANAVLFLASDDARYI
SGDNLFVDGGFTCTNHSLRVFR (SEQ ID NO: 92)

Figure 22A (Continued)

ATGACGACGGCTGGTTCGCGTGACAGTCCGCTGGTCGCTCAACGCCTGCTGGGCAAAGTGGCCC
TGGTTACGGGTGGTGCTACCGGCATTGGTGAAAGTATCGTGCGTCTGTTTCATAAACACGGCGC
GAAAGTTTGCGTGGTTGATATTAACGATGACCTGGGCCAGCATCTGTGTCAAACCCTGGGTCCG
ACCACCCGTTTCATTCACGGCGATGTTGCAATCGAAGATGATGTGAGCCGTGCGGTTGATTTTA
CCGTCGCCAACTTCGGTACGCTGGACATTATGGTGAACAATGCCGGTATGGGCGGTCCGCCGTG
CCCGGATATTCGTGAATTTCCGATCTCGACCTTTGAAAAAGTCTTCGACATTAACACCAAAGGC
ACGTTCATCGGTATGAAACATGCGGCCCGCGTGATGATTCCGAGTAAAAAAGGTAGTATTGTCA
GCATTAGCAGCGTGACCAGCGCGATTGGCGGCGCGGGTCCGCACGCCTATACCGCGAGCAAACA
TGCGGTGCTGGGCCTGACGAAATCTGTCGCGGCGGAACTGGGCCAGCACGGTATTCGTGTCAAC
TGTGTGTCTCCGTACGCCATCCTGACCAATCTGGCGCTGGCCCATCTGCACGAAGATGAACGTA
CGGATGACGCGCGTGCGGGTTTTCGTGCATTCATTGGTAAAAACGCTAATCTGCAAGGTGTTGA
TCTGGTCGAAGATGACGTGGCGAATGCCGTTCTGTTTCTGGCATCAGATGACGCTCGCTATATC
TCGGGCGATAACCTGTTCGTGGATGGCGGCTTCACCTGTACCAATCACTCCCTGCGTGTGTTCC
GTTAA (SEQ ID NO: 93)

>VvDH [Vitis vinifera]

MAATSIDNSPLPSQRLLGKVALVTGGATGIGESIVRLFLKQGAKVCIVDVQDDLGQKLCDTLGG
DPNVSFFHCDVTIEDDVCHAVDFTVTKFGTLDIMVNNAGMAGPPCSDIRNVEVSMFEKVFDVNV
KGVFLGMKHAARIMIPLKKGTIISLCSVSSAIAGVGPHAYTGSKCAVAGLTQSVAAEMGGHGIR
VNCISPYAIATGLALAHLPEDERTEDAMAGFRAFVGKNANLQGVELTVDDVAHAAVFLASDEAR
YISGLNLMLDGGFSCTNHSLRVFR (SEQ ID NO: 94)

ATGGCCGCAACGAGCATTGATAATTCTCCGCTGCCGAGTCAACGTCTGCTGGGTAAAGTCGCAC
TGGTCACGGGTGGCGCTACGGGTATTGGCGAAAGCATCGTGCGTCTGTTTCTGAAACAGGGTGC
TAAAGTGTGCATTGTGGACGTGCAAGATGACCTGGGCCAGAAACTGTGCGATACCCTGGGTGGC
GATCCGAACGTTAGCTTTTTCCATTGCGATGTGACCATCGAAGATGATGTGTGCCATGCAGTTG
ATTTTACCGTCACGAAATTCGGCACCCTGGATATTATGGTGAACAATGCGGGTATGGCAGGTCC
GCCGTGCTCGGACATCCGCAACGTGGAAGTCAGCATGTTTGAAAAGTGTTTGATGTGAATGTG
AAAGGTGTTTTCCTGGGCATGAAACATGCAGCCCGCATTATGATTCCGCTGAAAAAAGGCACCA
TTATCAGCCTGTGTTCAGTTTCCAGCGCTATCGCGGGCGTTGGTCCGCACGCATATACGGGTAG
CAAATGCGCAGTGGCGGGTCTGACGCAATCGGTCGCAGCAGAAATGGGTGGTCATGGCATTCGC
GTGAACTGTATCAGCCCGTATGCAATCGCAACGGGTCTGGCGCTGGCACATCTGCCGGAAGATG
AACGCACGGAAGATGCAATGGCGGGTTTCCGTGCGTTTGTGGGTAAAAATGCGAATCTGCAAGG
TGTTGAACTGACCGTGGATGATGTGGCGCACGCAGCGGTGTTTCTGGCAAGCGATGAAGCACGT
TACATCTCTGGTCTGAATCTGATGCTGGACGGCGGCTTTTCGTGTACCAACCACTCGCTGCGTG
TCTTTCGCTAA (SEQ ID NO: 95)

>VvDH1 [Vitis vinifera]

MSTASSGDVSLLSQRLVGKVALITGGATGIGESIARLFYRHGAKVCIVDIQDNPGQNLCRELGT
DDACFFHCDVSIEIDVIRAVDFVVNRFGKLDIMVNNAGIADPPCPDIRNTDLSIFEKVFDVNVK
GTFQCMKHAARVMVPQKKGSIISLTSVASVIGGAGPHAYTGSKHAVLGLTKSVAAELGLHGIRV
NCVSPYAVPTGMPLAHLPESEKTEDAMMGMRAFVGRNANLQGIELTVDDVANSVVFLASDEARY
VSGLNLMLDGGFSCVNHSLRVFR (SEQ ID NO: 96)

ATGTCAACGGCTTCCTCGGGTGATGTGTCGCTGCTGTCGCAACGCCTGGTCGGTAAAGTCGCTC
TGATTACGGGTGGTGCAACGGGCATTGGTGAATCGATTGCGCGTCTGTTTTACCGTCATGGTGC
GAAAGTGTGCATCGTTGACATTCAGGATAATCCGGGTCAAAACCTGTGCCGTGAACTGGGCACC
GACGATGCGTGCTTCTTTCACTGCGATGTGAGCATTGAAATCGATGTGATTCGTGCTGTTGACT
TTGTGGTTAACCGCTTTGGTAAACTGGACATTATGGTTAATAACGCGGGCATCGCAGATCCGCC
GTGCCCGGATATTCGCAACACCGATCTGAGCATTTTTGAAAAAGTGTTCGATGTGAACGTGAAA

Figure 22A (Continued)

GGCACCTTTCAGTGTATGAAACACGCAGCGCGCGTTATGGTGCCGCAGAAAAAGGTAGCATTA
TCAGCCTGACCTCGGTGGCGAGCGTGATTGGTGGCGCGGGTCCGCACGCCTATACGGGTAGCAA
ACACGCGGTTCTGGGTCTGACGAAAAGCGTTGCGGCAGAACTGGGTCTGCATGGTATTCGCGTG
AACTGTGTGAGTCCGTATGCAGTTCCGACGGGTATGCCGCTGGCACATCTGCCGGAATCGGAAA
AAACCGAAGATGCGATGATGGGTATGCGTGCATTTGTGGGTCGTAATGCCAACCTGCAAGGTAT
TGAACTGACCGTGGACGATGTCGCAAATAGCGTCGTGTTTCTGGCGTCGGATGAAGCGCGTTAT
GTTAGCGGTCTGAACCTGATGCTGGACGGCGGCTTCTCGTGTGTCAACCACTCGCTGCGTGTGT
TTCGCTAA (SEQ ID NO: 97)

>CsABA2 [Citrus sinensus]

MSNSNSTDSSPAVQRLVGRVALITGGATGIGESTVRLFHKHGAKVCIADVQDNLGQQVCQSLGG
EPDTFFCHCDVTKEEDVCSAVDLTVEKFGTLDIMVNNAGISGAPCPDIREADLSEFEKVFDINV
KGVFHGMKHAARIMIPQTKGTIISICSVAGAIGGLGPHAYTGSKHAVLGLNKNVAAELGKYGIR
VNCVSPYAVATGLALAHLPEEERTEDAMVGFRNFVARNANMQGTELTANDVANAVLFLASDEAR
YISGTNLMVDGGFTSVNHSLRVFR (SEQ ID NO: 98)

ATGTCCAATAGCAACTCTACGGATTCGTCGCCGGCAGTCCAACGCCTGGTCGGTCGTGTCGCCC
TGATTACGGGTGGTGCAACGGGTATTGGCGAAAGCACGGTGCGCCTGTTTCATAAACATGGCGC
GAAAGTGTGTATTGCCGACGTTCAGGATAACCTGGGTCAGCAAGTGTGTCAGAGTCTGGGTGGC
GAACCGGATACCTTTTTCTGCCATTGTGATGTGACGAAAGAAGAAGATGTGTGTAGCGCAGTTG
ATCTGACCGTGGAAAAATTTGGCACCCTGGACATTATGGTGAACAATGCGGGTATTAGCGGCGC
ACCGTGCCCGGACATTCGTGAAGCCGATCTGAGCGAATTTGAAAAAGTTTTCGACATCAACGTG
AAAGGCGTGTTTCACGGCATGAAACATGCAGCGCGTATTATGATCCCGCAAACCAAAGGCACCA
TTATCAGCATTTGCTCCGTGGCTGGTGCGATTGGTGGCCTGGGTCCGCACGCATATACCGGCTC
CAAACATGCAGTCCTGGGCCTGAACAAAAACGTGGCCGCGGAACTGGGCAAATACGGTATCCGT
GTGAATTGCGTCAGCCCGTATGCTGTTGCCACCGGCCTGGCTCTGGCACACCTGCCGGAAGAAG
AACGTACCGAAGATGCAATGGTGGGCTTTCGTAATTTTGTGGCACGCAACGCGAATATGCAAGG
CACCGAACTGACGGCGAATGATGTGGCAAACGCGGTCCTGTTTCTGGCCTCTGATGAAGCCCGT
TATATCAGCGGCACGAATCTGATGGTGGATGGCGGTTTTACCTCGGTCAATCACTCGCTGCGTG
TCTTCCGTTAA (SEQ ID NO: 99)

>BdDH [Brachypodium distachyon]

MSAAAAVSSSSSPRLEGKVALVTGGASGIGEAIVRLFRQHGAKVCIADVQDEAGQQVRDSLGDD
AGTDVLFVHCDVTVEEDVSRAVDAAAEKFGTLDIMVNNAGITGDKVTDIRNLDFAEVRKVFDIN
VHGMLLGMKHAARVMIPGKKGSIVSLASVASVMGGMGPHAYTASKHAVVGLTKSVALELGKHGI
RVNCVSPYAVPTALSMPHLPQGEHKGDAVRDFLAFVGGEANLKGVDLLPKDVAQAVLYLASDEA
RYISALNLVVDGGFTSVNPNLKAFED (SEQ ID NO: 100)

ATGTCCGCTGCTGCCGCCGTGTCCTCCTCATCGTCGCCGCGTCTGGAAGGCAAAGTCGCTCTGG
TTACGGGTGGTGCGTCAGGTATCGGCGAAGCCATTGTGCGCCTGTTCCGTCAACATGGTGCCAA
AGTGTGTATCGCGGATGTCCAAGACGAAGCGGGCCAACAGGTCCGTGATAGCCTGGGTGACGAT
GCCGGTACGGATGTGCTGTTTGTGCATTGCGACGTTACCGTGGAAGAAGATGTGTCACGCGCGG
TGGATGCCGCTGCGGAAAAATTCGGCACCCTGGACATTATGGTGAACAACGCAGGTATTACGGG
CGACAAAGTGACGGACATTCGCAACCTGGATTTCGCTGAAGTCCGTAAAGTGTTCGACATCAAT
GTGCACGGTATGCTGCTGGGCATGAAACATGCGGCCCGCGTGATGATTCCGGGTAAAAAGGCT
CGATTGTGAGCCTGGCATCGGTCGCAAGCGTTATGGGTGGTATGGGTCCGCACGCATATACCGC
AAGCAAACACGCGGTTGTGGGTCTGACGAAAAGCGTTGCACTGGAACTGGGCAAACATGGTATT
CGTGTCAACTGTGTGAGCCCGTATGCAGTTCCGACCGCACTGTCAATGCCGCACCTGCCGCAGG
GCGAACATAAAGGTGATGCGGTGCGTGATTTCCTGGCGTTTGTTGGCGGTGAAGCGAATCTGAA

Figure 22A (Continued)

AGGTGTCGATCTGCTGCCGAAAGATGTTGCACAGGCGGTTCTGTATCTGGCAAGCGACGAAGCG
CGCTATATTTCTGCGCTGAATCTGGTGGTTGATGGCGGTTTTACGAGCGTGAATCCGAATCTGA
AAGCATTTGAAGACTAA (SEQ ID NO: 101)

>ZzSDR [Zingiber zerumbet]

MRLEGKVALVTGGASGIGESIARLFIEHGAKICIVDVQDELGQQVSQRLGGDPHACYFHCDVTV
EDDVRRAVDFTAEKYGTIDIMVNNAGITGDKVIDIRDADFNEFKKVFDINVNGVFLGMKHAARI
MIPKMKGSIVSLASVSSVIAGAGPHGYTGAKHAVVGLTKSVAAELGRHGIRVNCVSPYAVPTRL
SMPYLPESEMQEDALRGFLTFVRSNANLKGVDLMPNDVAEAVLYLATEESKYVSGLNLVIDGGF
SIANHTLQVFE (SEQ ID NO: 102)

ATGCGTCTGGAAGGCAAAGTGGCTCTGGTCACGGGCGGTGCGTCGGGTATTGGCGAATCTATTG
CTCGTCTGTTTATTGAACACGGTGCAAAAATTTGCATCGTGGATGTCCAGGATGAACTGGGTCA
ACAGGTCTCTCAGCGTCTGGGTGGCGATCCGCACGCCTGTTATTTCCACTGTGATGTGACCGTG
GAAGATGACGTTCGTCGCGCGGTGGATTTTACGGCGGAAAAATATGGCACCATTGACATTATGG
TTAACAATGCGGGCATTACGGGCGATAAAGTGATCGATATTCGTGATGCGGATTTCAACGAATT
TAAAAAAGTGTTCGACATTAACGTGAATGGTGTCTTTCTGGGCATGAAACACGCAGCGCGTATT
ATGATCCCGAAAATGAAAGGCTCCATCGTTTCGCTGGCGTCCGTTAGCTCGGTGATTGCTGGTG
CAGGTCCGCATGGCTATACCGGCGCAAAACATGCGGTTGTGGGTCTGACCAAAAGCGTTGCAGC
CGAACTGGGTCGTCATGGTATTCGCGTGAACTGCGTTTCGCCGTATGCGGTGCCGACGCGCCTG
TCAATGCCGTATCTGCCGGAATCGGAAATGCAGGAAGATGCACTGCGCGGCTTTCTGACCTTTG
TGCGTAGCAATGCGAACCTGAAAGGCGTTGATCTGATGCCGAATGATGTGGCGGAAGCTGTTCT
GTATCTGGCGACCGAAGAAAGCAAATATGTTTCAGGTCTGAATCTGGTTATTGACGGCGGCTTC
TCCATCGCTAATCATACCCTGCAAGTGTTTGAATAA (SEQ ID NO: 103)

Figure 22B

```
CsDH3      MTTAGSRDSPIVAQRLLGKVALVTGGATGIGESIVRLFHKHGAKVCCVVDIN------------ 51
VvDH       MAATSIDNSPLPSQRLLGKVALVTGGATGIGESIVRLFLKQGAKVCIVDVQ------------ 51
VvDH1      MSTASSGDVSLLSQRIVGKVALITGGATGIGESIARLFYRHGAKVCIVDIQ------------ 51
CsABA2     MSNSNSTDSSPAVQRIVGRVALITGGATGIGESTVRLFHKHGAKVCIADVQ------------ 51
CsDH       MATPPIS--SLISQRLLGKVALVTGGASGIGEGIVRLFHRHGAKVCFVDVQ------------ 49
BdDH       -MSAAAAVSSSSSPRLEGKVALVTGGASGIGEAIVRLFRQHGAKVCIADVQ------------ 50
ZzSDR      ------------MRLEGKVALVTGGASGIGESIARLFIEHGAKICIVDVQ------------ 38
CsDH1      ----------MSKPRLQGKVAIIMGAASGIGEATAKLFAEHGAFVIIADIQ------------ 41
CsDH2      ----------MSNPRMEGKVALITGAASGIGEAAVRLFAEHGAFVVAADVQ------------ 41
ReCDH      ---------MARVEGQVALITGAARGQGRSHAIKLAEEGADVILVDVPNDVVDIGYP 48
                       *:*:**::  *.*  *             .   ..**     .   .  *:

CsDH3      ----DDLGQHLCQTLG-----PTTRFIHGDVAIEDDVSRAVDFTVANFGTLDIMVNNAGMG 103
VvDH       ----DDLGQKLCDTLGG----DPNVSFFHCDVTIEDDVCHAVDFTVTKFGTLDIMVNNAGMA 105
VvDH1      ----DNPGQNLCRELG-----TDDACFFHCDVSIEIDVIRAVDFVVNRFGKLDIMVNNAGIA 104
CsABA2     ----DNLGQQVCQSLGG----EPDTFFCHCDVTKEEDVCSAVDLTVEKFGTLDIMVNNAGIS 105
CsDH       ----DELGYRLQESLVGDKDSNIFYSHCDVTVEDDVRRAVDLTVTKFGTLDIMVNNAGIS 105
BdDH       ----DEAGQQVRDSLGDDAGTDVLFVHCDVTVEEDVSRAVDAAAEKFGTLDIMVNNAGIT 106
ZzSDR      ----DELGQQVSQRLGGDP--HACYFHCDVTVEDDVRRAVDFTAEKYGTIDIMVNNAGIT 92
CsDH1      ----DELGNQVVSSIGP----EKASYRHCDVRDEKQVEETVAYAIEKYGSLDIMYSNAGVA 94
CsDH2      ----DELGHQVAASVGT----DQVCYHHCDVRDEKQVEETVRYTLEKYGKLDVLFSNAGIM 94
ReCDH      LGTADELDQTAKDVENLG---RKAIVIHADVRDLESLTAEVDRAVSTLGRLDIVSANAGIA 106
               *:                    .   ***         . :  *  *:::  ***.

CsDH3      GPPCPDIREFPISTFEKVFDINTKGTFIGMKHHAARVMIPS-KKGSIVSISSVTSAIGGAG 162
VvDH       GPPCSDIRNVEVSMFEKVFDVNVKGVFLGMKHHAARIMIPL-KKGTIISLCSVSSAIAGVG 164
VvDH1      DPPCPDIRNTDLSIFEKVFDVNVKGTFQCMKHHAARVMVPQ-KKGSIISLTSVASVIGGAG 163
CsABA2     GAPCPDIREADLSEFEKVFDINVKGVFHGMKHHAARIMIPQ-TKGTIISICSVAGAIGGLG 164
CsDH       GTPSSDIRNVDVSEFEKVFDINVKGVFMGMKYAASVMIPR--KQGSIISLGSVGSVIGGIG 164
BdDH       GDKVTDIRNLDFAEVRKVFDINVHGMLLGMKHHAARVMIPG-KKGSIVSLASVASVMGGMG 165
ZzSDR      GDKVIDIRDADFNEFKKVFDINVNGVFLGMKHHAARIMIPK-MKGSIVSLASVSSVIAGAG 151
```

Figure 22B (Continued)

```
CsDH1    G-PVGTILDLDMAQFDRTIATNLAGSVMAVKYAARVMVANKIRGSIICTTSTASTVGGSG 153
CsDH2    G-PLTGILELDLTGFGNTMATNVCGVAATIKHAARAMVDKNIRGSIICTTSVASSLGGTA 153
ReCDH    SVPFLSH-DIPDNTWRQMIDINLTGVWHTAKVAVPHILAGERGGSIVLTSSAAGLKGYAQ 165
                  .   :   *    *:.  *    *  :  .   *:*:    *:.   .

CsDH3    PHAYTASKHAVLGLTKSVAAELGQHGIRVNCVSPYAILTNLA----LAHLHEDERTDDAR 218
VvDH     PHAYTGSKCAVAGLTQSVAAEMGGHGIRVNCISPYAIATGLA----LAHLPEDERTEDAM 220
VvDH1    PHAYTGSKHAVLGLTKSVAAELGLHGIRVNCVSPYAVPTGMP----LAHLPESEKTEDAM 219
CsABA2   PHAYTGSKHAVLGLNKNVAAELGKYGIRVNCVSPYAVATGLA----LAHLPEEERTEDAM 220
CsDH     PHHYISSKHAVVGLTRSIAAELGQHGIRVNCVSPYAVPTNLA----VAHLPEDERTEDMF 220
BdDH     PHAYTASKHAVVGLTKSVALELGKHGIRVNCVSPYAVPTALS----MPHLPQGEHKGDAV 221
ZzSDR    PHGYTGAKHAVVGLTKSVAAELGRHGIRVNCVSPYAVPTRLS----MPYLPESEMQEDAL 207
CsDH1    PHAYTISKHGLLGLLGLVRSAASELGKHGIRVNCVSPFGVATPFS----AGTIN------ 200
CsDH2    PHAYTTSKHALVGLVRTACSELGAYGIRVNCISPFGVATPLS----CTAYNLRP------ 203
ReCDH    ISHYSAAKHGVVGLMRSLALELAPHRVRVNSLHPTQVNTPMIQNEGTYRIFSPDLENPTR 225
          *  : ::    *: .   *  .  ****::  :    *       :   .

CsDH3    AGFRAFIGKNANLQGVDLVEDDVANAVLFLASDDARYISGDNLFVDGGFTCTNHSLRVFR--- 278
VvDH     AGFRAFVGKNANLQGVELTVDDVAHAAVFLASDEARYISGLNLMLDGGFSCTNHSLRVFR--- 280
VvDH1    MGMRAFVGRNANLQGIELTVDDVANSVVFLASDEARYVSGLNLMLDGGFSCVNHSLRVFR--- 279
CsABA2   VGFRNFVARNANMQGTELTANDVANAVLFLASDEARYISGTNLMVDGGFTSVNHSLRVFR--- 280
CsDH     TGFREFAKKNANLQGVELTVEDVANAVLFLASEDARYISGDNLIVDGGFTRVNHSFRVFR--- 280
BdDH     RDFLAFVGGEANLKGVDLLPKDVAQAVLYLASDEARYISALNLVVDGGFTSVNPNLKAFED-- 282
ZzSDR    RGFLTFVRSNANLKGVDLMPNDVAEAVLYLATEESKYVSGLNLVIDGGFSIANHTLQVFE--- 267
CsDH1    -DVEGFVCKVANLKGIVLKAKHVAEAALFLASDESAYVSGHDLVVDGGFTAVTNVMSMLEGHG 262
CsDH2    DEVEANSCALANLKGIVLKAKHIAEAALFLASDESAYISGHNLAVDGGFTVVNHSSSSAT--- 263
ReCDH    EDFEIASTTTNALPIPWVESVDVSNALLFLVSEDARYITGAAIPVDAGTTLK---------- 277
              .    :  :   : .  *:::.: *  :*.  .    :*. ..
```

Figure 23A

```
8rp-t20SrKO      -----MALLLAVFAVALAVALIFWYLKSYTSARRSQSNHLPRVPEVPGVPLLGNLLQLKEK
8rp-t20V00       -----MALLLAVFAVALAVALIFWYLKSYTSARRSQSNHLPRVPEVPGVPLLGNLLQLKEK
n22yhcB-t30V01   MAWEYALIGLVVGIIIGAVAMRWYLKSYTSARRSQSNRLPRVPEVPGVPLLGNLLQLKEK
n22yhcB-t30V02   MAWEYALIGLVVGIIIGAVAMRWYLKSYTSARRSQSNHLPRVPEVPGVPLLGNLLQLKEK
                      **.:  *..:  :...   :*********************:*********************

8rp-t20SrKO      KPYMTFTRWAATYGPIYSIKTGATSMVVVSSNEIAKEALVTRFQSISTRNLSKALKVLTA
8rp-t20V00       KPYMTFTRWAATYGPIYSIKTGATSMVVVSSNEIAKEALVTRFQSISTRNLSKALKVLTA
n22yhcB-t30V01   KPYMTFTRWAATYGPIYSIKTGATSMVVVSSNEIAKEALVTRFQSISTRNLSKALKVLTA
n22yhcB-t30V02   KPYMTFTKWAATYGPIYSIKTGATSVVVVSSNEIAKEALVTRFQSISTRNLSKALKVLTA
                 *******:*****************:**********************************

8rp-t20SrKO      DKTMVAMSDYDDYHKTVKRHILTAVLGPNAQKKHRIHRDIMMDNISTQLHEFVKNNPEQE
8rp-t20V00       DKTMVAMSDYDDYHKTVKRHILTAVLGPNAQKKHRIHRDIMMDNISTQLHEFVKNNPEQE
n22yhcB-t30V01   DKTMVAMSDYDDYHKTVKRHILTAVLGPNAQKKHRIHRDIMMDNISTQLHEFVKNNPEQE
n22yhcB-t30V02   DKQMVAMSDYDDYHKTVKRHILTAVLGPNAQKKHRIHRDIMMDNISTQLHEFVKNNPEQE
                 **  ********************************************************

8rp-t20SrKO      EVDLRKIFQSELFGLAMRQALGKDVESLYVEDLKITMNRDEIFQVLVVDPMMGAIDVDWR
8rp-t20V00       EVDLRKIFQSELFGLAMRQALGKDVESLYVEDLKITMNRDEIFQVLVVDPMMGAIDVDWR
n22yhcB-t30V01   EVDLRKIFQSELFGLAMRQALGKDVESLYVEDLKITMNRDEILQVLVVDPMMGAIDVDWR
n22yhcB-t30V02   EVDLRKIFQSELFGLAMRQALGKDVESLYVEDLKITMNRDEILQVLVVDPMMGAIDVDWR
                 *****************************************:******************

8rp-t20SrKO      DFFPYLKWVPNKKFENTIQQMYIRREAVMKSLIKEHKKRIASGEKLNSYIDYLLSEAQTL
8rp-t20V00       DFFPYLKWVPNKKFENTIQQMYIRREAVMKSLIKEHKKRIASGEKLNSYIDYLLSEAQTL
n22yhcB-t30V01   DFFPYLKWVPNKKFENTIQQMYIRREAVMKSLIKEQKKRIASGEKLNSYIDYLLSEAQTL
n22yhcB-t30V02   DFFPYLKWVPNKKFENTIQQMYIRREAVMKSLIKEQKKRIASGEKLNSYIDYLLSEAQTL
                 ***********************************:************************

8rp-t20SrKO      TDQQLLMSLWEPIIESSDTTMVTTEWAMYELAKNPKLQDRLYRDIKSVCGSEKITEEHLS
8rp-t20V00       TDQQLLMSLWEPIIESSDTTMVTTEWAMYELAKNPKLQDRLYRDIKSVCGSEKITEEHLS
n22yhcB-t30V01   TDQQLLMSLWEPIIESSDTTMVTTEWAMYELAKNPKLQDRLYRDIKSVCGSEKITEEHLS
n22yhcB-t30V02   TDQQLLMSLWEPIIESSDTTMVTTEWAMYELAKNPKLQDRLYRDIKSVCGSEKITEEHLS
                 ************************************************************

8rp-t20SrKO      QLPYITAIFHETLRRHSPVPIIPLRHVHEDTVLGGYHVPAGTELAVNIYGCNMDKNVWEN
8rp-t20V00       QLPYITAIFHETLRRHSPVPIIPLRHVHEDTVLGGYHVPAGTELAVNIYGCNMDKNVWEN
n22yhcB-t30V01   QLPYITAIFHETLRKHSPVPIIPLRHVHEDTQLGGYHVPAGTELAVNIYGCNMDKNVWEN
n22yhcB-t30V02   QLPYITAIFHETLRKHSPVPILPLRHVHEDTVLGGYHVPAGTELAVNIYGCNMDKNVWEN
                 **************:******:********* ****************************

8rp-t20SrKO      PEEWNPERFMKENETIDFQKTMAFGGGKRVCAGSLQALLTASIGIGRMVQEFEWKLKDMT
8rp-t20V00       PEEWNPERFMKENETIDFQKTMAFGGGKRVCAGSLQALLTASIGIGRMVQEFEWKLKDMT
n22yhcB-t30V01   PEEWNPERFMKENETADFQKTMAFGGGKRVCAGSLQALLTASIGIGRMVQEFEWKLKDMD
n22yhcB-t30V02   PEEWNPERFMKENETIDFQKTMAFGGGKRVCAGSLQALLIASIGIGRMVQEFEWKLKDMT
                 *************** *********************** *******************

8rp-t20SrKO      QEEVNTIGLTTQMLRPLRAIIKPRI
8rp-t20V00       QEEVNTIGLTNQMLRPLRAIIKPRI
n22yhcB-t30V01   QEEVNTIGLTNQMLRPLRAIIKPRI
n22yhcB-t30V02   QEEVNTIGLTNQMLRPLRAIIKPRI
                 **********:**************
```

Figure 23B

```
VO2     MDAVTGLLTVPATAITIGGTAVALAVALIFWYLKSYTSARRSQSNHLPRVPEVPGVPLLG
VO1     MDAVTGLLTVPATAITIGGTAVALAVALIFWYLKSYTSARRSQSNRLPRVPEVPGVPLLG
SrKO    MDAVTGLLTVPATAITIGGTAVALAVALIFWYLKSYTSARRSQSNHLPRVPEVPGVPLLG
VO0     MDAVTGLLTVPATAITIGGTAVALAVALIFWYLKSYTSARRSQSNHLPRVPEVPGVPLLG
        *********************************:**********

VO2     NLLQLKEKKPYMTFTKWAATYGPIYSIKTGATSVVVSSNEIAKEALVTRFQSISTRNLS
VO1     NLLQLKEKKPYMTFTRWAATYGPIYSIKTGATSMVVSSNEIAKEALVTRFQSISTRNLS
SrKO    NLLQLKEKKPYMTFTRWAATYGPIYSIKTGATSMVVSSNEIAKEALVTRFQSISTPNLS
VO0     NLLQLKEKKPYMTFTRWAATYGPIYSIKTGATSMVVSSNEIAKEALVTRFQSISTRNLS
        ***************:****************:**************************

VO2     KALKVLTADKQMVAMSDYDDYHKTVKRHILTAVLGPNAQKKHRIHRDIMMDNISTQLHEF
VO1     KALKVLTADKTMVAMSDYDDYHKTVKRHILTAVLGPNAQKKHRIHRDIMMDNISTQLHEF
SrKO    KALKVLTADKTMVAMSDYDDYHKTVKRHILTAVLGPNAQKKHRIHRDIMMDNISTQLHEF
VO0     KALKVLTADKTMVAMSDYDDYHKTVKRHILTAVLGPNAQKKHRIHRDIMMDNISTQLHEF
        ********* **************************************************

VO2     VKNNPEQEEVDLRKIFQSELFGLAMRQALGKDVESLYVEDLKITMNRDEILQVLVVDPMM
VO1     VKNNPEQEEVDLRKIFQSELFGLAMRQALGKDVESLYVEDLKITMNRDEILQVLVVDPMM
SrKO    VKNNPEQEEVDLRKIFQSELFGLAMRQALGKDVESLYVEDLKITMNRDEIFQVLVVDPMM
VO0     VKNNPEQEEVDLRKIFQSELFGLAMRQALGKDVESLYVEDLKITMNRDEIFQVLVVDPMM
        *************************************************:*********

VO2     GAIDVDWRDFFPYLKWVPNKKFENTIQQMYIRREAVMKSLIKEQKKRIASGEKLNSYIDY
VO1     GAIDVDWRDFFPYLKWVPNKKFENTIQQMYIRREAVMKSLIKEQKKRIASGEKLNSYIDY
SrKO    GAIDVDWRDFFPYLKWVPNKKFENTIQQMYIRREAVMKSLIKEHKKRIASGEKLNSYIDY
VO0     GAIDVDWRDFFPYLKWVPNKKFENTIQQMYIRREAVMKSLIKEHKKRIASGEKLNSYIDY
        *******************************************:****************

VO2     LLSEAQTLTDQQLLMSLWEPIIESSDTTMVTTEWAMYELAKNPKLQDRLYRDIKSVCGSE
VO1     LLSEAQTLTDQQLLMSLWEPIIESSDTTMVTTEWAMYELAKNPKLQDRLYRDIKSVCGSE
SrKO    LLSEAQTLTDQQLLMSLWEPIIESSDTTMVTTEWAMYELAKNPKLQDRLYRDIKSVCGSE
VO0     LLSEAQTLTDQQLLMSLWEPIIESSDTTMVTTEWAMYELAKNPKLQDRLYRDIKSVCGSE
        ************************************************************

VO2     KITEEHLSQLPYITAIFHETLRKHSPVPILPLRHVHEDTVLGGYHVPAGTELAVNIYGCN
VO1     KITEEHLSQLPYITAIFHETLRKHSPVPIIPLRHVHEDTQLGGYHVPAGTELAVNIYGCN
SrKO    KITEEHLSQLPYITAIFHETLRRHSPVPIIPLRHVHEDTVLGGYHVPAGTELAVNIYGCN
VO0     KITEEHLSQLPYITAIFHETLRRHSPVPIIPLRHVHEDTVLGGYHVPAGTELAVNIYGCN
        **********************:*****:*********:*********************

VO2     MDKNVWENPEEWNPERFMKENETIDFQKTMAFGGGKRVCAGSLQALLIASIGIGRMVQEF
VO1     MDKNVWENPEEWNPERFMKENETADFQKTMAFGGGKRVCAGSLQALLTASIGIGRMVQEF
SrKO    MDKNVWENPEEWNPERFMKENETIDFQKTMAFGGGKRVCAGSLQALLTASIGIGRMVQEF
VO0     MDKNVWENPEEWNPERFMKENETIDFQKTMAFGGGKRVCAGSLQALLTASIGIGRMVQEF
        ***********************:*********************** ************

VO2     EWKLKDMTQEEVNTIGLTNQMLRPLRAIIKPRI
VO1     EWKLKDMDQEEVNTIGLTNQMLRPLRAIIKPRI
SrKO    EWKLKDMTQEEVNTIGLTTQMLRPLRAIIKPRI
VO0     EWKLKDMTQEEVNTIGLTNQMLRPLRAIIKPRI
        ******* **********:**************
```

METHODS FOR PRODUCTION OF OXYGENATED TERPENES

PRIORITY

This application is a continuation of U.S. patent application Ser. No. 15/505,503, filed Feb. 21, 2017, now U.S. Pat. No. 10,934,564, which is a national stage application of PCT/US2015/046369 filed Aug. 21, 2015, which claims the benefit of U.S. Provisional Application No. 62/040,284 filed Aug. 21, 2014, each of which is hereby incorporated by reference in their entireties.

The claimed invention was made by, or on behalf of, one or more of the following parties to a joint research agreement: Manus Biosynthesis, Inc. (now MANUS BIO, Inc.) and Givaudan Schweiz AG (a wholly owned subsidiary of Givaudan SA). The agreement was in effect on and before the date the claimed invention was made, and the claimed invention was made as a result of activities undertaken within the scope of the agreement.

REFERENCE TO THE SEQUENCE LISTING

The instant application contains a Sequence Listing which has been submitted in ASCII format via EFS-Web and is hereby incorporated by reference in its entirety. Said ASCII copy, filed on Jan. 5, 2021 is named "SequenceListing.txt" and is 405,612 bytes in size.

FIELD OF THE INVENTION

The present invention relates to oxygenated sesquiterpenes (e.g., nootkatone) and methods for their production and use. The invention also provides enzymes for the production of oxygenated sesquiterpenes (e.g., nootkatone) and methods for identifying, selecting, making and using these enzymes.

BACKGROUND OF THE INVENTION

The food and beverage industries as well as other industries such as the perfume, cosmetic and health care industries routinely use terpenes and/or terpenoid products as flavours and fragrances. By way of example, many sesquiterpene compounds are used in perfumery (e.g. patchoulol) and in the flavour industry (e.g., nootkatone) and many are extracted from plants. However, factors such as: (i) the availability and high price of the plant raw material; (ii) the relatively low terpene content in plant; and (iii) the tedious and inefficient extraction processes to produce sufficient quantities of terpene products on an industrial scale all have stimulated research on the biosynthesis of terpenes using plant-independent systems. Consequently, effort has been expended in developing technologies to engineer microorganisms for converting renewable resources such as glucose into terpenoid products. By comparison with traditional methods, microorganisms have the advantage of fast growth without the need for land to sustain development.

Many microorganisms use either the methylerythritol 4-phosphate (MEP) pathway or the melavonate (MVA) pathway to supply intermediates necessary to produce terpenoid products. These MEP or MVA pathways can include an endogenous or an engineered MEP or MVA pathway or both. A detailed understanding of isoprenoid pathway engineering and optimization is disclosed in WO 2011/060057, US 2011/0189717, US 2012/107893, U.S. Pat. No. 8,512,988 and Ajikumar et al (2010) Science 330 which discloses the production of various terpenoid compounds including sesquiterpene compounds such as nootkatone, which is an oxidised sesquiterpene produced from a valencene sesquiterpene substrate.

Nootkatone (4,4a,5,6,7,8-hexahydro-6-isopropenyl-4,4a-dimethyl-2(3H)-naphtalenone) is an important flavour constituent of grapefruit and is used commercially to flavour soft drinks and other beverages, as well as being used in perfumery. The conventional method for nootkatone preparation is by oxidation of valencene (see U.S. Pat. Nos. 6,200,786 and 8,097,442). The starting material valencene is expensive and thus methods that consume valencene are less commercially acceptable. Because of these drawbacks, there is a need for commercially feasible and sustainable methods to prepare nootkatone and associated products.

SUMMARY OF THE INVENTION

An object of the present invention is to provide sustainable production of oxygenated sesquiterpene products. Specifically, the present invention provides enzyme catalysts for the ex vivo or in vivo production of certain oxygenated sesquiterpenes. In some embodiments, the invention provides host cells engineered for the biosynthesis of the oxygenated sesquiterpenes. Another object of the present invention is to provide engineered cytochrome P450 (CYP450) enzymes for synthesis of oxygenated sesquiterpenes, including in some embodiments functional expression alongside a reductase counterpart in E. coli, yeast, or other host cell. The invention thereby harnesses the unique capability of this class of enzymes to conduct oxidative chemistry.

In one aspect, the invention provides a method for making an oxygenated product of a sesquiterpene. The method comprises contacting the sesquiterpene with Stevia rebaudiana Kaurene Oxidase (SrKO) or derivative thereof having sesquiterpene oxidizing activity. Surprisingly, the wild type SrKO enzyme was shown to have activity on a sesquiterpene substrate even though its natural activity is understood to act on a diterpene substrate. Further, SrKO enzyme showed unique activities including oxygenation to the ketone, nootkatone), which requires two oxygenation cycles, and produced different oxygenated terpene products including hydroxygermacra-1(10)5-diene, and murolan-3,9(11) diene-10-peroxy. These activities are distinct from other P450 enzymes tested, which produced only one of the stereoisomers of the hydroxylated product (e.g., β-nootkatol), as the major product and/or produced only minor amounts of nootkatone.

In some embodiments, the method takes place in an ex vivo (e.g., cell free) system. In other embodiments, the sesquiterpene substrate and the SrKO or derivative thereof are contacted in a cell expressing the SrKO, such as a bacterium (e.g., E. coli). The oxygenated product of a sesquiterpene may be recovered, or may be the substrate for further chemical transformation. Functional expression of wild type cytochrome P450 in E. coli has inherent limitations attributable to the bacterial platforms (such as the absence of electron transfer machinery and cytochrome P450 reductases, and translational incompatibility of the membrane signal modules of P450 enzymes due to the lack of an endoplasmic reticulum). Thus, in some embodiments the SrKO enzyme is modified for functional expression in an E. coli host cell, for example, by replacing a portion of the SrKO N-terminal transmembrane region with a short peptide sequence that stabilizes interactions with the E. coli inner membrane and/or reduces cell stress.

In some embodiments, the SrKO derivative has at least one mutation with respect to the wild type SrKO that increases valencene oxidase activity (e.g., increases production of nootkatone). For example, the SrKO may have from 1 to 50 mutations independently selected from substitutions, deletions, or insertions relative to wild type SrKO (SEQ ID NO:37) or an SrKO modified for expression and activity in *E. coli* (e.g., SEQ ID NOS: 38 or 55). For example, the SrKO derivative may have from 1 to 40 mutations, from 1 to 30 mutations, from 1 to 20 mutations, or from 1 to 10 mutations relative to SrKO (SEQ ID NOS: 37, 38, or 55). In these or other embodiments, the SrKO derivative may comprise an amino acid sequence having at least 50% sequence identity, or at least 60% sequence identity, or at least 70% sequence identity, or at least 80% sequence identity, or at least 90% sequence identity to SrKO (SEQ ID NOS: 37, 38, or 55), and has valencene oxidase activity. The SrKO in various embodiments maintains valencene oxidase activity, or has increased valencene oxidase activity as compared to the wild type enzyme in an ex vivo or bacterial system (e.g. *E. coli*). Various mutations of SrKO which may maintain or enhance valencene oxidase activity are listed in Table 2 and Table 6. Thus, in various embodiments, the SrKO may have at least 2, at least 3, at least 4, at least 5, at least 6, at least 7, at least 8, at least 9, or at least 10 mutations selected from Table 2 and/or Table 6. Exemplary derivatives of SrKO, also referred to herein as "valencene oxidase" or "VO" are represented by SEQ ID NOS: 104 and 105, which may further be derivatized for improvements in desired activity. Mutations may be selected empirically for increases in oxygenated sesquiterpene titer, or selected by in silico evaluation, or both.

In accordance with aspects of the invention, oxygenated sesquiterpene products are obtainable by contacting a sesquiterpene substrate with *Stevia rebaudiana* Kaurene Oxidase (SrKO) or derivative thereof having valencene oxidizing activity. Unlike other CYP450 enzymes, when a SrKO enzyme is used with valencene sesquiterpene substrate, it produces a different oxygenated terpene product profile that can include hydroxygermacra-1(10)5-diene, murolan-3,9 (11) diene-10-peroxy, nootkatol, and nootkatone. By comparison, other CYP450's having the activity of hydroxylating valencene did not produce significant amounts of the ketone (nootkatone), which requires two oxygenation cycles. See Table 4 and FIG. 7.

In various embodiments, the sesquiterpene substrate is (or the predominant sesquiterpene substrate is) valencene, germacrene (A, B, C, D, or E), farnesene, farnesol, nootkatol, patchoulol, cadinene, cedrol, humulene, longifolene, and/or bergamotene, β-ylangene, β-santalol, β-santalene, α-santalene, α-santalol, ß-vetivone, a-vetivone, khusimol, bisabolene, β-aryophyllene, longifolene; α-sinensal; α-bisabolol, (–)-β-copaene, (–)-α-copaene, 4(Z),7(Z)-ecadienal, cedrol, cedrene, cedrol, guaiol, (–)-6,9-guaiadiene, bulnesol, guaiol, ledene, ledol, lindestrene, and alpha-bergamotene. In some embodiments, the predominant sesquiterpene substrate is valencene, and the predominant oxygenated product is nootkatone and/or nootkatol.

The invention, when applied in vivo, is applicable to a wide array of host cells. In some embodiments, the host cell is a microbial host, such as a bacterium selected from *E. coli, Bacillus subtillus*, or *Pseudomonas putida*; or a yeast, such as a species of *Saccharomyces, Pichia*, or *Yarrowia*, including *Saccharomyces cerevisiae, Pichia pastoris*, and *Yarrowia lipolytica*.

In some embodiments, the host cell produces isopentyl pyrophosphate (IPP), which acts as a substrate for the synthesis of the sesquiterpene. In some embodiments, the IPP is produced by metabolic flux through an endogenous or heterologous methylerythritol phosphate (MEP) or mevalonic acid (MVA) pathway. In some embodiments, the sesquiterpene is produced at least in part by metabolic flux through an MEP pathway, and wherein the host cell has at least one additional copy of a dxs, ispD, ispD, and/or idi gene.

In some embodiments, the host cell expresses a farnesyl pyrophosphate synthase (FPPS), which produces farnesyl pyrophosphate (FPP) from IPP or DMAPP. The host cell may further express a heterologous sesquiterpene synthase to produce the desired sesquiterpene scaffold. For example, in some embodiments the cell expresses a valencene synthase. Several valencene synthase enzymes are known including *Vitis vinifera* valencene synthase (VvVS) (SEQ ID NO:1) or *Citrus sinensus* valencene synthase (CsVS) (SEQ ID NO: 12), which may be employed with the present invention, or alternatively a derivative of the VvVS or CsVS. Exemplary derivative VvVS enzymes are disclosed herein. In certain embodiments, the sesquiterpene synthase is a valencene synthase selected from Vv1M1 (SEQ ID NO:3), Vv2M1 (SEQ ID NO:5), Vv1M5 (SEQ ID NO:7), Vv2M5 (SEQ ID NO:9), or VS2 (SEQ ID NO:11), as disclosed herein.

The SrKO or derivative thereof acts on the sesquiterpene (e.g., valencene) to produce the oxygenated terpene product. In some embodiments the SrKO is a fusion protein with a cytochrome P450 reductase partner (e.g., SrCPR), allowing the cofactor to be efficiently regenerated. In other embodiments, a P450 reductase is provided (e.g., to in vitro system) or expressed in the host cell separately, and may be expressed in the same operon as the SrKO in some embodiments. In some embodiments, the CPR enzyme is expressed separately, and the gene may be integrated into the host cell genome in some embodiments. Various exemplary CPR enzymes are disclosed herein, and which may be derivatized to improve oxygenated sesquiterpenoid titer and/or to improve P450 efficiency.

In some embodiments, the host cell expresses one or more enzymes that further direct oxygenated product to nootktone, such as the expression of one or more alcohol dehydrogenase (ADH) enzymes. Exemplary ADH enzymes are disclosed herein.

In other aspects, the invention provides a method for making a product containing an oxygenated sesquiterpene, which comprises incorporating the oxygenated sesquiterpene prepared and recovered according to the methods described herein into a consumer or industrial product. For example, the product may be a flavor product, a fragrance product, a cosmetic, a cleaning product, a detergent or soap, or a pest control product. In some embodiments, the oxygenated product recovered comprises nootkatone, and the product is a flavor product selected from a beverage, a chewing gum, a candy, or a flavor additive.

In other aspects, the invention provides engineered SrKO enzymes having enhanced valencene oxidase activity as compared to wild type, as well as host cells producing an oxygenated sesquiterpene as described herein, and which express all of the enzyme components for producing the desired oxygenated sesquiterpene from isopentyl pyrophosphate (IPP). For example, the host cell in various embodiments expresses a farnesyl pyrophosphate synthase, a sesquiterpene synthase, and the SrKO or derivative thereof. IPP may be produced through the MEP and/or MVA pathway, which may be endogenous to the host cell, and which may be enhanced through expression of heterologous enzymes or duplication of certain enzymes in the pathway. Host cells include various bacteria and yeast as described herein. The oxygenated sesquiterpene (e.g., nootkatone and/or nootkatol) may be recovered from the culture, and/or optionally may act as the substrate for further chemical transformation in the cell or ex vivo system.

In another aspect, the invention provides sesquiterpene-containing oil produced by the methods and host cells described herein. In some embodiments, the oil comprises hydroxygermacra-1(10)5-diene, murolan-3,9(11) diene-10-peroxy, nootkatol, and nootkatone. In some embodiments, the predominant oxygenated products of valencene is nootkatone and/or nootkatol.

In another aspect, there is provided an SrKO crystal model structure (CMS) based on the structural coordinates of P45017A1 (which catalyzes the biosynthesis of androgens). The CMS, including the terpene binding pocket domain (TBD) that comprises a terpene binding pocket (TBP) and a terpene (e.g., valencene) bound to the TBD, is illustrated in FIGS. 8A and 8B. This SrKO crystal model structure (CMS) facilitates in-silico testing of SrKO derivatives. In part aided by this homology model, the present disclosure illustrates the use of several mutational strategies to identify increases or improvements in sesquiterpene oxygenation activity, including back-to-consensus mutagenesis, site-saturation mutagenesis, and recombination library screening.

Additional aspects and embodiments of the invention will be apparent from the following detailed description.

DESCRIPTION OF THE DRAWINGS

FIG. 2 shows the number of VvVS mutants (y-axis) exhibiting certain levels of productivity (x-axis) versus the wild type.

FIG. 3A and FIG. 3B provide amino acid and nucleotide sequences of valencene synthases. FIG. 3A shows amino acid and nucleotide sequences from *Vitis vinifera* wild-type (WT) (VvVS) (SEQ ID NOS: 1 and 2) and derivatives Vv1M1 (SEQ ID NOS: 3 and 4), Vv2M1 (SEQ ID NOS: 5 and 6), Vv1M5 (SEQ ID NOS: 7 and 8), Vv2M5 (SEQ ID NOS: 9 and 10), and amino acid sequence of the derivative VS2 (SEQ ID NO:11); as well as amino acid sequence for *Citrus sinensus* wild-type (CsVS) (SEQ ID NO:12). FIG. 3B shows an alignment of wild-type VvVS and CsVS sequences, and the engineered Vv2M5 and VS2 sequences.

FIG. 4A and FIG. 4B provide the amino acid and nucleotide sequences of various CYP450 (Cytochrome P450) enzymes having activity on sesquiterpene scaffolds. FIG. 4A shows sequences of wild type amino acid sequences and amino acid and nucleotide sequences engineered for bacterial expression: ZzHO (SEQ ID NO: 13, 14, and 15 respectively), BsGAO (SEQ ID NO: 16, 17, and 18, respectively), HmPO (SEQ ID NO: 19, 20, and 21 respectively), LsGAO (SEQ ID NO: 22, 23, and 24, respectively), NtEAO (SEQ ID NO: 25, 26, and 27, respectively), CpVO (SEQ ID NO: 28, 29, and 30, respectively), AaAO (SEQ ID NO: 31, 32, and 33, respectively), AtKO (SEQ ID NO: 34, 35, and 36 respectively), SrKO (SEQ ID NO: 37, 38, and 39 respectively), PpKO (SEQ ID NO: 40, 41, and 42, respectively), BmVO (SEQ ID NO: 43 and SEQ ID NO: 44, respectively), PsVO (SEQ ID NO: 45 and SEQ ID NO: 46, respectively), PoLO (SEQ ID NO: 47 and SEQ ID NO: 48, respectively), CiVO (SEQ ID NO: 49, 50, and 51 respectively), HaGAO (SEQ ID NO: 52, 53, and 54, respectively). FIG. 4B shows amino acid sequences of engineered Valencene Oxidase enzymes based on the SrKO scaffold (SEQ ID NOS: 55-61).

FIG. 5A shows strain configuration of upstream MEP pathway genes and the two plasmids harboring downstream pathway genes. FIG. 5B shows construction of P450 fusions, whereby N-terminal regions of both the P450 and CPR (Cytochrome P450 reductase) are truncated and an exemplary leader sequence (MALLLAVF—SEQ ID NO:112) (8RP) is added while the two are fused with a short linker peptide.

FIG. 6A, FIG. 6B, FIG. 6C, and FIG. 6D provide the amino acid and nucleotide sequences of various CPR (Cytochrome P450 reductase) enzymes with sequence alignments. In FIG. 6A: *Stevia rebaudiana* (Sr)CPR (SEQ ID NOS: 62 and 63), *Stevia rebaudiana* (Sr)CPR1 (SEQ ID NOS: 76 and 77), *Arabidopsis thaliana* (At)CPR (SEQ ID NOS: 64 and 65), *Taxus cuspidata* (Tc) CPR (SEQ ID NOS: 66 and 67), *Artemisia annua* (Aa)CPR (SEQ ID NOS: 68 and 69), *Arabidopsis thaliana* (At)CPR1 (SEQ ID NOS: 70 and 71), *Arabidopsis thaliana* (At)CPR2 (SEQ ID NOS: 72 and 73), *Arabidopsis thaliana* (At)R2 (SEQ ID NOS: 74 and 75); *Stevia rebaudiana* (Sr)CPR2 (SEQ ID NOS: 78 and 79); *Stevia rebaudiana* (Sr)CPR3 (SEQ ID NOS: 80 and 81); *Pelargonium graveolens* (Pg)CPR (SEQ ID NO: 82 and 83). FIG. 6B shows an alignment of amino acid sequences for *Arabidopsis thaliana* and *Artemisia annua* CPR sequences (SEQ ID NOS:72, 74, 68, 64, and 70). FIG. 6C shows an alignment of *Stevia rebaudiana* CPR sequences (SEQ ID NOS: 78, 80, 62, and 76). FIG. 6D shows an alignment of eight CPR amino acid sequences (SEQ ID NO: 74, 72, 82, 68, 80, 62, 78, and 76).

FIG. 8B depicts a structural model of SrKO active site with valencene docked in its α-binding mode. Secondary structure motifs (B-C Loop and I-Helix) and amino acids targeted for mutagenesis are shown.

FIG. 11 illustrates an exemplary downstream pathway for expression in the host cell, for conversion of farnesyl diphosphate to nootkatone. Farnesyl diphosphate (produced from IPP/DMAPP by an expressed Farnesyl Pyrophosphate Synthase) is converted to valencene by the action of a Valencene Synthase (VS), which is oxidized by a Valencene Oxidase (VO), such as SrKO or an engineered derivative described herein. The VO cofactor is regenerated by a cytochrome P450 reductase (CPR). The products of oxidation by VO can include nootkatol and nookatone, which can be further directed to nootkatone by the action of an Alcohol Dehydrogenase (ADH).

FIG. 13A shows titer in mg/L. FIG. 13B shows fold change in oxygenated titer.

FIG. 16A shows oxygenated product in mg/L. FIG. 16B plots the fold change in oxygenation capacity (nootkatols require only one oxygenation cycle from valencene, while nootkatone requires two oxygenation cycles).

FIG. 22A and FIG. 22B depict alcohol dehydrogenase enzymes. FIG. 22A shows amino acid and nucleotide sequences including those for *Rhodococcus erythropolis* (Re)CDH (SEQ ID NOS: 84 and 85), *Citrus sinensus* (Cs)DH (SEQ ID NOS: 86 and 87), *Citrus sinensus* (Cs)DH1 (SEQ ID NOS: 88 and 89), *Citrus sinensus* (Cs)DH2 (SEQ ID NOS: 90 and 91), *Citrus sinensus* (Cs)DH3 (SEQ ID NOS: 92 and 93), *Vitis vinifera* (Vv)DH (SEQ ID NOS: 94 and 95), *Vitis vinifera* (Vv)DH1 (SEQ ID NOS: 96 and 97, *Citrus sinensus* (Cs)ABA2 (SEQ ID NOS: 98 and 99), *Brachypodium distachyon* (Bd)DH (SEQ ID NO: 100 and 101), *Zingiber zerumbet* (Zz)SDR (SEQ ID NOS: 102 and 103). FIG. 22B shows an alignment of the amino acid sequences.

FIG. 23A and FIG. 23B show alignments of several engineered valencene oxidase (VO) variants. In FIG. 23A: 8rp-t20SrKO (SEQ ID NO: 106) is the SrKO sequence with a 20-amino acid truncation at the N-terminus, and the addition of an 8-amino acid membrane anchor. 8rp-t20VO0 (SEQ ID NO: 107) has a truncation of 20 amino acids of the SrKO N-terminus, the addition of an 8-amino acid N-terminal anchor, and a single mutation at position 499 (numbered according to wild-type SrKO). n22yhcB-t30VO1 (SEQ ID NO: 104) has a 30-amino acid truncation of the SrKO N-terminus, a membrane anchor based on 22 amino acids from *E. coli* yhcB, and eight point mutations at positions 46, 231, 284, 383, 400, 444, 488, and 499 (with respect to SrKO wild-type). n22yhcB-t30VO2 (SEQ ID NO: 105) has a 30-amino acid truncation of the SrKO N-terminus, a membrane anchor based on 22 amino acids from *E. coli* yhcB, and nine point mutations at positions 76, 94, 131, 231, 284, 383, 390, 468, and 499 (with respect to SrKO wild-type). FIG. 23B, point mutations in VO0 (SEQ ID NO: 109), VO1 (SEQ ID NO: 110), and VO2 (SEQ ID NO: 111) are shown against wild-type SrKO (SEQ ID NO: 108) (all shown with the wild-type SrKO N-terminus for convenience).

DETAILED DESCRIPTION OF THE INVENTION

Figure 1:
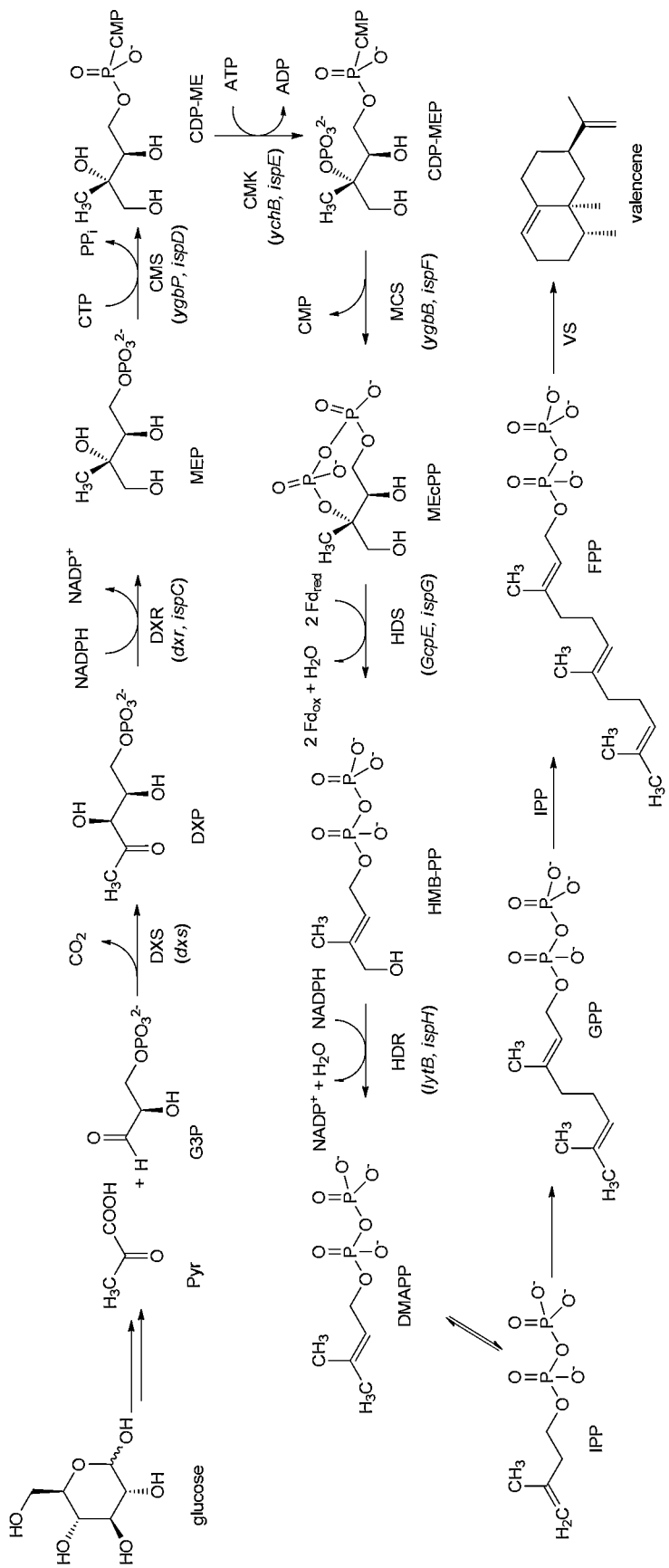
FIG. 1 shows a scheme for biosynthesis of valencene, which is a substrate for SrKO in accordance with the present disclosure.

The present invention in various aspects provides methods for making oxygenated terpenes or terpenoids in ex vivo or in cell systems. The invention further provides engineered or modified enzymes, polynucleotides, and host cells for use in such methods. The invention in various embodiments is directed to a method to produce nootkatone using an SrKO enzyme. Surprisingly, it was found that the SrKO enzyme can be used to catalyze sesquiterpene oxidation (e.g., valencene oxidation to nootkatol and nootkatone).

As used herein, SrKO refers to ent-kaurene oxidase CYP701A5 [*Stevia rebaudiana*] with Accession No AAQ63464.1 (SEQ ID NO:37). SrKO and its activity on diterpenes (and kaurene in particular) are known and are described in, for example, US 2012/0164678, which is hereby incorporated by reference in its entirety. It is a member of the CYP70 family of cytochrome p450 enzymes (CYP450). An SrKO sequence modified for expression in *E. coli* is shown as SEQ ID NO: 38. As shown herein, SrKO is active on sesquiterpene substrates (e.g., valencene), producing nootkatol and nootkatone, which are valuable terpenoid compounds. These oxygenation activities and product profiles (e.g., increasing production of nootkatone) can be further refined by mutagenesis of the SrKO using processes (and aided by in silico models) described in detail herein.

As used herein, the term "SrKO derivative" or "engineered SrKO" refers to an amino acid sequence that has substantial structural and/or sequence identity with SrKO, and catalyzes oxygenation of a sesquiterpene scaffold, such as valencene. SrKO enzymes engineered for the oxygenation of valencene are also referred to herein as "valencene oxidase" or "VO" enzymes. Generally, derivatives comprise mutated forms of SrKO having at least one mutation that increases the activity of the enzyme for the valencene substrate or for the production of nootkatone and/or other products. Some SrKO mutations are provided in Table 2. Some such additional SrKO mutations are provided in Table 6.

The term "contacting" means that the components are physically brought together, whether in vivo through co-expression of relevant protein products (e.g., sesquiterpene synthase and CYP450) in a host cell, or by adding or feeding a substrate of interest to a host cell expressing an SrKO or derivative thereof, or in vitro (or "ex vivo") by adding sesquiterpene substrate to purified P450 enzyme or cellular extract or partially purified extract containing the same. The terms in vitro and ex vivo refer to a cell free system, and may be performed in a reaction tube or well.

As used herein, "terpenes" are a large and varied class of hydrocarbons that have a simple unifying feature, despite their structural diversity. According to the "isoprene rule", all terpenes consist of isoprene (C5) units. This fact is used for a rational classification depending on the number of such units. Monoterpenes comprise 2 isoprene units and are classified as (C10) terpenes, sesquiterpenes comprise 3 isoprene units and are classified as (C15) terpenes, diterpenes comprise 4 isoprene units and are classified as (C20) terpenes, sesterterpenes (C25), triterpenes (C30) and rubber (C5)n. They occur as acyclic or mono- to pentacyclic derivatives with alcohol, ether, ester, aldehyde, or ketone groups (the so called "terpenoids"), everywhere in organisms, particularly in higher plants, and are characteristic of the individual type of plants. Terpenes such as Monoterpenes (C10), Sesquiterpenes (C15) and Diterpenes (C20) are derived from the prenyl diphosphate substrates, geranyl diphosphate (GPP), farnesyl diphosphate (FPP) and geranylgeranyl diphosphate (GGPP) respectively through the action of a very large group of enzymes called the terpene (terpenoid) synthases. These enzymes are often referred to as terpene cyclases since the product of the reactions are cyclised to various monoterpene, sesquiterpene and diterpene carbon skeleton products. Many of the resulting carbon skeletons undergo subsequence oxygenation by cytochrome p450 hydrolysase enzymes to give rise to large families of derivatives. The technical syntheses of top-selling flavours and fragrances can start from terpenes which can also serve as excellent solvents or diluting agents for dyes and varnishes. Natural or synthetic resins of terpenes are used and also many pharmaceutical syntheses of vitamins and insecticides start from terpenes. As used herein, the term "terpene" or "sesquiterpene" (for example) includes corresponding terpenoid or sesquiterpenoid compounds.

As used herein, the term "oxygenated sesquiterpene" refers to a sesquiterpene scaffold having one or more oxygenation events, producing a corresponding alcohol, aldehyde, carboxylic acid and/or ketone.

As used herein, the term "MEP pathway" refers to the (2-C-methyl-D-erythritol 4-phosphate) pathway, also called the MEP/DOXP (2-C-methyl-D-erythritol 4-phosphate/1-deoxy-D-xylulose 5-phosphate) pathway or the non-mevalonate pathway or the mevalonic acid-independent pathway. In the MEP pathway, pyruvate and D-glyceraldehyde-3-phosphate are converted via a series of reactions to IPP and DMAPP. The pathway typically involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH). The MEP pathway, and the genes and enzymes that make up the MEP pathway, are described in U.S. Pat. No. 8,512,988, which is hereby incorporated by reference in its entirety. For example, genes that make up the MEP pathway include dxs, ispC, ispD, ispE, ispF, ispG, ispH, idi, and ispA.

As used herein, the MVA pathway refers to the biosynthetic pathway that converts acetyl-CoA to IPP. The mevalonate pathway typically comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The MVA pathway, and the genes and enzymes that make up the MEP pathway, are described in U.S. Pat. No. 7,667,017, which is hereby incorporated by reference in its entirety.

As used herein, the term "cytochrome P450 reductase partner" or "CPR partner" refers to a cytochrome P450 reductase capable of regenerating the cofactor component of the cytochrome P450 oxidase of interest (e.g., SrKO) for oxidative chemistry. For example, SrCPR is a natural CPR partner for SrKO. In some embodiments, the CPR partner is not the natural CPR partner for SrKO. In some embodiments employing in vivo production of oxygenated sesquiterpene, the SrKO and SrCPR are co-expressed as separate proteins, or in some embodiments are expressed as a fusion protein.

The similarity of nucleotide and amino acid sequences, i.e. the percentage of sequence identity, can be determined via sequence alignments. Such alignments can be carried out with several art-known algorithms, such as with the mathematical algorithm of Karlin and Altschul (Karlin & Altschul (1993) Proc. Natl. Acad. Sci. USA 90: 5873-5877), with hmmalign (HMMER package) or with the CLUSTAL algorithm (Thompson, J. D., Higgins, D. G. & Gibson, T. J. (1994) Nucleic Acids Res. 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al (1990) J. Mol. Biol. 215: 403-410. BLAST polynucleotide searches can be performed with the BLASTN program, score=100, word length=12.

BLAST protein searches may be performed with the BLASTP program, score=word length=3. To obtain gapped alignments for comparative purposes, Gapped BLAST is utilized as described in Altschul et al (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups:
(1) hydrophobic: Met, Ala, Val, Leu, Ile;
(2) neutral hydrophilic: Cys, Ser, Thr; Asn, Gin;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt a-helices. Some preferred conservative substitutions within the above six groups are exchanges within the following sub-groups: (i) Ala, Val, Leu and He; (ii) Ser and Thr; (ii) Asn and Gin; (iv) Lys and Arg; and (v) Tyr and Phe.

As used herein, "non-conservative substitutions" or "non-conservative amino acid exchanges" are defined as exchanges of an amino acid by another amino acid listed in a different group of the six standard amino acid groups (1) to (6) shown above.

In one aspect, the invention provides a method for making an oxygenated product of a sesquiterpene. In various embodiments, the sesquiterpene substrate is (or the predominant sesquiterpene substrate is) valencene, germacrene (A, B, C, D, or E), farnesene, farnesol, nootkatol, patchoulol, cadinene, cedrol, humulene, longifolene, and/or bergamotene, β-ylangene, β-santalol, β-santalene, α-santalene, α-santalol, ß-vetivone, a-vetivone, khusimol, bisabolene, β-aryophyllene, Longifolene; α-sinensal; α-bisabolol, (-)-β-copaene, (-)-α-copaene, 4(Z),7(Z)-ecadienal, cedrol, cedrene, cedrol, guaiol, (-)-6,9-guaiadiene, bulnesol, guaiol, ledene, ledol, lindestrene, and alpha-bergamotene. In some embodiments, the predominant sesquiterpene substrate is valencene, and the predominant oxygenated product is nootkatone and/or nootkatol. In this context, the term "predominant" means that the particular sesquiterpene is present at a level higher than all other terpene or terpenoid species individually. In some embodiments, the predominant sesquiterpene (either the substrate or the oxygenated product after the reaction) makes up at least 25%, at least 40%, at least 50%, or at least 75% of the terpene or terpenoid component of the composition. In various embodiments involving in vivo production of oxygenated sesquiterpenes, the oxygenation product is recovered from the culture media, and can be fractionated to isolate or enrich for various components of the product, such as nootkatone. In some embodiments, Nootkatone is isolated and/or enriched, such that it makes up at least about 25%, at least about 40%, at least about 50%, at least about 60%, at least about 70%, at least about 80%, or at least about 90% of the sesquiterpene component (by weight), or makes up at least about 25%, at least about 40%, at least about 50%, at least about 60%, at least about 70%, at least about 80%, at least about 90%, or about 100% of the collective amount of nootkatol and nootkatone (by weight).

In various embodiments, the invention comprises contacting a sesquiterpene with a terpene oxidizing P450 enzyme, or derivative thereof. The contacting may take place in a host cell or in a cell free system. The substrate for oxidation (e.g., the sesquiterpene), may be produced by the cells (e.g., through metabolic flux through the MEP or MVA pathways), or alternatively fed to the host cells expressing the P450 enzyme. The oxygenated product may be recovered, or be the substrate for further chemical transformation either in the cellular system or cell free system. Table 1 below provides a list of exemplary P450 enzymes. While in certain embodiments the invention involves the use of the following P450 enzymes (optionally engineered to increase the oxygenation of valencene to nootkatone and/or nootkatol), a preferred enzyme in accordance with this disclosure is SrKO. Exemplary oxygenated sesquiterpene products obtained by these reactions in accordance with the disclosure are shown in Table 4.

TABLE 1

| # | Species | Name | Native Substrate | Native Reaction Product |
|---|---|---|---|---|
| 1 | Zingiber zerumbet | zzHO | α-humulene | 8-hydroxy-α-humulene |
| 2 | Barnadesia spinosa | BsGAO | germacrene A | germacra-1(10),4,11(13)-trien-12-ol |
| 3 | Hyoscyamus muticus | HmPO | premnaspirodiene | solavetivol |
| 4 | Latuca spicata | LsGAO | germacrene A | germacra-1(10),4,11(13)-trien-12-ol |
| 5 | Nicotiana tabacum | NlEAO | 5-epi-aristolochene | capsidiol |
| 6 | Citrus x paradisi | CpVO | valencene | nootkatol |
| 7 | Artemesia annua | AaAO | amorphadiene | artemisinic acid |
| 8 | Arabidopsis thaliana | AtKO | kaurene | kaurenoic acid |
| 9 | Stevia rebaudiana | SrKO | kaurene | kaurenoic acid |
| 10 | Pseudomonas putida | PpKO | kaurene | kaurenoic acid |
| 11 | Bacillus megaterium | BmVO | fatty acids | hydroxylated FAs |
| 12 | Pleurotus sapidus | PsVO | valencene | nootkatone |
| 13 | Pleurotus ostreatus | POLO | unknown | unknown |
| 14 | Cichorium intybus | CiVO | valencene | nootkatone |
| 15 | Helianthus annuus | HaGAO | germacrene A | germacrene A acid |

In various embodiments, the method comprises contacting the sesquiterpene with a protein comprising *Stevia rebaudiana* Kaurene Oxidase (SrKO) or derivative thereof. In some embodiments the SrKO is expressed in a host cell as described below, or is provided in a cell free system. For example, certain in vitro and in vivo systems for oxidizing terpenes with P450 enzymes are disclosed in U.S. Pat. No. 7,211,420, which are hereby incorporated by reference. McDougle D R, Palaria A, Magnetta E, Meling D D, Das A. *Functional Studies of N-terminally modified CYP2J2 epoxygenase in Model Lipid Bilayers*, Protein Sci. 2013 22:964-79; Luthra, A., Gregory, M., Grinkova, Y. V., Denisov, I. G., Sligar, S. G. (2013) "Nanodiscs in the studies of membrane-bound cytochrome P450 enzymes." Methods Mol. Biol., 987, 115-127).

In some embodiments, the SrKO derivative comprises an amino acid sequence that has from about 1 to about 50 mutations independently selected from substitutions, deletions, or insertions relative to SrKO (SEQ ID NO: 37), or relative to an SrKO enzyme modified at its N-terminus for functional expression in *E. coli* (SEQ ID NO:38 or 55) In various embodiments, the mutation or combination of mutations enhances the activity of the enzyme for oxygenation of valencene, such as the production of nootkatone. Protein modeling as described herein may be used to guide such substitutions, deletions, or insertions in the SrKO sequence.

For example, a structural model of the SrKO amino acid sequence may be created using the coordinates for P45017A1. As demonstrated herein, such a homology model is useful for directing improvement of SrKO for valencene oxygenation. Thus, in various embodiments, the SrKO derivative may have from about 1 to about 45 mutations, about 1 to about 40 mutations, about 1 to about 35 mutations, from about 1 to about 30 mutations, about 1 to about 25 mutations, from about 1 to about 20 mutations, about 1 to about 15 mutations, about 1 to about 10 mutations, or from about 1 to about 5 mutations relative to SrKO (SEQ ID NOS: 37, 38, or 55). In various embodiments, the SrKO comprises a sequence having at least 5 or at least 10 mutations with respect to SEQ ID NO: 37, 38, or 55 but not more than about 20 or 30 mutations. In various embodiments, the SrKO derivative may have about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, about 40 mutations, about 41 mutations, about 42 mutations, about 43 mutations, about 44 mutations, about 45 mutations, about 46 mutations, about 47 mutations, about 48 mutations, about 49 mutations, or about 50 mutations relative to SrKO (SEQ ID NO: 37, 38, or 55). SEQ ID NOS:37, and other WT enzymes disclosed herein, can optionally contain an Ala at position 2 where not present in the wild-type.

In these or other embodiments, the SrKO derivative may comprise an amino acid sequence having at least about 50% sequence identity, at least about 55% sequence identity, at least about 60% sequence identity, at least about 65% sequence identity, at least about 70% sequence identity, at least about 75% sequence identity, at least about 80% sequence identity, at least about 85% sequence identity, or at least about 90% sequence identity, or at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity, to SrKO (SEQ ID NO: 37, 38, or 55). In various embodiments, the SrKO derivative has higher activity for the oxygenation of valencene than the wild type enzyme, such as a higher production of oxygenated oil upon contact with valencene substrate than the wild type enzyme (SEQ ID NO:37) or the wild type enzyme as modified for functional expression in *E. coli*. For example, the SrKO derivative may comprise an amino acid sequence having at least: about 50% identity, about 51% identity, about 52% identity, about 53% identity, about 54% identity, about 55% identity, about 56% identity, about 57% identity, about 58% identity, about 59% identity, about 60% identity, about 61% identity, about 62% identity, about 63% identity, about 64% identity, about 65% identity, about 66% identity, about 67% identity, about 68% identity, about 69% identity, about 70% identity, about 71% identity, about 72% identity, about 73% identity, about 74% identity, about 75% identity, about 76% identity, about 77% identity, about 78% identity, about 79% identity, about 80% identity, about 81% identity, about 82% identity, about 83% identity, about 84% identity, about 85% identity, about 86% identity, about 87% identity, about 88% identity, about 89% identity, about 90% identity, about 91% sequence identity, about 92% sequence identity, about 93% sequence identity, about 94% sequence identity, about 95% sequence identity, about 96% sequence identity, about 97% sequence identity, about 98% sequence identity, or about 99% sequence identity to SrKO (SEQ ID NO: 37, 38, or 55).

In some embodiments, mutants are selected for an increase in production of oxygenated valencene, such as nootkatone. For example, the SrKO derivative may have one, two, three, four or more mutations at positions selected from 46, 76, 94, 131, 231, 284, 383, 390, 400, 444, 468, 488 and 499, relative to SEQ ID NO:37. For example, in some embodiments the SrKO is a derivative comprising an amino acid sequence having one or more (e.g, 2, 3, 4, or all) of the mutations selected from R76K, M94V, T131Q, F231L, H284Q, R383K, I390L, T468I, and T499N relative to SEQ ID NO:37. In some embodiments, the SrKO derivative comprises an amino acid sequence selected from SEQ ID NOS:55-61, 104, or 105, which were engineered according to this disclosure to improve activity for oxygenation of valencene (e.g., production of nootkatone). In some embodiments, the derivative comprises an amino acid sequence having from one to twenty, or from one to ten, or from one to five mutations relative to a sequence selected from SEQ ID NOS: 55-61, 104, and 105 with the proviso that the amino acid sequence has one or more mutations at positions selected from 46, 76, 94, 131, 231, 284, 383, 390, 400, 444, 468, 488 and 499 relative to SEQ ID NO:37, or the proviso that the SrKO derivative comprises an amino acid sequence having one, two, three or more (or all) of the mutations selected from R76K, M94V, T131Q, F231L, H284Q, R383K, I390L, T468I, and T499N relative to SEQ ID NO:37.

In some embodiments, the invention provides a recombinant polynucleotide encoding the SrKO derivative described above, which may be inserted into expression vectors for expression and optional purification. In some embodiments, the polynucleotide is incorporated into the genome of valencene-producing cells, such as valencene-producing *E. coli* cells.

The SrKO or derivative in various embodiments has valencene oxidase activity. Assays for determining and quantifying valencene oxidase activity are described herein and are known in the art. Assays include expressing the SrKO (or derivative) in valencene-producing cells (e.g., *E. coli* expressing FPPS and valencene synthase), and extracting the oxidized oil from the aqueous reaction media. The profile of terpenoid product can be determined quantitatively by GC/MS. Various mutations of SrKO tested for effect on valencene oxidase activity are listed in Table 2 or Table 6. Thus, in various embodiments, the SrKO may have at least about 1, at least about 2, at least about 3, at least about 4, at least about 5, at least about 6, at least about 7, at least about 8, at least about 9, or at least about 10 mutations selected from Table 2 or Table 6. In some embodiments, the SrKO derivative is a modified SrKO polypeptide comprising an amino acid sequence which has up to 25 mutations compared to the wild type protein according to SEQ ID NO: 37 (or its counterpart that is modified for expression in *E. coli*, and comprises at least the substitutions I310V, V375I or T487N in combination with at least any one or more of V375F, V375A, V375M, M120L, M120I, M120V, F129L, F129I, L114V, L114F and V121A (numbered according to SEQ ID NO:38), and optionally comprises a leader sequence (as shown in SEQ ID NO:38) supporting functional expression in *E. coli*.

TABLE 2.1

Summary of some *Stevia rebaudiana* kaurene oxidase mutations tested, numbered according to wild type SrKO (SEQ ID NO: 37) and 8rp-t20SrKO (SEQ ID NO: 38).

| No. | WT | Position SEQ ID NO: 37/ SEQ ID NO: 38 | Mutation |
|---|---|---|---|
| 1 | L | 59/47 | I |
| 2 | Y | 71/59 | H |
| 3 | M | 72/60 | K |
| 4 | T | 75/63 | A |
| 5 | A | 79/67 | E |
| 6 | K | 88/76 | R |
| 7 | T | 92/80 | C |
| 8 | M | 94/82 | V |
| 9 | V | 97/85 | L |
| 10 | V | 97/85 | I |
| 11 | S | 98/86 | N |
| 12 | Q | 112/100 | S |
| 13 | N | 118/106 | K |
| 14 | K | 124/112 | T |
| 15 | A | 128/116 | R |
| 16 | T | 131/119 | S |
| 17 | M | 135/123 | T |
| 18 | M | 135/123 | Q |
| 19 | M | 135/123 | F |
| 20 | M | 135/123 | T |
| 21 | D | 139/127 | G |
| 22 | Y | 141/129 | F |
| 23 | A | 152/140 | R |
| 24 | K | 161/149 | R |
| 25 | H | 162/150 | F |
| 26 | N | 183/171 | D |
| 27 | I | 192/180 | F |
| 28 | I | 195/183 | V |
| 29 | D | 220/208 | E |
| 30 | D | 244/232 | E |
| 31 | S | 279/267 | A |
| 32 | H | 284/272 | Q |
| 33 | S | 296/284 | C |
| 34 | I | 298/286 | L |
| 35 | Q | 306/294 | K |
| 36 | Q | 311/299 | E |
| 37 | I | 322/310 | T |
| 38 | I | 322/310 | V |
| 39 | R | 383/371 | K |
| 40 | R | 383/371 | I |
| 41 | V | 387/375 | T |
| 42 | V | 387/375 | I |
| 43 | V | 387/375 | L |
| 44 | I | 390/378 | V |
| 45 | H | 394/382 | Y |
| 46 | V | 400/388 | Q |
| 47 | V | 400/388 | M |
| 48 | H | 405/393 | D |
| 49 | L | 412/400 | I |
| 50 | V | 425/413 | D |
| 51 | V | 425/413 | K |
| 52 | F | 446/434 | L |
| 53 | G | 454/442 | A |
| 54 | S | 462/450 | A |
| 55 | L | 466/454 | M |
| 56 | G | 472/460 | A |
| 57 | M | 476/464 | L |
| 58 | M | 487/475 | G |
| 59 | T | 499/487 | N |
| 60 | P | 504/492 | K |
| 61 | I | 509/497 | L |
|  | T | 499/487 | S |
| 62 | M | 135/123 | Q |
|  | T | 499/487 | V |
| 63 | M | 135/123 | F |
|  | T | 499/487 | V |

TABLE 2.1-continued

Summary of some *Stevia rebaudiana* kaurene oxidase mutations tested, numbered according to wild type SrKO (SEQ ID NO: 37) and 8rp-t20SrKO (SEQ ID NO: 38).

| No. | WT | Position SEQ ID NO: 37/ SEQ ID NO: 38 | Mutation |
|---|---|---|---|
| 64 | M | 135/123 | F |
|  | T | 499/487 | F |
| 65 | M | 135/123 | F |
|  | T | 499/487 | M |
| 66 | M | 135/123 | F |
|  | T | 499/487 | G |

TABLE 2.2

The following mutants were evaluated in the VOI background (n22-yhcB-t30-VO1, SEQ ID NO: 110). Positions maintain numbering of SEQ ID NO: 37.

| No. | WT | Position | Mutation |
|---|---|---|---|
| 1 | A | 2 | T |
| 2 | H | 46 | R |
| 3 | E | 52 | A |
| 4 | R | 76 | K |
| 5 | M | 94 | V |
| 6 | T | 131 | K |
| 7 | T | 131 | Q |
| 8 | L | 150 | M |
| 9 | D | 191 | N |
| 10 | L | 231 | M |
| 11 | Q | 268 | T |
| 12 | E | 323 | L |
| 13 | K | 344 | D |
| 14 | R | 351 | Q |
| 15 | I | 389 | L |
| 16 | I | 389 | V |
| 17 | I | 389 | A |
| 18 | I | 390 | L |
| 19 | I | 390 | M |
| 20 | V | 400 | Q |
| 21 | I | 444 | A |
| 22 | T | 468 | I |
| 23 | T | 488 | D |
| 24 | E | 491 | K |
| 25 | I | 495 | V |

The SrKO may be expressed in a variety of host cells, either for recombinant protein production, or for sesquiterpene (e.g., valencene) oxidation. For example, the host cells include those described in U.S. Pat. No. 8,512,988, which is hereby incorporated by reference in its entirety. The host cell may be a prokaryotic or eukaryotic cell. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, such as, for example, *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. In an embodiment, the host cell is a bacterium selected from *E. coli, Bacillus subtillus*, or *Pseudomonas putida*. In an embodiment, the host cell is a yeast, and may be a species of *Saccharomyces, Pichia*, or *Yarrowia*, including *Saccharomyces cerevisiae, Pichia pastoris*, and *Yarrowia lipolytica*.

In some embodiments, the host cell produces isopentyl pyrophosphate (IPP), which acts as a substrate for the synthesis of the sesquiterpene. In some embodiments, the IPP is produced by metabolic flux (e.g., starting with a carbon source supplied to the cell) through an endogenous or heterologous methylerythritol phosphate (MEP) or mevalonic acid (MVA) pathway. In certain embodiments, the MEP or MVA pathway may be enhanced through expression of heterologous enzymes or duplication of certain enzymes in the pathway.

The MEP (2-C-methyl-D-erythritol 4-phosphate) pathway, also called the MEP/DOXP (2-C-methyl-D-erythritol 4-phosphate/1-deoxy-D-xylulose 5-phosphate) pathway or the non-mevalonate pathway or the mevalonic acid-independent pathway refers to the pathway that converts glyceraldehyde-3-phosphate and pyruvate to IPP and DMAPP. The pathway typically involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH). The MEP pathway, and the genes and enzymes that make up the MEP pathway, are described in U.S. Pat. No. 8,512,988, which is hereby incorporated by reference in its entirety. For example, genes that make up the MEP pathway include dxs, ispC, ispD, ispE, ispF, ispG, ispH, idi, and ispA. In some embodiments, the sesquiterpene is produced at least in part by metabolic flux through an MEP pathway, and wherein the host cell has at least one additional copy of a dxs ispD, ispF, and/or idi gene (e.g., dxs and idi; or dxs, ispD, ispF, and/or idi).

The MVA pathway refers to the biosynthetic pathway that converts acetyl-CoA to IPP. The mevalonate pathway typically comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The MVA pathway, and the genes and enzymes that make up the MEP pathway, are described in U.S. Pat. No. 7,667,017, which is hereby incorporated by reference in its entirety.

In some embodiments, the host cell expresses a farnesyl pyrophosphate synthase (FPPS), which produces farnesyl pyrophosphate from IPP or DMAPP. As shown in FIG. 1, farnesyl pyrophosphate is an intermediate for production of valencene. An exemplary farnesyl pyrophosphate synthase is ERG20 of *Saccharomyces cerevisiae* (NCBI accession P08524) and *E. coli* ispA. Various other prokaryotic, yeast, plant, and mammalian FPPS enzymes are known, and may be used in accordance with this aspect.

The host cell may further express a heterologous sesquiterpene synthase to produce the desired sesquiterpene, such as a valencene synthase. Several valencene synthase enzymes are known including valencene synthase from *Citrus x paradisi* or from *Citrus sinensis*. *Citrus sinensis* VS (e.g., AAQ04608.1) as well as various derivatives thereof are described in US 2012/0246767, which is hereby incorporated by reference. For example, the invention may employ an amino acid sequence of *Citrus sinensis* valencene synthase (SEQ ID NO: 12), or a derivative having from 1 to 30 mutations or from 1 to 20 or from 1 to 10 mutations with respect to the wild type amino acid sequence (SEQ ID NO:12). Such sequences may have at least 60% sequence identity, at least 70% sequence identity, at least 80% sequence identity, at least 90% sequence identity, at least 95% sequence identity, or at least about 96%, about 97%, about 98%, or about 99% sequence identity with the wild type sequence (SEQ ID NO:12). Further, valencene synthase from *Vitis vinifera* (VvVS) (SEQ ID NO: 1) has been described by Licker et al. (Phytochemistry (2004) 65: 2649-2659). In an embodiment, a valencene synthase comprising the amino acid sequence of VvVS or an engineered derivative thereof may be employed with the present invention. Various sesquiterpene synthase enzymes such as valencene synthase are known and are described in, for example, US 2012/0107893, US 2012/0246767, and U.S. Pat. No. 7,273,735, which are hereby incorporated by reference in their entireties.

For example, in some embodiments, the valencene synthase is a VvVS derivative that comprises an amino acid sequence having from about 1 to about 40 mutations, from about 1 to about 35 mutations, from about 1 to about 30 mutations, about 1 to about 25 mutations, from about 1 to about 20 mutations, about 1 to about 15 mutations, or from about 1 to about 10 mutations independently selected from substitutions, deletions, or insertions with respect to VvVS (SEQ ID NO: 1). For example, the VvVS derivative may comprise an amino acid sequence having at least about 5 or at least about 10, but less than about 30 or about 20 mutations with respect to SEQ ID NO: 1. In various embodiments, the VvVS derivative comprises an amino acid sequence that has about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, or about 40 mutations relative to VvVS (SEQ ID NO: 1). Such sequences may have at least 60% sequence identity, at least 70% sequence identity, at least 80% sequence identity, at least 90% sequence identity, at least 95% sequence identity, or at least about 96%, about 97%, about 98%, or about 99% sequence identity with SEQ ID NO:1. Exemplary mutations of VvVS are shown in Table 3.

Mutations can be guided by a homology model of *Vitis vinifera* valencene synthase (VvVS) based on the 5-epi-aristolochene synthase crystal structure as a template (PDB: 5EAT).

TABLE 3.1

Summary of *Vitis vinifera* valencene synthase mutations with respect to wild type (SEQ ID NO: 1)

| No. | WT | Position | Mutation |
|---|---|---|---|
| 1 | N | 23 | D |
| 2 | T | 37 | R |
| 3 | P | 38 | S |
| 4 | V | 42 | R |
| 5 | A | 45 | E |
| 6 | C | 46 | K |
| 7 | Q | 50 | R |
| 8 | K | 56 | E |
| 9 | K | 59 | R |
| 10 | R | 60 | K |
| 11 | K | 61 | M |
| 12 | T | 63 | R |
| 13 | T | 63 | K |
| 14 | N | 69 | Q |
| 15 | N | 69 | K |
| 16 | S | 71 | I |
| 17 | Q | 72 | R |
| 18 | L | 73 | K |
| 19 | N | 75 | E |
| 20 | F | 76 | M |
| 21 | F | 76 | L |
| 22 | V | 80 | M |
| 23 | V | 80 | L |
| 24 | V | 85 | I |
| 25 | A | 86 | S |
| 26 | Q | 91 | D |
| 27 | A | 96 | I |
| 28 | Q | 98 | E |
| 29 | Q | 98 | D |
| 30 | C | 101 | Y |
| 31 | N | 102 | H |
| 32 | S | 103 | D |
| 33 | F | 104 | D |
| 34 | F | 104 | N |
| 35 | D | 111 | E |
| 36 | N | 116 | T |
| 37 | I | 117 | S |
| 38 | I | 117 | V |
| 39 | I | 117 | T |
| 40 | G | 120 | R |
| 41 | Q | 127 | H |
| 42 | T | 130 | N |
| 43 | I | 131 | V |
| 44 | I | 135 | V |
| 45 | T | 140 | K |
| 46 | E | 142 | K |
| 47 | E | 148 | D |
| 48 | A | 149 | S |
| 49 | A | 149 | D |
| 50 | I | 151 | S |
| 51 | R | 155 | K |
| 52 | M | 157 | L |
| 53 | G | 159 | S |
| 54 | G | 159 | N |
| 55 | E | 162 | Q |
| 56 | E | 162 | K |
| 57 | A | 164 | S |
| 58 | V | 168 | T |
| 59 | G | 170 | D |
| 60 | L | 174 | M |
| 61 | A | 175 | E |
| 62 | A | 175 | D |
| 63 | K | 176 | E |
| 64 | T | 183 | K |
| 65 | A | 187 | S |
| 66 | M | 188 | L |
| 67 | E | 190 | N |
| 68 | G | 193 | K |
| 69 | A | 201 | S |
| 70 | N | 205 | E |
| 71 | R | 206 | Q |
| 72 | I | 208 | L |
| 73 | R | 209 | H |
| 74 | G | 211 | R |
| 75 | L | 212 | M |
| 76 | E | 213 | P |
| 77 | I | 221 | L |
| 78 | V | 223 | R |
| 79 | Q | 225 | D |
| 80 | Q | 225 | E |
| 81 | D | 226 | K |
| 82 | D | 226 | E |
| 83 | A | 228 | E |
| 84 | F | 229 | I |
| 85 | H | 230 | V |
| 86 | D | 231 | N |
| 87 | K | 232 | E |
| 88 | T | 233 | A |
| 89 | T | 233 | V |
| 90 | S | 247 | D |
| 91 | L | 248 | M |
| 92 | L | 248 | K |
| 93 | K | 250 | Q |
| 94 | E | 251 | K |
| 95 | S | 254 | K |
| 96 | N | 255 | E |
| 97 | A | 257 | S |
| 98 | K | 261 | A |
| 99 | E | 262 | D |
| 100 | D | 264 | G |
| 101 | Y | 280 | F |
| 102 | M | 283 | I |
| 103 | H | 284 | M |
| 104 | H | 284 | A |
| 105 | G | 285 | A |
| 106 | Y | 287 | F |
| 107 | Q | 291 | N |
| 108 | R | 294 | L |
| 109 | R | 297 | I |
| 110 | L | 299 | M |
| 111 | M | 305 | A |
| 112 | M | 305 | L |
| 113 | I | 308 | M |
| 114 | T | 318 | S |
| 115 | P | 319 | L |
| 116 | P | 319 | I |
| 117 | K | 323 | Q |
| 118 | R | 331 | K |
| 119 | D | 333 | E |
| 120 | I | 334 | E |
| 121 | I | 334 | V |
| 122 | N | 335 | K |
| 123 | N | 335 | Q |
| 124 | N | 335 | S |
| 125 | S | 336 | A |
| 126 | Y | 343 | W |
| 127 | Y | 348 | F |
| 128 | V | 349 | L |
| 129 | L | 352 | I |
| 130 | D | 353 | E |
| 131 | D | 353 | N |
| 132 | V | 354 | T |
| 133 | Y | 355 | F |
| 134 | K | 356 | E |
| 135 | K | 356 | N |
| 136 | I | 358 | V |
| 137 | E | 359 | D |
| 138 | E | 360 | Y |
| 139 | E | 363 | K |
| 140 | E | 363 | L |
| 141 | G | 366 | A |
| 142 | Y | 369 | N |

TABLE 3.1-continued

Summary of *Vitis vinifera* valencene synthase mutations with respect to wild type (SEQ ID NO: 1)

| No. | WT | Position | Mutation |
|---|---|---|---|
| 143 | R | 370 | V |
| 144 | V | 371 | I |
| 145 | H | 372 | E |
| 146 | H | 372 | P |
| 147 | A | 374 | G |
| 148 | A | 374 | L |
| 149 | E | 376 | D |
| 150 | M | 378 | I |
| 151 | N | 380 | I |
| 152 | N | 380 | K |
| 153 | R | 383 | Q |
| 154 | E | 394 | Q |
| 155 | E | 394 | D |
| 156 | E | 395 | N |
| 157 | E | 395 | G |
| 158 | H | 396 | Y |
| 159 | H | 396 | Q |
| 160 | E | 402 | D |
| 161 | R | 405 | E |
| 162 | C | 414 | R |
| 163 | L | 415 | M |
| 164 | A | 417 | L |
| 165 | T | 418 | V |
| 166 | T | 419 | H |
| 167 | V | 422 | L |
| 168 | M | 424 | V |
| 169 | A | 428 | V |
| 170 | T | 429 | S |
| 171 | T | 437 | F |
| 172 | S | 438 | G |
| 173 | D | 439 | Y |
| 174 | K | 441 | R |
| 175 | I | 442 | M |
| 176 | I | 442 | L |
| 177 | M | 443 | V |
| 178 | S | 444 | R |
| 179 | N | 447 | S |
| 180 | F | 448 | T |
| 181 | M | 453 | A |
| 182 | G | 466 | E |
| 183 | T | 469 | A |
| 184 | Q | 478 | E |
| 185 | Y | 479 | F |
| 186 | G | 480 | A |
| 187 | V | 481 | A |
| 188 | S | 482 | T |
| 189 | Y | 487 | C |
| 190 | S | 488 | E |
| 191 | E | 489 | H |
| 192 | F | 490 | I |
| 193 | F | 490 | L |
| 194 | Q | 491 | K |
| 195 | Q | 491 | N |
| 196 | Q | 493 | L |
| 197 | I | 494 | M |
| 198 | N | 496 | D |
| 199 | D | 500 | E |
| 200 | L | 506 | M |
| 201 | T | 509 | S |
| 202 | V | 511 | M |
| 203 | S | 512 | P |
| 204 | S | 512 | T |
| 205 | M | 513 | K |
| 206 | P | 514 | D |
| 207 | L | 519 | A |
| 208 | D | 527 | E |
| 209 | V | 528 | F |
| 210 | E | 532 | D |
| 211 | Q | 533 | E |
| 212 | Q | 533 | G |
| 213 | S | 535 | G |
| 214 | V | 539 | S |
| 215 | V | 542 | L |
| 216 | V | 542 | T |
| 217 | M | 543 | I |
| 218 | N | 546 | H |
| 219 | V | 550 | L |
| 220 | F | 551 | L |
| 221 | I | 552 | V |
| 222 | N | 553 | D |
| 223 | N | 553 | E |
| 224 | A | 554 | P |
| 225 | V | 555 | I |

TABLE 3.2

Summary of mutations evaluated in the Vv2M5 background (SEQ ID NO: 9).

| No. | WT | Position | Mutation |
|---|---|---|---|
| 226 | N | 18 | V |
| 227 | V | 21 | S |
| 228 | N | 23 | D |
| 229 | N | 27 | S |
| 230 | Q | 32 | H |
| 231 | I | 34 | L |
| 232 | T | 35 | S |
| 233 | T | 37 | S |
| 234 | K | 41 | S |
| 235 | V | 42 | E |
| 236 | A | 45 | E |
| 237 | K | 46 | C |
| 238 | K | 47 | M |
| 239 | Q | 50 | R |
| 240 | I | 51 | V |
| 241 | D | 53 | E |
| 242 | K | 56 | E |
| 243 | V | 67 | A |
| 244 | A | 68 | N |
| 245 | N | 69 | D |
| 246 | N | 69 | Q |
| 247 | S | 71 | L |
| 248 | Q | 72 | R |
| 249 | V | 80 | I |
| 250 | A | 86 | S |
| 251 | Q | 91 | K |
| 252 | C | 101 | Y |
| 253 | N | 102 | D |
| 254 | N | 102 | H |
| 255 | M | 110 | D |
| 256 | D | 111 | E |
| 257 | G | 112 | D |
| 258 | I | 117 | S |
| 259 | T | 130 | N |
| 260 | R | 143 | E |
| 261 | R | 145 | N |
| 262 | A | 149 | S |
| 263 | S | 152 | N |
| 264 | G | 159 | N |
| 265 | G | 159 | S |
| 266 | V | 168 | T |
| 267 | K | 176 | E |
| 268 | K | 186 | E |
| 269 | A | 187 | S |
| 270 | S | 191 | H |
| 271 | Y | 194 | P |
| 272 | H | 195 | P |
| 273 | N | 205 | E |
| 274 | L | 212 | M |
| 275 | E | 213 | P |
| 276 | W | 219 | H |
| 277 | V | 223 | I |
| 278 | D | 226 | E |
| 279 | A | 228 | E |

TABLE 3.2-continued

Summary of mutations evaluated in the Vv2M5 background (SEQ ID NO: 9).

| No. | WT | Position | Mutation |
|---|---|---|---|
| 280 | F | 229 | S |
| 281 | T | 233 | V |
| 282 | V | 245 | L |
| 283 | L | 248 | M |
| 284 | L | 256 | I |
| 285 | K | 261 | A |
| 286 | E | 262 | D |
| 287 | C | 347 | F |
| 288 | E | 363 | A |
| 289 | H | 372 | E |
| 290 | V | 377 | A |
| 291 | E | 395 | G |
| 292 | E | 395 | N |
| 293 | H | 396 | Y |
| 294 | A | 399 | T |
| 295 | C | 414 | R |
| 296 | E | 426 | D |
| 297 | S | 438 | G |
| 298 | M | 443 | I |
| 299 | T | 469 | A |
| 300 | S | 488 | E |
| 301 | K | 491 | R |
| 302 | M | 513 | K |
| 303 | A | 517 | E |
| 304 | L | 519 | V |
| 305 | E | 532 | D |
| 306 | V | 550 | L |
| 307 | N | 553 | D |

TABLE 3.3

Summary of mutations evaluated in VS2 background (SEQ ID NO: 11).

| No. | WT | Position | Mutation |
|---|---|---|---|
| 308 | P | 20 | R |
| 309 | N | 23 | D |
| 310 | I | 28 | F |
| 311 | K | 41 | P |
| 312 | K | 41 | S |
| 313 | V | 42 | D |
| 314 | R | 44 | H |
| 315 | Q | 50 | D |
| 316 | Q | 50 | R |
| 317 | E | 52 | R |
| 318 | K | 61 | M |
| 319 | N | 69 | Q |
| 320 | Q | 72 | R |
| 321 | L | 73 | K |
| 322 | A | 79 | I |
| 323 | A | 86 | S |
| 324 | H | 88 | L |
| 325 | Q | 91 | H |
| 326 | A | 96 | I |
| 327 | Q | 98 | R |
| 328 | C | 101 | Y |
| 329 | N | 102 | H |
| 330 | C | 107 | F |
| 331 | I | 117 | S |
| 332 | G | 120 | L |
| 333 | T | 140 | K |
| 334 | R | 145 | N |
| 335 | S | 152 | V |
| 336 | V | 154 | I |
| 337 | V | 154 | P |
| 338 | R | 155 | K |
| 339 | M | 157 | L |
| 340 | G | 159 | M |
| 341 | A | 175 | D |
| 342 | K | 176 | E |
| 343 | A | 177 | P |

TABLE 3.3-continued

Summary of mutations evaluated in VS2 background (SEQ ID NO: 11).

| No. | WT | Position | Mutation |
|---|---|---|---|
| 344 | L | 178 | I |
| 345 | H | 184 | Y |
| 346 | H | 184 | Q |
| 347 | A | 187 | S |
| 348 | S | 191 | H |
| 349 | H | 195 | N |
| 350 | L | 196 | P |
| 351 | A | 201 | R |
| 352 | L | 212 | M |
| 353 | E | 213 | P |
| 354 | A | 217 | Q |
| 355 | A | 228 | E |
| 356 | D | 231 | N |
| 357 | K | 232 | P |
| 358 | T | 233 | V |
| 359 | E | 236 | D |
| 360 | D | 241 | E |
| 361 | N | 255 | D |
| 362 | A | 257 | M |
| 363 | L | 276 | P |
| 364 | Y | 280 | F |
| 365 | M | 283 | I |
| 366 | V | 286 | A |
| 367 | T | 300 | M |
| 368 | T | 300 | I |
| 369 | T | 306 | L |
| 370 | T | 306 | I |
| 371 | L | 309 | I |
| 372 | A | 315 | V |
| 373 | E | 320 | D |
| 374 | K | 323 | R |
| 375 | S | 336 | T |
| 376 | E | 342 | D |
| 377 | C | 347 | L |
| 378 | A | 350 | I |
| 379 | N | 356 | H |
| 380 | E | 363 | G |
| 381 | Q | 368 | P |
| 382 | N | 380 | D |
| 383 | Q | 381 | L |
| 384 | E | 395 | G |
| 385 | A | 407 | G |
| 386 | A | 407 | S |
| 387 | C | 414 | P |
| 388 | A | 417 | I |
| 389 | A | 432 | I |
| 390 | V | 436 | L |
| 391 | I | 442 | P |
| 392 | I | 442 | L |
| 393 | S | 445 | R |
| 394 | S | 446 | M |
| 395 | T | 450 | C |
| 396 | S | 458 | T |
| 397 | H | 459 | Y |
| 398 | H | 459 | M |
| 399 | H | 467 | Q |
| 400 | T | 469 | A |
| 401 | E | 484 | P |
| 402 | Q | 485 | H |
| 403 | Q | 485 | E |
| 404 | V | 486 | A |
| 405 | Y | 487 | L |
| 406 | S | 488 | E |
| 407 | I | 494 | V |
| 408 | N | 496 | D |
| 409 | N | 496 | K |
| 410 | M | 513 | T |
| 411 | T | 523 | I |
| 412 | D | 527 | L |
| 413 | I | 529 | L |
| 414 | I | 529 | M |
| 415 | E | 532 | H |
| 416 | E | 532 | Y |
| 417 | S | 535 | A |
| 418 | R | 544 | H |

TABLE 3.3-continued

Summary of mutations evaluated in
VS2 background (SEQ ID NO: 11).

| No. | WT | Position | Mutation |
|-----|----|----------|----------|
| 419 | N  | 546      | Y        |
| 420 | N  | 546      | F        |
| 421 | A  | 548      | I        |
| 422 | V  | 550      | L        |
| 423 | V  | 555      | I        |

Thus, in various embodiments, the engineered VvVS may have at least about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, or about 40 mutations selected from Table 3. Exemplary recombinant valencene synthases Vv1M1 (SEQ ID NO:3), Vv2M1 (SEQ ID NO:5), Vv1M5 (SEQ ID NO:7), Vv2M5 (SEQ ID NO:9), and VS2 (SEQ ID NO: 11) are further depicted in FIGS. 3A-3B, including an alignment in FIG. 3B.

In certain aspects, the invention provides polynucleotides comprising a nucleotide sequence encoding a valencene synthase modified for increased expression of valencene as described above. Such polynucleotides may be expressed in host cells, either on extrachromosomal elements such as plasmids, or may be chromosomally integrated.

In various embodiments, the SrKO is expressed alongside a P450 reductase to regenerate the enzyme, or alternatively, the SrKO or derivative is expressed with the P450 reductase as a chimeric P450 enzyme. Functional expression of cytochrome P450 has been considered challenging due to the inherent limitations of bacterial platforms, such as the absence of electron transfer machinery and cytochrome P450 reductases, and translational incompatibility of the membrane signal modules of P450 enzymes due to the lack of an endoplasmic reticulum.

Accordingly, in some embodiments the SrKO is expressed as a fusion protein with a cytochrome P450 reductase partner. Cytochrome P450 reductase is a membrane protein found in the endoplasmic reticulum. It catalyzes pyridine nucleotide dehydration and electron transfer to membrane bound cytochrome P450s. Isozymes of similar structure are found in humans, plants, other mammals, and insects. Exemplary P450 reductase partners include, for example, *Stevia rebaudiana* (Sr)CPR (SEQ ID NOS: 62 and 63), *Stevia rebaudiana* (Sr)CPR1 (SEQ ID NOS: 76 and 77), *Arabidopsis thaliana* (At)CPR (SEQ ID NOS: 64 and 65), *Taxus cuspidata* (Tc) CPR (SEQ ID NOS: 66 and 67), *Artemisia annua* (Aa)CPR (SEQ ID NOS: 68 and 69), *Arabidopsis thaliana* (At)CPR1 (SEQ ID NOS: 70 and 71), *Arabidopsis thaliana* (At)CPR2 (SEQ ID NOS: 72 and 73), *Arabidopsis thaliana* (At)R2 (SEQ ID NOS: 74 and 75); *Stevia rebaudiana* (Sr)CPR2 (SEQ ID NOS: 78 and 79); *Stevia rebaudiana* (Sr)CPR3 (SEQ ID NOS: 80 and 81); *Pelargonium graveolens* (Pg)CPR (SEQ ID NO: 82 and 83).

Any of these P450s can be derivatized in some embodiments, for example, to introduce from 1 to about mutations, or from about 1 to about 10 mutations. FIG. 6B shows an alignment of amino acid sequences for *Arabidopsis thaliana* and *Artemisia annua* CPR sequences (SEQ ID NOS:72, 74, 68, 64, and 70). FIG. 6C shows an alignment of *Stevia rebaudiana* CPR sequences (SEQ ID NOS: 78, 80, 62, and 76). FIG. 6D shows an alignment of eight CPR amino acid sequences (SEQ ID NO: 74, 72, 82, 68, 80, 62, 78, and 76).

Engineering of P450 fusion proteins is disclosed, for example, in US 2012/0107893 and US 2012/0164678, both of which are hereby incorporated by reference in their entireties. In certain embodiments, the SrKO is fused to the cytochrome P450 reductase partner through a linker. Exemplary linker sequences, which are predominantly serine, glycine, and/or alanine, and optionally from one to five charged amino acids such as lysine or arginine, include, for example, GSG, GSGGGGS (SEQ ID NO: 113), GSGEAAAK (SEQ ID NO: 114), GSGEAAAKEAAAK (SEQ ID NO: 115), GSGMGSSSN (SEQ ID NO: 116), and GSTGS (SEQ ID NO: 117). The linker is generally flexible, and contains no more than one, two, or three hydrophobic residues, and is generally from three to fifty amino acids in length, such as from three to twenty amino acids in length. In other embodiments, a P450 reductase is expressed in the host cell separately, and may be expressed in the same operon as the SrKO in some embodiments. In some embodiments, the P450 reductase enzyme is expressed separately in the host cell, and the gene is optionally integrated into the genome or expressed from a plasmid.

In certain embodiments the N-terminus of the P450 enzymes may be engineered to increase their functional expression. The N-terminus of membrane-bound P450 plays important roles in enzyme expression, membrane association and substrate access. It has been reported that the use of rare codons in the N-terminus of P450 significantly improved the expression level of P450. Further, since most plant P450 enzymes are membrane-bound and hydrophobic substrates are thought to enter the enzymes through channels dynamically established between the P450 and membrane, N-terminal engineering can affect the association of the membrane and P450 and therefore the access of substrate to the enzyme. Accordingly, in an embodiment, N-terminal engineering of SrKO generates an SrKO derivative that either maintains or shows enhanced valencene oxidase activity in a host system such as *E. coli* or yeast. An exemplary N-terminal sequence is MALLLAVF (SEQ ID NO:112), and other exemplary sequences include sequences of from four to twenty amino acids (such as from four to fifteen amino acids, or from four to ten amino acids, or about eight amino acids) that are predominately hydrophobic, for example, constructed predominately of (at least 50%, or at least 75%) amino acids selected from leucine, valine, alanine, isoleucine, and phenylalanine.

In some embodiments, the SrKO is a derivative having a deletion of at least a portion of its N-terminal transmembrane region, and the addition of an inner membrane transmembrane domain from *E. coli* yhcB or derivative thereof. In these embodiments, the P450 enzyme has a more stable and/or productive association with the *E. coli* inner membrane, which reduces cell stress otherwise induced by the expression of a membrane-associated P450 enzyme. In some embodiments, the SrKO is a derivative having a deletion of from 15 to 35 amino acids of its N-terminal transmembrane domain, and the addition of from 15 to 25 amino acids of the transmembrane domain from *E. coli* yhcB or derivative thereof. In some embodiments, the N-terminal transmembrane domain of the derivative comprises the amino acid sequence MAWEYALIGLVVGIIIGAVA (SEQ ID NO:118), or an amino acid sequence having from 1 to 10 or from 1 to 5 amino acid mutations with respect to SEQ ID NO:118.

In some embodiments, the host cell further expresses one or more enzymes that divert product toward nootkatone. For example, the host cell may express an alcohol dehydrogenase enzyme producing nootkatone from nootkatol, examples of which include *Rhodococcus erythropolis* CDH (SEQ ID NO: 84), *Citrus sinensus* DH (SEQ ID NO: 86), *Citrus sinensus* DH1 (SEQ ID NO: 88), *Citrus sinensus* DH2 (SEQ ID NO: *Citrus sinensus* DH3 (SEQ ID NO: 92), *Vitis vinifera* DH (SEQ ID NO: 94), *Vitis vinifera* DH1 (SEQ ID NO: 96), *Citrus sinensus* ABA2 (SEQ ID NO: 98), *Brachypodium distachyon* DH (SEQ ID NO: 100), and *Zingiber zerumbet* SDR (SEQ ID NO: 102). The alcohol dehydrogenase may comprise an amino acid sequence having at least 70%, at least 80%, or at least 90% sequence identity to one or more of the enzymes described in this paragraph, and with the activity of converting nootkatol to nootkatone.

Sesquiterpenes (e.g., valencene and its oxygenated products) can be produced as biosynthetic products of the non-mevalonate pathway in *E. coli* comprising two modules: the native upstream pathway forming Isopentenyl Pyrophosphate (IPP) and a heterologous downstream terpenoid-forming pathway. A multivariate-modular approach to metabolic pathway engineering can be employed to optimize the production of sesquiterpenes in an engineered *E. coli*. The multivariate-modular pathway engineering approach is based on a systematic multivariate search to identify conditions that optimally balance the two pathway modules to minimize accumulation of inhibitory intermediates and flux diversion to side products.

WO 2011/060057, US 2011/0189717, US 2012/107893, and U.S. Pat. No. 8,512,988 (each of which are hereby incorporated by reference) describe methods and compositions for optimizing production of terpenoids in cells by controlling expression of genes or proteins participating in an upstream pathway and a downstream pathway. This can be achieved by grouping the enzyme pathways into two modules: an upstream (MEP) pathway module (e.g., containing one or more genes of the MEP pathway) and a downstream, heterologous pathway to sesquiterpene production. Using this basic configuration, parameters such as the effect of plasmid copy number on cell physiology, gene order and promoter strength in an expression cassette, and chromosomal integration are evaluated with respect to their effect on terpene and terpenoid (e.g., sesquiterpene) production. Expression of genes within the MEP pathway can thus be regulated in a modular method. As used herein, regulation by a modular method refers to regulation of multiple genes together. By way of example, multiple genes within the MEP pathway can be recombinantly expressed on a contiguous region of DNA, such as an operon. It should be appreciated that modules of genes within the MEP pathway, consistent with aspects of the invention, can contain any of the genes within the MEP pathway, in any order. In some embodiments, a gene within the MEP pathway is one of the following: dxs, ispC, ispD, ispE, ispF, ispG, ispH, idi, ispA or ispB. A non-limiting example of a module of genes within the MEP pathway is a module containing the genes dxs, idi, ispD and ispF, and referred to as dxs-idi-ispDF.

The manipulation of the expression of genes and/or proteins, including modules such as the dxs-idi-ispDF operon, and a FPPS-VS operon, can be achieved through methods known to one of ordinary skill in the art. For example, expression of the genes or operons can be regulated through selection of promoters, such as inducible promoters, with different strengths. Several non-limiting examples of promoters include Trc, T5 and T7. Additionally, expression of genes or operons can be regulated through manipulation of the copy number of the gene or operon in the cell.

The expression of one or more genes and/or proteins within the MEP pathway can be upregulated and/or downregulated. In certain embodiments, upregulation of one or more genes and/or proteins within the MEP pathway can be combined with downregulation of one or more genes and/or proteins within the MEP pathway. By way of example, in some embodiments, a cell that overexpresses one or more components of the non-mevalonate (MEP) pathway is used, at least in part, to amplify isopentyl diphosphate (IPP) and dimethylallyl diphosphate (DMAPP), substrates of GGPPS. In some embodiments, overexpression of one or more components of the non-mevalonate (MEP) pathway is achieved by increasing the copy number of one or more components of the non-mevalonate (MEP) pathway. In this regards, copy numbers of components at rate-limiting steps in the MEP pathway such as (dxs, ispD, ispF, idi) can be amplified, such as by additional episomal expression.

In some embodiments, the production of indole is used as a surrogate marker for sesquiterpene production, and/or the accumulation of indole in the culture is controlled to increase sesquiterpene production. For example, in various embodiments, accumulation of indole in the culture is controlled to below about 100 mg/L, or below about 75 mg/L, or below about 50 mg/L, or below about 25 mg/L, or below about 10 mg/L. The accumulation of indole can be controlled by balancing protein expression and activity using the multivariate modular approach described above, and/or is controlled by chemical means.

In other aspects, the invention provides a method for making a product containing an oxygenated sesquiterpene (as described), which comprises incorporating the oxygenated sesquiterpene prepared and recovered according to the method described above into a consumer or industrial product. For example, the product may be a flavor product, a fragrance product, a cosmetic, a cleaning product, a detergent or soap, or a pest control product (e.g., an insect repellant). In some embodiments, the oxygenated product recovered and optionally enriched by fractionation (e.g. fractional distillation) is nootkatone, and the product is a flavor product selected from a beverage, a chewing gum, a candy, or a flavor additive, or is an insect repellant.

The oxidized product can be recovered by any suitable process, including partitioning the desired product into an organic phase. The production of the desired product can be determined and/or quantified, for example, by gas chromatography (e.g., GC-MS). The desired product can be produced in batch or continuous bioreactor systems. Production of product, recovery, and/or analysis of the product can be done as described in US 2012/0246767, which is hereby incorporated by reference in its entirety. For example, in some embodiments, oxidized oil is extracted from aqueous reaction medium, which may be done by partitioning into an organic phase, e.g., using an organic solvent such as an alkane such as heptane, followed by fractional distillation. Sesquiterpene and sesquiterpenoid components of fractions may be measured quantitatively by GC/MS, followed by blending of the fractions to generate a desired nootkatone-containing ingredient for flavour (or other) applications.

In other aspects, the invention provides polynucleotides comprising a nucleotide sequence encoding a P450 derivative described herein. The polynucleotide may be codon optimized for expression in *E. coli* or yeast in some embodiments. In another example, the polynucleotide may comprise a nucleotide sequence encoding a SrKO fusion protein, optionally with a P450 reductase partner as described herein. In other embodiments, the invention provides polynucleotides comprising a nucleotide sequence encoding a sesquiterpene synthase variant described herein, which may likewise be codon optimized for expression in *E. coli* or yeast. Such polynucleotides may further comprise, in addition to sequences encoding the P450 or sesquiterpene synthase, one or more expression control elements. For example, the polynucleotide may comprise one or more promoters or transcriptional enhancers, ribosomal binding sites, transcription termination signals, and polyadenylation signals, as expression control elements. The polynucleotide may be inserted within any suitable vector, including an expression vector, and which may be contained within any suitable host cell for expression. The polynucleotide may be designed for introduction and/or protein expression in any suitable host cell, including bacterial cells and yeast cells, and may be expressed from a plasmid, or may be chromosomally integrated. In some embodiments, the recombinant nucleic acid molecule encodes an SrKO derivative with a higher activity for oxidation of valencene than the wild type enzyme (SEQ ID NO:37), and having a leader sequence as described, such as the leader sequence MALLLAVF (SEQ ID NO:117) or leader sequence derived from *E. coli* yhcB. In certain embodiments, the recombinant nucleic acid molecules further encodes either as an operon or as a fusion in frame with the SrKO derivative, an SrCPR or derivative thereof capable of regenerating the SrKO enzyme. When present as a fusion protein, the SrKO derivative and the SrCPR may be connected by a linking sequence of from 3 to 10 amino acids (e.g., 5 amino acids). In some embodiments, the linking sequence is predominately glycine, serine, and/or alanine and may comprise the sequence GSTGS.

In other aspects, the invention provides host cells producing an oxygenated sesquiterpene as described herein, and which express all of the enzyme components for producing the desired oxygenated sesquiterpene from isopentyl pyrophosphate (IPP). For example, the host cell in various embodiments expresses a farnesyl pyrophosphate synthase, a sesquiterpene synthase, and the SrKO or derivative thereof. IPP may be produced through the MEP and/or MVA pathway, which may be endogenous to the host cell or modified through expression of heterologous enzymes or duplication of certain enzymes in the pathway. Host cells include various bacteria and yeast as described herein.

In still other aspects, the invention provides sesquiterpene products produced by the methods and host cells described herein. As disclosed herein, SrKO enzyme showed unique activities by creating nootkatol and further oxidizing to the ketone, nootkatone, and produced different oxygenated terpene products including hydroxygermacra-1(10)5-diene, and murolan-3,9(11) di ene-10-peroxy.

Figure 7:
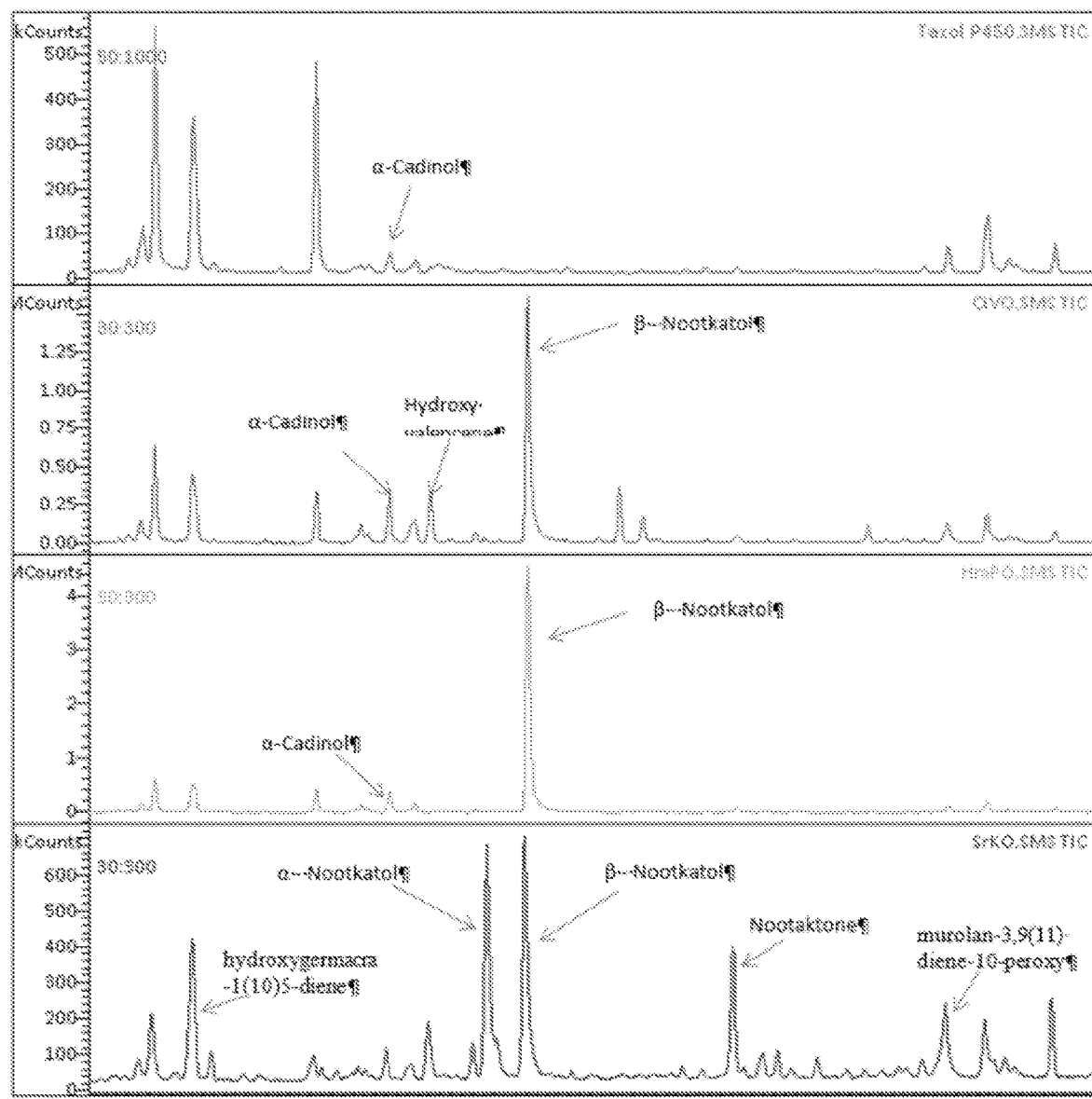
FIG. 7 provides GC-chromatographs which show the different activities of various CYP450 enzymes, as expressed in valencene-producing *E. coli* along with CPR partners as described in Example 2. Strains were cultured for four days and extracted with Methyl Tert-Butyl Ether (MTBE). 1 µl of MTBE was injected through GC-MS and the product profiles were monitored by comparing with a MS library. From top to bottom: Taxus 5-alpha hydroxylase, *Cichorium intybus* (CiVO) P450 (SEQ ID NO:50), *Hyoscyamus muticus* (HmPO) P450 (SEQ ID NO:20), and SrKO (SEQ ID NO:38).

Further, other P450 enzymes tested, including previously known sesquiterpene CYP450's or P450's having hydroxylating activity on the valencene substrate produced one of the stereoisomers (beta nootkatol) and only minor amounts of the ketone (nootkatone). Specifically, the other sesquiterpene CYP450 enzymes produced beta-nootkatol and hydroxyl valencene as major products, while Taxol CYP450 enzyme did not produce any oxygenated valencene (Table 4 and FIG. 7).

In certain aspects, the invention relates to SrKO derivative enzymes. For example, the SrKO derivative may comprise an amino acid sequence that has one or more mutations at positions selected from 46, 76, 94, 131, 231, 284, 383, 390, 400, 444, 468, 488 and 499 relative to SEQ ID NO:37. For example, in some embodiments the SrKO is a derivative comprising an amino acid sequence having one or more (two, three, four, or all) of the mutations selected from R76K, M94V, T131Q, F231L, H284Q, R383K, I390L, T468I, and T499N relative to SEQ ID NO:37. In some embodiments, the SrKO derivative comprises an amino acid sequence selected from SEQ ID NOS:55-61, 104, or 105 which were engineered according to this disclosure to improve activity for oxygenation of valencene (e.g., production of nootkatone). In some embodiments, the derivative comprises an amino acid sequence having from one to twenty mutations, or one to ten mutations, or one to five mutations relative to a sequence selected from SEQ ID NOS: 55-61, 104, or 105 with the proviso that the amino acid sequence has one, two, three or more mutations at positions selected from 46, 76, 94, 131, 231, 284, 383, 390, 400, 444, 468, 488 and 499 relative to SEQ ID NO:37, or the proviso that the SrKO derivative comprises an amino acid sequence having one, two, three or more (or all) of the mutations selected from R76K, M94V, T131Q, F231L, H284Q, R383K, I390L, T468I, and T499N relative to SEQ ID NO:37. As shown herein, these mutations increase the level of SrKOs valencene oxidation activity.

In these or other embodiments, the SrKO is a derivative having a deletion of at least a portion of its N-terminal transmembrane region, and the addition of an inner membrane transmembrane domain from *E. coli* yhcB or derivative thereof. In some embodiments, the SrKO is a derivative having a deletion of from 15 to 35 amino acids of its N-terminal transmembrane domain (relative to SEQ ID NO:37), and the addition of from 15 to 25 amino acids of the transmembrane domain from *E. coli* yhcB or derivative thereof. In some embodiments, the N-terminal transmembrane domain of the derivative comprises the amino acid sequence MAWEYALIGLVVGIIIGAVA (SEQ ID NO:118), or an amino acid sequence having from 1 to 10 or from 1 to 5 amino acid mutations with respect to SEQ ID NO:118.

In still other aspects, the invention provides a method of preparing the modified SrKO polypeptide, wherein the method comprises the steps of: (i) culturing a host cell expressing the modified polypeptide under conditions which permit expression of the polypeptide; and (ii) optionally recovering the polypeptide.

In still other aspects, the invention provides a method of producing an oxygenated sesquiterpene comprising the steps of: (i) providing the modified SrKO polypeptide, (ii) contacting a sesquiterpene with the modified SrKO polypeptide, and (iii) recovering the produced oxygenated sesquiterpene. The method may further comprise providing a CPR enzyme for regenerating the SrKO cofactor (e.g., SrCPR). In some embodiments, the oxygenated sesquiterpene is recovered as an oil. In some embodiments, the sesquiterpene is valencene. In some embodiments, the oxygenated sesquiterpene comprises hydroxygermacra-1(10)5-diene, murolan-3,9(11) diene-10-peroxy, nootkatol, and nootkatone. In some embodiments, the predominant oxygenated product is nootkatone and/or nootkatol.

Figure 8A:
FIGS. 8A and 8B illustrate a homology model of SrKO and its active site. The SrKO homology model is based on the known mutant P45017A1 (the crystal structure of membrane-bound cytochrome P450 17 A1 as disclosed in DeVore N M and Scott E E (*Nature*, 482, 116-119, 2012), which catalyzes the biosynthesis of androgens in human. The position of the heme is shown as sticks.
Figure 8B:
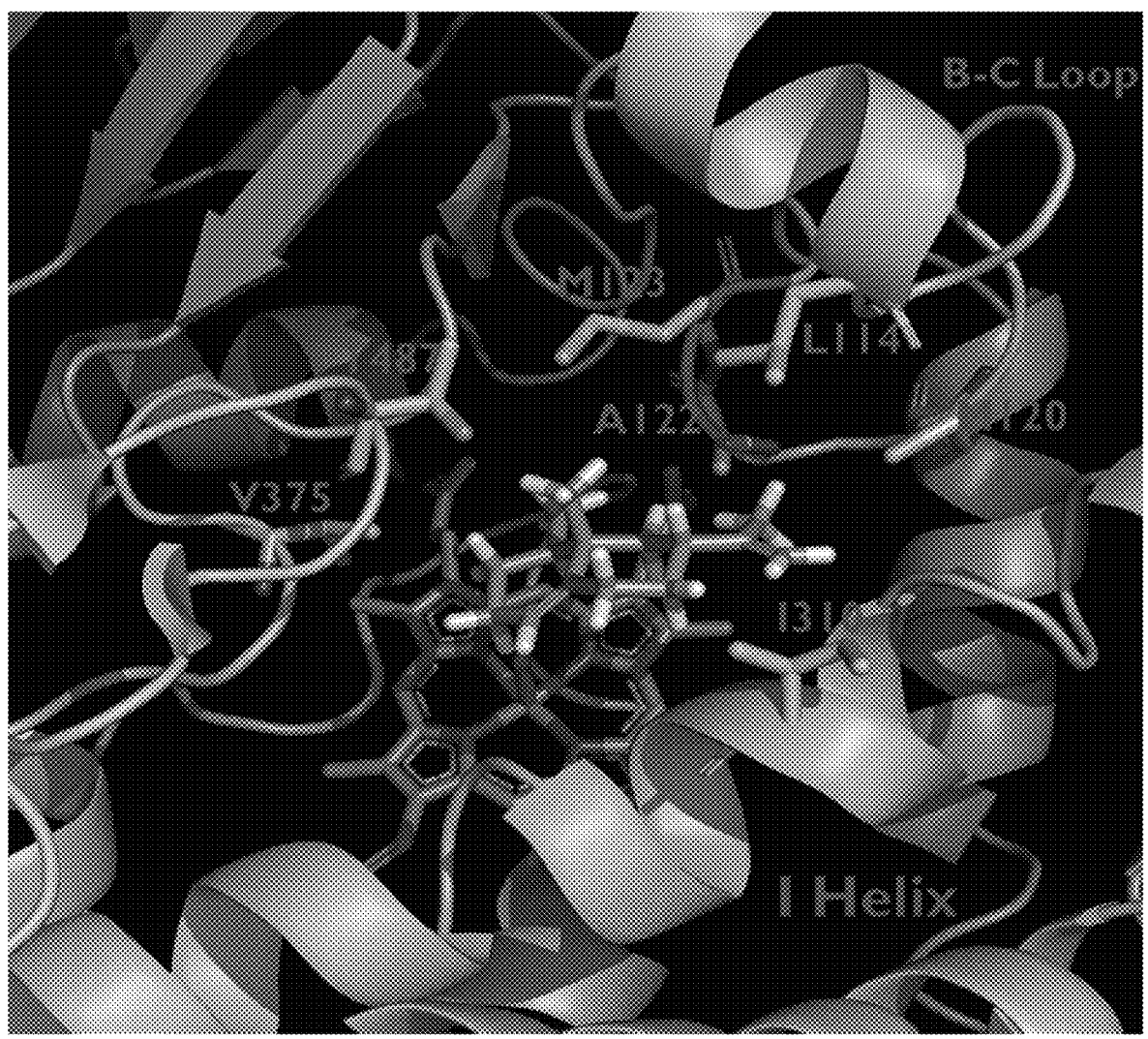

In another aspect, there is provided an SrKO crystal model structure (CMS) based on the structural coordinates of P45017A1, with an amino acid sequence of SrKO or derivative described herein. The CMS comprises a terpene binding pocket domain (TBD) that comprises a terpene binding pocket (TBP) and a terpene (e.g., valencene) bound to the TBD. FIGS. 8A and 8B. This SrKO crystal model structure (CMS) facilitates in-silico testing of SrKO derivatives.

Thus, in still other embodiments, the invention provides a method of screening for a terpene capable of binding to a TBD wherein the method comprises the use of the SrKO CMS. In another aspect, the invention provides a method for screening for a terpene capable of binding to the TBP, and the method comprises contacting the TBP with a test compound, and determining if said test compound binds to said TBP. In some embodiments, the method is to screen for a test compound (e.g., terpenes) useful in modulating the activity of a SrKO enzyme.

In another aspect, the invention provides a method for predicting, simulating or modelling the molecular characteristics and/or molecular interactions of a terpene binding domain (TBD) comprising the use of a computer model, said computer model comprising, using or depicting the structural coordinates of a terpene binding domain as defined above to provide an image of said ligand binding domain and to optionally display said image.

EXAMPLES

Example 1: Construction of Sesquiterpene Precursor (Valencene) Producing *E. coli* Strain

*E. coli* overexpressing upstream MEP pathway genes dxs, ispD, ispF, and idi was created, which facilitates flux to the isoprenoid precursor isopentyl-pyrophosphate (IPP) supporting more than 1 g/L titers of a heterologous diterpenoid product (3). Strains were constructed producing a variety of terpenoids including mono- and sesquiterpenes by replacing the geranylgeranyl pyrophosphate synthase (GGPS) and diterpene synthase with a farnesyl pyrophosphate synthase (FPPS) and sesquiterpene synthase or a geranyl pyrophosphate synthase (GPPS) and monoterpene synthase. For developing a sesquiterpene producing strain to test the CYP450s for novel oxygenated terpenes, a valencene synthase enzyme was cloned and expressed in the MEP pathway overexpressed *E. coli* strain. The high substrate flux helps identify the activity of the CYP450. Previously, research on an oxygenated taxadiene producing strain showed a significant drop in the productivity upon transferring the CYP450 pathway to the taxadiene producing strain (300 mg/L to ~10 mg/L).

Further, multivariate modular metabolic engineering (MMME) was applied for balancing the pathway for high level production of valencene. Naturally occurring valencene synthases, such as that from *Vitis vinifera*, often perform sub-optimally (~5 mg/L) even after MMME optimization, compared to previous results obtaining 100's of mg/L diterpenoids. Enzymes involved in the sesquiterpene biosynthesis can be difficult to express in *E. coli*, and also are deficient in kinetics relative to those involved in primary metabolism (17).

A homology model for the *Vitis vinifera* valencene synthase (VvVS) was constructed using the BioLuminate® software package (Schrodinger, Inc.) with the 5-epi-aristolochene synthase crystal structure as a template (PDB: 5EAT). Further, to identify the natural mutational landscape of terpene synthases, an extensive multiple sequence alignment incorporating hundreds of related terpene synthase sequences was created. Using this information, mutations were designed using a combination of back-to-consensus, in silico energetics, and structural analysis. Back-to-consensus mutations have been shown to be an important tool for improving stability (19,20) and expression (21). Energetics calculations based on atomic force-field models in BioLuminate were used to assess the ΔΔG of folding for individual mutations predicted for positions with low solvent-accessible surface area, which were predicted to affect folding and stability.

By applying the MMME approach, a balanced upstream and downstream valencene production strain was identified incorporating a codon-optimized version of VvVS on a plasmid with a p15A origin of replication and a T7 promoter. This strain background was then used to screen designed synthase enzyme mutations. Using the aforementioned protein engineering tools we designed over 200 unique point mutations (Table 3) which were then constructed in the p15A-T7 screening plasmid using site-directed mutagenesis. Mutated enzyme variants were transformed into the screening strain, triplicate colonies were cultured in selective LB cell culture medium overnight, and then inoculated into a minimal R-medium and cultured for four days at 22° C. Cultures were extracted using methyl tert-butyl ether (MTBE) and analyzed by combined gas chromatography/mass spectrometry for productivity of valencene.

Figure 2:
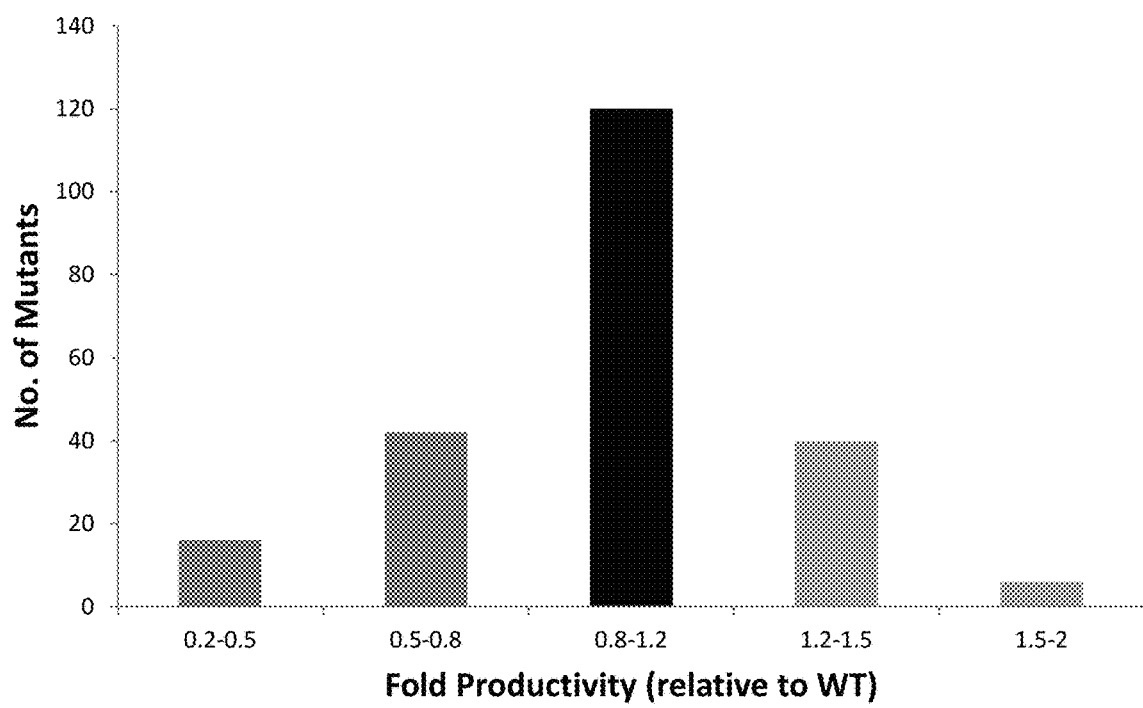
FIG. 2 depicts the fold productivities for site-directed mutants made to VvVS. 46 of the 225 point mutations convey an average improvement in productivity of valencene of at least 20% compared to the wild-type WT VvVS.

Approximately one-fifth of the designed point mutations increased valencene productivity in our screening strain by at least 20% (FIG. 2). Beneficial point mutations were then strategically combined to confer increasingly advantageous phenotypes. Recombined valencene synthase sequences are provided as Vv1M1 (Mutations—R331K, I334E, N335S, V371I, A374L, T418V, S482T, S512P, K356N, Q491K, E394D, A428V, Y348F, T318S, L352I, I442L, A554P), Vv2M1 (Mutations-R331K, I334E, N335S, V371I, A374L, T418V, S482T, S512P, K356N, Q491K, E394D, A428V, V542T, G480A, M305L, K441R, A554P), Vv1M5 (Mutations—R331K, I334E, N335S, V371I, A374L, T418V, S482T, S512P, K356N, Q491K, E394D, A428V, Y348F, T318S, L352I, I442L, A554P, H284M, C46K, F448T, Q533E), and Vv2M5 (Mutations—R331K, I334E, N335S, V371I, A374L, T418V, S482T, S512P, K356N, Q491K, E394D, A428V, V542T, G480A, M305L, K441R, A554P, H284M, C46K, F448T, Q533E) (FIGS. 3A-3B). When either of these enzymes was overexpressed in our MEP pathway strain with dxs-idi-ispDF overexpressed, and balanced using MMME, the titers of valencene obtained were sufficient to motivate incorporation of P450 enzymes to test their ability to catalyze the formation of oxygenated valencene. Titers of valencene before P450 incorporation were about 30 mg/L.

Example 2: Functional Activity of CYP450 Library on Valencene Scaffold

Valencene was used as a model system to validate the power of CYP450-based oxygenation chemistry for production terpene chemicals.

Figure 5A:
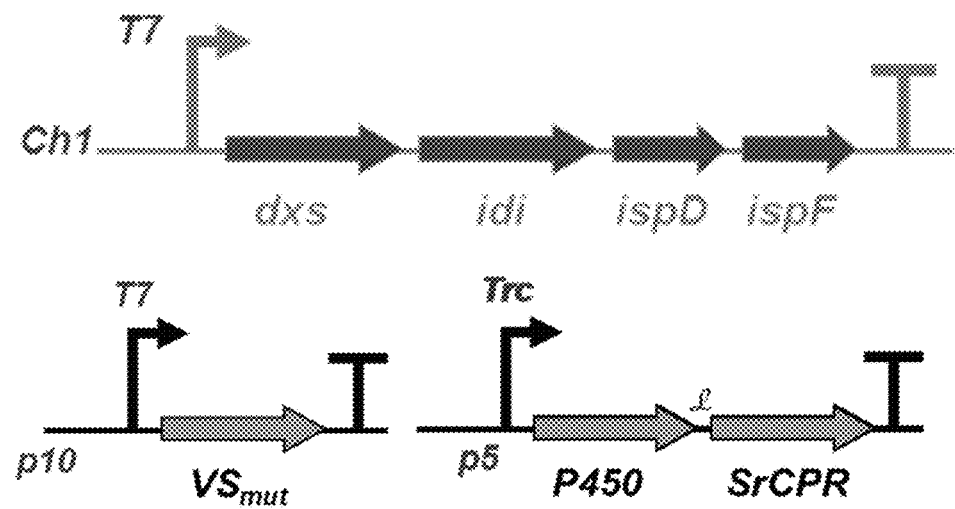
FIGS. 5A and 5B depict construct designs for expression of MEP, terpene and terpenoid synthases, and P450 enzymes in *E. coli*.
Figure 5B:
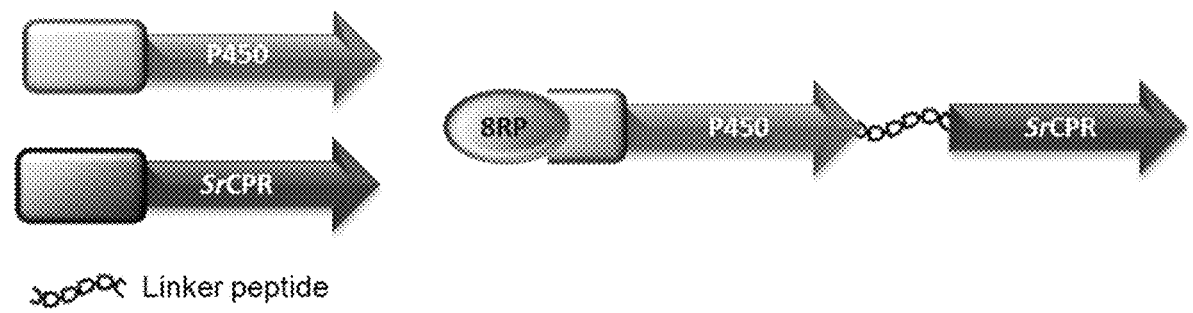

The CYPP450 candidate screening was conducted using the valencene producing *E. coli* strains as host background. For constructing the CYP450 for functional expression, a proprietary plasmid system, p5Trc (plasmid derived from pSC101) was used to construct a plasmid containing the candidate P450 fused to an N-terminal truncated *Stevia rebaudiana* cytochrome P450 reductase (SrCPR) through a flexible 5-amino acid linker (GSTGS, SEQ ID NO:117). The sequences of the various candidate P450s are shown in FIGS. 4A-4B. The candidate CYP450's were analyzed for N-terminal membrane associating regions which were truncated and a 8-amino acid leader sequence (MALLLAVF, SEQ ID NO:112) was added to the fusion (FIGS. 5A and 5B). CPR red/ox partners from *Arabidopsis thaliana* and *Taxus cuspidata* were also prepared in similar genetic constructions. Since the native SrCPR was effective, the level of activity of these constructs was not determined. The sequences of the various CPR red/ox partners are shown in FIG. 6A to FIG. 6D. Following transformation of p5Trc-CYP450-L-SrCPR to valencene producing strain, the strains were cultured overnight at in antibiotic selective LB media. These cultures were then used to inoculate 2 mL antibiotic selective R-media cultures in hungate tubes with 15 g/L glycerol and 0.1 mM IPTG which were subsequently cultured for 4-days at 22° C. before being extracted with methyl tert-butyl ether (MTBE).

A set of CYP450 enzymes, from those listed in Table 4, was selected and classified for both sesqui- and diterpene oxygenation in this *E. coli* system. Among the various CYP450 enzymes tested for oxygenation on valencene, kaurene oxidase from *Stevia rebaudiana* (SrKO) (16) was discovered to have a unique oxygenation chemistry on the valencene scaffold. SrKO natively oxidizes the diterpene (−)-kaurene at the C19 position to (−)-kaurenoic acid. SrKO enzyme showed unique activities in the present studies by creating different stereoisomers of the hydroxylated product (alpha and beta nootkatol and further oxidizing to the ketone, nootkatone), and produced different oxygenated terpene products including hydroxygermacra-1(10)5-diene, murolan-3,9(11) diene-10-peroxy, in addition to the alpha-nootkatol, beta-nootkatol, and nootkatone. Other P450's, including the previously known sesquiterpene CYP450's for hydroxylating valencene produced only one of the isomers (beta nootkatol) and only detectable amounts of ketone (nootkatone). Specifically, the other sesquiterpene CYP450 enzymes produced beta-nootkatol and hydroxyl valencene as major products while another diterpene CYP450 enzymes (e.g., Taxus 5-alpha hydroxylase) produced nootkatol as only a minor (detectable) product (Table 4 and FIG. 7).

TABLE 4

Major Products Formed From Valencene by Select P450 Enzymes in *E. coli*

| SPECIES | NAME | MAJOR PRODUCTS |
|---|---|---|
| *Cichorium intybus* | CiVO | β-nootkatol, α-cadinol, hydroxyl valencene. |
| *Hyoscyamus muticus* | HmPO | β-nootkatol, α-cadinol, hydroxyl valencene, nootkatone |
| *Latuca spicata* | LsGAO | β-nootkatol, α-cadinol, isovalencenol, nootkat-11-en-10-ol. |
| *Barnadesia spinosa* | BsGAO | β-nootkatol, α-cadinol, isovalencenol. |
| *Nicotiana tabacum* | NtEAO | α-cadinol, nootkat-11-en-10-ol. |
| *Stevia rebaudiana* | SrKO | α-nootkatol, hydroxygermacra-1(10)5-diene, β-nootkatol, nootkatone, murolan-3,9(11) diene-10-peroxy |
| *Zingiber zerumbet* | ZzHO | α-cadinol, nootkat-11-en-10-ol. |
| *Citrus x paradisi* | CpVO | α-cadinol, nootkat-11-en-10-ol. |
| *Mentha spicata* | MsL6OH | α-cadinol. |
| *Nicotiana tabacum* | NtVO | α-cadinol, nootkat-11-en-10-ol. |
| *Solanum tuberosum* | StVO | α-cadinol, β-nootkatol, globulol. |
| *Arabidopsis thaliana* | AtKO | α-cadinol, nootkat-11-en-10-ol. |
| *Cichorium intybus* | Ci2VO | β-nootkatol, α-cadinol, isovalencenol. |
| *Artemesia annua* | AaAO | α-cadinol, murolol, nootkat-11-en-10-ol. |
| Taxus 5-alpha hydroxylase P450 | | α-cadinol |

Example 3: Structural and Mutational Studies of SrKO

Once the unique activities of SrKO were identified, experiments were conducted to improve its ability to conduct its diverse oxidation of valencene. The crystal structure for SrKO has not been described. Blast search of SrKO against RCSB Protein Data Bank shows the sequence identity of SrKO to P450 enzymes with crystal structures are low (~20%). Given the conservative folding structures of P450s regardless of its low sequence identity, state-of-the-art protein modeling tools were used to build on SrKO. The crystal structure of membrane-bound cytochrome P450 17 A1 (see DeVore N. M., Scott E. E., *Nature*, 482, 116-119, 2012) which catalyses the biosynthesis of androgens in human was selected as the template for model development. Using BioLuminate protein modeling software, a homology model was developed (FIG. 8A) such that the positioning of key residues and characteristic motifs (see Gotoh O., *J. Biol Chem*, 267, 83-90, 1992) aligned well with the template. Furthermore, a homology model for SrKO which included the prosthetic heme-iron complex was also constructed. AutoDock VINA was then used to create an ensemble of possible binding modes for valencene in the SrKO active site (FIG. 8B) (29).

In addition, a Blast search of SrKO against NCBI non-redundant protein sequence library returned no orthologs with sequence identity greater than 80% (except the SrKO itself). The top hits are listed in the Table 5.

TABLE 5

BLAST search with SrKO in preparation of Homology Model

| Enzyme Name | Species | Sequence Identity | Accession |
|---|---|---|---|
| kaurene oxidase | *Stevia rebaudiana* | 99% | AAQ63464.1 |
| ent-kaurene oxidase 2 | *Lactuca sativa* | 79% | BAG71198.1 |
| ent-kaurene oxidase 1 | *Lactuca sativa* | 71% | BAG71197.1 |
| ent-kaurene oxidase | *Ricinus communis* | 63% | XP 002510288.1 |

Once the unique activities of SrKO were identified, experiments were conducted to improve its ability to conduct its diverse oxidation of valencene. Using the back-to-consensus mutagenesis strategy, a multiple sequence alignment of P450 enzymes was constructed including sequences (after clustering and elimination of sequences with greater than 90% identity) from a BLAST search of the Uniref100 database using 4 seed kaurene oxidase genes, from a BLAST search of the bacterial proteome using $P450_{Bm3}$, $P450_{CAM}$, and $P450_{eryF}$ as seed genes, and the most closely related SrKO homologs. Based on the homology model, the multiple sequence alignment, and the literature, various point mutations and double mutations were designed and tested. These cytochrome P450 derivatives were assessed for improvements in total oxygenated terpene productivity (e.g., total of the major peaks observed by GC/MS) in the in vivo testing system described above. Mutagenesis on active site positions guided by the model revealed several variants with significantly improved oxygenated products (Table 6 and Table 7 below).

TABLE 6

Binding pocket mutations and its fold productivity of total oxygenated oil as compared to the SrKO of SEQ ID NO: 38

| Mutant # (Table 2) | Mutants (numbered according to SEQ ID NO: 38) | Fold productivity |
|---|---|---|
| 38 | I310V | 1.5 |
| 37 | I310T | 0.0 |
| 42 | V375I | 1.4 |
| 41 | V375T | 0.0 |
| 19 | M123F | 0.0 |
| 20 | M123T | 0.3 |
| 18 | M123Q | 0.0 |
| 59 | T487N | 2.5 |
| 66 | M123F_T487G | 0.0 |
| 63 | M123F_T487V | 0.0 |
| 62 | M123Q_T487V | 0.0 |
| 59 | T487N_V375F | 2.2 |
| 59 | T487N_V375A | 1.8 |
| 59 | T487N_V121A | 2.0 |
| 59 | T487N_V375M | 1.9 |
| 59 | T487N_M120L | 1.8 |
| 59 | T487N_M120I | 1.8 |
| 59 | T487N_L114V | 1.4 |
| 59 | T487N_F219L | 3.5 |
| 59 | T487N_M120V | 1.1 |
| 59 | T487N_F219I | 3.3 |
| 59 | T487N_L114F | 1.2 |

TABLE 7

Non-binding pocket point mutations and productivity of total oxygenated oil compared to the SrKO of SEQ ID NO: 38

| Mutant # (Table 2) | Mutants (numbered according to SEQ ID NO: 38) | Fold productivity |
|---|---|---|
| 53 | G442A | 0.849153 |
| 55 | L454M | 0.717318 |
| 44 | I378V | 0.349005 |
| 47 | V388M | 0.792428 |
| 9 | V85I | 0.795913 |
| 51 | V413K | 0.902039 |
| 60 | P492K | 0.131657 |
| 40 | R371I | 0.657808 |
| 7 | T80C | 0.342501 |
| 23 | A140R | 0.014872 |
| 2 | Y59H | 0.406787 |
| 5 | A67E | 0.937429 |
| 8 | M82V | 1.585588 |
| 11 | S86N | 0.977752 |
| 22 | Y129F | 0.686276 |
| 24 | K149R | 0.990776 |
| 29 | D208E | 0.853446 |
| 31 | S267A | 0.79152 |
| 32 | H272Q | 0.958227 |
| 33 | S284C | 0.652348 |
| 39 | R371K | 1.443497 |
| 45 | H382Y | 0.609951 |
| 46 | V388Q | 0.924043 |
| 49 | L400I | 0.682775 |
| 50 | V413D | 0.039261 |
| 52 | F434L | 0.793926 |
| 57 | M464L | 0.689696 |
| 58 | M475G | 0.573906 |
| 61 | I497L | 0.679949 |
| 15 | A116R | 0.216353 |
| 1 | L47I | 0.88992 |
| 25 | H150F | 0.666723 |

Example 4: Isolation and Evaluation of Nootkatone

The product derived from oxidation of valencene by the cytochrome P450 enzyme SrKO (SEQ ID NO:38) was analysed by GC/MS (Agilent 6800; Column: Rtx-0.32 mm×60 m×1.0 μm film thickness; GC Temp. Program: 40° C. for 5 min, increased at 4° C./min to 300° C. and held for 30 min.) resulting in the data provided in Table 8A and 8B.

TABLE 8A

SrKO oxidation of valencene

| Ret.Time | Compound Name | CAS # | GC-FID Area % |
|---|---|---|---|
| 33.762 | dodecane | 112-40-3 | 6.70 |
| 35.440 | glyceryl diacetate I | | 5.26 |
| 38.767 | triacetin | 102-76-1 | 4.48 |
| 39.518 | unknown | | 10.17 |
| 40.176 | unknown | | 7.52 |
| 42.012 | unknown | | 2.53 |
| 44.437 | unknown | | 20.25 |
| 44.816 | valencene | 4630-07-3 | 1.97 |
| 45.546 | nootkatene | 5090-61-9 | 1.09 |
| 46.260 | unknown | | 2.14 |
| 46.395 | unknown | | 6.77 |
| 46.869 | unknown | | 4.01 |
| 47.394 | germacrene D-4-ol | 74841-87-5 | 1.23 |
| 48.273 | unknown | | 1.86 |
| 49.659 | T-muurolol | 19912-62-0 | 0.69 |
| 49.753 | an unknown sesquiterpene | | 0.56 |
| 50.336 | an unknown sesquiterpene | | 0.58 |
| 51.025 | epinootkatol (or alpha nootkatol) | 50763-66-1 | 1.96 |
| 51.430 | Nootkatol (or beta nootkatol) | 50763-67-2 | 3.54 |
| 54.138 | nootkatone | 4674-50-4 | 15.87 |
| 54.501 | 6-isopropenyl-4,8a-dimethyl-4a,5,6,7,8,8a-hexahydro-2(1H)-naphthalenone | 76784-84-4 | 0.84 |
| | TOTAL | | 100.00 |

TABLE 8B

SrKO oxidation of valencene

| Ret.Time | Compound Name | CAS # | GC-FID Area % |
|---|---|---|---|
| 33.763 | dodecane | 112-40-3 | 7.26 |
| 35.470 | glyceryl diacetate I | | 7.07 |
| 38.773 | triacetin | 102-76-1 | 6.19 |
| 39.526 | unknown | | 11.56 |
| 40.179 | unknown | | 8.10 |
| 44.440 | unknown | | 23.95 |
| 44.821 | valencene | 4630-07-3 | 6.88 |
| 45.545 | nootkatene | 5090-61-9 | 2.22 |
| 46.404 | unknown | | 5.08 |
| 46.879 | unknown | | 3.66 |
| 47.399 | germacrene D-4-ol | 74841-87-5 | 2.89 |
| 48.279 | unknown | | 2.27 |
| 49.665 | T-muurolol | 19912-62-0 | 0.94 |
| 50.342 | an unknown sesquiterpene | | 1.71 |
| 51.027 | epinootkatol | 50763-66-1 | 2.48 |
| 51.444 | nootkatol | 50763-67-2 | 5.24 |
| 54.152 | nootkatone | 4674-50-4 | 2.49 |
| | TOTAL | | 100.00 |

Similar analysis was conducted on the product produced by SrKO derivatives. It was confirmed that product profiles are comparable, and that the major products of nootkatone, nootkatol can be produced at higher levels based on mutagenesis of SrKO.

The oxidized oil product can then be extracted from the aqueous reaction medium using an appropriate solvent (e.g., heptane) followed by fractional distillation. The chemical composition of each fraction can be measured quantitatively by GC/MS. Fractions can be blended to generate the desired nootkatol and/or nootkatone ingredients for use in flavour or other applications.

Verification of acceptability can be carried out by direct comparison to a reference nootkatone flavouring product (for example, an existing natural flavouring commercial product obtained from Frutarom) with analysis provided in Table 9.

TABLE 9

Analysis of commercially available natural flavouring nootkatone from Frutarom

| Ret. Time | Compound Name | CAS # | GC-FID Area % |
|---|---|---|---|
| 42.307 | limonene glycol | 1946-00-5 | 0.201 |
| 42.792 | decanoic acid | 334-48-5 | 0.115 |
| 49.405 | valencene | 4630-07-3 | 0.039 |
| 50.362 | delta-cadinene | 483-76-1 | 0.268 |
| 52.757 | alpha-elemol | 639-99-6 | 2.178 |
| 53.11 | spathulenol | 6750-60-3 | 0.264 |
| 53.423 | caryophyllene oxide | 1139-30-6 | 0.394 |
| 53.748 | viridiflorol | 552-02-3 | 0.061 |
| 54.225 | unknown sesquiterpenoid (MW = 220, tent) | | 0.113 |
| 54.853 | unknown | | 2.985 |
| 55.386 | unknown | | 2.251 |
| 55.97 | T-muurolol | 19912-62-0 | 0.399 |
| 56.192 | bulnesol | 22451-73-6 | 0.722 |
| 56.523 | 7(11), 4b-selinenol; tentative | | 1.425 |
| 56.65 | unknown (MW = 232, tent) | | 0.663 |
| 56.937 | beta-sinensal | 3779-62-2 | 0.914 |
| 57.449 | unknown | | 0.285 |
| 57.589 | cedrenal; tentative | | 0.438 |
| 58.189 | unknown sesquiterpenoid(s) | | 1.077 |
| 58.73 | unknown sesquiterpenoids (MW = 220, 222, tent) | | 0.537 |
| 59.102 | beta, gamma-nootkatone | 35936-67-5 | 1.805 |
| 59.32 | myristic acid | 544-63-8 | 0.058 |
| 59.537 | 1,10-dihydronootkatone | 20489-53-6 | 0.582 |
| 59.75 | a nootkatone isomer | | 0.442 |
| 60.507 | nootkatone isomers (2); tentative | | 0.812 |
| 60.782 | unknowns (2) | | 0.605 |
| 61.034 | hexadecanal | 629-80-1 | 0.302 |
| 62.93 | nootkatone | 4674-50-4 | 74.287 |
| 63.057 | 3,11-eudesmadiene-2-one (5S,7R,10R) | 86917-81-9 | 1.909 |
| 63.14 | unknown (MW = 234, tent) | | 0.18 |
| 63.26 | unknown (MW = 232, tent) | | 0.105 |
| 64.112 | heptadecanal | 629-90-3 | 0.344 |
| 64.403 | unknown sesquiterpenoid | | 0.446 |
| 65.16 | unknown sesquiterpenoid | | 0.147 |
| 65.384 | palmitic acid | 57-10-3 | 0.154 |
| 65.599 | alpha-camphorene | 532-87-6 | 0.249 |
| 65.75 | unknown(s) | | 0.054 |
| 65.878 | dehydro-alpha-vetivenone; tentative | | 0.115 |
| 66.056 | nootkatone, 9-oxo | 86925-44-2 | 0.172 |
| 66.371 | ethyl palmitate | 628-97-7 | 0.185 |
| 66.856 | cis-9-octadecenal | 2423-10-1 | 0.239 |
| 66.986 | unknown sesquiterpenoids | | 0.114 |
| 67.556 | octadecanal | 638-66-4 | 0.096 |
| 74.551 | osthol | 484-12-8 | 0.367 |
| 80.543 | isomerazin | 1088-17-1 | 0.112 |
| 84.671 | unknown (MW = 298) | | 0.07 |
| | | TOTAL | 99.28 |

Example 5: N-Terminal Anchor Engineering

Figure 9:
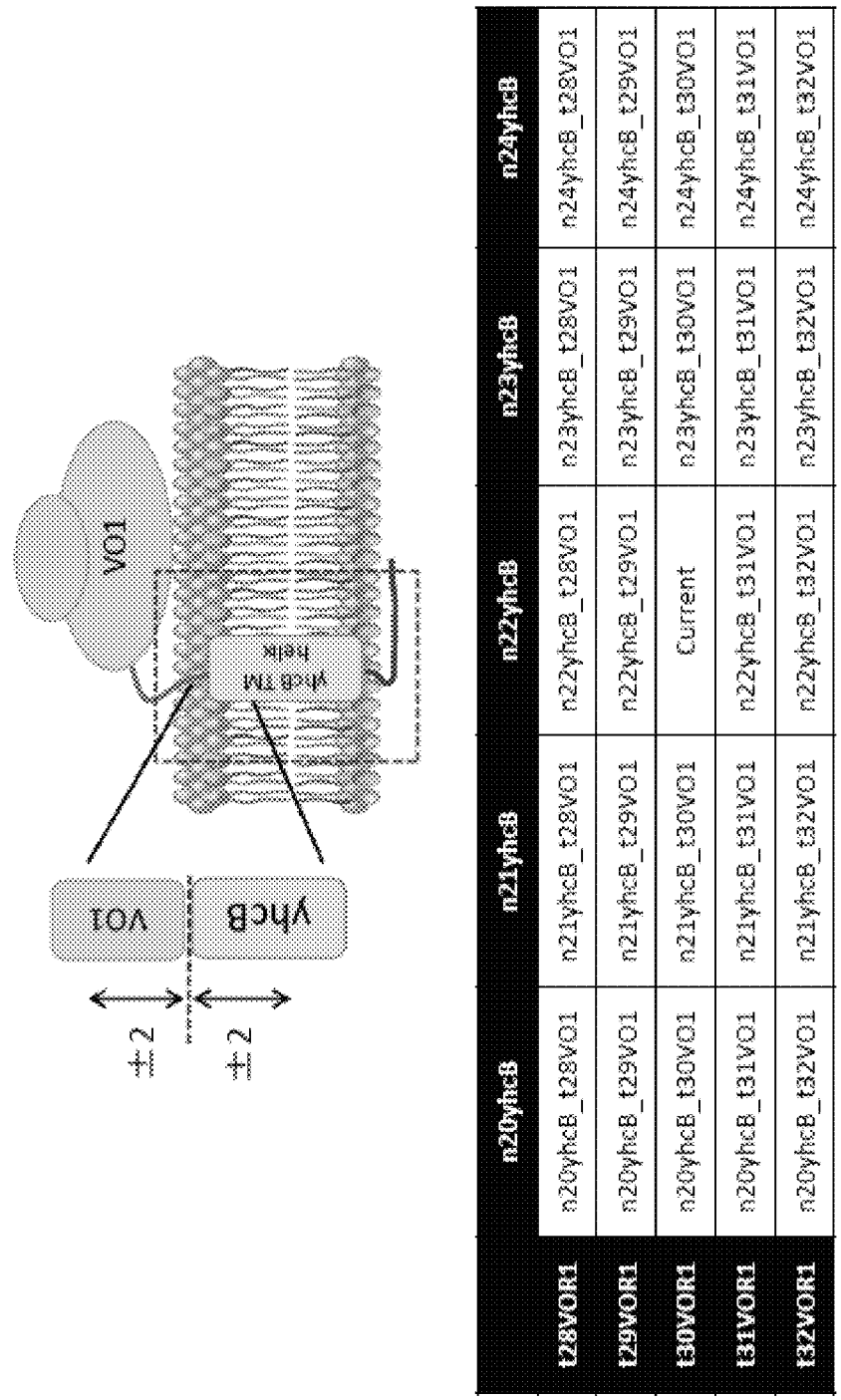
FIG. 9 shows optimizing the valencene oxidase (VO)N-terminal membrane anchor. The N-terminus of *E. coli* yhcB was selected as a membrane anchor sequence, which provides a single-pass transmembrane helix. The length of the anchor (from 20 to 24 amino acids) and the VO N-terminal truncation length (from 28 to 32 amino acids) were screened for improvements in oxygenation titer.

To optimize membrane interaction of the initial SrKO variants (referred to in these examples as Valencene Oxidase 1, or VO1), E. coli proteins anchored in the inner membrane with a cytoplasmic C-terminus were identified. An N-terminal sequence of E. coli yhcB was selected, which provides a single-pass transmembrane domain. 20-24 amino acids from the N-terminus of yhcB was exchanged for the original membrane anchor sequence MALLLAVF (SEQ ID NO:112), and the size of the SrKO N-terminal truncation was varied from 28 to 32. See FIG. 9. VO1 was expressed under control of a T7 promoter on a p5 plasmid. SrCPR was expressed independently from the chromosome. Strains were cultured in 96 deepwell plates at 30° C. for 48 hours, in R-medium plus glycerol and dodecane overlay as already described.

Figure 10:
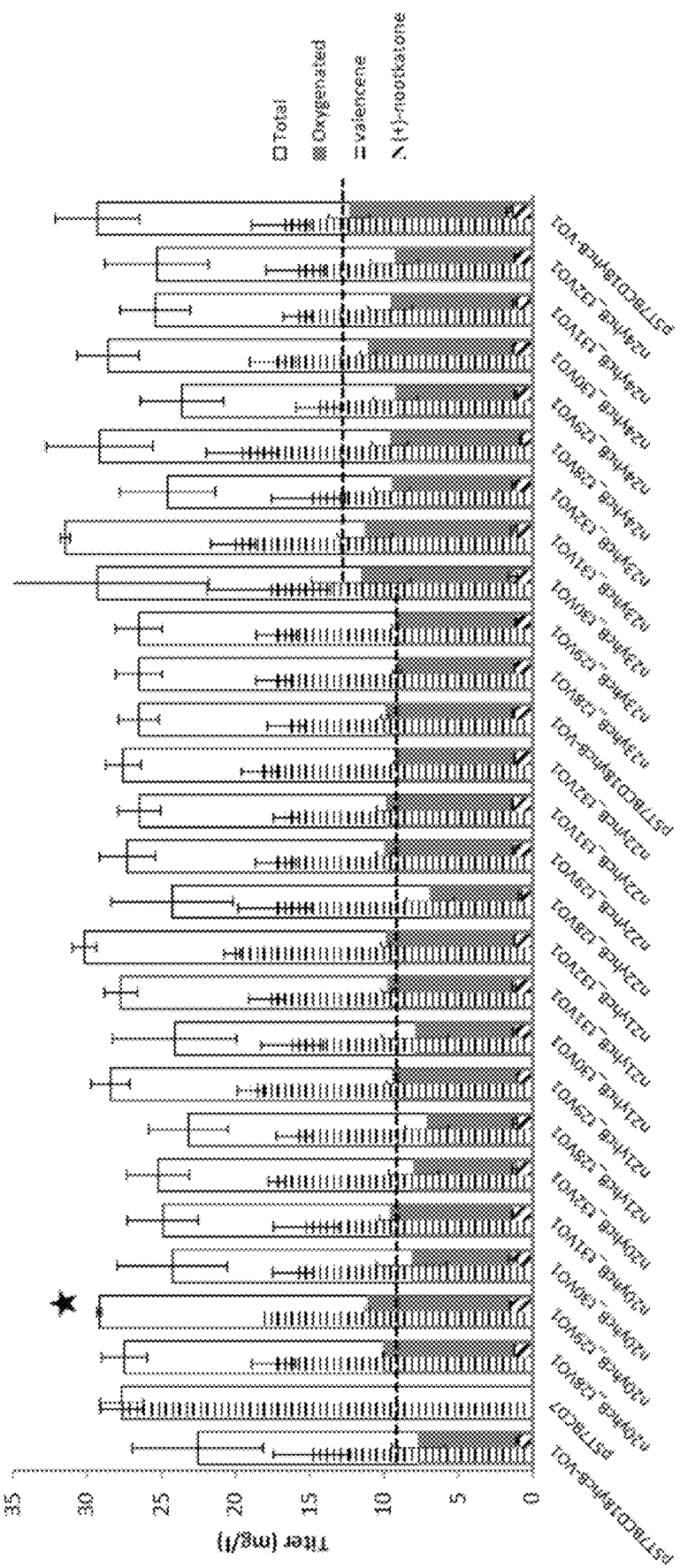
FIG. 10 shows that a truncation length of 29, and a 20 amino acid N-terminal anchor based on *E. coli* yhcB, led to a 1.2-fold increase in total oxygenated titer compared to the average of controls.
Figure 12:
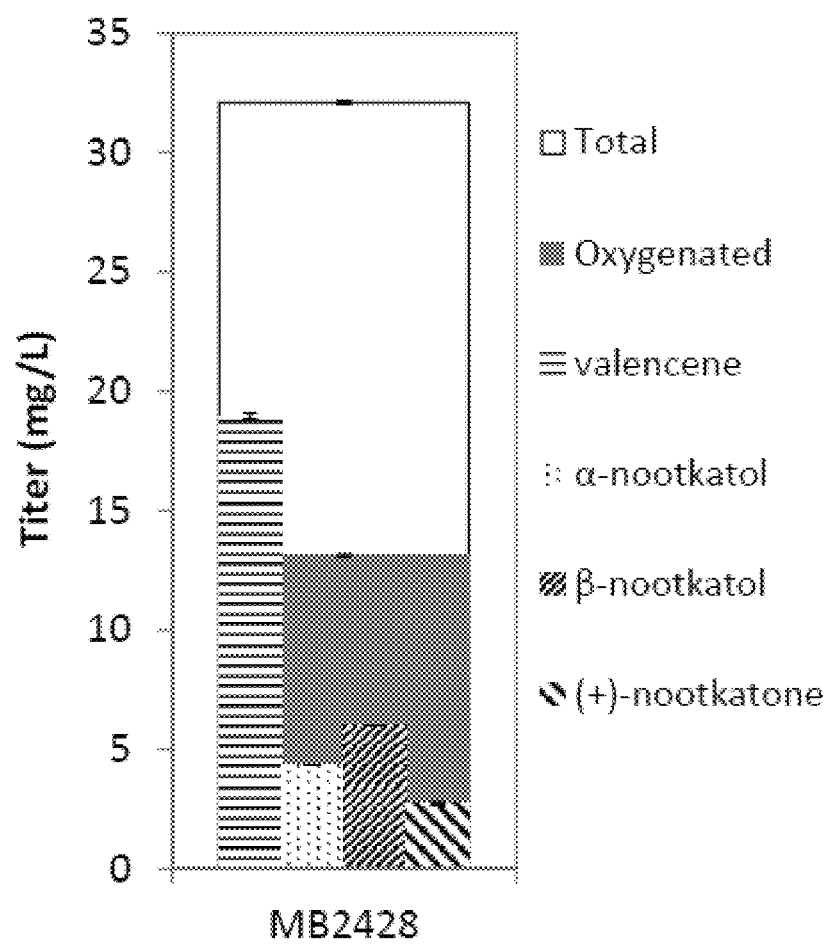
FIG. 12 shows the oxygenation profile for a strain expressing VO1-L-SrCPR. The oxygenation profile includes the single oxygenation products of β-nootkatol and α-nootkatol along with the two-step oxygenation product, nootkatone.

As shown in FIG. 10, n20yhcB t29VO1 exhibited 1.2-fold productivity in total oxygenated titer compared to the average of controls. N20yhcB t29VO1 exhibited a total oxygenated titer approximately 1.8 fold of the original 8RP anchor (not shown).

Example 6: Mutational Analysis of VO1

Mutational analysis of VO1 was conducted in an effort to increase oxygenated titers. Strain MB2509 (MP6-MEP MP1-ScFPPS Fab46-VS2 MP6-ScCPR) was used as the background, which when transformed with a p5-T7-yhcB-VO1 plasmid produces about 18% nootkatone. Strains were evaluated for higher production of nootkatone.

Guided by the homology model based on P450 17A1 (Example 3) site-saturation mutagenesis of the VO active site was conducted at 18 positions, and 5 paired position libraries were constructed. First shell residues were identified through substrate docking, and non-conserved first shell residues were selected based on relative proximity and position for altering the binding pocket geometry. Paired position libraries were constructed by overlap extension PCR and Gibson assembly.

TABLE 12

Paired Position Libraries (numbered according to SEQ ID NO: 37)

| Library | Pos. 1 | Allowed AA | Pos. 2 | Allowed AA |
|---|---|---|---|---|
| 1 | V387 | F,L,I,S,P,T,A,M | P388 | S,T,A |
| 2 | M132 | F,L,I,V,S,P,T,A | V133 | F,L,I,S,P,T,A,M |
| 3 | L123 | F,I,V,S,T,A,P,M | L126 | F,I,V,S,T,A,P,M |
| 4 | V387 | F,L,I,S,P,T,A,M | I322 | F,L,V,S,P,A,M,T |
| 5 | I322 | F,L,V,S,P,A,M,T | V133 | F,L,I,S,P,T,A,M |

Strains were evaluated as in Example 4 for total oxygenation of valencene. Strains were evaluated at 30° C. and 22° C.

Primary screening of paired position libraries revealed that many of the variants lost activity. Library 3 contained variants with improved activity at 22° C. but not 30° C. Thus, introducing two or more mutations simultaneously in the first shell residues can be detrimental to activity.

TABLE 13

The following single position SSM was conducted (numbered according to SEQ ID NO: 37)

| Residue | Location | |
|---|---|---|
| I390 | Channel | |
| L392 | Channel | |
| V387 | 1st Shell | |
| E323 | 1st Shell | I helix |
| I322 | 1st Shell | I helix |

TABLE 13-continued

The following single position SSM was conducted
(numbered according to SEQ ID NO: 37)

| Residue | Location | |
|---|---|---|
| T499 | 1st Shell | |
| Q500 | 1st Shell | |
| L231 | 1st Shell | F helix |
| L123 | 1st Shell | B-C loop |
| L126 | 1st Shell | B-C loop |
| V125 | 1st Shell | B-C loop |
| V133 | 1st Shell | F87 on BM3 |
| T131 | Channel | |
| M135 | 1st Shell | |
| L234 | 1st Shell | F helix |
| P238 | 1st Shell | F-G loop |
| M132 | 1st Shell | B-C loop |
| P388 | 1st Shell | |

Several variants improved oxygenated titers up to 1.7-fold. Mutations at positions E323, I390, and Q500 showed several hits with improved oxygenation titer, and these positions were selected for secondary screening.

Figure 13A:
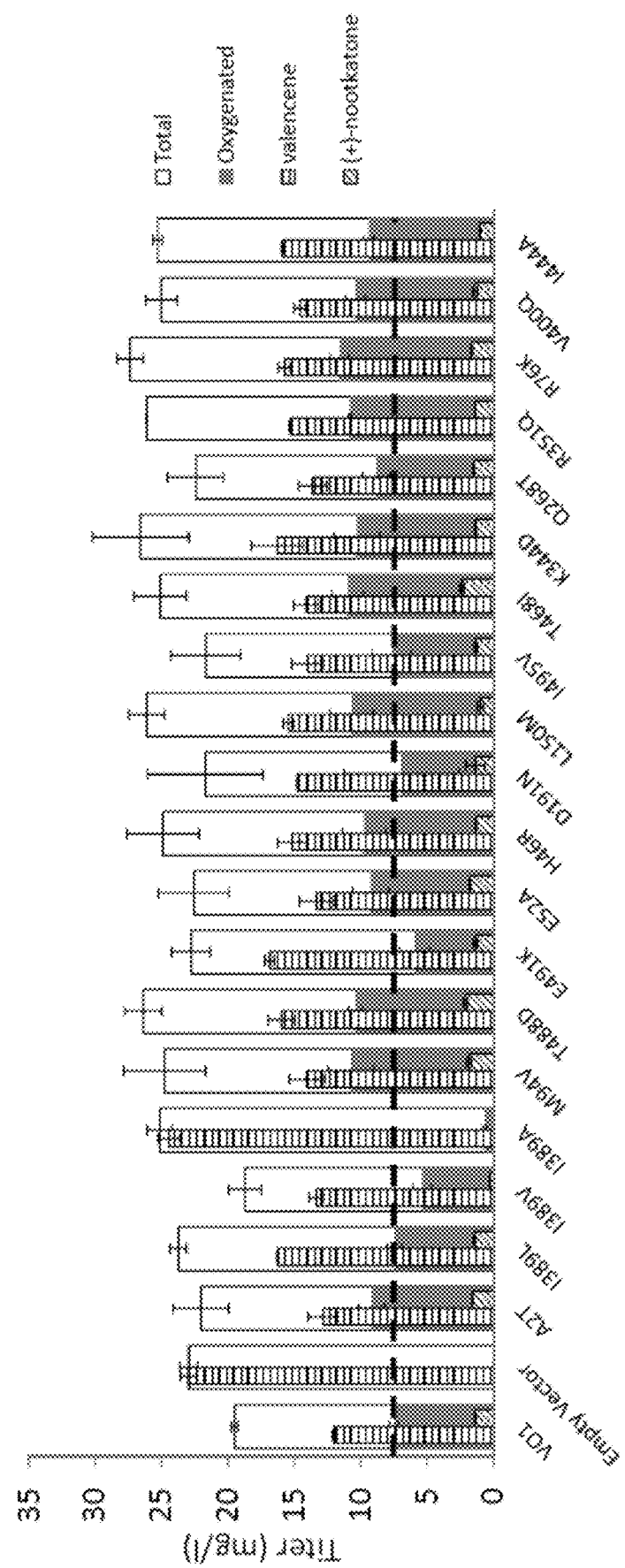
FIG. 13A and FIG. 13B show evaluation of mutations identified using a back-to-consensus strategy in wild-type SrKO, translated into an engineered valencene oxidase background (n22yhcB_t30VO1). More than 50% of the mutations resulted in a 1.2 to 1.45 fold improvement in total oxygenated titers.
Figure 13B:
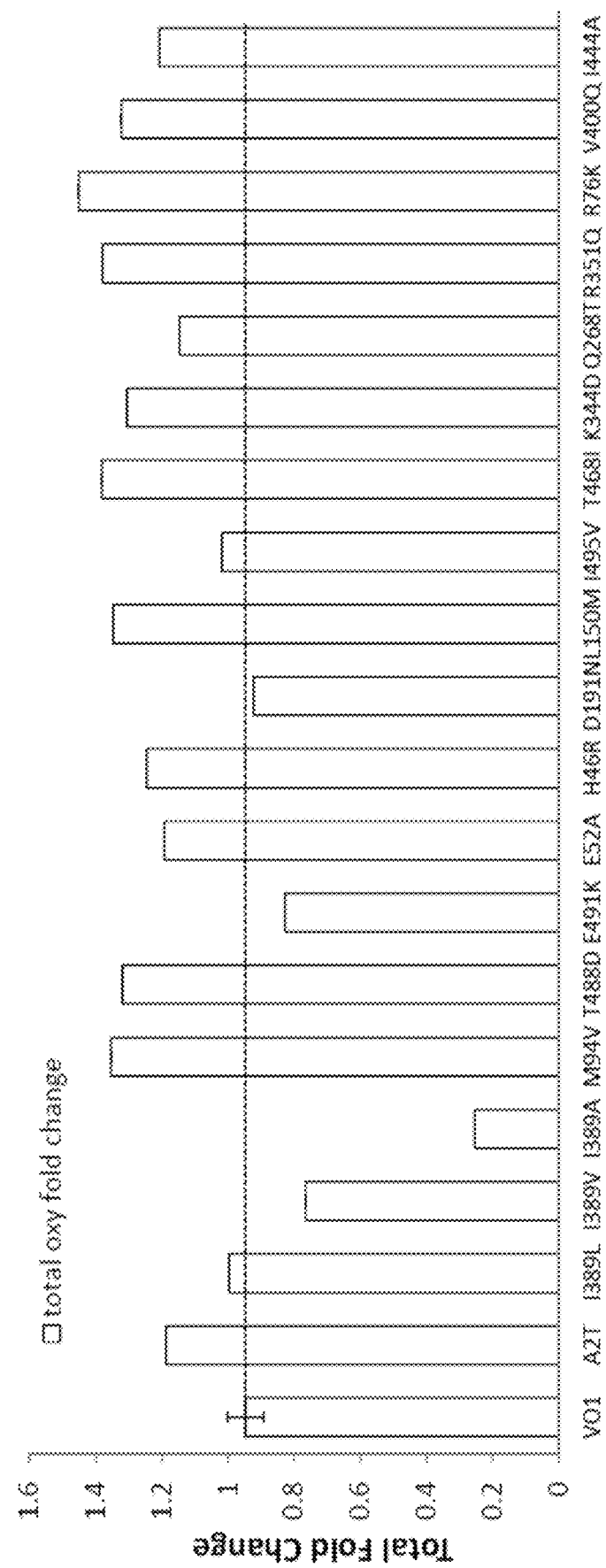

Next, back-to-consensus mutations (19 mutants) were screened in the VO1 background. Using the screening process described in Example 3, the following mutations were screened: A2T, I389L, I389V, I389A, M94V, T488D, E491K, E52A, H46R, D191N, L150M, I495V, T468I, K344D, Q268T, R351Q, R76K, V400Q, and I444A (numbered according to SEQ ID NO:37). As shown in FIG. 13A, more than 50% of the mutations resulted in 1.2 to 1.45 times oxygenated titers (shown as mg/L), without dramatic shifts in product profile. Improvements were seen with A2T, M94V, T488D, E52A, H46R, L150M, T468I, K344D, Q268T, R351Q, R76K, V400Q, and I444A, which were selected for secondary screening. FIG. 13B shows the same screen plotted versus fold total oxygenated product change.

Figure 14:
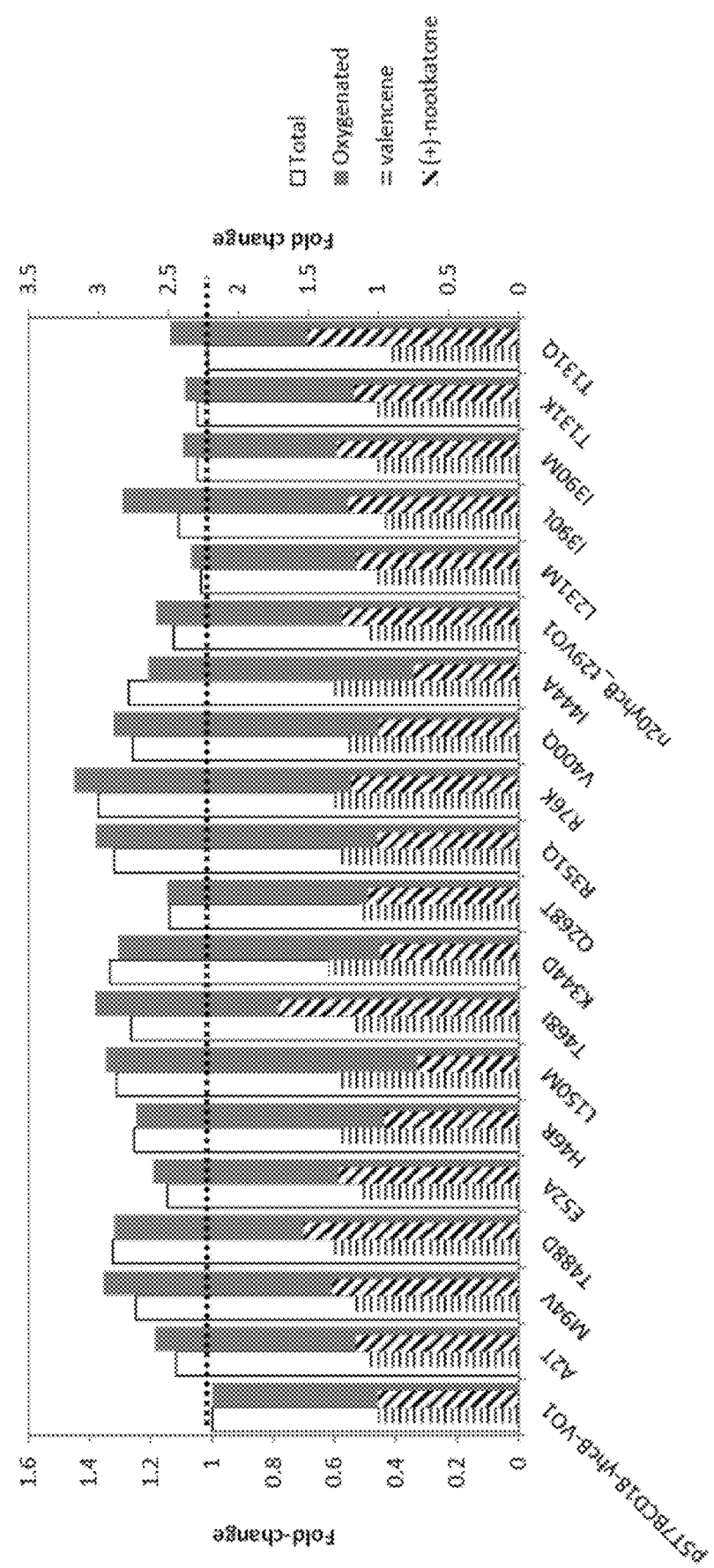
FIG. 14 shows results of secondary screening of back-to-consensus mutations, N-terminal anchor optimization, and site-saturation mutagenesis (SSM). Several mutations were identified that show a 1.1 to 1.4-fold improvement in oxygenated titers.
Figure 15:
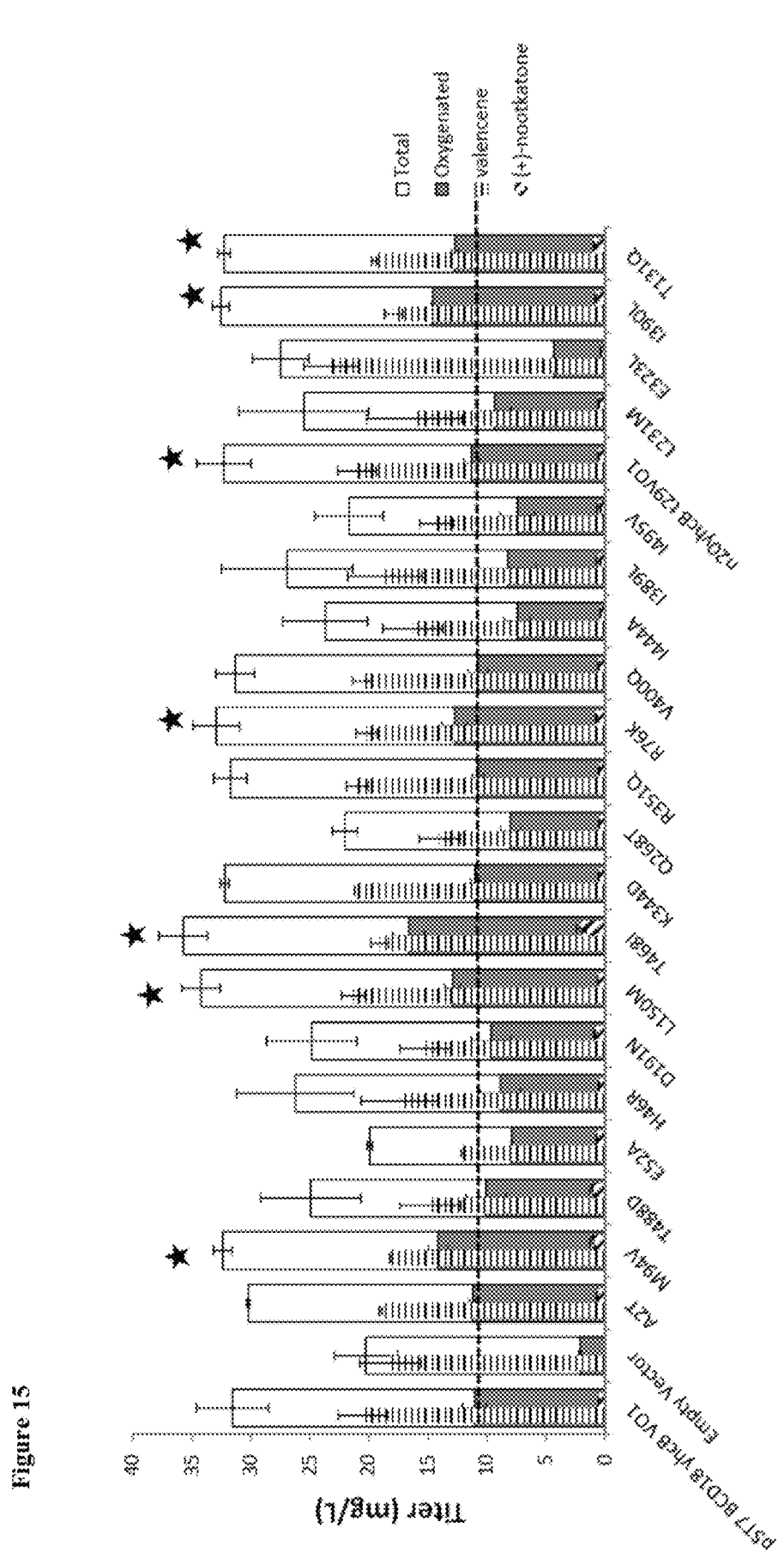
FIG. 15 shows performance of select VO1 variants at 33° C. Six mutations were identified that maintained improved productivities at 33° C.

Lead variants from active site SSM (L231M, I390L, I390M, T131K, and T131Q), the N-terminal anchor variant n20yhcB_t29VOR1, and back-to-consensus mutagenesis were selected, and re-screened. The results of this secondary screen are shown in FIG. 14. Several mutations showed a 1.1-1.4-fold improvement in oxygenated titers. To narrow the list of mutations for recombination, the same mutations were screened at 33° C. to differentiate stabilizing mutations which could enable a process shift to higher temperature. As shown in FIG. 15, six mutations (M94V, L150M, T468I, R76K, I390L, and T131Q) maintained improved productivities at 33° C. These six mutations, in addition to the lead N-terminal anchor, were selected for recombination.

Example 7: SrKO Recombination Library Screening

The seven mutations selected after secondary screening (Example 6) were randomly incorporated into a VO recombination library by allowing either the variant or wild type at each site. The background strain was MB2509 (EGV G2 MP6-CPR)+pBAC-T7-BCD7-yhcB-VO.

Figure 16A:
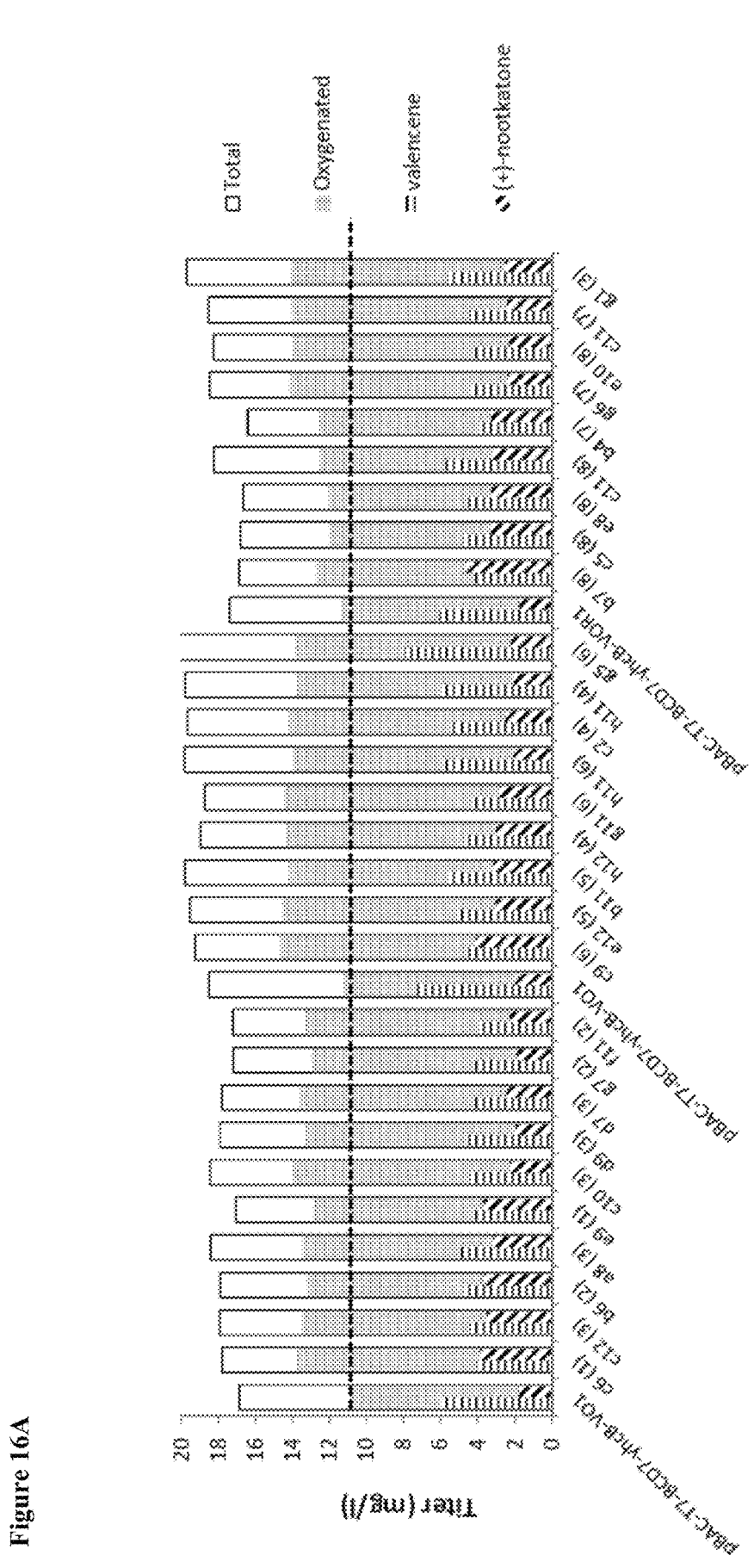
FIG. 16A and FIG. 16B show results from primary screening of the recombination library. Several variants (shown) exhibited up to 1.35-fold improvement in oxygenated product titer. There was a shift in profile to more (+)-nootkatone and higher oxygenation capacity for select variants.
Figure 16B:
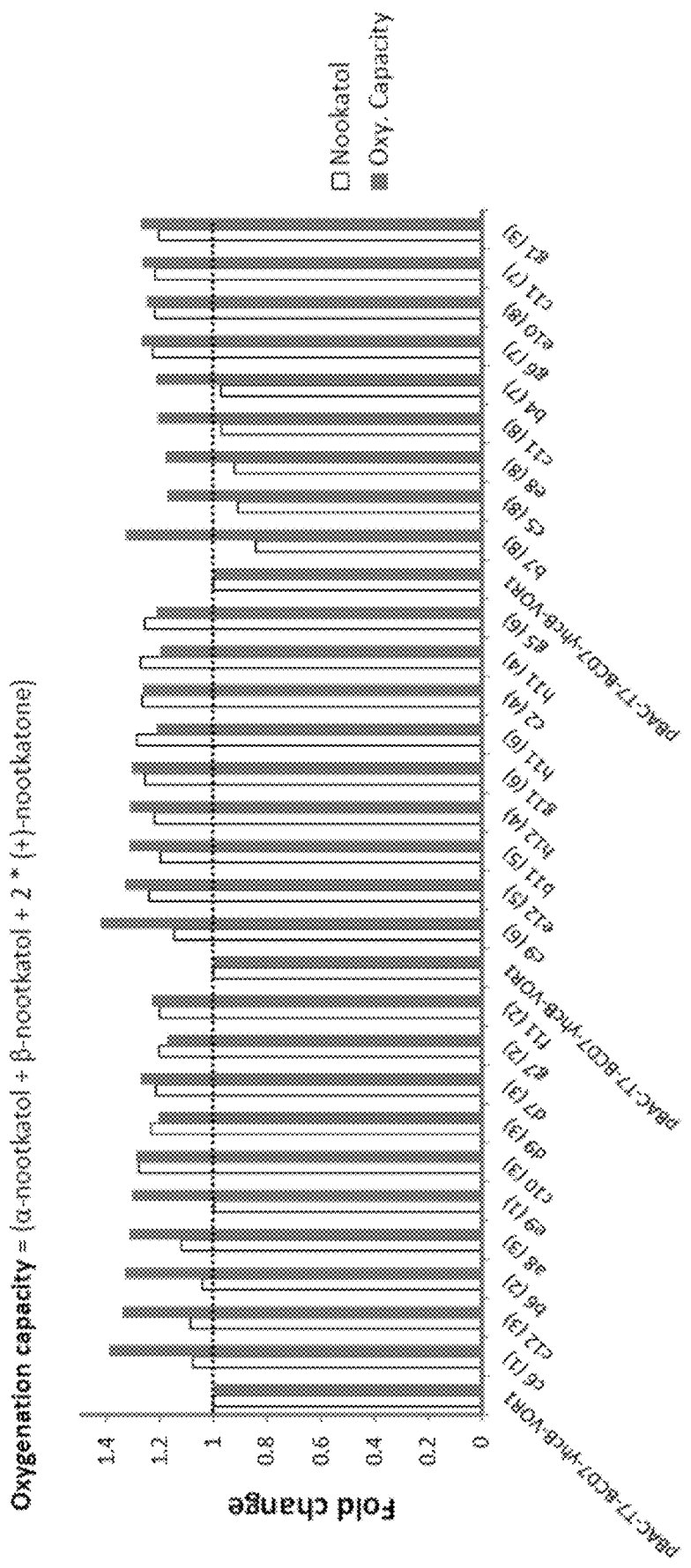

Primary screening at 30° C. (using the same process described in Example 5) identified several variants with up to 1.35-fold improvement in oxygenated product titers, compared to VO1. Further, select variants showed a shift in production to nootkatone, suggesting higher P450 activity (since production of nootkatone requires two oxygenation cycles). Results of primary screening are shown in FIG. 16A (strain versus titer in mg/L). FIG. 16B presents the same screen shown based on oxygenation capacity (total of nootkatone and nootkatol).

Figure 17:
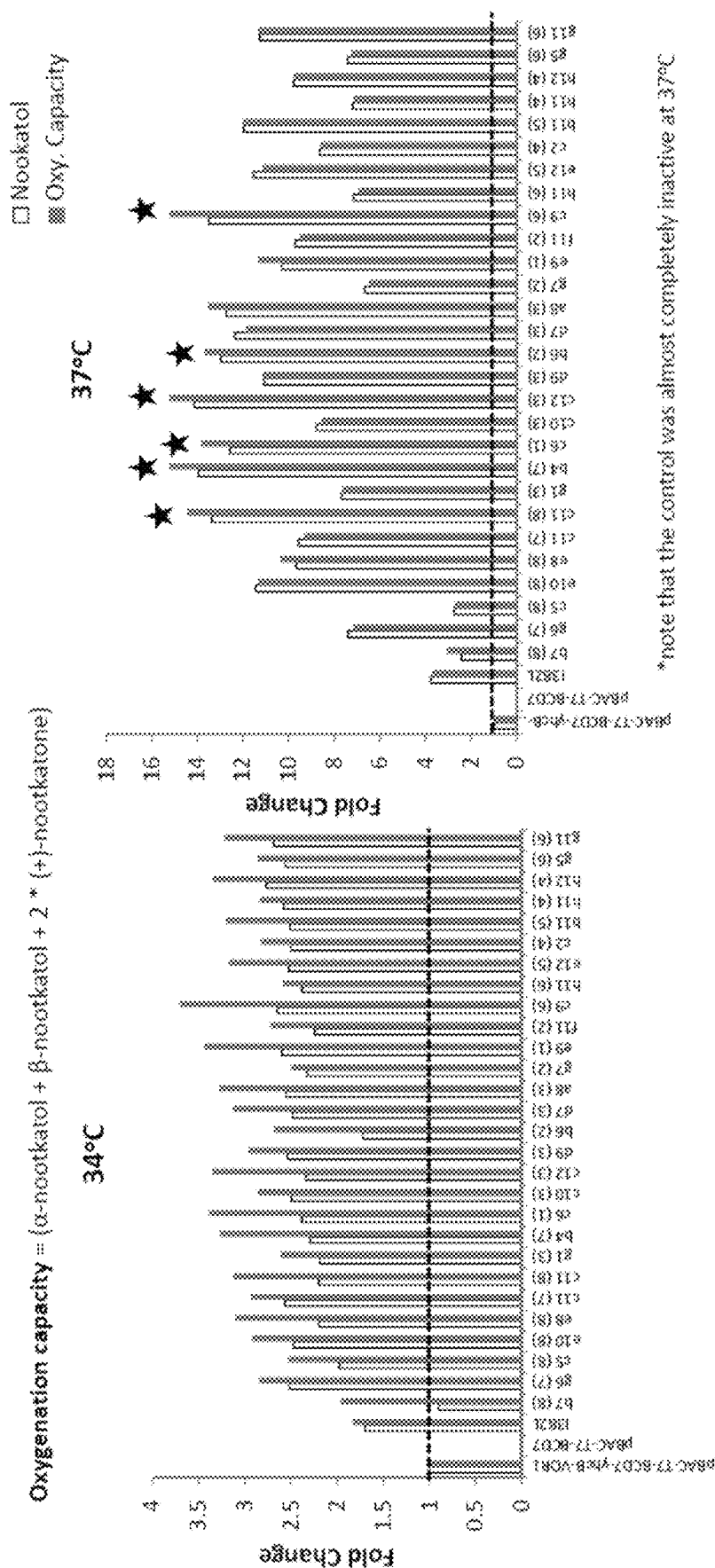
FIG. 17 shows oxygenation capacity at 34° C. and 37° C. for select VO recombination library variants.
Figure 18:
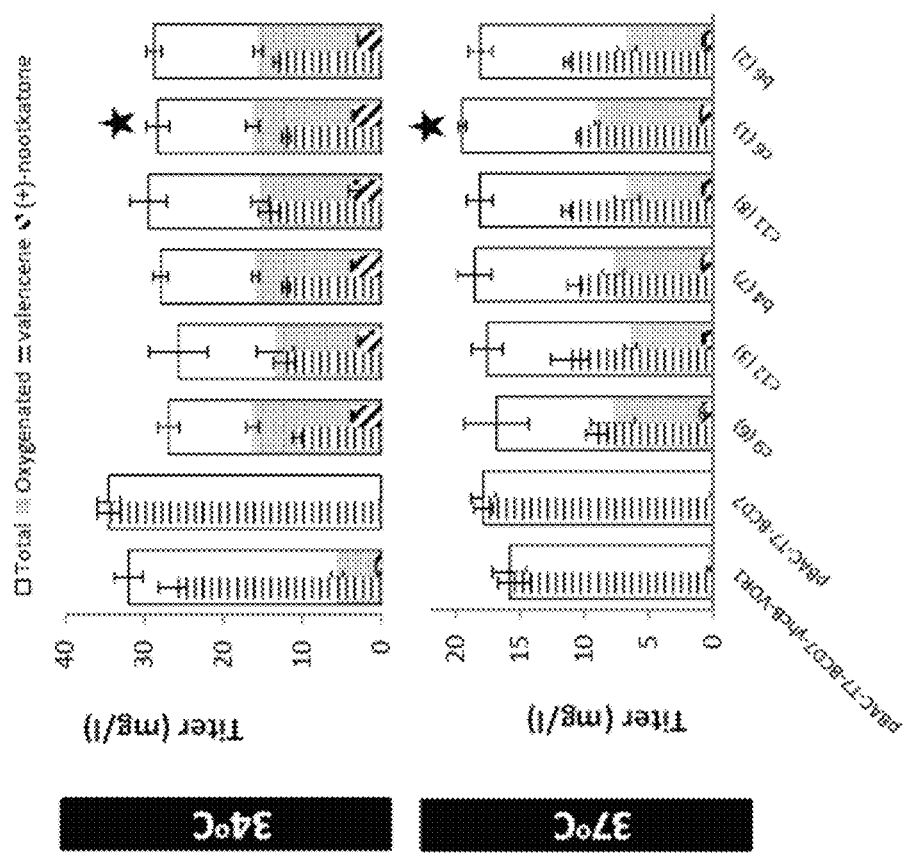
FIG. 18 shows oxygenation titer at 34° C. and 37° C. after re-screen of lead VO variants. C6(1) (R76K, M94V, T131Q, I390L, T468I) had the highest oxygenation capacity at 37° C., and was designated VO2.
Figure 19:
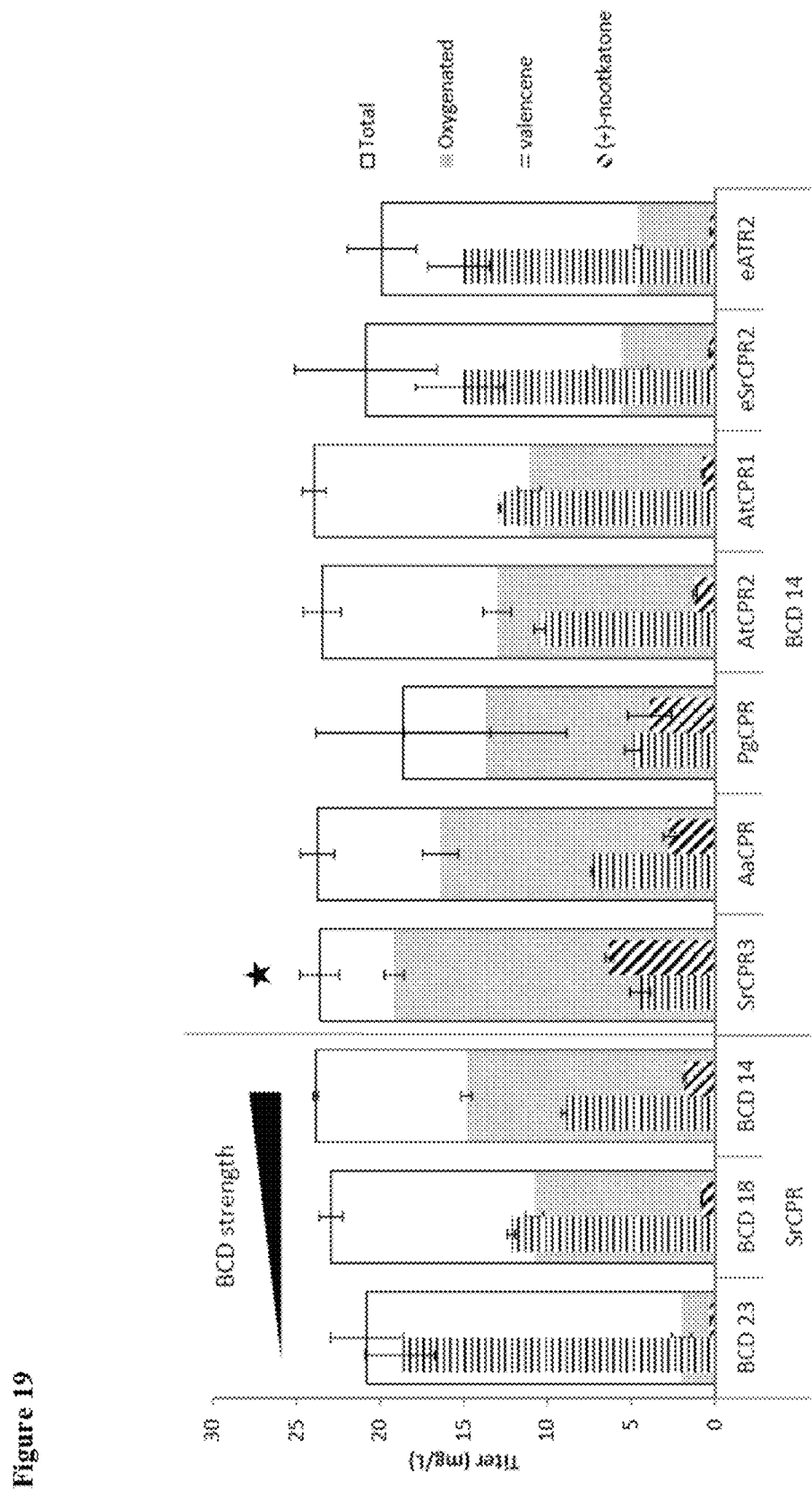
FIG. 19 shows screening of cytochrome P450 reductase (CPR) orthologs for enhanced valencene oxidase activity (30° C.). SrCPR3 shows increased oxygenation titer and higher production of Nootkatone.

The recombination variants were then screened at 34° C. and 37° C. to select leads with improved activity and stability at higher temperature. The results of the secondary screen are shown in FIG. 17. While the control was almost completely inactive at 37° C., six leads showed promising activity at the higher temperatures, and were selected for further screening (c11(8), b4(7), c6(1), c12(3), b6(2), and c9(6)). Based on this further screening (FIG. 18) c6(1) was selected as the best variant based on oxygenation capacity. The six leads contain the following sets of mutations.

TABLE 14

Sets of mutations in lead variants from recombination library

| | N20_t29yhcB | R76K | M94V | T131Q | L150M | I390L | T468I | A39H | Others |
|---|---|---|---|---|---|---|---|---|---|
| c9(6) | | | X | | | X | X | | V146L |
| c12(3) | | X | | X | | X | X | | |
| b4(7) | | | X | X | | X | X | X | |
| c11(8) | X | X | | X | | X | X | X | |
| c6(1) | | X | X | X | | X | X | | |
| b6(2) | | X | X | | | | X | | |

FIG. 23A and FIG. 23B show alignments of several engineered valencene oxidase (VO) variants as described herein, and highlights select mutations evaluated in the screening process. In FIG. 23A: 8rp-t20SrKO (SEQ ID NO:106) is the SrKO sequence with a 20-amino acid truncation at the N-terminus, and the addition of an 8-amino acid membrane anchor. 8rp-t20VO0 (SEQ ID NO:107) has a truncation of 20 amino acids of the SrKO N-terminus, the addition of an 8-amino acid N-terminal anchor, and a single mutation at position 499 (numbered according to wild-type SrKO). n22yhcB-t30VO1 (SEQ ID NO:104) has a 30-amino acid truncation of the SrKO N-terminus, a membrane anchor based on 22 amino acids from E. coli yhcB, and eight point mutations at positions 46, 231, 284, 383, 400, 488, and 499

(with respect to SrKO wild-type). n22yhcB-t30VO2 (SEQ ID NO:105) has a 30-amino acid truncation of the SrKO N-terminus, a membrane anchor based on 22 amino acids from *E. coli* yhcB, and nine point mutations at positions 76, 94, 131, 231, 284, 383, 390, 468, and 499 (with respect to SrKO wild-type). In FIG. 24B, point mutations in VO0 (SEQ ID NO:109), VO1 (SEQ ID NO:110), and VO2 (SEQ ID NO:111) are shown against wild-type SrKO (SEQ ID NO:108) (all shown with the wild-type SrKO N-terminus for convenience).

Example 8: Cytochrome P450 Reductase Screening

A set of cytochrome P450 reductases were screened for improved activity with VO1. This example was done using the strain MB2459 as the background, with pBAC-T7-BCD7-VO1(I382L)-T7BCDx-CPRx. BCD stands for BiCistronic Design, and is described in Mutalik et. al. *Nature Methods* 2013(10)4:354. Lower BCD numbers refer to higher translation rate. CPRs included SrCPR (SEQ ID NO:62), SrCPR3 (SEQ ID NO: 80), AaCPR (SEQ ID NO: 68), PgCPR (SEQ ID NO: 82), AtCPR2 (SEQ ID NO: 72), AtCPR1 (SEQ ID NO: 70), eSrCPR1 (SEQ ID NO: 76), and eATR2 (SEQ ID NO: 74). Strains were tested as in Example 5, at 30° C.

Figure 20:
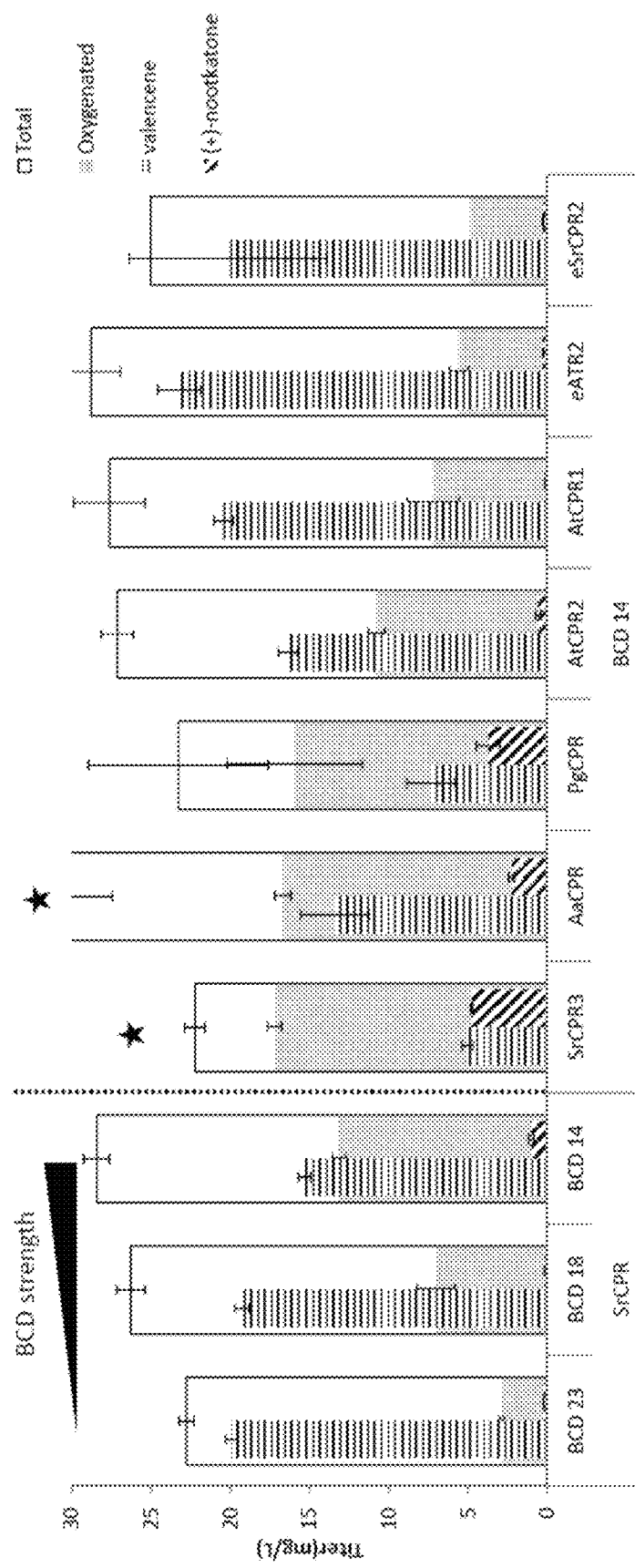
FIG. 20 shows screening of CPR orthologs at 34° C. SrCPR3 and AaCPR exhibit ~1.3-fold improvement in oxygenated titer, even at higher the higher temperature.

As shown in FIG. 20, SrCPR3, which was obtained through RNA sequencing studies, exhibited a 1.3-fold improvement in oxygenated titer.

The CPR orthologs were retested at 34° C. The results are shown in FIG. 20. Both SrCPR3 (SEQ ID NO: 80) and AaCPR (SEQ ID NO: 68) exhibited a 1.3-fold improvement in oxygenated titer, even at the higher temperature. Oxygenated titers are comparable to those obtained at 30° C.

Example 9: Alcohol Dehydrogenase Enzymes to Alter Product Profile

The ability of alcohol dehydrogenases to convert nootkatols to nootkatone was evaluated. The following ADH enzymes were evaluated:

TABLE 15

CPR enzymes

| Gene | UniProtID | Organism |
|---|---|---|
| reCDH | Q9RA05 | *Rhodococcus erythropolis* |
| csDH1 | A0A067H4B8 | *Citrus sinensis* |
| csDH2 | A0A067H4S0 | *Citrus sinensis* |
| csDH3 | | *Citrus sinensis* |
| vvDH | F6GX78 | *Vitis vinifera* |
| voDH1 | | |
| csABA2 | A0A067DRA0 | *Citrus sinensis* |
| csDH | A0A0A0KNF1 | *Cucumis sativus* |
| bdDH | I1GLS4 | *Brachypodium distachyon* |
| zzSDR | F1SWA0 | *Zingiber zerumbet* |

Strains were evaluated as in Example 5, using MB2490 as the background strain (MP6-MEP FAB46-ScFPPS-L-VS1 MP6-VO1-o-SrCPR+p5-T7-BCD14-ADH). Briefly, MP6, Fab46 and T7 refer to the promoter for the attached gene or operon. Here MEP is an operon overexpressing *E. coli* dxs, idi, and ispDF genes. The L between ScFPPS and VS1 refers to a short polypeptide linker encoding (GSTGS) while -o-between VO1 and SrCPR refers to an operonic construction in which an RBS sequence is inserted between the two genes. The plus denotes a plasmid following which is described as a p5 (five copy) plasmid with a promoter, BCD (described above) and the ADH in question.

Figure 21:
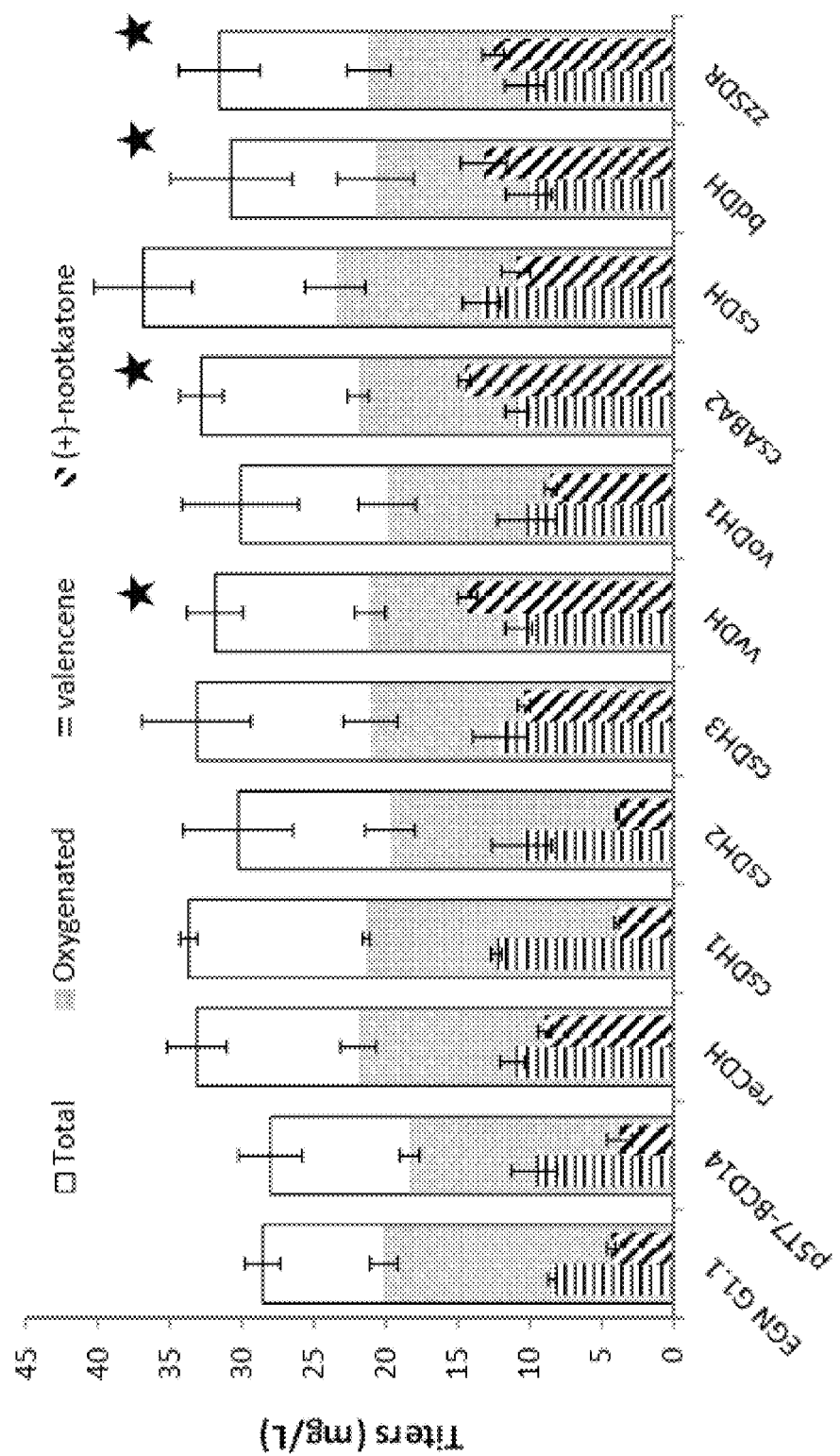
FIG. 21 shows conversion of nootkatols to nootkatone with an alcohol dehydrogenase. Four ADH orthologs (vvDH, csABA2, bdDH, and zzSDR) were identified that convert nootkatol to (+)-nootkatone, resulting in a 3-fold increase in (+)-nootkatone titers.

Four orthologs were identified (vvDH, csABA2, bdDH, and zzSDR) that convert nootkatol to nootkatone, resulting in more than a 3-fold increase in nootkatone titers. FIG. 21.

REFERENCES

1. Qualley A, Dudareva N. Plant Volatiles. Encycl. Life Sci. 2010; 1-9.
2. Ajikumar P, Tyo K, Carlsen S. Terpenoids: opportunities for biosynthesis of natural product drugs using engineered microorganisms. Mol. Pharm. [Internet]. 2008 [cited 2013 May 16]; 5(2):167-90.
3. Ajikumar P K, Xiao W-H, Tyo K E J, Wang Y, Simeon F, Leonard E, et al. Isoprenoid pathway optimization for Taxol precursor overproduction in *Escherichia coli*. Science [Internet]. 2010 Oct. 1 [cited 2013 May 22]; 330 (6000):70-4.
4. Ro D-K, Paradise E M, Ouellet M, Fisher K J, Newman K L, Ndungu J M, et al. Production of the antimalarial drug precursor artemisinic acid in engineered yeast. Nature [Internet]. 2006 Apr. 13 [cited 2013 Mar. 1]; 440(7086):940-3.
5. Sevrioukova I F, Li H, Zhang H, Peterson J a, Poulos T L. Structure of a cytochrome P450-redox partner electron-transfer complex. Proc. Natl. Acad. Sci. U.S.A. [Internet]. 1999 Mar. 2; 96(5):1863-8.
6. Sevrioukova I F, Poulos T L. Structural biology of redox partner interactions in P450cam monooxygenase: a fresh look at an old system. Arch. Biochem. Biophys. [Internet]. Elsevier Inc.; 2011 Mar. 1 [cited 2013 Mar. 26]; 507(1):66-74.
7. Ekroos M, Sjögren T. Structural basis for ligand promiscuity in cytochrome P450 3A4. Proc. Natl. Acad. Sci. U.S.A. [Internet]. 2006 Sep. 12; 103(37):13682-7.
8. Takahashi S, Yeo Y-S, Zhao Y, O'Maille P E, Greenhagen B T, Noel J P, et al. Functional characterization of premnaspirodiene oxygenase, a cytochrome P450 catalyzing regio- and stereo-specific hydroxylations of diverse sesquiterpene substrates. J. Biol. Chem. [Internet]. 2007 Oct. 26 [cited 2013 Mar. 10]; 282(43):31744-54.
9. Morrone D, Chen X, Coates R M, Peters R J. Characterization of the kaurene oxidase CYP701A3, a multifunctional cytochrome P450 from gibberellin biosynthesis. Biochem. J. [Internet]. 2010 Nov. 1 [cited 2013 Feb. 6]; 431(3):337-44.
10. Zhang Z, Sibbesen O. The substrate specificity of cytochrome P450 cam. Bioorganic Med. . . . [Internet]. 1998 [cited 2013 Sep. 24]; 6:1501-8.
11. Stjernschantz E, van Vugt-Lussenburg B M a, Bonifacio A, de Beer S B a, van der Zwan G, Gooijer C, et al. Structural rationalization of novel drug metabolizing mutants of cytochrome P450 BM3. Proteins [Internet]. 2008 April [cited 2013 May 16]; 71(1):336-52.
12. Chen M M Y, Snow C D, Vizcarra C L, Mayo S L, Arnold F H. Comparison of random mutagenesis and semi-rational designed libraries for improved cytochrome P450 BM3-catalyzed hydroxylation of small alkanes. Protein Eng. Des. Sel. [Internet]. 2012 April [cited 2013 Mar. 11]; 25(4):171-8.
13. Harford-Cross C F, Carmichael a B, Allan F K, England P a, Rouch D a, Wong L L. Protein engineering of cytochrome p450(cam) (CYP101) for the oxidation of polycyclic aromatic hydrocarbons. Protein Eng. [Internet]. 2000 February; 13(2):121-8.

14. Bell S G, Chen X, Sowden R J, Xu F, Williams J N, Wong L, et al. Molecular Recognition in (+)-r-Pinene Oxidation by Cytochrome P450cam. J. Am. Chem. Soc. 2003; 125:705-14.
15. Sowden R, Yasmin S, Rees N, Bell S G, Wong L-L. Biotransformation of the sesquiterpene (+)-valencene by cytochrome P450cam and P450BM-3. Org. Biomol. Chem. [Internet]. 2005 [cited 2013 May 16]; 3:57-64.
16. Brandle J E, Richman A, Swanson A K, Chapman B P. Leaf Ests from *Stevia rebaudiana*: a resource for gene discovery in diterpene synthesis. Plant Mol. Biol. [Internet]. 2002 November [cited 2013 Feb. 12]; 50(4-5):613-22.
17. Bar-even A, Noor E, Savir Y, Liebermeister W, Davidi D, Tawfik D S, et al. The Moderately Efficient Enzyme: Evolutionary and Physicochemical Trends Shaping Enzyme Parameters. Biochemistry. 2011;
18. Pleiss J. Protein design in metabolic engineering and synthetic biology. Curr. Opin. Biotechnol. [Internet]. 2011 October [cited 2013 Mar. 5]; 22(5):611-7.
19. Lehmann M, Pasamontes L, Lassen S F, Wyss M. The consensus concept for thermostability engineering of proteins. Biochim. Biophys. Acta [Internet]. 2000 Dec. 29 [cited 2013 Oct. 17]; 1543(2):408-15.
20. Vazquez-Figueroa E, Yeh V, Broering J M, Chaparro-Riggers J F, Bommarius A S. Thermostable variants constructed via the structure-guided consensus method also show increased stability in salts solutions and homogeneous aqueous-organic media. Protein Eng. Des. Sel. [Internet]. 2008 November [cited 2013 Oct. 17]; 21(10: 673-80.
21. Dai M, Fisher H E, Temirov J, Kiss C, Phipps M E, Pavlik P, et al. The creation of a novel fluorescent protein by guided consensus engineering. Protein Eng. Des. Sel. [Internet]. 2007 February [cited 2013 Sep. 19]; 20(2):69-79.
22. Fraatz M a., Riemer S J L, Stöber R, Kaspera R, Nimtz M, Berger R G, et al. A novel oxygenase from *Pleurotus sapidus* transforms valencene to nootkatone. J. Mol. Catal. B Enzym. [Internet]. 2009 December [cited 2013 Apr. 17]; 61(3-4):202-7.
23. Krügener S, Krings U, Zorn H, Berger R G. A dioxygenase of *Pleurotus sapidus* transforms (+)-valencene regio-specifically to (+)-nootkatone via a stereo-specific allylic hydroperoxidation. Bioresour. Technol. [Internet]. Elsevier Ltd; 2010 January [cited 2013 Apr. 12]; 101(2): 457-62.
24. Zorn H, Fraatz M A, Riemer S J L, Takenberg M. Enzymatic synthesis of nootkatone. GERMANY; 2010.
25. Kaspera R, Krings U, Nanzad T, Berger R G. Bioconversion of (+)-valencene in submerged cultures of the ascomycete *Chaetomium globosum*. Appl. Microbiol. Biotechnol. [Internet]. 2005 June [cited 2013 May 16]; 67(4):477-83.
26. Cankar K, van Houwelingen A, Bosch D, Sonke T, Bouwmeester H, Beekwilder J. A chicory cytochrome P450 mono-oxygenase CYP71AV8 for the oxidation of (+)-valencene. FEBS Lett. [Internet]. Federation of European Biochemical Societies; 2011 Jan. 3 [cited 2013 Mar. 6]; 585(4178-82.
27. Girhard M, Machida K, Itoh M, Schmid R D, Arisawa A, Urlacher V B. Regioselective biooxidation of (+)-valencene by recombinant *E. coli* expressing CYP109B1 from *Bacillus subtilis* in a two-liquid-phase system. Microb. Cell Fact. [Internet]. 2009 January [cited 2013 May 16]; 8(4):36.
28. Bm-P, Sowden R J, Yasmin S, Rees N H, Bell S G, Wong L. Biotransformation of the sesquiterpene (+)-valencene by cytochrome P450. 2005; 57-64.
29. Trott O, Olson A. AutoDock Vina: improving the speed and accuracy of docking with a new scoring function, efficient optimization, and multithreading. J. Comput. Chem. [Internet]. 2010 [cited 2013 Jul. 26]; 31(2):455-61.1

The invention claimed is:

1. A sesquiterpene oxidase comprising an amino acid sequence that has at least 80% sequence identity to the amino acid sequence SEQ ID NO: 37 or SEQ ID NO: 38, wherein the amino acid sequence of the sesquiterpene oxidase comprises a T499N substitution, and wherein the amino acid numbering corresponds to the amino acid sequence of SEQ ID NO: 37.

2. The sesquiterpene oxidase of claim 1, wherein the amino acid sequence has at least 85% sequence identity to the amino acid sequence of SEQ ID NO: 37 or SEQ ID NO: 38.

3. The sesquiterpene oxidase of claim 1, wherein the amino acid sequence has at least 90% sequence identity to the amino acid sequence of SEQ ID NO: 37 or SEQ ID NO: 38.

4. The sesquiterpene oxidase of claim 1, wherein the amino acid sequence has at least 95% sequence identity to the amino acid sequence of SEQ ID NO: 37 or SEQ ID NO: 38.

5. The sesquiterpene oxidase of claim 1, wherein the amino acid sequence of the sesquiterpene oxidase further comprises a F231L or F231I substitution, and wherein the amino acid numbering corresponds to the amino acid sequence of SEQ ID NO: 37.

\* \* \* \* \*

SEQUENCE LISTING

```
<160> NUMBER OF SEQ ID NOS: 118

<210> SEQ ID NO 1
<211> LENGTH: 556
<212> TYPE: PRT
<213> ORGANISM: Vitis vinifera

<400> SEQUENCE: 1

Met Ser Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Cys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110
```

```
Asp Leu Tyr Asn Ile Ala Leu Gly Phe Arg Leu Leu Arg Gln Gln Gly
            115                 120                 125

Tyr Thr Ile Ser Cys Asp Ile Phe Asn Lys Phe Thr Asp Glu Arg Gly
        130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met His Gly Val Tyr Phe
        275                 280                 285

Glu Pro Gln Tyr Leu Arg Gly Arg Arg Ile Leu Thr Lys Val Ile Ala
290                 295                 300

Met Thr Ser Ile Leu Asp Asp Ile His Asp Ala Tyr Gly Thr Pro Glu
305                 310                 315                 320

Glu Leu Lys Leu Phe Ile Glu Ala Ile Glu Arg Trp Asp Ile Asn Ser
                325                 330                 335

Ile Asn Gln Leu Pro Glu Tyr Met Lys Leu Cys Tyr Val Ala Leu Leu
            340                 345                 350

Asp Val Tyr Lys Glu Ile Glu Glu Met Glu Lys Glu Gly Asn Gln
        355                 360                 365

Tyr Arg Val His Tyr Ala Lys Glu Val Met Lys Asn Gln Val Arg Ala
370                 375                 380

Tyr Phe Ala Glu Ala Lys Trp Leu His Glu Glu His Val Pro Ala Phe
385                 390                 395                 400

Glu Glu Tyr Met Arg Val Ala Leu Ala Ser Ser Gly Tyr Cys Leu Leu
                405                 410                 415

Ala Thr Thr Ser Phe Val Gly Met Gly Glu Ile Ala Thr Lys Glu Ala
            420                 425                 430

Phe Asp Trp Val Thr Ser Asp Pro Lys Ile Met Ser Ser Asn Phe
        435                 440                 445

Ile Thr Arg Leu Met Asp Asp Ile Lys Ser His Lys Phe Glu Gln Lys
450                 455                 460

Arg Gly His Val Thr Ser Ala Val Glu Cys Tyr Met Lys Gln Tyr Gly
465                 470                 475                 480

Val Ser Glu Glu Gln Val Tyr Ser Glu Phe Gln Lys Gln Ile Glu Asn
                485                 490                 495

Ala Trp Leu Asp Ile Asn Gln Glu Cys Leu Lys Pro Thr Ala Val Ser
            500                 505                 510

Met Pro Leu Leu Ala Arg Leu Leu Asn Phe Thr Arg Thr Met Asp Val
        515                 520                 525
```

Ile Tyr Lys Glu Gln Asp Ser Tyr Thr His Val Gly Lys Val Met Arg
    530                 535                 540

Asp Asn Ile Ala Ser Val Phe Ile Asn Ala Val Ile
545                 550                 555

<210> SEQ ID NO 2
<211> LENGTH: 1671
<212> TYPE: DNA
<213> ORGANISM: Vitis vinifera

<400> SEQUENCE: 2

| | | |
|---|---|---|
| atggctacgc aggtctcagc ctcgtcactg gcacaaatcc cgcagccgaa aaatcgtccg | 60 |
| gtggcgaact tccatccgaa tatctggggt gaccagttta tcacgtatac cccggaagat | 120 |
| aaagtgaccc gtgcgtgcaa ggaagaacaa attgaagacc tgaaaaagga agtcaaacgc | 180 |
| aagctgaccg cagcagcagt ggcaaacccg tctcagctgc tgaatttat cgatgcggtt | 240 |
| caacgtctgg gcgtcgccta tcatttcgaa caggaaattg aagaagcact gcaacatatc | 300 |
| tgcaacagct ttcacgattg taatgatatg gacggcgatc tgtataacat tgctctgggt | 360 |
| ttccgtctgc tgcgccagca aggctacacg atttcctgtg acatctttaa taaattcacc | 420 |
| gatgaacgtg tcgctttaa ggaagcgctg atctcagacg ttcgtggcat gctgggtctg | 480 |
| tatgaagctg cgcatctgcg cgtccacggc gaagatattc tggccaaagc actggctttc | 540 |
| accacgaccc acctgaaggc gatggtcgaa tctctgggtt accatctggc agaacaggtg | 600 |
| gcacacgccc tgaaccgtcc gatccgcaaa ggcctggaac gtctggaagc gcgctggtat | 660 |
| attagtgtgt accaggacga agcatttcat gataaaaccc tgctggaact ggctaagctg | 720 |
| gatttcaacc tggttcaatc tctgcacaaa gaagaactga gtaatctggc ccgttggtgg | 780 |
| aaagaactgg actttgcgac caagctgccg ttcgcccgtg atcgcctggt gaaggctat | 840 |
| ttttggatgc atggtgtcta tttcgaaccg cagtacctgc gcggtcgtcg cattctgacg | 900 |
| aaagtgatcg caatgacctc gattctggat gacatccacg acgcttacgg cacccccggaa | 960 |
| gaactgaaac tgtttattga agcgatcgaa cgttgggata ttaacagcat caatcagctg | 1020 |
| ccggaatata tgaaactgtg ctacgtggcc ctgctggatg tttacaagga aatcgaagaa | 1080 |
| gaaatggaaa aggaaggtaa ccagtatcgt gttcattacg cgaaagaagt catgaagaat | 1140 |
| caagtgcgcg cctactttgc agaagctaaa tggctgcatg aagaacacgt gccggcgttc | 1200 |
| gaagaatata tgcgcgttgc gctggccagc tctggctact gtctgctggc cacgacctct | 1260 |
| tttgtgggca tgggtgaaat tgcaacgaaa gaagcgtttg actgggttac cagtgatccg | 1320 |
| aagattatga gttcctcaaa ctttatcacc cgtctgatgg atgacattaa atcccataag | 1380 |
| ttcgaacaga aacgcggtca cgtcacctca gccgtggaat gctatatgaa acagtacggc | 1440 |
| gtttcggaag aacaagtcta tagcgaattt cagaaacaaa tcgaaaacgc atggctggat | 1500 |
| attaatcagg aatgtctgaa accgacggca gtctccatgc cgctgctggc tcgtctgctg | 1560 |
| aattttacgc gcacgatgga tgtgatctat aaagaacagg attcgtacac ccatgtgggc | 1620 |
| aaggttatgc gcgataacat tgcaagcgtg ttcattaatg ctgttatcta a | 1671 |

<210> SEQ ID NO 3
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 3

```
Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Cys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met His Gly Val Tyr Phe
        275                 280                 285

Glu Pro Gln Tyr Leu Arg Gly Arg Ile Leu Thr Lys Val Ile Ala
    290                 295                 300

Met Thr Ser Ile Leu Asp Asp Ile His Asp Ala Tyr Gly Ser Pro Glu
305                 310                 315                 320

Glu Leu Lys Leu Phe Ile Glu Ala Ile Glu Lys Trp Asp Glu Ser Ser
                325                 330                 335

Ile Asn Gln Leu Pro Glu Tyr Met Lys Leu Cys Phe Val Ala Leu Ile
            340                 345                 350

Asp Val Tyr Asn Glu Ile Glu Glu Met Glu Lys Glu Gly Asn Gln
        355                 360                 365

Tyr Arg Ile His Tyr Leu Lys Glu Val Met Lys Asn Gln Val Arg Ala
    370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Ser Gly Tyr Cys Leu Leu
                405                 410                 415
```

```
Ala Val Thr Ser Phe Val Gly Met Gly Glu Ile Val Thr Lys Glu Ala
            420                 425                 430

Phe Asp Trp Val Thr Ser Asp Pro Lys Leu Met Ser Ser Asn Phe
        435                 440                 445

Ile Thr Arg Leu Met Asp Asp Ile Lys Ser His Lys Phe Glu Gln Lys
    450                 455                 460

Arg Gly His Val Thr Ser Ala Val Glu Cys Tyr Met Lys Gln Tyr Gly
465                 470                 475                 480

Val Thr Glu Glu Gln Val Tyr Ser Glu Phe Lys Lys Gln Ile Glu Asn
                485                 490                 495

Ala Trp Leu Asp Ile Asn Gln Glu Cys Leu Lys Pro Thr Ala Val Pro
            500                 505                 510

Met Pro Leu Leu Ala Arg Leu Leu Asn Phe Thr Arg Thr Met Asp Val
        515                 520                 525

Ile Tyr Lys Glu Gln Asp Ser Tyr Thr His Val Gly Lys Val Met Arg
    530                 535                 540

Asp Asn Ile Ala Ser Val Phe Ile Asn Pro Val Ile
545                 550                 555
```

<210> SEQ ID NO 4
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 4

```
atggcaaccc aggtgagtgc aagcagcctg gcccaaatcc ctcagccgaa aaaccgcccg      60
gttgcaaact tccaccctaa tatctggggc gatcagttca tcacctatac cccggaagat     120
aaagtgacaa gggcctgcaa agaggagcag atcgaggacc tgaaaaaaga ggtgaagcgc     180
aagctgaccg cagccgcagt ggcaaacccg agccaactgt taaacttcat cgatgccgtg     240
cagcgcctgg gcgttgccta tcacttcgag caggaaatcg aagaagccct acagcacatc     300
tgtaacagct ccacgattg taacgacatg gatggcgact tatacaacat agcattaggt     360
ttccgcttac tgcgtcagca gggctacacc ataagctgcg acatctttaa caagtttacc     420
gacgagcgcg gtcgttttaa agaggcgctg attagcgacg ttcgcggcat gttaggtctg     480
tacgaagccg cacatctgcg cgtgcacggc gaagacattc tggcgaaggc gctggcattc     540
acaaccacac acctgaaggc aatggtggaa agtctgggct accacttagc cgagcaggtt     600
gcccatgcac tgaatcgccc gattcgtaag ggcctggaac gcctggaagc ccgctggtac     660
atcagtgttt atcaggatga agcctttcat gataagaccc tgctggagct ggcaaagctg     720
gatttcaacc tggttcagag cctgcataag gaagagctga gcaacctggc ccgttggtgg     780
aaggagctgg atttcgcaac caagctgccg ttcgccaggg acaggttagt tgaaggctac     840
ttctggatgc acgcgtttta cttcgagccg caataccctgc gtggccgccg catcctgacg     900
aaggtgatcg ccatgaccag cattctggac gacatccacg atgcgtacgg gagccctgag     960
gagttaaagc tgttcatcga ggcaatcgag agtgggatg agagtagcat caaccaactg    1020
ccggagtata tgaaactgtg cttcgtggcc ctgattgatg tttacaatga gattgaagag    1080
gagatggaga agagggggaa ccagtaccgc atccactacc tgaaagaggt gatgaagaat    1140
caggtgcgcg catacttcgc agaggccaaa tggctgcatg atgagcatgt tcctgccttc    1200
gaggagtaca tgcgcgtggc cattagccag cagtggttact gtctgttagc cgttacgagc    1260
```

```
ttcgtgggta tgggcgagat cgtgaccaaa gaggcattcg actgggtgac gagcgacccg   1320
aagctgatga gcagcagcaa cttcatcacc cgtctgatgg acgacatcaa gagccacaag   1380
ttcgagcaga aacgcggtca cgttaccagc gccgtggagt gctacatgaa gcagtacggc   1440
gtgacagagg agcaagtgta cagcgagttc aagaaacaaa tcgagaacgc ctggctggac   1500
atcaaccaag agtgcctgaa accgaccgca gtgccgatgc ctctgttagc ccgtctgctg   1560
aatttcacac gcacgatgga cgttatctac aaggagcagg atagctacac ccacgttggt   1620
aaggtgatgc gcgacaacat cgccagtgtg ttcatcaacc cggtgatcta a             1671
```

<210> SEQ ID NO 5
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 5

```
Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Cys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met His Gly Val Tyr Phe
        275                 280                 285
```

```
Glu Pro Gln Tyr Leu Arg Gly Arg Arg Ile Leu Thr Lys Val Ile Ala
            290                 295                 300

Leu Thr Ser Ile Leu Asp Asp Ile His Asp Ala Tyr Gly Thr Pro Glu
305                 310                 315                 320

Glu Leu Lys Leu Phe Ile Glu Ala Ile Glu Lys Trp Asp Glu Ser Ser
                325                 330                 335

Ile Asn Gln Leu Pro Glu Tyr Met Lys Leu Cys Tyr Val Ala Leu Leu
            340                 345                 350

Asp Val Tyr Asn Glu Ile Glu Glu Met Glu Lys Glu Gly Asn Gln
            355                 360                 365

Tyr Arg Ile His Tyr Leu Lys Glu Val Met Lys Asn Gln Val Arg Ala
        370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Ser Gly Tyr Cys Leu Leu
                405                 410                 415

Ala Val Thr Ser Phe Val Gly Met Gly Glu Ile Val Thr Lys Glu Ala
            420                 425                 430

Phe Asp Trp Val Thr Ser Asp Pro Arg Ile Met Ser Ser Ser Asn Phe
        435                 440                 445

Ile Thr Arg Leu Met Asp Asp Ile Lys Ser His Lys Phe Glu Gln Lys
450                 455                 460

Arg Gly His Val Thr Ser Ala Val Glu Cys Tyr Met Lys Gln Tyr Ala
465                 470                 475                 480

Val Thr Glu Glu Gln Val Tyr Ser Glu Phe Lys Lys Gln Ile Glu Asn
                485                 490                 495

Ala Trp Leu Asp Ile Asn Gln Glu Cys Leu Lys Pro Thr Ala Val Pro
            500                 505                 510

Met Pro Leu Leu Ala Arg Leu Leu Asn Phe Thr Arg Thr Met Asp Val
        515                 520                 525

Ile Tyr Lys Glu Gln Asp Ser Tyr Thr His Val Gly Lys Thr Met Arg
530                 535                 540

Asp Asn Ile Ala Ser Val Phe Ile Asn Pro Val Ile
545                 550                 555

<210> SEQ ID NO 6
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 6
atggcaaccc aggtgagtgc aagcagcctg gcccaaatcc ctcagccgaa aaaccgcccg      60
gttgcaaact ccaccctaa tatctggggc gatcagttca tcacctatac cccggaagat     120
aaagtgacaa gggcctgcaa agaggagcag atcgaggacc tgaaaaaaga ggtgaagcgc     180
aagctgaccg cagccgcagt ggcaaacccg agccaactgt taaacttcat cgatgccgtg     240
cagcgcctgg gcgttgccta tcacttcgag caggaaatcg aagaagccct acagcacatc     300
tgtaacagct tccacgattg taacgacatg gatggcgact tatacaacat agcattaggt     360
ttccgcttac tgcgtcagca gggctacacc ataagctgcg acatctttaa caagtttacc     420
gacgagcgcg tcgttttaa agaggcgctg attagcgacg ttcgcggcat gttaggtctg     480
tacgaagccg cacatctgcg cgtgcacggc gaagacattc tggcgaaggc gctggcattc     540
```

```
acaaccacac acctgaaggc aatggtggaa agtctgggct accacttagc cgagcaggtt     600
gcccatgcac tgaatcgccc gattcgtaag ggcctggaac gcctggaagc ccgctggtac     660
atcagtgttt atcaggatga agcctttcat gataagaccc tgctggagct ggcaaagctg     720
gatttcaacc tggttcagag cctgcataag gaagagctga gcaacctggc ccgttggtgg     780
aaggagctgg atttcgcaac caagctgccg ttcgccaggg acaggttagt tgaaggctac     840
ttctggatgc acggcgttta cttcgagccg caatacctgc gtggccgccg catcctgacg     900
aaggtgatcg ccctgaccag cattctggac gacatccacg atgcgtacgg gacccctgag     960
gagttaaagc tgttcatcga ggcaatcgag aagtgggatg agagtagcat caaccaactg    1020
ccggagtata tgaaactgtg ctatgtggcc ctgctggatg tttacaatga gattgaagag    1080
gagatggaga agagggggaa ccagtaccgc atccactacc tgaaagaggt gatgaagaat    1140
caggtgcgcg catacttcgc agaggccaaa tggctgcatg atgagcatgt tcctgccttc    1200
gaggagtaca tgcgcgtggc attagccagc agtggttact gtctgttagc cgttacgagc    1260
ttcgtgggta tgggcgagat cgtgaccaaa gaggcattcg actgggtgac gagcgacccg    1320
cgtattatga gcagcagcaa cttcatcacc cgtctgatgg acgacatcaa gagccacaag    1380
ttcgagcaga aacgcggtca cgttaccagc gccgtggagt gctacatgaa gcagtacgca    1440
gtgacagagg agcaagtgta cagcgagttc aagaaacaaa tcgagaacgc ctggctggac    1500
atcaaccaag agtgcctgaa accgaccgca gtgccgatgc tctgttagcc cgtctgctg     1560 aatttcacac gcacgatgga cgttatctac aaggagcagg atagctacac ccacgttggt    1620
aagaccatgc gcgacaacat cgccagtgtg ttcatcaacc cggtgatcta a              1671
```

<210> SEQ ID NO 7
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 7

```
Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Lys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160
```

```
Tyr Glu Ala Ala His Leu Arg Val His Gly Glu Asp Ile Leu Ala Lys
            165                 170                 175

Ala Leu Ala Phe Thr Thr Thr His Leu Lys Ala Met Val Glu Ser Leu
        180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met Met Gly Val Tyr Phe
        275                 280                 285

Glu Pro Gln Tyr Leu Arg Gly Arg Arg Ile Leu Thr Lys Val Ile Ala
        290                 295                 300

Met Thr Ser Ile Leu Asp Asp Ile His Asp Ala Tyr Gly Ser Pro Glu
305                 310                 315                 320

Glu Leu Lys Leu Phe Ile Glu Ala Ile Glu Lys Trp Asp Glu Ser Ser
                325                 330                 335

Ile Asn Gln Leu Pro Glu Tyr Met Lys Leu Cys Phe Val Ala Leu Ile
            340                 345                 350

Asp Val Tyr Asn Glu Ile Glu Glu Met Glu Lys Glu Gly Asn Gln
        355                 360                 365

Tyr Arg Ile His Tyr Leu Lys Glu Val Met Lys Asn Gln Val Arg Ala
    370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Ser Gly Tyr Cys Leu Leu
                405                 410                 415

Ala Val Thr Ser Phe Val Gly Met Gly Glu Ile Val Thr Lys Glu Ala
            420                 425                 430

Phe Asp Trp Val Thr Ser Asp Pro Lys Leu Met Ser Ser Ser Asn Thr
        435                 440                 445

Ile Thr Arg Leu Met Asp Asp Ile Lys Ser His Lys Phe Glu Gln Lys
    450                 455                 460

Arg Gly His Val Thr Ser Ala Val Glu Cys Tyr Met Lys Gln Tyr Gly
465                 470                 475                 480

Val Thr Glu Glu Gln Val Tyr Ser Glu Phe Lys Lys Gln Ile Glu Asn
                485                 490                 495

Ala Trp Leu Asp Ile Asn Gln Glu Cys Leu Lys Pro Thr Ala Val Pro
            500                 505                 510

Met Pro Leu Leu Ala Arg Leu Leu Asn Phe Thr Arg Thr Met Asp Val
        515                 520                 525

Ile Tyr Lys Glu Glu Asp Ser Tyr Thr His Val Gly Lys Val Met Arg
    530                 535                 540

Asp Asn Ile Ala Ser Val Phe Ile Asn Pro Val Ile
545                 550                 555

<210> SEQ ID NO 8
<211> LENGTH: 1671
<212> TYPE: DNA
```

<213> ORGANISM: Artificial Sequence
<220> FEATURE:
<223> OTHER INFORMATION: Synthetic - Engineered valencene synthase

<400> SEQUENCE: 8

```
atggcaaccc aggtgagtgc aagcagcctg gcccaaatcc ctcagccgaa aaaccgcccg      60
gttgcaaaact tccaccctaa tatctggggc gatcagttca tcacctatac cccggaagat    120
aaagtgacaa gggccaaaaa agaggagcag atcgaggacc tgaaaaaaga ggtgaagcgc     180
aagctgaccg cagccgcagt ggcaaacccg agccaactgt taaacttcat cgatgccgtg     240
cagcgcctgg gcgttgccta tcacttcgag caggaaatcg aagaagccct acagcacatc     300
tgtaacagct ccacgattg taacgacatg gatggcgact tatacaacat agcattaggt      360
ttccgcttac tgcgtcagca gggctacacc ataagctgcg acatctttaa caagtttacc     420
gacgagcgcg tcgttttaa agaggcgctg attagcgacg ttcgcggcat gttaggtctg      480
tacgaagccg cacatctgcg cgtgcacggc gaagacattc tggcgaaggc gctggcattc     540
acaaccacac acctgaaggc aatggtgaaa gtctgggct accacttagc cgagcaggtt     600
gcccatgcac tgaatcgccc gattcgtaag ggcctggaac gcctggaagc ccgctggtac    660
atcagtgttt atcaggatga agccttcat gataagaccc tgctggagct ggcaaagctg      720
gatttcaacc tggttcagag cctgcataag gaagagctga gcaacctggc ccgttggtgg    780
aaggagctgg atttcgcaac caagctgccg ttcgccaggg acaggttagt tgaaggctac    840
ttctggatga tgggcgttta cttcgagccg caataccctgc gtggccgccg catcctgacg    900
aaggtgatcg ccatgaccag cattctggac gacatccacg atgcgtacgg gagccctgag   960
gagttaaagc tgttcatcga ggcaatcgag aagtgggatg agagtagcat caaccaactg   1020
ccggagtata tgaaactgtg cttcgtggcc ctgattgatg tttacaatga gattgaagag   1080
gagatggaga agagggggaa ccagtaccgc atccactacc tgaaagaggt gatgaagaat   1140
caggtgcgcg catacttcgc agaggccaaa tggctgcatg atgagcatgt tcctgccttc   1200
gaggagtaca tgcgcgtggc attagccagc agtggttact gtctgttagc cgttacgagc   1260
ttcgtgggta tgggcgagat cgtgaccaaa gaggcattcg actgggtgac gagcgacccg   1320
aagctgatga gcagcagcaa caccatcacc cgtctgatgg acgacatcaa gagccacaag   1380
ttcgagcaga aacgcggtca cgttaccagc gccgtggagt gctacatgaa gcagtacggc   1440
gtgacagagg agcaagtgta cagcgagttc aagaaacaaa tcgagaacgc ctggctggac   1500
atcaaccaag agtgcctgaa accgaccgca gtgccgatgc ctctgttagc ccgtctgctg   1560
aatttcacac gcacgatgga cgttatctac aaggaggaag atagctacac ccacgttggt   1620
aaggtgatgc gcgacaacat cgccagtgtg ttcatcaacc cggtgatcta a            1671
```

<210> SEQ ID NO 9
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 9

```
Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30
```

```
Phe Ile Thr Tyr Thr Pro Glu Asp Lys Val Thr Arg Ala Lys Lys Glu
            35                  40                  45

Glu Gln Ile Glu Asp Leu Lys Lys Glu Val Lys Arg Lys Leu Thr Ala
 50                  55                  60

Ala Ala Val Ala Asn Pro Ser Gln Leu Leu Asn Phe Ile Asp Ala Val
 65                  70                  75                  80

Gln Arg Leu Gly Val Ala Tyr His Phe Glu Gln Glu Ile Glu Glu Ala
                 85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
            115                 120                 125

Tyr Thr Ile Ser Cys Asp Ile Phe Asn Lys Phe Thr Asp Glu Arg Gly
            130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
            195                 200                 205

Arg Lys Gly Leu Glu Arg Leu Glu Ala Arg Trp Tyr Ile Ser Val Tyr
            210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met Met Gly Val Tyr Phe
            275                 280                 285

Glu Pro Gln Tyr Leu Arg Gly Arg Arg Ile Leu Thr Lys Val Ile Ala
            290                 295                 300

Leu Thr Ser Ile Leu Asp Asp Ile His Asp Ala Tyr Gly Thr Pro Glu
305                 310                 315                 320

Glu Leu Lys Leu Phe Ile Glu Ala Ile Glu Lys Trp Asp Glu Ser Ser
                325                 330                 335

Ile Asn Gln Leu Pro Glu Tyr Met Lys Leu Cys Tyr Val Ala Leu Leu
            340                 345                 350

Asp Val Tyr Asn Glu Ile Glu Glu Met Glu Lys Glu Gly Asn Gln
            355                 360                 365

Tyr Arg Ile His Tyr Leu Lys Glu Val Met Lys Asn Gln Val Arg Ala
            370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Ser Gly Tyr Cys Leu Leu
                405                 410                 415

Ala Val Thr Ser Phe Val Gly Met Gly Glu Ile Val Thr Lys Glu Ala
            420                 425                 430

Phe Asp Trp Val Thr Ser Asp Pro Arg Ile Met Ser Ser Ser Asn Thr
            435                 440                 445
```

```
Ile Thr Arg Leu Met Asp Asp Ile Lys Ser His Lys Phe Glu Gln Lys
            450                 455                 460
Arg Gly His Val Thr Ser Ala Val Glu Cys Tyr Met Lys Gln Tyr Ala
465                 470                 475                 480
Val Thr Glu Glu Gln Val Tyr Ser Glu Phe Lys Lys Gln Ile Glu Asn
                485                 490                 495
Ala Trp Leu Asp Ile Asn Gln Glu Cys Leu Lys Pro Thr Ala Val Pro
            500                 505                 510
Met Pro Leu Leu Ala Arg Leu Leu Asn Phe Thr Arg Thr Met Asp Val
        515                 520                 525
Ile Tyr Lys Glu Glu Asp Ser Tyr Thr His Val Gly Lys Thr Met Arg
    530                 535                 540
Asp Asn Ile Ala Ser Val Phe Ile Asn Pro Val Ile
545                 550                 555

<210> SEQ ID NO 10
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 10
atggcaaccc aggtgagtgc aagcagcctg gcccaaatcc ctcagccgaa aaaccgcccg      60 gttgcaaaact tccaccctaa tatctggggc gatcagttca tcacctatac cccggaagat    120
aaagtgacaa gggccaaaaa agaggagcag atcgaggacc tgaaaaaaga ggtgaagcgc     180
aagctgaccg cagccgcagt ggcaaacccg agccaactgt taaacttcat cgatgccgtg    240
cagcgcctgg gcgttgccta tcacttcgag caggaaatcg aagaagccct acagcacatc    300
tgtaacagct tccacgattg taacgacatg gatggcgact tatacaacat agcattaggt    360
ttccgcttac tgcgtcagca gggctacacc ataagctgcg acatctttaa caagtttacc    420
gacgagcgcg gtcgttttaa agaggcgctg attagcgacg ttcgcggcat gttaggtctg    480
tacgaagccg cacatctgcg cgtgcacggc gaagacattc tggcgaaggc gctggcattc    540
acaaccacac acctgaaggc aatggtggaa agtctgggct accacttagc cgagcaggtt    600
gcccatgcac tgaatcgccc gattcgtaag ggcctggaac gcctggaagc ccgctggtac    660
atcagtgttt atcaggatga agcctttcat gataagaccc tgctggagct ggcaaagctg    720
gatttcaacc tggttcagag cctgcataag gaagagctga gcaacctggc ccgttggtgg    780
aaggagctgg atttcgcaac caagctgccg ttcgccaggg acaggttagt tgaaggctac    840
ttctggatga tgggcgtta cttcgagccg caataccctgc gtggccgccg catcctgacg    900
aaggtgatcg ccctgaccag cattctggac gacatccacg atgcgtacgg gacccctgag    960
gagttaaagc tgttcatcga ggcaatcgag agtgggatg agagtagcat caaccaactg    1020
ccggagtata tgaaactgtg ctatgtggcc ctgctggatg tttacaatga gattgaagag    1080
gagatggaga agagggggaa ccagtaccgc atccactacc tgaaagaggt gatgaagaat    1140
caggtgcgcg catacttcgc agaggccaaa tggctgcatg atgagcatgt tcctgccttc    1200
gaggagtaca tgcgcgtggc attagccagc agtggttact gtctgttagc cgttacgagc    1260
ttcgtgggta tgggcgagat cgtgaccaaa gaggcattcg actgggtgac gagcgacccg    1320
cgtattatga gcagcagcaa caccatcacc cgtctgatgg acgacatcaa gagccacaag    1380
ttcgagcaga aacgcggtca cgttaccagc gccgtggagt gctacatgaa gcagtacgca    1440
```

-continued

```
gtgacagagg agcaagtgta cagcgagttc aagaaacaaa tcgagaacgc ctggctggac      1500
atcaaccaag agtgcctgaa accgaccgca gtgccgatgc tctgttagc ccgtctgctg      1560 aatttcacac gcacgatgga cgttatctac aaggaggaag atagctacac ccacgttggt      1620
aagaccatgc gcgacaacat cgccagtgtg ttcatcaacc cggtgatcta a              1671
```

<210> SEQ ID NO 11
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 11

```
Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Lys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met Met Gly Val Tyr Phe
        275                 280                 285

Glu Pro Gln Tyr Leu Arg Gly Arg Ile Leu Thr Lys Val Ile Ala
    290                 295                 300

Leu Thr Ser Ile Leu Asp Asp Ile His Asp Ala Tyr Gly Thr Pro Glu
305                 310                 315                 320
```

```
Glu Leu Lys Leu Phe Ile Glu Ala Ile Glu Lys Trp Asp Glu Ser Ser
            325                 330                 335

Ile Asn Gln Leu Pro Glu Tyr Met Lys Leu Cys Tyr Val Ala Leu Leu
        340                 345                 350

Asp Val Tyr Asn Glu Ile Glu Glu Met Glu Lys Glu Gly Asn Gln
        355                 360                 365

Tyr Arg Ile His Tyr Leu Lys Glu Val Met Lys Asn Gln Val Arg Ala
    370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Ser Gly Tyr Cys Leu Leu
                405                 410                 415

Ala Val Thr Ser Phe Val Gly Met Gly Glu Ile Val Thr Lys Glu Ala
                420                 425                 430

Phe Asp Trp Val Thr Ser Asp Pro Arg Ile Met Ser Ser Ser Asn Thr
            435                 440                 445

Ile Thr Arg Leu Met Asp Asp Ile Lys Ser His Lys Phe Glu Gln Lys
        450                 455                 460

Arg Gly His Val Thr Ser Ala Val Glu Cys Tyr Met Lys Gln Tyr Ala
465                 470                 475                 480

Val Thr Glu Glu Gln Val Tyr Ser Glu Phe Lys Lys Gln Ile Glu Asn
                485                 490                 495

Ala Trp Leu Asp Ile Asn Gln Glu Cys Leu Lys Pro Thr Ala Val Pro
            500                 505                 510

Met Pro Leu Leu Ala Arg Leu Leu Asn Phe Thr Arg Thr Met Asp Val
        515                 520                 525

Ile Tyr Lys Glu Glu Asp Ser Tyr Thr His Val Gly Lys Thr Met Arg
    530                 535                 540

Asp Asn Ile Ala Ser Val Phe Ile Asn Pro Val Ile
545                 550                 555

<210> SEQ ID NO 12
<211> LENGTH: 548
<212> TYPE: PRT
<213> ORGANISM: Citrus sinensus

<400> SEQUENCE: 12

Met Ala Ser Gly Glu Thr Phe Arg Pro Thr Ala Asp Phe His Pro Ser
1               5                   10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Glu Val
        35                  40                  45

Arg Arg Met Ile Thr Asp Ala Glu Asp Lys Pro Val Gln Lys Leu Arg
    50                  55                  60

Leu Ile Asp Glu Val Gln Arg Leu Gly Val Ala Tyr His Phe Glu Lys
65                  70                  75                  80

Glu Ile Gly Asp Ala Ile Gln Lys Leu Cys Pro Ile Tyr Ile Asp Ser
                85                  90                  95

Asn Arg Ala Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
        115                 120                 125

Asp Glu Gly Arg Phe Lys Ser Ser Leu Ile Asn Asp Val Gln Gly Met
    130                 135                 140
```

```
Leu Ser Leu Tyr Glu Ala Ala Tyr Met Ala Val Arg Gly Glu His Ile
145                 150                 155                 160
Leu Asp Glu Ala Ile Ala Phe Thr Thr Thr His Leu Lys Ser Leu Val
            165                 170                 175
Ala Gln Asp His Val Thr Pro Lys Leu Ala Glu Gln Ile Asn His Ala
        180                 185                 190
Leu Tyr Arg Pro Leu Arg Lys Thr Leu Pro Arg Leu Glu Ala Arg Tyr
    195                 200                 205
Phe Met Ser Met Ile Asn Ser Thr Ser Asp His Leu Cys Asn Lys Thr
210                 215                 220
Leu Leu Asn Phe Ala Lys Leu Asp Phe Asn Ile Leu Glu Leu His
225                 230                 235                 240
Lys Glu Glu Leu Asn Glu Leu Thr Lys Trp Trp Lys Asp Leu Asp Phe
                245                 250                 255
Thr Thr Lys Leu Pro Tyr Ala Arg Asp Arg Leu Val Glu Leu Tyr Phe
            260                 265                 270
Trp Asp Leu Gly Thr Tyr Phe Glu Pro Gln Tyr Ala Phe Gly Arg Lys
        275                 280                 285
Ile Met Thr Gln Leu Asn Tyr Ile Leu Ser Ile Ile Asp Asp Thr Tyr
    290                 295                 300
Asp Ala Tyr Gly Thr Leu Glu Glu Leu Ser Leu Phe Thr Glu Ala Val
305                 310                 315                 320
Gln Arg Trp Asn Ile Glu Ala Val Asp Met Leu Pro Glu Tyr Met Lys
                325                 330                 335
Leu Ile Tyr Arg Thr Leu Leu Asp Ala Phe Asn Glu Ile Glu Glu Asp
            340                 345                 350
Met Ala Lys Gln Gly Arg Ser His Cys Val Arg Tyr Ala Lys Glu Glu
        355                 360                 365
Asn Gln Lys Val Ile Gly Ala Tyr Ser Val Gln Ala Lys Trp Phe Ser
    370                 375                 380
Glu Gly Tyr Val Pro Thr Ile Glu Glu Tyr Met Pro Ile Ala Leu Thr
385                 390                 395                 400
Ser Cys Ala Tyr Thr Phe Val Ile Thr Asn Ser Phe Leu Gly Met Gly
                405                 410                 415
Asp Phe Ala Thr Lys Glu Val Phe Glu Trp Ile Ser Asn Asn Pro Lys
            420                 425                 430
Val Val Lys Ala Ala Ser Val Ile Cys Arg Leu Met Asp Asp Met Gln
        435                 440                 445
Gly His Glu Phe Glu Gln Lys Arg Gly His Val Ala Ser Ala Ile Glu
    450                 455                 460
Cys Tyr Thr Lys Gln His Gly Val Ser Lys Glu Ala Ile Lys Met
465                 470                 475                 480
Phe Glu Glu Val Ala Asn Ala Trp Lys Asp Ile Asn Glu Glu Leu
                485                 490                 495
Met Met Lys Pro Thr Val Val Ala Arg Pro Leu Leu Gly Thr Ile Leu
            500                 505                 510
Asn Leu Ala Arg Ala Ile Asp Phe Ile Tyr Lys Glu Asp Asp Gly Tyr
        515                 520                 525
Thr His Ser Tyr Leu Ile Lys Asp Gln Ile Ala Ser Val Leu Gly Asp
    530                 535                 540
His Val Pro Phe
545
```

<210> SEQ ID NO 13
<211> LENGTH: 513
<212> TYPE: PRT
<213> ORGANISM: Zingiber zerumbet

<400> SEQUENCE: 13

Met Glu Ala Ile Ser Leu Phe Ser Pro Phe Phe Ile Thr Leu Phe
1               5                   10                  15

Leu Gly Phe Phe Ile Thr Leu Leu Ile Lys Arg Ser Arg Ser Ser
                20                  25                  30

Val His Lys Gln Gln Val Leu Leu Ala Ser Leu Pro Pro Ser Pro Pro
            35                  40                  45

Arg Leu Pro Leu Ile Gly Asn Ile His Gln Leu Val Gly Gly Asn Pro
        50                  55                  60

His Arg Ile Leu Leu Gln Leu Ala Arg Thr His Gly Pro Leu Ile Cys
65                  70                  75                  80

Leu Arg Leu Gly Gln Val Asp Gln Val Val Ala Ser Ser Val Glu Ala
                85                  90                  95

Val Glu Glu Ile Ile Lys Arg His Asp Leu Lys Phe Ala Asp Arg Pro
            100                 105                 110

Arg Asp Leu Thr Phe Ser Arg Ile Phe Phe Tyr Asp Gly Asn Ala Val
        115                 120                 125

Val Met Thr Pro Tyr Gly Gly Glu Trp Lys Gln Met Arg Lys Ile Tyr
130                 135                 140

Ala Met Glu Leu Leu Asn Ser Arg Arg Val Lys Ser Phe Ala Ala Ile
145                 150                 155                 160

Arg Glu Asp Val Ala Arg Lys Leu Thr Gly Glu Ile Ala His Lys Ala
                165                 170                 175

Phe Ala Gln Thr Pro Val Ile Asn Leu Ser Glu Met Val Met Ser Met
            180                 185                 190

Ile Asn Ala Ile Val Ile Arg Val Ala Phe Gly Asp Lys Cys Lys Gln
        195                 200                 205

Gln Ala Tyr Phe Leu His Leu Val Lys Glu Ala Met Ser Tyr Val Ser
210                 215                 220

Ser Phe Ser Val Ala Asp Met Tyr Pro Ser Leu Lys Phe Leu Asp Thr
225                 230                 235                 240

Leu Thr Gly Leu Lys Ser Lys Leu Glu Gly Val His Gly Lys Leu Asp
                245                 250                 255

Lys Val Phe Asp Glu Ile Ile Ala Gln Arg Gln Ala Ala Leu Ala Ala
            260                 265                 270

Glu Gln Ala Glu Glu Asp Leu Ile Ile Asp Val Leu Leu Lys Leu Lys
        275                 280                 285

Asp Glu Gly Asn Gln Glu Phe Pro Ile Thr Tyr Thr Ser Val Lys Ala
290                 295                 300

Ile Val Met Glu Ile Phe Leu Ala Gly Thr Glu Thr Ser Ser Ser Val
305                 310                 315                 320

Ile Asp Trp Val Met Ser Glu Leu Ile Lys Asn Pro Lys Ala Met Glu
                325                 330                 335

Lys Val Gln Lys Glu Met Arg Glu Ala Met Gln Gly Lys Thr Lys Leu
            340                 345                 350

Glu Glu Ser Asp Ile Pro Lys Phe Ser Tyr Leu Asn Leu Val Ile Lys
        355                 360                 365

Glu Thr Leu Arg Leu His Pro Pro Gly Pro Leu Leu Phe Pro Arg Glu
370                 375                 380

```
Cys Arg Glu Thr Cys Glu Val Met Gly Tyr Arg Val Pro Ala Gly Ala
385                 390                 395                 400

Arg Leu Leu Ile Asn Ala Phe Ala Leu Ser Arg Asp Glu Lys Tyr Trp
            405                 410                 415

Gly Ser Asp Ala Glu Ser Phe Lys Pro Glu Arg Phe Glu Gly Ile Ser
        420                 425                 430

Val Asp Phe Lys Gly Ser Asn Phe Glu Phe Met Pro Phe Gly Ala Gly
        435                 440                 445

Arg Arg Ile Cys Pro Gly Met Thr Phe Gly Ile Ser Ser Val Glu Val
450                 455                 460

Ala Leu Ala His Leu Leu Phe His Phe Asp Trp Gln Leu Pro Gln Gly
465                 470                 475                 480

Met Lys Ile Glu Asp Leu Asp Met Met Glu Val Ser Gly Met Ser Ala
            485                 490                 495

Thr Arg Arg Ser Pro Leu Leu Val Leu Ala Lys Leu Ile Ile Pro Leu
                500                 505                 510

Pro
```

<210> SEQ ID NO 14
<211> LENGTH: 512
<212> TYPE: PRT
<213> ORGANISM: Zingiber zerumbet

<400> SEQUENCE: 14

```
Met Ala Leu Leu Leu Ala Val Phe Phe Phe Ile Thr Leu Phe Leu
1               5                   10                  15

Gly Phe Phe Ile Thr Leu Leu Ile Lys Arg Ser Ser Arg Ser Ser Val
                20                  25                  30

His Lys Gln Gln Val Leu Leu Ala Ser Leu Pro Pro Ser Pro Pro Arg
            35                  40                  45

Leu Pro Leu Ile Gly Asn Ile His Gln Leu Val Gly Gly Asn Pro His
        50                  55                  60

Arg Ile Leu Leu Gln Leu Ala Arg Thr His Gly Pro Leu Ile Cys Leu
65                  70                  75                  80

Arg Leu Gly Gln Val Asp Gln Val Val Ala Ser Ser Val Glu Ala Val
                85                  90                  95

Glu Glu Ile Ile Lys Arg His Asp Leu Lys Phe Ala Asp Arg Pro Arg
            100                 105                 110

Asp Leu Thr Phe Ser Arg Ile Phe Phe Tyr Asp Gly Asn Ala Val Val
        115                 120                 125

Met Thr Pro Tyr Gly Gly Glu Trp Lys Gln Met Arg Lys Ile Tyr Ala
130                 135                 140

Met Glu Leu Leu Asn Ser Arg Arg Val Lys Ser Phe Ala Ala Ile Arg
145                 150                 155                 160

Glu Asp Val Ala Arg Lys Leu Thr Gly Glu Ile Ala His Lys Ala Phe
                165                 170                 175

Ala Gln Thr Pro Val Ile Asn Leu Ser Glu Met Val Met Ser Met Ile
            180                 185                 190

Asn Ala Ile Val Ile Arg Val Ala Phe Gly Asp Lys Cys Lys Gln Gln
        195                 200                 205

Ala Tyr Phe Leu His Leu Val Lys Glu Ala Met Ser Tyr Val Ser Ser
210                 215                 220

Phe Ser Val Ala Asp Met Tyr Pro Ser Leu Lys Phe Leu Asp Thr Leu
225                 230                 235                 240
```

Thr Gly Leu Lys Ser Lys Leu Glu Gly Val His Gly Lys Leu Asp Lys
            245                 250                 255

Val Phe Asp Glu Ile Ile Ala Gln Arg Gln Ala Ala Leu Ala Ala Glu
        260                 265                 270

Gln Ala Glu Glu Asp Leu Ile Ile Asp Val Leu Leu Lys Leu Lys Asp
    275                 280                 285

Glu Gly Asn Gln Glu Phe Pro Ile Thr Tyr Thr Ser Val Lys Ala Ile
290                 295                 300

Val Met Glu Ile Phe Leu Ala Gly Thr Glu Thr Ser Ser Ser Val Ile
305                 310                 315                 320

Asp Trp Val Met Ser Glu Leu Ile Lys Asn Pro Lys Ala Met Glu Lys
                325                 330                 335

Val Gln Lys Glu Met Arg Glu Ala Met Gln Gly Lys Thr Lys Leu Glu
            340                 345                 350

Glu Ser Asp Ile Pro Lys Phe Ser Tyr Leu Asn Leu Val Ile Lys Glu
        355                 360                 365

Thr Leu Arg Leu His Pro Pro Gly Pro Leu Leu Phe Pro Arg Glu Cys
    370                 375                 380

Arg Glu Thr Cys Glu Val Met Gly Tyr Arg Val Pro Ala Gly Ala Arg
385                 390                 395                 400

Leu Leu Ile Asn Ala Phe Ala Leu Ser Arg Asp Glu Lys Tyr Trp Gly
                405                 410                 415

Ser Asp Ala Glu Ser Phe Lys Pro Glu Arg Phe Glu Gly Ile Ser Val
            420                 425                 430

Asp Phe Lys Gly Ser Asn Phe Glu Phe Met Pro Phe Gly Ala Gly Arg
        435                 440                 445

Arg Ile Cys Pro Gly Met Thr Phe Gly Ile Ser Ser Val Glu Val Ala
    450                 455                 460

Leu Ala His Leu Leu Phe His Phe Asp Trp Gln Leu Pro Gln Gly Met
465                 470                 475                 480

Lys Ile Glu Asp Leu Asp Met Met Glu Val Ser Gly Met Ser Ala Thr
                485                 490                 495

Arg Arg Ser Pro Leu Leu Val Leu Ala Lys Leu Ile Ile Pro Leu Pro
            500                 505                 510

<210> SEQ ID NO 15
<211> LENGTH: 1536
<212> TYPE: DNA
<213> ORGANISM: Zingiber zerumbet

<400> SEQUENCE: 15
atggctctgt tattagcagt gttcttcttt tcattacgc tgtttctggg tttctttatt      60
acgctgctga ttaaacgctc gtcccgtagc tctgtccata acagcaagt gctgctggcc     120 tctctgccgc cgagtccgcc gcgcctgccg ctgattggca catccatca actggtgggc     180 ggcaacccgc atcgtattct gctgcaactg gcgcgtaccc acggcccgct gatctgcctg     240
cgtctgggtc aggttgatca agtggttgca agttccgtgg aagctgttga agaaattatc     300
aaacgtcacg acctgaaatt tgcagatcgt ccgcgcgacc tgacctttag ccgtattttc     360
ttttatgatg gtaacgctgt cgtgatgacg ccgtacggcg gtgaatggaa acagatgcgt     420
aaaatctatg caatggaact gctgaacagc cgtcgtgtga atctttttgc ggccattcgt     480
gaagacgttg cacgcaaact gaccggcgaa atcgctcaca agcattcgc tcagacgccg     540 gtcattaacc tgtctgaaat ggtgatgagt atgatcaatg cgattgtcat ccgcgtggcc     600

```
tttggtgata aatgtaaaca gcaagcatac ttcctgcatc tggtgaaaga agctatgtcc    660
tatgtttcat cgtttcagt cgcggatatg tacccgtccc tgaaattcct ggacaccctg    720
acgggcctga aaagcaaact ggaaggcgtt cacggtaaac tggataaagt cttcgacgaa    780
atcatcgcac agcgtcaagc agcgctggcg gcggaacagg ctgaagaaga tctgattatc    840
gacgtgctgc tgaaactgaa agatgaaggc aaccaggaat tccgattac ctatacgtca     900
gttaaagcga ttgtcatgga aatcttcctg gccggcaccg aaaccagcag cagcgtgatt    960
gactgggtta tgagtgaact gatcaaaaac ccgaaagcga tggaaaaagt gcagaaagaa   1020
atgcgtgaag ccatgcaagg caaaaccaaa ctggaagaat cggatattcc gaaatttagc   1080
tacctgaatc tggttatcaa agaaaccctg cgtctgcatc cgccgggtcc gctgctgttc   1140
ccgcgtgaat gccgcgaaac ctgcgaagtg atgggctatc gtgttccggc gggtgcccgc   1200
ctgctgatta acgcatttgc tctgtctcgt gatgaaaat actggggttc cgacgccgaa    1260
tcatttaaac cggaacgctt tgaaggcatc tctgtggatt tcaaaggtag taattttgaa   1320
tttatgccgt tcggcgcggg ccgtcgtatt tgtccgggca tgacctttgg tatctcctca   1380
gttgaagtcg cgctggccca tctgctgttt cacttcgatt ggcaactgcc gcaaggcatg   1440
aaaattgaag atctggacat gatggaagtc tcgggtatga gcgcaacccg tcgtagcccg   1500
ctgctggttc tggccaaact gattatcccg ctgccg                             1536
```

<210> SEQ ID NO 16
<211> LENGTH: 496
<212> TYPE: PRT
<213> ORGANISM: Barnadesia spinosa

<400> SEQUENCE: 16

```
Met Glu Leu Thr Leu Thr Thr Ser Leu Gly Leu Ala Val Phe Val Phe
1               5                   10                  15

Ile Leu Phe Lys Leu Leu Thr Gly Ser Lys Thr Lys Asn Ser Leu
            20                  25                  30

Pro Glu Ala Trp Arg Leu Pro Ile Ile Gly His Met His His Leu Val
        35                  40                  45

Gly Thr Leu Pro His Arg Gly Val Thr Asp Met Ala Arg Lys Tyr Gly
    50                  55                  60

Ser Leu Met His Leu Gln Leu Gly Glu Val Ser Thr Ile Val Val Ser
65                  70                  75                  80

Ser Pro Arg Trp Ala Lys Glu Val Leu Thr Thr Tyr Asp Ile Thr Phe
                85                  90                  95

Ala Asn Arg Pro Glu Thr Leu Thr Gly Glu Ile Val Ala Tyr His Asn
            100                 105                 110

Thr Asp Ile Val Leu Ser Pro Tyr Gly Glu Tyr Trp Arg Gln Leu Arg
        115                 120                 125

Lys Leu Cys Thr Leu Glu Leu Leu Ser Ala Lys Val Lys Ser Phe
    130                 135                 140

Gln Ser Leu Arg Glu Glu Glu Cys Trp Asn Leu Val Lys Glu Val Arg
145                 150                 155                 160

Ser Ser Gly Ser Gly Ser Pro Val Asp Leu Ser Glu Ser Ile Phe Lys
                165                 170                 175

Leu Ile Ala Thr Ile Leu Ser Arg Ala Ala Phe Gly Lys Gly Ile Lys
            180                 185                 190

Asp Gln Arg Glu Phe Thr Glu Ile Val Lys Glu Ile Leu Arg Leu Thr
        195                 200                 205
```

```
Gly Gly Phe Asp Val Ala Asp Ile Phe Pro Ser Lys Lys Ile Leu His
    210                 215                 220

His Leu Ser Gly Lys Arg Ala Lys Leu Thr Asn Ile His Asn Lys Leu
225                 230                 235                 240

Asp Ser Leu Ile Asn Asn Ile Val Ser Glu His Pro Gly Ser Arg Thr
                245                 250                 255

Ser Ser Ser Gln Glu Ser Leu Leu Asp Val Leu Leu Arg Leu Lys Asp
            260                 265                 270

Ser Ala Glu Leu Pro Leu Thr Ser Asp Asn Val Lys Ala Val Ile Leu
        275                 280                 285

Asp Met Phe Gly Ala Gly Thr Asp Thr Ser Ser Ala Thr Ile Glu Trp
290                 295                 300

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
                325                 330                 335

Asp Ile Gln Glu Leu Ser Tyr Leu Lys Leu Val Ile Lys Glu Thr Leu
            340                 345                 350

Arg Leu His Pro Pro Leu Pro Leu Val Met Pro Arg Glu Cys Arg Glu
        355                 360                 365

Pro Cys Val Leu Ala Gly Tyr Glu Ile Pro Thr Lys Thr Lys Leu Ile
370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Asn Ile Met
                405                 410                 415

Gly Ser Glu Tyr Glu Tyr Leu Pro Phe Gly Ala Gly Arg Arg Met Cys
            420                 425                 430

Pro Gly Ala Ala Leu Gly Leu Ala Asn Val Glu Leu Pro Leu Ala His
        435                 440                 445

Ile Leu Tyr Tyr Phe Asn Trp Lys Leu Pro Asn Gly Ala Arg Leu Asp
450                 455                 460

Glu Leu Asp Met Ser Glu Cys Phe Gly Ala Thr Val Gln Arg Lys Ser
465                 470                 475                 480

Glu Leu Leu Leu Val Pro Thr Ala Tyr Lys Thr Ala Asn Asn Ser Ala
                485                 490                 495

<210> SEQ ID NO 17
<211> LENGTH: 496
<212> TYPE: PRT
<213> ORGANISM: Barnadesia spinosa

<400> SEQUENCE: 17

Met Ala Leu Leu Leu Ala Val Phe Leu Gly Leu Ala Val Phe Val Phe
1               5                   10                  15

Ile Leu Phe Lys Leu Leu Thr Gly Ser Lys Ser Thr Lys Asn Ser Leu
            20                  25                  30

Pro Glu Ala Trp Arg Leu Pro Ile Ile Gly His Met His His Leu Val
        35                  40                  45

Gly Thr Leu Pro His Arg Gly Val Thr Asp Met Ala Arg Lys Tyr Gly
    50                  55                  60

Ser Leu Met His Leu Gln Leu Gly Glu Val Ser Thr Ile Val Val Ser
65                  70                  75                  80

Ser Pro Arg Trp Ala Lys Glu Val Leu Thr Thr Tyr Asp Ile Thr Phe
                85                  90                  95
```

Ala Asn Arg Pro Glu Thr Leu Thr Gly Glu Ile Val Ala Tyr His Asn
            100                 105                 110

Thr Asp Ile Val Leu Ser Pro Tyr Gly Glu Tyr Trp Arg Gln Leu Arg
        115                 120                 125

Lys Leu Cys Thr Leu Glu Leu Ser Ala Lys Lys Val Lys Ser Phe
130                 135                 140

Gln Ser Leu Arg Glu Glu Cys Trp Asn Leu Val Lys Glu Val Arg
145                 150                 155                 160

Ser Ser Gly Ser Gly Ser Pro Val Asp Leu Ser Glu Ser Ile Phe Lys
                165                 170                 175

Leu Ile Ala Thr Ile Leu Ser Arg Ala Ala Phe Gly Lys Gly Ile Lys
            180                 185                 190

Asp Gln Arg Glu Phe Thr Glu Ile Val Lys Glu Ile Leu Arg Leu Thr
        195                 200                 205

Gly Gly Phe Asp Val Ala Asp Ile Phe Pro Ser Lys Lys Ile Leu His
210                 215                 220

His Leu Ser Gly Lys Arg Ala Lys Leu Thr Asn Ile His Asn Lys Leu
225                 230                 235                 240

Asp Ser Leu Ile Asn Asn Ile Val Ser Glu His Pro Gly Ser Arg Thr
                245                 250                 255

Ser Ser Ser Gln Glu Ser Leu Leu Asp Val Leu Leu Arg Leu Lys Asp
            260                 265                 270

Ser Ala Glu Leu Pro Leu Thr Ser Asp Asn Val Lys Ala Val Ile Leu
        275                 280                 285

Asp Met Phe Gly Ala Gly Thr Asp Thr Ser Ser Ala Thr Ile Glu Trp
290                 295                 300

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
                325                 330                 335

Asp Ile Gln Glu Leu Ser Tyr Leu Lys Leu Val Ile Lys Glu Thr Leu
            340                 345                 350

Arg Leu His Pro Pro Leu Pro Leu Val Met Pro Arg Glu Cys Arg Glu
        355                 360                 365

Pro Cys Val Leu Ala Gly Tyr Glu Ile Pro Thr Lys Thr Lys Leu Ile
370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Asn Ile Met
                405                 410                 415

Gly Ser Glu Tyr Glu Tyr Leu Pro Phe Gly Ala Gly Arg Arg Met Cys
            420                 425                 430

Pro Gly Ala Ala Leu Gly Leu Ala Asn Val Glu Leu Pro Leu Ala His
        435                 440                 445

Ile Leu Tyr Tyr Phe Asn Trp Lys Leu Pro Asn Gly Ala Arg Leu Asp
450                 455                 460

Glu Leu Asp Met Ser Glu Cys Phe Gly Ala Thr Val Gln Arg Lys Ser
465                 470                 475                 480

Glu Leu Leu Leu Val Pro Thr Ala Tyr Lys Thr Ala Asn Asn Ser Ala
                485                 490                 495

<210> SEQ ID NO 18
<211> LENGTH: 1488

<212> TYPE: DNA
<213> ORGANISM: Barnadesia spinosa

<400> SEQUENCE: 18

```
atggctctgt tattagcagt tttcctgggc ctggctgtct tcgtctttat cctgttcaaa      60
ctgctgaccg gctcaaaatc aaccaaaaat tcactgccgg aagcatggcg tctgccgatc     120
attggccaca tgcatcacct ggttggcacg ctgccgcatc gcggtgtgac cgacatggcg     180
cgtaaatacg gcagcctgat gcatctgcaa ctgggcgaag tgagcaccat tgtcgtctca     240
tcgccgcgtt gggcaaaaga agtgctgacg acgtatgata ttacctttgc gaatcgcccg     300
gaaaccctga ccggcgaaat tgttgcgtac cacaacacgg atattgtgct gtcaccgtat     360
ggcgaatact ggcgccaact gcgtaaactg tgcacgctgg aactgctgag cgccaaaaaa     420
gtgaaaagtt ttcagtcgct gcgtgaagaa gaatgctgga atctggtgaa agaagtgcgt     480
tcgagcggct caggttcccc ggtcgatctg tcggaatcca tctttaaact gattgcaacc     540
attctgagcc gcgcagcgtt tggcaaaggt atcaaagatc agcgtgaatt taccgaaatt     600
gtgaaagaaa tcctgcgcct gacgggcggt tttgatgtgg cggatatttt cccgtccaaa     660
aagatcctgc accacctgag cggcaaacgt gcgaaactga ccaacatcca caacaaactg     720
gattccctga ttaataacat tgtttctgaa catccgggtt cgcgtacctc gtcgagccag     780
gaaagcctgc tggatgtgct gctgcgcctg aaagattccg cggaactgcc gctgacctcg     840
gacaatgtta agccgtgat cctggatatg ttcggtgcgg cacggatac gtcgagcgcc     900
acgattgaat gggcgatcag cgaactgatc cgctgcccgc gtgcaatgga aaaagtgcaa     960
acggaactgc gtcaagcgct gaatggtaaa gaacgcattc aggaagaaga tattcaggaa    1020
ctgtcctatc tgaaactggt cattaaagaa accctgcgcc tgcatccgcc gctgccgctg    1080
gtgatgccgc gtgaatgtcg tgaaccgtgt gtcctggcgg gttacgaaat cccgaccaaa    1140
acgaaactga ttgtgaatgt cttgccatc aatcgtgacc cggaatactg gaaagatgca    1200
gaaaccttca tgccggaacg ctttgaaaac agcccgatta acatcatggg tagtgaatat    1260
gaatacctgc cgtttggcgc aggccgccgt atgtgtccgg tgcagctct gggtctggcg    1320
aatgtggaac tgccgctggc gcacatcctg tattatttta ctggaaaact gccgaatggc    1380
gctcgcctgg atgaactgga tatgtcggaa tgctttggcg cgacggtcca acgcaaaagc    1440
gaactgctgc tggtcccgac ggcatacaaa acggcaaaca actccgca               1488
```

<210> SEQ ID NO 19
<211> LENGTH: 502
<212> TYPE: PRT
<213> ORGANISM: Hyoscyamus muticus

<400> SEQUENCE: 19

```
Met Gln Phe Phe Ser Leu Val Ser Ile Phe Leu Phe Leu Ser Phe Leu
1               5                   10                  15

Phe Leu Leu Arg Lys Trp Lys Asn Ser Asn Ser Gln Ser Lys Lys Leu
                20                  25                  30

Pro Pro Gly Pro Trp Lys Leu Pro Leu Leu Gly Ser Met Leu His Met
            35                  40                  45

Val Gly Gly Leu Pro His His Val Leu Arg Asp Leu Ala Lys Lys Tyr
        50                  55                  60

Gly Pro Leu Met His Leu Gln Leu Gly Glu Val Ser Ala Val Val Val
65                  70                  75                  80
```

```
Thr Ser Pro Asp Met Ala Lys Glu Val Leu Lys Thr His Asp Ile Ala
                85                  90                  95

Phe Ala Ser Arg Pro Lys Leu Leu Ala Pro Glu Ile Val Cys Tyr Asn
            100                 105                 110

Arg Ser Asp Ile Ala Phe Cys Pro Tyr Gly Asp Tyr Trp Arg Gln Met
        115                 120                 125

Arg Lys Ile Cys Val Leu Glu Val Leu Ser Ala Lys Asn Val Arg Ser
    130                 135                 140

Phe Ser Ser Ile Arg Arg Asp Glu Val Leu Arg Leu Val Asn Phe Val
145                 150                 155                 160

Arg Ser Ser Thr Ser Glu Pro Val Asn Phe Thr Glu Arg Leu Phe Leu
                165                 170                 175

Phe Thr Ser Ser Met Thr Cys Arg Ser Ala Phe Gly Lys Val Phe Lys
            180                 185                 190

Glu Gln Glu Thr Phe Ile Gln Leu Ile Lys Glu Val Ile Gly Leu Ala
        195                 200                 205

Gly Gly Phe Asp Val Ala Asp Ile Phe Pro Ser Leu Lys Phe Leu His
    210                 215                 220

Val Leu Thr Gly Met Glu Gly Lys Ile Met Lys Ala His His Lys Val
225                 230                 235                 240

Asp Ala Ile Val Glu Asp Val Ile Asn Glu His Lys Lys Asn Leu Ala
                245                 250                 255

Met Gly Lys Thr Asn Gly Ala Leu Gly Gly Glu Asp Leu Ile Asp Val
            260                 265                 270

Leu Leu Arg Leu Met Asn Asp Gly Gly Leu Gln Phe Pro Ile Thr Asn
        275                 280                 285

Asp Asn Ile Lys Ala Ile Ile Phe Asp Met Phe Ala Ala Gly Thr Glu
    290                 295                 300

Thr Ser Ser Ser Thr Leu Val Trp Ala Met Val Gln Met Met Arg Asn
305                 310                 315                 320

Pro Thr Ile Leu Ala Lys Ala Gln Ala Glu Val Arg Glu Ala Phe Lys
                325                 330                 335

Gly Lys Glu Thr Phe Asp Glu Asn Asp Val Glu Glu Leu Lys Tyr Leu
            340                 345                 350

Lys Leu Val Ile Lys Glu Thr Leu Arg Leu His Pro Pro Val Pro Leu
        355                 360                 365

Leu Val Pro Arg Glu Cys Arg Glu Glu Thr Glu Ile Asn Gly Tyr Thr
    370                 375                 380

Ile Pro Val Lys Thr Lys Val Met Val Asn Val Trp Ala Leu Gly Arg
385                 390                 395                 400

Asp Pro Lys Tyr Trp Asp Asp Ala Asp Asn Phe Lys Pro Glu Arg Phe
                405                 410                 415

Glu Gln Cys Ser Val Asp Phe Ile Gly Asn Asn Phe Glu Tyr Leu Pro
            420                 425                 430

Phe Gly Gly Gly Arg Arg Ile Cys Pro Gly Ile Ser Phe Gly Leu Ala
        435                 440                 445

Asn Val Tyr Leu Pro Leu Ala Gln Leu Leu Tyr His Phe Asp Trp Lys
    450                 455                 460

Leu Pro Thr Gly Met Glu Pro Lys Asp Leu Asp Leu Thr Glu Leu Val
465                 470                 475                 480
```

Gly Val Thr Ala Ala Arg Lys Ser Asp Leu Met Leu Val Ala Thr Pro
            485                 490                 495

Tyr Gln Pro Ser Arg Glu
            500

<210> SEQ ID NO 20
<211> LENGTH: 508
<212> TYPE: PRT
<213> ORGANISM: Hyoscyamus muticus

<400> SEQUENCE: 20

Met Ala Leu Leu Leu Ala Val Phe Phe Phe Ser Leu Val Ser Ile Phe
1               5                   10                  15

Leu Phe Leu Ser Phe Leu Phe Leu Leu Arg Lys Trp Lys Asn Ser Asn
                20                  25                  30

Ser Gln Ser Lys Lys Leu Pro Pro Gly Pro Trp Lys Leu Pro Leu Leu
            35                  40                  45

Gly Ser Met Leu His Met Val Gly Gly Leu Pro His His Val Leu Arg
        50                  55                  60

Asp Leu Ala Lys Lys Tyr Gly Pro Leu Met His Leu Gln Leu Gly Glu
65                  70                  75                  80

Val Ser Ala Val Val Val Thr Ser Pro Asp Met Ala Lys Glu Val Leu
                85                  90                  95

Lys Thr His Asp Ile Ala Phe Ala Ser Arg Pro Lys Leu Leu Ala Pro
            100                 105                 110

Glu Ile Val Cys Tyr Asn Arg Ser Asp Ile Ala Phe Cys Pro Tyr Gly
        115                 120                 125

Asp Tyr Trp Arg Gln Met Arg Lys Ile Cys Val Leu Glu Val Leu Ser
130                 135                 140

Ala Lys Asn Val Arg Ser Phe Ser Ser Ile Arg Arg Asp Glu Val Leu
145                 150                 155                 160

Arg Leu Val Asn Phe Val Arg Ser Ser Thr Ser Glu Pro Val Asn Phe
                165                 170                 175

Thr Glu Arg Leu Phe Leu Phe Thr Ser Ser Met Thr Cys Arg Ser Ala
            180                 185                 190

Phe Gly Lys Val Phe Lys Glu Gln Glu Thr Phe Ile Gln Leu Ile Lys
        195                 200                 205

Glu Val Ile Gly Leu Ala Gly Gly Phe Asp Val Ala Asp Ile Phe Pro
210                 215                 220

Ser Leu Lys Phe Leu His Val Leu Thr Gly Met Glu Gly Lys Ile Met
225                 230                 235                 240

Lys Ala His His Lys Val Asp Ala Ile Val Glu Asp Val Ile Asn Glu
                245                 250                 255

His Lys Lys Asn Leu Ala Met Gly Lys Thr Asn Gly Ala Leu Gly Gly
            260                 265                 270

Glu Asp Leu Ile Asp Val Leu Leu Arg Leu Met Asn Asp Gly Gly Leu
        275                 280                 285

Gln Phe Pro Ile Thr Asn Asp Asn Ile Lys Ala Ile Ile Phe Asp Met
290                 295                 300

Phe Ala Ala Gly Thr Glu Thr Ser Ser Ser Thr Leu Val Trp Ala Met
305                 310                 315                 320

Val Gln Met Met Arg Asn Pro Thr Ile Leu Ala Lys Ala Gln Ala Glu
                325                 330                 335

Val Arg Glu Ala Phe Lys Gly Lys Glu Thr Phe Asp Glu Asn Asp Val
            340                 345                 350

| | | | | | | | | | | | | |
|---|---|---|---|---|---|---|---|---|---|---|---|---|
|Glu|Glu|Leu|Lys|Tyr|Leu|Lys|Leu|Val|Ile|Lys|Glu|Thr|Leu|Arg|Leu|
| | |355| | | |360| | | | |365| | | | |

His Pro Pro Val Pro Leu Leu Val Pro Arg Glu Cys Arg Glu Glu Thr
           370               375               380

Glu Ile Asn Gly Tyr Thr Ile Pro Val Lys Thr Lys Val Met Val Asn
385               390               395               400

Val Trp Ala Leu Gly Arg Asp Pro Lys Tyr Trp Asp Asp Ala Asp Asn
           405               410               415

Phe Lys Pro Glu Arg Phe Glu Gln Cys Ser Val Asp Phe Ile Gly Asn
           420               425               430

Asn Phe Glu Tyr Leu Pro Phe Gly Gly Gly Arg Arg Ile Cys Pro Gly
           435               440               445

Ile Ser Phe Gly Leu Ala Asn Val Tyr Leu Pro Leu Ala Gln Leu Leu
       450               455               460

Tyr His Phe Asp Trp Lys Leu Pro Thr Gly Met Glu Pro Lys Asp Leu
465               470               475               480

Asp Leu Thr Glu Leu Val Gly Val Thr Ala Ala Arg Lys Ser Asp Leu
           485               490               495

Met Leu Val Ala Thr Pro Tyr Gln Pro Ser Arg Glu
           500               505

<210> SEQ ID NO 21
<211> LENGTH: 1524
<212> TYPE: DNA
<213> ORGANISM: Hyoscyamus muticus

<400> SEQUENCE: 21

```
atggctctgt tattagcagt tttcttcttc tccctggtct caatctttct gttcctgtcc      60
tttctgttcc tgctgcgtaa atggaaaaac tcaaactccc aatcgaaaaa actgccgccg     120
ggtccgtgga aactgccgct gctgggctct atgctgcaca tggttggcgg cctgccgcat     180
cacgttctgc gtgatctggc gaaaaaatat ggtccgctga tgcatctgca actgggcgaa     240
gtctccgccg tggttgtcac ctcaccggat atggcaaaag aagtgctgaa aacgcatgac     300
attgcgttcg cctcccgtcc gaaactgctg gccccgaaaa ttgtgtgcta caaccgctca     360
gatattgcat tttgtccgta tggtgactac tggcgtcaaa tgcgcaaaat ttgcgtcctg     420
gaagtgctgt cggccaaaaa tgtgcgcagc tttagctcta ttcgtcgtga tgaagttctg     480
cgtctggtta acttcgtccg cagttccacc tcggagccgg tgaatttttac ggaacgtctg     540
tttctgttca cctcatcgat gacctgccgt agcgcatttg gtaaagtttt caaagaacag     600
gaaaccttca ttcaactgat caaagaagtc attggcctgg ccggcggttt tgatgtggca     660
gacatctttc gagtctgaa attcctgcat gttctgaccg gcatggaagg caaaattatg     720
aaagctcatc acaaagtcga tgcgattgtg aagacgttta tcaacgaaca aagaaaaaac     780
ctggcgatgg gcaaaacgaa cggcgcactg ggcggtgaag atctgatcga cgttctgctg     840
cgtctgatga tgatggcgg cctgcaattt ccgatcacca cgataatat caaagctatt     900
atctttgata tgtttgcggc gggcaccgaa accagcagca gcaccctggt gtgggcgatg     960
gtgcagatga tgcgtaaccc gacgattctg gcaaaagctc aagcggaagt gcgcgaagcc    1020
ttcaaaggca agaaaccctt tgatgaaaat gacgttgaag aactgaaata tctgaaactg    1080
gtcatcaaag aaacgctgcg tctgcatccg ccggttccgc tgctggtccc gcgtgaatgc    1140
cgcgaagaaa ccgaaattaa cggttatacc atcccggtta aaacgaaagt gatggttaat    1200
gtctgggctc tgggccgtga tccgaaatac tgggatgacg cggacaactt taaaccggaa    1260
```

-continued

```
cgcttttgaac agtgctctgt ggatttcatc ggcaacaact ttgaatatct gccgtttggc    1320
ggtggccgtc gcatttgtcc gggtatcagc ttcggcctgg ctaatgttta tctgccgctg    1380
gcgcaactgc tgtaccactt tgattggaaa ctgccgaccg gcatggaacc gaaagatctg    1440
gacctgaccg aactggtggg cgttacggca gctcgtaaat ctgatctgat gctggttgcg    1500
accccgtacc agccgagccg tgaa                                            1524
```

```
<210> SEQ ID NO 22
<211> LENGTH: 488
<212> TYPE: PRT
<213> ORGANISM: Lactuca sativa

<400> SEQUENCE: 22

Met Glu Leu Ser Ile Thr Thr Ser Ile Ala Leu Ala Thr Ile Val Phe
1               5                   10                  15

Phe Leu Tyr Lys Leu Ala Thr Arg Pro Lys Ser Thr Lys Lys Gln Leu
            20                  25                  30

Pro Glu Ala Ser Arg Leu Pro Ile Ile Gly His Met His His Leu Ile
        35                  40                  45

Gly Thr Met Pro His Arg Gly Val Met Asp Leu Ala Arg Lys His Gly
    50                  55                  60

Ser Leu Met His Leu Gln Leu Gly Glu Val Ser Thr Ile Val Val Ser
65                  70                  75                  80

Ser Pro Lys Trp Ala Lys Glu Ile Leu Thr Thr Tyr Asp Ile Thr Phe
                85                  90                  95

Ala Asn Arg Pro Glu Thr Leu Thr Gly Glu Ile Ile Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Val Lys Val Lys Ser Phe
    130                 135                 140

Gln Ser Ile Arg Glu Glu Glu Cys Trp Asn Leu Val Lys Glu Val Lys
145                 150                 155                 160

Glu Ser Gly Ser Gly Lys Pro Ile Asn Leu Ser Glu Ser Ile Phe Thr
                165                 170                 175

Met Ile Ala Thr Ile Leu Ser Arg Ala Ala Phe Gly Lys Gly Ile Lys
            180                 185                 190

Asp Gln Arg Glu Phe Thr Glu Ile Val Lys Glu Ile Leu Arg Gln Thr
        195                 200                 205

Gly Gly Phe Asp Val Ala Asp Ile Phe Pro Ser Lys Lys Phe Leu His
    210                 215                 220

His Leu Ser Gly Lys Arg Ala Arg Leu Thr Ser Ile His Lys Lys Leu
225                 230                 235                 240

Asp Asn Leu Ile Asn Asn Ile Val Ala Glu His His Val Ser Thr Ser
                245                 250                 255

Ser Lys Ala Asn Glu Thr Leu Leu Asp Val Leu Leu Arg Leu Lys Asp
            260                 265                 270

Ser Ala Glu Phe Pro Leu Thr Ala Asp Asn Val Lys Ala Ile Ile Leu
        275                 280                 285

Asp Met Phe Gly Ala Gly Thr Asp Thr Ser Ser Ala Thr Val Glu Trp
    290                 295                 300

Ala Ile Ser Glu Leu Ile Arg Cys Pro Arg Ala Met Glu Lys Val Gln
305                 310                 315                 320
```

```
Ala Glu Leu Arg Gln Ala Leu Asn Gly Lys Glu Lys Ile Gln Glu Glu
            325                 330                 335

Asp Ile Gln Asp Leu Ala Tyr Leu Asn Leu Val Ile Arg Glu Thr Leu
        340                 345                 350

Arg Leu His Pro Pro Leu Pro Leu Val Met Pro Arg Glu Cys Arg Glu
            355                 360                 365

Pro Val Asn Leu Ala Gly Tyr Glu Ile Ala Asn Lys Thr Lys Leu Ile
        370                 375                 380

Val Asn Val Phe Ala Ile Asn Arg Asp Pro Glu Tyr Trp Lys Asp Ala
385                 390                 395                 400

Glu Ala Phe Ile Pro Glu Arg Phe Glu Asn Asn Pro Asn Asn Ile Met
                405                 410                 415

Gly Ala Asp Tyr Glu Tyr Leu Pro Phe Gly Ala Gly Arg Arg Met Cys
            420                 425                 430

Pro Gly Ala Ala Leu Gly Leu Ala Asn Val Gln Leu Pro Leu Ala Asn
            435                 440                 445

Ile Leu Tyr His Phe Asn Trp Lys Leu Pro Asn Gly Ala Ser His Asp
        450                 455                 460

Gln Leu Asp Met Thr Glu Ser Phe Gly Ala Thr Val Gln Arg Lys Thr
465                 470                 475                 480

Glu Leu Leu Leu Val Pro Ser Phe
                485

<210> SEQ ID NO 23
<211> LENGTH: 488
<212> TYPE: PRT
<213> ORGANISM: Lactuca sativa

<400> SEQUENCE: 23

Met Ala Leu Leu Leu Ala Val Phe Ile Ala Leu Ala Thr Ile Val Phe
1               5                   10                  15

Phe Leu Tyr Lys Leu Ala Thr Arg Pro Lys Ser Thr Lys Lys Gln Leu
            20                  25                  30

Pro Glu Ala Ser Arg Leu Pro Ile Ile Gly His Met His His Leu Ile
        35                  40                  45

Gly Thr Met Pro His Arg Gly Val Met Asp Leu Ala Arg Lys His Gly
    50                  55                  60

Ser Leu Met His Leu Gln Leu Gly Glu Val Ser Thr Ile Val Val Ser
65                  70                  75                  80

Ser Pro Lys Trp Ala Lys Glu Ile Leu Thr Thr Tyr Asp Ile Thr Phe
                85                  90                  95

Ala Asn Arg Pro Glu Thr Leu Thr Gly Glu Ile Ile Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Val Lys Val Lys Ser Phe
    130                 135                 140

Gln Ser Ile Arg Glu Glu Glu Cys Trp Asn Leu Val Lys Glu Val Lys
145                 150                 155                 160

Glu Ser Gly Ser Gly Lys Pro Ile Asn Leu Ser Glu Ser Ile Phe Thr
                165                 170                 175

Met Ile Ala Thr Ile Leu Ser Arg Ala Ala Phe Gly Lys Gly Ile Lys
            180                 185                 190

Asp Gln Arg Glu Phe Thr Glu Ile Val Lys Glu Ile Leu Arg Gln Thr
        195                 200                 205
```

Gly Gly Phe Asp Val Ala Asp Ile Phe Pro Ser Lys Lys Phe Leu His
    210                 215                 220

His Leu Ser Gly Lys Arg Ala Arg Leu Thr Ser Ile His Lys Lys Leu
225                 230                 235                 240

Asp Asn Leu Ile Asn Asn Ile Val Ala Glu His His Val Ser Thr Ser
                245                 250                 255

Ser Lys Ala Asn Glu Thr Leu Leu Asp Val Leu Leu Arg Leu Lys Asp
            260                 265                 270

Ser Ala Glu Phe Pro Leu Thr Ala Asp Asn Val Lys Ala Ile Ile Leu
        275                 280                 285

Asp Met Phe Gly Ala Gly Thr Asp Thr Ser Ser Ala Thr Val Glu Trp
290                 295                 300

Ala Ile Ser Glu Leu Ile Arg Cys Pro Arg Ala Met Glu Lys Val Gln
305                 310                 315                 320

Ala Glu Leu Arg Gln Ala Leu Asn Gly Lys Glu Lys Ile Gln Glu Glu
                325                 330                 335

Asp Ile Gln Asp Leu Ala Tyr Leu Asn Leu Val Ile Arg Glu Thr Leu
            340                 345                 350

Arg Leu His Pro Pro Leu Pro Leu Val Met Pro Arg Glu Cys Arg Glu
        355                 360                 365

Pro Val Asn Leu Ala Gly Tyr Glu Ile Ala Asn Lys Thr Lys Leu Ile
370                 375                 380

Val Asn Val Phe Ala Ile Asn Arg Asp Pro Glu Tyr Trp Lys Asp Ala
385                 390                 395                 400

Glu Ala Phe Ile Pro Glu Arg Phe Glu Asn Asn Pro Asn Asn Ile Met
                405                 410                 415

Gly Ala Asp Tyr Glu Tyr Leu Pro Phe Gly Ala Gly Arg Arg Met Cys
            420                 425                 430

Pro Gly Ala Ala Leu Gly Leu Ala Asn Val Gln Leu Pro Leu Ala Asn
        435                 440                 445

Ile Leu Tyr His Phe Asn Trp Lys Leu Pro Asn Gly Ala Ser His Asp
450                 455                 460

Gln Leu Asp Met Thr Glu Ser Phe Gly Ala Thr Val Gln Arg Lys Thr
465                 470                 475                 480

Glu Leu Leu Leu Val Pro Ser Phe
                485

<210> SEQ ID NO 24
<211> LENGTH: 1464
<212> TYPE: DNA
<213> ORGANISM: Lactuca sativa

<400> SEQUENCE: 24
atggctctgt tattagcagt tttcatcgca ctggctacca tcgtcttctt cctgtataaa      60
ctggcaacgc gcccgaaatc taccaaaaaa caactgccgg aagcgagccg tctgccgatt     120
atcggccaca tgcatcacct gattggcacc atgccgcacc gtggtgtcat ggatctggcc     180
cgcaaacatg gctcgctgat gcatctgcaa ctgggcgaag tgagcaccat tgtggttagc     240
tctccgaaat gggcaaaaga aattctgacc acctatgata ttacctttgc taaccgcccg     300
gaaaccctga cgggcgaaat tatcgcgtac cataatacgg acattgtgct ggccccgtat     360
ggtgaatact ggcgtcaact gcgtaaactg tgcaccctgg aactgctgtc cgttaaaaaa     420
gtcaaatcat ttcaatcgat tcgtgaagaa gaatgttgga acctggtgaa agaagttaaa     480
gaaagcggct ctggtaaacc gattaatctg agtgaatcca tcttcaccat gattgcgacg     540

```
atcctgagtc gtgcggcctt tggcaaaggt attaaagatc agcgcgaatt taccgaaatt    600
gtcaaagaaa tcctgcgtca acgggcggt ttcgatgtgg cagacatttt tccgagcaaa     660
```

| | |
|---|---|
| atcctgagtc gtgcggcctt tggcaaaggt attaaagatc agcgcgaatt taccgaaatt | 600 |
| gtcaaagaaa tcctgcgtca acgggcggt ttcgatgtgg cagacatttt tccgagcaaa | 660 |
| aaattcctgc atcacctgtc tggcaaacgt gctcgcctga ccagtatcca taaaaaactg | 720 |
| gataacctga tcaacaatat cgtcgcggaa catcatgtga gcaccagcag caaagcgaat | 780 |
| gaaacgctgc tggatgttct gctgcgcctg aaagacagtg ccgaatttcc gctgaccgca | 840 |
| gacaacgtca agctattat cctggatatg ttcggtgcag caccgatac cagcagcgca | 900 |
| acggtggaat gggccattag cgaactgatc cgttgcccgc gcgcaatgga aaaagttcag | 960 |
| gcagaactgc gtcaagctct gaacggtaaa gaaaaaatcc aggaagaaga tattcaagac | 1020 |
| ctggcctatc tgaatctggt gattcgtgaa accctgcgtc tgcacccgcc gctgccgctg | 1080 |
| gttatgccgc gtgaatgccg tgagccggtg aacctggcgg gctatgaaat cgccaataaa | 1140 |
| accaaactga tcgtcaatgt gtttgcgatt aaccgtgacc cggaatactg gaaagacgcg | 1200 |
| gaagccttta tcccggaacg ttttgaaaac aatccgaaca atatcatggg tgcagattat | 1260 |
| gaatacctgc cgtttggcgc tggtcgtcgc atgtgtccgg gcgcagctct gggtctggca | 1320 |
| aacgttcaac tgccgctggc gaacattctg taccatttca actggaaact gccgaatggc | 1380 |
| gcgtcccacg atcaactgga catgaccgaa tcatttggtg ccaccgtgca acgtaaaacg | 1440 |
| gaactgctgc tggttccgag cttc | 1464 |

<210> SEQ ID NO 25
<211> LENGTH: 504
<212> TYPE: PRT
<213> ORGANISM: Nicotiani tabacum

<400> SEQUENCE: 25

```
Met Gln Phe Phe Ser Leu Val Ser Ile Phe Leu Phe Ser Phe Leu
1               5                   10                  15

Phe Leu Leu Arg Lys Trp Lys Asn Ser Asn Ser Gln Ser Lys Lys Leu
                20                  25                  30

Pro Pro Gly Pro Trp Lys Ile Pro Ile Leu Gly Ser Met Leu His Met
            35                  40                  45

Ile Gly Gly Glu Pro His His Val Leu Arg Asp Leu Ala Lys Lys Tyr
        50                  55                  60

Gly Pro Leu Met His Leu Gln Leu Gly Glu Ile Ser Ala Val Val Val
65                  70                  75                  80

Thr Ser Arg Asp Met Ala Lys Glu Val Leu Lys Thr His Asp Val Val
                85                  90                  95

Phe Ala Ser Arg Pro Lys Ile Val Ala Met Asp Ile Ile Cys Tyr Asn
            100                 105                 110

Gln Ser Asp Ile Ala Phe Ser Pro Tyr Gly Asp His Trp Arg Gln Met
        115                 120                 125

Arg Lys Ile Cys Val Met Glu Leu Leu Asn Ala Lys Asn Val Arg Ser
    130                 135                 140

Phe Ser Ser Ile Arg Arg Asp Glu Val Val Arg Leu Ile Asp Ser Ile
145                 150                 155                 160

Arg Ser Asp Ser Ser Gly Glu Leu Val Asn Phe Thr Gln Arg Ile
                165                 170                 175

Ile Trp Phe Ala Ser Ser Met Thr Cys Arg Ser Ala Phe Gly Gln Val
            180                 185                 190

Leu Lys Gly Gln Asp Ile Phe Ala Lys Lys Ile Arg Glu Val Ile Gly
        195                 200                 205
```

Leu Ala Glu Gly Phe Asp Val Val Asp Ile Phe Pro Thr Tyr Lys Phe
210                 215                 220

Leu His Val Leu Ser Gly Met Lys Arg Lys Leu Leu Asn Ala His Leu
225                 230                 235                 240

Lys Val Asp Ala Ile Val Glu Asp Val Ile Asn Glu His Lys Lys Asn
            245                 250                 255

Leu Ala Ala Gly Lys Ser Asn Gly Ala Leu Gly Gly Glu Asp Leu Ile
            260                 265                 270

Asp Val Leu Leu Arg Leu Met Asn Asp Thr Ser Leu Gln Phe Pro Ile
            275                 280                 285

Thr Asn Asp Asn Ile Lys Ala Val Ile Val Asp Met Phe Ala Ala Gly
290                 295                 300

Thr Glu Thr Ser Ser Thr Thr Thr Val Trp Ala Met Ala Glu Met Met
305                 310                 315                 320

Lys Asn Pro Ser Val Phe Thr Lys Ala Gln Ala Glu Val Arg Glu Ala
            325                 330                 335

Phe Arg Asp Lys Val Ser Phe Asp Glu Asn Asp Val Glu Glu Leu Lys
            340                 345                 350

Tyr Leu Lys Leu Val Ile Lys Glu Thr Leu Arg Leu His Pro Pro Ser
355                 360                 365

Pro Leu Leu Val Pro Arg Glu Cys Arg Glu Asp Thr Asp Ile Asn Gly
370                 375                 380

Tyr Thr Ile Pro Ala Lys Thr Lys Val Met Val Asn Val Trp Ala Leu
385                 390                 395                 400

Gly Arg Asp Pro Lys Tyr Trp Asp Asp Ala Glu Ser Phe Lys Pro Glu
            405                 410                 415

Arg Phe Glu Gln Cys Ser Val Asp Phe Phe Gly Asn Asn Phe Glu Phe
            420                 425                 430

Leu Pro Phe Gly Gly Gly Arg Arg Ile Cys Pro Gly Met Ser Phe Gly
            435                 440                 445

Leu Ala Asn Leu Tyr Leu Pro Leu Ala Gln Leu Leu Tyr His Phe Asp
            450                 455                 460

Trp Lys Leu Pro Thr Gly Ile Met Pro Arg Asp Leu Asp Leu Thr Glu
465                 470                 475                 480

Leu Ser Gly Ile Thr Ile Ala Arg Lys Gly Gly Leu Tyr Leu Asn Ala
            485                 490                 495

Thr Pro Tyr Gln Pro Ser Arg Glu
            500

<210> SEQ ID NO 26
<211> LENGTH: 510
<212> TYPE: PRT
<213> ORGANISM: Nicotiani tabacum

<400> SEQUENCE: 26

Met Ala Leu Leu Leu Ala Val Phe Phe Ser Leu Val Ser Ile Phe
1               5                   10                  15

Leu Phe Leu Ser Phe Leu Phe Leu Arg Lys Trp Lys Asn Ser Asn
                20                  25                  30

Ser Gln Ser Lys Lys Leu Pro Pro Gly Pro Trp Lys Ile Pro Ile Leu
            35                  40                  45

Gly Ser Met Leu His Met Ile Gly Gly Glu Pro His His Val Leu Arg
50                  55                  60

Asp Leu Ala Lys Lys Tyr Gly Pro Leu Met His Leu Gln Leu Gly Glu
65                  70                  75                  80

-continued

```
Ile Ser Ala Val Val Thr Ser Arg Asp Met Ala Lys Glu Val Leu
            85                  90                  95

Lys Thr His Asp Val Val Phe Ala Ser Arg Pro Lys Ile Val Ala Met
            100                 105                 110

Asp Ile Ile Cys Tyr Asn Gln Ser Asp Ile Ala Phe Ser Pro Tyr Gly
            115                 120                 125

Asp His Trp Arg Gln Met Arg Lys Ile Cys Val Met Glu Leu Leu Asn
    130                 135                 140

Ala Lys Asn Val Arg Ser Phe Ser Ser Ile Arg Arg Asp Glu Val Val
145                 150                 155                 160

Arg Leu Ile Asp Ser Ile Arg Ser Asp Ser Ser Gly Glu Leu Val
            165                 170                 175

Asn Phe Thr Gln Arg Ile Ile Trp Phe Ala Ser Ser Met Thr Cys Arg
            180                 185                 190

Ser Ala Phe Gly Gln Val Leu Lys Gly Gln Asp Ile Phe Ala Lys Lys
            195                 200                 205

Ile Arg Glu Val Ile Gly Leu Ala Glu Gly Phe Asp Val Val Asp Ile
    210                 215                 220

Phe Pro Thr Tyr Lys Phe Leu His Val Leu Ser Gly Met Lys Arg Lys
225                 230                 235                 240

Leu Leu Asn Ala His Leu Lys Val Asp Ala Ile Val Glu Asp Val Ile
            245                 250                 255

Asn Glu His Lys Lys Asn Leu Ala Ala Gly Lys Ser Asn Gly Ala Leu
            260                 265                 270

Gly Gly Glu Asp Leu Ile Asp Val Leu Arg Leu Met Asn Asp Thr
    275                 280                 285

Ser Leu Gln Phe Pro Ile Thr Asn Asp Asn Ile Lys Ala Val Ile Val
            290                 295                 300

Asp Met Phe Ala Ala Gly Thr Glu Thr Ser Ser Thr Thr Thr Val Trp
305                 310                 315                 320

Ala Met Ala Glu Met Met Lys Asn Pro Ser Val Phe Thr Lys Ala Gln
            325                 330                 335

Ala Glu Val Arg Glu Ala Phe Arg Asp Lys Val Ser Phe Asp Glu Asn
            340                 345                 350

Asp Val Glu Glu Leu Lys Tyr Leu Lys Leu Val Ile Lys Glu Thr Leu
            355                 360                 365

Arg Leu His Pro Pro Ser Pro Leu Leu Val Pro Arg Glu Cys Arg Glu
    370                 375                 380

Asp Thr Asp Ile Asn Gly Tyr Thr Ile Pro Ala Lys Thr Lys Val Met
385                 390                 395                 400

Val Asn Val Trp Ala Leu Gly Arg Asp Pro Lys Tyr Trp Asp Asp Ala
            405                 410                 415

Glu Ser Phe Lys Pro Glu Arg Phe Glu Gln Cys Ser Val Asp Phe Phe
            420                 425                 430

Gly Asn Asn Phe Glu Phe Leu Pro Phe Gly Gly Arg Arg Ile Cys
            435                 440                 445

Pro Gly Met Ser Phe Gly Leu Ala Asn Leu Tyr Leu Pro Leu Ala Gln
    450                 455                 460

Leu Leu Tyr His Phe Asp Trp Lys Leu Pro Thr Gly Ile Met Pro Arg
465                 470                 475                 480
```

Asp Leu Asp Leu Thr Glu Leu Ser Gly Ile Thr Ile Ala Arg Lys Gly
                485                 490                 495

Gly Leu Tyr Leu Asn Ala Thr Pro Tyr Gln Pro Ser Arg Glu
        500                 505                 510

<210> SEQ ID NO 27
<211> LENGTH: 1530
<212> TYPE: DNA
<213> ORGANISM: Nicotiani tabacum

<400> SEQUENCE: 27

| | | | | | | |
|---|---|---|---|---|---|---|
| atggctctgt | tattagcagt | tttcttcttc | tccctggtct | caatcttcct | gttcctgtcc | 60 |
| tttctgttcc | tgctgcgtaa | atggaaaaac | tctaatagcc | aatccaaaaa | actgccgccg | 120 |
| ggtccgtgga | aaattccgat | cctgggctct | atgctgcaca | tgattggcgg | tgaaccgcat | 180 |
| catgtgctgc | gtgatctggc | gaaaaaatat | ggtccgctga | tgcatctgca | actgggcgaa | 240 |
| atctctgcgg | tggttgtcac | gagtcgtgac | atggccaaag | aagtgctgaa | aacccatgat | 300 |
| gtggttttg | catctcgccc | gaaaatcgtt | gctatggata | ttatctgcta | taaccagtcg | 360 |
| gacatcgcgt | tcagcccgta | cggtgatcac | tggcgtcaaa | tgcgcaaaat | ttgtgtcatg | 420 |
| gaactgctga | acgccaaaaa | tgtgcgcagt | tttagctcta | ttcgtcgtga | tgaagtcgtg | 480 |
| cgtctgattg | attccatccg | ctcagacagt | tcctcaggcg | aactggtgaa | ttttacgcag | 540 |
| cgtattatct | ggttcgcatc | gagcatgacc | tgccgctcgg | cttttggtca | ggttctgaaa | 600 |
| ggccaagata | tttttgcgaa | gaaaattcgt | gaagtgatcg | gtctggccga | aggcttcgat | 660 |
| gttgtggata | ttttccgac | ctataaattc | ctgcatgtcc | tgagcggtat | gaaacgcaaa | 720 |
| ctgctgaacg | cgcacctgaa | agttgatgcc | attgtcgaag | acgtgatcaa | cgaacataag | 780 |
| aaaaaccctgg | cggcgggtaa | atccaacggc | gcactgggcg | gtgaagatct | gattgacgtg | 840 |
| ctgctgcgtc | tgatgaatga | taccagcctg | caatttccga | tcaccaacga | caacattaaa | 900 |
| gcggtgatcg | ttgatatgtt | cgcggcgggc | accgaaaacct | ctagtaccac | gaccgtttgg | 960 |
| gcgatggccg | aaatgatgaa | aaacccgtcg | gtgtttacca | agcacaagc | ggaagtgcgt | 1020 |
| gaagcgtttc | gtgataaagt | tagcttcgat | gaaaatgatg | tggaagaact | gaaatacctg | 1080 |
| aaactggtga | ttaaagaaac | gctgcgtctg | catccgccga | gcccgctgct | ggttccgcgt | 1140 |
| gaatgccgtg | aagataccga | cattaacggt | tatacgatcc | cggcaaaaac | caaagtcatg | 1200 |
| gtgaatgttt | gggctctggg | ccgtgacccg | aaatactggg | atgacgcaga | atcctttaaa | 1260 |
| ccggaacgct | ttgaacagtg | ctcagtggat | ttctttggta | caactttga | atttctgccg | 1320 |
| tttggcggtg | gccgtcgcat | tgtccgggt | atgtccttcg | gcctggcgaa | cctgtatctg | 1380 |
| ccgctggccc | aactgctgta | ccactttgat | tggaaactgc | cgacgggtat | tatgccgcgt | 1440 |
| gatctggacc | tgacggaact | gtctggcatt | accatcgcac | gcaaaggtgg | cctgtatctg | 1500 |
| aatgctaccc | cgtaccagcc | gagtcgtgaa | | | | 1530 |

<210> SEQ ID NO 28
<211> LENGTH: 522
<212> TYPE: PRT
<213> ORGANISM: Citrus x paradisi

<400> SEQUENCE: 28

Met Glu Leu Pro Leu Lys Ser Ile Ala Leu Thr Ile Val Ile Thr
1               5                   10                  15

Val Leu Thr Trp Ala Trp Arg Val Leu Asn Trp Val Trp Leu Arg Pro
            20                  25                  30

```
Lys Lys Leu Glu Lys Phe Leu Arg Gln Gln Gly Leu Lys Gly Asn Ser
             35                  40                  45
Tyr Arg Leu Leu Phe Gly Asp Leu Lys Glu Asn Ser Ile Glu Leu Lys
 50                  55                  60
Glu Ala Lys Ala Arg Pro Leu Ser Leu Asp Asp Ile Ala Ile Arg
 65                  70                  75                  80
Val Asn Pro Phe Leu His Lys Leu Val Asn Asp Tyr Gly Lys Asn Ser
             85                  90                  95
Phe Met Trp Phe Gly Pro Thr Pro Arg Val Asn Ile Met Asn Pro Asp
            100                 105                 110
Gln Ile Lys Ala Ile Phe Thr Lys Ile Asn Asp Phe Gln Lys Val Asn
            115                 120                 125
Ser Ile Pro Leu Ala Arg Leu Leu Ile Val Gly Leu Ala Thr Leu Glu
            130                 135                 140
Gly Glu Lys Trp Ala Lys His Arg Lys Leu Ile Asn Pro Ala Phe His
145                 150                 155                 160
Gln Glu Lys Leu Lys Leu Met Leu Pro Ala Phe Tyr Leu Ser Cys Ile
                165                 170                 175
Glu Ile Ile Thr Lys Trp Glu Lys Gln Met Ser Val Glu Gly Ser Ser
                180                 185                 190
Glu Leu Asp Val Trp Pro Tyr Leu Ala Asn Leu Thr Ser Asp Val Ile
                195                 200                 205
Ser Arg Thr Ala Phe Gly Ser Ser Tyr Glu Gly Arg Arg Ile Phe
            210                 215                 220
Gln Leu Gln Ala Glu Leu Ala Glu Leu Thr Met Gln Val Phe Arg Ser
225                 230                 235                 240
Val His Ile Pro Gly Trp Arg Phe Leu Pro Thr Lys Arg Asn Arg Arg
                245                 250                 255
Met Lys Glu Ile Asp Lys Glu Ile Arg Ala Ser Leu Met Gly Ile Ile
                260                 265                 270
Lys Asn Arg Glu Lys Ala Met Arg Ala Gly Glu Ala Ala Asn Asn Asp
            275                 280                 285
Leu Leu Gly Ile Leu Met Glu Thr Ser Phe Arg Glu Ile Glu Glu His
            290                 295                 300
Gly Asn Asn Lys Asn Val Gly Phe Ser Met Asn Asp Val Ile Glu Glu
305                 310                 315                 320
Cys Lys Leu Phe Tyr Phe Ala Gly Gln Glu Thr Thr Ser Val Leu Leu
                325                 330                 335
Asn Trp Thr Met Val Leu Leu Ser Lys His Gln Asp Trp Gln Glu Arg
                340                 345                 350
Ala Arg Gln Glu Val Leu Gln Val Phe Gly Asn Asn Lys Pro Asp Tyr
            355                 360                 365
Asp Gly Leu Asn His Leu Lys Ile Val Gln Met Ile Leu Tyr Glu Val
            370                 375                 380
Leu Arg Leu Tyr Pro Pro Val Thr Val Leu Ser Arg Ala Val Phe Lys
385                 390                 395                 400
Glu Thr Lys Leu Gly Asn Leu Thr Leu Pro Ala Gly Val Gln Ile Gly
                405                 410                 415
Leu Pro Met Ile Leu Val His Gln Asp Pro Glu Leu Trp Gly Asp Asp
                420                 425                 430
Ala Val Glu Phe Lys Pro Glu Arg Phe Ala Glu Gly Ile Ser Lys Ala
            435                 440                 445
```

```
Ala Lys Asn Gln Val Ser Tyr Phe Pro Phe Ala Leu Gly Pro Arg Ile
    450                 455                 460

Cys Val Gly Gln Asn Phe Ala Leu Val Glu Ala Lys Met Ala Thr Ala
465                 470                 475                 480

Met Ile Leu Gln Asn Tyr Ser Phe Glu Leu Ser Pro Ser Tyr Val His
                485                 490                 495

Ala Pro Thr Ala Val Pro Thr Leu His Pro Glu Leu Gly Thr Gln Leu
                500                 505                 510

Ile Leu Arg Lys Leu Trp Cys Lys Asn Asn
            515                 520

<210> SEQ ID NO 29
<211> LENGTH: 523
<212> TYPE: PRT
<213> ORGANISM: Citrus x paradisi

<400> SEQUENCE: 29

Met Ala Leu Leu Leu Ala Val Phe Ile Ala Leu Thr Ile Val Ile Val
1               5                   10                  15

Thr Val Leu Thr Trp Ala Trp Arg Val Leu Asn Trp Val Trp Leu Arg
            20                  25                  30

Pro Lys Lys Leu Glu Lys Phe Leu Arg Gln Gln Gly Leu Lys Gly Asn
            35                  40                  45

Ser Tyr Arg Leu Leu Phe Gly Asp Leu Lys Glu Asn Ser Ile Glu Leu
    50                  55                  60

Lys Glu Ala Lys Ala Arg Pro Leu Ser Leu Asp Asp Ile Ala Ile
65                  70                  75                  80

Arg Val Asn Pro Phe Leu His Lys Leu Val Asn Asp Tyr Gly Lys Asn
                85                  90                  95

Ser Phe Met Trp Phe Gly Pro Thr Pro Arg Val Asn Ile Met Asn Pro
            100                 105                 110

Asp Gln Ile Lys Ala Ile Phe Thr Lys Ile Asn Asp Phe Gln Lys Val
            115                 120                 125

Asn Ser Ile Pro Leu Ala Arg Leu Leu Ile Val Gly Leu Ala Thr Leu
    130                 135                 140

Glu Gly Glu Lys Trp Ala Lys His Arg Lys Leu Ile Asn Pro Ala Phe
145                 150                 155                 160

His Gln Glu Lys Leu Lys Leu Met Leu Pro Ala Phe Tyr Leu Ser Cys
                165                 170                 175

Ile Glu Ile Ile Thr Lys Trp Glu Lys Gln Met Ser Val Glu Gly Ser
            180                 185                 190

Ser Glu Leu Asp Val Trp Pro Tyr Leu Ala Asn Leu Thr Ser Asp Val
        195                 200                 205

Ile Ser Arg Thr Ala Phe Gly Ser Ser Tyr Glu Glu Gly Arg Arg Ile
    210                 215                 220

Phe Gln Leu Gln Ala Glu Leu Ala Glu Leu Thr Met Gln Val Phe Arg
225                 230                 235                 240

Ser Val His Ile Pro Gly Trp Arg Phe Leu Pro Thr Lys Arg Asn Arg
                245                 250                 255

Arg Met Lys Glu Ile Asp Lys Glu Ile Arg Ala Ser Leu Met Gly Ile
            260                 265                 270

Ile Lys Asn Arg Glu Lys Ala Met Arg Ala Gly Glu Ala Ala Asn Asn
        275                 280                 285

Asp Leu Leu Gly Ile Leu Met Glu Thr Ser Phe Arg Glu Ile Glu Glu
    290                 295                 300
```

```
       His Gly Asn Asn Lys Asn Val Gly Phe Ser Met Asn Asp Val Ile Glu
       305                 310                 315                 320

Glu Cys Lys Leu Phe Tyr Phe Ala Gly Gln Glu Thr Thr Ser Val Leu
                       325                 330                 335

Leu Asn Trp Thr Met Val Leu Leu Ser Lys His Gln Asp Trp Gln Glu
                   340                 345                 350

Arg Ala Arg Gln Glu Val Leu Gln Val Phe Gly Asn Asn Lys Pro Asp
               355                 360                 365

Tyr Asp Gly Leu Asn His Leu Lys Ile Val Gln Met Ile Leu Tyr Glu
           370                 375                 380

Val Leu Arg Leu Tyr Pro Pro Val Thr Val Leu Ser Arg Ala Val Phe
       385                 390                 395                 400

Lys Glu Thr Lys Leu Gly Asn Leu Thr Leu Pro Ala Gly Val Gln Ile
                       405                 410                 415

Gly Leu Pro Met Ile Leu Val His Gln Asp Pro Glu Leu Trp Gly Asp
                   420                 425                 430

Asp Ala Val Glu Phe Lys Pro Glu Arg Phe Ala Glu Gly Ile Ser Lys
               435                 440                 445

Ala Ala Lys Asn Gln Val Ser Tyr Phe Pro Phe Ala Leu Gly Pro Arg
       450                 455                 460

Ile Cys Val Gly Gln Asn Phe Ala Leu Val Glu Ala Lys Met Ala Thr
       465                 470                 475                 480

Ala Met Ile Leu Gln Asn Tyr Ser Phe Glu Leu Ser Pro Ser Tyr Val
                       485                 490                 495

His Ala Pro Thr Ala Val Pro Leu His Pro Glu Leu Gly Thr Gln
                   500                 505                 510

Leu Ile Leu Arg Lys Leu Trp Cys Lys Asn Asn
               515                 520

<210> SEQ ID NO 30
<211> LENGTH: 1569
<212> TYPE: DNA
<213> ORGANISM: Citrus x paradisi

<400> SEQUENCE: 30
atggctctgt tattagcagt tttcattgct ctgacgattg ttattgttac ggtgctgacc        60
tgggcgtggc gtgtgctgaa ctgggtttgg ctgcgtccga aaaaactgga aaaatttctg       120
cgccagcaag gcctgaaggg taacagctat cgtctgctgt tcggcgatct gaaagaaaat       180
tctattgaac tgaaagaagc gaaagcccgt ccgctgagtc tggatgacga tattgcaatc       240
cgcgttaacc cgtttctgca taaactggtc aacgattacg gcaaaaattc ttttatgtgg       300
ttcggtccga ccccgcgcgt gaacattatg aacccggatc agattaaagc gatctttacg       360
aaaatcaacg atttccaaaa agttaatagc attccgctgg cgcgtctgct gatcgtcggc       420
ctggccaccc tggaaggtga aaatgggca aacatcgca aactgattaa cccggctttt       480
caccaagaaa aactgaaact gatgctgccg gcgttctatc tgtcctgcat cgaaattatc       540
acgaaatggg aaaaacagat gtcagtggaa ggtagctctg aactggacgt tggccgtat       600 ctggccaatc tgaccagcga tgttatttct cgtacggcat tggcagttc ctacgaagaa       660 ggtcgtcgca tcttccagtt acaggcggaa ctggccgaac tgaccatgca ggttttcgt       720 tctgtccata ttccgggctg cgtttcctg ccgacgaaac gcaaccgtcg catgaaagaa       780
attgacaaag aaatccgcgc cagtctgatg ggtattatca aaaatcgtga aaagcaatg       840 cgcgctggcg aagcggccaa caatgatctg ctgggtattc tgatggaaac cagctttcgt       900
```

```
gaaatcgaag aacacggcaa caataaaaac gtcggtttca gcatgaatga cgtgatcgaa    960
gaatgtaaac tgttttattt cgctggccag gaaaccacgt cagttctgct gaactggacg   1020
atggtgctgc tgtcgaaaca tcaggattgg caagaacgtg cccgccagga agtcctgcaa   1080
gtgtttggca acaataaacc ggactacgat ggtctgaacc acctgaaaat tgtgcagatg   1140
atcctgtatg aagttctgcg tctgtatccg ccggtgacgg tgctgagccg tgcggtgttt   1200
aaagaaacca aactgggtaa tctgacgctg ccggcaggcg tccagattgg tctgccgatg   1260
atcctggtgc accaggaccc ggaactgtgg ggcgacgatg ctgtggaatt taaaccggaa   1320
cgtttcgcgg aaggtattag taaagcagct aaaaatcagg tttcctattt tccgttcgcg   1380
ctgggtccgc gtatttgcgt cggtcaaaac tttgcactgg tggaagctaa aatggcaacc   1440
gctatgatcc tgcaaaatta tagctttgaa ctgtcaccga gctatgttca tgcgccgacc   1500
gccgttccga cgctgcaccc ggaactgggc acgcaactga ttctgcgtaa actgtggtgt   1560
aaaaacaat                                                           1569
```

<210> SEQ ID NO 31
<211> LENGTH: 495
<212> TYPE: PRT
<213> ORGANISM: Artemesia annua

<400> SEQUENCE: 31

```
Met Lys Ser Ile Leu Lys Ala Met Ala Leu Ser Leu Thr Thr Ser Ile
1               5                   10                  15

Ala Leu Ala Thr Ile Leu Leu Phe Val Tyr Lys Phe Ala Thr Arg Ser
            20                  25                  30

Lys Ser Thr Lys Lys Ser Leu Pro Glu Pro Trp Arg Leu Pro Ile Ile
        35                  40                  45

Gly His Met His His Leu Ile Gly Thr Thr Pro His Arg Gly Val Arg
    50                  55                  60

Asp Leu Ala Arg Lys Tyr Gly Ser Leu Met His Leu Gln Leu Gly Glu
65                  70                  75                  80

Val Pro Thr Ile Val Val Ser Ser Pro Lys Trp Ala Lys Glu Ile Leu
                85                  90                  95

Thr Thr Tyr Asp Ile Thr Phe Ala Asn Arg Pro Glu Thr Leu Thr Gly
            100                 105                 110

Glu Ile Val Leu Tyr His Asn Thr Asp Val Val Leu Ala Pro Tyr Gly
        115                 120                 125

Glu Tyr Trp Arg Gln Leu Arg Lys Ile Cys Thr Leu Glu Leu Leu Ser
    130                 135                 140

Val Lys Lys Val Lys Ser Phe Gln Ser Leu Arg Glu Glu Glu Cys Trp
145                 150                 155                 160

Asn Leu Val Gln Glu Ile Lys Ala Ser Gly Ser Gly Arg Pro Val Asn
                165                 170                 175

Leu Ser Glu Asn Val Phe Lys Leu Ile Ala Thr Ile Leu Ser Arg Ala
            180                 185                 190

Ala Phe Gly Lys Gly Ile Lys Asp Gln Lys Glu Leu Thr Glu Ile Val
        195                 200                 205

Lys Glu Ile Leu Arg Gln Thr Gly Gly Phe Asp Val Ala Asp Ile Phe
    210                 215                 220

Pro Ser Lys Lys Phe Leu His His Leu Ser Gly Lys Arg Ala Arg Leu
225                 230                 235                 240

Thr Ser Leu Arg Lys Lys Ile Asp Asn Leu Ile Asp Asn Leu Val Ala
                245                 250                 255
```

Glu His Thr Val Asn Thr Ser Ser Lys Thr Asn Glu Thr Leu Leu Asp
             260                 265                 270

Val Leu Leu Arg Leu Lys Asp Ser Ala Glu Phe Pro Leu Thr Ser Asp
         275                 280                 285

Asn Ile Lys Ala Ile Ile Leu Asp Met Phe Gly Ala Gly Thr Asp Thr
     290                 295                 300

Ser Ser Ser Thr Ile Glu Trp Ala Ile Ser Glu Leu Ile Lys Cys Pro
305                 310                 315                 320

Lys Ala Met Glu Lys Val Gln Ala Glu Leu Arg Lys Ala Leu Asn Gly
                 325                 330                 335

Lys Glu Lys Ile His Glu Asp Ile Gln Glu Leu Ser Tyr Leu Asn
             340                 345                 350

Met Val Ile Lys Glu Thr Leu Arg Leu His Pro Pro Leu Pro Leu Val
             355                 360                 365

Leu Pro Arg Glu Cys Arg Gln Pro Val Asn Leu Ala Gly Tyr Asn Ile
     370                 375                 380

Pro Asn Lys Thr Lys Leu Ile Val Asn Val Phe Ala Ile Asn Arg Asp
385                 390                 395                 400

Pro Glu Tyr Trp Lys Asp Ala Glu Ala Phe Ile Pro Glu Arg Phe Glu
                 405                 410                 415

Asn Ser Ser Ala Thr Val Met Gly Ala Glu Tyr Glu Tyr Leu Pro Phe
             420                 425                 430

Gly Ala Gly Arg Arg Met Cys Pro Gly Ala Ala Leu Gly Leu Ala Asn
             435                 440                 445

Val Gln Leu Pro Leu Ala Asn Ile Leu Tyr His Phe Asn Trp Lys Leu
     450                 455                 460

Pro Asn Gly Val Ser Tyr Asp Gln Ile Asp Met Thr Glu Ser Ser Gly
465                 470                 475                 480

Ala Thr Met Gln Arg Lys Thr Glu Leu Leu Val Pro Ser Phe
                 485                 490                 495

<210> SEQ ID NO 32
<211> LENGTH: 488
<212> TYPE: PRT
<213> ORGANISM: Artemesia annua

<400> SEQUENCE: 32

Met Ala Leu Leu Leu Ala Val Phe Ile Ala Leu Ala Thr Ile Leu Leu
1               5                   10                  15

Phe Val Tyr Lys Phe Ala Thr Arg Ser Lys Ser Thr Lys Lys Ser Leu
             20                  25                  30

Pro Glu Pro Trp Arg Leu Pro Ile Ile Gly His Met His His Leu Ile
         35                  40                  45

Gly Thr Thr Pro His Arg Gly Val Arg Asp Leu Ala Arg Lys Tyr Gly
     50                  55                  60

Ser Leu Met His Leu Gln Leu Gly Glu Val Pro Thr Ile Val Val Ser
65                  70                  75                  80

Ser Pro Lys Trp Ala Lys Glu Ile Leu Thr Thr Tyr Asp Ile Thr Phe
                 85                  90                  95

Ala Asn Arg Pro Glu Thr Leu Thr Gly Glu Ile Val Leu Tyr His Asn
             100                 105                 110

Thr Asp Val Val Leu Ala Pro Tyr Gly Glu Tyr Trp Arg Gln Leu Arg
         115                 120                 125

Lys Ile Cys Thr Leu Glu Leu Leu Ser Val Lys Lys Val Lys Ser Phe
     130                 135                 140

```
Gln Ser Leu Arg Glu Glu Cys Trp Asn Leu Val Gln Glu Ile Lys
145                 150                 155                 160

Ala Ser Gly Ser Gly Arg Pro Val Asn Leu Ser Glu Asn Val Phe Lys
                165                 170                 175

Leu Ile Ala Thr Ile Leu Ser Arg Ala Ala Phe Gly Lys Gly Ile Lys
            180                 185                 190

Asp Gln Lys Glu Leu Thr Glu Ile Val Lys Glu Ile Leu Arg Gln Thr
        195                 200                 205

Gly Gly Phe Asp Val Ala Asp Ile Phe Pro Ser Lys Lys Phe Leu His
    210                 215                 220

His Leu Ser Gly Lys Arg Ala Arg Leu Thr Ser Leu Arg Lys Lys Ile
225                 230                 235                 240

Asp Asn Leu Ile Asp Asn Leu Val Ala Glu His Thr Val Asn Thr Ser
                245                 250                 255

Ser Lys Thr Asn Glu Thr Leu Leu Asp Val Leu Leu Arg Leu Lys Asp
            260                 265                 270

Ser Ala Glu Phe Pro Leu Thr Ser Asp Asn Ile Lys Ala Ile Ile Leu
        275                 280                 285

Asp Met Phe Gly Ala Gly Thr Asp Thr Ser Ser Ser Thr Ile Glu Trp
    290                 295                 300

Ala Ile Ser Glu Leu Ile Lys Cys Pro Lys Ala Met Glu Lys Val Gln
305                 310                 315                 320

Ala Glu Leu Arg Lys Ala Leu Asn Gly Lys Glu Lys Ile His Glu Glu
                325                 330                 335

Asp Ile Gln Glu Leu Ser Tyr Leu Asn Met Val Ile Lys Glu Thr Leu
            340                 345                 350

Arg Leu His Pro Pro Leu Pro Leu Val Leu Pro Arg Glu Cys Arg Gln
        355                 360                 365

Pro Val Asn Leu Ala Gly Tyr Asn Ile Pro Asn Lys Thr Lys Leu Ile
    370                 375                 380

Val Asn Val Phe Ala Ile Asn Arg Asp Pro Glu Tyr Trp Lys Asp Ala
385                 390                 395                 400

Glu Ala Phe Ile Pro Glu Arg Phe Glu Asn Ser Ser Ala Thr Val Met
                405                 410                 415

Gly Ala Glu Tyr Glu Tyr Leu Pro Phe Gly Ala Gly Arg Arg Met Cys
            420                 425                 430

Pro Gly Ala Ala Leu Gly Leu Ala Asn Val Gln Leu Pro Leu Ala Asn
        435                 440                 445

Ile Leu Tyr His Phe Asn Trp Lys Leu Pro Asn Gly Val Ser Tyr Asp
    450                 455                 460

Gln Ile Asp Met Thr Glu Ser Ser Gly Ala Thr Met Gln Arg Lys Thr
465                 470                 475                 480

Glu Leu Leu Leu Val Pro Ser Phe
                485

<210> SEQ ID NO 33
<211> LENGTH: 1464
<212> TYPE: DNA
<213> ORGANISM: Artemesia annua

<400> SEQUENCE: 33
atggctctgt tattagcagt tttcatcgca ctggcaacca ttctgctgtt tgtgtataaa      60
ttcgctaccc gttccaaatc aacgaaaaaa tcactgccgg aaccgtggcg cctgccgatt     120
atcggtcaca tgcatcacct gatcggcacc accccgcatc gtggcgtgcg tgatctggca     180
```

```
cgcaaatatg gctcgctgat gcatctgcaa ctgggtgaag tcccgaccat tgtggttagc    240
tctccgaaat gggcgaaaga aatcctgacc acctatgata ttacctttgc caaccgcccg    300
gaaaccctga cgggcgaaat cgtgctgtac cacaatacgg atgtggtgct ggcgccgtat    360
ggtgaatact ggcgtcaact gcgtaaaatt tgcaccctgg aactgctgag tgtgaaaaaa    420
gttaaatctt tccagagcct gcgtgaagaa gaatgttgga acctggttca agaaattaaa    480
gcatcgggca gcgtcgcccc ggttaacctg agtgaaaatg tctttaaact gattgctacc    540
atcctgtccc gtgcggcctt cggcaaaggt atcaaagatc agaaagaact gaccgaaatt    600
gtcaaagaaa tcctgcgcca aacgggcggt tttgatgtgg cggacatttt tccgtcgaaa    660
aaattcctgc atcacctgag cggtaaacgt gcccgcctga ccagcctgcg taagaaaatt    720
gataacctga tcgacaatct ggtcgcggaa cataccgtga acacgagttc caaaaccaat    780
gaaacgctgc tggatgtgct gctgcgcctg aaagactccg ccgaatttcc gctgacctca    840
gataatatca aagcgattat cctggatatg ttcggtgcag gcaccgatac cagcagcagc    900
accattgaat gggcaatctc agaactgatt aaatgcccga agctatggaa aaagtccag    960 gcagaactgc gcaaagctct gaacggcaaa gaaaaaatcc atgaagaaga tattcaagaa    1020
ctgtcttacc tgaacatggt tatcaaagaa accctgcgtc tgcacccgcc gctgccgctg    1080
gtgctgccgc gtgaatgtcg ccagccggtt aacctggcag gctataacat cccgaataaa    1140
acgaaactga tcgttaacgt ctttgctatt aaccgtgacc cggaatactg gaagacgcg    1200 gaagccttta tcccggaacg ctttgaaaac agcagcgcga ccgtgatggg tgccgaatat    1260
gaatacctgc cgtttggcgc gggtcgtcgc atgtgtccgg cgcagctct gggtctggca    1320 aacgtgcaac tgccgctggc taatatcctg tatcacttca actggaaact gccgaatggc    1380
gttagctacg atcaaattga catgaccgaa agctcaggtg ccacgatgca acgcaaaacc    1440
gaactgctgc tggtgccgtc cttc                                           1464
```

<210> SEQ ID NO 34
<211> LENGTH: 509
<212> TYPE: PRT
<213> ORGANISM: Arabidopsis thaliana

<400> SEQUENCE: 34

```
Met Ala Phe Phe Ser Met Ile Ser Ile Leu Leu Gly Phe Val Ile Ser
1               5                   10                  15

Ser Phe Ile Phe Ile Phe Phe Lys Lys Leu Ser Phe Ser Arg
            20                  25                  30

Lys Asn Met Ser Glu Val Ser Thr Leu Pro Ser Val Pro Val Pro
        35                  40                  45

Gly Phe Pro Val Ile Gly Asn Leu Leu Gln Leu Lys Glu Lys Pro
    50                  55                  60

His Lys Thr Phe Thr Arg Trp Ser Glu Ile Tyr Gly Pro Ile Tyr Ser
65                  70                  75                  80

Ile Lys Met Gly Ser Ser Ser Leu Ile Val Leu Asn Ser Thr Glu Thr
                85                  90                  95

Ala Lys Glu Ala Met Val Thr Arg Phe Ser Ser Ile Ser Thr Arg Lys
            100                 105                 110

Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
    130                 135                 140
```

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
            165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
    210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
            245                 250                 255

Ala Arg Ile Gln Gln Lys His Lys Arg Arg Leu Ala Val Met Asn Ala
            260                 265                 270

Leu Ile Gln Asp Arg Leu Lys Gln Asn Gly Ser Glu Ser Asp Asp Asp
        275                 280                 285

Cys Tyr Leu Asn Phe Leu Met Ser Glu Ala Lys Thr Leu Thr Lys Glu
    290                 295                 300

Gln Ile Ala Ile Leu Val Trp Glu Thr Ile Ile Glu Thr Ala Asp Thr
305                 310                 315                 320

Thr Leu Val Thr Thr Glu Trp Ala Ile Tyr Glu Leu Ala Lys His Pro
            325                 330                 335

Ser Val Gln Asp Arg Leu Cys Lys Glu Ile Gln Asn Val Cys Gly Gly
            340                 345                 350

Glu Lys Phe Lys Glu Glu Gln Leu Ser Gln Val Pro Tyr Leu Asn Gly
        355                 360                 365

Val Phe His Glu Thr Leu Arg Lys Tyr Ser Pro Ala Pro Leu Val Pro
    370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
            405                 410                 415

Lys Arg Trp Glu Arg Pro Glu Asp Trp Trp Pro Glu Arg Phe Leu Asp
            420                 425                 430

Asp Gly Lys Tyr Glu Thr Ser Asp Leu His Lys Thr Met Ala Phe Gly
        435                 440                 445

Ala Gly Lys Arg Val Cys Ala Gly Ala Leu Gln Ala Ser Leu Met Ala
    450                 455                 460

Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
            485                 490                 495

Leu Tyr Pro Leu Met Ala Ile Ile Asn Pro Arg Arg Ser
            500                 505

<210> SEQ ID NO 35
<211> LENGTH: 513
<212> TYPE: PRT
<213> ORGANISM: Arabidopsis thaliana

<400> SEQUENCE: 35

```
Met Ala Leu Leu Leu Ala Val Phe Ser Met Ile Ser Ile Leu Leu Gly
1               5                   10                  15

Phe Val Ile Ser Ser Phe Ile Phe Ile Phe Phe Lys Lys Leu Leu
            20                  25                  30

Ser Phe Ser Arg Lys Asn Met Ser Glu Val Ser Thr Leu Pro Ser Val
        35                  40                  45

Pro Val Val Pro Gly Phe Pro Val Ile Gly Asn Leu Leu Gln Leu Lys
    50                  55                  60

Glu Lys Lys Pro His Lys Thr Phe Thr Arg Trp Ser Glu Ile Tyr Gly
65              70                  75                  80

Pro Ile Tyr Ser Ile Lys Met Gly Ser Ser Ser Leu Ile Val Leu Asn
                85                  90                  95

Ser Thr Glu Thr Ala Lys Glu Ala Met Val Thr Arg Phe Ser Ser Ile
            100                 105                 110

Ser Thr Arg Lys Leu Ser Asn Ala Leu Thr Val Leu Thr Cys Asp Lys
        115                 120                 125

Ser Met Val Ala Thr Ser Asp Tyr Asp Asp Phe His Lys Leu Val Lys
    130                 135                 140

Arg Cys Leu Leu Asn Gly Leu Leu Gly Ala Asn Ala Gln Lys Arg Lys
145                 150                 155                 160

Arg His Tyr Arg Asp Ala Leu Ile Glu Asn Val Ser Ser Lys Leu His
                165                 170                 175

Ala His Ala Arg Asp His Pro Gln Glu Pro Val Asn Phe Arg Ala Ile
            180                 185                 190

Phe Glu His Glu Leu Phe Gly Val Ala Leu Lys Gln Ala Phe Gly Lys
        195                 200                 205

Asp Val Glu Ser Ile Tyr Val Lys Glu Leu Gly Val Thr Leu Ser Lys
    210                 215                 220

Asp Glu Ile Phe Lys Val Leu Val His Asp Met Met Glu Gly Ala Ile
225                 230                 235                 240

Asp Val Asp Trp Arg Asp Phe Phe Pro Tyr Leu Lys Trp Ile Pro Asn
                245                 250                 255

Lys Ser Phe Glu Ala Arg Ile Gln Gln Lys His Lys Arg Arg Leu Ala
            260                 265                 270

Val Met Asn Ala Leu Ile Gln Asp Arg Leu Lys Gln Asn Gly Ser Glu
        275                 280                 285

Ser Asp Asp Asp Cys Tyr Leu Asn Phe Leu Met Ser Glu Ala Lys Thr
    290                 295                 300

Leu Thr Lys Glu Gln Ile Ala Ile Leu Val Trp Glu Thr Ile Ile Glu
305                 310                 315                 320

Thr Ala Asp Thr Thr Leu Val Thr Thr Glu Trp Ala Ile Tyr Glu Leu
                325                 330                 335

Ala Lys His Pro Ser Val Gln Asp Arg Leu Cys Lys Glu Ile Gln Asn
            340                 345                 350

Val Cys Gly Gly Glu Lys Phe Lys Glu Glu Gln Leu Ser Gln Val Pro
    355                 360                 365

Tyr Leu Asn Gly Val Phe His Glu Thr Leu Arg Lys Tyr Ser Pro Ala
370                 375                 380

Pro Leu Val Pro Ile Arg Tyr Ala His Glu Asp Thr Gln Ile Gly Gly
385                 390                 395                 400

Tyr His Val Pro Ala Gly Ser Glu Ile Ala Ile Asn Ile Tyr Gly Cys
                405                 410                 415
```

```
Asn Met Asp Lys Lys Arg Trp Glu Arg Pro Glu Asp Trp Trp Pro Glu
            420                 425                 430

Arg Phe Leu Asp Asp Gly Lys Tyr Glu Thr Ser Asp Leu His Lys Thr
        435                 440                 445

Met Ala Phe Gly Ala Gly Lys Arg Val Cys Gly Ala Leu Gln Ala
    450                 455                 460

Ser Leu Met Ala Gly Ile Ala Ile Gly Arg Leu Val Gln Glu Phe Glu
465                 470                 475                 480

Trp Lys Leu Arg Asp Gly Glu Glu Glu Asn Val Asp Thr Tyr Gly Leu
                485                 490                 495

Thr Ser Gln Lys Leu Tyr Pro Leu Met Ala Ile Ile Asn Pro Arg Arg
            500                 505                 510

Ser

<210> SEQ ID NO 36
<211> LENGTH: 1539
<212> TYPE: DNA
<213> ORGANISM: Arabidopsis thaliana

<400> SEQUENCE: 36
atggctctgt tattagcagt tttttcgatg atttctatcc tgctgggctt tgttatctcg      60
tcctttatct ttatcttctt cttcaaaaaa ctgctgtcgt tttctcgtaa aaacatgtcc     120
gaagtttcaa ccctgccgag tgtcccggtg gttccgggtt ttccggttat cggtaatctg     180
ctgcagctga agaaaagaa accgcataag accttcacgc gctggtccga atctatggc       240 ccgatctact caattaaaat gggtagctct agtctgattg tgctgaactc taccgaaacg     300
gcaaaagaag ctatggttac ccgttttttcc tcaatttcga cgcgcaagct gagcaatgcg    360
ctgaccgtcc tgacgtgcga caaatctatg gtggccacca gtgattacga tgacttccat     420
aaactggtta agcgttgtct gctgaacggc ctgctgggtg cgaatgccca gaagcgtaag     480
cgccactatc gcgacgccct gattgaaaac gtgtcgagca aactgcatgc acacgctcgt     540
gatcatccgc aggaaccggt caattttcgc gcaatcttcg aacacgaact gtttggcgtg     600
gcgctgaaac aagccttcgg caaggatgtt gaatcgattt acgtcaaaga actgggcgtg     660
accctgagca agacgaaat cttttaaggtc ctggtgcatg atatgatgga aggtgcaatt     720
gacgttgatt ggcgtgattt cttttccgtat ctgaaatgga ttccgaacaa gtcattcgaa     780
gctcgcattc agcaaaaaca caagcgtcgc ctggcagtga tgaacgctct gattcaggat     840
cgtctgaaac aaaatggctc tgaaagtgat gacgattgct atctgaattt tctgatgtcc     900
gaagcaaaaa ccctgacgaa ggaacagatt gctatcctgg tttgggaaac cattatcgaa     960
acggcggaca ccacgctggt caccacggaa tgggcgatct acgaactggc caagcatccg    1020
agcgttcagg atcgcctgtg caaagaaatt caaaacgtct gtggcggtga aaaatttaag    1080
gaagaacagc tgtcgcaagt gccgtatctg aatggtgttt ccacgaaaac cctgcgtaaa    1140
tatagcccgg caccgctggt cccgatccgt tacgcccatg aagataccca gattggcggt    1200
tatcacgtgc cggcaggcag tgaaattgct atcaacattt acggttgcaa tatggacaaa    1260
aagcgttggg aacgcccgga agattggtgg ccggaacgtt ttctggacga tggcaaatat    1320
gaaacctctg atctgcataa gacgatggcg ttcggtgcag gtaaacgtgt gtgtgcaggt    1380
gcactgcaag caagtctgat ggcaggcatc gctattggtc gtctggtgca agaatttgaa    1440
tggaaactgc gcgacggcga agaagaaaac gttgatacct atggtctgac gtcccagaaa    1500
ctgtacccgc tgatggccat tatcaatccg cgtcgctca                           1539
```

```
<210> SEQ ID NO 37
<211> LENGTH: 513
<212> TYPE: PRT
<213> ORGANISM: Stevia rebaudiana

<400> SEQUENCE: 37

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Arg His
    370                 375                 380
```

```
Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
            405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
            435                 440                 445

Thr Met Ala Phe Gly Gly Lys Arg Val Cys Ala Gly Ser Leu Gln
            450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
            485                 490                 495

Leu Thr Thr Gln Met Leu Arg Pro Leu Arg Ala Ile Ile Lys Pro Arg
            500                 505                 510

Ile

<210> SEQ ID NO 38
<211> LENGTH: 501
<212> TYPE: PRT
<213> ORGANISM: Stevia rebaudiana

<400> SEQUENCE: 38

Met Ala Leu Leu Leu Ala Val Phe Ala Val Ala Leu Ala Val Ala Leu
1               5                   10                  15

Ile Phe Trp Tyr Leu Lys Ser Tyr Thr Ser Ala Arg Arg Ser Gln Ser
            20                  25                  30

Asn His Leu Pro Arg Val Pro Glu Val Pro Gly Val Pro Leu Leu Gly
            35                  40                  45

Asn Leu Leu Gln Leu Lys Glu Lys Lys Pro Tyr Met Thr Phe Thr Arg
50                  55                  60

Trp Ala Ala Thr Tyr Gly Pro Ile Tyr Ser Ile Lys Thr Gly Ala Thr
65                  70                  75                  80

Ser Met Val Val Val Ser Ser Asn Glu Ile Ala Lys Glu Ala Leu Val
            85                  90                  95

Thr Arg Phe Gln Ser Ile Ser Thr Arg Asn Leu Ser Lys Ala Leu Lys
            100                 105                 110

Val Leu Thr Ala Asp Lys Thr Met Val Ala Met Ser Asp Tyr Asp Asp
            115                 120                 125

Tyr His Lys Thr Val Lys Arg His Ile Leu Thr Ala Val Leu Gly Pro
            130                 135                 140

Asn Ala Gln Lys Lys His Arg Ile His Arg Asp Ile Met Met Asp Asn
145                 150                 155                 160

Ile Ser Thr Gln Leu His Glu Phe Val Lys Asn Asn Pro Glu Gln Glu
            165                 170                 175

Glu Val Asp Leu Arg Lys Ile Phe Gln Ser Glu Leu Phe Gly Leu Ala
            180                 185                 190

Met Arg Gln Ala Leu Gly Lys Asp Val Glu Ser Leu Tyr Val Glu Asp
            195                 200                 205

Leu Lys Ile Thr Met Asn Arg Asp Glu Ile Phe Gln Val Leu Val Val
            210                 215                 220

Asp Pro Met Met Gly Ala Ile Val Asp Trp Arg Asp Phe Phe Pro
225                 230                 235                 240
```

```
Tyr Leu Lys Trp Val Pro Asn Lys Lys Phe Glu Asn Thr Ile Gln Gln
                245                 250                 255

Met Tyr Ile Arg Arg Glu Ala Val Met Lys Ser Leu Ile Lys Glu His
            260                 265                 270

Lys Lys Arg Ile Ala Ser Gly Glu Lys Leu Asn Ser Tyr Ile Asp Tyr
        275                 280                 285

Leu Leu Ser Glu Ala Gln Thr Leu Thr Asp Gln Gln Leu Leu Met Ser
    290                 295                 300

Leu Trp Glu Pro Ile Ile Glu Ser Ser Asp Thr Thr Met Val Thr Thr
305                 310                 315                 320

Glu Trp Ala Met Tyr Glu Leu Ala Lys Asn Pro Lys Leu Gln Asp Arg
                325                 330                 335

Leu Tyr Arg Asp Ile Lys Ser Val Cys Gly Ser Glu Lys Ile Thr Glu
            340                 345                 350

Glu His Leu Ser Gln Leu Pro Tyr Ile Thr Ala Ile Phe His Glu Thr
        355                 360                 365

Leu Arg Arg His Ser Pro Val Pro Ile Ile Pro Leu Arg His Val His
    370                 375                 380

Glu Asp Thr Val Leu Gly Gly Tyr His Val Pro Ala Gly Thr Glu Leu
385                 390                 395                 400

Ala Val Asn Ile Tyr Gly Cys Asn Met Asp Lys Asn Val Trp Glu Asn
                405                 410                 415

Pro Glu Glu Trp Asn Pro Glu Arg Phe Met Lys Glu Asn Glu Thr Ile
            420                 425                 430

Asp Phe Gln Lys Thr Met Ala Phe Gly Gly Gly Lys Arg Val Cys Ala
        435                 440                 445

Gly Ser Leu Gln Ala Leu Leu Thr Ala Ser Ile Gly Ile Gly Arg Met
    450                 455                 460

Val Gln Glu Phe Glu Trp Lys Leu Lys Asp Met Thr Gln Glu Glu Val
465                 470                 475                 480

Asn Thr Ile Gly Leu Thr Thr Gln Met Leu Arg Pro Leu Arg Ala Ile
                485                 490                 495

Ile Lys Pro Arg Ile
            500

<210> SEQ ID NO 39
<211> LENGTH: 1503
<212> TYPE: DNA
<213> ORGANISM: Stevia rebaudiana

<400> SEQUENCE: 39
atggctctgt tattagcagt ttttgccgtc gctctggcgg tagcactgat cttctggtat      60
ctgaaatctt acactagcgc gcgccgctct cagtccaacc acctgccgcg tgtgccggaa     120
gttccgggtg tgccactgct gggcaacctg ctgcaactga agaaaagaa accgtacatg      180 acctttaccc gctgggcagc gacttatggt cctatctaca gcattaaaac cggcgctacg     240
tctatggttg tggtttcttc aacgaaatc gcgaagaag ccctggtgac tcgtttccag      300
tccattagca cccgcaacct gtccaaagcg ctgaaggttc tgacggctga caagactatg     360
gtggctatga gcgactatga tgactaccac aaaaccgtta acgtcacat cctgaccgca      420 gtactgggtc gaacgcaca gaaaaaacat cgcatccacc gcgacattat gatggataac     480
atctccacgc agctgcatga gttcgttaag aacaatccag aacaggaaga ggtagatctg     540
cgtaaaattt ttcagtccga actgttcggt ctggctatgc gtcaggcgct gggcaaagac     600
```

```
gttgaaagcc tgtatgtcga agacctgaaa attaccatga accgtgatga gatcttccag    660
gttctggttg tagatccgat gatgggcgcc atcgacgtgg attggcgtga cttctttccg    720
tacctgaaat gggtcccgaa caagaagttc gaaaacacca tccagcaaat gtacatccgt    780
cgtgaagcgg tgatgaaaag cctgatcaaa gaacacaaaa agcgtattgc ttctggtgag    840
aaactgaact cctacatcga ttatctgctg tccgaagcgc agaccctgac cgaccaacag    900
ctgctgatgt ctctgtggga accgattatc gaaagcagcg acaccactat ggtcactacc    960
gaatgggcaa tgtatgagct ggccaaaaac ccgaaactgc aggatcgtct gtaccgtgac   1020
atcaaaagcg tttgcggctc cgagaaaatc actgaagaac acctgtctca gctgccgtac   1080
atcactgcta ttttccacga aaccctgcgt cgccattctc cggttccgat cattccgctg   1140
cgtcacgttc acgaagatac tgtgctgggt ggttaccatg taccggcagg cactgaactg   1200
gctgtcaaca tctacggctg taacatggat aaaaacgttt gggagaatcc tgaagaatgg   1260
aacccggaac gcttcatgaa agagaacgaa accatcgact ccagaaaaac gatggctttc   1320
ggcggtggta acgtgtgtg cgcaggttct ctgcaggcgc tgctgacggc gtccattggt   1380
atcggtcgca tggtacagga atttgaatgg aagctgaaag acatgaccca agaagaggtg   1440
aataccattg gtctgactac ccagatgctg cgtccactgc gtgcaatcat caaacctcgt   1500
att                                                                  1503
```

<210> SEQ ID NO 40
<211> LENGTH: 546
<212> TYPE: PRT
<213> ORGANISM: Physcomitrella patens

<400> SEQUENCE: 40

```
Met Ala Lys His Leu Ala Thr Gln Leu Leu Gln Gln Trp Asn Glu Ala
1               5                   10                  15

Leu Lys Thr Met Pro Pro Gly Phe Arg Thr Ala Gly Lys Ile Leu Val
            20                  25                  30

Trp Glu Glu Leu Ala Ser Asn Lys Val Leu Ile Thr Ile Ala Leu Ala
        35                  40                  45

Trp Val Leu Leu Phe Val Ala Arg Thr Cys Leu Arg Asn Lys Lys Arg
    50                  55                  60

Leu Pro Pro Ala Ile Pro Gly Leu Pro Val Leu Gly Asn Leu Leu
65                  70                  75                  80

Gln Leu Thr Glu Lys Lys Pro His Arg Thr Phe Thr Ala Trp Ser Lys
                85                  90                  95

Glu His Gly Pro Ile Phe Thr Ile Lys Val Gly Ser Val Pro Gln Ala
            100                 105                 110

Val Val Asn Asn Ser Glu Ile Ala Lys Glu Val Leu Val Thr Lys Phe
        115                 120                 125

Ala Ser Ile Ser Lys Arg Gln Met Pro Met Ala Leu Arg Val Leu Thr
    130                 135                 140

Arg Asp Lys Thr Met Val Ala Met Ser Asp Tyr Gly Glu Glu His Arg
145                 150                 155                 160

Met Leu Lys Lys Leu Val Met Thr Asn Leu Gly Pro Thr Thr Gln
                165                 170                 175

Asn Lys Asn Arg Ser Leu Arg Asp Asp Ala Leu Ile Gly Met Ile Glu
            180                 185                 190

Gly Val Leu Ala Glu Leu Lys Ala Ser Pro Thr Ser Pro Lys Val Val
        195                 200                 205
```

```
Asn Val Arg Asp Tyr Val Gln Arg Ser Leu Phe Pro Phe Ala Leu Gln
    210                 215                 220

Gln Val Phe Gly Tyr Ile Pro Asp Gln Val Glu Val Leu Glu Leu Gly
225                 230                 235                 240

Thr Cys Val Ser Thr Trp Asp Met Phe Asp Ala Leu Val Val Ala Pro
                245                 250                 255

Leu Ser Ala Val Ile Asn Val Asp Trp Arg Asp Phe Phe Pro Ala Leu
                260                 265                 270

Arg Trp Ile Pro Asn Arg Ser Val Glu Asp Leu Val Arg Thr Val Asp
            275                 280                 285

Phe Lys Arg Asn Ser Ile Met Lys Ala Leu Ile Arg Ala Gln Arg Met
    290                 295                 300

Arg Leu Ala Asn Leu Lys Glu Pro Pro Arg Cys Tyr Ala Asp Ile Ala
305                 310                 315                 320

Leu Thr Glu Ala Thr His Leu Thr Glu Lys Gln Leu Glu Met Ser Leu
                325                 330                 335

Trp Glu Pro Ile Ile Glu Ser Ala Asp Thr Thr Leu Val Thr Ser Glu
            340                 345                 350

Trp Ala Met Tyr Glu Ile Ala Lys Asn Pro Asp Cys Gln Asp Arg Leu
    355                 360                 365

Tyr Arg Glu Ile Val Ser Val Ala Gly Thr Glu Arg Met Val Thr Glu
370                 375                 380

Asp Asp Leu Pro Asn Met Pro Tyr Leu Gly Ala Ile Ile Lys Glu Thr
385                 390                 395                 400

Leu Arg Lys Tyr Thr Pro Val Pro Leu Ile Pro Ser Arg Phe Val Glu
                405                 410                 415

Glu Asp Ile Thr Leu Gly Gly Tyr Asp Ile Pro Lys Gly Tyr Gln Ile
            420                 425                 430

Leu Val Asn Leu Phe Ala Ile Ala Asn Asp Pro Ala Val Trp Ser Asn
    435                 440                 445

Pro Glu Lys Trp Asp Pro Glu Arg Met Leu Ala Asn Lys Lys Val Asp
    450                 455                 460

Met Gly Phe Arg Asp Phe Ser Leu Met Pro Phe Gly Ala Gly Lys Arg
465                 470                 475                 480

Met Cys Ala Gly Ile Thr Gln Ala Met Phe Ile Ile Pro Met Asn Val
                485                 490                 495

Ala Ala Leu Val Gln His Cys Glu Trp Arg Leu Ser Pro Gln Glu Ile
            500                 505                 510

Ser Asn Ile Asn Asn Lys Ile Glu Asp Val Val Tyr Leu Thr Thr His
    515                 520                 525

Lys Leu Ser Pro Leu Ser Cys Glu Ala Thr Pro Arg Ile Ser His Arg
530                 535                 540

Leu Pro
545

<210> SEQ ID NO 41
<211> LENGTH: 548
<212> TYPE: PRT
<213> ORGANISM: Physcomitrella patens

<400> SEQUENCE: 41

Met Ala Leu Leu Leu Ala Val Phe Thr Gln Leu Leu Gln Gln Trp Asn
1               5                   10                  15

Glu Ala Leu Lys Thr Met Pro Pro Gly Phe Arg Thr Ala Gly Lys Ile
                20                  25                  30
```

```
Leu Val Trp Glu Glu Leu Ala Ser Asn Lys Val Leu Ile Thr Ile Ala
         35                  40                  45

Leu Ala Trp Val Leu Leu Phe Val Ala Arg Thr Cys Leu Arg Asn Lys
 50                  55                  60

Lys Arg Leu Pro Pro Ala Ile Pro Gly Gly Leu Pro Val Leu Gly Asn
 65                  70                  75                  80

Leu Leu Gln Leu Thr Glu Lys Lys Pro His Arg Thr Phe Thr Ala Trp
                 85                  90                  95

Ser Lys Glu His Gly Pro Ile Phe Thr Ile Lys Val Gly Ser Val Pro
                100                 105                 110

Gln Ala Val Val Asn Asn Ser Glu Ile Ala Lys Glu Val Leu Val Thr
                115                 120                 125

Lys Phe Ala Ser Ile Ser Lys Arg Gln Met Pro Met Ala Leu Arg Val
130                 135                 140

Leu Thr Arg Asp Lys Thr Met Val Ala Met Ser Asp Tyr Gly Glu Glu
145                 150                 155                 160

His Arg Met Leu Lys Lys Leu Val Met Thr Asn Leu Leu Gly Pro Thr
                165                 170                 175

Thr Gln Asn Lys Asn Arg Ser Leu Arg Asp Asp Ala Leu Ile Gly Met
                180                 185                 190

Ile Glu Gly Val Leu Ala Glu Leu Lys Ala Ser Pro Thr Ser Pro Lys
        195                 200                 205

Val Val Asn Val Arg Asp Tyr Val Gln Arg Ser Leu Phe Pro Phe Ala
210                 215                 220

Leu Gln Gln Val Phe Gly Tyr Ile Pro Asp Gln Val Glu Val Leu Glu
225                 230                 235                 240

Leu Gly Thr Cys Val Ser Thr Trp Asp Met Phe Asp Ala Leu Val Val
                245                 250                 255

Ala Pro Leu Ser Ala Val Ile Asn Val Asp Trp Arg Asp Phe Phe Pro
                260                 265                 270

Ala Leu Arg Trp Ile Pro Asn Arg Ser Val Glu Asp Leu Val Arg Thr
        275                 280                 285

Val Asp Phe Lys Arg Asn Ser Ile Met Lys Ala Leu Ile Arg Ala Gln
290                 295                 300

Arg Met Arg Leu Ala Asn Leu Lys Glu Pro Pro Arg Cys Tyr Ala Asp
305                 310                 315                 320

Ile Ala Leu Thr Glu Ala Thr His Leu Thr Lys Gln Leu Glu Met
                325                 330                 335

Ser Leu Trp Glu Pro Ile Ile Glu Ser Ala Asp Thr Thr Leu Val Thr
                340                 345                 350

Ser Glu Trp Ala Met Tyr Glu Ile Ala Lys Asn Pro Asp Cys Gln Asp
                355                 360                 365

Arg Leu Tyr Arg Glu Ile Val Ser Val Ala Gly Thr Glu Arg Met Val
        370                 375                 380

Thr Glu Asp Asp Leu Pro Asn Met Pro Tyr Leu Gly Ala Ile Ile Lys
385                 390                 395                 400

Glu Thr Leu Arg Lys Tyr Thr Pro Val Pro Leu Ile Pro Ser Arg Phe
                405                 410                 415

Val Glu Glu Asp Ile Thr Leu Gly Gly Tyr Asp Ile Pro Lys Gly Tyr
                420                 425                 430

Gln Ile Leu Val Asn Leu Phe Ala Ile Ala Asn Asp Pro Ala Val Trp
        435                 440                 445
```

```
Ser Asn Pro Glu Lys Trp Asp Pro Glu Arg Met Leu Ala Asn Lys Lys
    450                 455                 460
Val Asp Met Gly Phe Arg Asp Phe Ser Leu Met Pro Phe Gly Ala Gly
465                 470                 475                 480
Lys Arg Met Cys Ala Gly Ile Thr Gln Ala Met Phe Ile Ile Pro Met
                485                 490                 495
Asn Val Ala Ala Leu Val Gln His Cys Glu Trp Arg Leu Ser Pro Gln
            500                 505                 510
Glu Ile Ser Asn Ile Asn Asn Lys Ile Glu Asp Val Val Tyr Leu Thr
        515                 520                 525
Thr His Lys Leu Ser Pro Leu Ser Cys Glu Ala Thr Pro Arg Ile Ser
    530                 535                 540
His Arg Leu Pro
545

<210> SEQ ID NO 42
<211> LENGTH: 1644
<212> TYPE: DNA
<213> ORGANISM: Physcomitrella patens

<400> SEQUENCE: 42
atggctctgt tattagcagt ttttacgcaa ctgctgcaac aatggaatga agctctgaag     60
acgatgccgc cgggttttcg caccgctggc aaaattctgg tgtgggaaga actggcaagc    120
aataaagttc tgattacgat cgcactggct tgggtcctgc tgtttgtggc tcgtacctgc    180
ctgcgcaata aaaagcgtct gccgccggca atcccgggcg tctgccggt gctgggcaac    240 ctgctgcagc tgacggaaaa gaaaccgcat cgtaccttta cggcgtggag caaggaacac    300
ggcccgattt tcaccatcaa agtcggttcg gtgccgcagg ctgtggttaa caatagcgaa    360
attgcgaaag aagtcctggt gaccaagttc gccagcatct ctaaacgtca aatgccgatg    420
gcactgcgcg tcctgacgcg tgataaaacg atggtggcta tgtctgacta tggcgaagaa    480
catcgcatgc tgaaaaagct ggtgatgacg aatctgctgg gtccgaccac gcagaacaaa    540
aatcgtagtc tgcgcgatga cgcactgatt ggcatgatcg aaggtgttct ggcggaactg    600
aaggccagtc cgacctcccc gaaagtcgtg aacgttcgcg attatgtcca gcgttctctg    660
tttccgttcg cgctgcagca agtgtttggc tacattccgg atcaagttga agtcctggaa    720
ctgggcacgt gtgtttctac ctgggatatg ttcgacgcac tggttgtcgc tccgctgagt    780
gcggttatta acgtcgattg cgtgactttt ttccggcc tgcgctggat tccgaatcgt    840
tccgtggaag atctggtgcg caccgttgac tttaagcgta actcaattat gaaagccctg    900
atccgtgcac agcgtatgcg cctggctaac ctgaaggaac gccgcgctg ctacgcagat    960 attgctctga ccgaagcgac gcacctgacc gaaaaacaac tggaaatgag tctgtgggaa   1020
ccgattatcg aatccgccga taccacgctg gtgacctcag aatgggctat gtatgaaatt   1080
gcgaaaaatc cggattgtca ggaccgtctg taccgcgaaa tcgtgtccgt tgccggcacg   1140
gaacgcatgg ttaccgaaga tgacctgccg aacatgccgt atctgggtgc aattatcaaa   1200
gaaacgctgc gcaagtacac cccggttccg ctgattccga tcgtttttgt cgaagaagat   1260
atcaccctgg gcggttatga cattccgaaa ggttaccaga tcctggtcaa cctgttcgcg   1320
attgccaatg atccggccgt ttggtcgaac ccggaaaaat gggacccgga acgcatgctg   1380
gcaaataaaa aggtggatat gggctttcgt gacttcagcc tgatgccgtt tggcgccggt   1440
aaacgcatgt gcgccggtat cacccaagca atgttcatta tcccgatgaa tgtggcggcc   1500
```

```
ctggttcagc attgtgaatg gcgcctgagc ccgcaagaaa tctctaacat caacaacaag    1560
atcgaagatg tggtttacct gaccacgcat aaactgtcac cgctgtcgtg cgaagcaacc    1620
ccgcgtatca gccaccgtct gccg                                           1644
```

<210> SEQ ID NO 43
<211> LENGTH: 1049
<212> TYPE: PRT
<213> ORGANISM: Bacillus megaterium

<400> SEQUENCE: 43

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ile Pro Ala Phe Ser Leu Tyr Ala
                325                 330                 335

Lys Glu Asp Thr Val Leu Gly Gly Glu Tyr Pro Leu Glu Lys Gly Asp
            340                 345                 350
```

```
Glu Leu Met Val Leu Ile Pro Gln Leu His Arg Asp Lys Thr Ile Trp
            355                 360                 365

Gly Asp Asp Val Glu Glu Phe Arg Pro Glu Arg Phe Glu Asn Pro Ser
        370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Glu Gly Phe Val Val Lys
                435                 440                 445

Ala Lys Ser Lys Lys Ile Pro Leu Gly Gly Ile Pro Ser Pro Ser Thr
        450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
        500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
        530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
                580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
        610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
                660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
        690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
        740                 745                 750

Tyr Val Glu Leu Gln Asp Pro Val Thr Arg Thr Gln Leu Arg Ala Met
        755                 760                 765
```

```
Ala Ala Lys Thr Val Cys Pro Pro His Lys Val Glu Leu Glu Ala Leu
770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
                820                 825                 830
Ser Ser Ser Pro Arg Val Asp Glu Lys Gln Ala Ser Ile Thr Val Ser
            835                 840                 845
Val Val Ser Gly Glu Ala Trp Ser Gly Tyr Gly Glu Tyr Lys Gly Ile
850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
                900                 905                 910
Gly Phe Val Gln Ala Arg Lys Gln Leu Lys Glu Gln Gly Gln Ser Leu
                915                 920                 925
Gly Glu Ala His Leu Tyr Phe Gly Cys Arg Ser Pro His Glu Asp Tyr
            930                 935                 940
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Asp
                980                 985                 990
Gln Gly Ala His Phe Tyr Ile Cys Gly Asp Gly Ser Gln Met Ala Pro
            995                 1000                1005
Ala Val Glu Ala Thr Leu Met Lys Ser Tyr Ala Asp Val His Gln
    1010                1015                1020
Val Ser Glu Ala Asp Ala Arg Leu Trp Leu Gln Gln Leu Glu Glu
    1025                1030                1035
Lys Gly Arg Tyr Ala Lys Asp Val Trp Ala Gly
    1040                1045
```

<210> SEQ ID NO 44
<211> LENGTH: 3150
<212> TYPE: DNA
<213> ORGANISM: Bacillus megaterium

<400> SEQUENCE: 44

| | |
|---|---|
| atgacgatta aagaaatgcc gcaaccgaag acgtttggcg aactgaagaa cctgccgctg | 60 |
| ctgaacacgg ataagccggt gcaagccctg atgaagattg ctgatgaact gggcgaaatc | 120 |
| tttaaattcg aagcgccggg tcgtgtgacc cgttatctga gcagccagcg tctgattaaa | 180 |
| gaagcctgcg atgaatcgcg ctttgacaag aacctgagcc aggcactgaa atttgttcgt | 240 |
| gatttcgcag gtgacggtct ggccaccagc tggacgcatg aaaagaactg gaaaaaggcc | 300 |
| cacaatattc tgctgccgtc gttcagccag caagcaatga aggctacca tgctatgatg | 360 |
| gtcgatatcg cggttcagct ggtccaaaaa tgggaacgtc tgaatgcgga cgaacacatt | 420 |
| gaagtgccgg aagatatgac cgcctgacg ctggacacca tcgtctgtg tggctttaac | 480 |
| tatcgttttta attcgttcta ccgcgatcag ccgcatccgt tcattaccag catggtgcgt | 540 |

```
gcgctggacg aagccatgaa caaactgcag cgtgcaaacc cggatgaccc ggcgtatgat      600
gaaaacaagc gtcagtttca agaagacatc aaagtgatga atgatctggt tgacaagatt      660
atcgcagatc gcaaagcgag cggcgaacag tcagatgacc tgctgacgca catgctgaac      720
ggcaaagacc cggaaaccgg tgaaccgctg atgacgaaaa acatccgtta tcagatcatc      780
acctttctga tcgcaggcca tgaaaccacg tcgggtctgc tgagctttgc gctgtacttc      840
ctggtcaaga cccgcacgt gctgcagaaa gcggccgaag aagcagctcg tgtgctggtt      900
gatccggttc cgtcgtataa acaggtcaag caactgaaat acgtgggtat ggttctgaat      960
gaagcgctgc cctgtggcc gacgattccg gcatttagcc tgtatgctaa ggaagatacc     1020
gttctgggcg gtgaataccc gctggaaaaa ggcgatgaac tgatggtcct gattccgcag     1080
ctgcatcgcg acaaaaccat ctggggtgat gacgtggaag aatttcgccc ggaacgcttc     1140
gaaaacccga gcgcgattcc gcagcatgcc tttaaaccgt tcggcaatgg tcaacgtgcg     1200
tgcatcggcc agcaatttgc gctgcacgaa gccacgctgg ttctgggtat gatgctgaaa     1260
cattttgatt tcgaagacca caccaactat gaactggata ttaaggaaac cctgacgctg     1320
aaaccggaag gcttcgtggt taaagcgaag tctaaaaaga ttccgctggg cggtatcccg     1380
tctccgagta cggaacagag tgccaaaaag gtccgtaaaa aggcggaaaa cgcccataat     1440
accccgctgc tggtgctgta tggttctaac atgggcacgg cagaaggcac cgctcgcgat     1500
ctggcagaca ttgctatgtc taaaggtttt gcgccgcagg tggccacgct ggatagtcat     1560
gcaggcaatc tgccgcgtga aggtgctgtc ctgatcgtga ccgcaagcta caacggtcac     1620
ccgccggata atgcgaagca gttcgttgat ggctggacc aagcgtcggc cgatgaagtt     1680
aaaggtgtcc gctatagcgt gtttggctgt ggtgacaaga actgggctac cacgtaccag     1740
aaagttccgg cgttcattga tgaaacgctg cggccaaag gcgcagaaaa tatcgctgat     1800
cgtggtgaag cagacgcttc cgatgacttt gaaggcacct atgaagaatg gcgcgaacac     1860
atgtggtcgg atgtggcagc ttacttcaac ctggatattg aaaacagcga agacaataaa     1920
tccaccctgt cactgcagtt tgttgatagt gcggccgaca tgccgctggc aaagatgcac     1980
ggcgctttct ccacgaatgt cgtggcttca aaagaactgc agcaaccggg ttcggcacgt     2040
agcacccgcc atctggaaat tgaactgccg aaagaagcca gctatcagga aggcgatcac     2100
ctgggtgtga ttccgcgtaa ctacgaaggc atcgtgaatc gtgttacggc cgctttggt     2160 ctggatgcat cccagcaaat ccgcctggaa gcggaagaag aaaagctggc gcatctgccg     2220
ctggccaaaa ccgtctcagt ggaagaactg ctgcagtatg tggaactgca agatccggtt     2280
acccgtacgc agctgcgtgc gatggcggct aagaccgtct gcccgccgca caaagtggaa     2340
ctggaagctc tgctggaaaa gcaggcgtat aagaacaag tgctggcgaa acgcctgacc     2400
atgctggaac tgctggaaaa gtacccggcc tgtgaaatga gttctctga atttatcgca     2460 ctgctgccgt ctatccgtcc gcgttattac agtattagtt cctcaccgcg tgtggatgaa     2520
aaacaggcca gtatcaccgt ttctgttgtc agtggcgaag catggtctgg ctatggtgaa     2580
tacaagggta tcgcaagtaa ctacctggct gaactgcagg aaggcgatac cattacgtgc     2640
tttatctcta cgccgcaaag tgaatttacc ctgccgaaag accggaaac gccgctgatc     2700 atggttggcc cgggcaccgg tgtcgcaccg tttcgtggtt tcgtgcaggc acgcaagcaa     2760
ctgaaagaac agggccaatc cctgggtgaa gcgcatctgt attttggctg tcgctcaccg     2820
cacgaagatt atctgtacca ggaagaactg gaaaacgcgc aatccgaagg tattatcacg     2880
ctgcataccg ccttctcacg tatgccgaat cagccgaaaa cctacgtcca gcacgtgatg     2940
```

-continued

```
gaacaagatg gcaaaaagct gattgaactg ctggaccagg gtgcgcattt ttatatctgc   3000
ggtgatggca gccaaatggc accggcagtg aagcaaccc tgatgaaatc ctacgcagat    3060
gttcaccagg tctcagaagc agacgctcgt ctgtggctgc agcaactgga agaaaagggc    3120
cgctatgcga agatgtttg ggccggttaa                                      3150
```

```
<210> SEQ ID NO 45
<211> LENGTH: 396
<212> TYPE: PRT
<213> ORGANISM: Pleurotus sapidus

<400> SEQUENCE: 45

Met Arg Tyr Gly Cys Ala Ala Val Ala Leu Phe Tyr Leu Thr Ala Met
1               5                   10                  15

Gly Lys Leu His Pro Leu Ala Ile Ile Pro Asp Tyr Lys Gly Ser Met
            20                  25                  30

Ala Ala Ser Val Thr Ile Phe Asn Lys Arg Thr Asn Pro Leu Asp Ile
        35                  40                  45

Ser Val Asn Gln Ala Asn Asp Trp Pro Trp Arg Tyr Ala Lys Thr Cys
    50                  55                  60

Val Leu Ser Ser Asp Trp Ala Leu His Glu Met Ile Ile His Leu Asn
65                  70                  75                  80

Asn Thr His Leu Val Glu Glu Ala Val Ile Val Ala Ala Gln Arg Lys
                85                  90                  95

Leu Ser Pro Ser His Ile Val Phe Arg Leu Leu Glu Pro His Trp Val
            100                 105                 110

Val Thr Leu Ser Leu Asn Ala Leu Ala Arg Ser Val Leu Ile Pro Glu
        115                 120                 125

Val Ile Val Pro Ile Ala Gly Phe Ser Ala Pro His Ile Phe Gln Phe
    130                 135                 140

Ile Arg Glu Ser Phe Thr Asn Phe Asp Trp Lys Ser Leu Tyr Val Pro
145                 150                 155                 160

Ala Asp Leu Glu Ser Arg Gly Phe Pro Val Asp Gln Leu Asn Ser Pro
                165                 170                 175

Lys Phe His Asn Tyr Ala Tyr Ala Arg Asp Ile Asn Asp Met Trp Thr
            180                 185                 190

Thr Leu Lys Lys Phe Val Ser Ser Val Leu Gln Asp Ala Gln Tyr Tyr
        195                 200                 205

Pro Asp Asp Ala Ser Val Ala Gly Asp Thr Gln Ile Gln Ala Trp Cys
    210                 215                 220

Asp Glu Met Arg Ser Gly Met Gly Ala Gly Met Thr Asn Phe Pro Glu
225                 230                 235                 240

Ser Ile Thr Thr Val Asp Asp Leu Val Asn Met Val Thr Met Cys Ile
                245                 250                 255

His Ile Ala Ala Pro Gln His Thr Ala Val Asn Tyr Leu Gln Gln Tyr
            260                 265                 270

Tyr Gln Thr Phe Val Ser Asn Lys Pro Ser Ala Leu Phe Ser Pro Leu
        275                 280                 285

Pro Thr Ser Ile Ala Gln Leu Gln Lys Tyr Thr Glu Ser Asp Leu Met
    290                 295                 300

Ala Ala Leu Pro Leu Asn Ala Lys Arg Gln Trp Leu Leu Met Ala Gln
305                 310                 315                 320

Ile Pro Tyr Leu Leu Ser Met Gln Val Gln Glu Asp Glu Asn Ile Val
                325                 330                 335
```

```
Thr Tyr Ala Ala Asn Ala Ser Thr Asp Lys Asp Pro Ile Ile Ala Ser
                340                 345                 350

Ala Gly Arg Gln Leu Ala Ala Asp Leu Lys Lys Leu Ala Ala Val Phe
            355                 360                 365

Leu Val Asn Ser Ala Gln Leu Asp Asp Gln Asn Thr Pro Tyr Asp Val
        370                 375                 380

Leu Ala Pro Glu Gln Leu Ala Asn Ala Ile Val Ile
385                 390                 395

<210> SEQ ID NO 46
<211> LENGTH: 1191
<212> TYPE: DNA
<213> ORGANISM: Pleurotus sapidus

<400> SEQUENCE: 46
atgcgttatg gctgtgctgc tgtggctctg ttctatctga ccgctatggg caaactgcac      60
ccgctggcta ttatcccgga ctacaagggt agcatggcgg cctctgtcac cattttttaac    120 aaacgtacga atccgctgga tatcagcgtt aaccaggcaa atgactggcc gtggcgctat     180
gctaagacgt gcgtgctgag cagcgattgg gcgctgcatg aaatgattat ccacctgaac     240
aatacccatc tggtggaaga agccgtcatt gtggcagctc agcgtaaaact gtcaccgtcg    300 cacatcgttt ttcgcctgct ggaaccgcat tgggtggtta ccctgtcgct gaacgcactg     360
gctcgtagcg tgctgatccc ggaagttatt gtcccgatcg cgggtttctc tgccccgcac    420 attttttcagt tcatccgcga atcttttacc aatttcgatt ggaaaagtct gtacgtcccg    480
gcggacctgg aatcgcgtgg ctttccggtg atcagctga acagcccgaa gttccataat     540
tatgcgtacg cccgcgatat caacgacatg tggaccacgc tgaaaaagtt tgtgagttcc    600
gttctgcagg atgcccaata ttacccggat gacgcaagtg tggctggtga tacgcagatt    660
caagcatggt gcgacgaaat gcgttccggc atgggtgcgg gcatgaccaa cttcccggaa    720
tcaatcacca cggttgatga cctggtcaat atggtgacca tgtgtattca catcgcggcc    780
ccgcagcata cggcggttaa ctatctgcag caatactacc aaaaccttcgt cagtaacaag   840 ccgtccgcac tgttctcacc gctgccgacc tctattgctc agctgcaaaa atacacggaa    900
agtgatctga tggcagctct gccgctgaac gcgaagcgtc agtggctgct gatggcccaa    960
attccgtatc tgctgtcgat gcaggtgcaa gaagatgaaa acatcgttac ctacgcggcc  1020
aatgcgtcca cggataaaga cccgattatc gcatcagctg gccgccagct ggcagctgac  1080
ctgaaaaagc tggcggccgt ttttctggtc aactcagccc agctggatga ccaaaatacc  1140
ccgtatgatg tgctggcacc ggaacagctg gcgaatgcca ttgttatcta a            1191

<210> SEQ ID NO 47
<211> LENGTH: 640
<212> TYPE: PRT
<213> ORGANISM: Pleurotus ostreatus

<400> SEQUENCE: 47

Met Ala Pro Thr Met Ser Leu Ser Arg Ser Ala Leu Lys Asn Val His
1               5                   10                  15

Leu Pro Tyr Met Val Gln His Pro Glu Pro Thr Asp Cys Ser Thr Ala
            20                  25                  30

Met Lys His Ala Ala Glu Gly Tyr Asp Arg Ala Arg Gln Met Ile Ala
        35                  40                  45

Phe Leu Phe Asp Ile Leu Asp Tyr Glu Ser Ser Val Pro Gln Lys Phe
    50                  55                  60
```

Thr Pro Glu Glu Lys Lys Glu Lys Tyr Thr Trp Ser His Ser Asp Lys
65                  70                  75                  80

Phe Pro Pro His Leu Ala Ile Ile Pro Glu Asp Ile Asp Val Pro Ala
                85                  90                  95

Tyr Ile Ile Phe Ser Ile Val Arg Leu Val Gln Thr Leu Ser Ile Met
            100                 105                 110

Ser Gly Ile Gln Cys Asn Glu Arg Leu Ala Pro Gly Pro Glu Gln Asn
        115                 120                 125

Thr Met Glu Lys Leu Thr Lys Trp Asn Ala Glu Arg His Lys Asn Gln
    130                 135                 140

Gly Trp Val Lys Asp Met Phe Asn Glu Pro Asn Ile Gly Leu Arg Asn
145                 150                 155                 160

Asp Trp Tyr Thr Asp Ala Val Phe Ala Gln Gln Phe Thr Gly Pro
                165                 170                 175

Asn Pro Thr Thr Ile Thr Leu Ala Ser Asp Thr Trp Met Lys Ala Phe
                180                 185                 190

Thr Glu Glu Ala Ala Ser Gln Gly Lys Arg Asp Leu Ile Ser Leu Phe
            195                 200                 205

Arg Ser Ala Pro Pro Asn Ser Phe Tyr Val Gln Asp Phe Ser Asp Phe
    210                 215                 220

Arg Ala Arg Met Gly Ala Lys Pro Asp Glu Glu Leu Cys Ala Thr Ser
225                 230                 235                 240

Asp Gly Gly Val Thr Arg Tyr Gly Cys Ala Ala Val Ala Leu Phe Tyr
                245                 250                 255

Leu Pro Pro Thr Gly Glu Leu His Pro Leu Ala Ile Val Pro Asp Tyr
            260                 265                 270

Lys Gly Ser Met Ala Ala Ser Ile Thr Leu Phe Asn Lys Arg Val Asp
            275                 280                 285

Pro Ser Asp Ala Ser Val Asp Gln Ala Asn Asp Trp Pro Trp Arg Tyr
    290                 295                 300

Ala Lys Thr Cys Val Leu Ser Ala Asp Trp Val Leu His Glu Met Ile
305                 310                 315                 320

Ile His Leu Asn Asn Thr His Leu Val Gln Glu Ala Val Ile Val Ala
                325                 330                 335

Val Gln Arg Thr Leu Pro Asp Ser His Ile Val Phe Arg Leu Leu Lys
            340                 345                 350

Pro His Trp Val Val Thr Leu Ser Leu Asn Ala Gln Ala Arg Ser Val
    355                 360                 365

Leu Ile Pro Glu Val Ile Val Pro Ile Ala Gly Phe Ser Glu Leu Arg
    370                 375                 380

Ile Phe Gln Phe Val Gly His Ala Phe Thr Asn Phe Asp Trp Lys Ala
385                 390                 395                 400

Leu Tyr Val Pro Thr Asp Leu Glu Phe Arg Gly Phe Pro Leu Asp Arg
                405                 410                 415

Leu Asp Asp Asp Lys Phe His Asn Tyr Ala Tyr Ala Lys Asp Ile Lys
                420                 425                 430

Asp Met Trp Met Ala Leu Arg Lys Phe Val Ser Ser Val Leu Lys Asp
            435                 440                 445

Gly Lys Tyr Tyr Pro Asp Ser Ala Val Ala Ala Asp Ala Gln Ile
            450                 455                 460

Gln Asp Trp Cys Asp Glu Met Arg Ser Glu Lys Gly Ala Gly Met Lys
465                 470                 475                 480

Lys Phe Pro Glu Ser Ile Ser Thr Leu Asp Asp Leu Ile Asp Met Val
                485                 490                 495

Thr Met Cys Ile His Ile Ala Ala Pro Gln His Thr Ala Val Asn Tyr
            500                 505                 510

Leu Gln Gln Tyr Tyr Gln Thr Phe Val Pro Asn Lys Pro Ser Ala Leu
        515                 520                 525

Phe Ser Pro Leu Pro Thr Leu Leu Ser Gln Leu Glu Ser Tyr Thr Glu
    530                 535                 540

Ser Asp Leu Met Ala Ala Leu Pro Leu Gly Ala Lys Gln Glu Trp Leu
545                 550                 555                 560

Leu Met Ala Gln Val Pro Tyr Leu Leu Ser Lys Glu Val Glu Gln Asp
                565                 570                 575

Gly Asn Ile Val Thr Tyr Ala Gly Thr Ala Ser Asn Asn Glu Asp Pro
            580                 585                 590

Ile Ile Ala Ala Ala Gly Lys Glu Leu Ser Ala Asp Leu Val Ile Leu
        595                 600                 605

Ala Gly Val Phe Leu Lys Asn Ser Glu Lys Leu Asp Asp Gln Asn Thr
    610                 615                 620

Ala Tyr Asn Val Leu Ala Pro Asp Gln Leu Ala Asn Ala Ile Val Ile
625                 630                 635                 640

<210> SEQ ID NO 48
<211> LENGTH: 1923
<212> TYPE: DNA
<213> ORGANISM: Pleurotus ostreatus

<400> SEQUENCE: 48
atggccccga cgatgtcact gtctcgctcc gcactgaaga atgtccacct gccgtatatg      60
gtccaacacc cggaaccgac cgattgcagc accgcgatga acacgcggc cgaaggttat     120 gatcgtgctc gccagatgat tgcgtttctg ttcgacatcc tggattacga aagctctgtt     180
ccgcaaaaat ttaccccgga agaaaagaaa gaaaaatata cgtggtcaca ctcggataag     240
ttcccgccgc atctggccat tatcccggaa gacattgatg tgccggcata cattatcttt     300
agcatcgttc gtctggtcca gaccctgagt attatgtccg gcatccaatg caacgaacgt     360
ctggcaccgg ggccggaaca gaatacgatg gaaaaactga cgaagtggaa cgcggaacgt     420
cataaaaatc aaggctgggt caaggatatg tttaacgaac cgaatattgg tctgcgcaac     480
gactggtata ccgatgctgt gttcgcgcag caattttttca cgggtccgaa tccgaccacg     540
attaccctgg cctctgatac gtggatgaaa gcatttaccg aagaagcagc tagtcagggc     600
aagcgtgacc tgatcagcct gtttcgctct gccccgccga actccttcta cgttcaggac     660
ttttcagatt tccgtgctcg catgggcgcg aaaccggacg aagaactgtg cgcgaccctc t     720 gatggcggtg ttacccgtta tggctgtgca gcagtcgcac tgttttacct gccgccgacc     780
ggtgaactgc atccgctggc cattgtgccg gattataaag cagtatggc agcttccatc     840 acgctgttca caagcgtgt ggacccgtca gatgcctcgg ttgaccaggc aaatgattgg     900
ccgtggcgct acgctaaaac ctgtgttctg tccgcggatt gggtcctgca tgaaatgatt     960
atccacctga caatacccca tctggtgcag gaagccgtca ttgtggcagt tcaacgtacg    1020
ctgccggatt cacacatcgt ttttcgcctg ctgaaaccgc attgggtggt tacccttgtcg    1080 ctgaatgccc aggcacgtag cgttctgatc ccggaagtca ttgtgccgat cgcgggcttc    1140
agtgaactgc gcatctttca gttcgttggt cacgcctttca ccaacttcga ctggaaagca    1200
ctgtatgtcc gacggatct ggaatttcgt ggtttcccgc tggaccgcct ggatgacgat    1260

-continued

```
aagttccata actatgctta cgcgaaggac attaaggata tgtggatggc cctgcgtaag      1320
ttcgtgagtt ccgttctgaa agatggcaag tattacccgg acgattcggc tgttgcagca      1380
gacgcgcaga ttcaagactg gtgcgatgaa atgcgcagcg aaaaaggcgc gggtatgaaa      1440
aagttcccgg aaagcatttc taccctggac gatctgatcg atatggtgac gatgtgtatt      1500
cacatcgcag ctccgcagca taccgccgtg aactatctgc agcaatatta ccaaacgttt      1560
gttccgaata accgtcagc actgttctcg ccgctgccga ccctgctgag ccagctggaa       1620
tcttacacgg aaagtgatct gatggcggcc ctgccgctgg gtgctaaaca ggaatggctg      1680
ctgatggcgc aagtgccgta tctgctgtct aaggaagtcg aacaggatgg caacattgtg      1740
acctacgccg gtacggcaag taacaatgaa gatccgatta tcgcagctgc gggcaaagaa      1800
ctgtccgctg acctggtcat cctggcgggt gtgtttctga aaaactcaga aaagctggac      1860
gatcagaaca ccgcctataa tgtcctggca ccggatcaac tggccaatgc aattgtgatc      1920
taa                                                                    1923
```

<210> SEQ ID NO 49
<211> LENGTH: 495
<212> TYPE: PRT
<213> ORGANISM: Cichorium intybus

<400> SEQUENCE: 49

```
Met Glu Ile Ser Ile Pro Thr Thr Leu Gly Leu Ala Val Ile Ile Phe
1               5                   10                  15

Ile Ile Phe Lys Leu Leu Thr Arg Thr Thr Ser Lys Lys Asn Leu Leu
            20                  25                  30

Pro Glu Pro Trp Arg Leu Pro Ile Ile Gly His Met His His Leu Ile
        35                  40                  45

Gly Thr Met Pro His Arg Gly Val Met Glu Leu Ala Arg Lys His Gly
    50                  55                  60

Ser Leu Met His Leu Gln Leu Gly Glu Val Ser Thr Ile Val Val Ser
65                  70                  75                  80

Ser Pro Arg Trp Ala Lys Glu Val Leu Thr Thr Tyr Asp Ile Thr Phe
                85                  90                  95

Ala Asn Arg Pro Glu Thr Leu Thr Gly Glu Ile Val Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Asn Lys Lys Val Lys Ser Phe
    130                 135                 140

Gln Ser Leu Arg Glu Glu Glu Cys Trp Asn Leu Val Lys Asp Ile Arg
145                 150                 155                 160

Ser Thr Gly Gln Gly Ser Pro Ile Asn Leu Ser Glu Asn Ile Phe Lys
                165                 170                 175

Met Ile Ala Thr Ile Leu Ser Arg Ala Ala Phe Gly Lys Gly Ile Lys
            180                 185                 190

Asp Gln Met Lys Phe Thr Glu Leu Val Lys Glu Ile Leu Arg Leu Thr
        195                 200                 205

Gly Gly Phe Asp Val Ala Asp Ile Phe Pro Ser Lys Lys Leu Leu His
    210                 215                 220

His Leu Ser Gly Lys Arg Ala Lys Leu Thr Asn Ile His Asn Lys Leu
225                 230                 235                 240

Asp Asn Leu Ile Asn Asn Ile Ile Ala Glu His Pro Gly Asn Arg Thr
                245                 250                 255
```

Ser Ser Ser Gln Glu Thr Leu Leu Asp Val Leu Leu Arg Leu Lys Glu
        260                 265                 270

Ser Ala Glu Phe Pro Leu Thr Ala Asp Asn Val Lys Ala Val Ile Leu
        275                 280                 285

Asp Met Phe Gly Ala Gly Thr Asp Thr Ser Ser Ala Thr Ile Glu Trp
290                 295                 300

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
                325                 330                 335

Asp Leu Gln Glu Leu Asn Tyr Leu Lys Leu Val Ile Lys Glu Thr Leu
        340                 345                 350

Arg Leu His Pro Pro Leu Pro Leu Val Met Pro Arg Glu Cys Arg Glu
        355                 360                 365

Pro Cys Val Leu Gly Gly Tyr Asp Ile Pro Ser Lys Thr Lys Leu Ile
        370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Thr Val Met
                405                 410                 415

Gly Ser Glu Tyr Glu Tyr Leu Pro Phe Gly Ala Gly Arg Arg Met Cys
        420                 425                 430

Pro Gly Ala Ala Leu Gly Leu Ala Asn Val Glu Leu Pro Leu Ala His
        435                 440                 445

Ile Leu Tyr Phe Asn Trp Lys Leu Pro Asn Gly Lys Thr Phe Glu Asp
        450                 455                 460

Leu Asp Met Thr Glu Ser Phe Gly Ala Thr Val Gln Arg Lys Thr Glu
465                 470                 475                 480

Leu Leu Leu Val Pro Thr Asp Phe Gln Thr Leu Thr Ala Ser Thr
                485                 490                 495

<210> SEQ ID NO 50
<211> LENGTH: 493
<212> TYPE: PRT
<213> ORGANISM: Cichorium intybus

<400> SEQUENCE: 50

Met Ala Leu Leu Leu Ala Val Phe Leu Ala Val Ile Ile Phe Ile Ile
1               5                   10                  15

Phe Lys Leu Leu Thr Arg Thr Thr Ser Lys Lys Asn Leu Leu Pro Glu
            20                  25                  30

Pro Trp Arg Leu Pro Ile Ile Gly His Met His His Leu Ile Gly Thr
        35                  40                  45

Met Pro His Arg Gly Val Met Glu Leu Ala Arg Lys His Gly Ser Leu
    50                  55                  60

Met His Leu Gln Leu Gly Glu Val Ser Thr Ile Val Val Ser Ser Pro
65                  70                  75                  80

Arg Trp Ala Lys Glu Val Leu Thr Thr Tyr Asp Ile Thr Phe Ala Asn
                85                  90                  95

Arg Pro Glu Thr Leu Thr Gly Glu Ile Val Ala Tyr Asn Thr Asp
            100                 105                 110

Ile Val Leu Ala Pro Tyr Gly Glu Tyr Trp Arg Gln Leu Arg Lys Leu
        115                 120                 125

Cys Thr Leu Glu Leu Leu Ser Asn Lys Lys Val Lys Ser Phe Gln Ser
    130                 135                 140

```
Leu Arg Glu Glu Glu Cys Trp Asn Leu Val Lys Asp Ile Arg Ser Thr
145                 150                 155                 160

Gly Gln Gly Ser Pro Ile Asn Leu Ser Glu Asn Ile Phe Lys Met Ile
            165                 170                 175

Ala Thr Ile Leu Ser Arg Ala Ala Phe Gly Lys Gly Ile Lys Asp Gln
            180                 185                 190

Met Lys Phe Thr Glu Leu Val Lys Glu Ile Leu Arg Leu Thr Gly Gly
            195                 200                 205

Phe Asp Val Ala Asp Ile Phe Pro Ser Lys Lys Leu Leu His His Leu
210                 215                 220

Ser Gly Lys Arg Ala Lys Leu Thr Asn Ile His Asn Lys Leu Asp Asn
225                 230                 235                 240

Leu Ile Asn Asn Ile Ile Ala Glu His Pro Gly Asn Arg Thr Ser Ser
                245                 250                 255

Ser Gln Glu Thr Leu Leu Asp Val Leu Leu Arg Leu Lys Glu Ser Ala
            260                 265                 270

Glu Phe Pro Leu Thr Ala Asp Asn Val Lys Ala Val Ile Leu Asp Met
            275                 280                 285

Phe Gly Ala Gly Thr Asp Thr Ser Ser Ala Thr Ile Glu Trp Ala Ile
290                 295                 300

Ser Glu Leu Ile Arg Cys Pro Arg Ala Met Glu Lys Val Gln Thr Glu
305                 310                 315                 320

Leu Arg Gln Ala Leu Asn Gly Lys Glu Arg Ile Gln Glu Glu Asp Leu
                325                 330                 335

Gln Glu Leu Asn Tyr Leu Lys Leu Val Ile Lys Glu Thr Leu Arg Leu
            340                 345                 350

His Pro Pro Leu Pro Leu Val Met Pro Arg Glu Cys Arg Glu Pro Cys
            355                 360                 365

Val Leu Gly Gly Tyr Asp Ile Pro Ser Lys Thr Lys Leu Ile Val Asn
370                 375                 380

Val Phe Ala Ile Asn Arg Asp Pro Glu Tyr Trp Lys Asp Ala Glu Thr
385                 390                 395                 400

Phe Met Pro Glu Arg Phe Glu Asn Ser Pro Ile Thr Val Met Gly Ser
                405                 410                 415

Glu Tyr Glu Tyr Leu Pro Phe Gly Ala Gly Arg Arg Met Cys Pro Gly
            420                 425                 430

Ala Ala Leu Gly Leu Ala Asn Val Glu Leu Pro Leu Ala His Ile Leu
            435                 440                 445

Tyr Phe Asn Trp Lys Leu Pro Asn Gly Lys Thr Phe Glu Asp Leu Asp
450                 455                 460

Met Thr Glu Ser Phe Gly Ala Thr Val Gln Arg Lys Thr Glu Leu Leu
465                 470                 475                 480

Leu Val Pro Thr Asp Phe Gln Thr Leu Thr Ala Ser Thr
            485                 490

<210> SEQ ID NO 51
<211> LENGTH: 1482
<212> TYPE: DNA
<213> ORGANISM: Cichorium intybus

<400> SEQUENCE: 51
atggctctgt tattagcagt ttttctggct gtcattatct ttatcatctt caaactgctg      60
acccgcacca cctcgaagaa aaacctgctg ccggaaccgt ggcgtctgcc gattatcggc     120
cacatgcatc acctgattgg caccatgccg caccgtggtg tgatggaact ggcgcgcaaa     180
```

```
catggctcac tgatgcacct gcagctgggt gaagtgagca ccatcgtggt tagctctccg    240
cgttgggcga aagaagttct gaccacgtat gatattaccg ttgccaaccg cccggaaacc    300
ctgacgggcg aaatcgtggc ataccataat acggacattg ttctggctcc gtatggtgaa    360
tactggcgtc agctgcgcaa actgtgcacc ctggaactgc tgagtaacaa aaaagtcaaa    420
tcttttcaaa gtctgcgtga agaagaatgt tggaatctgg tgaaagatat ccgctccacc    480
ggccagggtt caccgatcaa cctgtcggaa aacatcttca aaatgatcgc gacgatcctg    540
tctcgtgcgg cctttggcaa aggtattaaa gaccaaatga aattcaccga actggttaaa    600
gaaatcctgc gcctgacggg cggttttgat gtcgcagaca ttttcccgag taaaaaactg    660
ctgcatcacc tgtccggcaa acgtgctaaa ctgaccaaca tccataacaa actggataac    720
ctgatcaaca acattatcgc cgaacacccg ggtaatcgta ccagttcctc acaggaaacg    780
ctgctggatg ttctgctgcg cctgaaagaa agcgcagaat tccgctgac cgcggacaat    840
gttaaagccg tcattctgga tatgttcggt gcaggcaccg acacgtcgag cgcaaccatt    900
gaatgggcta tctctgaact gattcgttgc ccgcgcgcga tggaaaaagt gcagacggaa    960
ctgcgtcaag ccctgaacgg caaagaacgc atccaggaag aagatctgca agaactgaac   1020
tacctgaaac tggttatcaa agaaaccctg cgcctgcatc cgccgctgcc gctggtcatg   1080
ccgcgtgaat ccgcgaaacc gtgtgtgctg ggcggttatg atatcccgag caaaaccaaa   1140
ctgatcgtca acgtgtttgc aattaatcgt gacccgaat actggaaaga cgctgaaacc   1200
tttatgccgg aacgcttcga aaacagcccg attacggtta tgggttctga atatgaatac   1260
ctgccgtttg gtgcaggtcg tcgcatgtgt ccgggtgcag ctctgggtct ggcgaatgtc   1320
gaactgccgc tggcccacat cctgtattac ttcaactgga aactgccgaa tggcaaaacc   1380
tttgaagatc tggacatgac cgaatccttc ggtgcaacgg tgcaacgcaa aaccgaactg   1440
ctgctggtgc cgacggattt ccaaacgctg accgcatcaa cg                      1482
```

<210> SEQ ID NO 52
<211> LENGTH: 488
<212> TYPE: PRT
<213> ORGANISM: Helianthus annuus

<400> SEQUENCE: 52

```
Met Glu Val Ser Leu Thr Thr Ser Ile Ala Leu Ala Thr Ile Val Phe
1               5                   10                  15

Phe Leu Tyr Lys Leu Leu Thr Arg Pro Thr Ser Ser Lys Asn Arg Leu
            20                  25                  30

Pro Glu Pro Trp Arg Leu Pro Ile Ile Gly His Met His His Leu Ile
        35                  40                  45

Gly Thr Met Pro His Arg Gly Val Met Asp Leu Ala Arg Lys Tyr Gly
    50                  55                  60

Ser Leu Met His Leu Gln Leu Gly Glu Val Ser Ala Ile Val Val Ser
65                  70                  75                  80

Ser Pro Lys Trp Ala Lys Glu Ile Leu Thr Thr Tyr Asp Ile Pro Phe
                85                  90                  95

Ala Asn Arg Pro Glu Thr Leu Thr Gly Glu Ile Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Val Lys Lys Val Lys Ser Phe
    130                 135                 140
```

Gln Ser Leu Arg Glu Glu Cys Trp Asn Leu Val Gln Glu Ile Lys
145                 150                 155                 160

Ala Ser Gly Ser Gly Thr Pro Phe Asn Leu Ser Glu Gly Ile Phe Lys
                165                 170                 175

Val Ile Ala Thr Val Leu Ser Arg Ala Ala Phe Gly Lys Gly Ile Lys
            180                 185                 190

Asp Gln Lys Gln Phe Thr Glu Ile Val Lys Glu Ile Leu Arg Glu Thr
        195                 200                 205

Gly Gly Phe Asp Val Ala Asp Ile Phe Pro Ser Lys Lys Phe Leu His
210                 215                 220

His Leu Ser Gly Lys Arg Gly Arg Leu Thr Ser Ile His Asn Lys Leu
225                 230                 235                 240

Asp Ser Leu Ile Asn Asn Leu Val Ala Glu His Thr Val Ser Lys Ser
                245                 250                 255

Ser Lys Val Asn Glu Thr Leu Leu Asp Val Leu Leu Arg Leu Lys Asn
            260                 265                 270

Ser Glu Glu Phe Pro Leu Thr Ala Asp Asn Val Lys Ala Ile Ile Leu
        275                 280                 285

Asp Met Phe Gly Ala Gly Thr Asp Thr Ser Ser Ala Thr Val Glu Trp
290                 295                 300

Ala Ile Ser Glu Leu Ile Arg Cys Pro Arg Ala Met Glu Lys Val Gln
305                 310                 315                 320

Ala Glu Leu Arg Gln Ala Leu Asn Gly Lys Glu Arg Ile Lys Glu Glu
                325                 330                 335

Glu Ile Gln Asp Leu Pro Tyr Leu Asn Leu Val Ile Arg Glu Thr Leu
            340                 345                 350

Arg Leu His Pro Pro Leu Pro Leu Val Met Pro Arg Glu Cys Arg Gln
        355                 360                 365

Ala Met Asn Leu Ala Gly Tyr Asp Val Ala Asn Lys Thr Lys Leu Ile
370                 375                 380

Val Asn Val Phe Ala Ile Asn Arg Asp Pro Glu Tyr Trp Lys Asp Ala
385                 390                 395                 400

Glu Ser Phe Asn Pro Glu Arg Phe Glu Asn Ser Asn Thr Thr Ile Met
                405                 410                 415

Gly Ala Asp Tyr Glu Tyr Leu Pro Phe Gly Ala Gly Arg Arg Met Cys
            420                 425                 430

Pro Gly Ser Ala Leu Gly Leu Ala Asn Val Gln Leu Pro Leu Ala Asn
        435                 440                 445

Ile Leu Tyr Tyr Phe Lys Trp Lys Leu Pro Asn Gly Ala Ser His Asp
450                 455                 460

Gln Leu Asp Met Thr Glu Ser Phe Gly Ala Thr Val Gln Arg Lys Thr
465                 470                 475                 480

Glu Leu Met Leu Val Pro Ser Phe
                485

<210> SEQ ID NO 53
<211> LENGTH: 488
<212> TYPE: PRT
<213> ORGANISM: Helianthus annuus

<400> SEQUENCE: 53

Met Ala Leu Leu Leu Ala Val Phe Ile Ala Leu Ala Thr Ile Val Phe
1               5                   10                  15

Phe Leu Tyr Lys Leu Leu Thr Arg Pro Thr Ser Ser Lys Asn Arg Leu
                20                  25                  30

-continued

```
Pro Glu Pro Trp Arg Leu Pro Ile Ile Gly His Met His Leu Ile
         35                  40                  45

Gly Thr Met Pro His Arg Gly Val Met Asp Leu Ala Arg Lys Tyr Gly
 50                  55                  60

Ser Leu Met His Leu Gln Leu Gly Glu Val Ser Ala Ile Val Val Ser
 65                  70                  75                  80

Ser Pro Lys Trp Ala Lys Glu Ile Leu Thr Thr Tyr Asp Ile Pro Phe
                 85                  90                  95

Ala Asn Arg Pro Glu Thr Leu Thr Gly Glu Ile Ile Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Val Lys Lys Val Lys Ser Phe
130                 135                 140

Gln Ser Leu Arg Glu Glu Glu Cys Trp Asn Leu Val Gln Glu Ile Lys
145                 150                 155                 160

Ala Ser Gly Ser Gly Thr Pro Phe Asn Leu Ser Glu Gly Ile Phe Lys
                165                 170                 175

Val Ile Ala Thr Val Leu Ser Arg Ala Ala Phe Gly Lys Gly Ile Lys
            180                 185                 190

Asp Gln Lys Gln Phe Thr Glu Ile Val Lys Glu Ile Leu Arg Glu Thr
        195                 200                 205

Gly Gly Phe Asp Val Ala Asp Ile Phe Pro Ser Lys Lys Phe Leu His
210                 215                 220

His Leu Ser Gly Lys Arg Gly Arg Leu Thr Ser Ile His Asn Lys Leu
225                 230                 235                 240

Asp Ser Leu Ile Asn Asn Leu Val Ala Glu His Thr Val Ser Lys Ser
                245                 250                 255

Ser Lys Val Asn Glu Thr Leu Leu Asp Val Leu Leu Arg Leu Lys Asn
            260                 265                 270

Ser Glu Glu Phe Pro Leu Thr Ala Asp Asn Val Lys Ala Ile Ile Leu
        275                 280                 285

Asp Met Phe Gly Ala Gly Thr Asp Thr Ser Ser Ala Thr Val Glu Trp
290                 295                 300

Ala Ile Ser Glu Leu Ile Arg Cys Pro Arg Ala Met Glu Lys Val Gln
305                 310                 315                 320

Ala Glu Leu Arg Gln Ala Leu Asn Gly Lys Glu Arg Ile Lys Glu Glu
                325                 330                 335

Glu Ile Gln Asp Leu Pro Tyr Leu Asn Leu Val Ile Arg Glu Thr Leu
            340                 345                 350

Arg Leu His Pro Pro Leu Pro Leu Val Met Pro Arg Glu Cys Arg Gln
        355                 360                 365

Ala Met Asn Leu Ala Gly Tyr Asp Val Ala Asn Lys Thr Lys Leu Ile
370                 375                 380

Val Asn Val Phe Ala Ile Asn Arg Asp Pro Glu Tyr Trp Lys Asp Ala
385                 390                 395                 400

Glu Ser Phe Asn Pro Glu Arg Phe Glu Asn Ser Asn Thr Thr Ile Met
                405                 410                 415

Gly Ala Asp Tyr Glu Tyr Leu Pro Phe Gly Ala Gly Arg Arg Met Cys
            420                 425                 430

Pro Gly Ser Ala Leu Gly Leu Ala Asn Val Gln Leu Pro Leu Ala Asn
        435                 440                 445
```

Ile Leu Tyr Tyr Phe Lys Trp Lys Leu Pro Asn Gly Ala Ser His Asp
        450                 455                 460

Gln Leu Asp Met Thr Glu Ser Phe Gly Ala Thr Val Gln Arg Lys Thr
465                 470                 475                 480

Glu Leu Met Leu Val Pro Ser Phe
                485

<210> SEQ ID NO 54
<211> LENGTH: 1464
<212> TYPE: DNA
<213> ORGANISM: Helianthus annuus

<400> SEQUENCE: 54

```
atggctctgt tattagcagt tttcatcgcc ctggcaacca ttgtcttttt cctgtataaa      60
ctgctgaccc gtccgacctc atctaaaaac cgtctgccgg aaccgtggcg cctgccgatt     120
atcggccaca tgcatcacct gattggcacc atgccgcacc gtggtgtcat ggatctggca     180
cgcaaatatg gcagcctgat gcatctgcaa ctgggtgaag tttctgcgat tgtggttagc     240
tctccgaaat gggccaaaga aattctgacc acctatgata ttccgtttgc gaaccgcccg     300
gaaaccctga cgggcgaaat tatcgcatac acaataccg acattgtgct ggctccgtat      360
ggtgaatact ggcgtcaact gcgtaaactg tgcacgctgg aactgctgag tgttaaaaaa     420
gtcaaaagtt ccagagcct gcgtgaagaa gaatgttgga acctggttca agaaattaaa      480
gcgagcggca cggcacccc gtttaatctg agtgaaggta ttttcaaagt gattgcgacc      540
gtgctgagcc gtgcggcatt tggtaaaggt atcaaagatc agaaacaatt caccgaaatt     600
gtcaaagaaa tcctgcgcga acgggcggt tttgatgtgg cggacatctt ccgagcaaa       660 aaattcctgc atcacctgtc tggcaaacgt ggtcgcctga cctcaattca taacaaactg     720
gattcgctga tcaacaatct ggtcgccgaa cataccgtga gcaaaagcag caaagtgaat     780
gaaacgctgc tggatgtcct gctgcgtctg aaaaactcgg aagaatttcc gctgaccgca     840
gacaatgtga agctattat cctggatatg ttcggtgcag caccgatac cagcagcgca       900 acggtggaat gggccattag cgaactgatc cgttgcccgc gcgcaatgga aaaagttcag     960
gcagaactgc gtcaagctct gaacggcaaa gaacgcatta agaagaaga atccaggat      1020 ctgccgtatc tgaatctggt tattcgtgaa accctgcgtc tgcatccgcc gctgccgctg    1080
gtcatgccgc gtgaatgtcg ccaagcaatg aacctggctg gctatgacgt ggcaaataaa    1140
accaaactga tcgtcaatgt gtttgcgatt aaccgtgacc cggaatactg gaaagacgcg    1200
gaaagtttta acccggaacg ctttgaaaac agcaacacca cgattatggg tgcggattat    1260
gaatacctgc gtttggcgc cggtcgtcgc atgtgtccgg gcagcgcgct gggtctggcc     1320
aacgttcaac tgccgctggc caatatcctg tattacttca atggaaaact gccgaatggc    1380
gcctcacacg atcaactgga catgaccgaa tcgtttggtg caaccgtgca acgcaaaacg    1440
gaactgatgc tggttccgtc tttc                                           1464
```

<210> SEQ ID NO 55
<211> LENGTH: 504
<212> TYPE: PRT
<213> ORGANISM: Artificial Sequence
<220> FEATURE:
<223> OTHER INFORMATION: Synthetic - Engineered valencene oxidase

<400> SEQUENCE: 55

```
Met Ala Trp Glu Tyr Ala Leu Ile Gly Leu Val Val Gly Ile Ile Ile
1               5                   10                  15

Gly Ala Val Ala Ala Trp Tyr Leu Lys Ser Tyr Thr Ser Ala Arg Arg
            20                  25                  30

Ser Gln Ser Asn His Leu Pro Arg Val Pro Glu Val Pro Gly Val Pro
        35                  40                  45

Leu Leu Gly Asn Leu Leu Gln Leu Lys Glu Lys Pro Tyr Met Thr
    50                  55                  60

Phe Thr Arg Trp Ala Ala Thr Tyr Gly Pro Ile Tyr Ser Ile Lys Thr
65                  70                  75                  80

Gly Ala Thr Ser Met Val Val Ser Ser Asn Glu Ile Ala Lys Glu
                85                  90                  95

Ala Leu Val Thr Arg Phe Gln Ser Ile Ser Thr Arg Asn Leu Ser Lys
                100                 105                 110

Ala Leu Lys Val Leu Thr Ala Asp Lys Thr Met Val Ala Met Ser Asp
            115                 120                 125

Tyr Asp Asp Tyr His Lys Thr Val Lys Arg His Ile Leu Thr Ala Val
130                 135                 140

Leu Gly Pro Asn Ala Gln Lys Lys His Arg Ile His Arg Asp Ile Met
145                 150                 155                 160

Met Asp Asn Ile Ser Thr Gln Leu His Glu Phe Val Lys Asn Asn Pro
                165                 170                 175

Glu Gln Glu Glu Val Asp Leu Arg Lys Ile Phe Gln Ser Glu Leu Phe
            180                 185                 190

Gly Leu Ala Met Arg Gln Ala Leu Gly Lys Asp Val Glu Ser Leu Tyr
        195                 200                 205

Val Glu Asp Leu Lys Ile Thr Met Asn Arg Asp Glu Ile Phe Gln Val
    210                 215                 220

Leu Val Val Asp Pro Met Met Gly Ala Ile Asp Val Asp Trp Arg Asp
225                 230                 235                 240

Phe Phe Pro Tyr Leu Lys Trp Val Pro Asn Lys Lys Phe Glu Asn Thr
                245                 250                 255

Ile Gln Gln Met Tyr Ile Arg Arg Glu Ala Val Met Lys Ser Leu Ile
            260                 265                 270

Lys Glu His Lys Lys Arg Ile Ala Ser Gly Glu Lys Leu Asn Ser Tyr
        275                 280                 285

Ile Asp Tyr Leu Leu Ser Glu Ala Gln Thr Leu Thr Asp Gln Gln Leu
    290                 295                 300

Leu Met Ser Leu Trp Glu Pro Ile Ile Glu Ser Ser Asp Thr Thr Met
305                 310                 315                 320

Val Thr Thr Glu Trp Ala Met Tyr Glu Leu Ala Lys Asn Pro Lys Leu
                325                 330                 335

Gln Asp Arg Leu Tyr Arg Asp Ile Lys Ser Val Cys Gly Ser Glu Lys
            340                 345                 350

Ile Thr Glu Glu His Leu Ser Gln Leu Pro Tyr Ile Thr Ala Ile Phe
        355                 360                 365

His Glu Thr Leu Arg Arg His Ser Pro Val Pro Ile Ile Pro Leu Arg
    370                 375                 380

His Val His Glu Asp Thr Val Leu Gly Gly Tyr His Val Pro Ala Gly
385                 390                 395                 400

Thr Glu Leu Ala Val Asn Ile Tyr Gly Cys Asn Met Asp Lys Asn Val
                405                 410                 415
```

-continued

```
Trp Glu Asn Pro Glu Glu Trp Asn Pro Glu Arg Phe Met Lys Glu Asn
                420                 425                 430

Glu Thr Ile Asp Phe Gln Lys Thr Met Ala Phe Gly Gly Gly Lys Arg
            435                 440                 445

Val Cys Ala Gly Ser Leu Gln Ala Leu Leu Thr Ala Ser Ile Gly Ile
        450                 455                 460

Gly Arg Met Val Gln Glu Phe Glu Trp Lys Leu Lys Asp Met Thr Gln
465                 470                 475                 480

Glu Glu Val Asn Thr Ile Gly Leu Thr Thr Gln Met Leu Arg Pro Leu
                485                 490                 495

Arg Ala Ile Ile Lys Pro Arg Ile
                500
```

<210> SEQ ID NO 56
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 56

```
Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
            20                  25                  30

Arg Ser Gln Ser Asn His Leu Pro Arg Val Pro Glu Val Pro Gly Val
        35                  40                  45

Pro Leu Leu Gly Asn Leu Leu Gln Leu Lys Glu Lys Lys Pro Tyr Met
    50                  55                  60

Thr Phe Thr Arg Trp Ala Ala Thr Tyr Gly Pro Ile Tyr Ser Ile Lys
65                  70                  75                  80

Thr Gly Ala Thr Ser Val Val Val Ser Ser Asn Glu Ile Ala Lys
                85                  90                  95

Glu Ala Met Val Thr Arg Phe Gln Ser Ile Ser Thr Arg Asn Leu Ser
                100                 105                 110

Lys Ala Leu Lys Val Leu Thr Ala Asp Lys Thr Met Val Ala Met Ser
            115                 120                 125

Asp Tyr Asp Asp Tyr His Lys Thr Val Lys Arg His Ile Leu Thr Ala
        130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
        195                 200                 205

Tyr Val Glu Asp Leu Lys Ile Thr Met Asn Arg Asp Glu Ile Leu Gln
    210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270
```

```
Ile Lys Glu His Lys Lys Arg Ile Ala Ser Gly Glu Lys Leu Asn Ser
            275                 280                 285

Tyr Ile Asp Tyr Leu Leu Ser Glu Ala Gln Thr Leu Thr Asp Gln Gln
        290                 295                 300

Leu Leu Met Ser Leu Trp Glu Pro Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Leu Pro Leu
    370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
        435                 440                 445

Arg Val Cys Ala Gly Ser Leu Gln Ala Leu Leu Ile Ala Ser Ile Gly
    450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
            500                 505

<210> SEQ ID NO 57
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 57

Met Ala Trp Glu Tyr Ala Leu Ile Gly Leu Val Val Gly Ile Ile
1               5                   10                  15

Gly Ala Val Ala Met Arg Trp Tyr Leu Lys Ser Tyr Thr Ser Ala Arg
            20                  25                  30

Arg Ser Gln Ser Asn His Leu Pro Arg Val Pro Glu Val Pro Gly Val
        35                  40                  45

Pro Leu Leu Gly Asn Leu Leu Gln Leu Lys Glu Lys Pro Tyr Met
    50                  55                  60

Thr Phe Thr Lys Trp Ala Ala Thr Tyr Gly Pro Ile Tyr Ser Ile Lys
65                  70                  75                  80

Thr Gly Ala Thr Ser Met Val Val Ser Ser Asn Glu Ile Ala Lys
                85                  90                  95

Glu Ala Met Val Thr Arg Phe Gln Ser Ile Ser Thr Arg Asn Leu Ser
            100                 105                 110

Lys Ala Leu Lys Val Leu Thr Ala Asp Lys Gln Met Val Ala Met Ser
        115                 120                 125
```

```
Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
        195                 200                 205

Tyr Val Glu Asp Leu Lys Ile Thr Met Asn Arg Asp Glu Ile Leu Gln
210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu His Lys Lys Arg Ile Ala Ser Gly Glu Lys Leu Asn Ser
        275                 280                 285

Tyr Ile Asp Tyr Leu Leu Ser Glu Ala Gln Thr Leu Thr Asp Gln Gln
290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Leu Pro Leu
370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
        435                 440                 445

Arg Val Cys Ala Gly Ser Leu Gln Ala Leu Leu Ile Ala Ser Ile Gly
450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
            500                 505

<210> SEQ ID NO 58
<211> LENGTH: 505
<212> TYPE: PRT
<213> ORGANISM: Artificial Sequence
<220> FEATURE:
<223> OTHER INFORMATION: Synthetic - Engineered valencene oxidase
```

<400> SEQUENCE: 58

```
Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
            20                  25                  30

Arg Ser Gln Ser Asn His Leu Pro Arg Val Pro Glu Val Pro Gly Val
        35                  40                  45

Pro Leu Leu Gly Asn Leu Leu Gln Leu Lys Glu Lys Lys Pro Tyr Met
    50                  55                  60

Thr Phe Thr Arg Trp Ala Ala Thr Tyr Gly Pro Ile Tyr Ser Ile Lys
65                  70                  75                  80

Thr Gly Ala Thr Ser Val Val Val Ser Ser Asn Glu Ile Ala Lys
                85                  90                  95

Glu Ala Met Val Thr Arg Phe Gln Ser Ile Ser Thr Arg Asn Leu Ser
            100                 105                 110

Lys Ala Leu Lys Val Leu Thr Ala Asp Lys Gln Met Val Ala Met Ser
        115                 120                 125

Asp Tyr Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
        195                 200                 205

Tyr Val Glu Asp Leu Lys Ile Thr Met Asn Arg Asp Glu Ile Leu Gln
    210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu His Lys Lys Arg Ile Ala Ser Gly Glu Lys Leu Asn Ser
        275                 280                 285

Tyr Ile Asp Tyr Leu Leu Ser Glu Ala Gln Thr Leu Thr Asp Gln Gln
    290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Leu Pro Leu
    370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415
```

Val Trp Glu Asn Pro Glu Glu Trp Asn Pro Glu Arg Phe Met Lys Glu
                420                 425                 430

Asn Glu Thr Ile Asp Phe Gln Lys Thr Met Ala Phe Gly Gly Gly Lys
            435                 440                 445

Arg Val Cys Ala Gly Ser Leu Gln Ala Leu Leu Ile Ala Ser Ile Gly
        450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
                500                 505

<210> SEQ ID NO 59
<211> LENGTH: 504
<212> TYPE: PRT
<213> ORGANISM: Artificial Sequence
<220> FEATURE:
<223> OTHER INFORMATION: Synthetic - Engineered valencene oxidase

<400> SEQUENCE: 59

Met Ala Trp Glu Tyr Ala Leu Ile Gly Leu Val Val Gly Ile Ile Ile
1               5                   10                  15

Gly Ala Val Ala Ala Trp Tyr Leu Lys Ser Tyr Thr Ser Ala Arg Arg
            20                  25                  30

Ser Gln Ser Asn His Leu Pro Arg Val Pro Glu Val Pro Gly Val Pro
        35                  40                  45

Leu Leu Gly Asn Leu Leu Gln Leu Lys Glu Lys Lys Pro Tyr Met Thr
    50                  55                  60

Phe Thr Lys Trp Ala Ala Thr Tyr Gly Pro Ile Tyr Ser Ile Lys Thr
65                  70                  75                  80

Gly Ala Thr Ser Met Val Val Ser Ser Asn Glu Ile Ala Lys Glu
                85                  90                  95

Ala Met Val Thr Arg Phe Gln Ser Ile Ser Thr Arg Asn Leu Ser Lys
                100                 105                 110

Ala Leu Lys Val Leu Thr Ala Asp Lys Gln Met Val Ala Met Ser Asp
            115                 120                 125

Tyr Asp Asp Tyr His Lys Thr Val Lys Arg His Ile Leu Thr Ala Val
130                 135                 140

Leu Gly Pro Asn Ala Gln Lys Lys His Arg Ile His Arg Asp Ile Met
145                 150                 155                 160

Met Asp Asn Ile Ser Thr Gln Leu His Glu Phe Val Lys Asn Pro
                165                 170                 175

Glu Gln Glu Glu Val Asp Leu Arg Lys Ile Phe Gln Ser Glu Leu Phe
                180                 185                 190

Gly Leu Ala Met Arg Gln Ala Leu Gly Lys Asp Val Glu Ser Leu Tyr
            195                 200                 205

Val Glu Asp Leu Lys Ile Thr Met Asn Arg Asp Glu Ile Leu Gln Val
    210                 215                 220

Leu Val Val Asp Pro Met Met Gly Ala Ile Asp Val Asp Trp Arg Asp
225                 230                 235                 240

Phe Phe Pro Tyr Leu Lys Trp Val Pro Asn Lys Lys Phe Glu Asn Thr
                245                 250                 255

Ile Gln Gln Met Tyr Ile Arg Arg Glu Ala Val Met Lys Ser Leu Ile
            260                 265                 270

```
Lys Glu His Lys Lys Arg Ile Ala Ser Gly Glu Lys Leu Asn Ser Tyr
            275                 280                 285

Ile Asp Tyr Leu Leu Ser Glu Ala Gln Thr Leu Thr Asp Gln Gln Leu
    290                 295                 300

Leu Met Ser Leu Trp Glu Pro Ile Ile Glu Ser Ser Asp Thr Thr Met
305                 310                 315                 320

Val Thr Thr Glu Trp Ala Met Tyr Glu Leu Ala Lys Asn Pro Lys Leu
                325                 330                 335

Gln Asp Arg Leu Tyr Arg Asp Ile Lys Ser Val Cys Gly Ser Glu Lys
            340                 345                 350

Ile Thr Glu Glu His Leu Ser Gln Leu Pro Tyr Ile Thr Ala Ile Phe
        355                 360                 365

His Glu Thr Leu Arg Lys His Ser Pro Val Pro Ile Leu Pro Leu Arg
    370                 375                 380

His Val His Glu Asp Thr Val Leu Gly Gly Tyr His Val Pro Ala Gly
385                 390                 395                 400

Thr Glu Leu Ala Val Asn Ile Tyr Gly Cys Asn Met Asp Lys Asn Val
                405                 410                 415

Trp Glu Asn Pro Glu Glu Trp Asn Pro Glu Arg Phe Met Lys Glu Asn
            420                 425                 430

Glu Thr Ile Asp Phe Gln Lys Thr Met Ala Phe Gly Gly Gly Lys Arg
        435                 440                 445

Val Cys Ala Gly Ser Leu Gln Ala Leu Leu Ile Ala Ser Ile Gly Ile
    450                 455                 460

Gly Arg Met Val Gln Glu Phe Glu Trp Lys Leu Lys Asp Met Thr Gln
465                 470                 475                 480

Glu Glu Val Asn Thr Ile Gly Leu Thr Asn Gln Met Leu Arg Pro Leu
                485                 490                 495

Arg Ala Ile Ile Lys Pro Arg Ile
            500

<210> SEQ ID NO 60
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 60

Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
            20                  25                  30

Arg Ser Gln Ser Asn His Leu Pro Arg Val Pro Glu Val Pro Gly Val
        35                  40                  45

Pro Leu Leu Gly Asn Leu Leu Gln Leu Lys Glu Lys Pro Tyr Met
    50                  55                  60

Thr Phe Thr Lys Trp Ala Ala Thr Tyr Gly Pro Ile Tyr Ser Ile Lys
65                  70                  75                  80

Thr Gly Ala Thr Ser Val Val Val Ser Ser Asn Glu Ile Ala Lys
                85                  90                  95

Glu Ala Met Val Thr Arg Phe Gln Ser Ile Ser Thr Arg Asn Leu Ser
            100                 105                 110

Lys Ala Leu Lys Val Leu Thr Ala Asp Lys Thr Met Val Ala Met Ser
        115                 120                 125
```

Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
        195                 200                 205

Tyr Val Glu Asp Leu Lys Ile Thr Met Asn Arg Asp Glu Ile Leu Gln
210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu His Lys Lys Arg Ile Ala Ser Gly Glu Lys Leu Asn Ser
        275                 280                 285

Tyr Ile Asp Tyr Leu Leu Ser Glu Ala Gln Thr Leu Thr Asp Gln Gln
290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Ile Pro Leu
370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
        435                 440                 445

Arg Val Cys Ala Gly Ser Leu Gln Ala Leu Leu Ile Ala Ser Ile Gly
450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
            500                 505

<210> SEQ ID NO 61
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 61

```
Met Ala Trp Glu Tyr Ala Leu Ile Gly Leu Val Val Gly Ile Ile Ile
1               5                   10                  15
Gly Ala Val Ala Met Arg Trp Tyr Leu Lys Ser Tyr Thr Ser Ala Arg
                20                  25                  30
Arg Ser Gln Ser Asn His Leu Pro Arg Val Pro Glu Val Pro Gly Val
            35                  40                  45
Pro Leu Leu Gly Asn Leu Leu Gln Leu Lys Glu Lys Lys Pro Tyr Met
        50                  55                  60
Thr Phe Thr Lys Trp Ala Ala Thr Tyr Gly Pro Ile Tyr Ser Ile Lys
65                  70                  75                  80
Thr Gly Ala Thr Ser Val Val Val Ser Ser Asn Glu Ile Ala Lys
                85                  90                  95
Glu Ala Leu Val Thr Arg Phe Gln Ser Ile Ser Thr Arg Asn Leu Ser
                100                 105                 110
Lys Ala Leu Lys Val Leu Thr Ala Asp Lys Gln Met Val Ala Met Ser
            115                 120                 125
Asp Tyr Asp Asp Tyr His Lys Thr Val Lys Arg His Ile Leu Thr Ala
130                 135                 140
Val Leu Gly Pro Asn Ala Gln Lys Lys His Arg Ile His Arg Asp Ile
145                 150                 155                 160
Met Met Asp Asn Ile Ser Thr Gln Leu His Glu Phe Val Lys Asn Asn
                165                 170                 175
Pro Glu Gln Glu Glu Val Asp Leu Arg Lys Ile Phe Gln Ser Glu Leu
            180                 185                 190
Phe Gly Leu Ala Met Arg Gln Ala Leu Gly Lys Asp Val Glu Ser Leu
        195                 200                 205
Tyr Val Glu Asp Leu Lys Ile Thr Met Asn Arg Asp Glu Ile Leu Gln
210                 215                 220
Val Leu Val Val Asp Pro Met Met Gly Ala Ile Asp Val Asp Trp Arg
225                 230                 235                 240
Asp Phe Phe Pro Tyr Leu Lys Trp Val Pro Asn Lys Lys Phe Glu Asn
                245                 250                 255
Thr Ile Gln Gln Met Tyr Ile Arg Arg Glu Ala Val Met Lys Ser Leu
            260                 265                 270
Ile Lys Glu Gln Lys Lys Arg Ile Ala Ser Gly Glu Lys Leu Asn Ser
        275                 280                 285
Tyr Ile Asp Tyr Leu Leu Ser Glu Ala Gln Thr Leu Thr Asp Gln Gln
290                 295                 300
Leu Leu Met Ser Leu Trp Glu Pro Ile Ile Glu Ser Ser Asp Thr Thr
305                 310                 315                 320
Met Val Thr Thr Glu Trp Ala Met Tyr Glu Leu Ala Lys Asn Pro Lys
                325                 330                 335
Leu Gln Asp Arg Leu Tyr Arg Asp Ile Lys Ser Val Cys Gly Ser Glu
            340                 345                 350
Lys Ile Thr Glu Glu His Leu Ser Gln Leu Pro Tyr Ile Thr Ala Ile
        355                 360                 365
Phe His Glu Thr Leu Arg Lys His Ser Pro Val Pro Ile Leu Pro Leu
370                 375                 380
Arg His Val His Glu Asp Thr Val Leu Gly Gly Tyr His Val Pro Ala
385                 390                 395                 400
Gly Thr Glu Leu Ala Val Asn Ile Tyr Gly Cys Asn Met Asp Lys Asn
                405                 410                 415
```

```
Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
        435                 440                 445

Arg Val Cys Ala Gly Ser Leu Gln Ala Leu Leu Ile Ala Ser Ile Gly
    450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
                500                 505

<210> SEQ ID NO 62
<211> LENGTH: 710
<212> TYPE: PRT
<213> ORGANISM: Stevia rebaudiana

<400> SEQUENCE: 62

Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
            20                  25                  30

Asp Pro Thr Thr Leu Pro Ala Leu Lys Met Leu Val Glu Asn Arg Glu
        35                  40                  45

Leu Leu Thr Leu Phe Thr Thr Ser Phe Ala Val Leu Ile Gly Cys Leu
    50                  55                  60

Val Phe Leu Met Trp Arg Arg Ser Ser Lys Lys Leu Val Gln Asp
65              70                  75                  80

Pro Val Pro Gln Val Ile Val Lys Lys Glu Lys Glu Ser Glu
                85                  90                  95

Val Asp Asp Gly Lys Lys Val Ser Ile Phe Tyr Gly Thr Gln Thr
                100                 105                 110

Gly Thr Ala Glu Gly Phe Ala Lys Ala Leu Val Glu Glu Ala Lys Val
            115                 120                 125

Arg Tyr Glu Lys Thr Ser Phe Lys Val Ile Asp Leu Asp Asp Tyr Ala
    130                 135                 140

Ala Asp Asp Asp Glu Tyr Glu Glu Lys Leu Lys Lys Glu Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Asp Lys Gly Glu Trp
            180                 185                 190

Leu Lys Lys Leu Gln Tyr Gly Val Phe Gly Leu Gly Asn Arg Gln Tyr
        195                 200                 205

Glu His Phe Asn Lys Ile Ala Ile Val Val Asp Asp Lys Leu Thr Glu
    210                 215                 220

Met Gly Ala Lys Arg Leu Val Pro Val Gly Leu Gly Asp Asp Asp Gln
225                 230                 235                 240

Cys Ile Glu Asp Asp Phe Thr Ala Trp Lys Glu Leu Val Trp Pro Glu
                245                 250                 255

Leu Asp Gln Leu Leu Arg Asp Glu Asp Asp Thr Ser Val Thr Thr Pro
            260                 265                 270

Tyr Thr Ala Ala Val Leu Glu Tyr Arg Val Val Tyr His Asp Lys Pro
        275                 280                 285
```

```
Ala Asp Ser Tyr Ala Glu Asp Gln Thr His Thr Asn Gly His Val Val
    290                 295                 300

His Asp Ala Gln His Pro Ser Arg Ser Asn Val Ala Phe Lys Lys Glu
305                 310                 315                 320

Leu His Thr Ser Gln Ser Asp Arg Ser Cys Thr His Leu Glu Phe Asp
                325                 330                 335

Ile Ser His Thr Gly Leu Ser Tyr Glu Thr Gly Asp His Val Gly Val
            340                 345                 350

Tyr Ser Glu Asn Leu Ser Glu Val Val Asp Glu Ala Leu Lys Leu Leu
        355                 360                 365

Gly Leu Ser Pro Asp Thr Tyr Phe Ser Val His Ala Asp Lys Glu Asp
370                 375                 380

Gly Thr Pro Ile Gly Gly Ala Ser Leu Pro Pro Phe Pro Pro Cys
385                 390                 395                 400

Thr Leu Arg Asp Ala Leu Thr Arg Tyr Ala Asp Val Leu Ser Ser Pro
                405                 410                 415

Lys Lys Val Ala Leu Leu Ala Leu Ala Ala His Ala Ser Asp Pro Ser
            420                 425                 430

Glu Ala Asp Arg Leu Lys Phe Leu Ala Ser Pro Ala Gly Lys Asp Glu
        435                 440                 445

Tyr Ala Gln Trp Ile Val Ala Asn Gln Arg Ser Leu Leu Glu Val Met
    450                 455                 460

Gln Ser Phe Pro Ser Ala Lys Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
            500                 505                 510

Thr Thr Pro Ala Gly Arg Ile His Arg Gly Leu Cys Ser Thr Trp Met
        515                 520                 525

Lys Asn Ala Val Pro Leu Thr Glu Ser Pro Asp Cys Ser Gln Ala Ser
530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Phe Phe Gly Cys Arg Asn Arg Lys Val Asp Phe Ile
        595                 600                 605

Tyr Glu Asp Glu Leu Asn Asn Phe Val Glu Thr Gly Ala Leu Ser Glu
    610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
            660                 665                 670

Val His Arg Thr Leu His Thr Ile Val Gln Glu Gln Gly Ser Leu Asp
        675                 680                 685
```

Ser Ser Lys Ala Glu Leu Tyr Val Lys Asn Leu Gln Met Ser Gly Arg
    690                 695                 700

Tyr Leu Arg Asp Val Trp
705                 710

<210> SEQ ID NO 63
<211> LENGTH: 2133
<212> TYPE: DNA
<213> ORGANISM: Stevia rebaudiana

<400> SEQUENCE: 63

| | | | | |
|---|---|---|---|---|
| atgcagagcg | attctgttaa | agtatccccg | ttcgacctgg | tctctgcggc | tatgaacggc | 60 |
| aaagcaatgg | agaaactgaa | cgcgagcgaa | tctgaagatc | caaccaccct | gccggcactg | 120 |
| aaaatgctgg | tagaaaaccg | tgaactgctg | actctgttca | ccacctcctt | cgccgttctg | 180 |
| attggttgcc | tggtcttcct | gatgtggcgc | cgttcctctt | ccaagaagct | ggtacaggac | 240 |
| ccggttcctc | aggtgatcgt | cgttaaaaag | aaagagaagg | aaagcgaagt | cgatgacggc | 300 |
| aaaaagaagg | tttccatttt | ctacggtact | cagaccggca | ccgctgaggg | ttttgccaaa | 360 |
| gcactggttg | aagaggcaaa | agtgcgttac | gaaaaaactt | ccttcaaagt | gattgacctg | 420 |
| gacgactatg | ctgcggatga | tgatgaatac | gaggaaaaac | tgaaaaaaga | agcctggcc | 480 |
| ttcttcttcc | tggcaaccta | tggcgatggt | gaaccgaccg | acaacgcggc | gaacttctac | 540 |
| aaatggttta | ccgaaggcga | cgacaaaggt | gaatggctga | agaaactgca | gtatggtgtt | 600 |
| ttcggtctgg | gcaatcgcca | gtacgaacat | tttaacaaaa | tcgcaatcgt | tgttgatgac | 660 |
| aaactgactg | aaatgggtgc | gaaacgtctg | gtgccggttg | gctgggtga | cgatgatcaa | 720 |
| tgcatcgaag | atgacttcac | cgcatggaaa | gaactggttt | ggccggaact | ggatcagctg | 780 |
| ctgcgcgacg | aagacgacac | ttccgtgacc | accccgtata | ccgctgcagt | gctggagtac | 840 |
| cgtgttgttt | accacgataa | accggcggac | tcttacgccg | aagatcagac | tcacactaac | 900 |
| ggtcacgtcg | tacatgacgc | acagcacccg | tctcgtagca | atgttgcgtt | taagaaagag | 960 |
| ctgcacacga | gccagtccga | ccgctcttgt | acgcacctgg | agttcgatat | ctcccacacc | 1020 |
| ggtctgtcct | atgaaaccgg | tgaccatgtt | ggcgtttaca | gcgaaaacct | gagcgaggta | 1080 |
| gttgatgaag | cgctgaaact | gctgggcctg | tctccagaca | cctactttag | cgtgcatgct | 1140 |
| gacaaggaag | atggtactcc | gattggcggc | gcttccctgc | cgccaccgtt | ccaccttgc | 1200 |
| actctgcgtg | atgctctgac | tcgttacgct | gatgttctgt | ctagcccgaa | aaaggttgcg | 1260 |
| ctgctggcgc | tggccgcaca | tgcttctgac | ccgtctgaag | ctgaccgtct | gaaattcctg | 1320 |
| gcgtctccgg | ccggcaaaga | cgaatacgcg | cagtggattg | tcgctaacca | gcgctctctg | 1380 |
| ctggaagtga | tgcagtcctt | cccgtctgcc | aaaccgccac | tgggcgtgtt | tttcgcagct | 1440 |
| gtggctccgc | gcctgcagcc | gcgctactat | tctatctcta | gctccccgaa | aatgagcccg | 1500 |
| aaccgcatcc | acgttacttg | tgctctggtt | tacgaaacca | ccctgcgggc | cgtatccac | 1560 |
| cgtggtctgt | gctctacgtg | gatgaaaaat | gccgtgccgc | tgaccgaatc | cccggactgc | 1620 |
| tctcaggcgt | ccatcttcgt | gcgtacctct | aacttccgtc | tgccggtgga | cccgaaagtt | 1680 |
| cctgttatca | tgatcggtcc | tggcacgggt | ctggcccgt | tcgtggtttt | ctgcaggag | 1740 |
| cgtctggctc | tgaaagaatc | cggtactgag | ctgggctctt | ccatctttt | cttcggttgt | 1800 |
| cgtaaccgca | agtcgatttt | catctatgaa | gacgaactga | caacttcgt | agagactggt | 1860 |
| gcactgtccg | aactgattgt | ggcattctct | cgtgaaggca | cggcgaaaga | atacgttcaa | 1920 |
| cacaaaatgt | ctcagaaagc | gagcgatatc | tggaaactgc | tgtccgaggg | tgcgtatctg | 1980 |

```
tatgtttgtg gcgacgcgaa aggcatggct aaagatgtac accgcaccct gcacaccatt    2040
gtacaagaac aaggctctct ggatagctcc aaggcagaac tgtacgtgaa aaacctgcag    2100
atgtctggcc gttacctgcg tgatgtatgg taa                                 2133
```

<210> SEQ ID NO 64
<211> LENGTH: 692
<212> TYPE: PRT
<213> ORGANISM: Arabidopsis thaliana

<400> SEQUENCE: 64

```
Met Thr Ser Ala Leu Tyr Ala Ser Asp Leu Phe Lys Gln Leu Lys Ser
1               5                   10                  15

Ile Met Gly Thr Asp Ser Leu Ser Asp Asp Val Val Leu Val Ile Ala
            20                  25                  30

Thr Thr Ser Leu Ala Leu Val Ala Gly Phe Val Val Leu Leu Trp Lys
        35                  40                  45

Lys Thr Thr Ala Asp Arg Ser Gly Glu Leu Lys Pro Leu Met Ile Pro
    50                  55                  60

Lys Ser Leu Met Ala Lys Asp Glu Asp Asp Leu Asp Leu Gly Ser
65                  70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
            100                 105                 110

Lys Ala Ala Val Lys Val Ile Asp Leu Asp Asp Tyr Ala Ala Asp Asp
        115                 120                 125

Asp Gln Tyr Glu Glu Lys Leu Lys Lys Glu Thr Leu Ala Phe Phe Cys
    130                 135                 140

Val Ala Thr Tyr Gly Asp Gly Glu Pro Thr Asp Asn Ala Ala Arg Phe
145                 150                 155                 160

Ser Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
            180                 185                 190

Asn Lys Ile Gly Ile Val Leu Asp Glu Glu Leu Cys Lys Lys Gly Ala
        195                 200                 205

Lys Arg Leu Ile Glu Val Gly Leu Gly Asp Asp Gln Ser Ile Glu
    210                 215                 220

Asp Asp Phe Asn Ala Trp Lys Glu Ser Leu Trp Ser Glu Leu Asp Lys
225                 230                 235                 240

Leu Leu Lys Asp Glu Asp Lys Ser Val Ala Thr Pro Tyr Thr Ala
                245                 250                 255

Val Ile Pro Glu Tyr Arg Val Val Thr His Asp Pro Arg Phe Thr Thr
            260                 265                 270

Gln Lys Ser Met Glu Ser Asn Val Ala Asn Gly Asn Thr Thr Ile Asp
        275                 280                 285

Ile His His Pro Cys Arg Val Asp Val Ala Val Gln Lys Glu Leu His
    290                 295                 300

Thr His Glu Ser Asp Arg Ser Cys Ile His Leu Glu Phe Asp Ile Ser
305                 310                 315                 320

Arg Thr Gly Ile Thr Tyr Glu Thr Gly Asp His Val Gly Val Tyr Ala
                325                 330                 335

Glu Asn His Val Glu Ile Val Glu Glu Ala Gly Lys Leu Leu Gly His
            340                 345                 350
```

Ser Leu Asp Leu Val Phe Ser Ile His Ala Asp Lys Glu Asp Gly Ser
            355                 360                 365

Pro Leu Glu Ser Ala Val Pro Pro Phe Pro Gly Pro Cys Thr Leu
370                 375                 380

Gly Thr Gly Leu Ala Arg Tyr Ala Asp Leu Leu Asn Pro Pro Arg Lys
385                 390                 395                 400

Ser Ala Leu Val Ala Leu Ala Ala Tyr Ala Thr Glu Pro Ser Glu Ala
                405                 410                 415

Glu Lys Leu Lys His Leu Thr Ser Pro Asp Gly Lys Asp Glu Tyr Ser
            420                 425                 430

Gln Trp Ile Val Ala Ser Gln Arg Ser Leu Leu Glu Val Met Ala Ala
            435                 440                 445

Phe Pro Ser Ala Lys Pro Pro Leu Gly Val Phe Phe Ala Ala Ile Ala
450                 455                 460

Pro Arg Leu Gln Pro Arg Tyr Tyr Ser Ile Ser Ser Cys Gln Asp Trp
465                 470                 475                 480

Ala Pro Ser Arg Val His Val Thr Ser Ala Leu Val Tyr Gly Pro Thr
                485                 490                 495

Pro Thr Gly Arg Ile His Lys Gly Val Cys Ser Thr Trp Met Lys Asn
            500                 505                 510

Ala Val Pro Ala Glu Lys Ser His Glu Cys Ser Gly Ala Pro Ile Phe
            515                 520                 525

Ile Arg Ala Ser Asn Phe Lys Leu Pro Ser Asn Pro Ser Thr Pro Ile
530                 535                 540

Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Leu Gly Ser Ser
                565                 570                 575

Leu Leu Phe Phe Gly Cys Arg Asn Arg Gln Met Asp Phe Ile Tyr Glu
            580                 585                 590

Asp Glu Leu Asn Asn Phe Val Asp Gln Gly Val Ile Ser Glu Leu Ile
            595                 600                 605

Met Ala Phe Ser Arg Glu Gly Ala Gln Lys Glu Tyr Val Gln His Lys
610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Glu Gln Glu Gly Val Ser Ser Ser
            660                 665                 670

Glu Ala Glu Ala Ile Val Lys Lys Leu Gln Thr Glu Gly Arg Tyr Leu
            675                 680                 685

Arg Asp Val Trp
690

<210> SEQ ID NO 65
<211> LENGTH: 2079
<212> TYPE: DNA
<213> ORGANISM: Arabidopsis thaliana

<400> SEQUENCE: 65
atgaccagcg cactgtacgc aagcgacctg tttaagcaac tgaagagcat tatgggcacc     60
gatagcctga gcgatgatgt tgtcctggtc attgcgacca cgagcctggc actggtggct    120
ggttttgtgg ttctgctgtg gaaaaagacc acggccgatc gttctggcga actgaaaccg    180

```
ctgatgattc cgaaaagtct gatggcaaag gacgaagatg acgatctgga tctgggctcc    240
ggtaaaaccc gtgtgtcaat cttttcggt acccagacgg gcaccgcaga aggtttcgca    300
aaagctctgt ctgaagaaat taaggcgcgc tatgaaaaag cggccgttaa ggtcatcgat    360
ctggacgatt atgcagctga cgatgaccag tacgaagaaa aactgaaaaa ggaaaccctg    420 gcgttttct gcgttgccac ctacggcgac ggtgaaccga cggataacgc ggcccgtttt    480
agtaaatggt tcaccgaaga aaatgaacgc gacattaagc tgcagcaact ggcgtatggc    540
gtgtttgctc tgggtaaccg tcagtacgaa catttcaaca agatcggtat cgtcctggat    600
gaagaactgt gtaaaaggg cgcgaagcgc ctgattgaag tgggcctggg tgatgacgat    660
caatccatcg aagacgattt taacgcctgg aaagaatctc tgtggagtga actggacaaa    720
ctgctgaagg atgaagacga taagagcgtg gcgacgccgt ataccgccgt tattccggaa    780
taccgtgtcg tgacccatga tccgcgcttc accacgcaga aaagcatgga atcaaatgtt    840
gcgaacggta ataccacgat tgacatccat caccctgtgcc gtgtggatgt tgccgtccaa    900
aaagaactgc ataccacgat atcggaccgt agctgtatcc acctggaatt tgatattagc    960
cgcacgggca tcacctatga aacgggcgac catgtgggtg tttacgcaga aaaccacgtg   1020
gaaattgttg aagaagctgg caaactgctg ggtcattcgc tggatctggt ttttagcatc   1080
cacgcggaca aggaagatgg ttcgccgctg gaaagcgcag tgccgccgcc gttcccgggt   1140
ccgtgcaccc tgggtacggg tctggcacgt tatgcagatc tgctgaatcc gccgcgcaaa   1200
tccgcactgg tggctctggc agcttacgca accgaaccgt cagaagctga aaaactgaag   1260
catctgacgt cgccggacgg taaagatgaa tatagccagt ggattgttgc gtctcaacgc   1320
agtctgctgg aagtcatggc agcatttccg tcggcaaaac cgccgctggg cgtgttttt c  1380 gcagctattg caccgcgtct gcagccgcgc tattacagca tcagctcttg tcaagattgg   1440
gcgccgtctc gtgtccatgt gaccagtgca ctggtgtatg gtccgacgcc gaccggtcgc   1500
attcacaaag gcgtgtgctc tacctggatg aaaaacgcgg ttccggccga aaagtctcac   1560
gaatgtagtg gtgcgccgat tttatccgt gccagtaact tcaaactgcc gtccaatccg   1620
tcaaccccga tcgttatggt cggtccgggt acgggtctgg caccgtttcg tggtttcctg   1680
caggaacgca tggctctgaa agaagatggc gaagaactgg gtagttccct gctgttttc   1740 ggctgccgta atcgccagat ggacttcatc tacgaagatg aactgaacaa cttcgtcgat   1800
caaggtgtga tttccgaact gatcatggca tttcacgcg aaggcgctca gaaagaatac   1860
gtccaacata aaatgatgga aaaggcggcc caagtgtggg atctgatcaa gaagaaggc   1920 tatctgtacg tttgtggcga cgcaaagggt atggctcgtg atgtccatcg caccctgcac   1980
acgattgttc aggaacaaga aggtgtctca tcgagcgaag cggaagccat cgtgaaaaag   2040
ctgcagaccg aaggccgtta tctgcgcgat gtttggtaa                           2079
```

<210> SEQ ID NO 66
<211> LENGTH: 717
<212> TYPE: PRT
<213> ORGANISM: Taxus cuspidata

<400> SEQUENCE: 66

Met Gln Ala Asn Ser Asn Thr Val Glu Gly Ala Ser Gln Gly Lys Ser
1               5                   10                  15

Leu Leu Asp Ile Ser Arg Leu Asp His Ile Phe Ala Leu Leu Leu Asn
            20                  25                  30

```
Gly Lys Gly Gly Asp Leu Gly Ala Met Thr Gly Ser Ala Leu Ile Leu
            35                  40                  45

Thr Glu Asn Ser Gln Asn Leu Met Ile Leu Thr Thr Ala Leu Ala Val
 50                  55                  60

Leu Val Ala Cys Val Phe Phe Phe Val Trp Arg Arg Gly Gly Ser Asp
 65                  70                  75                  80

Thr Gln Lys Pro Ala Val Arg Pro Thr Pro Leu Val Lys Glu Glu Asp
                 85                  90                  95

Glu Glu Glu Glu Asp Asp Ser Ala Lys Lys Lys Val Thr Ile Phe Phe
            100                 105                 110

Gly Thr Gln Thr Gly Thr Ala Glu Gly Phe Ala Lys Ala Leu Ala Glu
            115                 120                 125

Glu Ala Lys Ala Arg Tyr Glu Lys Ala Val Phe Lys Val Val Asp Leu
130                 135                 140

Asp Asn Tyr Ala Ala Asp Asp Glu Gln Tyr Glu Glu Lys Leu Lys Lys
145                 150                 155                 160

Glu Lys Leu Ala Phe Phe Met Leu Ala Thr Tyr Gly Asp Gly Glu Pro
                165                 170                 175

Thr Asp Asn Ala Ala Arg Phe Tyr Lys Trp Phe Leu Glu Gly Lys Glu
            180                 185                 190

Arg Glu Pro Trp Leu Ser Asp Leu Thr Tyr Gly Val Phe Gly Leu Gly
            195                 200                 205

Asn Arg Gln Tyr Glu His Phe Asn Lys Val Ala Lys Ala Val Asp Glu
            210                 215                 220

Val Leu Ile Glu Gln Gly Ala Lys Arg Leu Val Pro Val Gly Leu Gly
225                 230                 235                 240

Asp Asp Asp Gln Cys Ile Glu Asp Phe Thr Ala Trp Arg Glu Gln
                245                 250                 255

Val Trp Pro Glu Leu Asp Gln Leu Leu Arg Asp Glu Asp Asp Glu Pro
                260                 265                 270

Thr Ser Ala Thr Pro Tyr Thr Ala Ala Ile Pro Glu Tyr Arg Val Glu
            275                 280                 285

Ile Tyr Asp Ser Val Val Ser Val Tyr Glu Glu Thr His Ala Leu Lys
            290                 295                 300

Gln Asn Gly Gln Ala Val Tyr Asp Ile His His Pro Cys Arg Ser Asn
305                 310                 315                 320

Val Ala Val Arg Arg Glu Leu His Thr Pro Leu Ser Asp Arg Ser Cys
                325                 330                 335

Ile His Leu Glu Phe Asp Ile Ser Asp Thr Gly Leu Ile Tyr Glu Thr
            340                 345                 350

Gly Asp His Val Gly Val His Thr Glu Asn Ser Ile Glu Thr Val Glu
            355                 360                 365

Glu Ala Ala Lys Leu Leu Gly Tyr Gln Leu Asp Thr Ile Phe Ser Val
            370                 375                 380

His Gly Asp Lys Glu Asp Gly Thr Pro Leu Gly Gly Ser Ser Leu Pro
385                 390                 395                 400

Pro Pro Phe Pro Gly Pro Cys Thr Leu Arg Thr Ala Leu Ala Arg Tyr
                405                 410                 415

Ala Asp Leu Leu Asn Pro Pro Arg Lys Ala Ala Phe Leu Ala Leu Ala
            420                 425                 430

Ala His Ala Ser Asp Pro Ala Glu Ala Glu Arg Leu Lys Phe Leu Ser
            435                 440                 445
```

| | | | | | | | | | | | | |
|---|---|---|---|---|---|---|---|---|---|---|---|---|
|Ser|Pro|Ala|Gly|Lys|Asp|Glu|Tyr|Ser|Gln|Trp|Val|Thr|Ala|Ser|Gln|
| |450| | | | |455| | | | |460| |

Arg Ser Leu Leu Glu Ile Met Ala Glu Phe Pro Ser Ala Lys Pro Pro
465                 470                 475                 480

Leu Gly Val Phe Phe Ala Ala Ile Ala Pro Arg Leu Gln Pro Arg Tyr
                485                 490                 495

Tyr Ser Ile Ser Ser Ser Pro Arg Phe Ala Pro Ser Arg Ile His Val
            500                 505                 510

Thr Cys Ala Leu Val Tyr Gly Pro Ser Pro Thr Gly Arg Ile His Lys
            515                 520                 525

Gly Val Cys Ser Asn Trp Met Lys Asn Ser Leu Pro Ser Glu Glu Thr
530                 535                 540

His Asp Cys Ser Trp Ala Pro Val Phe Val Arg Gln Ser Asn Phe Lys
545                 550                 555                 560

Leu Pro Ala Asp Ser Thr Thr Pro Ile Val Met Val Gly Pro Gly Thr
                565                 570                 575

Gly Phe Ala Pro Phe Arg Gly Phe Leu Gln Glu Arg Ala Lys Leu Gln
                580                 585                 590

Glu Ala Gly Glu Lys Leu Gly Pro Ala Val Leu Phe Phe Gly Cys Arg
                595                 600                 605

Asn Arg Gln Met Asp Tyr Ile Tyr Glu Asp Glu Leu Lys Gly Tyr Val
                610                 615                 620

Glu Lys Gly Ile Leu Thr Asn Leu Ile Val Ala Phe Ser Arg Glu Gly
625                 630                 635                 640

Ala Thr Lys Glu Tyr Val Gln His Lys Met Leu Glu Lys Ala Ser Asp
                645                 650                 655

Thr Trp Ser Leu Ile Ala Gln Gly Gly Tyr Leu Tyr Val Cys Gly Asp
                660                 665                 670

Ala Lys Gly Met Ala Arg Asp Val His Arg Thr Leu His Thr Ile Val
                675                 680                 685

Gln Glu Gln Glu Ser Val Asp Ser Ser Lys Ala Glu Phe Leu Val Lys
                690                 695                 700

Lys Leu Gln Met Asp Gly Arg Tyr Leu Arg Asp Ile Trp
705                 710                 715

<210> SEQ ID NO 67
<211> LENGTH: 2154
<212> TYPE: DNA
<213> ORGANISM: Taxus cuspidata

<400> SEQUENCE: 67

```
atgcaggcta attccaacac ggtggaaggt gcctcccagg ggaagagcct gctggacata      60
tctcggctgg accatatttt tgcgctgctg ttgaacggca agggaggaga tctgggagcc     120
atgaccggct cggctttgat tttgacagag aattcgcaga atttgatgat tttgaccacg     180
gctttggctg ttttggtcgc gtgtgttttc ttcttcgttt ggaggagggg aggatcggat     240
acgcagaagc cggcggtgag accgacgcct ctggtgaagg aggaagatga ggaggaagaa     300
gacgattctg caaagaagaa agtcacgatt tctttttgga cacagactgg acggccgag      360 ggatttgcca aggctctagc agaagaggca aaggcaagat gagaaagc tgtgtttaaa       420 gtcgtagatt tggacaacta tgcagcagat gatgagcagt atgaagaaaa attgaaaaag     480
gaaaaattag cattttttat gctagcaacg tatgagaatg gggagcccac tgacaatgca     540
gcaagatttt ataagtggtt tcttgagggc aaggagaggg agccatggct ttctgatctc     600
```

-continued

```
acttatgggg tgtttggatt aggcaacaga caatatgaac attttaataa ggtggctaaa    660
gcagtagatg aagtcttaat tgaacaaggt gcaaagcgac ttgttccagt gggccttggt    720
gatgatgacc aatgcattga agatgacttt actgcttggc gagagcaggt ttggcctgaa    780
ctggatcagt tactccggga tgaagatgat gagcccacaa gtgctacacc ttatacagct    840
gccatacctg agtatagggt tgaaatttat gattccgtgg tttcagtgta cgaggaaact    900
catgctctca agcaaaatgg ccaagctgtt tatgatatcc atcacccctg cagatctaat    960
gtggcagtga aagagagct tcatacacct ttgtctgacc gctcttgcat ccatttggaa    1020
tttgatatat cagacactgg ccttatatat gagacaggag atcatgttgg tgtccataca    1080
gaaaacagca ttgaaactgt ggaggaagca gcaaagctac taggctacca attggacact    1140
atattctcag tccacggtga caagaagat ggcacgccac ttggagggtc ttctttgcca    1200
ccacctttcc ctggtccatg caccctacga actgctcttg ctcgttatgc tgatttgctg    1260
aatcctcctc ggaaggccgc ctttcttgca ttggcagctc atgcatctga tccagcagag    1320
gcagagcggt tgaagttcct ctcatcacca gctggaaagg atgaatattc tcaatgggtc    1380
actgcaagtc agagaagtct tttagaaata atggcagaat ttccatcagc aaaaccaccc    1440
cttggtgttt tctttgcagc aatagcccct cgtctgcaac cccgatatta ttctatttct    1500
tcctctccca ggtttgcacc ctcaagaata catgtgacat gtgctcttgt ttacgggccc    1560
agtccaaccg gtagaattca caaggtgtt tgttctaact ggatgaagaa ttcgctaccc    1620
tcagaagaaa cccatgactg tagctgggct ccagtctttg tcaggcaatc aaattttaaa    1680
ttgccagcag attctactac tcctattgtc atggtgggtc ctggaactgg ttttgcacct    1740
tttagaggtt ttttgcagga aagagcaaaa cttcaagaag ctggtgagaa gctcggtccg    1800
gctgttttat tttttgggtg caggaatcgc caaatggact acatttatga agatgagctg    1860
aagggctatg tggagaaagg aatactgacc aatctcattg ttgctttctc tcgtgaagga    1920
gcaaccaaag agtatgtcca gcacaagatg ctggaaaagg catccgatac ctggagtctc    1980
attgctcagg gtgggtatct ttatgtatgt ggtgatgcca agggtatggc tagggatgta    2040
cacaggacac tgcacactat tgtccaagag caggaatctg tggatagcag caaagcagag    2100
tttctagtga agaaattaca gatggatgga agatacttac gagatatatg gtga          2154
```

<210> SEQ ID NO 68
<211> LENGTH: 705
<212> TYPE: PRT
<213> ORGANISM: Artemisia annua

<400> SEQUENCE: 68

```
Met Ala Gln Ser Thr Thr Ser Val Lys Leu Ser Pro Phe Asp Leu Met
1               5                   10                  15

Thr Ala Leu Leu Asn Gly Lys Val Ser Phe Asp Thr Ser Asn Thr Ser
            20                  25                  30

Asp Thr Asn Ile Pro Leu Ala Val Phe Met Glu Asn Arg Glu Leu Leu
        35                  40                  45

Met Ile Leu Thr Thr Ser Val Ala Val Leu Ile Gly Cys Val Val Val
    50                  55                  60

Leu Val Trp Arg Arg Ser Ser Ser Ala Ala Lys Lys Ala Ala Glu Ser
65                  70                  75                  80

Pro Val Ile Val Val Pro Lys Lys Val Thr Glu Asp Glu Val Asp Asp
                85                  90                  95
```

```
Gly Arg Lys Lys Val Thr Val Phe Phe Gly Thr Gln Thr Gly Thr Ala
            100                 105                 110

Glu Gly Phe Ala Lys Ala Leu Val Glu Glu Ala Lys Ala Arg Tyr Glu
        115                 120                 125

Lys Ala Val Phe Lys Val Ile Asp Leu Asp Asp Tyr Ala Ala Glu Asp
130                 135                 140

Asp Glu Tyr Glu Glu Lys Leu Lys Lys Glu Ser Leu Ala Phe Phe Phe
145                 150                 155                 160

Leu Ala Thr Tyr Gly Asp Gly Glu Pro Thr Asp Asn Ala Ala Arg Phe
                165                 170                 175

Tyr Lys Trp Phe Thr Glu Gly Glu Lys Gly Glu Trp Leu Asp Lys
                180                 185                 190

Leu Gln Tyr Ala Val Phe Gly Leu Gly Asn Arg Gln Tyr Glu His Phe
        195                 200                 205

Asn Lys Ile Ala Lys Val Val Asp Glu Lys Leu Val Glu Gln Gly Ala
            210                 215                 220

Lys Arg Leu Val Pro Val Gly Met Gly Asp Asp Gln Cys Ile Glu
225                 230                 235                 240

Asp Asp Phe Thr Ala Trp Lys Glu Leu Val Trp Pro Glu Leu Asp Gln
                245                 250                 255

Leu Leu Arg Asp Glu Asp Asp Thr Ser Val Ala Thr Pro Tyr Thr Ala
            260                 265                 270

Ala Val Ala Glu Tyr Arg Val Val Phe His Asp Lys Pro Glu Thr Tyr
                275                 280                 285

Asp Gln Asp Gln Leu Thr Asn Gly His Ala Val His Asp Ala Gln His
290                 295                 300

Pro Cys Arg Ser Asn Val Ala Val Lys Lys Glu Leu His Ser Pro Leu
305                 310                 315                 320

Ser Asp Arg Ser Cys Thr His Leu Glu Phe Asp Ile Ser Asn Thr Gly
                325                 330                 335

Leu Ser Tyr Glu Thr Gly Asp His Val Gly Val Tyr Val Glu Asn Leu
            340                 345                 350

Ser Glu Val Val Asp Glu Ala Glu Lys Leu Ile Gly Leu Pro Pro His
        355                 360                 365

Thr Tyr Phe Ser Val His Ala Asp Asn Glu Asp Gly Thr Pro Leu Gly
370                 375                 380

Gly Ala Ser Leu Pro Pro Phe Pro Cys Thr Leu Arg Lys Ala
385                 390                 395                 400

Leu Ala Ser Tyr Ala Asp Val Leu Ser Ser Pro Lys Lys Ser Ala Leu
                405                 410                 415

Leu Ala Leu Ala Ala His Ala Thr Asp Ser Thr Glu Ala Asp Arg Leu
            420                 425                 430

Lys Phe Leu Ala Ser Pro Ala Gly Lys Asp Glu Tyr Ala Gln Trp Ile
        435                 440                 445

Val Ala Ser His Arg Ser Leu Leu Glu Val Met Glu Ala Phe Pro Ser
450                 455                 460

Ala Lys Pro Pro Leu Gly Val Phe Phe Ala Ser Val Ala Pro Arg Leu
465                 470                 475                 480

Gln Pro Arg Tyr Tyr Ser Ile Ser Ser Ser Pro Arg Phe Ala Pro Asn
                485                 490                 495

Arg Ile His Val Thr Cys Ala Leu Val Tyr Glu Gln Thr Pro Ser Gly
            500                 505                 5100
```

Arg Val His Lys Gly Val Cys Ser Thr Trp Met Lys Asn Ala Val Pro
        515                 520                 525

Met Thr Glu Ser Gln Asp Cys Ser Trp Ala Pro Ile Tyr Val Arg Thr
530                 535                 540

Ser Asn Phe Arg Leu Pro Ser Asp Pro Lys Val Pro Val Ile Met Ile
545                 550                 555                 560

Gly Pro Gly Thr Gly Leu Ala Pro Phe Arg Gly Phe Leu Gln Glu Arg
                565                 570                 575

Leu Ala Gln Lys Glu Ala Gly Thr Glu Leu Gly Thr Ala Ile Leu Phe
            580                 585                 590

Phe Gly Cys Arg Asn Arg Lys Val Asp Phe Ile Tyr Glu Asp Glu Leu
        595                 600                 605

Asn Asn Phe Val Glu Thr Gly Ala Leu Ser Glu Leu Val Thr Ala Phe
    610                 615                 620

Ser Arg Glu Gly Ala Thr Lys Glu Tyr Val Gln His Lys Met Thr Gln
625                 630                 635                 640

Lys Ala Ser Asp Ile Trp Asn Leu Leu Ser Glu Gly Ala Tyr Leu Tyr
                645                 650                 655

Val Cys Gly Asp Ala Lys Gly Met Ala Lys Asp Val His Arg Thr Leu
            660                 665                 670

His Thr Ile Val Gln Glu Gln Gly Ser Leu Asp Ser Ser Lys Ala Glu
        675                 680                 685

Leu Tyr Val Lys Asn Leu Gln Met Ala Gly Arg Tyr Leu Arg Asp Val
    690                 695                 700

Trp
705

<210> SEQ ID NO 69
<211> LENGTH: 2118
<212> TYPE: DNA
<213> ORGANISM: Artemisia annua

<400> SEQUENCE: 69
atggcgcagt ctaccaccag cgtgaaattg tccccttttg atctcatgac cgctctgctg      60
aatgggaaag tctcattcga tacaagcaac acaagtgata ccaacatccc tttggcggtt     120
tttatggaga atagagagtt actcatgatt ttaacgactt ccgtggccgt gctcattggg     180
tgcgtcgtcg tacttgtctg cgccggtca agtagcgcag caagaaggc ggcggagtcc     240 ccggttatcg tcgtcccaaa gaaggttaca gaggacgagg tggacgacgg acgcaaaaaa     300
gtgacggtat tctttggtac acagaccgga accgcggaag gatttgctaa agcgctggtg     360
gaagaagcta aagcccgtta cgaaaaagcg gtattcaaag tgatagacct ggatgactat     420
gcggcagagg acgacgagta cgaggaaaaa ttgaaaaaag aatctcttgc gttcttttt     480 ctcgccactt acggcgatgg agaacctact gataatgcgg ctcggtttta taagtggttc     540
actgagggtg aagaaaaagg tgaatggctg acaaattgc agtacgcagt atttggactc     600
gggaatcgtc aatatgaaca ttttaacaaa attgctaagg tcgtcgatga aaaactggtt     660
gagcagggtg cgaaacgtct ggtcccggtt ggaatgggcg atgacgacca gtgcattgaa     720
gacgacttta cagcatggaa ggaactggtg tggccggaac tggaccaact tttgcgtgac     780
gaggatgaca catctgtagc tacgccgtac actgctgcgg tagccgagta tagggtcgtt     840
tttcacgata aaccggaaac ctacgaccaa gaccagctca caaatggtca tgcagtacat     900
gatgcgcaac atcctTgcag gtcaaatgtg gcggtgaaga aagagctgca cagtcctctg     960

```
tcagatcgtt cttgcaccca cctggaattt gacatatcca atacgggcct ttcgtatgaa    1020
accggagatc acgttggtgt ctatgttgaa aatctgtcgg aagtggttga tgaggcggaa    1080
aaacttatcg gtctgccgcc tcatacgtac ttttcagtcc acgctgataa tgaagacgga    1140
accccgctgg gtggcgcatc gttaccccca cccttccac catgcactct gcgtaaggcg     1200
cttgccagtt atgctgatgt tttgtctagt cccaaaaaga gtgcacttct cgcactggcg    1260
gcccatgcca ctgatagtac agaggccgac aggctgaaat ttctggcgtc accagcggga    1320
aaagacgaat acgcccaatg gatcgttgcc agtcatcggt ctttactgga agtgatggaa    1380 gcgttcccctt ccgctaagcc acctctgggg gtctttttcg ctagtgtggc accccgtcta   1440
cagccccggt attactcaat atctagctca cccagatttg ctccgaatag aatacacgta    1500
acatgcgcgc tggtctatga gcagacccca agtggacggg tgcataaagg gtttgttct     1560 acctggatga agaacgccgt cccaatgacc gagtctcagg attgttcctg ggcacctata    1620
tatgttagaa catcaaactt tcgactgcca agtgacccga agttccggt aattatgata     1680 ggtccaggaa cagggctggc tccctttcgc gggttcctcc aggaacgtct ggcgcagaag    1740
gaggcgggaa ctgaactggg gacggcgatt ttattttcg ggtgtagaaa tcgtaaagtc     1800
gattttatat atgaagatga gttgaacaat ttcgtggaaa ccggggcatt atcggaatta    1860
gttacggctt ttagcaggga gggggcgact aaagagtatg tccagcacaa gatgactcag    1920
aaagcctcag atatatggaa cctgctgtcg gagggagcct atctttatgt ttgcggtgat    1980 gcaaaggaa tggccaaaga tgtccaccgg accctccaca ctattgtgca ggaacagggt     2040
tcattagact caagtaaagc cgaactttac gtaaaaaatc tacagatggc gggccgttac    2100
ctccgtgacg tttggtaa                                                  2118
```

<210> SEQ ID NO 70
<211> LENGTH: 693
<212> TYPE: PRT
<213> ORGANISM: Arabidopsis thaliana

<400> SEQUENCE: 70

```
Met Ala Thr Ser Ala Leu Tyr Ala Ser Asp Leu Phe Lys Gln Leu Lys
1               5                   10                  15

Ser Ile Met Gly Thr Asp Ser Leu Ser Asp Val Val Leu Val Ile
            20                  25                  30

Ala Thr Thr Ser Leu Ala Leu Val Ala Gly Phe Val Val Leu Leu Trp
        35                  40                  45

Lys Lys Thr Thr Ala Asp Arg Ser Gly Glu Leu Lys Pro Leu Met Ile
    50                  55                  60

Pro Lys Ser Leu Met Ala Lys Asp Glu Asp Asp Leu Asp Leu Gly
65                  70                  75                  80

Ser Gly Lys Thr Arg Val Ser Ile Phe Phe Gly Thr Gln Thr Gly Thr
                85                  90                  95

Ala Glu Gly Phe Ala Lys Ala Leu Ser Glu Glu Ile Lys Ala Arg Tyr
            100                 105                 110

Glu Lys Ala Ala Val Lys Val Ile Asp Leu Asp Asp Tyr Ala Ala Asp
        115                 120                 125

Asp Asp Gln Tyr Glu Glu Lys Leu Lys Lys Glu Thr Leu Ala Phe Phe
    130                 135                 140

Cys Val Ala Thr Tyr Gly Asp Gly Glu Pro Thr Asp Asn Ala Ala Arg
145                 150                 155                 160
```

```
Phe Tyr Lys Trp Phe Thr Glu Glu Asn Glu Arg Asp Ile Lys Leu Gln
            165                 170                 175

Gln Leu Ala Tyr Gly Val Phe Ala Leu Gly Asn Arg Gln Tyr Glu His
        180                 185                 190

Phe Asn Lys Ile Gly Ile Val Leu Asp Glu Glu Leu Cys Lys Lys Gly
            195                 200                 205

Ala Lys Arg Leu Ile Glu Val Gly Leu Gly Asp Asp Gln Ser Ile
210                 215                 220

Glu Asp Asp Phe Asn Ala Trp Lys Glu Ser Leu Trp Ser Glu Leu Asp
225                 230                 235                 240

Lys Leu Leu Lys Asp Glu Asp Lys Ser Val Ala Thr Pro Tyr Thr
            245                 250                 255

Ala Val Ile Pro Glu Tyr Arg Val Val Thr His Asp Pro Arg Phe Thr
            260                 265                 270

Thr Gln Lys Ser Met Glu Ser Asn Val Ala Asn Gly Asn Thr Thr Ile
            275                 280                 285

Asp Ile His His Pro Cys Arg Val Asp Val Ala Val Gln Lys Glu Leu
            290                 295                 300

His Thr His Glu Ser Asp Arg Ser Cys Ile His Leu Glu Phe Asp Ile
305                 310                 315                 320

Ser Arg Thr Gly Ile Thr Tyr Glu Thr Gly Asp His Val Gly Val Tyr
                325                 330                 335

Ala Glu Asn His Val Glu Ile Val Glu Glu Ala Gly Lys Leu Leu Gly
            340                 345                 350

His Ser Leu Asp Leu Val Phe Ser Ile His Ala Asp Lys Glu Asp Gly
            355                 360                 365

Ser Pro Leu Glu Ser Ala Val Pro Pro Phe Pro Gly Pro Cys Thr
370                 375                 380

Leu Gly Thr Gly Leu Ala Arg Tyr Ala Asp Leu Leu Asn Pro Pro Arg
385                 390                 395                 400

Lys Ser Ala Leu Val Ala Leu Ala Ala Tyr Ala Thr Glu Pro Ser Glu
                405                 410                 415

Ala Glu Lys Leu Lys His Leu Thr Ser Pro Asp Gly Lys Asp Glu Tyr
                420                 425                 430

Ser Gln Trp Ile Val Ala Ser Gln Arg Ser Leu Leu Glu Val Met Ala
            435                 440                 445

Ala Phe Pro Ser Ala Lys Pro Leu Gly Val Phe Phe Ala Ala Ile
            450                 455                 460

Ala Pro Arg Leu Gln Pro Arg Tyr Tyr Ser Ile Ser Ser Ser Pro Arg
465                 470                 475                 480

Leu Ala Pro Ser Arg Val His Val Thr Ser Ala Leu Val Tyr Gly Pro
                485                 490                 495

Thr Pro Thr Gly Arg Ile His Lys Gly Val Cys Ser Thr Trp Met Lys
                500                 505                 510

Asn Ala Val Pro Ala Glu Lys Ser His Glu Cys Ser Gly Ala Pro Ile
            515                 520                 525

Phe Ile Arg Ala Ser Asn Phe Lys Leu Pro Ser Asn Pro Ser Thr Pro
            530                 535                 540

Ile Val Met Val Gly Pro Gly Thr Gly Leu Ala Pro Phe Arg Gly Phe
545                 550                 555                 560

Leu Gln Glu Arg Met Ala Leu Lys Glu Asp Gly Glu Glu Leu Gly Ser
                565                 570                 575
```

| Ser | Leu | Leu | Phe | Phe | Gly | Cys | Arg | Asn | Arg | Gln | Met | Asp | Phe | Ile | Tyr |
| | | | | 580 | | | | | 585 | | | | | 590 | |

Glu Asp Glu Leu Asn Asn Phe Val Asp Gln Gly Val Ile Ser Glu Leu
              595                 600                 605

Ile Met Ala Phe Ser Arg Glu Gly Ala Gln Lys Glu Tyr Val Gln His
    610                 615                 620

Lys Met Met Glu Lys Ala Ala Gln Val Trp Asp Leu Ile Lys Glu Glu
625                 630                 635                 640

Gly Tyr Leu Tyr Val Cys Gly Asp Ala Lys Gly Met Ala Arg Asp Val
                645                 650                 655

His Arg Thr Leu His Thr Ile Val Gln Glu Gln Glu Gly Val Ser Ser
            660                 665                 670

Ser Glu Ala Glu Ala Ile Val Lys Lys Leu Gln Thr Glu Gly Arg Tyr
    675                 680                 685

Leu Arg Asp Val Trp
    690

<210> SEQ ID NO 71
<211> LENGTH: 2082
<212> TYPE: DNA
<213> ORGANISM: Arabidopsis thaliana

<400> SEQUENCE: 71

```
atggcgacca gcgctctgta tgctagtgac cttttttaaac agctcaaaag catcatgggc     60
actgatagcc tgtccgacga tgttgtcctg gtaatcgcaa ccacttccct tgcgcttgtt    120
gcgggctttg tggtgttact gtggaagaag actaccgcag ataggagtgg tgaattgaaa    180
ccgctgatga tcccaaaaag tctgatggcc aaagatgagg atgatgatct ggatcttgga    240
tcagggaaga cgcgagtcag tatttttttc gggacccaga cgggcaccgc ggagggcttc    300
gccaaagctc tgtccgagga ataaaggcc agatacgaga aagccgccgt aaaggttata    360
gacctagatg attacgccgc tgatgacgat cagtatgagg agaaacttaa aaaggagact    420
ctggcgtttt tttgcgtggc aacttacgga gacggcgagc ccaccgataa tgcagctagg    480
ttttacaagt ggtttaccga ggagaacgaa cgagatataa agttacagca gttggcctat    540
ggcgtgtttg ccctgggtaa tcggcaatat gagcatttca acaaaattgg catcgttctg    600
gatgaggaat tgtgcaaaaa gggtgcaaaa cggctgatag aggtgggtct aggtgacgat    660
gatcaatcta tagaagacga ttttaatgcg tggaaagaga gcttatggag tgaactggat    720
aagctcttga agatgaaga cgacaagtca gtggcgaccc cttataccgc ggtaatcccg    780
gaataccgcg tcgtgacaca cgatccgagg tttacaaccc aaaaatctat ggagtctaat    840
gtcgccaatg gcaacacaac gattgatatt caccacccct gtcgtgttga cgtggctgtt    900
caaaaagaac ttcatacaca cgaaagtgac cgaagttgca tacacttgga atttgacatt    960
agtcgcaccg gaattacgta tgaaactggt gatcacgtgg gtgtatacgc agaaaatcat   1020
gtcgaaatag tagaagaagc tggcaaactg ctgggacatt cactcgatct agtgtttagt   1080
atacatgccg ataaagagga tggcagccca ttggaaagtg ccgtccctcc gccgtttcct   1140
ggaccgtgta ctctggggac gggactcgcc cgctatgctg acctgttaaa cccccctcgt   1200
aaaagcgccc ttgtggccct gcggcatac gcaactgaac cgagcgaagc ggagaagctg   1260
aaacatctga catcaccgga tgcaaagac gagtatagtc agtggatagt agcctctcag   1320
cgctctctgc tggaagtgat ggccgcattt ccgtccgcca aaccaccctt gggagtattt   1380
ttcgctgcta tcgcacctcg gctccagccg cgctattaca gcatatcttc aagtccccgc   1440
```

-continued

```
ttagcaccgt ctcgtgtcca tgtcacttct gcgttggttt atggtccgac tccaacaggt      1500
cgcatccaca aagtgtgctg ttcaacctgg atgaaaaacg cggtgcccgc ggagaaatct      1560
catgagtgca gtggtgcacc tattttatc cgcgcaagta acttcaaact ccttctaat       1620 ccgagcacgc ccattgtgat ggttggccca ggcactggcc ttgctccgtt cgcggtttt      1680 ctacaggagc ggatggccct taagaagat ggggaagaat tgggatcatc gttgctcttt      1740
tttggctgcc gaaatcgcca gatggatttt atctacgaag acgagttgaa taactttgtc      1800
gatcaaggag taatttcgga gttgattatg gcattttcac gcgaaggggc tcagaaagag      1860
tatgtccaac acaagatgat ggaaaaagcg cacaagtgt gggatcttat taaagaagaa      1920
ggctatcttt atgtatgtgg ggatgcgaaa ggtatggccc gtgatgtcca tcgcaccctg      1980
cacacgattg tacaggaaca ggaaggtgtg tcctcgtccg aagcagaagc aatcgttaaa      2040
aaactgcaaa cagagggtcg ttaccttcgc gacgtgtggt aa                         2082
```

<210> SEQ ID NO 72
<211> LENGTH: 712
<212> TYPE: PRT
<213> ORGANISM: Arabidopsis thaliana

<400> SEQUENCE: 72

```
Met Ala Ser Ser Ser Ser Ser Ser Thr Ser Met Ile Asp Leu Met
1               5                   10                  15

Ala Ala Ile Ile Lys Gly Glu Pro Val Ile Val Ser Asp Pro Ala Asn
                20                  25                  30

Ala Ser Ala Tyr Glu Ser Val Ala Ala Glu Leu Ser Ser Met Leu Ile
        35                  40                  45

Glu Asn Arg Gln Phe Ala Met Ile Val Thr Thr Ser Ile Ala Val Leu
    50                  55                  60

Ile Gly Cys Ile Val Met Leu Val Trp Arg Arg Ser Gly Ser Gly Asn
65                  70                  75                  80

Ser Lys Arg Val Glu Pro Leu Lys Pro Leu Val Ile Lys Pro Arg Glu
                85                  90                  95

Glu Glu Ile Asp Asp Gly Arg Lys Lys Val Thr Ile Phe Phe Gly Thr
            100                 105                 110

Gln Thr Gly Thr Ala Glu Gly Phe Ala Lys Ala Leu Gly Glu Glu Ala
        115                 120                 125

Lys Ala Arg Tyr Glu Lys Thr Arg Phe Lys Ile Val Asp Leu Asp Asp
    130                 135                 140

Tyr Ala Ala Asp Asp Asp Glu Tyr Glu Glu Lys Leu Lys Lys Glu Asp
145                 150                 155                 160

Val Ala Phe Phe Phe Leu Ala Thr Tyr Gly Asp Gly Glu Pro Thr Asp
                165                 170                 175

Asn Ala Ala Arg Phe Tyr Lys Trp Phe Thr Glu Gly Asn Asp Arg Gly
            180                 185                 190

Glu Trp Leu Lys Asn Leu Lys Tyr Gly Val Phe Gly Leu Gly Asn Arg
        195                 200                 205

Gln Tyr Glu His Phe Asn Lys Val Ala Lys Val Val Asp Asp Ile Leu
    210                 215                 220

Val Glu Gln Gly Ala Gln Arg Leu Val Gln Val Gly Leu Gly Asp Asp
225                 230                 235                 240

Asp Gln Cys Ile Glu Asp Asp Phe Thr Ala Trp Arg Glu Ala Leu Trp
                245                 250                 255
```

```
Pro Glu Leu Asp Thr Ile Leu Arg Glu Gly Asp Thr Ala Val Ala
            260                 265                 270

Thr Pro Tyr Thr Ala Ala Val Leu Glu Tyr Arg Val Ser Ile His Asp
            275                 280                 285

Ser Glu Asp Ala Lys Phe Asn Asp Ile Asn Met Ala Asn Gly Asn Gly
290                 295                 300

Tyr Thr Val Phe Asp Ala Gln His Pro Tyr Lys Ala Asn Val Ala Val
305                 310                 315                 320

Lys Arg Glu Leu His Thr Pro Glu Ser Asp Arg Ser Cys Ile His Leu
                325                 330                 335

Glu Phe Asp Ile Ala Gly Ser Gly Leu Thr Tyr Glu Thr Gly Asp His
            340                 345                 350

Val Gly Val Leu Cys Asp Asn Leu Ser Glu Thr Val Asp Glu Ala Leu
            355                 360                 365

Arg Leu Leu Asp Met Ser Pro Asp Thr Tyr Phe Ser Leu His Ala Glu
            370                 375                 380

Lys Glu Asp Gly Thr Pro Ile Ser Ser Ser Leu Pro Pro Pro Phe Pro
385                 390                 395                 400

Pro Cys Asn Leu Arg Thr Ala Leu Thr Arg Tyr Ala Cys Leu Leu Ser
                405                 410                 415

Ser Pro Lys Lys Ser Ala Leu Val Ala Leu Ala Ala His Ala Ser Asp
            420                 425                 430

Pro Thr Glu Ala Glu Arg Leu Lys His Leu Ala Ser Pro Ala Gly Lys
            435                 440                 445

Asp Glu Tyr Ser Lys Trp Val Val Glu Ser Gln Arg Ser Leu Leu Glu
450                 455                 460

Val Met Ala Glu Phe Pro Ser Ala Lys Pro Pro Leu Gly Val Phe Phe
465                 470                 475                 480

Ala Gly Val Ala Pro Arg Leu Gln Pro Arg Phe Tyr Ser Ile Ser Ser
                485                 490                 495

Ser Pro Lys Ile Ala Glu Thr Arg Ile His Val Thr Cys Ala Leu Val
            500                 505                 510

Tyr Glu Lys Met Pro Thr Gly Arg Ile His Lys Gly Val Cys Ser Thr
            515                 520                 525

Trp Met Lys Asn Ala Val Pro Tyr Glu Lys Ser Glu Asn Cys Ser Ser
530                 535                 540

Ala Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
            580                 585                 590

Leu Gly Pro Ser Val Leu Phe Phe Gly Cys Arg Asn Arg Arg Met Asp
            595                 600                 605

Phe Ile Tyr Glu Glu Glu Leu Gln Arg Phe Val Glu Ser Gly Ala Leu
610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
            660                 665                 670
```

Arg Asp Val His Arg Ser Leu His Thr Ile Ala Gln Glu Gln Gly Ser
        675                 680                 685

Met Asp Ser Thr Lys Ala Glu Gly Phe Val Lys Asn Leu Gln Thr Ser
        690                 695                 700

Gly Arg Tyr Leu Arg Asp Val Trp
705                 710

<210> SEQ ID NO 73
<211> LENGTH: 2139
<212> TYPE: DNA
<213> ORGANISM: Arabidopsis thaliana

<400> SEQUENCE: 73

| | | | | | |
|---|---|---|---|---|---|
| atggcgtcca | gcagttcatc | gagttctaca | agcatgatcg | atctgatggc | cgctattatc | 60 |
| aaaggggaac | ccgtaattgt | ctctgatcca | gcaaatgcct | cggcatacga | gtcggtggct | 120 |
| gccgaattat | catctatgtt | aattgaaaat | agacaatttg | ccatgattgt | gacaacttct | 180 |
| attgctgtgc | tgataggttg | catcgtcatg | ctcgtgtggc | gccgtagcgg | atcaggcaac | 240 |
| tcaaagcgcg | tcgagccttt | gaaaccctg | gttatcaaac | cgcgagagga | ggaaatcgat | 300 |
| gatggcagaa | aaaggttac | tatcttttt | ggcacacaga | cggggacagc | ggaaggtttc | 360 |
| gcgaaagcac | tcggagagga | agcgaaagcc | cgatacgaga | aaacacggtt | caaaattgtg | 420 |
| gatctggatg | actatgcggc | tgatgatgat | gagtatgaag | aaaaactgaa | aaagaagat | 480 |
| gtggcgtttt | tttttcttgc | cacttatggc | gacggagagc | ccaccgataa | tgcagcgcgg | 540 |
| ttttacaagt | ggttcaccga | aggaaatgat | cggggagaat | ggttaaaaaa | tctgaaatac | 600 |
| ggtgtgttcg | gtcttggcaa | tcgccaatat | gagcatttta | taaagtcgc | gaaagtggtc | 660 |
| gatgatatat | tggtagaaca | gggcgctcag | cgcctcgtcc | aggtgggct | tggcgacgat | 720 |
| gatcagtgca | tagaagatga | ttttactgca | tggcgtgaag | cgctgtggcc | ggagctggac | 780 |
| accattttac | gtgaagaggg | cgatacagca | gtggcaaccc | cgtacacggc | tgccgtctta | 840 |
| gagtatcgtg | tgtccattca | tgatagcgag | gatgccaaat | tcaatgacat | caatatggcg | 900 |
| aatggaaatg | ggtacaccgt | gtttgacgcg | cagcacccgt | ataaggcaaa | cgttgcagtc | 960 |
| aagagggaac | tgcatactcc | tgaaagtgat | cgcagttgca | tccacctgga | gttcgatatt | 1020 |
| gcgggatcag | gtttaacgta | cgaaacgggc | gaccacgtag | gtgtgctgtg | cgacaatctt | 1080 |
| tcagagacag | tggacgaagc | tctgcgcctg | ctggatatga | gcccggatac | ctatttagc | 1140 |
| ttgcacgctg | agaagaaga | tgggactcca | attgcagta | gcttacctcc | acccttccg | 1200 |
| ccgtgtaatt | tgcgtaccgc | ccttacgcgc | tatgcgtgtc | tgctgagttc | gccaagaag | 1260 |
| tcggcccttg | tggcactggc | ggcacatgca | agtgacccga | ccgaggcgga | gaggctgaaa | 1320 |
| catctggctt | ctccagcggg | caaagatgaa | tacagcaaat | gggtggtaga | atcacagcgt | 1380 |
| tccctactag | aagtaatggc | cgaatttccc | tcagctaaac | caccgctggg | agtgttcttt | 1440 |
| gcgggcgttg | ctccccgctt | gcaaccacgc | ttttattcaa | ttagctcaag | tcctaagata | 1500 |
| gcggaaacac | ggatacatgt | aacttgcgca | ttggtttatg | aaaaaatgcc | aaccgggagg | 1560 |
| atacataaag | gcgtatgttc | aacctggatg | aaaaatgctg | tgccatacga | aaagtcggag | 1620 |
| aattgctcct | ctgccccaat | tttcgtgcgt | caaagcaact | ttaaactgcc | gagtgattca | 1680 |
| aaggtgccta | ttattatgat | aggccctggt | acaggactcg | ccccgtttcg | tggttttctt | 1740 |
| caagaaagac | tggctctggt | cgaatcaggc | gtggaattag | accctccgt | gttatttttt | 1800 |
| ggctgccgca | accgtcgaat | ggacttcatc | tatgaagaag | aattgcaacg | ttttgtggag | 1860 |

-continued

```
tcaggcgctc tggcggaact atccgtcgcc tttagtagag aaggcccaac caaagaatac  1920
gtacagcata agatgatgga taaagcgagc gacatttgga atatgatctc acaaggggcg  1980
tacctgtacg tatgtggaga tgccaaagga atggcacgag acgtacatag atcgttgcat  2040
actattgctc aagaacaggg aagcatggat tcgactaaag cagaaggctt tgttaaaaat  2100
ctacagacat ctggtcgcta tctgcgtgac gtgtggtaa                         2139
```

<210> SEQ ID NO 74
<211> LENGTH: 713
<212> TYPE: PRT
<213> ORGANISM: Arabidopsis thaliana

<400> SEQUENCE: 74

```
Met Ala Ser Ser Ser Ser Ser Ser Thr Ser Met Ile Asp Leu Met
1               5                   10                  15

Ala Ala Ile Ile Lys Gly Glu Pro Val Ile Ser Asp Pro Ala Asn
                20                  25                  30

Ala Ser Ala Tyr Glu Ser Val Ala Ala Glu Leu Ser Ser Met Leu Ile
            35                  40                  45

Glu Asn Arg Gln Phe Ala Met Ile Val Thr Thr Ser Ile Ala Val Leu
50                  55                  60

Ile Gly Cys Ile Val Met Leu Val Trp Arg Arg Ser Gly Ser Gly Asn
65                  70                  75                  80

Ser Lys Arg Val Glu Pro Leu Lys Pro Leu Val Ile Lys Pro Arg Glu
                85                  90                  95

Glu Glu Ile Asp Asp Gly Arg Lys Lys Val Thr Ile Phe Phe Gly Thr
            100                 105                 110

Gln Thr Gly Thr Ala Glu Gly Phe Ala Lys Ala Leu Gly Glu Glu Ala
        115                 120                 125

Lys Ala Arg Tyr Glu Lys Thr Arg Phe Lys Ile Val Asp Leu Asp Asp
    130                 135                 140

Tyr Ala Ala Asp Asp Asp Glu Tyr Glu Glu Lys Leu Lys Lys Glu Asp
145                 150                 155                 160

Val Ala Phe Phe Phe Leu Ala Thr Tyr Gly Asp Gly Glu Pro Thr Asp
                165                 170                 175

Asn Ala Ala Arg Phe Tyr Lys Trp Phe Thr Glu Gly Asn Asp Arg Gly
            180                 185                 190

Glu Trp Leu Lys Asn Leu Lys Tyr Gly Val Phe Gly Leu Gly Asn Arg
        195                 200                 205

Gln Tyr Glu His Phe Asn Lys Val Ala Lys Val Val Asp Asp Ile Leu
    210                 215                 220

Val Glu Gln Gly Ala Gln Arg Leu Val Gln Val Gly Leu Gly Asp Asp
225                 230                 235                 240

Asp Gln Cys Ile Glu Asp Asp Phe Thr Ala Trp Arg Glu Ala Leu Trp
                245                 250                 255

Pro Glu Leu Asp Thr Ile Leu Arg Glu Glu Gly Asp Thr Ala Val Ala
            260                 265                 270

Thr Pro Tyr Thr Ala Ala Val Leu Glu Tyr Arg Val Ser Ile His Asp
        275                 280                 285

Ser Glu Asp Ala Lys Phe Asn Asp Ile Thr Leu Ala Asn Gly Asn Gly
    290                 295                 300

Tyr Thr Val Phe Asp Ala Gln His Pro Tyr Lys Ala Asn Val Ala Val
305                 310                 315                 320
```

```
Lys Arg Glu Leu His Thr Pro Glu Ser Asp Arg Ser Cys Ile His Leu
                325                 330                 335

Glu Phe Asp Ile Ala Gly Ser Gly Leu Thr Met Lys Leu Gly Asp His
            340                 345                 350

Val Gly Val Leu Cys Asp Asn Leu Ser Glu Thr Val Asp Glu Ala Leu
        355                 360                 365

Arg Leu Leu Asp Met Ser Pro Asp Thr Tyr Phe Ser Leu His Ala Glu
    370                 375                 380

Lys Glu Asp Gly Thr Pro Ile Ser Ser Ser Leu Pro Pro Phe Pro
385                 390                 395                 400

Pro Cys Asn Leu Arg Thr Ala Leu Thr Arg Tyr Ala Cys Leu Leu Ser
                405                 410                 415

Ser Pro Lys Lys Ser Ala Leu Val Ala Leu Ala His Ala Ser Asp
            420                 425                 430

Pro Thr Glu Ala Glu Arg Leu Lys His Leu Ala Ser Pro Ala Gly Lys
        435                 440                 445

Asp Glu Tyr Ser Lys Trp Val Val Glu Ser Gln Arg Ser Leu Leu Glu
    450                 455                 460

Val Met Ala Glu Phe Pro Ser Ala Lys Pro Pro Leu Gly Val Phe Phe
465                 470                 475                 480

Ala Gly Val Ala Pro Arg Leu Gln Pro Arg Phe Tyr Ser Ile Ser Ser
                485                 490                 495

Ser Pro Lys Ile Ala Glu Thr Arg Ile His Val Thr Cys Ala Leu Val
            500                 505                 510

Tyr Glu Lys Met Pro Thr Gly Arg Ile His Lys Gly Val Cys Ser Thr
        515                 520                 525

Trp Met Lys Asn Ala Val Pro Tyr Glu Lys Ser Glu Lys Leu Phe Leu
    530                 535                 540

Gly Arg Pro Ile Phe Val Arg Gln Ser Asn Phe Lys Leu Pro Ser Asp
545                 550                 555                 560

Ser Lys Val Pro Ile Ile Met Ile Gly Pro Gly Thr Gly Leu Ala Pro
                565                 570                 575

Phe Arg Gly Phe Leu Gln Glu Arg Leu Ala Leu Val Glu Ser Gly Val
            580                 585                 590

Glu Leu Gly Pro Ser Val Leu Phe Phe Gly Cys Arg Asn Arg Arg Met
        595                 600                 605

Asp Phe Ile Tyr Glu Glu Glu Leu Gln Arg Phe Val Glu Ser Gly Ala
    610                 615                 620

Leu Ala Glu Leu Ser Val Ala Phe Ser Arg Glu Gly Pro Thr Lys Glu
625                 630                 635                 640

Tyr Val Gln His Lys Met Met Asp Lys Ala Ser Asp Ile Trp Asn Met
                645                 650                 655

Ile Ser Gln Gly Ala Tyr Leu Tyr Val Cys Gly Asp Ala Lys Gly Met
            660                 665                 670

Ala Arg Asp Val His Arg Ser Leu His Thr Ile Ala Gln Glu Gln Gly
        675                 680                 685

Ser Met Asp Ser Thr Lys Ala Glu Gly Phe Val Lys Asn Leu Gln Thr
    690                 695                 700

Ser Gly Arg Tyr Leu Arg Asp Val Trp
705                 710

<210> SEQ ID NO 75
<211> LENGTH: 2142
```

```
<212> TYPE: DNA
<213> ORGANISM: Arabidopsis thaliana

<400> SEQUENCE: 75
atggcgagca gttcgtcctc ctcttctacc agtatgatcg atctgatggc cgctattata      60
aaaggagaac cagtcattgt gtctgatcct gcaaacgcat cagcctacga atctgtggct     120
gctgaactgt cctcgatgct gatcgaaaat cgccaatttg caatgattgt tacaaccagc     180
atcgctgttc ttatcgggtg tattgtcatg ctggtttggc ggcggagtgg cagcggcaat     240
tctaaaagag tggagccact gaagcctctg gtaatcaaac cccgcgaaga agaaatcgat     300
gatggacgta agaaagttac aattttttttt ggtacacaga caggtacagc agagggcttt     360
gccaaagctc ttggagaaga agcaaaagct cgatatgaga aaacacgctt caagatcgtc     420
gatctggatg actacgcggc agacgacgat gagtacgaag aaaaactcaa aaaagaggat     480
gtggctttt ttttcctggc aacttatggg acggcgagc ctaccgacaa tgcagcgcgg     540
ttttacaaat ggtttaccga aggcaatgat agaggggagt ggctcaaaaa tctcaaatac     600
ggagttttcg gattggggaa tagacaatac gaacacttta ataaggttgc gaaagtggta     660
gatgatattc tggtcgagca gggcgcgcaa cgtttagtac aggtcggcct gggtgatgac     720
gaccagtgca tcgaagatga ctttacggcc tggcgagaag cgctctggcc ggaattagat     780
acaatccttc gggaagaggg ggacactgct gtcgctaccc cgtacactgc cgcagtgctg     840
gaatatcgtg tttcaataca tgattcggaa gatgccaagt ttaatgacat caccctggca     900
aacggcaacg gatataccgt atttgacgct caacatccgt ataaggccaa tgtagcagta     960
aagcgggaac tccatactcc cgaaagtgac agaagttgca tccatctgga gttcgatata    1020
gcgggaagcg gactgactat gaaactggga gatcatgtag gggtcctgtg cgataatttg    1080
agcgaaaccg ttgacgaagc gctccggctt ttagatatgt cccctgatac ttatttctct    1140
ttgcacgccg agaaggaaga tggtacacct atatcctcct cgctgccgcc gccttttcca    1200
ccatgtaatc tgcgtacggc cttgactagg tatgcatgtc ttcttagctc cccgaaaaag    1260
tccgcactgg tagcgttggc agctcatgcc agcgatccca cggaggcaga gcgtttaaaa    1320
cacctggcga gtcctgctgg caaagatgaa tacagcaaat gggtggttga gtcgcagagg    1380
tccctgctgg aagtcatggc tgaatttccg tctgcgaaac cgcctctggg agttttcttc    1440
gcaggagtag ccccacgttt acaaccgcgt ttctattcta tttcttcctc ccccaagatc    1500
gcggaaactc gaatacacgt aacgtgcgca ttggtgtatg aaaagatgcc aactggtcgt    1560
atccacaagg gagtgtgctc aacctggatg aaaaacgccg ttccgtatga aaaatcggaa    1620
aaattgtttt tgggtagacc catattcgtt cggcagtcaa actttaaact accttctgat    1680
agcaaggttc cgattattat gattggaccg ggtactggcc tggcgccgtt ccgtggtttc    1740
ctgcaagaac ggttggcgct ggtggaatcc ggcgtgaacc ttgggccatc ggttttgttt    1800
ttcgggtgcc gcaatcgtcg catggacttc atctacgagg aagaactcca gcgttttgtc    1860
gaaagcggtg cccttgctga attgtccgtt gcattcagcc gcgaaggtcc aactaaggag    1920
tatgtgcagc acaaaatgat ggacaaagcg agcgatattt ggaatatgat tagccagggc    1980
gcatacctttt atgtgtgcgg tgatgctaag ggaatggcgc gcgatgtcca tagatcttta    2040
cataccattg cacaggagca gggctctatg gattcaacaa aagctgaagg ttttgtgaaa    2100
aaccttcaga ccagcgggcg gtatcttcgc gatgtttggt aa                      2142
```

```
<210> SEQ ID NO 76
<211> LENGTH: 711
<212> TYPE: PRT
<213> ORGANISM: Stevia rebaudiana

<400> SEQUENCE: 76
```

| Met | Ala | Gln | Ser | Asp | Ser | Val | Lys | Val | Ser | Pro | Phe | Asp | Leu | Val | Ser |
|---|---|---|---|---|---|---|---|---|---|---|---|---|---|---|---|
| 1 | | | | 5 | | | | | 10 | | | | | 15 | |

| Ala | Ala | Met | Asn | Gly | Lys | Ala | Met | Glu | Lys | Leu | Asn | Ala | Ser | Glu | Ser |
|---|---|---|---|---|---|---|---|---|---|---|---|---|---|---|---|
| | | | 20 | | | | | 25 | | | | | 30 | | |

| Glu | Asp | Pro | Thr | Thr | Leu | Pro | Ala | Leu | Lys | Met | Leu | Val | Glu | Asn | Arg |
|---|---|---|---|---|---|---|---|---|---|---|---|---|---|---|---|
| | | 35 | | | | | 40 | | | | | 45 | | | |

| Glu | Leu | Leu | Thr | Leu | Phe | Thr | Thr | Ser | Phe | Ala | Val | Leu | Ile | Gly | Cys |
|---|---|---|---|---|---|---|---|---|---|---|---|---|---|---|---|
| | 50 | | | | | 55 | | | | | 60 | | | | |

| Leu | Val | Phe | Leu | Met | Trp | Arg | Arg | Ser | Ser | Lys | Lys | Leu | Val | Gln |
|---|---|---|---|---|---|---|---|---|---|---|---|---|---|---|
| 65 | | | | 70 | | | | | 75 | | | | | 80 |

| Asp | Pro | Val | Pro | Gln | Val | Ile | Val | Val | Lys | Lys | Glu | Lys | Glu | Ser |
|---|---|---|---|---|---|---|---|---|---|---|---|---|---|---|
| | | | | 85 | | | | 90 | | | | | 95 | |

| Glu | Val | Asp | Asp | Gly | Lys | Lys | Lys | Val | Ser | Ile | Phe | Tyr | Gly | Thr | Gln |
|---|---|---|---|---|---|---|---|---|---|---|---|---|---|---|---|
| | | | 100 | | | | | 105 | | | | | 110 | | |

| Thr | Gly | Thr | Ala | Glu | Gly | Phe | Ala | Lys | Ala | Leu | Val | Glu | Glu | Ala | Lys |
|---|---|---|---|---|---|---|---|---|---|---|---|---|---|---|---|
| | | 115 | | | | | 120 | | | | | 125 | | | |

| Val | Arg | Tyr | Glu | Lys | Thr | Ser | Phe | Lys | Val | Ile | Asp | Leu | Asp | Asp | Tyr |
|---|---|---|---|---|---|---|---|---|---|---|---|---|---|---|---|
| | 130 | | | | | 135 | | | | | 140 | | | | |

| Ala | Ala | Asp | Asp | Asp | Glu | Tyr | Glu | Glu | Lys | Leu | Lys | Lys | Glu | Ser | Leu |
|---|---|---|---|---|---|---|---|---|---|---|---|---|---|---|---|
| 145 | | | | | 150 | | | | | 155 | | | | | 160 |

| Ala | Phe | Phe | Phe | Leu | Ala | Thr | Tyr | Gly | Asp | Gly | Glu | Pro | Thr | Asp | Asn |
|---|---|---|---|---|---|---|---|---|---|---|---|---|---|---|---|
| | | | 165 | | | | | 170 | | | | | 175 | | |

| Ala | Ala | Asn | Phe | Tyr | Lys | Trp | Phe | Thr | Glu | Gly | Asp | Asp | Lys | Gly | Glu |
|---|---|---|---|---|---|---|---|---|---|---|---|---|---|---|---|
| | | 180 | | | | | 185 | | | | | 190 | | | |

| Leu | Leu | Lys | Lys | Leu | Gln | Tyr | Gly | Val | Phe | Gly | Leu | Gly | Asn | Arg | Gln |
|---|---|---|---|---|---|---|---|---|---|---|---|---|---|---|---|
| | | 195 | | | | | 200 | | | | | 205 | | | |

| Tyr | Glu | His | Phe | Asn | Lys | Ile | Ala | Ile | Val | Val | Asp | Asp | Lys | Leu | Thr |
|---|---|---|---|---|---|---|---|---|---|---|---|---|---|---|---|
| | 210 | | | | | 215 | | | | | 220 | | | | |

| Glu | Met | Gly | Ala | Lys | Arg | Leu | Val | Pro | Val | Gly | Leu | Gly | Asp | Asp | Asp |
|---|---|---|---|---|---|---|---|---|---|---|---|---|---|---|---|
| 225 | | | | | 230 | | | | | 235 | | | | | 240 |

| Gln | Cys | Ile | Glu | Asp | Asp | Phe | Thr | Ala | Trp | Lys | Glu | Leu | Val | Trp | Pro |
|---|---|---|---|---|---|---|---|---|---|---|---|---|---|---|---|
| | | | 245 | | | | | 250 | | | | | 255 | | |

| Glu | Leu | Asp | Gln | Leu | Leu | Arg | Asp | Glu | Asp | Thr | Ser | Val | Thr | Thr |
|---|---|---|---|---|---|---|---|---|---|---|---|---|---|---|
| | | | 260 | | | | | 265 | | | | | 270 | |

| Pro | Tyr | Thr | Ala | Ala | Val | Leu | Glu | Tyr | Arg | Val | Val | Tyr | His | Asp | Lys |
|---|---|---|---|---|---|---|---|---|---|---|---|---|---|---|---|
| | | 275 | | | | | 280 | | | | | 285 | | | |

| Pro | Ala | Asp | Ser | Tyr | Ala | Glu | Asp | Gln | Thr | His | Thr | Asn | Gly | His | Val |
|---|---|---|---|---|---|---|---|---|---|---|---|---|---|---|---|
| | 290 | | | | | 295 | | | | | 300 | | | | |

| Val | His | Asp | Ala | Gln | His | Pro | Ser | Arg | Ser | Asn | Val | Ala | Phe | Lys | Lys |
|---|---|---|---|---|---|---|---|---|---|---|---|---|---|---|---|
| 305 | | | | | 310 | | | | | 315 | | | | | 320 |

| Glu | Leu | His | Thr | Ser | Gln | Ser | Asp | Arg | Ser | Cys | Thr | His | Leu | Glu | Phe |
|---|---|---|---|---|---|---|---|---|---|---|---|---|---|---|---|
| | | | 325 | | | | | 330 | | | | | 335 | | |

| Asp | Ile | Ser | His | Thr | Gly | Leu | Ser | Tyr | Glu | Thr | Gly | Asp | His | Val | Gly |
|---|---|---|---|---|---|---|---|---|---|---|---|---|---|---|---|
| | | | 340 | | | | | 345 | | | | | 350 | | |

| Val | Tyr | Ser | Glu | Asn | Leu | Ser | Glu | Val | Val | Asp | Glu | Ala | Leu | Lys | Leu |
|---|---|---|---|---|---|---|---|---|---|---|---|---|---|---|---|
| | | 355 | | | | | 360 | | | | | 365 | | | |

| Leu | Gly | Leu | Ser | Pro | Asp | Thr | Tyr | Phe | Ser | Val | His | Ala | Asp | Lys | Glu |
|---|---|---|---|---|---|---|---|---|---|---|---|---|---|---|---|
| | 370 | | | | | 375 | | | | | 380 | | | | |

Asp Gly Thr Pro Ile Gly Gly Ala Ser Leu Pro Pro Phe Pro Pro
385                 390                 395                 400

Cys Thr Leu Arg Asp Ala Leu Thr Arg Tyr Ala Asp Val Leu Ser Ser
            405                 410                 415

Pro Lys Lys Val Ala Leu Leu Ala Leu Ala Ala His Ala Ser Asp Pro
            420                 425                 430

Ser Glu Ala Asp Arg Leu Lys Phe Leu Ala Ser Pro Ala Gly Lys Asp
            435                 440                 445

Glu Tyr Ala Gln Trp Ile Val Ala Asn Gln Arg Ser Leu Leu Glu Val
        450                 455                 460

Met Gln Ser Phe Pro Ser Ala Lys Pro Pro Leu Gly Val Phe Phe Ala
465                 470                 475                 480

Ala Val Ala Pro Arg Leu Gln Pro Arg Tyr Tyr Ser Ile Ser Ser Ser
                485                 490                 495

Pro Lys Met Ser Pro Asn Arg Ile His Val Thr Cys Ala Leu Val Tyr
            500                 505                 510

Glu Thr Thr Pro Ala Gly Arg Ile His Arg Gly Leu Cys Ser Thr Trp
            515                 520                 525

Met Lys Asn Ala Val Pro Leu Thr Glu Ser Pro Asp Cys Ser Gln Ala
530                 535                 540

Ser Ile Phe Val Arg Thr Ser Asn Phe Arg Leu Pro Val Asp Pro Lys
545                 550                 555                 560

Val Pro Val Ile Met Ile Gly Pro Gly Thr Gly Leu Ala Pro Phe Arg
                565                 570                 575

Gly Phe Leu Gln Glu Arg Leu Ala Leu Lys Glu Ser Gly Thr Glu Leu
            580                 585                 590

Gly Ser Ser Ile Phe Phe Gly Cys Arg Asn Arg Lys Val Asp Phe
            595                 600                 605

Ile Tyr Glu Asp Glu Leu Asn Asn Phe Val Glu Thr Gly Ala Leu Ser
        610                 615                 620

Glu Leu Ile Val Ala Phe Ser Arg Glu Gly Thr Ala Lys Glu Tyr Val
625                 630                 635                 640

Gln His Lys Met Ser Gln Lys Ala Ser Asp Ile Trp Lys Leu Leu Ser
            645                 650                 655

Glu Gly Ala Tyr Leu Tyr Val Cys Gly Asp Ala Lys Gly Met Ala Lys
            660                 665                 670

Asp Val His Arg Thr Leu His Thr Ile Val Gln Glu Gln Gly Ser Leu
            675                 680                 685

Asp Ser Ser Lys Ala Glu Leu Tyr Val Lys Asn Leu Gln Met Ser Gly
            690                 695                 700

Arg Tyr Leu Arg Asp Val Trp
705                 710

<210> SEQ ID NO 77
<211> LENGTH: 2136
<212> TYPE: DNA
<213> ORGANISM: Stevia rebaudiana

<400> SEQUENCE: 77
atggctcaga gcgattctgt taaagtatcc ccgttcgacc tggtctctgc ggctatgaac      60
ggcaaagcaa tggagaaact gaacgcgagc gaatctgaag atccaaccac cctgccggca     120
ctgaaaatgc tggtagaaaa ccgtgaactg ctgactctgt tcaccacctc cttcgccgtt     180
ctgattggtt gcctggtctt cctgatgtgg cgccgttcct cttccaagaa gctggtacag     240

```
gacccggttc ctcaggtgat cgtcgttaaa aagaaagaga aggaaagcga agtcgatgac    300
ggcaaaaaga aggtttccat tttctacggt actcagaccg gcaccgctga gggttttgcc    360
aaagcactgg ttgaagaggc aaaagtgcgt tacgaaaaaa cttccttcaa agtgattgac    420
ctggacgact atgctgcgga tgatgatgaa tacgaggaaa aactgaaaaa agaaagcctg    480
gccttcttct tcctggcaac ctatggcgat ggtgaaccga ccgacaacgc ggcgaacttc    540
tacaaatggt ttaccgaagg cgacgacaaa ggtgaattgc tgaagaaact gcagtatggt    600
gttttcggtc tgggcaatcg ccagtacgaa cattttaaca aaatcgcaat cgttgttgat    660
gacaaactga ctgaaatggg tgcgaaacgt ctggtgccgg ttggcctggg tgacgatgat    720
caatgcatcg aagatgactt caccgcatgg aaagaactgg tttggccgga actggatcag    780
ctgctgcgcg acgaagacga cacttccgtg accaccccgt ataccgctgc agtgctggag    840
taccgtgttg tttaccacga taaaccggcg gactcttacg ccgaagatca gactcacact    900
aacggtcacg tcgtacatga cgcacagcac ccgtctcgta gcaatgttgc gtttaagaaa    960
gagctgcaca cgagccagtc cgaccgctct tgtacgcacc tggagttcga tatctcccac   1020
accggtctgt cctatgaaac cggtgaccat gttggcgttt acagcgaaaa cctgagcgag   1080
gtagttgatg aagcgctgaa actgctgggc ctgtctccag acacctactt tagcgtgcat   1140
gctgacaagg aagatggtac tccgattggc ggcgcttccc tgccgccacc gtttccacct   1200
tgcactctgc gtgatgctct gactcgttac gctgatgttc tgtctagccc gaaaaaggtt   1260
gcgctgctgg cgctggccgc acatgcttct gacccgtctg aagctgaccg tctgaaattc   1320
ctggcgtctc cggccggcaa agacgaatac gcgcagtgga ttgtcgctaa ccagcgctct   1380
ctgctggaag tgatgcagtc cttcccgtct gccaaaccgc cactgggcgt gttttttcgca  1440 gctgtggctc cgcgcctgca gccgcgctac tattctatct ctagctcccc gaaaatgagc   1500
ccgaaccgca tccacgttac ttgtgctctg gtttacgaaa ccaccccctgc gggccgtatc   1560 caccgtggtc tgtgctctac gtggatgaaa aatgccgtgc cgctgaccga atccccggac   1620
tgctctcagg cgtccatctt cgtgcgtacc tctaacttcc gtctgccggt ggacccgaaa   1680
gttcctgtta tcatgatcgg tcctggcacg ggtctggccc cgtttcgtgg ttttctgcag   1740
gagcgtctgg ctctgaaaga atccggtact gagctgggct cttccatctt tttcttcggt   1800
tgtcgtaacc gcaaagtcga tttcatctat gaagacgaac tgaacaactt cgtagagact   1860
ggtgcactgt ccgaactgat tgtggcattc tctcgtgaag gcacggcgaa agaatacgtt   1920
caacacaaaa tgtctcagaa agcgagcgat atctggaaac tgctgtccga gggtgcgtat   1980
ctgtatgttt gtggcgacgc gaaaggcatg gctaaagatg tacaccgcac cctgcacacc   2040
attgtacaag aacaaggctc tctggatagc tccaaggcag aactgtacgt gaaaaacctg   2100
cagatgtctg gccgttacct gcgtgatgta tggtaa                            2136
```

```
<210> SEQ ID NO 78
<211> LENGTH: 710
<212> TYPE: PRT
<213> ORGANISM: Stevia rebaudiana

<400> SEQUENCE: 78

Met Ala Gln Ser Glu Ser Val Glu Ala Ser Thr Ile Asp Leu Met Thr
1               5                   10                  15

Ala Val Leu Lys Asp Thr Val Ile Asp Thr Ala Asn Ala Ser Asp Asn
            20                  25                  30
```

```
Gly Asp Ser Lys Met Pro Pro Ala Leu Ala Met Met Phe Glu Ile Arg
         35                  40                  45

Asp Leu Leu Leu Ile Leu Thr Thr Ser Val Ala Val Leu Val Gly Cys
 50                  55                  60

Phe Val Val Leu Val Trp Lys Arg Ser Ser Gly Lys Lys Ser Gly Lys
 65                  70                  75                  80

Glu Leu Glu Pro Pro Lys Ile Val Val Pro Lys Arg Arg Leu Glu Gln
                 85                  90                  95

Glu Val Asp Asp Gly Lys Lys Val Thr Ile Phe Phe Gly Thr Gln
             100                 105                 110

Thr Gly Thr Ala Glu Gly Phe Ala Lys Ala Leu Phe Glu Glu Ala Lys
         115                 120                 125

Ala Arg Tyr Glu Lys Ala Ala Phe Lys Val Ile Asp Leu Asp Asp Tyr
130                 135                 140

Ala Ala Asp Leu Asp Glu Tyr Ala Glu Lys Leu Lys Lys Glu Thr Tyr
145                 150                 155                 160

Ala Phe Phe Phe Leu Ala Thr Tyr Gly Asp Gly Glu Pro Thr Asp Asn
                 165                 170                 175

Ala Ala Lys Phe Tyr Lys Trp Phe Thr Glu Gly Asp Glu Lys Gly Val
             180                 185                 190

Trp Leu Gln Lys Leu Gln Tyr Gly Val Phe Gly Leu Gly Asn Arg Gln
         195                 200                 205

Tyr Glu His Phe Asn Lys Ile Gly Ile Val Val Asp Asp Gly Leu Thr
210                 215                 220

Glu Gln Gly Ala Lys Arg Ile Val Pro Val Gly Leu Gly Asp Asp Asp
225                 230                 235                 240

Gln Ser Ile Glu Asp Asp Phe Ser Ala Trp Lys Glu Leu Val Trp Pro
                 245                 250                 255

Glu Leu Asp Leu Leu Leu Arg Asp Glu Asp Asp Lys Ala Ala Ala Thr
             260                 265                 270

Pro Tyr Thr Ala Ala Ile Pro Glu Tyr Arg Val Val Phe His Asp Lys
         275                 280                 285

Pro Asp Ala Phe Ser Asp His Thr Gln Thr Asn Gly His Ala Val
290                 295                 300

His Asp Ala Gln His Pro Cys Arg Ser Asn Val Ala Val Lys Lys Glu
305                 310                 315                 320

Leu His Thr Pro Glu Ser Asp Arg Ser Cys Thr His Leu Glu Phe Asp
                 325                 330                 335

Ile Ser His Thr Gly Leu Ser Tyr Glu Thr Gly Asp His Val Gly Val
             340                 345                 350

Tyr Cys Glu Asn Leu Ile Glu Val Val Glu Glu Ala Gly Lys Leu Leu
         355                 360                 365

Gly Leu Ser Thr Asp Thr Tyr Phe Ser Leu His Ile Asp Asn Glu Asp
370                 375                 380

Gly Ser Pro Leu Gly Gly Pro Ser Leu Gln Pro Pro Phe Pro Pro Cys
385                 390                 395                 400

Thr Leu Arg Lys Ala Leu Thr Asn Tyr Ala Asp Leu Leu Ser Ser Pro
                 405                 410                 415

Lys Lys Ser Thr Leu Leu Ala Leu Ala Ala His Ala Ser Asp Pro Thr
             420                 425                 430

Glu Ala Asp Arg Leu Arg Phe Leu Ala Ser Arg Glu Gly Lys Asp Glu
         435                 440                 445
```

Tyr Ala Glu Trp Val Val Ala Asn Gln Arg Ser Leu Leu Glu Val Met
        450                 455                 460

Glu Ala Phe Pro Ser Ala Arg Pro Pro Leu Gly Val Phe Phe Ala Ala
465                 470                 475                 480

Val Ala Pro Arg Leu Gln Pro Arg Tyr Tyr Ser Ile Ser Ser Pro
            485                 490                 495

Lys Met Glu Pro Asn Arg Ile His Val Thr Cys Ala Leu Val Tyr Glu
                500                 505                 510

Lys Thr Pro Ala Gly Arg Ile His Lys Gly Ile Cys Ser Thr Trp Met
            515                 520                 525

Lys Asn Ala Val Pro Leu Thr Glu Ser Gln Asp Cys Ser Trp Ala Pro
530                 535                 540

Ile Phe Val Arg Thr Ser Asn Phe Arg Leu Pro Ile Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Leu Phe Phe Gly Cys Arg Asn Arg Lys Val Asp Tyr Ile
            595                 600                 605

Tyr Glu Asn Glu Leu Asn Asn Phe Val Glu Asn Gly Ala Leu Ser Glu
            610                 615                 620

Leu Asp Val Ala Phe Ser Arg Asp Gly Pro Thr Lys Glu Tyr Val Gln
625                 630                 635                 640

His Lys Met Thr Gln Lys Ala Ser Glu Ile Trp Asn Met Leu Ser Glu
                645                 650                 655

Gly Ala Tyr Leu Tyr Val Cys Gly Asp Ala Lys Gly Met Ala Lys Asp
            660                 665                 670

Val His Arg Thr Leu His Thr Ile Val Gln Glu Gln Gly Ser Leu Asp
            675                 680                 685

Ser Ser Lys Ala Glu Leu Tyr Val Lys Asn Leu Gln Met Ser Gly Arg
            690                 695                 700

Tyr Leu Arg Asp Val Trp
705                 710

<210> SEQ ID NO 79
<211> LENGTH: 2133
<212> TYPE: DNA
<213> ORGANISM: Stevia rebaudiana

<400> SEQUENCE: 79
atggcgcaat ctgaaagtgt tgaggccagt accatcgacc ttatgacggc agtgttgaag      60
gatacagtta ttgacactgc aaatgcttca gataacggcg attctaaaat gcctcctgcg     120
cttgcgatga tgttcgagat ccgcgatctt ctgctgatcc ttaccacatc agtagcggtg     180
ctggtgggat gctttgtggt actcgtgtgg aaacgttcgt cgggcaaaaa atcaggtaag     240
gagctggaac cgcctaagat tgtcgtaccg aaacgccgac tggaacaaga agttgatgat     300
ggcaaaaaaa aagtgactat atttttggg acacagacag gcacagcgga gggatttgcg     360
aaagccttat tcgaggaggc gaaggcacgt tacgagaaag cagcttttaa agtcattgat     420
ctggatgact atgcagcaga cctagatgaa tacgcagaga aactgaaaaa agaaacttat     480
gcgttttctc tcctggccac atacggagac ggtgaaccga cggacaatgc cgccaagttt     540
tataagtggt tcactgaagg ggatgagaaa ggtgtatggc ttcagaaatt gcaatacgga     600

-continued

```
gtgttcggac taggaaatcg gcaatatgag cactttaata aaataggcat agtagtagac    660
gatgggctaa ccgagcaggg ggccaaacgg attgtacccg tgggcctggg ggacgatgat    720
cagtctattg aggatgattt tagtgcttgg aaagagcttg tttggcctga actggactta    780
ctcctgcgtg atgaagacga taaagcggca gcgactccat acacggcagc aatccccgag    840
tatagagtcg tattccatga taaaccggat gctttctctg atgaccatac ccaaactaat    900
ggtcatgcgg tccatgatgc acaacatccc tgccgcagca atgtagcggt gaaaaaggag    960
ctgcatacgc ctgaaagtga tcgctcatgt acgcatctgg agtttgatat ttcacacaca   1020
ggtcttagct acgagactgg agatcacgtc ggagtctatt gcgaaaatct gatcgaagtg   1080
gttgaagagg ccgggaaact gttgggacta agtacagata cttattttc tttacatata    1140
gataacgagg atggttcccc acttggcggt ccatctcttc agcctccatt cccaccatgt   1200
accttacgca aagcgctgac taactacgca gatctgctgt ctagcccaaa gaaatcaacg   1260
cttctggcgt tggctgctca tgcctcagat ccgaccgaag ctgatcgcct tcgttttctg   1320
gcatcccgag aaggtaaaga tgaatatgca gaatgggtgg tagcgaatca gcgttctttg   1380
ctggaagtca tggaggcatt ccccagcgcg cgccctccgc tgggtgtttt cttcgcagcg   1440
gtggccccgc ggctccagcc gcgttattat tcaattagca gttctcctaa gatggaacct   1500
aatcgaatcc atgtaacatg tgcattggtc tatgagaaaa cgccggctgg ccgcatccat   1560
aaaggtatat gtagcacatg gatgaaaaat gcagtacccc tcacggagtc ccaggattgt   1620
agttgggcgc cgatatttgt tcggacgagc aattttagac ttcctataga cccaaaggtt   1680
ccagttatta tgattggtcc tggcaccgga cttgcgccat tccggggggtt tctgcaagaa   1740
agactggctc tgaaagaaag cggtacagaa ctcggctcca gtatattgtt tttcggctgt   1800
cgcaaccgga aagtagatta tatatatgaa aacgagctga ataacttcgt tgaaaatggt   1860
gccctgtctg aactcgatgt cgcttttttcg cgagatggcc cgacaaaaga atacgtgcag   1920
cataaaatga cccagaaagc aagtgaaatc tggaatatgc tgtcagaagg ggcatatctg   1980
tatgtgtgcg gagatgcaaa gggcatggcc aaagacgttc acagaaacctt gcataccata   2040
gtacaagagc agggctctct ggatagctca aaagccgagc tgtacgtgaa aaatctccag   2100
atgagtggac gctacctgag ggatgtttgg taa                                2133
```

<210> SEQ ID NO 80
<211> LENGTH: 708
<212> TYPE: PRT
<213> ORGANISM: Stevia rebaudiana

<400> SEQUENCE: 80

```
Met Ala Gln Ser Asn Ser Val Lys Ile Ser Pro Leu Asp Leu Val Thr
1               5                   10                  15

Ala Leu Phe Ser Gly Lys Val Leu Asp Thr Ser Asn Ala Ser Glu Ser
            20                  25                  30

Gly Glu Ser Ala Met Leu Pro Thr Ile Ala Met Ile Met Glu Asn Arg
        35                  40                  45

Glu Leu Leu Met Ile Leu Thr Thr Ser Val Ala Val Leu Ile Gly Cys
    50                  55                  60

Val Val Val Leu Val Trp Arg Arg Ser Ser Thr Lys Lys Ser Ala Leu
65                  70                  75                  80

Glu Pro Pro Val Ile Val Pro Lys Arg Val Gln Glu Glu Glu Val
            85                  90                  95
```

-continued

```
Asp Asp Gly Lys Lys Val Thr Val Phe Gly Thr Gln Thr Gly
            100                 105                 110

Thr Ala Glu Gly Phe Ala Lys Ala Leu Val Glu Glu Ala Lys Ala Arg
        115                 120                 125

Tyr Glu Lys Ala Val Phe Lys Val Ile Asp Leu Asp Asp Tyr Ala Ala
        130                 135                 140

Asp Asp Asp Glu Tyr Glu Glu Lys Leu Lys Lys Glu Ser Leu Ala Phe
145                 150                 155                 160

Phe Phe Leu Ala Thr Tyr Gly Asp Gly Glu Pro Thr Asp Asn Ala Ala
                165                 170                 175

Arg Phe Tyr Lys Trp Phe Thr Glu Gly Asp Ala Lys Gly Glu Trp Leu
                180                 185                 190

Asn Lys Leu Gln Tyr Gly Val Phe Gly Leu Gly Asn Arg Gln Tyr Glu
                195                 200                 205

His Phe Asn Lys Ile Ala Lys Val Val Asp Asp Gly Leu Val Glu Gln
            210                 215                 220

Gly Ala Lys Arg Leu Val Pro Val Gly Leu Gly Asp Asp Gln Cys
225                 230                 235                 240

Ile Glu Asp Asp Phe Thr Ala Trp Lys Glu Leu Val Trp Pro Glu Leu
                245                 250                 255

Asp Gln Leu Leu Arg Asp Glu Asp Thr Thr Val Ala Thr Pro Tyr
                260                 265                 270

Thr Ala Ala Val Ala Glu Tyr Arg Val Val Phe His Glu Lys Pro Asp
                275                 280                 285

Ala Leu Ser Glu Asp Tyr Ser Tyr Thr Asn Gly His Ala Val His Asp
            290                 295                 300

Ala Gln His Pro Cys Arg Ser Asn Val Ala Val Lys Lys Glu Leu His
305                 310                 315                 320

Ser Pro Glu Ser Asp Arg Ser Cys Thr His Leu Glu Phe Asp Ile Ser
                325                 330                 335

Asn Thr Gly Leu Ser Tyr Glu Thr Gly Asp His Val Gly Val Tyr Cys
                340                 345                 350

Glu Asn Leu Ser Glu Val Val Asn Asp Ala Glu Arg Leu Val Gly Leu
                355                 360                 365

Pro Pro Asp Thr Tyr Phe Ser Ile His Thr Asp Ser Glu Asp Gly Ser
370                 375                 380

Pro Leu Gly Gly Ala Ser Leu Pro Pro Phe Pro Pro Cys Thr Leu
385                 390                 395                 400

Arg Lys Ala Leu Thr Cys Tyr Ala Asp Val Leu Ser Ser Pro Lys Lys
                405                 410                 415

Ser Ala Leu Leu Ala Leu Ala Ala His Ala Thr Asp Pro Ser Glu Ala
                420                 425                 430

Asp Arg Leu Lys Phe Leu Ala Ser Pro Ala Gly Lys Asp Glu Tyr Ser
                435                 440                 445

Gln Trp Ile Val Ala Ser Gln Arg Ser Leu Leu Glu Val Met Glu Ala
            450                 455                 460

Phe Pro Ser Ala Lys Pro Ser Leu Gly Val Phe Phe Ala Ser Val Ala
465                 470                 475                 480

Pro Arg Leu Gln Pro Arg Tyr Tyr Ser Ile Ser Ser Ser Pro Lys Met
                485                 490                 495

Ala Pro Asp Arg Ile His Val Thr Cys Ala Leu Val Tyr Glu Lys Thr
                500                 505                 510
```

```
Pro Ala Gly Arg Ile His Lys Gly Val Cys Ser Thr Trp Met Lys Asn
        515                 520                 525

Ala Val Pro Met Thr Glu Ser Gln Asp Cys Ser Trp Ala Pro Ile Tyr
    530                 535                 540

Val Arg Thr Ser Asn Phe Arg Leu Pro Ser Asp Pro Lys Val Pro Val
545                 550                 555                 560

Ile Met Ile Gly Pro Gly Thr Gly Leu Ala Pro Phe Arg Gly Phe Leu
                565                 570                 575

Gln Glu Arg Leu Ala Leu Lys Glu Ala Gly Thr Asp Leu Gly Leu Ser
            580                 585                 590

Ile Leu Phe Phe Gly Cys Arg Asn Arg Lys Val Asp Phe Ile Tyr Glu
        595                 600                 605

Asn Glu Leu Asn Asn Phe Val Glu Thr Gly Ala Leu Ser Glu Leu Ile
    610                 615                 620

Val Ala Phe Ser Arg Glu Gly Pro Thr Lys Glu Tyr Val Gln His Lys
625                 630                 635                 640

Met Ser Glu Lys Ala Ser Asp Ile Trp Asn Leu Leu Ser Glu Gly Ala
                645                 650                 655

Tyr Leu Tyr Val Cys Gly Asp Ala Lys Gly Met Ala Lys Asp Val His
            660                 665                 670

Arg Thr Leu His Thr Ile Val Gln Glu Gln Gly Ser Leu Asp Ser Ser
        675                 680                 685

Lys Ala Glu Leu Tyr Val Lys Asn Leu Gln Met Ser Gly Arg Tyr Leu
    690                 695                 700

Arg Asp Val Trp
705
```

<210> SEQ ID NO 81
<211> LENGTH: 2127
<212> TYPE: DNA
<213> ORGANISM: Stevia rebaudiana

<400> SEQUENCE: 81

```
atggcgcaat ctaattctgt gaaaatctct ccattggatc tggttacagc actctttagc      60
gggaaggtac tggatacaag taacgccagt gaaagcgggg aatccgcgat gctgccaaca     120
atcgcgatga tcatggaaaa tcgggaactg ctaatgattc tgacaacgtc tgtagcagtt     180
ttaatcggtt gcgttgtggt tctggtgtgg cgtcgatcat ccacgaaaaa gagcgcatta     240
gaaccgcctg ttatcgtagt accaaaaaga gttcaggagg aagaggtgga tgatgggaaa     300
aaaaaagtca ccgttttctt cgggacccaa actggtacgg cagaaggttt tgcgaaagca     360
ctggtcgaag aggcgaaagc ccgctatgag aaggcggttt ttaaggttat tgaccttgat     420
gactatgcgg cggacgatga tgaatacgaa gaaaaattaa agaaagaatc acttgccttt     480
ttttttttgg caacatacgg tgatggcgag ccgactgata cgcggcacg gtttacaaaa     540
tggtttaccg aaggcgacgc gaaggggag tggttgaaca agttacagta cggtgtgttc     600
ggcttgggga accgccagta cgagcacttt aacaagatag ctaaagttgt cgatgatggt     660
ctggtagaac agggagcgaa gcgtctcgtg ccagtagggc tggcgatga tgatcagtgt     720
atagaagatg attttacggc ttggaaggag ttagtttggc cggaactgga ccaactgctg     780
cgcgatgagg atgatacaac tgtcgctacc ccgtatacag cagcggtagc tgaatacagg     840
gtggtttttc acgagaaacc tgatgcgctg agtgaggact attcgtatac taacggccat     900
gccgttcacg atgcacagca cccgtgccgt tctaatgtcg ccgtaaaaaa ggaactgcat     960
```

```
agcccggagt cggaccgcag ttgtacccat ctggagtttg atatttcaaa taccgggctg    1020
agttacgaaa cgggcgatca cgttggcgtg tactgtgaga atctaagcga ggttgttaac    1080
gatgcagaac gactggtcgg tttgcctcca gatacttatt tctcgatcca cactgatagc    1140
gaagatggct ctccactcgg ggggcgagt ctgccgcccc cgtttccccc gtgtacgctg     1200
agaaaggccc ttacatgtta tgcagatgta ctctcttccc ccaaaaaaag tgccttgctc    1260
gcattagcag cccacgctac cgatccctcg gaagcagatc gtctgaaatt cttggcatcg    1320
ccggcgggca agatgaata cagccaatgg atagttgcaa gtcagcgcag tctcttagaa      1380 gtgatgaag cgtttccgtc cgcaaagccg tccttaggtg tgttttcgc gtccgtggca       1440 ccgcgtcttc agcctagata ttacagcatt agttcctctc caaaaatggc cccggaccgt    1500
attcacgtga cttgtgctct tgtatatgag aaaaccccgg caggtcgtat tcacaaaggc    1560
gtgtgcagca cctggatgaa gaatgcagtg ccgatgaccg aaagccagga ttgttcatgg    1620
gcgccaatct atgtcaggac aagtaatttc agacttccgt ctgatcctaa agttccagtc    1680
ataatgattg gccccggcac gggactggct ccttttcgtg gtttcctgca agagcgcttg    1740
gcactgaaag aagcaggcac tgacctggga ctgtccatcc tgttctttgg gtgccgtaat    1800
cgtaaggtcg atttatata tgaaaatgaa ttgaacaact tgtagaaac aggcgcatta     1860 tccgaactga tcgtagcttt tagtagagag gggccgacga agaatatgt acaacacaag    1920 atgtctgaga aggcttcgga tatatggaac ctgctctctg agggtgccta tctgtacgtt    1980
tgcggtgatg ccaaaggaat ggccaaagat gtgcaccgca ctttacatac aatcgtccaa    2040
gagcagggta gcttggactc atctaaagct gaactgtatg tgaagaactt acagatgagc    2100
gggcgctatt tgcgagatgt tttggtaa                                        2127
```

<210> SEQ ID NO 82
<211> LENGTH: 706
<212> TYPE: PRT
<213> ORGANISM: Pelargonium graveolens

<400> SEQUENCE: 82

```
Met Ala Gln Ser Ser Gly Ser Met Ser Pro Phe Asp Phe Met Thr
1               5                   10                  15

Ala Ile Ile Lys Gly Lys Met Glu Pro Ser Asn Ala Ser Leu Gly Ala
                20                  25                  30

Ala Gly Glu Val Thr Ala Met Ile Leu Asp Asn Arg Glu Leu Val Met
            35                  40                  45

Ile Leu Thr Thr Ser Ile Ala Val Leu Ile Gly Cys Val Val Val Phe
        50                  55                  60

Ile Trp Arg Arg Ser Ser Ser Gln Thr Pro Thr Ala Val Gln Pro Leu
65                  70                  75                  80

Lys Pro Leu Leu Ala Lys Glu Thr Glu Ser Glu Val Asp Asp Gly Lys
                85                  90                  95

Gln Lys Val Thr Ile Phe Phe Gly Thr Gln Thr Gly Thr Ala Glu Gly
            100                 105                 110

Phe Ala Lys Ala Leu Ala Asp Glu Ala Lys Ala Arg Tyr Asp Lys Val
        115                 120                 125

Thr Phe Lys Val Val Asp Leu Asp Asp Tyr Ala Ala Asp Asp Glu Glu
    130                 135                 140

Tyr Glu Glu Lys Leu Lys Lys Glu Thr Leu Ala Phe Phe Phe Leu Ala
145                 150                 155                 160
```

```
Thr Tyr Gly Asp Gly Glu Pro Thr Asp Asn Ala Ala Arg Phe Tyr Lys
            165                 170                 175
Trp Phe Leu Glu Gly Lys Glu Arg Gly Glu Trp Leu Gln Asn Leu Lys
        180                 185                 190
Phe Gly Val Phe Gly Leu Gly Asn Arg Gln Tyr Glu His Phe Asn Lys
        195                 200                 205
Ile Ala Ile Val Val Asp Glu Ile Leu Ala Glu Gln Gly Gly Lys Arg
        210                 215                 220
Leu Ile Ser Val Gly Leu Gly Asp Asp Asp Gln Cys Ile Glu Asp Asp
225                 230                 235                 240
Phe Thr Ala Trp Arg Glu Ser Leu Trp Pro Glu Leu Asp Gln Leu Leu
                245                 250                 255
Arg Asp Glu Asp Asp Thr Thr Val Ser Thr Pro Tyr Thr Ala Ala Val
                260                 265                 270
Leu Glu Tyr Arg Val Val Phe His Asp Pro Ala Asp Ala Pro Thr Leu
            275                 280                 285
Glu Lys Ser Tyr Ser Asn Ala Asn Gly His Ser Val Val Asp Ala Gln
            290                 295                 300
His Pro Leu Arg Ala Asn Val Ala Val Arg Arg Glu Leu His Thr Pro
305                 310                 315                 320
Ala Ser Asp Arg Ser Cys Thr His Leu Glu Phe Asp Ile Ser Gly Thr
                325                 330                 335
Gly Ile Ala Tyr Glu Thr Gly Asp His Val Gly Val Tyr Cys Glu Asn
                340                 345                 350
Leu Ala Glu Thr Val Glu Glu Ala Leu Glu Leu Leu Gly Leu Ser Pro
            355                 360                 365
Asp Thr Tyr Phe Ser Val His Ala Asp Lys Glu Asp Gly Thr Pro Leu
        370                 375                 380
Ser Gly Ser Ser Leu Pro Pro Phe Pro Pro Cys Thr Leu Arg Thr
385                 390                 395                 400
Ala Leu Thr Leu His Ala Asp Leu Leu Ser Pro Lys Lys Ser Ala
                405                 410                 415
Leu Leu Ala Leu Ala Ala His Ala Ser Asp Pro Thr Glu Ala Asp Arg
                420                 425                 430
Leu Arg His Leu Ala Ser Pro Ala Gly Lys Asp Glu Tyr Ala Gln Trp
            435                 440                 445
Ile Val Ala Ser Gln Arg Ser Leu Leu Glu Val Met Ala Glu Phe Pro
        450                 455                 460
Ser Ala Lys Pro Pro Leu Gly Val Phe Phe Ala Ser Val Ala Pro Arg
465                 470                 475                 480
Leu Gln Pro Arg Tyr Tyr Ser Ile Ser Ser Pro Arg Ile Ala Pro
                485                 490                 495
Ser Arg Ile His Val Thr Cys Ala Leu Val Tyr Glu Lys Thr Pro Thr
                500                 505                 510
Gly Arg Val His Lys Gly Val Cys Ser Thr Trp Met Lys Asn Ser Val
            515                 520                 525
Pro Ser Glu Lys Ser Asp Glu Cys Ser Trp Ala Pro Ile Phe Val Arg
        530                 535                 540
Gln Ser Asn Phe Lys Leu Pro Ala Asp Ala Lys Val Pro Ile Ile Met
545                 550                 555                 560
Ile Gly Pro Gly Thr Gly Leu Ala Pro Phe Arg Gly Phe Leu Gln Glu
                565                 570                 575
```

Arg Leu Ala Leu Lys Glu Ala Gly Thr Glu Leu Gly Pro Ser Ile Leu
              580                 585                 590

Phe Phe Gly Cys Arg Asn Ser Lys Met Asp Tyr Ile Tyr Glu Asp Glu
          595                 600                 605

Leu Asp Asn Phe Val Gln Asn Gly Ala Leu Ser Glu Leu Val Leu Ala
      610                 615                 620

Phe Ser Arg Glu Gly Pro Thr Lys Glu Tyr Val Gln His Lys Met Met
625                 630                 635                 640

Glu Lys Ala Ser Asp Ile Trp Asn Leu Ile Ser Gln Gly Ala Tyr Leu
                  645                 650                 655

Tyr Val Cys Gly Asp Ala Lys Gly Met Ala Arg Asp Val His Arg Thr
              660                 665                 670

Leu His Thr Ile Ala Gln Glu Gln Gly Ser Leu Asp Ser Ser Lys Ala
          675                 680                 685

Glu Ser Met Val Lys Asn Leu Gln Met Ser Gly Arg Tyr Leu Arg Asp
      690                 695                 700

Val Trp
705

<210> SEQ ID NO 83
<211> LENGTH: 2121
<212> TYPE: DNA
<213> ORGANISM: Pelargonium graveolens

<400> SEQUENCE: 83
atggcgcagt caagcagtgg atcaatgagc cctttcgatt ttatgaccgc tataataaaa      60
ggtaaaatgg agccaagtaa tgcgtcttta ggagcggcag gtgaagtcac agcaatgata     120
cttgataata gggagctggt tatgattctg acgaccagca ttgcagtgct gatcggttgc     180
gttgtagtgt tcatttggcg tcgttcatca tcccagaccc ctaccgcggt gcagccatta     240
aaaccacttt tagcgaagga acagagagc gaagtagacg atggcaaaca gaaagtaact     300
atcttttttg gtactcaaac tggaaccgct gaaggtttcg cgaaagcgct cgcagacgag     360
gccaaagcac ggtatgataa agtcactttt aaagtggttg atctggacga ttatgccgca     420
gatgacgaag aatatgaaga aaagctgaag aaggaaacgt tagcattctt ttttcttgcg     480
acgtatggag atggtgaacc tactgacaat gctgcaaggt tttataagtg gtttctggaa     540
ggtaaagaac gcggagaatg gcttcagaat ctaaaatttg gtgtgtttgg tttaggcaac     600
cgtcagtatg agcatttcaa taaaattgcc attgtggttg atgaaatcct tgcagaacaa     660
ggtggtaagc gtctcatttc agttggcctg ggcgatgatg atcagtgtat tgaggatgac     720
tttactgcct ggagggaatc gctgtggccg gagctagatc agttattacg cgatgaggat     780
gatactacgg tttctacgcc gtataccgcc gcggtgctgg aatacagagt cgttttcat      840 gatccggcag atgccccaac tctcgaaaaa agctacagca acgctaacgg catagcgtg      900 gttgatgcgc aacatccgtt acgggcaaat gttgccgtca gacgggagtt gcatactcct     960
gcgtctgacc gctcatgtac ccatctggaa tttgatatat ctggtactgg catcgcatac    1020
gagacgggtg atcatgttgg cgtgtattgc gagaatcttg cagagacggt agaagaagcg    1080
ttggaacttt taggtctttc cccggataca tacttctccg tacacgcaga taagaggac    1140 ggtacgcctc tctcaggctc atctctcccg ccgccatttc caccgtgcac tttacgtaca    1200
gccctgacgt tacatgctga cttactgtct tccccaaaga aatctgcatt gctcgcgctt    1260
gcagctcatg catcagaccc cactgaagct gatcgattgc ggcacctagc aagccctgcg    1320

```
ggcaaggacg aatacgctca gtggatagtt gctagtcagc gttccttgct ggaagtgatg    1380
gcggagttcc ccagtgccaa gccccgctg ggagtattct tcgcatcggt tgctccaaga    1440
ttgcagcccc ggtactactc tatttcttct tccccaagaa tagcgccgtc tcgcatacac    1500
gtgacctgcg cgttagttta cgagaaaaca cctacgggca gagtacacaa aggagtttgc    1560
tccacttgga tgaaaaactc agtgccctct gaaaagagtg atgaatgttc atgggcacca    1620 atttcgtac gacagagcaa ctttaaactg cccgccgatg cgaaagtacc cataattatg     1680
attggtccag gaacgggtct ggcaccattt cgcggcttcc tccaggagcg gcttgcattg    1740
aaagaagcag ggacagaact gggaccttcc atattatttt ttgggtgccg caacagcaaa    1800
atggactata tatacgagga tgaactggat aattttgtac agaatggggc actctctgaa    1860
ctcgtgttgg cgttctcacg tgaaggtcct accaaagagt atgtgcaaca taagatgatg    1920
gagaaagcct cagatatatg gaaccttatt tcacagggag cttatttgta tgtgtgcggg    1980
gacgcaaaag gcatggcgcg tgatgtgcac cgcacgttac ataccatcgc tcaggagcag    2040
gggtcattag atagctcaaa agcagagagt atggtgaaga tcttcagat gtcaggcaga     2100 tacctgcgcg atgtctggta a                                              2121
```

<210> SEQ ID NO 84
<211> LENGTH: 277
<212> TYPE: PRT
<213> ORGANISM: Rhodococcus erythropolis

<400> SEQUENCE: 84

```
Met Ala Arg Val Glu Gly Gln Val Ala Leu Ile Thr Gly Ala Ala Arg
1               5                   10                  15

Gly Gln Gly Arg Ser His Ala Ile Lys Leu Ala Glu Gly Ala Asp
                20                  25                  30

Val Ile Leu Val Asp Val Pro Asn Asp Val Val Asp Ile Gly Tyr Pro
            35                  40                  45

Leu Gly Thr Ala Asp Glu Leu Asp Gln Thr Ala Lys Asp Val Glu Asn
        50                  55                  60

Leu Gly Arg Lys Ala Ile Val Ile His Ala Asp Val Arg Asp Leu Glu
65                  70                  75                  80

Ser Leu Thr Ala Glu Val Asp Arg Ala Val Ser Thr Leu Gly Arg Leu
                85                  90                  95

Asp Ile Val Ser Ala Asn Ala Gly Ile Ala Ser Val Pro Phe Leu Ser
            100                 105                 110

His Asp Ile Pro Asp Asn Thr Trp Arg Gln Met Ile Asp Ile Asn Leu
        115                 120                 125

Thr Gly Val Trp His Thr Ala Lys Val Ala Val Pro His Ile Leu Ala
    130                 135                 140

Gly Glu Arg Gly Gly Ser Ile Val Leu Thr Ser Ser Ala Ala Gly Leu
145                 150                 155                 160

Lys Gly Tyr Ala Gln Ile Ser His Tyr Ser Ala Ala Lys His Gly Val
                165                 170                 175

Val Gly Leu Met Arg Ser Leu Ala Leu Glu Leu Ala Pro His Arg Val
            180                 185                 190

Arg Val Asn Ser Leu His Pro Thr Gln Val Asn Thr Pro Met Ile Gln
        195                 200                 205

Asn Glu Gly Thr Tyr Arg Ile Phe Ser Pro Asp Leu Glu Asn Pro Thr
    210                 215                 220
```

```
Arg Glu Asp Phe Glu Ile Ala Ser Thr Thr Thr Asn Ala Leu Pro Ile
225                 230                 235                 240

Pro Trp Val Glu Ser Val Asp Val Ser Asn Ala Leu Leu Phe Leu Val
            245                 250                 255

Ser Glu Asp Ala Arg Tyr Ile Thr Gly Ala Ala Ile Pro Val Asp Ala
        260                 265                 270

Gly Thr Thr Leu Lys
        275

<210> SEQ ID NO 85
<211> LENGTH: 834
<212> TYPE: DNA
<213> ORGANISM: Rhodococcus erythropolis

<400> SEQUENCE: 85
atggcccgtg tggaaggtca agtggctctg attaccggcg ctgctcgtgg tcaaggtcgt      60
agtcatgcga ttaaactggc ggaagaaggc gcggatgtga ttctggttga cgtcccgaat     120
gatgtggttg acatcggcta tccgctgggt acggcagatg aactggacca gaccgctaaa     180
gatgttgaaa acctgggtcg taaggcgatt gtcatccatg ccgatgtgcg cgacctggaa     240
tcactgacgg cagaagtgga tcgtgctgtt agtaccctgg ccgcctggaa cattgtttcc     300
gcaaatgctg gtatcgccag cgtcccgttt ctgtctcacg atattccgga caacacctgg     360
cgtcagatga ttgatatcaa tctgacgggc gtctggcata ccgcgaaagt ggccgttccg     420
cacattctgg ccggtgaacg cggcggttcc atcgttctga ccagctctgc ggccggcctg     480
aaaggttatg cacaaattag tcattactcc gcagctaagc acggcgtcgt gggtctgatg     540
cgttcactgg cactggaact ggctccgcat cgtgtccgcg tgaactcgct gcacccgacg     600
caggtgaaca ccccgatgat tcaaaatgaa ggcacgtatc gtatctttag cccggatctg     660
gaaaacccga cccgcgaaga cttcgaaatt gcgtctacca cgaccaatgc cctgccgatc     720
ccgtgggtgg aatcagttga tgtctcgaac gcactgctgt tcctggttag cgaagacgca     780
cgttacatta ccggtgcagc aatcccggtg gatgccggta cgaccctgaa gtaa          834

<210> SEQ ID NO 86
<211> LENGTH: 280
<212> TYPE: PRT
<213> ORGANISM: Citrus sinensus

<400> SEQUENCE: 86

Met Ala Thr Pro Pro Ile Ser Ser Leu Ile Ser Gln Arg Leu Leu Gly
1               5                   10                  15

Lys Val Ala Leu Val Thr Gly Gly Ala Ser Gly Ile Gly Glu Gly Ile
            20                  25                  30

Val Arg Leu Phe His Arg His Gly Ala Lys Val Cys Phe Val Asp Val
        35                  40                  45

Gln Asp Glu Leu Gly Tyr Arg Leu Gln Glu Ser Leu Val Gly Asp Lys
    50                  55                  60

Asp Ser Asn Ile Phe Tyr Ser His Cys Asp Val Thr Val Glu Asp Asp
65                  70                  75                  80

Val Arg Arg Ala Val Asp Leu Thr Val Thr Lys Phe Gly Thr Leu Asp
                85                  90                  95

Ile Met Val Asn Asn Ala Gly Ile Ser Gly Thr Pro Ser Ser Asp Ile
            100                 105                 110

Arg Asn Val Asp Val Ser Glu Phe Glu Lys Val Phe Asp Ile Asn Val
        115                 120                 125
```

```
Lys Gly Val Phe Met Gly Met Lys Tyr Ala Ala Ser Val Met Ile Pro
    130                 135                 140

Arg Lys Gln Gly Ser Ile Ile Ser Leu Gly Ser Val Gly Ser Val Ile
145                 150                 155                 160

Gly Gly Ile Gly Pro His His Tyr Ile Ser Ser Lys His Ala Val Val
                165                 170                 175

Gly Leu Thr Arg Ser Ile Ala Ala Glu Leu Gly Gln His Gly Ile Arg
            180                 185                 190

Val Asn Cys Val Ser Pro Tyr Ala Val Pro Thr Asn Leu Ala Val Ala
        195                 200                 205

His Leu Pro Glu Asp Glu Arg Thr Glu Asp Met Phe Thr Gly Phe Arg
    210                 215                 220

Glu Phe Ala Lys Lys Asn Ala Asn Leu Gln Gly Val Glu Leu Thr Val
225                 230                 235                 240

Glu Asp Val Ala Asn Ala Val Leu Phe Leu Ala Ser Glu Asp Ala Arg
                245                 250                 255

Tyr Ile Ser Gly Asp Asn Leu Ile Val Asp Gly Gly Phe Thr Arg Val
            260                 265                 270

Asn His Ser Phe Arg Val Phe Arg
        275                 280

<210> SEQ ID NO 87
<211> LENGTH: 843
<212> TYPE: DNA
<213> ORGANISM: Citrus sinensus

<400> SEQUENCE: 87
atggcaacgc cgccgatttc atccctgatt tcacaacgcc tgctgggtaa agtcgccctg      60
gtcacgggtg gtgcttctgg tattggtgaa ggcatcgtgc gtctgtttca ccgtcatggc     120
gcgaaagtgt gctttgttga tgtgcaggat gaactgggct accgtctgca agaatctctg     180
gtgggcgaca aagattcaaa catctttat agccactgtg atgtcaccgt ggaagacgat     240
gtgcgccgcg ctgtggatct gaccgtgacg aaattcggta cgctggatat tatggtcaat     300
aacgcgggta ttagtggcac cccgtccagc gatattcgta tgttgatgt gagcgaattt     360 gaaaaagtgt ttgatattaa cgtcaaaggc gtgtttatgg gcatgaaata tgccgcgagc     420
gtgatgatcc cgcgcaaaca gggtagcatc atctccctgg gttctgttgg cagcgtgatc     480
ggtggcattg gcccgcacca ttatatcagc tcgaaacatg cggttgtggg cctgacccgc     540
agcattgcag cggaactggg tcagcatggc attcgtgtga actgtgtgtc tccgtatgcg     600
gttccgacca atctggcggt tgcacacctg ccggaagatg aacgtaccga agatatgttt     660
acgggcttcc gtgaatttgc gaaaaagaat gccaacctgc aaggtgttga actgaccgtc     720
gaagatgtgg ccaatgcggt gctgtttctg gccagcgaag atgcacgcta cattagcggt     780
gataatctga tcgttgatgg cggctttacc cgtgtgaacc actcatttcg tgttttccgt     840
taa                                                                    843

<210> SEQ ID NO 88
<211> LENGTH: 262
<212> TYPE: PRT
<213> ORGANISM: Citrus sinensus

<400> SEQUENCE: 88

Met Ser Lys Pro Arg Leu Gln Gly Lys Val Ala Ile Ile Met Gly Ala
1               5                   10                  15
```

Ala Ser Gly Ile Gly Glu Ala Thr Ala Lys Leu Phe Ala Glu His Gly
         20                  25                  30

Ala Phe Val Ile Ile Ala Asp Ile Gln Asp Glu Leu Gly Asn Gln Val
     35                  40                  45

Val Ser Ser Ile Gly Pro Glu Lys Ala Ser Tyr Arg His Cys Asp Val
 50                  55                  60

Arg Asp Glu Lys Gln Val Glu Thr Val Ala Tyr Ala Ile Glu Lys
 65                  70                  75                  80

Tyr Gly Ser Leu Asp Ile Met Tyr Ser Asn Ala Gly Val Ala Gly Pro
                 85                  90                  95

Val Gly Thr Ile Leu Asp Leu Asp Met Ala Gln Phe Asp Arg Thr Ile
            100                 105                 110

Ala Thr Asn Leu Ala Gly Ser Val Met Ala Val Lys Tyr Ala Ala Arg
        115                 120                 125

Val Met Val Ala Asn Lys Ile Arg Gly Ser Ile Ile Cys Thr Thr Ser
130                 135                 140

Thr Ala Ser Thr Val Gly Gly Ser Gly Pro His Ala Tyr Thr Ile Ser
145                 150                 155                 160

Lys His Gly Leu Leu Gly Leu Val Arg Ser Ala Ala Ser Glu Leu Gly
                165                 170                 175

Lys His Gly Ile Arg Val Asn Cys Val Ser Pro Phe Gly Val Ala Thr
            180                 185                 190

Pro Phe Ser Ala Gly Thr Ile Asn Asp Val Glu Gly Phe Val Cys Lys
        195                 200                 205

Val Ala Asn Leu Lys Gly Ile Val Leu Lys Ala Lys His Val Ala Glu
    210                 215                 220

Ala Ala Leu Phe Leu Ala Ser Asp Glu Ser Ala Tyr Val Ser Gly His
225                 230                 235                 240

Asp Leu Val Val Asp Gly Gly Phe Thr Ala Val Thr Asn Val Met Ser
                245                 250                 255

Met Leu Glu Gly His Gly
            260

<210> SEQ ID NO 89
<211> LENGTH: 789
<212> TYPE: DNA
<213> ORGANISM: Citrus sinensus

<400> SEQUENCE: 89
atgtcaaaac cgcgtctgca aggcaaagtg gctattatta tgggtgctgc gtctggcatc      60
ggtgaagcta cggctaaact gttcgctgaa catggcgcat ttgtgattat cgctgatatt     120
caggacgaac tgggcaacca ggtggttagc tctatcggcc cggaaaaagc gtcttatcgt     180
cactgcgatg tgcgtgatga aaaacaggtt gaagaaaccg tcgcgtatgc gattgaaaaa     240
tacggcagcc tggatattat gtactccaat gcgggcgtgg ccggtccggt tggcacgatt     300
ctggatctgg acatggccca attcgaccgt accatcgcaa cgaacctggc tggtagtgtt     360
atggcagtca aatatgcggc ccgtgtcatg gtggcgaata aaattcgcgg tagcattatc     420
tgtaccacga gtaccgcctc cacggtgggc ggcagcggcc cgcacgccta ccattagc       480 aaacacggtc tgctgggcct ggttcgttca gcagcttcgg aactgggtaa acatggcatc     540
cgcgtgaact gcgttagccc gtttggtgtt gcgaccccgt tctctgccgg tacgattaac     600
gatgtcgaag gctttgtctg taaagtggcg aatctgaaag catcgtcct gaaagcgaag      660 catgtggccg aagcggccct gttcctggca agcgatgaat ctgcttatgt gagcggtcac     720

```
gacctggtgg tggatggtgg ctttacggca gttacgaatg tcatgtcaat gctggaaggt    780
cacggctaa                                                            789
```

<210> SEQ ID NO 90
<211> LENGTH: 263
<212> TYPE: PRT
<213> ORGANISM: Citrus sinensus

<400> SEQUENCE: 90

```
Met Ser Asn Pro Arg Met Glu Gly Lys Val Ala Leu Ile Thr Gly Ala
1               5                   10                  15

Ala Ser Gly Ile Gly Glu Ala Ala Val Arg Leu Phe Ala Glu His Gly
            20                  25                  30

Ala Phe Val Val Ala Ala Asp Val Gln Asp Glu Leu Gly His Gln Val
        35                  40                  45

Ala Ala Ser Val Gly Thr Asp Gln Val Cys Tyr His His Cys Asp Val
    50                  55                  60

Arg Asp Glu Lys Gln Val Glu Glu Thr Val Arg Tyr Thr Leu Glu Lys
65                  70                  75                  80

Tyr Gly Lys Leu Asp Val Leu Phe Ser Asn Ala Gly Ile Met Gly Pro
                85                  90                  95

Leu Thr Gly Ile Leu Glu Leu Asp Leu Thr Gly Phe Gly Asn Thr Met
            100                 105                 110

Ala Thr Asn Val Cys Gly Val Ala Ala Thr Ile Lys His Ala Ala Arg
        115                 120                 125

Ala Met Val Asp Lys Asn Ile Arg Gly Ser Ile Cys Thr Thr Ser
    130                 135                 140

Val Ala Ser Ser Leu Gly Gly Thr Ala Pro His Ala Tyr Thr Thr Ser
145                 150                 155                 160

Lys His Ala Leu Val Gly Leu Val Arg Thr Ala Cys Ser Glu Leu Gly
                165                 170                 175

Ala Tyr Gly Ile Arg Val Asn Cys Ile Ser Pro Phe Gly Val Ala Thr
            180                 185                 190

Pro Leu Ser Cys Thr Ala Tyr Asn Leu Arg Pro Asp Glu Val Glu Ala
        195                 200                 205

Asn Ser Cys Ala Leu Ala Asn Leu Lys Gly Ile Val Leu Lys Ala Lys
    210                 215                 220

His Ile Ala Glu Ala Ala Leu Phe Leu Ala Ser Asp Glu Ser Ala Tyr
225                 230                 235                 240

Ile Ser Gly His Asn Leu Ala Val Asp Gly Gly Phe Thr Val Val Asn
                245                 250                 255

His Ser Ser Ser Ser Ala Thr
            260
```

<210> SEQ ID NO 91
<211> LENGTH: 792
<212> TYPE: DNA
<213> ORGANISM: Citrus sinensus

<400> SEQUENCE: 91

```
atgtcaaacc cgcgtatgga aggcaaagtc gcactgatta cgggcgcagc atctggtatc    60
ggtgaagcag cagtccgtct gttcgctgaa catggtgcgt ttgtcgtggc ggcagatgtg   120
caagacgaac tgggtcatca ggtggcggca tctgtgggta cggaccaggt gtgctaccat   180
cactgcgatg tgcgcgatga aaaacaagtg aagaaaccg tgcgttatac cctggaaaaa   240
```

```
tacggcaaac tggatgtcct gttttcaaac gcgggcatca tgggtccgct gaccggcatt    300
ctggaactgg atctgaccgg cttcggtaac acgatggcaa ccaatgtgtg cggtgttgcc    360
gcgaccatta aacacgcggc acgcgcaatg gtggacaaaa acattcgcgg tagcattatc    420
tgcaccacca gcgtggcttc atcgctgggt ggcaccgcgc cgcacgcata caccacgagc    480
aaacacgcac tggtgggcct ggttcgtacg gcatgttcgg aactgggtgc gtatggcatt    540
cgtgtgaact gtatcagccc gtttggtgtt gcaacgccgc tgtcttgcac ggcctataac    600
ctgcgcccgg atgaagtgga agcaaactca tgcgcactgg cgaacctgaa aggtattgtg    660
ctgaaagcga aacacattgc ggaagcagcg ctgttcctgg cgagcgatga aagcgcgtat    720
attagcggtc ataatctggc ggtggatggt ggtttcacgg tggttaatca ttcaagttcg    780
tcggcgacgt aa    792

<210> SEQ ID NO 92
<211> LENGTH: 278
<212> TYPE: PRT
<213> ORGANISM: Citrus sinensus

<400> SEQUENCE: 92

Met Thr Thr Ala Gly Ser Arg Asp Ser Pro Leu Val Ala Gln Arg Leu
1               5                   10                  15

Leu Gly Lys Val Ala Leu Val Thr Gly Gly Ala Thr Gly Ile Gly Glu
            20                  25                  30

Ser Ile Val Arg Leu Phe His Lys His Gly Ala Lys Val Cys Val Val
        35                  40                  45

Asp Ile Asn Asp Asp Leu Gly Gln His Leu Cys Gln Thr Leu Gly Pro
    50                  55                  60

Thr Thr Arg Phe Ile His Gly Asp Val Ala Ile Glu Asp Asp Val Ser
65                  70                  75                  80

Arg Ala Val Asp Phe Thr Val Ala Asn Phe Gly Thr Leu Asp Ile Met
                85                  90                  95

Val Asn Asn Ala Gly Met Gly Gly Pro Pro Cys Pro Asp Ile Arg Glu
            100                 105                 110

Phe Pro Ile Ser Thr Phe Glu Lys Val Phe Asp Ile Asn Thr Lys Gly
        115                 120                 125

Thr Phe Ile Gly Met Lys His Ala Ala Arg Val Met Ile Pro Ser Lys
    130                 135                 140

Lys Gly Ser Ile Val Ser Ile Ser Ser Val Thr Ser Ala Ile Gly Gly
145                 150                 155                 160

Ala Gly Pro His Ala Tyr Thr Ala Ser Lys His Ala Val Leu Gly Leu
                165                 170                 175

Thr Lys Ser Val Ala Ala Glu Leu Gly Gln His Gly Ile Arg Val Asn
            180                 185                 190

Cys Val Ser Pro Tyr Ala Ile Leu Thr Asn Leu Ala Leu Ala His Leu
        195                 200                 205

His Glu Asp Glu Arg Thr Asp Asp Ala Arg Ala Gly Phe Arg Ala Phe
    210                 215                 220

Ile Gly Lys Asn Ala Asn Leu Gln Gly Val Asp Leu Val Glu Asp Asp
225                 230                 235                 240

Val Ala Asn Ala Val Leu Phe Leu Ala Ser Asp Ala Arg Tyr Ile
                245                 250                 255
```

```
Ser Gly Asp Asn Leu Phe Val Asp Gly Gly Phe Thr Cys Thr Asn His
            260                 265                 270
Ser Leu Arg Val Phe Arg
        275

<210> SEQ ID NO 93
<211> LENGTH: 837
<212> TYPE: DNA
<213> ORGANISM: Citrus sinensus

<400> SEQUENCE: 93
atgacgacgg ctggttcgcg tgacagtccg ctggtcgctc aacgcctgct gggcaaagtg    60
gccctggtta cgggtggtgc taccggcatt ggtgaaagta tcgtgcgtct gtttcataaa   120
cacggcgcga aagtttgcgt tggttgatatt aacgatgacc tgggccagca tctgtgtcaa   180
accctgggtc cgaccacccg tttcattcac ggcgatgttg caatcgaaga tgatgtgagc   240
cgtgcggttg attttaccgt cgccaacttc ggtacgctgg acattatggt gaacaatgcc   300
ggtatgggcg gtccgccgtg cccggatatt cgtgaatttc cgatctcgac ctttgaaaaa   360
gtcttcgaca ttaacaccaa aggcacgttc atcggtatga acatgcggc cgcgtgatg    420 attccgagta aaaaaggtag tattgtcagc attagcagcg tgaccagcgc gattggcggc   480
gcgggtccgc acgcctatac cgcgagcaaa catgcggtgc tgggcctgac gaaatctgtc   540
gcggcggaac tgggccagca cggtattcgt gtcaactgtg tgtctccgta cgccatcctg   600
accaatctgg cgctggccca tctgcacgaa gatgaacgta cggatgacgc gcgtgcgggt   660
tttcgtgcat tcattggtaa aaacgctaat ctgcaaggtg ttgatctggt cgaagatgac   720
gtggcgaatg ccgttctgtt tctggcatca gatgacgctc gctatatctc gggcgataac   780
ctgttcgtgg atggcggctt cacctgtacc aatcactccc tgcgtgtgtt ccgttaa     837

<210> SEQ ID NO 94
<211> LENGTH: 280
<212> TYPE: PRT
<213> ORGANISM: Vitis vinifera

<400> SEQUENCE: 94

Met Ala Ala Thr Ser Ile Asp Asn Ser Pro Leu Pro Ser Gln Arg Leu
1               5                   10                  15
Leu Gly Lys Val Ala Leu Val Thr Gly Gly Ala Thr Gly Ile Gly Glu
            20                  25                  30
Ser Ile Val Arg Leu Phe Leu Lys Gln Gly Ala Lys Val Cys Ile Val
        35                  40                  45
Asp Val Gln Asp Asp Leu Gly Gln Lys Leu Cys Asp Thr Leu Gly Gly
    50                  55                  60
Asp Pro Asn Val Ser Phe His Cys Asp Val Thr Ile Glu Asp Asp
65                  70                  75                  80
Val Cys His Ala Val Asp Phe Thr Val Thr Lys Phe Gly Thr Leu Asp
                85                  90                  95
Ile Met Val Asn Asn Ala Gly Met Ala Gly Pro Pro Cys Ser Asp Ile
            100                 105                 110
Arg Asn Val Glu Val Ser Met Phe Glu Lys Val Phe Asp Val Asn Val
        115                 120                 125
Lys Gly Val Phe Leu Gly Met Lys His Ala Ala Arg Ile Met Ile Pro
    130                 135                 140
Leu Lys Lys Gly Thr Ile Ile Ser Leu Cys Ser Val Ser Ser Ala Ile
145                 150                 155                 160
```

Ala Gly Val Gly Pro His Ala Tyr Thr Gly Ser Lys Cys Ala Val Ala
            165                 170                 175

Gly Leu Thr Gln Ser Val Ala Ala Glu Met Gly Gly His Gly Ile Arg
            180                 185                 190

Val Asn Cys Ile Ser Pro Tyr Ala Ile Ala Thr Gly Leu Ala Leu Ala
            195                 200                 205

His Leu Pro Glu Asp Glu Arg Thr Glu Asp Ala Met Ala Gly Phe Arg
            210                 215                 220

Ala Phe Val Gly Lys Asn Ala Asn Leu Gln Gly Val Glu Leu Thr Val
225                 230                 235                 240

Asp Asp Val Ala His Ala Ala Val Phe Leu Ala Ser Asp Glu Ala Arg
            245                 250                 255

Tyr Ile Ser Gly Leu Asn Leu Met Leu Asp Gly Gly Phe Ser Cys Thr
            260                 265                 270

Asn His Ser Leu Arg Val Phe Arg
            275                 280

<210> SEQ ID NO 95
<211> LENGTH: 843
<212> TYPE: DNA
<213> ORGANISM: Vitis vinifera

<400> SEQUENCE: 95

```
atggccgcaa cgagcattga taattctccg ctgccgagtc aacgtctgct gggtaaagtc      60
gcactggtca cgggtggcgc tacgggtatt ggcgaaagca tcgtgcgtct gtttctgaaa     120
cagggtgcta agtgtgcat tgtggacgtg caagatgacc tgggccagaa actgtgcgat      180
accctgggtg gcgatccgaa cgttagcttt ttccattgcg atgtgaccat cgaagatgat     240
gtgtgccatg cagttgattt taccgtcacg aaattcggca ccctggatat tatggtgaac     300
aatgcgggta tggcaggtcc gccgtgctcg gacatccgca acgtggaagt cagcatgttt     360
gaaaaagtgt ttgatgtgaa tgtgaaaggt gttttcctgg catgaaaca tgcagcccgc      420
attatgattc cgctgaaaaa aggcaccatt atcagcctgt gttcagtttc agcgctatc      480
gcgggcgttg gtccgcacgc atatacgggt agcaaatgcg cagtggcggg tctgacgcaa     540
tcggtcgcag cagaaatggg tggtcatggc attcgcgtga actgtatcag cccgtatgca     600
atcgcaacgg gtctggcgct ggcacatctg ccggaagatg aacgcacgga agatgcaatg     660
gcgggttttc ccgtgcgtttgt gggtaaaaat gcgaatctgc aaggtgttga actgaccgtg     720
gatgatgtgg cgcacgcagc ggtgtttctg gcaagcgatg aagcacgtta catctctggt     780
ctgaatctga tgctggacgg cggcttttcg tgtaccaacc actcgctgcg tgtctttcgc     840
taa                                                                  843
```

<210> SEQ ID NO 96
<211> LENGTH: 279
<212> TYPE: PRT
<213> ORGANISM: Vitis vinifera

<400> SEQUENCE: 96

Met Ser Thr Ala Ser Ser Gly Asp Val Ser Leu Leu Ser Gln Arg Leu
1               5                   10                  15

Val Gly Lys Val Ala Leu Ile Thr Gly Gly Ala Thr Gly Ile Gly Glu
            20                  25                  30

Ser Ile Ala Arg Leu Phe Tyr Arg His Gly Ala Lys Val Cys Ile Val
            35                  40                  45

```
Asp Ile Gln Asp Asn Pro Gly Gln Asn Leu Cys Arg Glu Leu Gly Thr
 50                  55                  60

Asp Asp Ala Cys Phe Phe His Cys Asp Val Ser Ile Glu Ile Asp Val
 65                  70                  75                  80

Ile Arg Ala Val Asp Phe Val Val Asn Arg Phe Gly Lys Leu Asp Ile
                 85                  90                  95

Met Val Asn Asn Ala Gly Ile Ala Asp Pro Pro Cys Pro Asp Ile Arg
            100                 105                 110

Asn Thr Asp Leu Ser Ile Phe Glu Lys Val Phe Asp Val Asn Val Lys
            115                 120                 125

Gly Thr Phe Gln Cys Met Lys His Ala Ala Arg Val Met Val Pro Gln
130                 135                 140

Lys Lys Gly Ser Ile Ile Ser Leu Thr Ser Val Ala Ser Val Ile Gly
145                 150                 155                 160

Gly Ala Gly Pro His Ala Tyr Thr Gly Ser Lys His Ala Val Leu Gly
                165                 170                 175

Leu Thr Lys Ser Val Ala Ala Glu Leu Gly Leu His Gly Ile Arg Val
            180                 185                 190

Asn Cys Val Ser Pro Tyr Ala Val Pro Thr Gly Met Pro Leu Ala His
            195                 200                 205

Leu Pro Glu Ser Glu Lys Thr Glu Asp Ala Met Met Gly Met Arg Ala
210                 215                 220

Phe Val Gly Arg Asn Ala Asn Leu Gln Gly Ile Glu Leu Thr Val Asp
225                 230                 235                 240

Asp Val Ala Asn Ser Val Val Phe Leu Ala Ser Asp Glu Ala Arg Tyr
                245                 250                 255

Val Ser Gly Leu Asn Leu Met Leu Asp Gly Gly Phe Ser Cys Val Asn
            260                 265                 270

His Ser Leu Arg Val Phe Arg
            275

<210> SEQ ID NO 97
<211> LENGTH: 840
<212> TYPE: DNA
<213> ORGANISM: Vitis vinifera

<400> SEQUENCE: 97
atgtcaacgg cttcctcggg tgatgtgtcg ctgctgtcgc aacgcctggt cggtaaagtc      60
gctctgatta cgggtggtgc aacgggcatt ggtgaatcga ttgcgcgtct gttttaccgt     120
catggtgcga aagtgtgcat cgttgacatt caggataatc cgggtcaaaa cctgtgccgt     180
gaactgggca ccgacgatgc gtgcttcttt cactgcgatg tgagcattga aatcgatgtg     240
attcgtgctg ttgactttgt ggttaaccgc tttggtaaac tggacattat ggttaataac     300
gcgggcatcg cagatccgcc gtgcccggat attcgcaaca ccgatctgag cattttttgaa     360 aaagtgttcg atgtgaacgt gaaaggcacc tttcagtgta tgaaacacgc agcgcgcgtt     420
atggtgccgc agaaaaaagg tagcattatc agcctgacct cggtggcgag cgtgattggt     480
ggcgcgggtc cgcacgccta cgggtagc aaacacgcgg ttctgggtct gacgaaaagc     540
gttgcggcag aactgggtct gcatggtatt cgcgtgaact gtgtgagtcc gtatgcagtt     600
ccgacgggta tgccgctggc acatctgccg gaatcggaaa aaaccgaaga tgcgatgatg     660
ggtatgcgtg catttgtggg tcgtaatgcc aacctgcaag gtattgaact gaccgtggac     720
```
gatgtcgcaa atagcgtcgt gtttctggcg tcggatgaag cgcgttatgt tagcggtctg    780
aacctgatgc tggacggcgg cttctcgtgt gtcaaccact cgctgcgtgt gtttcgctaa    840

<210> SEQ ID NO 98
<211> LENGTH: 280
<212> TYPE: PRT
<213> ORGANISM: Citrus sinensus

<400> SEQUENCE: 98

Met Ser Asn Ser Asn Ser Thr Asp Ser Ser Pro Ala Val Gln Arg Leu
1               5                   10                  15

Val Gly Arg Val Ala Leu Ile Thr Gly Gly Ala Thr Gly Ile Gly Glu
            20                  25                  30

Ser Thr Val Arg Leu Phe His Lys His Gly Ala Lys Val Cys Ile Ala
        35                  40                  45

Asp Val Gln Asp Asn Leu Gly Gln Gln Val Cys Gln Ser Leu Gly Gly
    50                  55                  60

Glu Pro Asp Thr Phe Phe Cys His Cys Asp Val Thr Lys Glu Glu Asp
65                  70                  75                  80

Val Cys Ser Ala Val Asp Leu Thr Val Glu Lys Phe Gly Thr Leu Asp
                85                  90                  95

Ile Met Val Asn Asn Ala Gly Ile Ser Gly Ala Pro Cys Pro Asp Ile
            100                 105                 110

Arg Glu Ala Asp Leu Ser Glu Phe Glu Lys Val Phe Asp Ile Asn Val
        115                 120                 125

Lys Gly Val Phe His Gly Met Lys His Ala Ala Arg Ile Met Ile Pro
    130                 135                 140

Gln Thr Lys Gly Thr Ile Ile Ser Ile Cys Ser Val Ala Gly Ala Ile
145                 150                 155                 160

Gly Gly Leu Gly Pro His Ala Tyr Thr Gly Ser Lys His Ala Val Leu
                165                 170                 175

Gly Leu Asn Lys Asn Val Ala Ala Glu Leu Gly Lys Tyr Gly Ile Arg
            180                 185                 190

Val Asn Cys Val Ser Pro Tyr Ala Val Ala Thr Gly Leu Ala Leu Ala
        195                 200                 205

His Leu Pro Glu Glu Glu Arg Thr Glu Asp Ala Met Val Gly Phe Arg
    210                 215                 220

Asn Phe Val Ala Arg Asn Ala Asn Met Gln Gly Thr Glu Leu Thr Ala
225                 230                 235                 240

Asn Asp Val Ala Asn Ala Val Leu Phe Leu Ala Ser Asp Glu Ala Arg
                245                 250                 255

Tyr Ile Ser Gly Thr Asn Leu Met Val Asp Gly Gly Phe Thr Ser Val
            260                 265                 270

Asn His Ser Leu Arg Val Phe Arg
        275                 280

<210> SEQ ID NO 99
<211> LENGTH: 843
<212> TYPE: DNA
<213> ORGANISM: Citrus sinensus

<400> SEQUENCE: 99
atgtccaata gcaactctac ggattcgtcg ccggcagtcc aacgcctggt cggtcgtgtc     60
gccctgatta cggtggtgc aacgggtatt ggcgaaagca cggtgcgcct gtttcataaa    120
catggcgcga aagtgtgtat tgccgacgtt caggataacc tgggtcagca agtgtgtcag    180

```
agtctgggtg gcgaaccgga tacctttttc tgccattgtg atgtgacgaa agaagaagat    240
gtgtgtagcg cagttgatct gaccgtggaa aaatttggca ccctggacat tatggtgaac    300
aatgcgggta ttagcggcgc accgtgcccg gacattcgtg aagccgatct gagcgaattt    360
gaaaaagttt tcgacatcaa cgtgaaaggc gtgtttcacg gcatgaaaca tgcagcgcgt    420
attatgatcc cgcaaaccaa aggcaccatt atcagcattt gctccgtggc tggtgcgatt    480
ggtggcctgg gtccgcacgc atataccggc tccaaacatg cagtcctggg cctgaacaaa    540
aacgtggccg cggaactggg caaatacggt atccgtgtga attgcgtcag cccgtatgct    600
gttgccaccg gctggctct ggcacacctg ccggaagaag aacgtaccga agatgcaatg    660
gtgggctttc gtaattttgt ggcacgcaac gcgaatatgc aaggcaccga actgacggcg    720
aatgatgtgg caaacgcggt cctgtttctg gcctctgatg aagcccgtta tatcagcggc    780
acgaatctga tggtggatgg cggttttacc tcggtcaatc actcgctgcg tgtcttccgt    840
taa                                                                  843
```

```
<210> SEQ ID NO 100
<211> LENGTH: 282
<212> TYPE: PRT
<213> ORGANISM: Brachypodium distachyon

<400> SEQUENCE: 100
```

| | | | | | | | | | | | | | | | |
|---|---|---|---|---|---|---|---|---|---|---|---|---|---|---|---|
| Met | Ser | Ala | Ala | Ala | Val | Ser | Ser | Ser | Ser | Pro | Arg | Leu | Glu | | |
| 1 | | | | 5 | | | | | 10 | | | | | 15 | |
| Gly | Lys | Val | Ala | Leu | Val | Thr | Gly | Gly | Ala | Ser | Gly | Ile | Gly | Glu | Ala |
| | | | 20 | | | | | 25 | | | | | 30 | | |
| Ile | Val | Arg | Leu | Phe | Arg | Gln | His | Gly | Ala | Lys | Val | Cys | Ile | Ala | Asp |
| | | 35 | | | | | 40 | | | | | 45 | | | |
| Val | Gln | Asp | Glu | Ala | Gly | Gln | Gln | Val | Arg | Asp | Ser | Leu | Gly | Asp | Asp |
| | 50 | | | | | 55 | | | | | 60 | | | | |
| Ala | Gly | Thr | Asp | Val | Leu | Phe | Val | His | Cys | Asp | Val | Thr | Val | Glu | Glu |
| 65 | | | | | 70 | | | | | 75 | | | | | 80 |
| Asp | Val | Ser | Arg | Ala | Val | Asp | Ala | Ala | Ala | Glu | Lys | Phe | Gly | Thr | Leu |
| | | | | 85 | | | | | 90 | | | | | 95 | |
| Asp | Ile | Met | Val | Asn | Asn | Ala | Gly | Ile | Thr | Gly | Asp | Lys | Val | Thr | Asp |
| | | | 100 | | | | | 105 | | | | | 110 | | |
| Ile | Arg | Asn | Leu | Asp | Phe | Ala | Glu | Val | Arg | Lys | Val | Phe | Asp | Ile | Asn |
| | | 115 | | | | | 120 | | | | | 125 | | | |
| Val | His | Gly | Met | Leu | Leu | Gly | Met | Lys | His | Ala | Ala | Arg | Val | Met | Ile |
| | 130 | | | | | 135 | | | | | 140 | | | | |
| Pro | Gly | Lys | Lys | Gly | Ser | Ile | Val | Ser | Leu | Ala | Ser | Val | Ala | Ser | Val |
| 145 | | | | | 150 | | | | | 155 | | | | | 160 |
| Met | Gly | Gly | Met | Gly | Pro | His | Ala | Tyr | Thr | Ala | Ser | Lys | His | Ala | Val |
| | | | | 165 | | | | | 170 | | | | | 175 | |
| Val | Gly | Leu | Thr | Lys | Ser | Val | Ala | Leu | Glu | Leu | Gly | Lys | His | Gly | Ile |
| | | | 180 | | | | | 185 | | | | | 190 | | |
| Arg | Val | Asn | Cys | Val | Ser | Pro | Tyr | Ala | Val | Pro | Thr | Ala | Leu | Ser | Met |
| | | 195 | | | | | 200 | | | | | 205 | | | |
| Pro | His | Leu | Pro | Gln | Gly | Glu | His | Lys | Gly | Asp | Ala | Val | Arg | Asp | Phe |
| | 210 | | | | | 215 | | | | | 220 | | | | |
| Leu | Ala | Phe | Val | Gly | Gly | Glu | Ala | Asn | Leu | Lys | Gly | Val | Asp | Leu | Leu |
| 225 | | | | | 230 | | | | | 235 | | | | | 240 |
| Pro | Lys | Asp | Val | Ala | Gln | Ala | Val | Leu | Tyr | Leu | Ala | Ser | Asp | Glu | Ala |
| | | | | 245 | | | | | 250 | | | | | 255 | |

Arg Tyr Ile Ser Ala Leu Asn Leu Val Val Asp Gly Gly Phe Thr Ser
            260                 265                 270

Val Asn Pro Asn Leu Lys Ala Phe Glu Asp
        275                 280

<210> SEQ ID NO 101
<211> LENGTH: 849
<212> TYPE: DNA
<213> ORGANISM: Brachypodium distachyon

<400> SEQUENCE: 101
atgtccgctg ctgccgccgt gtcctcctca tcgtcgccgc gtctggaagg caaagtcgct      60
ctggttacgg gtggtgcgtc aggtatcggc gaagccattg tgcgcctgtt ccgtcaacat     120
ggtgccaaag tgtgtatcgc ggatgtccaa gacgaagcgg ccaacaggt ccgtgatagc     180 ctgggtgacg atgccggtac ggatgtgctg tttgtgcatt gcgacgttac cgtggaagaa     240
gatgtgtcac gcgcggtgga tgccgctgcg gaaaaattcg gcaccctgga cattatggtg     300
aacaacgcag gtattacggg cgacaaagtg acgacattc gcaacctgga tttcgctgaa     360
gtccgtaaag tgttcgacat caatgtgcac ggtatgctgc tgggcatgaa acatgcggcc     420
cgcgtgatga ttccgggtaa aaaaggctcg attgtgagcc tggcatcggt cgcaagcgtt     480
atgggtggta tgggtccgca cgcatatacc gcaagcaaac acgcggttgt gggtctgacg     540
aaaagcgttg cactggaact gggcaaacat ggtattcgtg tcaactgtgt gagcccgtat     600
gcagttccga ccgcactgtc aatgccgcac ctgccgcagg gcgaacataa aggtgatgcg     660
gtgcgtgatt tcctggcgtt tgttggcggt gaagcgaatc tgaaaggtgt cgatctgctg     720
ccgaaagatg ttgcacaggc ggttctgtat ctggcaagcg acgaagcgcg ctatatttct     780
gcgctgaatc tggtggttga tggcggtttt acgagcgtga atccgaatct gaaagcattt     840
gaagactaa                                                              849

<210> SEQ ID NO 102
<211> LENGTH: 267
<212> TYPE: PRT
<213> ORGANISM: Zingiber zerumbet

<400> SEQUENCE: 102

Met Arg Leu Glu Gly Lys Val Ala Leu Val Thr Gly Gly Ala Ser Gly
1               5                   10                  15

Ile Gly Glu Ser Ile Ala Arg Leu Phe Ile Glu His Gly Ala Lys Ile
            20                  25                  30

Cys Ile Val Asp Val Gln Asp Glu Leu Gly Gln Gln Val Ser Gln Arg
        35                  40                  45

Leu Gly Gly Asp Pro His Ala Cys Tyr Phe His Cys Asp Val Thr Val
    50                  55                  60

Glu Asp Asp Val Arg Arg Ala Val Asp Phe Thr Ala Glu Lys Tyr Gly
65                  70                  75                  80

Thr Ile Asp Ile Met Val Asn Asn Ala Gly Ile Thr Gly Asp Lys Val
                85                  90                  95

Ile Asp Ile Arg Asp Ala Asp Phe Asn Glu Phe Lys Lys Val Phe Asp
            100                 105                 110

Ile Asn Val Asn Gly Val Phe Leu Gly Met Lys His Ala Ala Arg Ile
        115                 120                 125

Met Ile Pro Lys Met Lys Gly Ser Ile Val Ser Leu Ala Ser Val Ser
    130                 135                 140

```
Ser Val Ile Ala Gly Ala Gly Pro His Gly Tyr Thr Gly Ala Lys His
145                 150                 155                 160

Ala Val Val Gly Leu Thr Lys Ser Val Ala Glu Leu Gly Arg His
                165                 170                 175

Gly Ile Arg Val Asn Cys Val Ser Pro Tyr Ala Val Pro Thr Arg Leu
            180                 185                 190

Ser Met Pro Tyr Leu Pro Glu Ser Glu Met Gln Glu Asp Ala Leu Arg
        195                 200                 205

Gly Phe Leu Thr Phe Val Arg Ser Asn Ala Asn Leu Lys Gly Val Asp
    210                 215                 220

Leu Met Pro Asn Asp Val Ala Glu Ala Val Leu Tyr Leu Ala Thr Glu
225                 230                 235                 240

Glu Ser Lys Tyr Val Ser Gly Leu Asn Leu Val Ile Asp Gly Gly Phe
                245                 250                 255

Ser Ile Ala Asn His Thr Leu Gln Val Phe Glu
            260                 265

<210> SEQ ID NO 103
<211> LENGTH: 804
<212> TYPE: DNA
<213> ORGANISM: Zingiber zerumbet

<400> SEQUENCE: 103
```

| | | | | | |
|---|---|---|---|---|---|
| atgcgtctgg | aaggcaaagt | ggctctggtc | acgggcggtg | cgtcgggtat | tggcgaatct | 60 |
| attgctcgtc | tgtttattga | acacggtgca | aaaatttgca | tcgtggatgt | ccaggatgaa | 120 |
| ctgggtcaac | aggtctctca | gcgtctgggt | ggcgatccgc | acgcctgtta | tttccactgt | 180 |
| gatgtgaccg | tggaagatga | cgttcgtcgc | gcggtggatt | ttacggcgga | aaaatatggc | 240 |
| accattgaca | ttatggttaa | caatgcgggc | attacgggcg | ataaagtgat | cgatattcgt | 300 |
| gatgcggatt | tcaacgaatt | taaaaaagtg | ttcgacatta | acgtgaatgg | tgtcttttctg | 360 |
| ggcatgaaac | acgcagcgcg | tattatgatc | ccgaaaatga | aggctccat | cgtttcgctg | 420 |
| gcgtccgtta | gctcggtgat | tgctggtgca | ggtccgcatg | gctataccgg | cgcaaaacat | 480 |
| gcggttgtgg | gtctgaccaa | aagcgttgca | gccgaactgg | gtcgtcatgg | tattcgcgtg | 540 |
| aactgcgttt | cgccgtatgc | ggtgccgacg | cgcctgtcaa | tgccgtatct | gccggaatcg | 600 |
| gaaatgcagg | aagatgcact | gcgcggcttt | ctgacctttg | tgcgtagcaa | tgcgaacctg | 660 |
| aaaggcgttg | atctgatgcc | gaatgatgtg | gcggaagctg | ttctgtatct | ggcgaccgaa | 720 |
| gaaagcaaat | atgtttcagg | tctgaatctg | gttattgacg | gcggcttctc | catcgctaat | 780 |
| cataccctgc | aagtgtttga | ataa | | | | 804 |

<210> SEQ ID NO 104
<211> LENGTH: 505
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 104

```
Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
                20                  25                  30

Arg Ser Gln Ser Asn Arg Leu Pro Arg Val Pro Glu Val Pro Gly Val
            35                  40                  45
```

```
Pro Leu Leu Gly Asn Leu Leu Gln Leu Lys Glu Lys Pro Tyr Met
     50                  55                  60
Thr Phe Thr Arg Trp Ala Ala Thr Tyr Gly Pro Ile Tyr Ser Ile Lys
 65                  70                  75                  80
Thr Gly Ala Thr Ser Met Val Val Ser Ser Asn Glu Ile Ala Lys
                 85                  90                  95
Glu Ala Leu Val Thr Arg Phe Gln Ser Ile Ser Thr Arg Asn Leu Ser
                100                 105                 110
Lys Ala Leu Lys Val Leu Thr Ala Asp Lys Thr Met Val Ala Met Ser
            115                 120                 125
Asp Tyr Asp Asp Tyr His Lys Thr Val Lys Arg His Ile Leu Thr Ala
130                 135                 140
Val Leu Gly Pro Asn Ala Gln Lys Lys His Arg Ile His Arg Asp Ile
145                 150                 155                 160
Met Met Asp Asn Ile Ser Thr Gln Leu His Glu Phe Val Lys Asn Asn
                165                 170                 175
Pro Glu Gln Glu Glu Val Asp Leu Arg Lys Ile Phe Gln Ser Glu Leu
                180                 185                 190
Phe Gly Leu Ala Met Arg Gln Ala Leu Gly Lys Asp Val Glu Ser Leu
            195                 200                 205
Tyr Val Glu Asp Leu Lys Ile Thr Met Asn Arg Asp Glu Ile Leu Gln
210                 215                 220
Val Leu Val Val Asp Pro Met Met Gly Ala Ile Asp Val Asp Trp Arg
225                 230                 235                 240
Asp Phe Phe Pro Tyr Leu Lys Trp Val Pro Asn Lys Lys Phe Glu Asn
                245                 250                 255
Thr Ile Gln Gln Met Tyr Ile Arg Arg Glu Ala Val Met Lys Ser Leu
            260                 265                 270
Ile Lys Glu Gln Lys Lys Arg Ile Ala Ser Gly Glu Lys Leu Asn Ser
        275                 280                 285
Tyr Ile Asp Tyr Leu Leu Ser Glu Ala Gln Thr Leu Thr Asp Gln Gln
290                 295                 300
Leu Leu Met Ser Leu Trp Glu Pro Ile Ile Glu Ser Ser Asp Thr Thr
305                 310                 315                 320
Met Val Thr Thr Glu Trp Ala Met Tyr Glu Leu Ala Lys Asn Pro Lys
                325                 330                 335
Leu Gln Asp Arg Leu Tyr Arg Asp Ile Lys Ser Val Cys Gly Ser Glu
            340                 345                 350
Lys Ile Thr Glu Glu His Leu Ser Gln Leu Pro Tyr Ile Thr Ala Ile
        355                 360                 365
Phe His Glu Thr Leu Arg Lys His Ser Pro Val Pro Ile Ile Pro Leu
370                 375                 380
Arg His Val His Glu Asp Thr Gln Leu Gly Gly Tyr His Val Pro Ala
385                 390                 395                 400
Gly Thr Glu Leu Ala Val Asn Ile Tyr Gly Cys Asn Met Asp Lys Asn
                405                 410                 415
Val Trp Glu Asn Pro Glu Glu Trp Asn Pro Glu Arg Phe Met Lys Glu
            420                 425                 430
Asn Glu Thr Ala Asp Phe Gln Lys Thr Met Ala Phe Gly Gly Gly Lys
        435                 440                 445
Arg Val Cys Ala Gly Ser Leu Gln Ala Leu Leu Thr Ala Ser Ile Gly
450                 455                 460
```

Ile Gly Arg Met Val Gln Glu Phe Glu Trp Lys Leu Lys Asp Met Asp
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
            500                 505

<210> SEQ ID NO 105
<211> LENGTH: 505
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 105

Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
            20                  25                  30

Arg Ser Gln Ser Asn His Leu Pro Arg Val Pro Glu Val Pro Gly Val
        35                  40                  45

Pro Leu Leu Gly Asn Leu Leu Gln Leu Lys Glu Lys Lys Pro Tyr Met
    50                  55                  60

Thr Phe Thr Lys Trp Ala Ala Thr Tyr Gly Pro Ile Tyr Ser Ile Lys
65                  70                  75                  80

Thr Gly Ala Thr Ser Val Val Val Ser Ser Asn Glu Ile Ala Lys
            85                  90                  95

Glu Ala Leu Val Thr Arg Phe Gln Ser Ile Ser Thr Arg Asn Leu Ser
            100                 105                 110

Lys Ala Leu Lys Val Leu Thr Ala Asp Lys Gln Met Val Ala Met Ser
            115                 120                 125

Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
        195                 200                 205

Tyr Val Glu Asp Leu Lys Ile Thr Met Asn Arg Asp Glu Ile Leu Gln
    210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu Gln Lys Arg Ile Ala Ser Gly Glu Lys Leu Asn Ser
            275                 280                 285

Tyr Ile Asp Tyr Leu Leu Ser Glu Ala Gln Thr Leu Thr Asp Gln Gln
    290                 295                 300

Leu Leu Met Ser Leu Trp Glu Pro Ile Ile Glu Ser Ser Asp Thr Thr
305                 310                 315                 320

```
Met Val Thr Thr Glu Trp Ala Met Tyr Glu Leu Ala Lys Asn Pro Lys
            325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
            355                 360                 365

Phe His Glu Thr Leu Arg Lys His Ser Pro Val Pro Ile Leu Pro Leu
            370                 375                 380

Arg His Val His Glu Asp Thr Val Leu Gly Tyr His Val Pro Ala
385                 390                 395                 400

Gly Thr Glu Leu Ala Val Asn Ile Tyr Gly Cys Asn Met Asp Lys Asn
            405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
            435                 440                 445

Arg Val Cys Ala Gly Ser Leu Gln Ala Leu Leu Ile Ala Ser Ile Gly
            450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
            485                 490                 495

Leu Arg Ala Ile Ile Lys Pro Arg Ile
            500                 505

<210> SEQ ID NO 106
<211> LENGTH: 501
<212> TYPE: PRT
<213> ORGANISM: Artificial Sequence
<220> FEATURE:
<223> OTHER INFORMATION: Synthetic - Engineered valencene oxidase
     variant

<400> SEQUENCE: 106

Met Ala Leu Leu Leu Ala Val Phe Ala Val Ala Leu Ala Val Ala Leu
1               5                   10                  15

Ile Phe Trp Tyr Leu Lys Ser Tyr Thr Ser Ala Arg Arg Ser Gln Ser
            20                  25                  30

Asn His Leu Pro Arg Val Pro Glu Val Pro Gly Val Pro Leu Leu Gly
            35                  40                  45

Asn Leu Leu Gln Leu Lys Glu Lys Lys Pro Tyr Met Thr Phe Thr Arg
            50                  55                  60

Trp Ala Ala Thr Tyr Gly Pro Ile Tyr Ser Ile Lys Thr Gly Ala Thr
65                  70                  75                  80

Ser Met Val Val Val Ser Ser Asn Glu Ile Ala Lys Glu Ala Leu Val
            85                  90                  95

Thr Arg Phe Gln Ser Ile Ser Thr Arg Asn Leu Ser Lys Ala Leu Lys
            100                 105                 110

Val Leu Thr Ala Asp Lys Thr Met Val Ala Met Ser Asp Tyr Asp Asp
            115                 120                 125

Tyr His Lys Thr Val Lys Arg His Ile Leu Thr Ala Val Leu Gly Pro
            130                 135                 140

Asn Ala Gln Lys Lys His Arg Ile His Arg Asp Ile Met Met Asp Asn
145                 150                 155                 160

Ile Ser Thr Gln Leu His Glu Phe Val Lys Asn Asn Pro Glu Gln Glu
            165                 170                 175
```

```
Glu Val Asp Leu Arg Lys Ile Phe Gln Ser Glu Leu Phe Gly Leu Ala
                180                 185                 190

Met Arg Gln Ala Leu Gly Lys Asp Val Glu Ser Leu Tyr Val Glu Asp
            195                 200                 205

Leu Lys Ile Thr Met Asn Arg Asp Glu Ile Phe Gln Val Leu Val Val
        210                 215                 220

Asp Pro Met Met Gly Ala Ile Asp Val Asp Trp Arg Asp Phe Phe Pro
225                 230                 235                 240

Tyr Leu Lys Trp Val Pro Asn Lys Lys Phe Glu Asn Thr Ile Gln Gln
                245                 250                 255

Met Tyr Ile Arg Arg Glu Ala Val Met Lys Ser Leu Ile Lys Glu His
            260                 265                 270

Lys Lys Arg Ile Ala Ser Gly Glu Lys Leu Asn Ser Tyr Ile Asp Tyr
        275                 280                 285

Leu Leu Ser Glu Ala Gln Thr Leu Thr Asp Gln Gln Leu Leu Met Ser
        290                 295                 300

Leu Trp Glu Pro Ile Ile Glu Ser Ser Asp Thr Thr Met Val Thr Thr
305                 310                 315                 320

Glu Trp Ala Met Tyr Glu Leu Ala Lys Asn Pro Lys Leu Gln Asp Arg
                325                 330                 335

Leu Tyr Arg Asp Ile Lys Ser Val Cys Gly Ser Glu Lys Ile Thr Glu
            340                 345                 350

Glu His Leu Ser Gln Leu Pro Tyr Ile Thr Ala Ile Phe His Glu Thr
        355                 360                 365

Leu Arg Arg His Ser Pro Val Pro Ile Ile Pro Leu Arg His Val His
        370                 375                 380

Glu Asp Thr Val Leu Gly Gly Tyr His Val Pro Ala Gly Thr Glu Leu
385                 390                 395                 400

Ala Val Asn Ile Tyr Gly Cys Asn Met Asp Lys Asn Val Trp Glu Asn
                405                 410                 415

Pro Glu Glu Trp Asn Pro Glu Arg Phe Met Lys Glu Asn Glu Thr Ile
            420                 425                 430

Asp Phe Gln Lys Thr Met Ala Phe Gly Gly Gly Lys Arg Val Cys Ala
        435                 440                 445

Gly Ser Leu Gln Ala Leu Leu Thr Ala Ser Ile Gly Ile Gly Arg Met
450                 455                 460

Val Gln Glu Phe Glu Trp Lys Leu Lys Asp Met Thr Gln Glu Glu Val
465                 470                 475                 480

Asn Thr Ile Gly Leu Thr Thr Gln Met Leu Arg Pro Leu Arg Ala Ile
                485                 490                 495

Ile Lys Pro Arg Ile
            500

<210> SEQ ID NO 107
<211> LENGTH: 501
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 107

Met Ala Leu Leu Leu Ala Val Phe Ala Val Ala Leu Ala Val Ala Leu
1               5                   10                  15

Ile Phe Trp Tyr Leu Lys Ser Tyr Thr Ser Ala Arg Arg Ser Gln Ser
            20                  25                  30
```

Asn His Leu Pro Arg Val Pro Glu Val Pro Gly Val Pro Leu Leu Gly
         35                  40                  45

Asn Leu Leu Gln Leu Lys Glu Lys Pro Tyr Met Thr Phe Thr Arg
 50                  55                  60

Trp Ala Ala Thr Tyr Gly Pro Ile Tyr Ser Ile Lys Thr Gly Ala Thr
 65                  70                  75                  80

Ser Met Val Val Val Ser Ser Asn Glu Ile Ala Lys Glu Ala Leu Val
                 85                  90                  95

Thr Arg Phe Gln Ser Ile Ser Thr Arg Asn Leu Ser Lys Ala Leu Lys
                100                 105                 110

Val Leu Thr Ala Asp Lys Thr Met Val Ala Met Ser Asp Tyr Asp Asp
            115                 120                 125

Tyr His Lys Thr Val Lys Arg His Ile Leu Thr Ala Val Leu Gly Pro
        130                 135                 140

Asn Ala Gln Lys Lys His Arg Ile His Arg Asp Ile Met Met Asp Asn
145                 150                 155                 160

Ile Ser Thr Gln Leu His Glu Phe Val Lys Asn Asn Pro Glu Gln Glu
                165                 170                 175

Glu Val Asp Leu Arg Lys Ile Phe Gln Ser Glu Leu Phe Gly Leu Ala
            180                 185                 190

Met Arg Gln Ala Leu Gly Lys Asp Val Glu Ser Leu Tyr Val Glu Asp
        195                 200                 205

Leu Lys Ile Thr Met Asn Arg Asp Glu Ile Phe Gln Val Leu Val Val
        210                 215                 220

Asp Pro Met Met Gly Ala Ile Asp Val Asp Trp Arg Asp Phe Phe Pro
225                 230                 235                 240

Tyr Leu Lys Trp Val Pro Asn Lys Lys Phe Glu Asn Thr Ile Gln Gln
                245                 250                 255

Met Tyr Ile Arg Arg Glu Ala Val Met Lys Ser Leu Ile Lys Glu His
                260                 265                 270

Lys Lys Arg Ile Ala Ser Gly Glu Lys Leu Asn Ser Tyr Ile Asp Tyr
        275                 280                 285

Leu Leu Ser Glu Ala Gln Thr Leu Thr Asp Gln Gln Leu Leu Met Ser
290                 295                 300

Leu Trp Glu Pro Ile Ile Glu Ser Ser Asp Thr Thr Met Val Thr Thr
305                 310                 315                 320

Glu Trp Ala Met Tyr Glu Leu Ala Lys Asn Pro Lys Leu Gln Asp Arg
                325                 330                 335

Leu Tyr Arg Asp Ile Lys Ser Val Cys Gly Ser Glu Lys Ile Thr Glu
            340                 345                 350

Glu His Leu Ser Gln Leu Pro Tyr Ile Thr Ala Ile Phe His Glu Thr
        355                 360                 365

Leu Arg Arg His Ser Pro Val Pro Ile Ile Pro Leu Arg His Val His
        370                 375                 380

Glu Asp Thr Val Leu Gly Gly Tyr His Val Pro Ala Gly Thr Glu Leu
385                 390                 395                 400

Ala Val Asn Ile Tyr Gly Cys Asn Met Asp Lys Asn Val Trp Glu Asn
                405                 410                 415

Pro Glu Glu Trp Asn Pro Glu Arg Phe Met Lys Glu Asn Glu Thr Ile
            420                 425                 430

Asp Phe Gln Lys Thr Met Ala Phe Gly Gly Gly Lys Arg Val Cys Ala
        435                 440                 445

```
Gly Ser Leu Gln Ala Leu Leu Thr Ala Ser Ile Gly Ile Gly Arg Met
    450                 455                 460

Val Gln Glu Phe Glu Trp Lys Leu Lys Asp Met Thr Gln Glu Glu Val
465                 470                 475                 480

Asn Thr Ile Gly Leu Thr Asn Gln Met Leu Arg Pro Leu Arg Ala Ile
                485                 490                 495

Ile Lys Pro Arg Ile
            500

<210> SEQ ID NO 108
<211> LENGTH: 513
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 108

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
                20                  25                  30

Leu Lys Ser Tyr Thr Ser Ala Arg Arg Ser Gln Ser Asn His Leu Pro
            35                  40                  45

Arg Val Pro Glu Val Pro Gly Val Pro Leu Leu Gly Asn Leu Leu Gln
        50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
                100                 105                 110

Ser Ile Ser Thr Arg Asn Leu Ser Lys Ala Leu Lys Val Leu Thr Ala
            115                 120                 125

Asp Lys Thr Met Val Ala Met Ser Asp Tyr Asp Asp Tyr His Lys Thr
130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
    290                 295                 300
```

```
Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
            325                 330                 335

Tyr Glu Leu Ala Lys Asn Pro Lys Leu Gln Asp Arg Leu Tyr Arg Asp
                340                 345                 350

Ile Lys Ser Val Cys Gly Ser Glu Lys Ile Thr Glu His Leu Ser
            355                 360                 365

Gln Leu Pro Tyr Ile Thr Ala Ile Phe His Glu Thr Leu Arg Arg His
        370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
                420                 425                 430

Asn Pro Glu Arg Phe Met Lys Glu Asn Glu Thr Ile Asp Phe Gln Lys
            435                 440                 445

Thr Met Ala Phe Gly Gly Gly Lys Arg Val Cys Ala Gly Ser Leu Gln
    450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Val Asn Thr Ile Gly
                485                 490                 495

Leu Thr Thr Gln Met Leu Arg Pro Leu Arg Ala Ile Ile Lys Pro Arg
                500                 505                 510

Ile

<210> SEQ ID NO 109
<211> LENGTH: 513
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 109

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
                20                  25                  30

Leu Lys Ser Tyr Thr Ser Ala Arg Arg Ser Gln Ser Asn His Leu Pro
            35                  40                  45

Arg Val Pro Glu Val Pro Gly Val Pro Leu Leu Gly Asn Leu Leu Gln
        50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
                100                 105                 110

Ser Ile Ser Thr Arg Asn Leu Ser Lys Ala Leu Lys Val Leu Thr Ala
            115                 120                 125

Asp Lys Thr Met Val Ala Met Ser Asp Tyr Asp Asp Tyr His Lys Thr
        130                 135                 140
```

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
            165                 170                 175

Leu His Glu Phe Val Lys Asn Asn Pro Glu Gln Glu Glu Val Asp Leu
        180                 185                 190

Arg Lys Ile Phe Gln Ser Glu Leu Phe Gly Leu Ala Met Arg Gln Ala
    195                 200                 205

Leu Gly Lys Asp Val Glu Ser Leu Tyr Val Glu Asp Leu Lys Ile Thr
210                 215                 220

Met Asn Arg Asp Glu Ile Phe Gln Val Leu Val Asp Pro Met Met
225                 230                 235                 240

Gly Ala Ile Asp Val Asp Trp Arg Asp Phe Phe Pro Tyr Leu Lys Trp
            245                 250                 255

Val Pro Asn Lys Lys Phe Glu Asn Thr Ile Gln Gln Met Tyr Ile Arg
        260                 265                 270

Arg Glu Ala Val Met Lys Ser Leu Ile Lys Glu His Lys Lys Arg Ile
    275                 280                 285

Ala Ser Gly Glu Lys Leu Asn Ser Tyr Ile Asp Tyr Leu Leu Ser Glu
290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
            325                 330                 335

Tyr Glu Leu Ala Lys Asn Pro Lys Leu Gln Asp Arg Leu Tyr Arg Asp
        340                 345                 350

Ile Lys Ser Val Cys Gly Ser Glu Lys Ile Thr Glu Glu His Leu Ser
    355                 360                 365

Gln Leu Pro Tyr Ile Thr Ala Ile Phe His Glu Thr Leu Arg Arg His
370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
            405                 410                 415

Tyr Gly Cys Asn Met Asp Lys Asn Val Trp Glu Asn Pro Glu Glu Trp
        420                 425                 430

Asn Pro Glu Arg Phe Met Lys Glu Asn Glu Thr Ile Asp Phe Gln Lys
    435                 440                 445

Thr Met Ala Phe Gly Gly Gly Lys Arg Val Cys Ala Gly Ser Leu Gln
450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
            485                 490                 495

Leu Thr Asn Gln Met Leu Arg Pro Leu Arg Ala Ile Ile Lys Pro Arg
        500                 505                 510

Ile

<210> SEQ ID NO 110
<211> LENGTH: 513
<212> TYPE: PRT
<213> ORGANISM: Artificial Sequence
<220> FEATURE:
<223> OTHER INFORMATION: Synthetic - Engineered valencene oxidase
      variant

```
<400> SEQUENCE: 110

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn Arg Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Leu Gln Val Leu Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu Gln Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Lys His
    370                 375                 380

Ser Pro Val Pro Ile Ile Pro Leu Arg His Val His Glu Asp Thr Gln
385                 390                 395                 400

Leu Gly Gly Tyr His Val Pro Ala Gly Thr Glu Leu Ala Val Asn Ile
                405                 410                 415
```

```
Tyr Gly Cys Asn Met Asp Lys Asn Val Trp Glu Asn Pro Glu Glu Trp
                420                 425                 430

Asn Pro Glu Arg Phe Met Lys Glu Asn Glu Thr Ala Asp Phe Gln Lys
            435                 440                 445

Thr Met Ala Phe Gly Gly Lys Arg Val Cys Ala Gly Ser Leu Gln
450                 455                 460

Ala Leu Leu Thr Ala Ser Ile Gly Ile Gly Arg Met Val Gln Glu Phe
465                 470                 475                 480

Glu Trp Lys Leu Lys Asp Met Asp Gln Glu Val Asn Thr Ile Gly
                485                 490                 495

Leu Thr Asn Gln Met Leu Arg Pro Leu Arg Ala Ile Ile Lys Pro Arg
                500                 505                 510

Ile
```

<210> SEQ ID NO 111
<211> LENGTH: 513
<212> TYPE: PRT
<213> ORGANISM: Artificial Sequence
<220> FEATURE:
<223> OTHER INFORMATION: Synthetic - Engineered valencene oxidase variant

<400> SEQUENCE: 111

```
Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
                20                  25                  30

Leu Lys Ser Tyr Thr Ser Ala Arg Arg Ser Gln Ser Asn His Leu Pro
            35                  40                  45

Arg Val Pro Glu Val Pro Gly Val Pro Leu Leu Gly Asn Leu Leu Gln
        50                  55                  60

Leu Lys Glu Lys Lys Pro Tyr Met Thr Phe Thr Lys Trp Ala Ala Thr
65                  70                  75                  80

Tyr Gly Pro Ile Tyr Ser Ile Lys Thr Gly Ala Thr Ser Val Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Gln Met Val Ala Met Ser Asp Tyr Asp Tyr His Lys Thr
130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Leu Gln Val Leu Val Asp Pro Met Met
225                 230                 235                 240

Gly Ala Ile Asp Val Asp Trp Arg Asp Phe Phe Pro Tyr Leu Lys Trp
                245                 250                 255
```

-continued

```
Val Pro Asn Lys Lys Phe Glu Asn Thr Ile Gln Gln Met Tyr Ile Arg
            260                 265                 270

Arg Glu Ala Val Met Lys Ser Leu Ile Lys Gln Lys Lys Arg Ile
        275                 280                 285

Ala Ser Gly Glu Lys Leu Asn Ser Tyr Ile Asp Tyr Leu Leu Ser Glu
        290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu His Leu Ser
        355                 360                 365

Gln Leu Pro Tyr Ile Thr Ala Ile Phe His Glu Thr Leu Arg Lys His
            370                 375                 380

Ser Pro Val Pro Ile Leu Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Gly Lys Arg Val Cys Ala Gly Ser Leu Gln
450                 455                 460

Ala Leu Leu Ile Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Asn Gln Met Leu Arg Pro Leu Arg Ala Ile Ile Lys Pro Arg
            500                 505                 510

Ile

<210> SEQ ID NO 112
<211> LENGTH: 8
<212> TYPE: PRT
<213> ORGANISM: Artificial Sequence
<220> FEATURE:
<223> OTHER INFORMATION: Synthetic - Leader sequence

<400> SEQUENCE: 112

Met Ala Leu Leu Leu Ala Val Phe
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic - Linker sequence

<400> SEQUENCE: 113

Gly Ser Gly Gly Gly Gly Ser
1               5

<210> SEQ ID NO 114
<211> LENGTH: 8
```

```
<212> TYPE: PRT
<213> ORGANISM: Artificial Sequence
<220> FEATURE:
<223> OTHER INFORMATION: Synthetic - Linker sequence

<400> SEQUENCE: 114

Gly Ser Gly Glu Ala Ala Ala Lys
1               5

<210> SEQ ID NO 115
<211> LENGTH: 13
<212> TYPE: PRT
<213> ORGANISM: Artificial Sequence
<220> FEATURE:
<223> OTHER INFORMATION: Synthetic - Linker sequence

<400> SEQUENCE: 115

Gly Ser Gly Glu Ala Ala Ala Lys Glu Ala Ala Ala Lys
1               5                   10

<210> SEQ ID NO 116
<211> LENGTH: 9
<212> TYPE: PRT
<213> ORGANISM: Artificial Sequence
<220> FEATURE:
<223> OTHER INFORMATION: Synthetic - Linker sequence

<400> SEQUENCE: 116

Gly Ser Gly Met Gly Ser Ser Ser Asn
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic - Linker sequence

<400> SEQUENCE: 117

Gly Ser Thr Gly Ser
1               5

<210> SEQ ID NO 118
<211> LENGTH: 20
<212> TYPE: PRT
<213> ORGANISM: Artificial Sequence
<220> FEATURE:
<223> OTHER INFORMATION: Synthetic sequence

<400> SEQUENCE: 118

Met Ala Trp Glu Tyr Ala Leu Ile Gly Leu Val Val Gly Ile Ile Ile
1               5                   10                  15

Gly Ala Val Ala
            20
```